(12) United States Patent
Apte et al.

(10) Patent No.: US 10,395,777 B2
(45) Date of Patent: *Aug. 27, 2019

(54) METHOD AND SYSTEM FOR CHARACTERIZING MICROORGANISM-ASSOCIATED SLEEP-RELATED CONDITIONS

(71) Applicant: uBiome, Inc., San Francisco, CA (US)

(72) Inventors: Zachary Apte, San Francisco, CA (US); Jessica Richman, San Francisco, CA (US); Daniel Almonacid, San Francisco, CA (US); Inti Pedroso, Santiago (CL); Catalina Valdivia, Santiago (CL); Rodrigo Ortiz, Santiago (CL); Paz Tapia, Santiago (CL)

(*) Notice: Subject to any disclaimer, the term of this patent is extended or adjusted under 35 U.S.C. 154(b) by 0 days.

This patent is subject to a terminal disclaimer.

(21) Appl. No.: 15/997,654

(22) Filed: Jun. 4, 2018

(65) Prior Publication Data

US 2018/0286520 A1 Oct. 4, 2018

Related U.S. Application Data

(63) Continuation-in-part of application No. 15/606,743, filed on May 26, 2017, which is a continuation of application No. 14/919,614, filed on Oct. 21, 2015, now Pat. No. 9,703,929.

(60) Provisional application No. 62/514,356, filed on Jun. 2, 2017, provisional application No. 62/515,396, filed on Jun. 5, 2017, provisional application No. 62/066,369, filed on Oct. 21, 2014, provisional application No. 62/087,551, filed on Dec. 4, 2014, provisional application No. 62/092,999, filed on Dec. 17, 2014, provisional application No. 62/147,376, filed on Apr. 14, 2015, provisional application No. 62/147,212, filed on Apr. 14, 2015, provisional application No. 62/147,362, filed on Apr. 14, 2015, provisional application No. 62/146,855, filed on Apr. 13, 2015, provisional application No. 62/206,654, filed on Aug. 18, 2015.

(51) Int. Cl.
```
G01N 33/48    (2006.01)
G16H 50/70    (2018.01)
G16H 10/40    (2018.01)
G16B 50/00    (2019.01)
G16H 50/20    (2018.01)
G06G 7/58     (2006.01)
```

(52) U.S. Cl.
CPC ............ G16H 50/70 (2018.01); G16B 50/00 (2019.02); G16H 10/40 (2018.01); G16H 50/20 (2018.01); *Y02A 90/26* (2018.01)

(58) Field of Classification Search
None
See application file for complete search history.

(56) References Cited

U.S. PATENT DOCUMENTS

| | | |
|---|---|---|
| 6,033,864 A | 3/2000 | Braun et al. |
| 6,309,643 B1 | 10/2001 | Braun et al. |
| 6,632,641 B1 | 10/2003 | Brennan et al. |
| 6,861,053 B1 | 3/2005 | Lin et al. |
| D521,843 S | 5/2006 | Hung |
| 7,048,906 B2 | 5/2006 | Lin et al. |
| 7,176,002 B2 | 2/2007 | Lao et al. |
| 8,478,544 B2 | 7/2013 | Colwell et al. |
| 8,598,203 B2 | 12/2013 | Tarcic et al. |
| 8,883,264 B2 | 11/2014 | Yang et al. |
| 9,028,841 B2 | 5/2015 | Henn et al. |
| 9,149,473 B2 | 10/2015 | Ecker et al. |
| 9,433,651 B2 | 9/2016 | Jones et al. |
| 9,447,195 B2 | 9/2016 | Cordova et al. |
| 9,506,109 B2 | 11/2016 | Savelkoul et al. |
| 9,663,831 B2 | 5/2017 | Apte et al. |
| 9,703,929 B2 | 7/2017 | Apte et al. |
| 9,710,606 B2 | 7/2017 | Apte et al. |
| 10,242,160 B2 | 3/2019 | Apte et al. |
| 2002/0012926 A1 | 1/2002 | Quake et al. |
| 2003/0190314 A1 | 10/2003 | Campbell et al. |
| 2005/0196785 A1 | 9/2005 | Quake et al. |
| 2006/0073501 A1 | 4/2006 | Van Den Boom et al. |
| 2006/0089310 A1 | 4/2006 | Goldstein et al. |
| 2007/0134652 A1 | 6/2007 | Slepnev et al. |

(Continued)

FOREIGN PATENT DOCUMENTS

| | | |
|---|---|---|
| CN | 105407728 A | 3/2015 |
| EP | 2631240 A1 | 8/2013 |

(Continued)

OTHER PUBLICATIONS

Avila, Maria et al., The Oral Microbiota: Living with a Permanent Guest, DNA and Cell Biology, Nov. 8, 2009, vol. 28, No. 8.

Carroll et al. "Alterations in composition and diversity of the intestinal microbiota in patients with diarrhea-predominant irritable bowel syndrome," Feb. 20, 2012 (Feb. 29, 2012), vol. 24, pp. 1-19 [Original pp. 5215-5230].

Cho et al. "The Human Microbiome: at the Interface of Health and Disease," Nature Reviews Genetics, Apr. 1, 2012 (Apr. 1, 2012), vol. 13, pp. 260-270.

(Continued)

*Primary Examiner* — Eric S Dejong
(74) *Attorney, Agent, or Firm* — Kilpatrick Townsend & Stockton LLP

(57) ABSTRACT

Embodiments of a method and/or system for characterizing one or more sleep-related conditions can include determining a microorganism dataset associated with a set of subjects; and/or performing a characterization process associated with the one or more sleep-related conditions, based on the microorganism dataset, where performing the characterization process can additionally or alternatively include performing a sleep-related characterization process for the one or more sleep-related conditions, and/or determining one or more therapies S140.

30 Claims, 12 Drawing Sheets

(56) References Cited

U.S. PATENT DOCUMENTS

| | | |
|---|---|---|
| 2007/0259337 A1 | 11/2007 | Hully et al. |
| 2008/0131556 A1 | 6/2008 | De Simone et al. |
| 2010/0035232 A1 | 2/2010 | Ecker et al. |
| 2010/0129816 A1 | 5/2010 | Savelkoul et al. |
| 2010/0172874 A1 | 7/2010 | Turnbaugh et al. |
| 2011/0027219 A1 | 2/2011 | Tarcic et al. |
| 2011/0177976 A1 | 7/2011 | Gordon et al. |
| 2012/0045771 A1 | 2/2012 | Beier et al. |
| 2012/0129794 A1 | 5/2012 | Dowd et al. |
| 2012/0149584 A1 | 6/2012 | Olle et al. |
| 2012/0252775 A1 | 10/2012 | Finegold |
| 2013/0017999 A1 | 1/2013 | Fremont et al. |
| 2013/0045874 A1 | 2/2013 | Ehrlich |
| 2013/0108598 A1 | 5/2013 | Oresic et al. |
| 2013/0121968 A1 | 5/2013 | Quay |
| 2013/0184302 A1 | 7/2013 | Bortey et al. |
| 2014/0093478 A1 | 4/2014 | Turnbaugh et al. |
| 2014/0136120 A1 | 5/2014 | Colwell et al. |
| 2014/0179726 A1 | 6/2014 | Bajaj et al. |
| 2014/0199281 A1 | 7/2014 | Henn et al. |
| 2014/0315929 A1 | 10/2014 | Chiosis |
| 2014/0341853 A1 | 11/2014 | Hovanky |
| 2014/0363399 A1 | 12/2014 | Jones et al. |
| 2015/0050245 A1 | 2/2015 | Herman et al. |
| 2015/0211055 A1 | 7/2015 | Apte et al. |
| 2015/0211078 A1 | 7/2015 | Apte et al. |
| 2015/0213193 A1 | 7/2015 | Apte et al. |
| 2015/0259728 A1 | 9/2015 | Cutliffe et al. |
| 2015/0374761 A1 | 12/2015 | Sadowsky et al. |
| 2016/0032363 A1 | 2/2016 | Stintzi et al. |
| 2016/0040216 A1 | 2/2016 | Akins et al. |
| 2016/0110515 A1 | 4/2016 | Apte et al. |
| 2016/0138089 A1 | 5/2016 | Harris et al. |
| 2016/0228003 A1 | 8/2016 | Apte et al. |
| 2016/0232313 A1 | 8/2016 | Apte et al. |
| 2016/0263166 A1 | 9/2016 | Elinav et al. |
| 2017/0024527 A1 | 1/2017 | Apte et al. |
| 2017/0039347 A1 | 2/2017 | Apte et al. |
| 2017/0262608 A1 | 9/2017 | Apte et al. |
| 2017/0268045 A1 | 9/2017 | Apte et al. |
| 2017/0268046 A1 | 9/2017 | Apte et al. |
| 2017/0270268 A1 | 9/2017 | Apte et al. |
| 2017/0270269 A1 | 9/2017 | Apte et al. |
| 2017/0270270 A1 | 9/2017 | Apte et al. |
| 2017/0270271 A1 | 9/2017 | Apte et al. |
| 2017/0270272 A1 | 9/2017 | Apte et al. |
| 2017/0286619 A1 | 10/2017 | Apte et al. |
| 2017/0286620 A1 | 10/2017 | Apte et al. |
| 2017/0327864 A1 | 11/2017 | Apte et al. |
| 2017/0344719 A1 | 11/2017 | Apte et al. |
| 2017/0357763 A1 | 12/2017 | Apte et al. |
| 2017/0357767 A1 | 12/2017 | Apte et al. |
| 2017/0357768 A1 | 12/2017 | Apte et al. |
| 2017/0372027 A1 | 12/2017 | Apte et al. |
| 2018/0070827 A1 | 3/2018 | Apte et al. |
| 2019/0085396 A1 | 3/2019 | Apte et al. |

FOREIGN PATENT DOCUMENTS

| | | |
|---|---|---|
| EP | 2994756 B1 | 3/2016 |
| WO | 2012/050513 A1 | 4/2012 |
| WO | 2014/121298 A2 | 8/2014 |
| WO | 2014/138999 A1 | 9/2014 |
| WO | 2014/144092 A1 | 9/2014 |
| WO | 2014/145958 A2 | 9/2014 |
| WO | 2015/013214 A2 | 1/2015 |
| WO | 2013/085326 A1 | 6/2015 |
| WO | 2015/095241 A2 | 6/2015 |
| WO | 2015/103165 A1 | 7/2015 |
| WO | 2015/112352 A2 | 7/2015 |
| WO | 2015/112352 A8 | 7/2015 |
| WO | 2015/170979 A1 | 11/2015 |
| WO | 2015/095241 A4 | 12/2015 |
| WO | 2016/065075 A1 | 4/2016 |
| WO | 2016/138337 A1 | 9/2016 |
| WO | 2016/172643 A2 | 10/2016 |
| WO | 2016/172643 A3 | 10/2016 |
| WO | 2017/044885 A1 | 3/2017 |
| WO | 2017/044902 A1 | 3/2017 |

OTHER PUBLICATIONS

Dewhirst, Floyd et al., The Human Oral Microbiome, Journal of Bacteriology, Oct. 2010, vol. 192, No. 19, pp. 5002-5017.

Evans, Morgan, Prosthetic valve endocarditis due to *Neisseria elongata* subsp. elongata in a patient with Klinefelter's syndrome, Journal of Medical Microbiology, Jun. 1, 2007, vol. 56, No. 6, pp. 860-862.

Greenblum et al. "Metagenomic Systems Biology of the Human Gut Microbiome Reveals Topological Shifts Associated with Obesity and Inflammatory Bowel Disease," Proceeding of the National Academy of Sciences, Dec. 19, 2011 (Dec. 19, 2011), vol. 109, pp. 594.

Kanehisa et al. "KEGG: Kyoto encyclopedia of genes and genomes," Nucleic Acids Research, Jan. 1, 2000 (Jan. 1, 2000), vol. 28, No. 1, pp. 27-30.

K03100: IepB: signal peptidase I, KEGG, Aug. 7, 2012 (Aug. 7, 2012), p. 1 of 1. Retrieved from the Internet: on Jun. 12, 2016 (Jun. 12, 2016).

KEGG: Aminoacyl-tRNA biosynthesis—Reference pathway, Jul. 20, 2013 (Jul. 20, 2013). Retrieved from the internet: 1 <http://lweb:archive.org/web/20130720015616/http:www.genome.jp/kegg-bin/show _pathway?map=map00970&show_description=show. On Jun. 20, 2016 (20.06.

Mak et al. "Metabolyzer: A Novel Statistical Workflow for Analyzing Post Processed LC/MS Metabolomics Data," Anal Chem, Jan. 7, 2014 (Jan. 7, 2014), vol. 86, pp. 506-513.

Morgan et al. "Dysfunction of the intestinal microbiome in inflammatory bowel disease and treatment," Genome Biol., Apr. 16, 2012 (Apr. 16, 2012), vol. 13(9):R79, pp. 1-18.

Mutlu et al. "A Compositional Look at the Human Gastrointestinal Microbiome and Immune Activation Parameters in HIV Infected Subjects," PLoS Pathogens, Feb. 20, 2014 (Feb. 20, 2014), vol. 10, pp. 1-18.

Nakayama et al. "Aberrant Structures of Fecal Bacterial Community in Allergic Infants Profiled by 16S rRNA Gene Pyrosequencing," FEMS Immunology & Medical Microbiology, Dec. 1, 2011 (Dec. 1, 2011 ), vol. 63, pp. 397-406.

Pqnnusamy et al. "Microbial community and metabolomic comparison of irritable bowel syndrome faeces," Feb. 17, 2011 (Feb. 17, 2011), vol. 60, pp. 817-827. entire document.

Benedict et al., "Gut Microbiota and Glucometabolic Alterations in Response to Recurrent Partial Sleep Deprivation in Normal-Weight Young Individuals", Molecular Metabolism, vol. 5, 2016, pp. 1175-1186.

International Application No. PCT/US2015/056767, International Preliminary Report on Patentability dated May 4, 2017, 9 pages.

International Application No. PCT/US2015/056767, International Search Report and Written Opinion dated Jan. 11, 2016, 10 pages.

International Application No. PCT/US2018/035912, International Search Report and Written Opinion dated Sep. 12, 2018, 17 pages.

Nagy-Szakal et al., "Fecal Metagenomic Profiles in Subgroups of Patients with Myalgic Encephalomyelitis/Chronic Fatigue Syndrome", Microbiome, vol. 5, No. 44, 2017, pp. 1-17.

U.S. Appl. No. 14/919,614, Non-Final Office Action dated Jul. 14, 2016, 10 pages.

U.S. Appl. No. 14/919,614, Notice of Allowance dated May 19, 2017, 10 pages.

U.S. Appl. No. 15/606,743, Non Final Office Action dated Dec. 19, 2017, 10 pages.

U.S. Appl. No. 15/606,743, Notice of Allowance dated Sep. 20, 2018, 5 pages.

Canadian Application No. 2,962,466, Examination Report dated Mar. 23, 2018, 4 pages.

European Application No. 15852829.9, Extended European Search Report dated May 14, 2018, 8 pages.

(56) References Cited

OTHER PUBLICATIONS

European Application No. 16780673.6, Extended European Search Report dated Oct. 25, 2018, 12 pages.
International Application No. PCT/US2016/027365, International Preliminary Report on Patentability dated Oct. 17, 2017, 13 pages.
International Application No. PCT/US2016/027365, International Search Report and Written Opinion dated Jul. 27, 2016, 14 pages.
International Application No. PCT/US2017/067003, International Search Report and Written Opinion dated Apr. 26, 2018, 17 pages.
Kinross, et al.. "Gut Microbiome-host Interactions in Health and Disease", Genome Medicine, vol. 3, No. 14, 2011, pp. 1-12.
Morgan, et al., "Biodiversity and Functional Genomics in the Human Microbiome", Trends Genet., vol. 29, No. 1, Jan. 2013, pp. 51-58.
U.S. Appl. No. 15/098,236, Non-Final Office Action dated Jul. 12, 2018, 14 pages.
U.S. Appl. No. 15/606,824, Final Office Action dated Sep. 20, 2018, 8 pages.
U.S. Appl. No. 15/606,824, Non-Final Office Action dated Jan. 16, 2018, 10 pages.
U.S. Appl. No. 15/606,874, Final Office Action dated Aug. 31, 2018, 8 pages.
U.S. Appl. No. 15/606,874, Non-Final Office Action dated Feb. 9, 2018, 10 pages.
U.S. Appl. No. 15/606,874, Notice of Allowance dated Jan. 17, 2019, 5 pages.
U.S. Appl. No. 15/606,909, Final Office Action dated Sep. 20, 2018, 8 pages.
U.S. Appl. No. 15/606,909, Non-Final Office Action dated Mar. 9, 2018, 10 pages.
U.S. Appl. No. 15/606,909, Notice of Allowance dated Feb. 20, 2019, 5 pages.
U.S. Appl. No. 15/606,943, Final Office Action dated Nov. 1, 2018, 7 pages.
U.S. Appl. No. 15/606,943, Non-Final Office Action dated Apr. 10, 2018, 10 pages.
U.S. Appl. No. 15/606,943, Notice of Allowance dated Mar. 8, 2019, 5 pages.
U.S. Appl. No. 15/606,975, Final Office Action dated Jun. 14, 2018, 8 pages.
U.S. Appl. No. 15/606,975, Non-Final Office Action dated Sep. 25, 2017, 10 pages.
U.S. Appl. No. 15/606,975, Notice of Allowance dated Oct. 19, 2018, 5 pages.
U.S. Appl. No. 15/621,144, Final Office Action dated Nov. 1, 2018, 7 pages.
U.S. Appl. No. 15/621,144, Non-Final Office Action dated Apr. 10, 2018, 10 pages.
U.S. Appl. No. 15/621,144, Notice of Allowance dated Mar. 8, 2019, 6 pages.
U.S. Appl. No. 15/621,152, Final Office Action dated Nov. 1, 2018, 7 pages.
U.S. Appl. No. 15/621,152, Non-Final Office Action dated Apr. 10, 2018, 10 pages.
U.S. Appl. No. 15/621,152, Notice of Allowance dated Mar. 8, 2019, 6 pages.
U.S. Appl. No. 15/668,595, Non-Final Office Action dated Oct. 5, 2018, 13 pages.
U.S. Appl. No. 15/668,620, Non-Final Office Action dated Oct. 5, 2018, 13 pages.
U.S. Appl. No. 15/668,636, Non-Final Office Action dated Oct. 5, 2018, 12 pages.
U.S. Appl. No. 15/668,653, Non-Final Office Action dated Oct. 5, 2018, 13 pages.
U.S. Appl. No. 15/845,190, Non-Final Office Action dated Nov. 1, 2018, 13 pages.
U.S. Appl. No. 15/098,236, "Notice of Allowance", dated Apr. 3, 2019, 7 pages.
U.S. Appl. No. 15/606,824, "Notice of Allowance", dated Mar. 26, 2019, 5 pages.
U.S. Appl. No. 15/606,975, "Notice of Allowance", dated Apr. 3, 2019, 5 pages.
U.S. Appl. No. 15/845,190, "Notice of Allowance", dated Apr. 3, 2019, 5 pages.

METHOD AND SYSTEM FOR CHARACTERIZING MICROORGANISM-ASSOCIATED SLEEP-RELATED CONDITIONS

CROSS-REFERENCE TO RELATED APPLICATIONS

This application is a continuation-in-part of U.S. application Ser. No. 15/606,743, filed 26 May 2017, which is a continuation of U.S. application Ser. No. 14/919,614, filed 21 Oct. 2017, which claims the benefit of U.S. Provisional Application Ser. No. 62/066,369 filed 21 Oct. 2014, U.S. Provisional Application Ser. No. 62/087,551 filed 4 Dec. 2014, U.S. Provisional Application Ser. No. 62/092,999 filed 17 Dec. 2014, U.S. Provisional Application Ser. No. 62/147,376 filed 14 Apr. 2015, U.S. Provisional Application Ser. No. 62/147,212 filed 14 Apr. 2015, U.S. Provisional Application Ser. No. 62/147,362 filed 14 Apr. 2015, U.S. Provisional Application Ser. No. 62/146,855 filed 13 Apr. 2015, and U.S. Provisional Application Ser. No. 62/206,654 filed 18 Aug. 2015, which are each incorporated in its entirety herein by this reference.

This application additionally claims the benefit of U.S. Provisional Application Ser. No. 62/514,356 filed 2 Jun. 2017 and U.S. Provisional Application Ser. No. 62/515,396 filed 5 Jun. 2017, which are each herein incorporated in their entirety by this reference.

TECHNICAL FIELD

The disclosure generally relates to genomics and microbiology.

BACKGROUND

A microbiome can include an ecological community of commensal, symbiotic, and pathogenic microorganisms that are associated with an organism. Characterization of the human microbiome is a complex process. The human microbiome includes over 10 times more microbial cells than human cells, but characterization of the human microbiome is still in nascent stages such as due to limitations in sample processing techniques, genetic analysis techniques, and resources for processing large amounts of data. Present knowledge has clearly established the role of microbiome associations with multiple health conditions, and has become an increasingly appreciated mediator of host genetic and environmental factors on human disease development. The microbiome is suspected to play at least a partial role in a number of health/disease-related states. Further, the microbiome may mediate effects of environmental factors on human, plant, and/or animal health. Given the profound implications of the microbiome in affecting a user's health, efforts related to the characterization of the microbiome, the generation of insights from the characterization, and the generation of therapeutics configured to rectify states of dysbiosis should be pursued. Methods and systems for analyzing the microbiomes of humans and/or providing therapeutic measures based on gained insights have, however, left many questions unanswered.

As such, there is a need in the field of microbiology for a new and useful method and/or system for characterizing, monitoring, diagnosing, and/or intervening in one or more microorganism-related health conditions, such as for individualized and/or population-wide use.

DESCRIPTION OF THE EMBODIMENTS

The following description of the embodiments is not intended to limit the embodiments, but rather to enable any person skilled in the art to make and use.

1. Overview

Figure 1A:
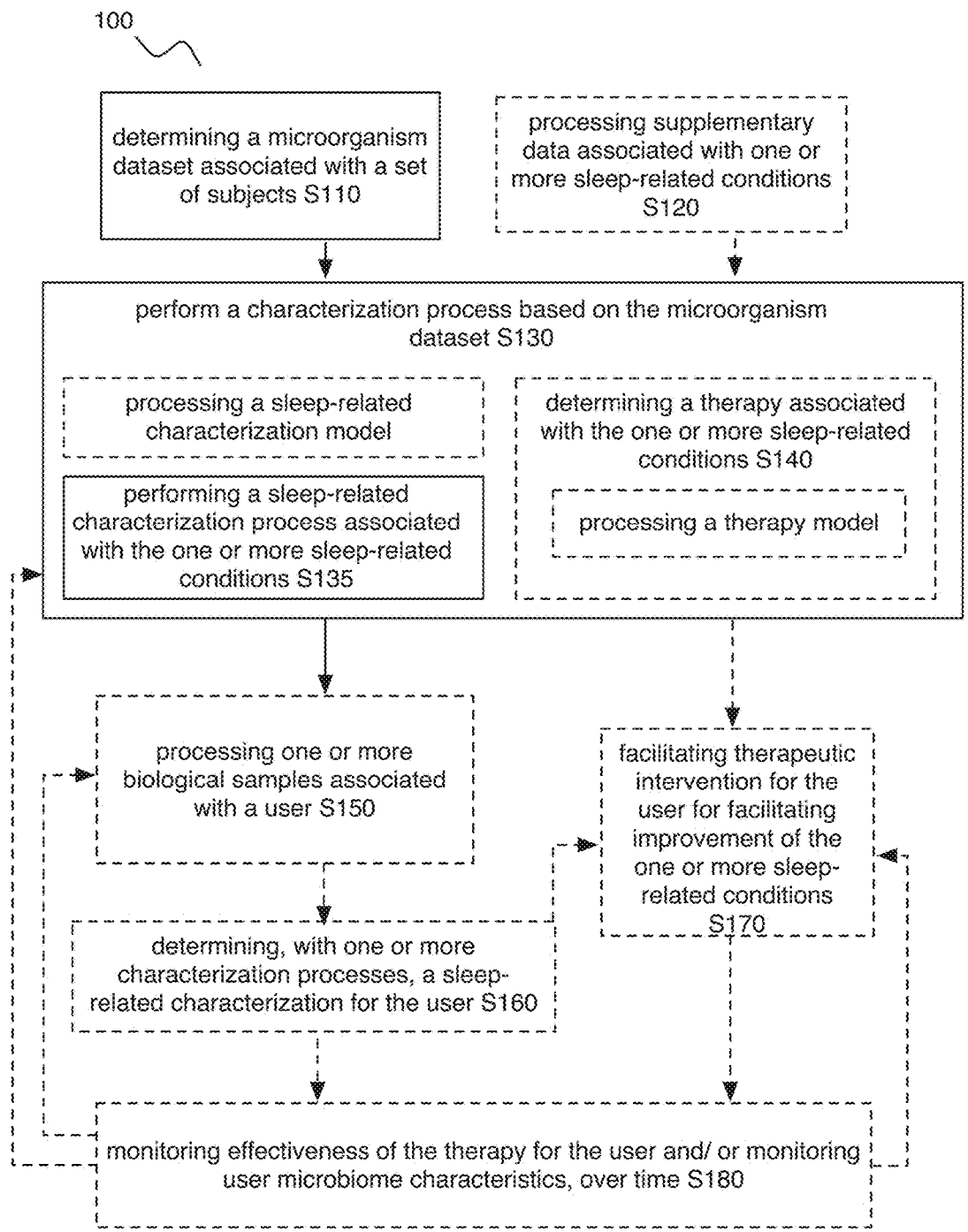
FIGS. 1A-1B show a flowchart representation of variations of an embodiment of a method.
Figure 1B:
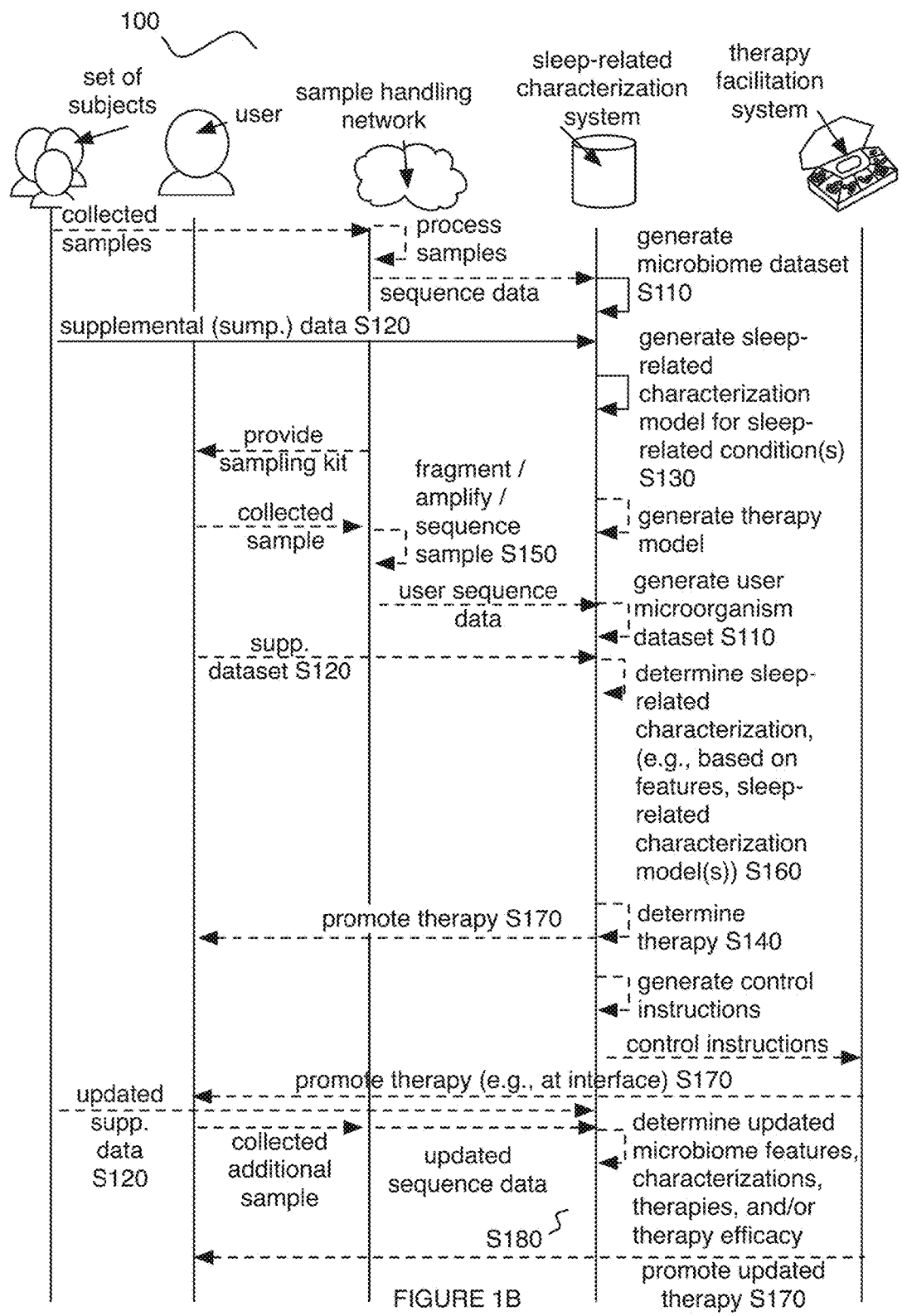

As shown in FIGS. 1A-1B, embodiments of a method 100 for characterizing one or more sleep-related conditions can include: determining a microorganism dataset (e.g., microorganism sequence dataset, microbiome composition diversity dataset such as based upon a microorganism sequence dataset, microbiome functional diversity dataset such as based upon a microorganism sequence dataset, etc.) associated with a set of subjects S110; and/or performing a characterization process (e.g., pre-processing, feature determination, feature processing, sleep-related characterization model processing, etc.) associated with the one or more sleep-related conditions, based on the microorganism dataset (e.g., based on microbiome composition features and/or microbiome functional features derived from the microorganism dataset and associated with the one or more sleep-related conditions; etc.) S130, where performing the characterization process can additionally or alternatively include performing a sleep-related characterization process for the one or more sleep-related conditions S135, and/or determining one or more therapies (e.g., determining therapies for preventing, ameliorating, reducing the risk of, and/or otherwise improving the one or more sleep-related conditions, etc.) S140.

Embodiments of the method 100 can additionally or alternatively include one or more of: processing supplementary data associated with (e.g., informative of; describing; indicative of; correlated with, etc.) one or more sleep-related conditions S120; processing one or more biological samples associated with a user (e.g., subject, human, animal, patient; etc.) S150; determining, with one or more characterization processes, a sleep-related characterization for the user for one or more sleep-related conditions, based on a user microorganism dataset (e.g., user microorganism sequence dataset; user microbiome composition dataset; user microbiome function dataset; user microbiome features derived from the user microorganism dataset, where the user microbiome features can correspond to feature values for the microbiome features determined from one or more characterization processes; etc.) associated with a biological sample of the user S160; facilitating therapeutic intervention for the one or more sleep-related conditions for the user (e.g., based upon the sleep-related characterization and/or a therapy model; etc.) S170; monitoring effectiveness of one or more therapies and/or monitoring other suitable components (e.g., microbiome characteristics, etc.) for the user (e.g., based upon processing a series of biological samples from the user), over time (e.g., such as to assess user microbiome characteristics such as user microbiome composition features and/or functional features associated with the therapy, for the user over time, etc.) S180; and/or any other suitable processes.

Embodiments of the method 100 and/or system 200 can function to characterize (e.g., assess, evaluate, diagnose, describe, etc.) one or more sleep-related conditions (e.g., characterizing the sleep-related conditions themselves, such as determining microbiome features correlated with and/or otherwise associated with the sleep-related conditions; characterizing one or more sleep-related conditions for one or more users, such as determining propensity metrics for the one or more sleep-related conditions for the one or more users; etc.). In an example, the method 100 can include: determining a microorganism dataset associated with a set of subjects (e.g., including subjects with one or more sleep-related conditions, subjects without the one or more sleep-related conditions, etc.), based on microorganism nucleic acids from biological samples associated with the set of subjects, where the microorganism nucleic acids are associated with one or more sleep-related conditions; processing (e.g., collecting, etc.), for the set of subjects, supplementary data associated with the one or more sleep-related conditions; determining microbiome features (e.g., at least one of a set of microbiome composition features and a set of microbiome functional features, etc.) associated with the set of subjects, based on the microorganism dataset (and/or the supplementary data and/or other suitable data); generating a sleep-related characterization model (e.g., for determining sleep-related characterizations; a therapy model; etc.) based on the supplementary data and the microbiome features, where the sleep-related characterization model is associated with the one or more sleep-related conditions; determining a sleep-related characterization for a user for the one or more sleep-related conditions based on the sleep-related characterization model; and facilitating therapeutic intervention (e.g., providing a therapy to the user, etc.) for facilitating improvement of the one or more sleep-related conditions, based on the sleep-related characterization. In another example, the method 100 can include: collecting a biological sample from a user (e.g., via sample kit provision and collection, etc.), where the biological sample includes microorganism nucleic acids associated with one or more sleep-related conditions; determining a microorganism dataset associated with the user based on the microorganism nucleic acids of the biological sample (e.g., based on sample preparation and/or sequencing with the biological sample, etc.); determining user microbiome features (e.g., including at least one of user microbiome composition features and user microbiome functional features, based on the microorganism dataset, etc.), where the user microbiome features are associated with the one or more sleep-related conditions; determining a sleep-related characterization for a user for the one or more sleep-related conditions based on the user microbiome features; and facilitating therapeutic intervention in relation to a therapy for the user for facilitating improvement of the one or more sleep-related conditions, based on the sleep-related characterization.

Additionally or alternatively, embodiments of the method 100 and/or system 200 can identify microbiome features and/or other suitable data associated with (e.g., positive correlated with, negatively correlated with, etc.) one or more sleep-related conditions, such as for use as biomarkers (e.g., for diagnostic processes, for treatment processes, etc.). In examples, sleep-related characterization can be associated with at least one or more of user microbiome composition (e.g., microbiome composition diversity, etc.), microbiome function (e.g., microbiome functional diversity, etc.), and/or other suitable microbiome-related aspects. In an example, microorganism features (e.g., describing composition, function, and/or diversity of recognizable patterns, such as in relation to relative abundance of microorganisms that are present in a subject's microbiome, such as for subjects exhibiting one or more sleep-related conditions; etc.) and/or microorganism datasets (e.g., from which microbiome features can be derived, etc.) can be used for diagnostics, characterizations, therapeutic intervention facilitation, monitoring, and/or other suitable purposes, such as by using bioinformatics pipelines, analytical techniques, and/or other suitable approaches described herein. Additionally or alternatively, embodiments of the method 100 and/or system 200 can function to perform cross-condition analyses for a plurality of sleep-related conditions (e.g., performing characterization processes for a plurality of sleep-related conditions, such as determining correlation, covariance, comorbidity, and/or other suitable relationships between different sleep-related conditions, etc.), such as in the context of characterizing, diagnosing, and/or treating a user.

Additionally or alternatively, embodiments can function to facilitate therapeutic intervention (e.g., therapy selection; therapy promotion and/or provision; therapy monitoring; therapy evaluation; etc.) for one or more sleep-related conditions, such as through promotion of associated therapies (e.g., in relation to specific physiological sites gut, skin, nose, mouth, genitals, other suitable physiological sites, other collection sites; therapies determined by therapy models; etc.). Additionally or alternatively, embodiments can function to generate models (e.g., sleep-related characterization models such as for phenotypic prediction; therapy models such as for therapy determination; machine learning models such as for feature processing, etc.), such as models that can be used to characterize and/or diagnose users based on their microbiome (e.g., user microbiome features; as a clinical diagnostic; as a companion diagnostic, etc.), and/or that can be used to select and/or provide therapies for subjects in relation to one or more sleep-related conditions. Additionally or alternatively, embodiments can perform any suitable functionality described herein.

As such, data from populations of subjects (e.g., associated with one or more sleep-related conditions; positively or negatively correlated with one or more sleep-related conditions; etc.) can be used to characterize subsequent users, such as for indicating microorganism-related states of health and/or areas of improvement, and/or to facilitate therapeutic intervention (e.g., promoting one or more therapies; facilitating modulation of the composition and/or functional diversity of a user's microbiome toward one or more of a set of desired equilibrium states, such as states correlated with improved health states associated with one or more sleep-related conditions; etc.), such as in relation to one or more sleep-related conditions. Variations of the method 100 can further facilitate selection, monitoring (e.g., efficacy monitoring, etc.) and/or adjusting of therapies provided to a user, such as through collection and analysis (e.g., with sleep-related characterization models) of additional samples from a subject over time (e.g., throughout the course of a therapy regimen, through the extent of a user's experiences with sleep-related conditions; etc.), across collection sites, in addition or alternative to processing supplementary data over time (e.g., sleep-tracking data, etc.), such as for one or more sleep-related conditions. However, data from populations, subgroups, individuals, and/or other suitable entities can be used by any suitable portions of the method 100 and/or system 200 for any suitable purpose.

Embodiments of the method 100 and/or system 200 can preferably determine and/or promote (e.g., provide; present; notify regarding; etc.) characterizations and/or therapies for one or more sleep-related conditions, and/or any suitable portions of the method 100 and/or system 200 can be performed in relation to sleep-related conditions. Sleep-related conditions can include any one or more of: insomnias (e.g., short sleeping, child insomnia, etc.), hypersomnias (e.g., narcolepsy, idiopathic hypersomnia, Kleine-Levin syndrome, insufficient sleep syndrome, long sleeping, idiopathic hypersomnia, etc.), sleep-related breathing disorders (e.g., sleep apnea, obstructive sleep apnea, snoring, central sleep apnea, child sleep apnea, infant sleep apnea, sleep-related groaning, catathrenia, hypopnea syndrome, etc.), circadian rhythm-related sleep disorders (e.g., delayed sleep-wake phase, advanced sleep-wake phase, irregular sleep-wake rhythm, non-24-hour sleep-wake rhythm, shift work sleep disorders, jet lag, etc.), parasomnias (e.g., sleep-walking, confusional arousals, sleep terrors, sleep eating disorders, REM sleep behavior disorders, sleep paralysis, nightmares, bedwetting, hallucinations, exploding head syndrome, sleep talking, etc.), sleep-related movement disorders (e.g., periodic limb movements, sleep leg cramps, sleep rhythmic movement, bruxism, restless legs syndrome, etc.), dyssomnias, sleeping sickness, nocturia, somniphobia, abnormal sleep behavior disorders, daytime sleepiness disorders, comorbid conditions, and/or any other suitable conditions associated with sleep.

Additionally or alternatively, sleep-related conditions can include one or more of: diseases, symptoms, causes (e.g., triggers, etc.), disorders, associated risk (e.g., propensity scores, etc.), associated severity, behaviors (e.g., physical activity behavior; alcohol consumption; smoking behaviors; stress-related characteristics; other psychological characteristics; sickness; social behaviors; caffeine consumption; alcohol consumption; sleep habits such as sleep time, wake time, naps, length, quality, sleep phases, consistence, variance and/or other sleep behaviors; other habits; diet-related behaviors; meditation and/or other relaxation behaviors; lifestyle conditions associated with sleep-related conditions; lifestyle conditions affecting sleep quality; lifestyle conditions informative of, correlated with, indicative of, facilitative of, and/or otherwise associated with diagnosis and/or therapeutic intervention for sleep-related conditions; behaviors affecting and/or otherwise associated with sleep and/or sleep-related conditions; etc.), environmental factors (e.g., location of sleep; bed, mattress, pillow, blanket, and/or other bedding and/or sleeping environment factors; lighting; other visual factors; noise; other audio factors; touch factors; etc.), demographic-related characteristics (e.g., age, weight, race, gender, etc.), phenotypes (e.g., phenotypes measurable for a human, animal, plant, fungi body; phenotypes associated with sleep and/or other related aspects, etc.), and/or any other suitable aspects associated with sleep-related conditions. In examples, one or more sleep-related conditions can include a medical disorder affecting the sleep patterns of a human, animal, and/or other suitable entity. In an example, one or more sleep-related conditions can interfere with normal physical, mental, social and/or emotional function. In an example, one or more sleep-related conditions can be characterized by and/or diagnosed by medical interview, medical history, survey, sensor data, medical exams, data activities including and/or requiring monitoring individuals as they sleep, other supplementary data, and/or through any suitable techniques (e.g., techniques available for diagnosis for sleep-related conditions, etc.).

Embodiments of the method 100 and/or system 200 can be implemented for a single user, such as in relation to applying one or more sample handling processes and/or characterization processes for processing one or more biological samples (e.g., collected across one or more collection sites, etc.) from the user, for sleep-related characterization, facilitating therapeutic intervention, and/or for any other suitable purpose. Additionally or alternatively, embodiments can be implemented for a population of subjects (e.g., including the user, excluding the user), where the population of subjects can include subjects similar to and/or dissimilar to any other subjects for any suitable type of characteristics (e.g., in relation to sleep-related conditions, demographic characteristics, behaviors, microbiome composition and/or function, etc.); implemented for a subgroup of users (e.g., sharing characteristics, such as characteristics affecting sleep-related characterization and/or therapy determination; etc.); implemented for plants, animals, microorganisms, and/or any other suitable entities. Thus, information derived from a set of subjects (e.g., population of subjects, set of subjects, subgroup of users, etc.) can be used to provide additional insight for subsequent users. In a variation, an aggregate set of biological samples is preferably associated with and processed for a wide variety of subjects, such as including subjects of one or more of: different demographic characteristics (e.g., genders, ages, marital statuses, ethnicities, nationalities, socioeconomic statuses, sexual orientations, etc.), different sleep-related conditions (e.g., health and disease states; different genetic dispositions; etc.), different living situations (e.g., living alone, living with pets, living with a significant other, living with children, etc.), different dietary habits (e.g., omnivorous, vegetarian, vegan, sugar consumption, acid consumption, caffeine consumption, etc.), different behavioral tendencies (e.g., levels of physical activity, drug use, alcohol use, etc.), different levels of mobility (e.g., related to distance traveled within a given time period), and/or any other suitable characteristic (e.g., characteristics influencing, correlated with, and/or otherwise associated with microbiome composition and/or function, etc.). In examples, as the number of subjects increases, the predictive power of processes implemented in portions of the method 100 and/or system 200 can increase, such as in relation to characterizing subsequent users (e.g., with varying characteristics, etc.) based upon their microbiomes (e.g., in relation to different collection sites for samples for the users, etc.). However, portions of the method 100 and/or system 200 can be performed and/or configured in any suitable manner for any suitable entity or entities.

Data described herein (e.g., microbiome features, microorganism datasets, models, sleep-related characterizations, supplementary data, notifications, etc.) can be associated with any suitable temporal indicators (e.g., seconds, minutes, hours, days, weeks, etc.) including one or more: temporal indicators indicating when the data was collected (e.g., temporal indicators indicating when a sample was collected; etc.), determined, transmitted, received, and/or otherwise processed; temporal indicators providing context to content described by the data (e.g., temporal indicators associated with sleep-related characterizations, such as where the sleep-related characterization describes the sleep-related conditions and/or user microbiome status at a particular time; etc.); changes in temporal indicators (e.g., changes in sleep-related characterizations over time, such as in response to receiving a therapy; latency between sample collection, sample analysis, provision of a sleep-related characterization or therapy to a user, and/or other suitable portions of the method 100; etc.); and/or any other suitable indicators related to time.

Additionally or alternatively, parameters, metrics, inputs, outputs, and/or other suitable data can be associated with value types including: scores (e.g., sleep-related condition propensity scores; feature relevance scores; correlation scores, covariance scores, microbiome diversity scores, severity scores; etc.), individual values (e.g., individual sleep-related condition scores, such as condition propensity scores, for different collection sites, etc.), aggregate values, (e.g., overall scores based on individual microorganism-related scores for different collection sites, etc.), binary values (e.g., presence or absence of a microbiome feature; presence or absence of a sleep-related condition; etc.), relative values (e.g., relative taxonomic group abundance, relative microbiome function abundance, relative feature abundance, etc.), classifications (e.g., sleep-related condition classifications and/or diagnoses for users; feature classifications; behavior classifications; demographic characteristic classifications; etc.), confidence levels (e.g., associated with microorganism sequence datasets; with microbiome diversity scores; with other sleep-related characterizations; with other outputs; etc.), identifiers, values along a spectrum, and/or any other suitable types of values. Any suitable types of data described herein can be used as inputs (e.g., for different analytical techniques, models, and/or other suitable components described herein), generated as outputs (e.g., of different analytical techniques, models, etc.), and/or manipulated in any suitable manner for any suitable components associated with the method 100 and/or system 200.

One or more instances and/or portions of the method 100 and/or processes described herein can be performed asynchronously (e.g., sequentially), concurrently (e.g., parallel data processing; concurrent cross-condition analysis; multiplex sample processing, such as multiplex amplification of microorganism nucleic acid fragments corresponding to target sequences associated with sleep-related conditions; performing sample processing and analysis for substantially concurrently evaluating a panel of sleep-related conditions; computationally determining microorganism datasets, microbiome features, and/or characterizing sleep-related conditions in parallel for a plurality of users; such as concurrently on different threads for parallel computing to improve system processing ability; etc.), in temporal relation (e.g., substantially concurrently with, in response to, serially, prior to, subsequent to, etc.) to a trigger event (e.g., performance of a portion of the method 100), and/or in any other suitable order at any suitable time and frequency by and/or using one or more instances of the system 200, components, and/or entities described herein. In an example, the method 100 can include generating a microorganism dataset based on processing microorganism nucleic acids of one or more biological samples with a bridge amplification substrate of a next generation sequencing platform (and/or other suitable sequencing system) of a sample handling system, and determining microbiome features and microbiome functional diversity features at computing devices operable to communicate with the next generation sequencing platform. However, the method 100 and/or system 200 can be configured in any suitable manner.

2. Benefits.

Microbiome analysis can enable accurate and/or efficient characterization and/or therapy provision (e.g., according to portions of the method 100, etc.) for sleep-related conditions caused by, correlated with, and/or otherwise associated with microorganisms. Specific examples of the technology can overcome several challenges faced by conventional approaches in characterizing a sleep-related conditions and/or facilitating therapeutic intervention. First, conventional approaches can require patients to visit one or more care providers to receive a characterization and/or a therapy recommendation for a sleep-related condition (e.g., through diagnostic medical procedures such as in-hospital sleep-tracking; etc.), which can amount to inefficiencies and/or health-risks associated with the amount of time elapsed before diagnosis and/or treatment, with inconsistency in healthcare quality, and/or with other aspects of care provider visitation. Second, conventional genetic sequencing and analysis technologies for human genome sequencing can be incompatible and/or inefficient when applied to the microbiome (e.g., where the human microbiome can include over 10 times more microbial cells than human cells; where viable analytical techniques and the means of leveraging the analytical techniques can differ; where optimal sample processing techniques can differ, such as for reducing amplification bias; where different approaches to sleep-related characterizations can be employed; where the types of conditions and correlations can differ; where causes of the associated conditions and/or viable therapies for the associated conditions can differ; where sequence reference databases can differ; where the microbiome can vary across different body regions of the user such as at different collection sites; etc.). Third, the onset of sequencing technologies (e.g., next-generation sequencing, associated technologies, etc.) has given rise to technological issues (e.g., data processing and analysis issues for the plethora of generated sequence data; issues with processing a plurality of biological samples in a multiplex manner; information display issues; therapy prediction issues; therapy provision issues, etc.) that would not exist but for the unprecedented advances in speed and data generation associated with sequencing genetic material. Specific examples of the method 100 and/or system 200 can confer technologically-rooted solutions to at least the challenges described above.

First, specific examples of the technology can transform entities (e.g., users, biological samples, therapy facilitation systems including medical devices, etc.) into different states or things. For example, the technology can transform a biological sample into components able to be sequenced and analyzed to generate microorganism dataset and/or microbiome features usable for characterizing users in relation to one or more sleep-related conditions (e.g., such as through use of next-generation sequencing systems, multiplex amplification operations; etc.). In another example, the technology can identify, promote (e.g., present, recommend, etc.), discourage, and/or provide therapies (e.g., personalized therapies based on a sleep-related characterization; etc.) and/or otherwise facilitate therapeutic intervention (e.g., facilitating modification of a user's microbiome composition, microbiome functionality, etc.), which can prevent and/or ameliorate one or more sleep-related conditions, thereby transforming the microbiome and/or health of the patient (e.g., improving a health state associated with a sleep-related condition; etc.). In another example, the technology can transform microbiome composition and/or function at one or more different physiological sites of a user (e.g., one or more different collection sites, etc.), such as targeting and/or transforming microorganisms associated with a gut, nose, skin, mouth, and/or genitals microbiome. In another example, the technology can control therapy facilitation systems (e.g., dietary systems; automated medication dispensers; behavior modification systems; diagnostic systems; disease therapy facilitation systems; etc.) to promote therapies (e.g., by generating control instructions for the therapy facilitation system to execute; etc.), thereby transforming the therapy facilitation system.

Second, specific examples of the technology can confer improvements in computer-related technology (e.g., improving computational efficiency in storing, retrieving, and/or processing microorganism-related data for sleep-related conditions; computational processing associated with biological sample processing, etc.) such as by facilitating computer performance of functions not previously performable. For example, the technology can apply a set of analytical techniques in a non-generic manner to non-generic microorganism datasets and/or microbiome features (e.g., that are recently able to be generated and/or are viable due to advances in sample processing techniques and/or sequencing technology, etc.) for improving sleep-related characterizations and/or facilitating therapeutic intervention for sleep-related conditions.

Third, specific examples of the technology can confer improvements in processing speed, sleep-related characterization, accuracy, microbiome-related therapy determination and promotion, and/or other suitable aspects in relation to sleep-related conditions. For example, the technology can leverage non-generic microorganism datasets to determine, select, and/or otherwise process microbiome features of particular relevance to one or more sleep-related conditions (e.g., processed microbiome features relevant to a sleep-related condition; cross-condition microbiome features with relevance to a plurality of sleep-related conditions, etc.), which can facilitate improvements in accuracy (e.g., by using the most relevant microbiome features; by leveraging tailored analytical techniques; etc.), processing speed (e.g., by selecting a subset of relevant microbiome features; by performing dimensionality reduction techniques; by leveraging tailored analytical techniques; etc.), and/or other computational improvements in relation to phenotypic prediction (e.g., indications of the sleep-related conditions, etc.), other suitable characterizations, therapeutic intervention facilitation, and/or other suitable purposes. In a specific example, the technology can apply feature-selection rules (e.g., microbiome feature-selection rules for composition, function; for supplemental features extracted from supplementary datasets; etc.) to select an optimized subset of features (e.g., microbiome functional features relevant to one or more sleep-related conditions; microbiome composition diversity features such as reference relative abundance features indicative of healthy, presence, absence, and/or other suitable ranges of taxonomic groups associated with sleep-related conditions; user relative abundance features that can be compared to reference relative abundance features correlated with sleep-related conditions and/or therapy responses; etc.) out of a vast potential pool of features (e.g., extractable from the plethora of microbiome data such as sequence data; identifiable by univariate statistical tests; etc.) for generating, applying, and/or otherwise facilitating characterization and/or therapies (e.g., through models, etc.). The potential size of microbiomes (e.g., human microbiomes, animal microbiomes, etc.) can translate into a plethora of data, giving rise to questions of how to process and analyze the vast array of data to generate actionable microbiome insights in relation to sleep-related conditions. However, the feature-selection rules and/or other suitable computer-implementable rules can enable one or more of: shorter generation and execution times (e.g., for generating and/or applying models; for determining sleep-related characterizations and/or associated therapies; etc.); optimized sample processing techniques (e.g., improving transformation of microorganism nucleic acids from biological samples through using primer types, other biomolecules, and/or other sample processing components identified through computational analysis of taxonomic groups, sequences, and/or other suitable data associated with sleep-related conditions, such as while optimizing for improving specificity, reducing amplification bias, and/or other suitable parameters; etc.); model simplification facilitating efficient interpretation of results; reduction in overfitting; network effects associated with generating, storing, and applying sleep-related characterizations for a plurality of users over time in relation to sleep-related conditions (e.g., through collecting and processing an increasing amount of microbiome-related data associated with an increasing number of users to improve predictive power of the sleep-related characterizations and/or therapy determinations; etc.); improvements in data storage and retrieval (e.g., storing and/or retrieving sleep-related characterization models; storing specific models such as in association with different users and/or sets of users, with different sleep-related conditions; storing microorganism datasets in association with user accounts; storing therapy monitoring data in association with one or more therapies and/or users receiving the therapies; storing features, sleep-related characterizations, and/or other suitable data in association with a user, set of users, and/or other entities to improve delivery of personalized characterizations and/or treatments for the sleep-related conditions, etc.), and/or other suitable improvements to technological areas.

Fourth, specific examples of the technology can amount to an inventive distribution of functionality across a network including a sample handling system, a sleep-related characterization system, and a plurality of users, where the sample handling system can handle substantially concurrent processing of biological samples (e.g., in a multiplex manner) from the plurality of users, which can be leveraged by the sleep-related characterization system in generating personalized characterizations and/or therapies (e.g., customized to the user's microbiome such as in relation to the user's dietary behavior, probiotics-associated behavior, medical history, demographic characteristics, other behaviors, preferences, etc.) for sleep-related conditions.

Fifth, specific examples of the technology can improve the technical fields of at least genomics, microbiology, microbiome-related computation, diagnostics, therapeutics, microbiome-related digital medicine, digital medicine generally, modeling, and/or other relevant fields. In an example, the technology can model and/or characterize different sleep-related conditions, such as through computational identification of relevant microorganism features (e.g., which can act as biomarkers to be used in diagnoses, facilitating therapeutic intervention, etc.) for sleep-related conditions. In another example, the technology can perform cross-condition analysis to identify and evaluate cross-condition microbiome features associated with (e.g., shared across, correlated across, etc.) a plurality of a sleep-related conditions (e.g., diseases, phenotypes, etc.). Such identification and characterization of microbiome features can facilitate improved health care practices (e.g., at the population and individual level, such as by facilitating diagnosis and therapeutic intervention, etc.), by reducing risk and prevalence of comorbid and/or multi-morbid sleep-related conditions (e.g., which can be associated with environmental factors, and thereby associated with the microbiome, etc.).

Sixth, the technology can leverage specialized computing devices (e.g., devices associated with the sample handling system, such as next-generation sequencing systems; sleep-related characterization systems; therapy facilitation systems; etc.) in performing suitable portions associated with the method 100 and/or system 200.

Specific examples of the technology can, however, provide any other suitable benefit(s) in the context of using non-generalized computer systems for sleep-related characterization, microbiome modulation, and/or for performing other suitable portions of the method 100.

3. System.

Figure 2:
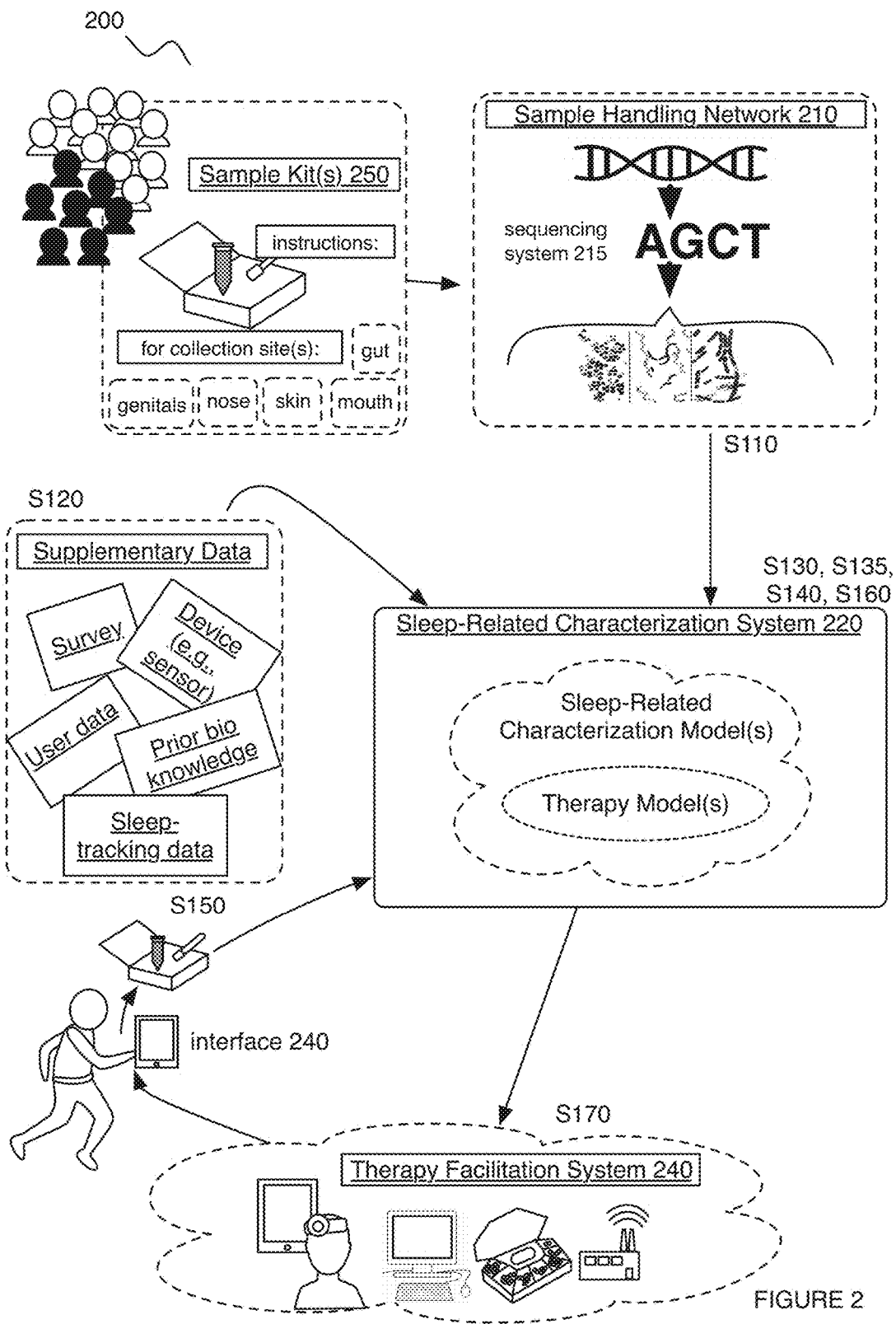
FIG. 2 depicts embodiments of a method and system.

As shown in FIG. 2, embodiments of the system 200 (e.g., for characterizing a sleep-related condition) can include any one or more of: a handling system (e.g., a sample handling system, etc.) 210 operable to collect and/or process biological samples (e.g., collected by users and included in containers including pre-processing reagents; etc.) from one or more users (e.g., a human subject, patient, animal subject, environmental ecosystem, care provider, etc.) for facilitating determination of a microorganism dataset (e.g., microorganism genetic sequences; microorganism sequence dataset; etc.); a sleep-related characterization system 220 operable to determine user microbiome features (e.g., microbiome composition features; microbiome functional features; diversity features; relative abundance ranges; such as based on a microorganism dataset and/or other suitable data; etc.), determine sleep-related characterizations (e.g., sleep-related condition characterizations, therapy-related characterizations, characterizations for users, etc.); and/or a therapy facilitation system 230 operable to facilitate therapeutic intervention (e.g., promote a therapy, etc.) for one or more sleep-related conditions (e.g., based on one or more sleep-related conditions; for improving one or more sleep-related conditions; etc.).

The handling system 210 of the system 200 can function to receive and/or process (e.g., fragment, amplify, sequence, generate associated datasets, etc.) biological samples to transform microorganism nucleic acids and/or other components of the biological samples into data (e.g., genetic sequences that can be subsequently aligned and analyzed; microorganism datasets; etc.) for facilitating generation of sleep-related characterizations and/or therapeutic intervention. The handling system 210 can additionally or alternatively function to provide sample kits 250 (e.g., including sample containers, instructions for collecting samples from one or more collection sites, etc.) to a plurality of users (e.g., in response to a purchase order for a sample kit 250), such as through a mail delivery system. The handling system 210 can include one or more sequencing systems 215 (e.g., a next-generation sequencing systems, sequencing systems for targeted amplicon sequencing, metatranscriptomic sequencing, metagenomic sequencing, sequencing-by-synthesis techniques, capillary sequencing technique, Sanger sequencing, pyrosequencing techniques, nanopore sequencing techniques, etc.) for sequencing one or more biological samples (e.g., sequencing microorganism nucleic acids from the biological samples, etc.), such as in generating microorganism data (e.g., microorganism sequence data, other data for microorganism datasets, etc.). The handling system 210 can additionally or alternatively include a library preparation system operable to automatically prepare biological samples (e.g., fragment and amplify using primers compatible with genetic targets associated with the sleep-related condition) in a multiplex manner to be sequenced by a sequencing system; and/or any suitable components. The handling system can perform any suitable sample processing techniques described herein. However, the handling system 210 and associated components can be configured in any suitable manner.

The sleep-related characterization system 220 of the system 200 can function to determine, analyze, characterize, and/or otherwise process microorganism datasets (e.g., based on processed biological samples leading to microorganism genetic sequences; alignments to reference sequences; etc.), microbiome features (e.g., individual variables; groups of variables; features relevant for phenotypic prediction, for statistical description; variables associated with a sample obtained from an individual; variables associated with sleep-related conditions; variables describing fully or partially, in relative or absolute quantities the sample's microbiome composition and/or functionality; etc.), models, and/or other suitable data for facilitating sleep-related characterization and/or therapeutic intervention. In examples, the sleep-related characterization system 220 can identify data associated with the information of the features that statistically describe the differences between samples associated with one or more sleep-related conditions (e.g., samples associated with presence, absence, risk of, propensity for, and/or other aspects related to sleep-related conditions etc.), such as where the differing analyses can provide complementing views into the features differentiating the different samples (e.g., differentiating the subgroups associated with presence or absence of a condition, etc.). In a specific example, individual predictors, a specific biological process, and/or statistically inferred latent variables can provide complementary information at different levels of data complexity to facilitate varied downstream opportunities in relation to characterization, diagnosis, and/or treatment. In another specific example, the sleep-related characterization system 220 process supplementary data for performing one or more characterization processes.

The sleep-related characterization system 220 can include, generate, apply, and/or otherwise process sleep-related characterization models, which can include any one or more of sleep-related condition models for characterizing one or more sleep-related conditions (e.g., determining propensity of one or more sleep-related conditions for one or more users, etc.), therapy models for determining therapies, and/or any other suitable models for any suitable purposes associated with the system 200 and/or method 100. In a specific example, the sleep-related characterization system 220 can generate and/or apply a therapy model (e.g., based on cross-condition analyses, etc.) for identifying and/or characterizing a therapy used to treat one or more sleep-related conditions. Different sleep-related characterization models (e.g., different combinations of sleep-related characterization models; different models applying different analytical techniques; different inputs and/or output types; applied in different manners such as in relation to time and/or frequency; etc.) can be applied (e.g., executed, selected, retrieves, stored, etc.) based on one or more of: sleep-related conditions (e.g., using different sleep-related characterization models depending on the sleep-related condition or conditions being characterized, such as where different sleep-related characterization models possess differing levels of suitability for processing data in relation to different sleep-related conditions and/or combinations of conditions, etc.), users (e.g., different sleep-related characterization models based on different user data and/or characteristics, demographic characteristics, genetics, environmental factors, etc.), sleep-related characterizations (e.g., different sleep-related characterization models for different types of characterizations, such as a therapy-related characterization versus a diagnosis-related characterization, such as for identifying relevant microbiome composition versus determining a propensity score for a sleep-related condition; etc.), therapies (e.g., different sleep-related characterization models for monitoring efficacy of different therapies, etc.), collection sites (e.g., different sleep-related characterization models for processing microorganism datasets corresponding to biological samples from different collection sites; etc.), supplementary data, and/or any other suitable components. In examples, different sleep-related characterization models can be tailored to different types of inputs, outputs, sleep-related characterizations, sleep-related conditions (e.g., different phenotypic measures that need to be characterized), and/or any other suitable entities. However, sleep-related characterization models can be tailored and/or used in any suitable manner for facilitating sleep-related characterization and/or therapeutic intervention.

Sleep-related characterization models, other models, other components of the system 200, and/or suitable portions of the method 100 (e.g., characterization processes, determining microbiome features, determining sleep-related characterizations, etc.) can employ analytical techniques including any one or more of: univariate statistical tests, multivariate statistical tests, dimensionality reduction techniques, artificial intelligence approaches (e.g., machine learning approaches, etc.), performing pattern recognition on data (e.g., identifying correlations between sleep-related conditions and microbiome features; etc.), fusing data from multiple sources (e.g., generating characterization models based on microbiome data and/or supplementary data from a plurality of users associated with one or more sleep-related conditions, such as based on microbiome features extracted from the data; etc.), combination of values (e.g., averaging values, etc.), compression, conversion (e.g., digital-to-analog conversion, analog-to-digital conversion), performing statistical estimation on data (e.g. ordinary least squares regression, non-negative least squares regression, principal components analysis, ridge regression, etc.), wave modulation, normalization, updating (e.g., of characterization models and/or therapy models based on processed biological samples over time; etc.), ranking (e.g., microbiome features; therapies; etc.), weighting (e.g., microbiome features; etc.), validating, filtering (e.g., for baseline correction, data cropping, etc.), noise reduction, smoothing, filling (e.g., gap filling), aligning, model fitting, binning, windowing, clipping, transformations, mathematical operations (e.g., derivatives, moving averages, summing, subtracting, multiplying, dividing, etc.), data association, multiplexing, demultiplexing, interpolating, extrapolating, clustering, image processing techniques, other signal processing operations, other image processing operations, visualizing, and/or any other suitable processing operations. Artificial intelligence approaches can include any one or more of: supervised learning (e.g., using logistic regression, using back propagation neural networks, using random forests, decision trees, etc.), unsupervised learning (e.g., using an Apriori algorithm, using K-means clustering), semi-supervised learning, a deep learning algorithm (e.g., neural networks, a restricted Boltzmann machine, a deep belief network method, a convolutional neural network method, a recurrent neural network method, stacked auto-encoder method, etc.) reinforcement learning (e.g., using a Q-learning algorithm, using temporal difference learning), a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), an ensemble method (e.g., boosting, boostrapped aggregation, AdaBoost, stacked generalization, gradient boosting machine method, random forest method, etc.), and/or any suitable artificial intelligence approach. However, data processing can be employed in any suitable manner.

The sleep-related characterization system 220 can preferably perform cross-condition analyses for a plurality of sleep-related conditions (e.g., generating multi-condition characterizations based on outputs of different sleep-related characterization models, such as multi-condition microbiome features; etc.). For example, the sleep-related characterization system can characterize relationships between sleep-related conditions based on microorganism data, microbiome features, and/or other suitable microbiome characteristics of users associated with (e.g., diagnosed with, characterized by, etc.) a plurality of sleep-related conditions. In a specific example, cross-condition analyses can be performed based on characterizations for individual sleep-related conditions (e.g., outputs from sleep-related characterization models for individual sleep-related conditions, etc.). Cross-condition analyses can include identification of condition-specific features (e.g., associated exclusively with a single sleep-related condition, etc.), multi-condition features (e.g., associated with two or more sleep-related conditions, etc.), and/or any other suitable types of features. Cross-condition analyses can include determination of parameters informing correlation, concordance, and/or other similar parameters describing relationships between two or more sleep-related conditions, such as by evaluating different pairs of sleep-related conditions. However, the sleep-related characterization system and/or other suitable components can be configured in any suitable manner to facilitate cross-condition analyses (e.g., applying analytical techniques for cross-condition analysis purposes; generating cross-condition characterizations, etc.).

The sleep-related characterization system 220 preferably includes a remote computing system (e.g., for applying sleep-related characterization models, etc.), but can additionally or alternatively include any suitable computing systems (e.g., local computing systems, user devices, handling system components, etc.). However, the sleep-related characterization system 220 can be configured in any suitable manner.

The therapy facilitation system 230 of the system 200 can function to facilitate therapeutic intervention (e.g., promote one or more therapies, etc.) for one or more sleep-related conditions (e.g., facilitating modulation of a user microbiome composition and functional diversity for improving a state of the user in relation to one or more sleep-related conditions, etc.). The therapy facilitation system 230 can facilitate therapeutic intervention for any number of sleep-related conditions associated with any number of collection sites, such as based on multi-site characterizations, multi-condition characterizations, other characterizations, and/or any other suitable data. The therapy facilitation system 230 can include any one or more of: a communications system (e.g., to communicate therapy recommendations, selections, discouragements, and/or other suitable therapy-related information to a computing device (e.g., user device and/or care provider device; mobile device; smart phone; desktop computer; at a website, web application, and/or mobile application accessed by the computing device; etc.); to enable telemedicine between a care provider and a subject in relation to a sleep-related condition; etc.), an application executable on a user device (e.g., indicating microbiome composition and/or functionality for a user; etc.), a medical device (e.g., a biological sampling device, such as for collecting samples from different collection sites; medication provision devices; surgical systems; etc.), a user device (e.g., biometric sensors), and/or any other suitable component. One or more therapy facilitation systems 230 can be controllable, communicable with, and/or otherwise associated with the sleep-related characterization system 220. For example, the sleep-related characterization system 220 can generate characterizations of one or more sleep-related conditions for the therapy facilitation system 230 to present (e.g., transmit, communicate, etc.) to a corresponding user (e.g., at an interface 240, etc.). In another example, the therapy facilitation system 230 can update and/or otherwise modify an application and/or other software of a device (e.g., user smartphone) to promote a therapy (e.g., promoting, at a to-do list application, lifestyle changes for improving a user state associated with one or more sleep-related conditions, etc.). However, the therapy facilitation system 230 can be configured in any other manner.

Figure 9:
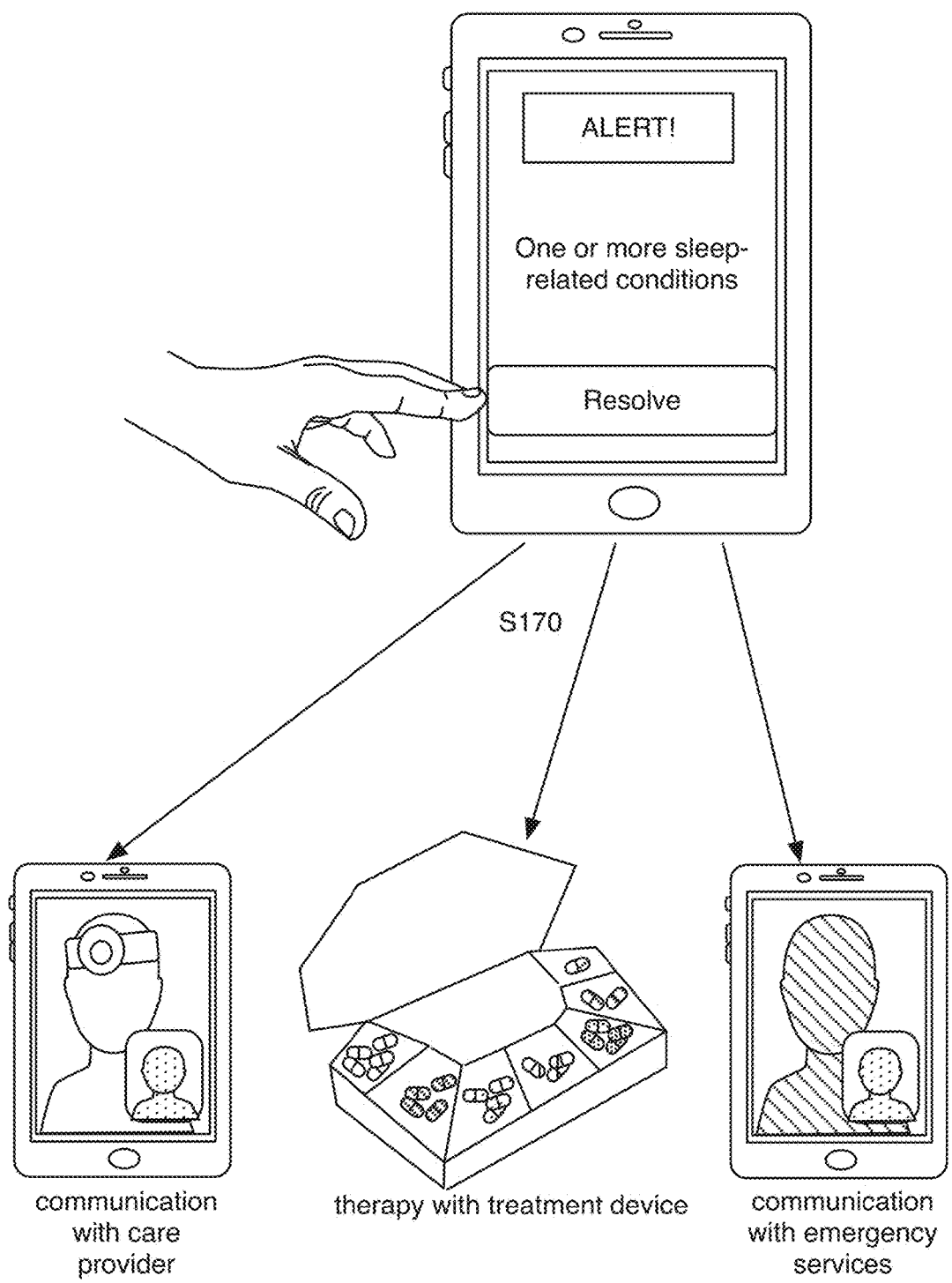
FIG. 9 depicts promoting a therapy in an embodiment of a method.

As shown in FIG. 9, the system 200 can additionally or alternatively include an interface 240, which can function to improve presentation of microbiome characteristics, sleep-related condition information (e.g., propensity metrics; therapy recommendations; comparisons to other users; other characterizations; etc.). In examples, the interface 240 can present sleep-related condition information including a microbiome composition (e.g., taxonomic groups; relative abundances; etc.), functional diversity (e.g., relative abundance of genes associated with particular functions, and propensity metrics for one or more sleep-related conditions, such as relative to user groups sharing a demographic characteristic (e.g., smokers, exercisers, users on different dietary regimens, consumers of probiotics, antibiotic users, groups undergoing particular therapies, etc.). However, the interface 240 can be configured in any suitable manner.

While the components of the system 200 are generally described as distinct components, they can be physically and/or logically integrated in any manner. For example, a computing system (e.g., a remote computing system, a user device, etc.) can implement portions and/or all of the sleep-related characterization system 220 (e.g., apply a microbiome-related condition model to generate a characterization of sleep-related conditions for a user, etc.) and the therapy facilitation system 230 (e.g., facilitate therapeutic intervention through presenting insights associated with microbiome composition and/or function; presenting therapy recommendations and/or information; scheduling daily events at a calendar application of the smartphone to notify the user in relation to therapies for improving sleep-related, etc.). However, the functionality of the system 200 can be distributed in any suitable manner amongst any suitable system components. However, the components of the system 200 can be configured in any suitable manner 4.1 Determining a Microorganism Dataset.

Block S110 can include determining a microorganism dataset (e.g., microorganism sequence dataset, microbiome composition diversity dataset such as based upon a microorganism sequence dataset, microbiome functional diversity dataset such as based upon a microorganism sequence dataset, etc.) associated with a set of subjects S110. Block S110 can function to process biological samples (e.g., an aggregate set of biological samples associated with a population of subjects, a subpopulation of subjects, a subgroup of subjects sharing a demographic characteristic and/or other suitable characteristics; a user biological sample; etc.), in order to determine compositional, functional, pharmacogenomics, and/or other suitable aspects associated with the corresponding microbiomes, such as in relation to one or more sleep-related conditions. Compositional and/or functional aspects can include one or more of aspects at the microorganism level (and/or other suitable granularity), including parameters related to distribution of microorganisms across different groups of kingdoms, phyla, classes, orders, families, genera, species, subspecies, strains, and/or any other suitable infraspecies taxon (e.g., as measured in total abundance of each group, relative abundance of each group, total number of groups represented, etc.). Compositional and/or functional aspects can also be represented in terms of operational taxonomic units (OTUs). Compositional and/or functional aspects can additionally or alternatively include compositional aspects at the genetic level (e.g., regions determined by multilocus sequence typing, 16S sequences, 18S sequences, ITS sequences, other genetic markers, other phylogenetic markers, etc.). Compositional and functional aspects can include the presence or absence or the quantity of genes associated with specific functions (e.g. enzyme activities, transport functions, immune activities, etc.). Outputs of Block 110 can thus be used to facilitate determination of microbiome features (e.g., generation of a microorganism sequence dataset usable for identifying microbiome features; etc.) for the characterization process of Block S130 and/or other suitable portions of the method 100 (e.g., where Block S110 can lead to outputs of microbiome composition datasets, microbiome functional datasets, and/or other suitable microorganism datasets from which microbiome features can be extracted, etc.), where the features can be microorganism-based (e.g., presence of a genus of bacteria), genetic-based (e.g., based upon representation of specific genetic regions and/or sequences), functional-based (e.g., presence of a specific catalytic activity), and/or any other suitable microbiome features.

In a variation, Block S110 can include assessment and/or processing based upon phylogenetic markers (e.g., for generating microorganism datasets, etc.) derived from bacteria and/or archaea in relation to gene families associated with one or more of: ribosomal protein S2, ribosomal protein S3, ribosomal protein S5, ribosomal protein S7, ribosomal protein S8, ribosomal protein S9, ribosomal protein S10, ribosomal protein S11, ribosomal protein S12/S23, ribosomal protein S13, ribosomal protein S15P/S13e, ribosomal protein S17, ribosomal protein S19, ribosomal protein L1, ribosomal protein L2, ribosomal protein L3, ribosomal protein L4/L1e, ribosomal protein L5, ribosomal protein L6, ribosomal protein L10, ribosomal protein L11, ribosomal protein L14b/L23e, ribosomal protein L15, ribosomal protein L16/L10E, ribosomal protein L18P/L5E, ribosomal protein L22, ribosomal protein L24, ribosomal protein L25/L23, ribosomal protein L29, translation elongation factor EF-2, translation initiation factor IF-2, metalloendopeptidase, ffh signal recognition particle protein, phenylalanyl-tRNA synthetase beta subunit, phenylalanyl-tRNA synthetase alpha subunit, tRNA pseudouridine synthase B, Porphobilinogen deaminase, ribosomal protein L13, phosphoribosylformylglycinamidine cyclo-ligase, and ribonuclease HII. Additionally or alternatively, markers can include target sequences (e.g., sequences associated with a microorganism taxonomic group; sequences associated with functional aspects; sequences correlated with sleep-related conditions; sequences indicative of user responsiveness to different therapies; sequences that are invariant across a population and/or any suitable set of subjects, such as to facilitate multiplex amplification using a primer type sharing a primer sequence; conserved sequences; sequences including mutations, polymorphisms; nucleotide sequences; amino acid sequences; etc.), proteins (e.g., serum proteins, antibodies, etc.), peptides, carbohydrates, lipids, other nucleic acids, whole cells, metabolites, natural products, genetic predisposition biomarkers, diagnostic biomarkers, prognostic biomarkers, predictive biomarkers, other molecular biomarkers, gene expression markers, imaging biomarkers, and/or other suitable markers. However, markers can include any other suitable marker(s) associated with microbiome composition, microbiome functionality, and/or sleep-related conditions.

Figure 5:
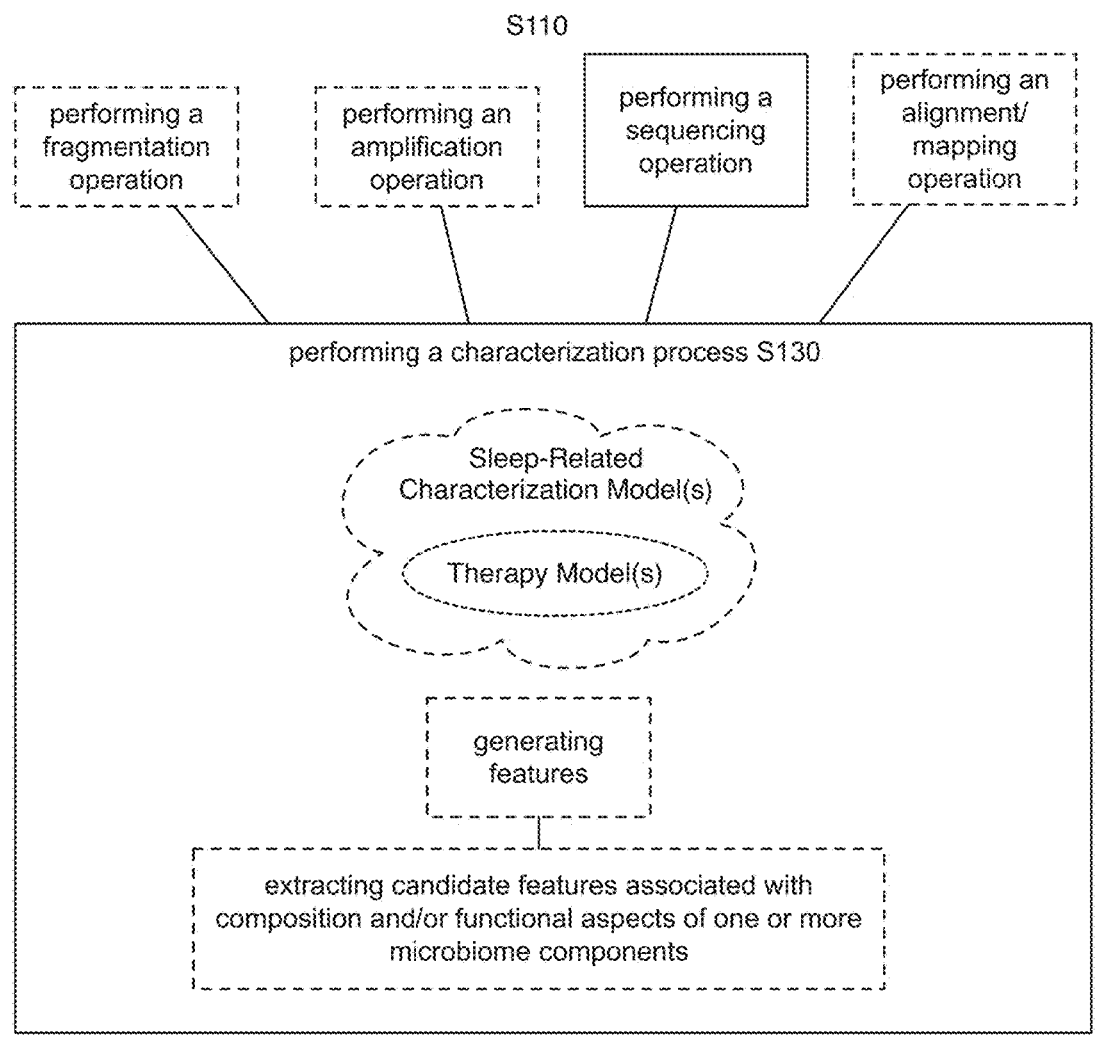
FIG. 5 depicts variations of sample processing in an embodiment of a method.

Characterizing the microbiome composition and/or functional aspects for each of the aggregate set of biological samples thus preferably includes a combination of sample processing techniques (e.g., wet laboratory techniques; as shown in FIG. 5), including, but not limited to, amplicon sequencing (e.g., 16S, 18S, ITS), UMIs, 3 step PCR, Crispr, metagenomic approaches, metatranscriptomics, use of random primers, and computational techniques (e.g., utilizing tools of bioinformatics), to quantitatively and/or qualitatively characterize the microbiome and functional aspects associated with each biological sample from a subject or population of subjects.

In variations, sample processing in Block 110 can include any one or more of: lysing a biological sample, disrupting membranes in cells of a biological sample, separation of undesired elements (e.g., RNA, proteins) from the biological sample, purification of nucleic acids (e.g., DNA) in a biological sample, amplification of nucleic acids from the biological sample, further purification of amplified nucleic acids of the biological sample, and sequencing of amplified nucleic acids of the biological sample. In an example, Block 110 can include: collecting biological samples from a set of users (e.g., biological samples collected by the user with a sampling kit including a sample container, etc.), where the biological samples include microorganism nucleic acids associated with the sleep-related condition (e.g., microorganism nucleic acids including target sequences correlated with a sleep-related condition; etc.). In another example, Block S110 can include providing a set of sampling kits to a set of users, each sampling kit of the set of sampling kits including a sample container (e.g., including pre-processing reagents, such as lysing reagents; etc.) operable to receive a biological sample from a user of the set of users.

In variations, lysing a biological sample and/or disrupting membranes in cells of a biological sample preferably includes physical methods (e.g., bead beating, nitrogen decompression, homogenization, sonication), which omit certain reagents that produce bias in representation of certain bacterial groups upon sequencing. Additionally or alternatively, lysing or disrupting in Block 110 can involve chemical methods (e.g., using a detergent, using a solvent, using a surfactant, etc.). Additionally or alternatively, lysing or disrupting in Block 110 can involve biological methods. In variations, separation of undesired elements can include removal of RNA using RNases and/or removal of proteins using proteases. In variations, purification of nucleic acids can include one or more of: precipitation of nucleic acids from the biological samples (e.g., using alcohol-based precipitation methods), liquid-liquid based purification techniques (e.g., phenol-chloroform extraction), chromatography-based purification techniques (e.g., column adsorption), purification techniques involving use of binding moiety-bound particles (e.g., magnetic beads, buoyant beads, beads with size distributions, ultrasonically responsive beads, etc.) configured to bind nucleic acids and configured to release nucleic acids in the presence of an elution environment (e.g., having an elution solution, providing a pH shift, providing a temperature shift, etc.), and any other suitable purification techniques.

In variations, amplification of purified nucleic acids can include one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. In amplification of purified nucleic acids, the primers used are preferably selected to prevent or minimize amplification bias, as well as configured to amplify nucleic acid regions/sequences (e.g., of the 16S region, the 18S region, the ITS region, etc.) that are informative taxonomically, phylogenetically, for diagnostics, for formulations (e.g., for probiotic formulations), and/or for any other suitable purpose. Thus, universal primers (e.g., a F27-R338 primer set for 16S RNA, a F515-R806 primer set for 16S RNA, etc.) configured to avoid amplification bias can be used in amplification. Additionally or alternatively include incorporated barcode sequences and/or UMIs specific to biological samples, to users, to sleep-related conditions, to taxa, to target sequences, and/or to any other suitable components, which can facilitate a post-sequencing identification process (e.g., for mapping sequence reads to microbiome composition and/or microbiome function aspects; etc.). Primers used in variations of Block 110 can additionally or alternatively include adaptor regions configured to cooperate with sequencing techniques involving complementary adaptors (e.g., Illumina Sequencing). Additionally or alternatively, Block S110 can implement any other step configured to facilitate processing (e.g., using a Nextera kit). In a specific example, performing amplification and/or sample processing operations can be in a multiplex manner (e.g., for a single biological sample, for a plurality of biological samples across multiple users; etc.). In another specific example, performing amplification can include normalization steps to balance libraries and detect all amplicons in a mixture independent of the amount of starting material, such as 3 step PCR, bead based normalization, and/or other suitable techniques.

In variations, sequencing of purified nucleic acids can include methods involving targeted amplicon sequencing, metatranscriptomic sequencing, and/or metagenomic sequencing, implementing techniques including one or more of: sequencing-by-synthesis techniques (e.g., Illumina sequencing), capillary sequencing techniques (e.g., Sanger sequencing), pyrosequencing techniques, and nanopore sequencing techniques (e.g., using an Oxford Nanopore technique).

In a specific example, amplification and sequencing of nucleic acids from biological samples of the set of biological samples includes: solid-phase PCR involving bridge amplification of DNA fragments of the biological samples on a substrate with oligo adapters, where amplification involves primers having a forward index sequence (e.g., corresponding to an Illumina forward index for MiSeq/NextSeq/HiSeq platforms), a forward barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, UMIs, a sequence for targeting a specific target region (e.g., 16S region, 18S region, ITS region), a reverse index sequence (e.g., corresponding to an Illumina reverse index for MiSeq/HiSeq platforms), and a reverse barcode sequence. In the specific example, sequencing can include Illumina sequencing (e.g., with a HiSeq platform, with a MiSeq platform, with a NextSeq platform, etc.) using a sequencing-by-synthesis technique. In another specific example, the method 100 can include: identifying one or more primer types compatible with one or more genetic targets associated with one or more sleep-related conditions (e.g., a biomarker of the one or more sleep-related conditions; positively correlated with; negatively correlated with; causative of; etc.); determining a microorganism dataset (e.g., microorganism sequence dataset; such as with a next-generation sequencing system; etc.) for one or more users (e.g., set of subjects) based on the one or more primer types (e.g., based on primers corresponding to the one or more primer types, and on the microorganism nucleic acids included in collected biological samples, etc.), such as through fragmenting the microorganism nucleic acids, and/ or performing a singleplex amplification process and/or a multiplex amplification process for the fragmented microorganism nucleic acids based on the one or more identified primer types (e.g., primers corresponding to the primer types, etc.) compatible with the one or more genetic targets associated with the sleep-related condition; and/or promoting (e.g., providing), based on a sleep-related characterization derived from the a microorganism dataset a therapy for the user condition (e.g., enabling selective modulation of a microbiome of the user in relation to at least one of a population size of a desired taxon and a desired microbiome function, etc.). In a specific example, the biological samples can correspond to a set of collection sites including at least one of a gut site, a skin site, a nose site, a mouth site, and a genitals site, and where determining a microorganism dataset (e.g., microorganism sequence dataset, etc.) can include identifying a first primer type compatible with a first genetic target associated with one or more sleep-related conditions and a first collection site of the set of collection sites; identifying a second primer type compatible with a second genetic target associated with the one or more sleep-related conditions and a second collection site of the set of collection sites; and generating the microorganism dataset for the set of subjects based on the microorganism nucleic acids, the first primers corresponding to the first primer type, and second primers corresponding to the second primer type. In the specific example, the first collection site type can include the gut site (e.g., which can be evaluated through stool samples, etc.), where determining the microorganism dataset can include determining at least one of a metagenomic library and a metatranscriptomic library based on a subset of the microorganism nucleic acids and the first primers, and where determining the at least one of the set of microbiome composition features and the set of microbiome functional features can include determining the at least one of the set of microbiome composition features and the set of microbiome functional features based on the at least one of the metagenomic library and the metatranscriptomic library. However, processing metagenomic libraries and/or metatranscriptomic libraries (e.g., for any suitable portions of the method 100 and/or system 200) can be performed in any suitable manner.

In variations, primers (e.g., of a primer type corresponding to a primer sequence; etc.) used in Block S110 and/or other suitable portions of the method 100 can include primers associated with protein genes (e.g., coding for conserved protein gene sequences across a plurality of taxa, such as to enable multiplex amplification for a plurality of targets and/or taxa; etc.). Primers can additionally or alternatively be associated with sleep-related conditions (e.g., primers compatible with genetic targets including microorganism sequence biomarkers for microorganisms correlated with sleep-related conditions; etc.), microbiome composition features (e.g., identified primers compatible with a genetic target corresponding to microbiome composition features associated with a group of taxa correlated with a sleep-related condition; genetic sequences from which relative abundance features are derived etc.), functional diversity features, supplementary features, and/or other suitable features and/or data. Primers (and/or other suitable molecules, markers, and/or biological material described herein) can possess any suitable size (e.g., sequence length, number of base pairs, conserved sequence length, variable region length, etc.). Additionally or alternatively, any suitable number of primers can be used in sample processing for performing characterizations (e.g., sleep-related characterizations; etc.), improving sample processing (e.g., through reducing amplification bias, etc.), and/or for any suitable purposes. The primers can be associated with any suitable number of targets, sequences, taxa, conditions, and/or other suitable aspects. Primers used in Block 110 and/or other suitable portions of the method 100 can be selected through processes described in Block 110 (e.g., primer selection based on parameters used in generating the taxonomic database) and/or any other suitable portions of the method 100. Additionally or alternatively, primers (and/or processes associated with primers) can include and/or be analogous to that described in U.S. application Ser. No. 14/919,614, filed 21 Oct. 2015, which is herein incorporated in its entirety by this reference. However, identification and/or usage of primers can be configured in any suitable manner.

Some variations of sample processing can include further purification of amplified nucleic acids (e.g., PCR products) prior to sequencing, which functions to remove excess amplification elements (e.g., primers, dNTPs, enzymes, salts, etc.). In examples, additional purification can be facilitated using any one or more of: purification kits, buffers, alcohols, pH indicators, chaotropic salts, nucleic acid binding filters, centrifugation, and/or any other suitable purification technique.

In variations, computational processing in Block 110 can include any one or more of: identification of microbiome-derived sequences (e.g., as opposed to subject sequences and contaminants), alignment and mapping of microbiome-derived sequences (e.g., alignment of fragmented sequences using one or more of single-ended alignment, ungapped alignment, gapped alignment, pairing), and generating features associated with (e.g., derived from) compositional and/or functional aspects of the microbiome associated with a biological sample.

Identification of microbiome-derived sequences can include mapping of sequence data from sample processing to a subject reference genome (e.g., provided by the Genome Reference Consortium), in order to remove subject genome-derived sequences. Unidentified sequences remaining after mapping of sequence data to the subject reference genome can then be further clustered into operational taxonomic units (OTUs) based upon sequence similarity and/or reference-based approaches (e.g., using VAMPS, using MG-RAST, using QIIME databases), aligned (e.g., using a genome hashing approach, using a Needleman-Wunsch algorithm, using a Smith-Waterman algorithm), and mapped to reference bacterial genomes (e.g., provided by the National Center for Biotechnology Information), using an alignment algorithm (e.g., Basic Local Alignment Search Tool, FPGA accelerated alignment tool, BWT-indexing with BWA, BWT-indexing with SOAP, BWT-indexing with Bowtie, etc.). Mapping of unidentified sequences can additionally or alternatively include mapping to reference archaeal genomes, viral genomes and/or eukaryotic genomes. Furthermore, mapping of taxa can be performed in relation to existing databases, and/or in relation to custom-generated databases.

However, processing biological samples, generating a microorganism dataset, and/or other aspects associated with Block 110 can be performed in any suitable manner.

4.2 Processing Supplementary Data.

The method 100 can additionally or alternatively include Block S120, which can include processing (e.g., receiving, collecting, transforming, determining supplementary features, ranking supplementary features, identifying correlations, etc.) supplementary data (e.g., one or more supplementary datasets, etc.) associated with (e.g., informative of; describing; indicative of; correlated with; etc.) one or more sleep-related conditions, one or more users, and/or other suitable entities. Block S120 can function to process data for supplementing microorganism datasets, microbiome features (e.g., in relation to determining sleep-related characterizations and/or facilitating therapeutic intervention, etc.), and/or can function to supplement any suitable portion of the method 100 and/or system 200 (e.g., processing supplementary data for facilitating one or more characterization processes, such as in Block S130; such as for facilitating training, validating, generating, determining, applying and/or otherwise processing sleep-related characterization models, etc.). In an example, supplementary data can include at least one of survey-derived data, user data, site-specific data, and device data (and/or other suitable supplementary data), where the method 100 can include determining a set of supplementary features based on the at least one of the survey-derived data, the user data, the site-specific data, and the device data (and/or other suitable supplementary data); and generating one or more sleep-related characterization models based on the supplementary features, microbiome features, and/or other suitable data.

Supplementary data can include any one or more of: survey-derived data (e.g., data from responses to one or more surveys surveying for one or more sleep-related conditions, for any suitable types of data described herein; etc.); site-specific data (e.g., data informative of different collection sites, such as prior biological knowledge indicating correlations between microbiomes at specific collection sites and one or more sleep-related conditions; etc.); sleep-related condition data (e.g., data informative of different sleep-related conditions, such as in relation to microbiome characteristics, therapies, users, etc.); device data (e.g.,سensor data; contextual sensor data associated with sleep; wearable device data; medical device data; user device data such as mobile phone application data; web application data; etc.); user data (e.g., user medical data current and historical medical data such as historical therapies, historical medical examination data; medical device-derived data; physiological data; data associated with medical tests; social media data; demographic data; family history data; behavior data describing behaviors; environmental factor data describing environmental factors; diet-related data such as data from food establishment check-ins, data from spectrophotometric analysis, user-inputted data, nutrition data associated with probiotic and/or prebiotic food items, types of food consumed, amount of food consumed, caloric data, diet regimen data, and/or other suitable diet-related data; etc.); prior biological knowledge (e.g., informative of sleep-related conditions, microbiome characteristics, associations between microbiome characteristics and sleep-related conditions, etc.); and/or any other suitable type of supplementary data.

In variations, processing supplementary data can include processing survey-derived data, where the survey-derived data can provide physiological data, demographic data, behavior data, environmental factor data (e.g., describing environmental factors, etc.), other types of supplementary data, and/or any other suitable data. Physiological data can include information related to physiological features (e.g., height, weight, body mass index, body fat percent, body hair level, medical history, etc.). Demographic data can include information related to demographic characteristics (e.g., gender, age, ethnicity, marital status, number of siblings, socioeconomic status, sexual orientation, etc.). Behavioral data can describe behaviors including one or more: health-associated states (e.g., health and disease states), dietary habits (e.g., alcohol consumption, caffeine consumption, omnivorous, vegetarian, vegan, sugar consumption, acid consumption, consumption of wheat, egg, soy, treenut, peanut, shellfish, food preferences, allergy characteristics, consumption and/or avoidance of other food items, etc.), behavioral tendencies (e.g., levels of physical activity, drug use, alcohol use, habit development, etc.), different levels of mobility (e.g., amount of exercise such as low, moderate, and/or extreme physical exercise activity; related to distance traveled within a given time period; indicated by mobility sensors such as motion and/or location sensors; etc.), different levels of sexual activity (e.g., related to numbers of partners and sexual orientation), and any other suitable behavioral data. Survey-derived data can include quantitative data, qualitative data, and/or other suitable types of survey-derived data, such as where qualitative data can be converted to quantitative data (e.g., using scales of severity, mapping of qualitative responses to quantified scores, etc.). Processing survey-derived data can include facilitating collection of survey-derived data, such as including providing one or more surveys to one or more users, subjects, and/or other suitable entities. Surveys can be provided in-person (e.g., in coordination with sample kit provision and/or reception of samples; etc.), electronically (e.g., during account setup; at an application executing at an electronic device of a subject, at a web application and/or website accessible through an internet connection; etc.), and/or in any other suitable manner.

Additionally or alternatively, processing supplementary data can include processing sensor data (e.g., sensors of sleep-related devices, wearable computing devices, mobile devices; biometric sensors associated with the user, such as biometric sensors of a user smart phone; etc.). Sensor data can include any one or more of: physical activity- and/or physical action-related data (e.g., accelerometer data, gyroscope data, location sensor data such as GPS data, and/or other mobility sensor data from one or more devices such as a mobile device and/or wearable electronic device, etc.), sensor data describing environmental factors (e.g., temperature data, elevation data, climate data, light parameter data, pressure data, air quality data, etc.), biometric sensor data (e.g., heart rate sensor data; fingerprint sensor data; optical sensor data such as facial images and/or video; data recorded through sensors of a mobile device; data recorded through a wearable or other peripheral device; etc.), and/or any other suitable data associated with sensors. Additionally or alternatively, sensor data can include data sampled at one or more: optical sensors (e.g., image sensors, light sensors, cameras, etc.), audio sensors (e.g., microphones, etc.), temperature sensors, volatile compound sensors, air quality sensors, weight sensors, humidity sensors, depth sensors, location sensors (GPS receivers; beacons; indoor positioning systems; compasses; etc.), motion sensors (e.g., accelerators, gyroscope, magnetometer, remote motion detection systems such as for monitoring motion of a user when sleeping, motion sensors integrated with a device worn by a user during sleep, etc.), biometric sensors (e.g., heart rate sensors such as for monitoring heart rate during a time period associated with user sleep; fingerprint sensors; facial recognition sensors; bio-impedance sensors, etc.), pressure sensors (e.g., integrated with a bedding-related component, such as for detecting user motion when sleeping on a bed, etc.), proximity sensors (e.g., for monitoring motion and/or other aspects of third-party objects associated with user sleep periods; etc.), flow sensors, power sensors (e.g., Hall effect sensors), virtual reality-related sensors, augmented reality-related sensors, and/or or any other suitable types of sensors.

Additionally or alternatively, supplementary data can include medical record data and/or clinical data. As such, portions of the supplementary dataset can be derived from one or more electronic health records (EHRs). Additionally or alternatively, supplementary data can include any other suitable diagnostic information (e.g., clinical diagnosis information). Any suitable supplementary data (e.g., in the form of extracted supplementary features, etc.) can be combined with and/or used with microbiome features and/or other suitable data for performing portions of the method 100 (e.g., performing characterization processes, etc.) and/or system 200. For example, supplementary data associated with (e.g., derived from, etc.) a colonoscopy, biopsy, blood test, diagnostic imaging, other suitable diagnostic procedures, survey-related information, and/or any other suitable test can be used to supplement (e.g., for any suitable portions of the method 100 and/or system 200).

Additionally or alternatively, supplementary data can include therapy-related data including one or more of: therapy regimens, types of therapies, recommended therapies, therapies used by the user, therapy adherence, and/or other suitable data related to therapies. For example, supplementary data can include user adherence metrics (e.g., medication adherence, probiotic adherence, physical exercise adherence, dietary adherence, etc.) in relation to one or more therapies (e.g., a recommended therapy, etc.). However, processing supplementary data can be performed in any suitable manner.

4.2 Performing a Characterization Process.

Block S130 can include, performing a characterization process (e.g., pre-processing, feature generation, feature processing, multi-site characterization for a plurality of collection sites, cross-condition analysis for a plurality of sleep-related conditions, model generation, etc.) associated with one or more sleep-related conditions, such as based on a microorganism dataset (e.g., derived in Block 110, etc.) and/or other suitable data (e.g., supplementary dataset; etc.) S130. Block S130 can function to identify, determine, extract, and/or otherwise process features and/or feature combinations that can be used to determine sleep-related characterizations for users or and sets of users, based upon their microbiome composition (e.g., microbiome composition diversity features, etc.), function (e.g., microbiome functional diversity features, etc.), and/or other suitable microbiome features (e.g., such as through the generation and application of a characterization model for determining sleep-related characterizations, etc.). As such, the characterization process can be used as a diagnostic tool that can characterize a subject (e.g., in terms of behavioral traits, in terms of medical conditions, in terms of demographic characteristics, etc.) based upon their microbiome composition and/or functional features, in relation to one or more of their health condition states (e.g., sleep-related condition states), behavioral traits, medical conditions, demographic characteristics, and/or any other suitable traits. Such characterizations can be used to determine, recommend, and/or provide therapies (e.g., personalized therapies, such as determined by way of a therapy model, etc.), and/or otherwise facilitate therapeutic intervention.

Performing a characterization process S130 can include pre-processing microorganism datasets, microbiome features, and/or other suitable data for facilitation of downstream processing (e.g., determining sleep-related characterizations, etc.). In an example, performing a characterization process can include, filtering a microorganism dataset (e.g., filtering a microorganism sequence dataset, such as prior to applying a set of analytical techniques to determine the microbiome features, etc.), by at least one of: a) removing first sample data corresponding to first sample outliers of a set of biological samples (e.g., associated with one or more sleep-related conditions, etc.), such as where the first sample outliers are determined by at least one of principal component analysis, a dimensionality reduction technique, and a multivariate methodology; b) removing second sample data corresponding to second sample outliers of the set of biological samples, where the second sample outliers can determined based on corresponding data quality for the set of microbiome features (e.g., removing samples corresponding to a number of microbiome features with high quality data below a threshold condition, etc.); and c) removing one or more microbiome features from the set of microbiome features based on a sample number for the microbiome feature failing to satisfy a threshold sample number condition, where the sample number corresponds to a number of samples associated with high quality data for the microbiome feature. However, pre-processing can be performed with any suitable analytical techniques in any suitable manner.

In performing the characterization process, Block S130 can use computational methods (e.g., statistical methods, machine learning methods, artificial intelligence methods, bioinformatics methods, etc.) to characterize a subject as exhibiting features (e.g., where determining user microbiome features can include determining feature values for microbiome features identified by characterization processes as correlated with and/or otherwise associated with one or more sleep-related conditions, etc.) associated with one or more sleep-related conditions (e.g., features characteristic of a set of users with the one or more sleep-related conditions, etc.).

Figure 3:
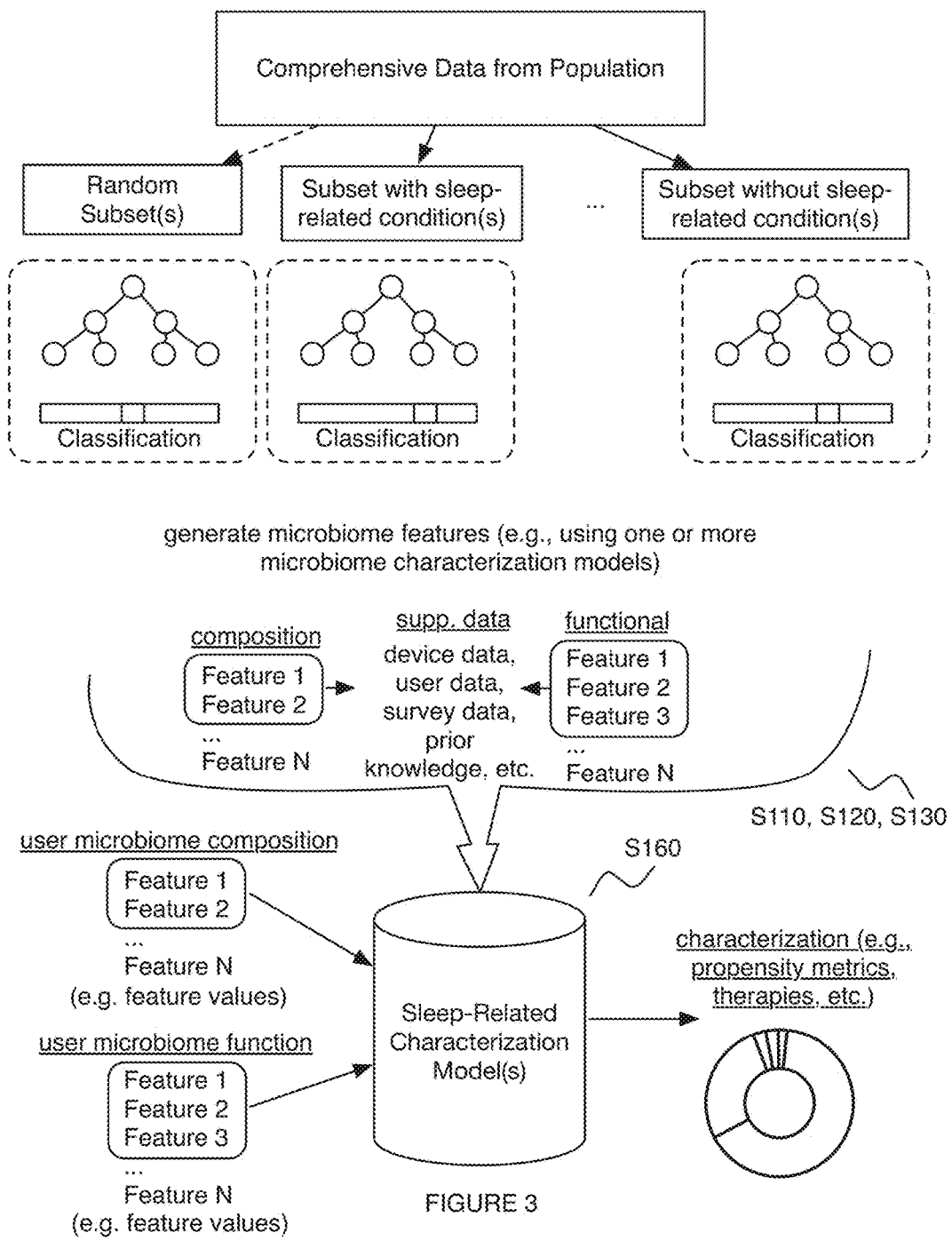
FIG. 3 depicts a variation of a process for generation of a characterization model in an embodiment of a method.

As shown in FIG. 3, performing characterization processes can include determining one or more microbiome features associated with one or more sleep-related conditions (e.g., identifying microbiome features with greatest relevance to one or more sleep-related conditions; determining user microbiome features, such as presence, absence, and/or values of user microbiome features corresponding to the identified microbiome features associated with the one or more sleep-related conditions, etc.), such as through applying one or more analytical techniques. In an example, determining microbiome features (e.g., microbiome composition features, microbiome functional features, etc.) can applying a set of analytical techniques including at least one of a univariate statistical test, a multivariate statistical test, a dimensionality reduction technique, and an artificial intelligence approach, such as based on a microorganism dataset (e.g., microorganism sequence dataset, etc.), and where the microbiome features configured to improve computing system-related functionality associated with the determining of the sleep-related characterization for the user (e.g., in relation to accuracy, reducing error, processing speed, scaling, etc.). In an example, determining microbiome features (e.g., user microbiome features, etc.) can include applying a set of analytical techniques to determine at least one of presence of at least one of a microbiome composition diversity feature and a microbiome functional diversity feature, absence of the at least one of the microbiome composition diversity feature and the microbiome functional diversity feature, a relative abundance feature describing relative abundance of different taxonomic groups associated with the first sleep-related condition, a ratio feature describing a ratio between at least two microbiome features associated with the different taxonomic groups, an interaction feature describing an interaction between the different taxonomic groups, and a phylogenetic distance feature describing phylogenetic distance between the different taxonomic groups, such as based on the microorganism dataset, and where the set of analytical techniques can include at least one of a univariate statistical test, a multivariate statistical test, a dimensionality reduction technique, and an artificial intelligence approach.

In variations, upon identification of represented groups of microorganisms of the microbiome associated with a biological sample, generating features associated with (e.g., derived from) compositional and functional aspects of the microbiome associated with a biological sample can be performed. In a variation, generating features can include generating features based upon multilocus sequence typing (MSLT), in order to identify markers useful for characterization in subsequent blocks of the method 100. Additionally or alternatively, generated features can include generating features that describe the presence or absence of certain taxonomic groups of microorganisms, and/or ratios between exhibited taxonomic groups of microorganisms. Additionally or alternatively, generating features can include generating features describing one or more of: quantities of represented taxonomic groups, networks of represented taxonomic groups, correlations in representation of different taxonomic groups, interactions between different taxonomic groups, products produced by different taxonomic groups, interactions between products produced by different taxonomic groups, ratios between dead and alive microorganisms (e.g., for different represented taxonomic groups, based upon analysis of RNAs), phylogenetic distance (e.g., in terms of Kantorovich-Rubinstein distances, Wasserstein distances etc.), any other suitable taxonomic group-related feature(s), any other suitable genetic or functional aspect(s).

Additionally or alternatively, generating features can include generating features describing relative abundance of different microorganism groups, for instance, using a sparCC approach, using Genome Relative Abundance and Average size (GAAS) approach and/or using a Genome Relative Abundance using Mixture Model theory (GRAMMy) approach that uses sequence-similarity data to perform a maximum likelihood estimation of the relative abundance of one or more groups of microorganisms. Additionally or alternatively, generating features can include generating statistical measures of taxonomic variation, as derived from abundance metrics. Additionally or alternatively, generating features can include generating features associated with (e.g., derived from) relative abundance factors (e.g., in relation to changes in abundance of a taxon, which affects abundance of other taxa). Additionally or alternatively, generating features can include generation of qualitative features describing presence of one or more taxonomic groups, in isolation and/or in combination. Additionally or alternatively, generating features can include generation of features related to genetic markers (e.g., representative 16S, 18S, and/or ITS sequences) characterizing microorganisms of the microbiome associated with a biological sample. Additionally or alternatively, generating features can include generation of features related to functional associations of specific genes and/or organisms having the specific genes. Additionally or alternatively, generating features can include generation of features related to pathogenicity of a taxon and/or products attributed to a taxon. Block S130 can, however, include determination of any other suitable feature(s) derived from sequencing and mapping of nucleic acids of a biological sample. For instance, the feature(s) can be combinatory (e.g. involving pairs, triplets), correlative (e.g., related to correlations between different features), and/or related to changes in features (e.g., temporal changes, changes across sample sites, etc., spatial changes, etc.). However, determining microbiome features can be performed in any suitable manner.

In variations, performing a characterization process can include performing one or more multi-site analyses (e.g., with sleep-related characterization models; generating a multi-site characterization, etc.) associated with a plurality of collection sites. However, multi-site analyses can be performed in any suitable manner.

In variations, performing a characterization process can include performing one or more cross-condition analyses (e.g., using sleep-related characterization models, etc.) for a plurality of sleep-related conditions. In an example, performing cross-condition analyses can include determining a set of cross-condition features (e.g., as part of determining microbiome features, etc.) associated with a plurality of sleep-related conditions (e.g., a first sleep-related condition and a second sleep-related condition, etc.) based on one or more analytical techniques, where determining a sleep-related characterization can include determining the sleep-related characterization for a user for the plurality of sleep-related conditions (e.g., first and the second sleep-related conditions, etc.) based on one or more sleep-related characterization models, and where the set of cross-condition features is configured to improve the computing system-related functionality associated with the determining of the sleep-related characterization for the user for the plurality of sleep-related conditions. Performing cross-condition analyses can include determining cross-condition correlation metrics (e.g., correlation and/or covariance between data corresponding to different sleep-related conditions, etc.) and/or other suitable metrics associated with cross-condition analyses. However, performing cross-condition analyses can be performed in any suitable manner.

In a variation, characterization can be based upon features associated with (e.g., derived from) a statistical analysis (e.g., an analysis of probability distributions) of similarities and/or differences between a first group of subjects exhibiting a target state (e.g., a sleep-related condition state) and a second group of subjects not exhibiting the target state (e.g., a "normal" state). In implementing this variation, one or more of a Kolmogorov-Smirnov (KS) test, a permutation test, a Cramer-von Mises test, any other statistical test (e.g., t-test, z-test, chi-squared test, test associated with distributions, etc.), and/or other suitable analytical techniques can be used. In particular, one or more such statistical hypothesis tests can be used to assess a set of features having varying degrees of abundance in a first group of subjects exhibiting a target state (e.g., a sick state) and a second group of subjects not exhibiting the target state (e.g., having a normal state). In more detail, the set of features assessed can be constrained based upon percent abundance and/or any other suitable parameter pertaining to diversity in association with the first group of subjects and the second group of subjects, in order to increase or decrease confidence in the characterization. In a specific implementation of this example, a feature can be derived from a taxon of bacteria that is abundant in a certain percentage of subjects of the first group and subjects of the second group, where a relative abundance of the taxon between the first group of subjects and the second group of subjects can be determined from the KS test, with an indication of significance (e.g., in terms of p-value). Thus, an output of Block S130 can include a normalized relative abundance value (e.g., 25% greater abundance of a taxon in subjects with a sleep-related condition vs. subjects without the sleep-related condition; in sick subjects vs. healthy subjects) with an indication of significance (e.g., a p-value of 0.0013). Variations of feature generation can additionally or alternatively implement or be derived from functional features or metadata features (e.g., non-bacterial markers). Additionally or alternatively, any suitable microbiome features can be derived based on statistical analyses (e.g., applied to a microorganism sequence dataset and/or other suitable microorganism dataset, etc.) including any one or more of: a prediction analysis, multi hypothesis testing, a random forest test, principal component analysis, and/or other suitable analytical techniques.

In performing the characterization process, Block S130 can additionally or alternatively transform input data from at least one of the microbiome composition diversity dataset and microbiome functional diversity dataset into feature vectors that can be tested for efficacy in predicting characterizations of the population of subjects. Data from the supplementary dataset can be used to provide indication of one or more characterizations of a set of characterizations, where the characterization process is trained with a training dataset of candidate features and candidate classifications to identify features and/or feature combinations that have high degrees (or low degrees) of predictive power in accurately predicting a classification. As such, refinement of the characterization process with the training dataset identifies feature sets (e.g., of subject features, of combinations of features) having high correlation with specific classifications of subjects.

In variations, feature vectors (and/or any suitable set of features) effective in predicting classifications of the characterization process can include features related to one or more of: microbiome diversity metrics (e.g., in relation to distribution across taxonomic groups, in relation to distribution across archaeal, bacterial, viral, and/or eukaryotic groups), presence of taxonomic groups in one's microbiome, representation of specific genetic sequences (e.g., 16S sequences) in one's microbiome, relative abundance of taxonomic groups in one's microbiome, microbiome resilience metrics (e.g., in response to a perturbation determined from the supplementary dataset), abundance of genes that encode proteins or RNAs with given functions (enzymes, transporters, proteins from the immune system, hormones, interference RNAs, etc.) and any other suitable features associated with (e.g., derived from) the microbiome diversity dataset and/or the supplementary dataset. In variations, microbiome features can be associated with (e.g., include, correspond to, typify, etc.) at least one of: presence of a microbiome feature from the microbiome features (e.g., user microbiome features, etc.), absence of the microbiome features from the microbiome features, relative abundance of different taxonomic groups associated with the sleep-related condition; a ratio between at least two microbiome features associated with the different taxonomic groups, interactions between the different taxonomic groups, and phylogenetic distance between the different taxonomic groups. In a specific example, microbiome features can include one or more relative abundance characteristics associated with at least one of the microbiome composition diversity features (e.g., relative abundance associated with different taxa, etc.) and the microbiome functional diversity features (e.g., relative abundance of sequences corresponding to different functional features; etc.). Relative abundance characteristics and/or other suitable microbiome features (and/or other suitable data described herein) can be extracted and/or otherwise determined based on: a normalization, a feature vector derived from at least one of linear latent variable analysis and non-linear latent variable analysis, linear regression, non-linear regression, a kernel method, a feature embedding method, a machine learning method, a statistical inference method, and/or other suitable analytical techniques. Additionally or alternatively, combinations of features can be used in a feature vector, where features can be grouped and/or weighted in providing a combined feature as part of a feature set. For example, one feature or feature set can include a weighted composite of the number of represented classes of bacteria in one's microbiome, presence of a specific genus of bacteria in one's microbiome, representation of a specific 16S sequence in one's microbiome, and relative abundance of a first phylum over a second phylum of bacteria. However, the feature vectors can additionally or alternatively be determined in any other suitable manner.

In a variation, the characterization process can be generated and trained according to a random forest predictor (RFP) algorithm that combines bagging (e.g., bootstrap aggregation) and selection of random sets of features from a training dataset to construct a set of decision trees, T, associated with the random sets of features. In using a random forest algorithm, N cases from the set of decision trees are sampled at random with replacement to create a subset of decision trees, and for each node, m prediction features are selected from all of the prediction features for assessment. The prediction feature that provides the best split at the node (e.g., according to an objective function) is used to perform the split (e.g., as a bifurcation at the node, as a trifurcation at the node). By sampling many times from a large dataset, the strength of the characterization process, in identifying features that are strong in predicting classifications can be increased substantially. In this variation, measures to prevent bias (e.g., sampling bias) and/or account for an amount of bias can be included during processing, such as to increase robustness of the model.

In a variation, Block S130 and/or other portions of the method 100 can include applying computer-implemented rules (e.g., models, feature selection rules, etc.) to process population-level data, but can additionally or alternatively include applying computer-implemented rules to process microbiome-related data on a demographic characteristic-specific basis (e.g., subgroups sharing one or more demographic characteristics such as therapy regimens, dietary regimens, physical activity regimens, ethnicity, age, gender, weight, sleeping behaviors, etc.), condition-specific basis (e.g., subgroups exhibiting a specific sleep-related condition, a combination of sleep-related conditions, triggers for the sleep-related conditions, associated symptoms, etc.), a sample type-specific basis (e.g., applying different computer-implemented rules to process microbiome data derived from different collection sites; etc.), a user basis (e.g., different computer-implemented rules for different users; etc.) and/or any other suitable basis. As such, Block S130 can include assigning users from the population of users to one or more subgroups; and applying different computer-implemented rules for determining features (e.g., the set of feature types used; the types of characterization models generated from the features; etc.) for the different subgroups. However, applying computer-implemented rules can be performed in any suitable manner.

In another variation, Block S130 can include processing (e.g., generating, training, updating, executing, storing, etc.) one or more sleep-related characterization models (e.g., sleep-related condition models, therapy models, etc.) for one or more sleep-related conditions (e.g., for outputting characterizations for users describing user microbiome characteristics in relation to sleep-related conditions; therapy models for outputting therapy determinations for one or more sleep-related conditions; etc.). The characterization models preferably leverage microbiome features as inputs, and preferably output sleep-related characterizations and/or any suitable components thereof; but characterization models can use any suitable inputs to generate any suitable outputs. In an example, Block S130 can include transforming the supplementary data, the microbiome composition diversity features, and the microbiome functional diversity features, other microbiome features, outputs of sleep-related characterization models, and/or other suitable data into one or more characterization models (e.g., training a sleep-related characterization model based on the supplementary data and microbiome features; etc.) for one or more sleep-related conditions. In another example, the method 100 can include: determining a population microorganism sequence dataset (e.g., including microorganism sequence outputs for different users of the population; etc.) for a population of users associated with one or more sleep-related conditions, based on a set of samples from the population of users (e.g., and/or based on one or more primer types associated with the sleep-related condition; etc.); collecting a supplementary dataset associated with diagnosis of the one or more sleep-related conditions for the population of subjects; and generating the sleep-related characterization model based on the population microorganism sequence dataset and the supplementary dataset. In an example, the method 100 can include determining a set of user microbiome features for the user based on a sample from the user, where the set of user microbiome features is associated with microbiome features associated with a set of subjects (e.g., microbiome features determined to be correlated with one or more sleep-related conditions, based on processing biological samples corresponding to a set of subjects associated with the one or more sleep-related conditions; a set microbiome composition features and the set of microbiome functional features; etc.); determining a sleep-related characterization, including determining a therapy for the user for the one or more sleep-related conditions based on a therapy model and the set of user microbiome features; providing the therapy (e.g., providing a recommendation for the therapy to the user at a computing device associated with the user, etc.) and/or otherwise facilitating therapeutic intervention.

Figure 8A:
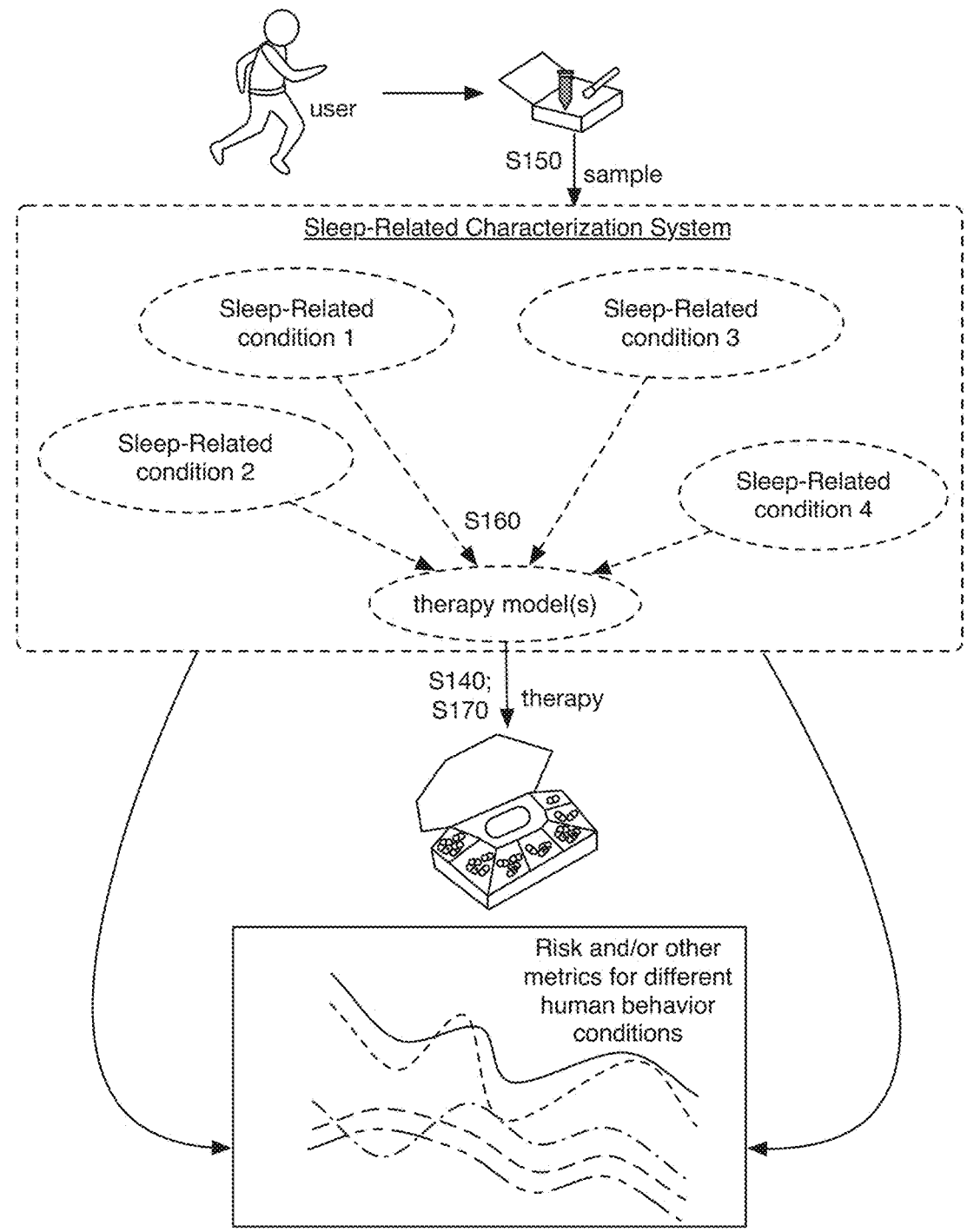
FIGS. 8A-8C depicts variations of performing characterization processes with models.
Figure 8B:
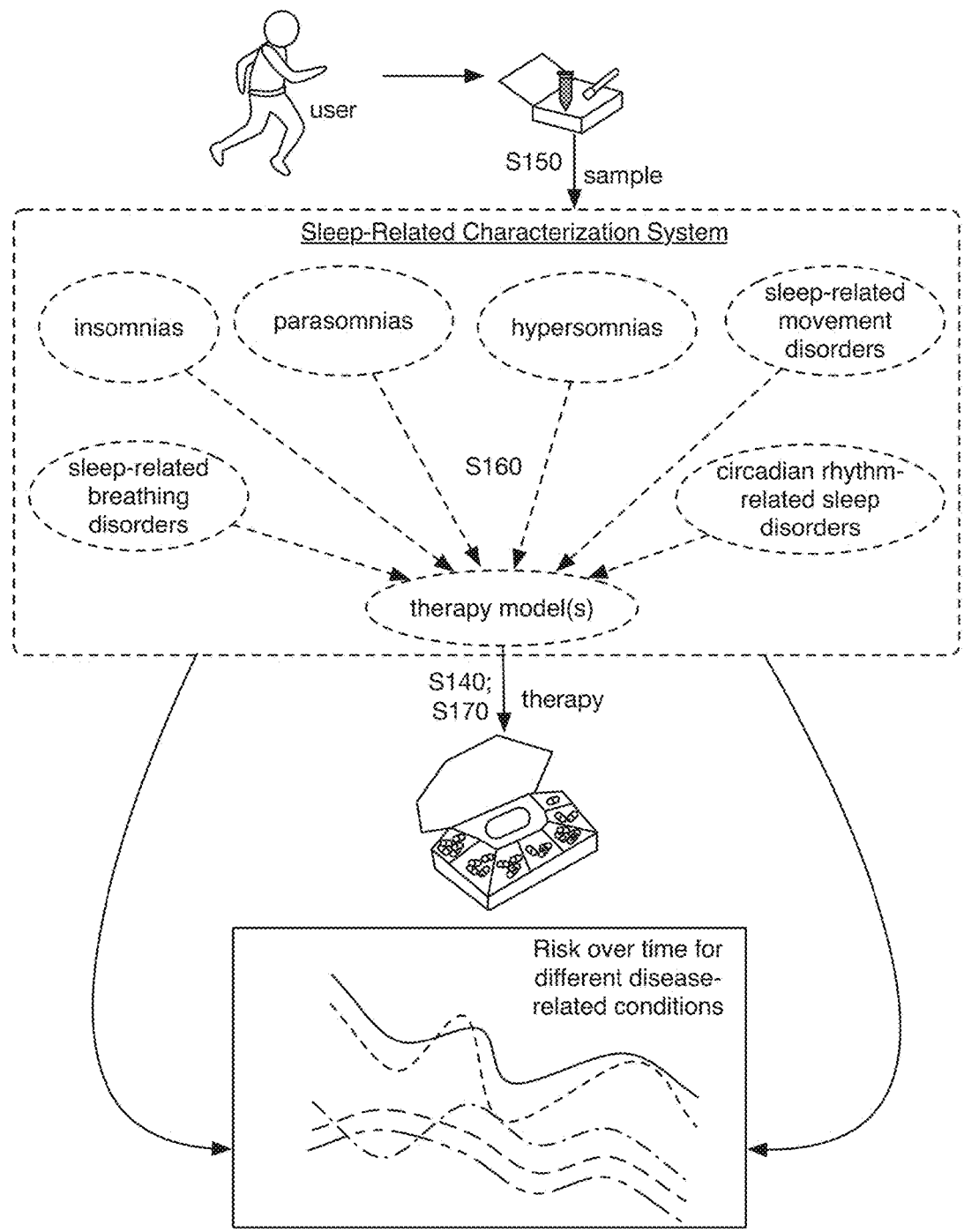
Figure 8C:
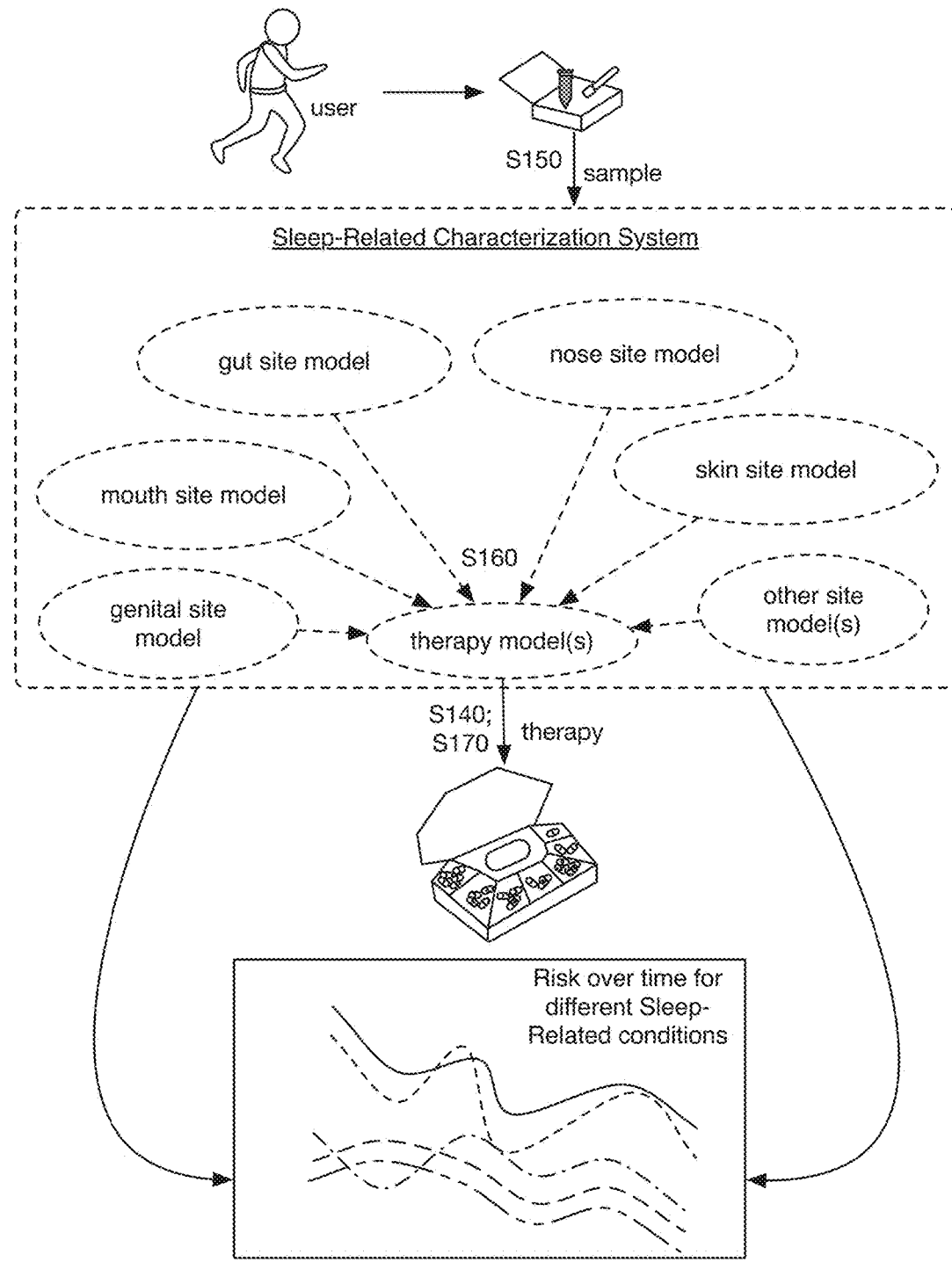

In another variation, as shown in FIGS. 8A-8C, different sleep-related characterization models and/or other suitable models (e.g., generated with different algorithms, with different sets of features, with different input and/or output types, applied in different manners such as in relation to time, frequency, component applying the model, etc.) can be generated for different sleep-related conditions, different user demographic characteristics (e.g., based on age, gender, weight, height, ethnicity; etc.), different physiological sites (e.g., a gut site model, a nose site model, a skin site model, a mouth site model, a genitals site model, etc.), individual users, supplementary data (e.g., models incorporating prior knowledge of microbiome features, sleep-related conditions, and/or other suitable components; features associated with biometric sensor data and/or survey response data vs. models independent of supplementary data, etc.), and/or other suitable criteria.

In variations, determining sleep-related characterizations and/or any other suitable characterizations can include determining sleep-related characterizations in relation to specific physiological sites (e.g., gut, healthy gut, skin, nose, mouth, genitals, other suitable physiological sites, other sample collection sites, etc.), such as through any one or more of: determining a sleep-related characterization based on a sleep-related characterization model derived based on site-specific data (e.g., defining correlations between a sleep-related condition and microbiome features associated with one or more physiological sites); determining a sleep-related characterization based on a user biological sample collected at one or more physiological sites, and/or any other suitable site-related processes. In examples, machine learning approaches (e.g., classifiers, deep learning algorithms, SVM, random forest), parameter optimization approaches (e.g., Bayesian Parameter Optimization), validation approaches (e.g., cross validation approaches), statistical tests (e.g., univariate statistical techniques, multivariate statistical techniques, correlation analysis such as canonical correlation analysis, etc.), dimension reduction techniques (e.g. PCA), and/or other suitable analytical techniques (e.g., described herein) can be applied in determining site-related (e.g., physiological site-related, etc.) characterizations (e.g., using a one or more approaches for one or more sample collection sites, such as for each type of sample collection site, etc.), other suitable characterizations, therapies, and/or any other suitable outputs. In a specific example, performing a characterization process (e.g., determining a sleep-related characterization; determining microbiome features; based on a sleep-related characterization model; etc.) can include applying at least one of: machine learning approaches, parameter optimization approaches, statistical tests, dimension reduction approaches, and/or other suitable approaches (e.g., where microbiome features such as a set of microbiome composition diversity features and/or a set of microbiome functional diversity features can be associated with microorganisms collected at least at one of a gut site, a skin site, a nose site, a mouth site, a genitals site, etc.). In another specific example, characterization processes performed for a plurality of sample collection sites can be used to generate individual characterizations that can be combined to determine an aggregate characterization (e.g., an aggregate microbiome score, such as for one or more conditions described herein, etc.). However, the method 100 can include determining any suitable site-related (e.g., site-specific) outputs, and/or performing any suitable portions of the method 100 (e.g., collecting samples, processing samples, determining therapies) with site-specificity and/or other site-relatedness in any suitable manner.

Characterization of the subject(s) can additionally or alternatively implement use of a high false positive test and/or a high false negative test to further analyze sensitivity of the characterization process in supporting analyses generated according to embodiments of the method 100. However, performing one or more characterization processes S130 can be performed in any suitable manner.

4.3.A Sleep-related characterization process.

Performing a characterization process S130 can include performing a sleep-related characterization process (e.g., determining a characterization for one or more sleep-related conditions; determining and/or applying one or more sleep-related characterization model; etc.) S135, such as for one or more users (e.g., for data corresponding to samples from a set of subjects for generating one or more sleep-related characterization models; for a single user for generating a sleep-related characterization for the user, such as through using one or more sleep-related characterization models; etc.) and/or for one or more sleep-related conditions.

In a variation, performing a sleep-related characterization process can include determining microbiome features associated with one or more sleep-related conditions (e.g., a sleep order condition. In an example, performing a sleep-related characterization process can include applying one or more analytical techniques (e.g., statistical analyses) to identify the sets of microbiome features (e.g., microbiome composition features, microbiome composition diversity features, microbiome functional features, microbiome functional diversity features, etc.) that have the highest correlations with one or more sleep-related conditions (e.g., features associated with a single sleep-related condition, cross-condition features associated with multiple sleep-related conditions and/or other suitable sleep-related conditions, etc.). In a specific example, performing a sleep-related characterization process can facilitate therapeutic intervention for one or more sleep-related conditions, such as through facilitating intervention associated with therapies having a positive effect on a state of one or more users in relation to the one or more sleep-related conditions. In another specific example, performing a sleep-related characterization process (e.g., determining features highest correlations to one or more sleep-related conditions, etc.) can be based upon a random forest predictor algorithm trained with a training dataset derived from a subset of the population of subjects (e.g., subjects having the one or more sleep-related conditions; subjects not having the one or more sleep-related conditions; etc.), and validated with a validation dataset derived from a subset of the population of subjects. However, determining microbiome features and/or other suitable aspects associated with one or more sleep-related conditions can be performed in any suitable manner.

Microbiome features associated with one or more sleep-related conditions (e.g., positively correlated with; negatively correlated with; useful for diagnosis; etc.) can include features associated with any combination of one or more of the following taxa (e.g., features describing abundance of; features describing relative abundance of; features describing functional aspects associated with; features derived from; features describing presence and/or absence of; etc.) described in Table 1 (e.g., in relation to a sleep-related condition of bad sleep quality, etc.) and/or Table 2 (e.g., in relation to a sleep-related condition of shift work, such as night time shift work with day time sleeping periods, etc.) and/or: *Acetitomaculum* (genus), Acidaminococcaceae (family), *Acidaminococcus* (genus), *Acidaminococcus* sp. D21 (species), Actinobacteria (class), Actinobacteria (phylum), *Actinomyces* (genus), *Actinomyces* sp. ICM47 (species), *Actinomyces* sp. ICM54 (species), *Actinomyces* sp. S9 PR-21 (species), *Akkermansia muciniphila* (species), Alcaligenaceae (family), *Alistipes indistinctus* (species), *Alistipes* sp. 627 (species), *Anaerococcus* (genus), *Anaerococcus hydrogenalis* (species), *Anaerococcus octavius* (species), *Anaerococcus* sp. 8404299 (species), *Anaerococcus* sp. 8405254 (species), *Anaerococcus tetradius* (species), *Anaerofustis* (genus), *Anaerofustis stercorihominis* (species), *Anaeroplasma* (genus), *Anaerosporobacter* (genus), *Anaerostipes* sp. 1y-2 (species), *Anaerostipes* sp. 3_2_56FAA (species), *Anaerotruncus colihominis* (species), *Anaerotruncus* sp. NML 070203 (species), *Atopobium* (genus), *Atopobium vaginae* (species), *Bacteroides clarus* (species), *Bacteroides coprocola* (species), *Bacteroides nordii* (species), *Bacteroides plebeius* (species), *Bacteroides* sp. 2_2_4 (species), *Bacteroides* sp. CB57 (species), *Bacteroides* sp. DJF_B097 (species), *Bacteroides* sp. EBA5-17 (species), *Bacteroides* sp. SLC1-38 (species), *Bacteroides* sp. XB12B (species), *Bacteroides stercorirosoris* (species), Bifidobacteriaceae (family), Bifidobacteriales (order), *Bifidobacterium* (genus), *Bifidobacterium biavatii* (species), *Bifidobacterium bifidum* (species), *Bifidobacterium choerinum* (species), *Bifidobacterium longum* (species), *Bifidobacterium merycicum* (species), *Bifidobacterium* sp. MSX5B (species), *Bifidobacterium stercoris* (species), *Blautia glucerasea* (species), *Blautia hydrogenotrophica* (species), *Blautia* sp. Ser8 (species), *Blautia* sp. YHC-4 (species), *Brevibacterium massiliense* (species), *Butyricicoccus* (genus), *Butyricicoccus pullicaecorum* (species), *Butyricimonas synergistica* (species), *Butyrivibrio* (genus), *Butyrivibrio crossotus* (species), *Campylobacter* (genus), *Campylobacter hominis* (species), *Campylobacter ureolyticus* (species), Campylobacteraceae (family), Campylobacterales (order), *Candidatus Soleaferrea* (genus), *Candidatus Stoquefichus* (genus), *Catabacter hongkongensis* (species), *Catenibacterium mitsuokai* (species), *Cellulosilyticum* (genus), *Collinsella aerofaciens* (species), *Collinsella intestinalis* (species), *Coprobacillus* (genus), *Coprobacillus* sp. D6 (species), *Coprobacter* (genus), *Coprobacter fastidiosus* (species), *Corynebacterium* sp. (species), *Corynebacterium ulcerans* (species), Cyanobacteria (phylum), *Dermabacter* (genus), *Dermabacter hominis* (species), Dermabacteraceae (family), *Desulfovibrio desulfuricans* (species), *Desulfovibrio piger* (species), *Desulfovibrio* sp. (species), *Dialister* (genus), *Dialister invisus* (species), *Dialister propionicifaciens* (species), *Dielma* (genus), *Dielma fastidiosa* (species), *Eggerthella* (genus), *Eggerthella* sp. HGA1 (species), *Eisenbergiella tayi* (species), *Enterobacter* (genus), *Enterobacter* sp. BS2-1 (species), *Enterococcus* sp. C6I11 (species), Epsilonproteobacteria (class), *Erysipelatoclostridium ramosum* (species), Eubacteriaceae (family), *Eubacterium* (genus), *Eubacterium callanderi* (species), *Eubacterium* sp. SA11 (species), *Facklamia* sp. 1440-97 (species), *Fibro-*

*bacter* (genus), *Flavobacterium* (genus), *Flavonifractor plautii* (species), Fusobacteria (phylum), Fusobacteriaceae (family), Fusobacteriales (order), Fusobacteriia (class), *Fusobacterium* (genus), *Fusobacterium equinum* (species), *Fusobacterium ulcerans* (species), *Gardnerella* (genus), *Gardnerella vaginalis* (species), *Gelria* (genus), *Gordonibacter* (genus), *Gordonibacter pamelaeae* (species), *Granulicatella* (genus), *Granulicatella adiacens* (species), *Haemophilus* (genus), *Haemophilus parainfluenzae* (species), *Herbaspirillum* (genus), *Herbaspirillum seropedicae* (species), *Holdemania* (genus), *Holdemania filiformis* (species), *Howardella* (genus), *Hydrogenoanaerobacterium* (genus), *Intestinibacter* (genus), *Klebsiella* (genus), *Kluyvera georgiana* (species), *Lachnospira* (genus), *Lactobacillus crispatus* (species), *Lactobacillus rhamnosus* (species), *Lactobacillus* sp. 66c (species), *Lactobacillus* sp. Akhmr01 (species), *Lactobacillus* sp. BL302 (species), *Lactobacillus* sp. TAB-30 (species), *Lactonifactor* (genus), *Lactonifactor longoviformis* (species), Leptotrichiaceae (family), *Leuconostoc* (genus), Leuconostocaceae (family), *Megamonas* (genus), *Megamonas funiformis* (species), *Megasphaera* (genus), *Megasphaera genomosp.* C1 (species), *Megasphaera* sp. S6-MB2 (species), *Megasphaera* sp. UPII 199-6 (species), *Mobiluncus* (genus), *Mobiluncus mulieris* (species), *Moryella* (genus), *Negativicoccus* (genus), *Negativicoccus succinicivorans* (species), Negativicutes (class), *Oligella* (genus), *Oligella urethralis* (species), *Olsenella sp.* 1183 (species), Oscillospiraceae (family), *Pantoea* (genus), *Papillibacter* (genus), *Parabacteroides goldsteinii* (species), *Parabacteroides* sp. 157 (species), *Paraprevotella clara* (species), *Parvimonas micra* (species), Pasteurellaceae (family), Pasteurellales (order), *Peptoniphilus* (genus), *Peptoniphilus coxii* (species), *Peptoniphilus* sp. 2002-2300004 (species), *Peptoniphilus* sp. 7-2 (species), *Peptoniphilus* sp. gpac018A (species), *Phascolarctobacterium* (genus), *Phascolarctobacterium succinatutens* (species), Phyllobacteriaceae (family), *Phyllobacterium* (genus), *Porphyromonas uenonis* (species), *Prevotella bivia* (species), *Prevotella disiens* (species), Propionibacteriaceae (family), *Propionibacterium* (genus), Proteobacteria (phylum), *Pseudobutyrivibrio* (genus), *Pseudoclavibacter* sp. *Timone*(species), Rhizobiales (order), *Roseburia* (genus), Ruminococcaceae (family), *Sarcina ventriculi* (species), Selenomonadales order *Shuttleworthia* (genus), Sphingomonadaceae (family), Sphingomonadales (order), *Stenotrophomonas* (genus), *Stenotrophomonas* sp. C-S-TSA3 (species), *Streptococcus agalactiae* (species), *Streptococcus gordonii* (species), *Streptococcus pasteurianus* (species), *Streptococcus peroris* (species), *Streptococcus* sp. BS35a (species), *Streptococcus* sp. oral taxon G59 (species), *Sutterella* (genus), *Sutterella* sp. YIT 12072 (species), *Sutterella stercoricanis* (species), *Sutterella wadsworthensis* (species), *Terrisporobacter glycolicus* (species), Thermoanaerobacteraceae (family), Thermoanaerobacterales (order), *Turicibacter* (genus), *Turicibacter sanguinis* (species), *Varibaculum* (genus), *Varibaculum cambriense* (species), *Veillonella* sp. AS16 (species), Veillonellaceae (family), *Weissella hellenica* (species), Xanthomonadaceae (family), Xanthomonadales (order), *Alistipes massiliensis* (species), *Butyricimonas virosa* (species), *Alistipes putredinis* (species), *Actinobacillus porcinus* (species), *Actinobacillus* (genus), *Butyricimonas* (genus), *Howardella ureilytica* (species), Firmicutes (phylum), *Clostridium* (genus), Lentisphaeria (class), Anaeroplasmataceae (family), Pseudomonadaceae (family), Victivallaceae (family), *Blautia* (genus), *Asteroleplasma* (genus), *Delftia* (genus), *Victivallis* (genus), *Peptostreptococcus* (genus), *Pseudomonas* (genus), *Alloprevotella* (genus), *Catenibacterium* (genus), Anaeroplasmatales (order), Pseudomonadales (order), Lentisphaerae (phylum), *Veillonella* sp. CM60 (species), *Porphyromonas* sp. 2026 (species), *Delftia* sp. BN-SKY3 (species), *Peptostreptococcus anaerobius* (species), *Citrobacter* sp. BW4 (species), *Alistipes* sp. RMA 9912 (species), *Bacteroides vulgatus* (species), *Lactobacillus* sp. BL302 (species), *Lactobacillus* sp. TAB-26 (species), *Bifidobacterium kashiwanohense* (species), *Butyricimonas* sp. JCM 18677 (species) and/or any other suitable taxa (e.g., described herein, etc.).

In a first variation, microbiome features associated with one or more sleep-related conditions can include features associated with one or more of the following taxa: *Acetitomaculum* (genus), Acidaminococcaceae (family), *Acidaminococcus* (genus), *Acidaminococcus* sp. D21 (species), Actinobacteria (class), Actinobacteria (phylum), *Actinomyces* (genus), *Actinomyces* sp. ICM47 (species), *Actinomyces* sp. ICM54 (species), *Actinomyces* sp. S9 PR-21 (species), *Akkermansia muciniphila* (species), Alcaligenaceae (family), *Alistipes indistinctus* (species), *Alistipes* sp. 627 (species), *Anaerococcus* (genus), *Anaerococcus hydrogenalis* (species), *Anaerococcus octavius* (species), *Anaerococcus* sp. 8404299 (species), *Anaerococcus* sp. 8405254 (species), *Anaerococcus tetradius* (species), *Anaerofustis* (genus), *Anaerofustis stercorihominis* (species), *Anaeroplasma* (genus), *Anaerosporobacter* (genus), *Anaerostipes* sp. 1y-2 (species), *Anaerostipes* sp. 3—2_56FAA (species), *Anaerotruncus colihominis* (species), *Anaerotruncus* sp. NML 070203 (species), *Atopobium* (genus), *Atopobium vaginae* (species), *Bacteroides clarus* (species), *Bacteroides coprocola* (species), *Bacteroides nordii* (species), *Bacteroides plebeius* (species), *Bacteroides* sp. 2_2_4 (species), *Bacteroides* sp. CB57 (species), *Bacteroides* sp. DJF_B097 (species), *Bacteroides* sp. EBA5-17 (species), *Bacteroides* sp. SLC1-38 (species), *Bacteroides* sp. XB12B (species), *Bacteroides stercorirosoris* (species), Bifidobacteriaceae (family), Bifidobacteriales (order), *Bifidobacterium* (genus), *Bifidobacterium biavatii* (species), *Bifidobacterium bifidum* (species), *Bifidobacterium choerinum* (species), *Bifidobacterium longum* (species), *Bifidobacterium merycicum* (species), *Bifidobacterium* sp. MSX5B (species), *Bifidobacterium stercoris* (species), *Blautia glucerasea* (species), *Blautia hydrogenotrophica* (species), *Blautia* sp. Ser8 (species), *Blautia* sp. YHC-4 (species), *Brevibacterium massiliense* (species), *Butyricicoccus* (genus), *Butyricicoccus pullicaecorum* (species), *Butyricimonas synergistica* (species), *Butyrivibrio* (genus), *Butyrivibrio crossotus* (species), *Campylobacter* (genus), *Campylobacter hominis* (species), *Campylobacter ureolyticus* (species), Campylobacteraceae (family), Campylobacterales (order), *Candidatus Soleaferrea* (genus), *Candidatus Stoquefichus* (genus), *Catabacter hongkongensis* (species), *Catenibacterium mitsuokai* (species), *Cellulosilyticum* (genus), *Collinsella aerofaciens* (species), *Collinsella intestinalis* (species), *Coprobacillus* (genus), *Coprobacillus* sp. D6 (species), *Coprobacter* (genus), *Coprobacter fastidiosus* (species), *Corynebacterium* sp. (species), *Corynebacterium ulcerans* (species), Cyanobacteria (phylum), *Dermabacter* (genus), *Dermabacter hominis* (species), Dermabacteraceae (family), *Desulfovibrio desulfuricans* (species), *Desulfovibrio piger* (species), *Desulfovibrio* sp. (species), *Dialister* (genus), *Dialister invisus* (species), *Dialister propionicifaciens* (species), *Dielma* (genus), *Dielma fastidiosa* (species), *Eggerthella* (genus), *Eggerthella* sp. HGA1 (species), *Eisenbergiella tayi* (species), *Enterobacter* (genus), *Enterobacter* sp. BS2-1 (species), *Enterococcus* sp. C6I11 (species), Epsilonproteobacteria (class), *Erysipelatoclostridium*

*ramosum* (species), Eubacteriaceae (family), *Eubacterium* (genus), *Eubacterium callanderi* (species), *Eubacterium* sp. SA11 (species), *Facklamia* sp. 1440-97 (species), *Fibrobacter* (genus), *Flavobacterium* (genus), *Flavonifractor plautii* (species), Fusobacteria (phylum), Fusobacteriaceae (family), Fusobacteriales (order), Fusobacteriia (class), *Fusobacterium* (genus), *Fusobacterium equinum* (species), *Fusobacterium ulcerans* (species), *Gardnerella* (genus), *Gardnerella vaginalis* (species), *Gelria* (genus), *Gordonibacter* (genus), *Gordonibacter pamelaeae* (species), *Granulicatella* (genus), *Granulicatella adiacens* (species), *Haemophilus* (genus), *Haemophilus parainfluenzae* (species), *Herbaspirillum* (genus), *Herbaspirillum seropedicae* (species), *Holdemania* (genus), *Holdemania filiformis* (species), *Howardella* (genus), *Hydrogenoanaerobacterium* (genus), *Intestinibacter* (genus), *Klebsiella* (genus), *Kluyvera georgiana* (species), *Lachnospira* (genus), *Lactobacillus crispatus* (species), *Lactobacillus rhamnosus* (species), *Lactobacillus* sp. 66c (species), *Lactobacillus* sp. Akhmr01 (species), *Lactobacillus* sp. BL302 (species), *Lactobacillus* sp. TAB-30 (species), *Lactonifactor* (genus), *Lactonifactor longoviformis* (species), Leptotrichiaceae (family), *Leuconostoc* (genus), Leuconostocaceae (family), *Megamonas* (genus), *Megamonas funiformis* (species), *Megasphaera* (genus), *Megasphaera genomosp.* C1 (species), *Megasphaera* sp. S6-MB2 (species), *Megasphaera* sp. UPII 199-6 (species), *Mobiluncus* (genus), *Mobiluncus mulieris* (species), *Moryella* (genus), *Negativicoccus* (genus), *Negativicoccus succinicivorans* (species), Negativicutes (class), *Oligella* (genus), *Oligella urethralis* (species), *Olsenella* sp. 1183 (species), Oscillospiraceae (family), *Pantoea* (genus), *Papillibacter* (genus), *Parabacteroides goldsteinii* (species), *Parabacteroides* sp. 157 (species), *Paraprevotella clara* (species), *Parvimonas micra* (species), Pasteurellaceae (family), Pasteurellales (order), *Peptoniphilus* (genus), *Peptoniphilus coxii* (species), *Peptoniphilus* sp. 2002-2300004 (species), *Peptoniphilus* sp. 7-2 (species), *Peptoniphilus* sp. gpac018A (species), *Phascolarctobacterium* (genus), *Phascolarctobacterium succinatutens* (species), Phyllobacteriaceae (family), *Phyllobacterium* (genus), *Porphyromonas uenonis* (species), *Prevotella bivia* (species), *Prevotella disiens* (species), Propionibacteriaceae (family), *Propionibacterium* (genus), Proteobacteria (phylum), *Pseudobutyrivibrio* (genus), *Pseudoclavibacter* sp. *Timone* (species), Rhizobiales (order), *Roseburia* (genus), Ruminococcaceae (family), *Sarcina ventriculi* (species), Selenomonadales order *Shuttleworthia* (genus), Sphingomonadaceae (family), Sphingomonadales (order), *Stenotrophomonas* (genus), *Stenotrophomonas* sp. C-S-TSA3 (species), *Streptococcus agalactiae* (species), *Streptococcus gordonii* (species), *Streptococcus pasteurianus* (species), *Streptococcus peroris* (species), *Streptococcus* sp. BS35a (species), *Streptococcus* sp. oral taxon G59 (species), *Sutterella* (genus), *Sutterella* sp. YIT 12072 (species), *Sutterella stercoricanis* (species), *Sutterella wadsworthensis* (species), (species), Thermoanaerobacteraceae (family), Thermoanaerobacterales (order), *Turicibacter* (genus), *Turicibacter sanguinis* (species), *Varibaculum* (genus), *Varibaculum cambriense* (species), *Veillonella* sp. AS16 (species), Veillonellaceae (family), *Weissella hellenica* (species), Xanthomonadaceae (family), Xanthomonadales (order), and/or any other suitable taxa.

In a second variation, microbiome features associated with one or more sleep-related conditions (e.g., and/or behaviors and/or lifestyle conditions such as shift work, etc.) can include features associated with one or more of the following taxa: *Alistipes massiliensis* (species), *Butyricimonas virosa* (species), Leuconostocaceae (family), *Lactobacillus* sp. TAB-30 (species), *Alistipes putredinis* (species), *Actinobacillus porcinus* (species), *Bifidobacterium stercoris* (species), *Actinobacillus* (genus), *Butyricimonas* (genus), *Howardella* (genus), *Catenibacterium mitsuokai* (species), *Howardella ureilytica* (species), Firmicutes (phylum), *Clostridium* (genus), Lentisphaeria (class), Anaeroplasmataceae (family), Pseudomonadaceae (family), Victivallaceae (family), *Blautia* (genus), *Asteroleplasma* (genus), *Delftia* (genus), *Victivallis* (genus), *Peptostreptococcus* (genus), *Pseudomonas* (genus), *Bifidobacterium* (genus), *Alloprevotella* (genus), *Catenibacterium* (genus), Anaeroplasmatales (order), Pseudomonadales (order), Lentisphaerae (phylum), *Veillonella* sp. CM60 (species), *Lactobacillus* sp. Akhmr01 (species), *Porphyromonas* sp. 2026 (species), *Weissella hellenica* (species), *Delftia* sp. BN-SKY3 (species), *Peptostreptococcus anaerobius* (species), *Citrobacter* sp. BW4 (species), *Collinsella intestinalis* (species), *Alistipes* sp. RMA 9912 (species), *Bacteroides vulgatus* (species), *Lactobacillus* sp. BL302 (species), *Lactobacillus* sp. TAB-26 (species), *Bifidobacterium* sp. (species), *Prevotella bivia* (species), *Bifidobacterium kashiwanohense* (species), *Butyricimonas* sp. JCM 18677 (species), *Bifidobacterium stercoris* (species), and/or any other suitable taxa.

In an example, the method 100 can include determining a sleep-related characterization for the user for a first sleep-related condition and a second sleep-related condition based on a first set of composition features (e.g., including at least one or more of the microbiome features described above in relation to the first variation; including any suitable combination of microbiome features; etc.), a first sleep-related characterization model, a second set of composition features (e.g., including at least one or more of the microbiome features described above in relation to the second variation; including any suitable combination of microbiome features; etc.), and a second sleep-related characterization model, where the first sleep-related characterization model is associated with the first sleep-related condition (e.g., where the first sleep-related characterization model determines characterizations for the first sleep-related condition, etc.), and where the second sleep-related characterization model is associated with the second sleep-related condition (e.g., where the second sleep-related characterization model determines characterizations for the second sleep-related condition, etc.). In the example, determining user microbiome features can include determining first user microbiome functional features associated with first functions from at least one of Cluster of Orthologous Groups (COG) database and Kyoto Encyclopedia of Genes and Genomes (KEGG) database, where the first user microbiome functional features are associated with the first sleep-related condition; and determining second user microbiome functional features associated with second functions from at least one of the COG database and the KEGG database, where the second user microbiome functional features are associated with the second sleep-related condition, where determining the sleep-related characterization can include determining the sleep-related characterization for the user for the first sleep-related condition and the second sleep-related condition based on the first set of composition features, the first user microbiome functional features, the first sleep-related characterization model, the second set of composition features, the second user microbiome functional features, and the second sleep-related characterization model. Additionally or alternatively, any combinations of microbiome features can be used with any suitable number and types of sleep-related characterization models to determine sleep-related characterization for one or more sleep-related conditions, in any suitable manner.

Additionally or alternatively, microbiome features associated with one or more sleep-related conditions can include microbiome functional features (e.g., features describing functions associated with one or more microorganisms, such as microorganisms classified under taxa described herein; features describing functional diversity; features describing presence, absence, abundance, and/or relative abundance; etc.) corresponding to functions from and/or otherwise associated with the Clusters of Orthologous Groups (COG) database, Kyoto Encyclopedia of Genes and Genomes (KEGG) database, and/or any other suitable database available (e.g., databases with microorganism function data, etc.). However, microbiome features can include any suitable microbiome functional features associated with any suitable microorganism function, human function, and/or other suitable functionality. In examples, the method 100 can include generating one or more sleep-related characterization models based on any suitable combination of microbiome features described above and/or herein (e.g., based on a set of microbiome composition features including features associated with at least one of the taxa described herein; and/or based on microbiome functional features described herein, such as corresponding to functions from databases described herein; etc.) In an example, performing a characterization process for a user can include characterizing a user as having one or more sleep-related conditions, such as based upon detection of, values corresponding to, and/or other aspects related to microbiome features described herein (e.g., microbiome features described above, etc.), and such as in a manner that is an additional (e.g., supplemental to, complementary to, etc.) or alternative to typical approaches of diagnosis, other characterizations (e.g., treatment-related characterizations, etc.), treatment, monitoring, and/or other suitable approaches associated with sleep-related conditions. In variations, the microbiome features can be used for diagnostics, other characterizations, treatment, monitoring, and/or any other suitable purposes and/or approaches associated with sleep-related conditions. However, determining one or more sleep-related characterizations can be performed in any suitable manner.

4.3.B Determining a therapy.

Performing a characterization process S130 (e.g., performing a sleep-related therapy) can include Block S140, which can include determining one or more therapies (e.g., therapies configured to modulate microbiome composition, function, diversity, and/or other suitable aspects, such as for improving one or more aspects associated with sleep-related conditions, such as in users characterized based on one or more characterization processes; etc.). Block S140 can function to identify, select, rank, prioritize, predict, discourage, and/or otherwise determine therapies (e.g., facilitate therapy determination, etc.). For example, Block S140 can include determining one or more of probiotic-based therapies, bacteriophage-based therapies, small molecule-based therapies, and/or other suitable therapies, such as therapies that can shift a subject's microbiome composition, function, diversity, and/or other characteristics (e.g., microbiomes at any suitable sites, etc.) toward a desired state (e.g., equilibrium state, etc.) in promotion of a user's health, for modifying a state of one or more sleep-related conditions, and/or for other suitable purposes.

Therapies (e.g., sleep-related therapies, etc.) can include any one or more of: consumables (e.g., probiotic therapies, prebiotic therapies, medication, sleeping pills, melatonin supplements, allergy or cold medication, bacteriophage-based therapies, consumables for underlying conditions, small molecule therapies, etc.); device-related therapies (e.g., sleep-monitoring devices, such as a user device executing a sleep-monitoring application, sensor-based devices; dental guards; breathing devices; medical devices; implantable medical devices; sleep apnea devices such as continuous positive airway pressure devices, mandibular advancement devices, tongue retaining devices; stimulation devices such as electrostimulation devices, nerve stimulation devices; snoring prevention devices; catheters such as transtracheal catheters; nasal air filters; air quality devices such as air filtration devices; audio-based devices such as white noise machines; etc.); surgical operations (e.g., sleep apnea surgery; tonsillectomy; adenoidectomy; supraglottoplasty; turbinoplasty; septoplasty; septorhinoplasty; nasal surgeries; soft palate surgeries; oropharyngeal surgeries; hypopharyngeal surgeries; tracheostomies; maxillomandibular advancement; uvulopalatopharyngoplasty; hyoid suspension; genioglossus advancement; etc.); psychological-associated therapies (e.g., cognitive behavioral therapy, anxiety therapy, talking therapy, psychodynamic therapy, action-oriented therapy, rational emotive behavior therapy, interpersonal psychotherapy, relaxation training, deep breathing techniques, progressive muscle relaxation, sleep restriction therapy, meditation, etc.); behavior modification therapies (e.g., physical activity recommendations such as increased exercise; dietary recommendations such as reducing sugar intake, increased vegetable intake, increased fish intake, decreased caffeine consumption, decreased alcohol consumption, decreased carbohydrate intake; smoking recommendations such as decreasing tobacco intake; weight-related recommendations; sleep habit recommendations; device recommendations such as decreased electronic device usage before bedtime; recommendations in relation to other behaviors; etc.); topical administration therapies (e.g., bacteriophage-based therapies); environmental factor modification therapies; (e.g., adjusting lighting for sleep time and/or wake time; adjusting bedding-related factors; modification of other environmental factors; etc.); modification of any other suitable aspects associated with one or more sleep-related conditions; and/or any other suitable therapies (e.g., for improving a health state associated with one or more sleep-related conditions, such as therapies for improving one or more sleep-related conditions, therapies for reducing the risk of one or more sleep-related conditions, etc.). In examples, types of therapies can include any one or more of: probiotic therapies, bacteriophage-based therapies, small molecule-based therapies, cognitive/behavioral therapies, physical rehabilitation therapies, clinical therapies, medication-based therapies, diet-related therapies, and/or any other suitable therapy designed to operate in any other suitable manner in promoting a user's health.

In a variation, therapies can include one or more bacteriophage-based therapies (e.g., in the form of a consumable, in the form of a topical administration therapy, etc.), where one or more populations (e.g., in terms of colony forming units) of bacteriophages specific to a certain bacteria (or other microorganism) represented in the subject can be used to down-regulate or otherwise eliminate populations of the certain bacteria. As such, bacteriophage-based therapies can be used to reduce the size(s) of the undesired population(s) of bacteria represented in the subject. Additionally or alternatively, bacteriophage-based therapies can be used to increase the relative abundances of bacterial populations not targeted by the bacteriophage(s) used. However, bacteriophage-based therapies can be used to modulate characteristics of microbiomes (e.g., microbiome composition, microbiome function, etc.) in any suitable manner, and/or can be used for any suitable purpose.

In a variation, therapies can include one or more probiotic therapies and/or prebiotic therapies associated with any combination of at least one or more of (e.g., including any combination of one or more of, etc.) any suitable taxa described in Table 1 (e.g., in relation to therapies for a sleep-related condition of bad sleep quality, etc.) and/or Table 2 (e.g., in relation to therapies for a sleep-related condition for shift work, etc.) and/or: *Anaerococcus* sp. 8405254, *Bacteroides nordii, Bacteroides* sp. SLC1-38, *Bifidobacterium merycicum, Blautia glucerasea, Blautia* sp. YHC-4, *Butyrivibrio crossotus, Catabacter hongkongensis, Catenibacterium mitsuokai, Collinsella aerofaciens, Collinsella intestinalis, Desulfovibrio piger, Eubacterium* sp. SA11, *Fusobacterium ulcerans, Lactobacillus* sp. TAB-30, *Megamonas funiformis, Megasphaera* sp. S6-MB2, *Olsenella* sp. 1183, *Phascolarctobacterium succinatutens, Streptococcus gordonii, Sutterella* sp. YIT 12072, *Sutterella wadsworthensis, Veillonella* sp. AS16, *Fusobacterium equinum, Facklamia* sp. 1440-97, *Anaerostipes* sp. 3_2_56FAA, *Pseudoclavibacter* sp. *Timone, Parvimonas micra, Lactobacillus* sp. 66c, *Bacteroides coprocola, Corynebacterium ulcerans, Anaerostipes* sp. 1y-2, *Sarcina ventriculi, Lactonifactor longoviformis, Enterococcus* sp. C6I11, *Eubacterium callanderi, Dialister invisus, Blautia* sp. Ser8, *Bacteroides plebeius, Bacteroides* sp. 2_2_4, *Anaerotruncus colihominis, Varibaculum cambriense, Actinomyces* sp. S9 PR-21, *Desulfovibrio* sp., *Prevotella disiens, Mobiluncus mulieris, Lactobacillus rhamnosus, Bifidobacterium* sp. MSX5B, *Acidaminococcus* sp. D21, *Bifidobacterium bifidum, Bacteroides* sp. EBA5-17, *Anaerococcus hydrogenalis, Alistipes* sp. 627, *Negativicoccus succinicivorans, Anaerococcus* sp. 8404299, *Butyricimonas synergistica, Actinomyces* sp. ICM54, *Turicibacter sanguinis, Blautia hydrogenotrophica, Parabacteroides goldsteinii, Bifidobacterium biavatii, Erysipelatoclostridium ramosum, Anaerofustis stercorihominis, Gardnerella vaginalis, Gordonibacter pamelaeae, Campylobacter hominis, Lactobacillus* sp. BL302, *Megasphaera* sp. UPII 199-6, *Peptoniphilus* sp. gpac018A, *Bifidobacterium stercoris, Butyricicoccus pullicaecorum, Megasphaera* sp. S6-MB2, *Corynebacterium* sp., *Dialister propionicifaciens, Anaerococcus tetradius, Eggerthella* sp. HGA1, *Peptoniphilus* sp. 7-2, *Terrisporobacter glycolicus, Peptoniphilus* sp. 2002-2300004, *Bacteroides* sp. CB57, *Streptococcus pasteurianus, Megasphaera genomosp.* C1, *Holdemania filiformis, Coprobacillus* sp. D6, *Dielma fastidiosa, Sutterella stercoricanis, Brevibacterium massiliense, Bacteroides stercorirosoris, Lactobacillus* sp. Akhmr01, *Actinomyces* sp. ICM47, *Lactobacillus crispatus, Prevotella bivia, Enterobacter* sp. BS2-1, *Streptococcus* sp. BS35a, *Anaerotruncus* sp. NML 070203, *Haemophilus parainfluenzae, Peptoniphilus coxii, Granulicatella adiacens, Campylobacter ureolyticus, Bifidobacterium longum, Bacteroides clarus, Bacteroides* sp. XB12B, *Streptococcus agalactiae, Kluyvera georgiana, Flavonifractor plautii, Paraprevotella clara, Stenotrophomonas* sp. C-S-TSA3, *Bacteroides* sp. DJF_B097, *Herbaspirillum seropedicae, Streptococcus* sp. oral taxon G59, *Eisenbergiella tayi, Coprobacter fastidiosus, Oligella urethralis, Akkermansia muciniphila, Desulfovibrio desulfuricans, Streptococcus peroris, Anaerococcus octavius, Atopobium vaginae, Parabacteroides* sp. 157, *Bifidobacterium choerinum, Porphyromonas uenonis, Dermabacter hominis, Alistipes indistinctus, Weissella hellenica, Alistipes massiliensis, Butyricimonas virosa, Alistipes putredinis, Actinobacillus porcinus, Howardella ureilytica, Veil-* *lonella* sp. CM60, *Porphyromonas* sp. 2026, *Delftia* sp. BN-SKY3, *Peptostreptococcus anaerobius, Citrobacter* sp. BW4, *Alistipes* sp. RMA 9912, *Bacteroides vulgatus, Lactobacillus* sp. TAB-26, *Bifidobacterium* sp., *Bifidobacterium kashiwanohense, Butyricimonas* sp. JCM 18677, and/or any other suitable microorganisms associated with any suitable taxonomic groups (e.g., microorganisms from taxa described herein, such as in relation to microbiome features, etc.). For one or more probiotic therapies and/or other suitable therapies, microorganisms associated with a given taxonomic group, and/or any suitable combination of microorganisms can be provided at dosages of 0.1 million to 10 billion CFU, and/or at any suitable amount (e.g., as determined from a therapy model that predicts positive adjustment of a patient's microbiome in response to the therapy, etc.). In an example, a subject can be instructed to ingest capsules including the probiotic formulation according to a regimen tailored to one or more of his/her: physiology (e.g., body mass index, weight, height), demographic characteristics (e.g., gender, age), severity of dysbiosis, sensitivity to medications, and any other suitable factor.

Figure 4:
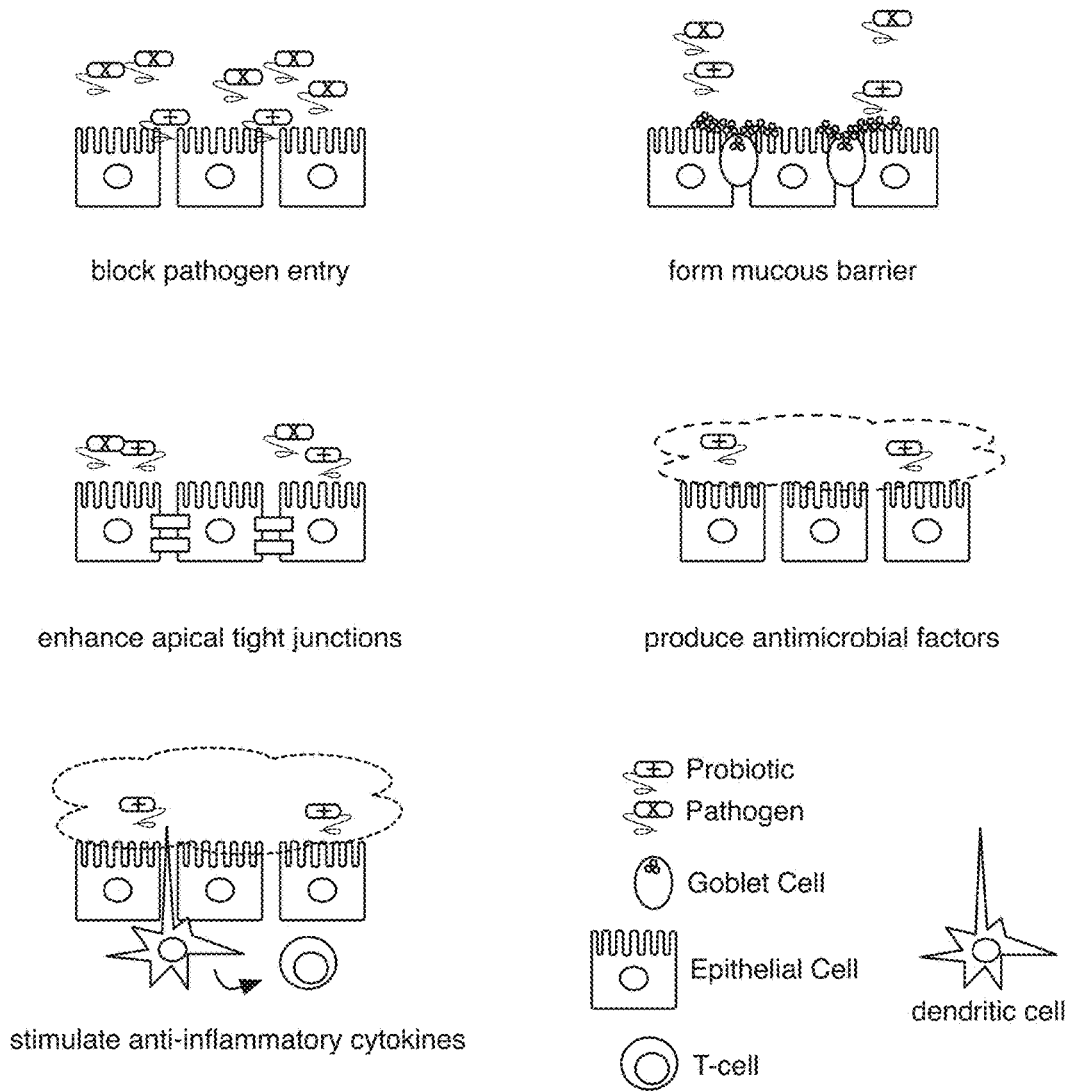
FIG. 4 depicts variations of mechanisms by which probiotic-based therapies operate in an embodiment of a method.

In a specific example of probiotic therapies, as shown in FIG. 4, candidate therapies of the therapy model can perform one or more of: blocking pathogen entry into an epithelial cell by providing a physical barrier (e.g., by way of colonization resistance), inducing formation of a mucous barrier by stimulation of goblet cells, enhance integrity of apical tight junctions between epithelial cells of a subject (e.g., by stimulating up regulation of zona-occludens 1, by preventing tight junction protein redistribution), producing antimicrobial factors, stimulating production of anti-inflammatory cytokines (e.g., by signaling of dendritic cells and induction of regulatory T-cells), triggering an immune response, and performing any other suitable function that adjusts a subject's microbiome away from a state of dysbiosis. In another specific example, therapies can include medical-device based therapies (e.g., associated with human behavior modification, associated with treatment of disease-related conditions, etc.).

In variations, the therapy model is preferably based upon data from a large population of subjects, which can include the population of subjects from which the microbiome diversity datasets are derived in Block S110, where microbiome composition and/or functional features or states of health, prior exposure to and post exposure to a variety of therapeutic measures, are well characterized. Such data can be used to train and validate the therapy provision model, in identifying therapeutic measures that provide desired outcomes for subjects based upon different sleep-related characterizations. In variations, support vector machines, as a supervised machine learning algorithm, can be used to generate the therapy provision model. However, any other suitable machine learning algorithm described above can facilitate generation of the therapy provision model.

Additionally or alternatively, the therapy model can be derived in relation to identification of a "normal" or baseline microbiome composition and/or functional features, as assessed from subjects of a population of subjects who are identified to be in good health. Upon identification of a subset of subjects of the population of subjects who are characterized to be in good health (e.g., using features of the characterization process), therapies that modulate microbiome compositions and/or functional features toward those of subjects in good health can be generated in Block S140. Block S140 can thus include identification of one or more baseline microbiome compositions and/or functional features (e.g., one baseline microbiome for each of a set of demographic characteristics), and potential therapy formulations and therapy regimens that can shift microbiomes of subjects who are in a state of dysbiosis toward one of the identified baseline microbiome compositions and/or functional features. The therapy model can, however, be generated and/or refined in any other suitable manner.

Microorganism compositions associated with probiotic therapies and/or prebiotic therapies (e.g., associated with probiotic therapies determined by a therapy model applied by a therapy facilitation system, etc.) can include microorganisms that are culturable (e.g., able to be expanded to provide a scalable therapy) and/or non-lethal (e.g., non-lethal in their desired therapeutic dosages). Furthermore, microorganism compositions can include a single type of microorganism that has an acute or moderated effect upon a subject's microbiome. Additionally or alternatively, microorganism compositions can include balanced combinations of multiple types of microorganisms that are configured to cooperate with each other in driving a subject's microbiome toward a desired state. For instance, a combination of multiple types of bacteria in a probiotic therapy can include a first bacteria type that generates products that are used by a second bacteria type that has a strong effect in positively affecting a subject's microbiome. Additionally or alternatively, a combination of multiple types of bacteria in a probiotic therapy can include several bacteria types that produce proteins with the same functions that positively affect a subject's microbiome.

Probiotic and/or prebiotic compositions can be naturally or synthetically derived. For instance, in one application, a probiotic composition can be naturally derived from fecal matter or other biological matter (e.g., of one or more subjects having a baseline microbiome composition and/or functional features, as identified using the characterization process and the therapy model). Additionally or alternatively, probiotic compositions can be synthetically derived (e.g., derived using a benchtop method) based upon a baseline microbiome composition and/or functional features, as identified using the characterization process and the therapy model. In variations, microorganism agents that can be used in probiotic therapies can include one or more of: yeast (e.g., *Saccharomyces boulardii*), gram-negative bacteria (e.g., *E. coli* Nissle), gram-positive bacteria (e.g., *Bifidobacteria bifidum, Bifidobacteria infantis, Lactobacillus rhamnosus, Lactococcus lactis, Lactobacillus plantarum, Lactobacillus acidophilus, Lactobacillus casei, Bacillus polyfermenticus*, etc.), and any other suitable type of microorganism agent. However, probiotic therapies, prebiotic therapies and/or other suitable therapies can include any suitable combination of microorganisms associated with any suitable taxa described herein, and/or therapies can be configured in any suitable manner.

Block S140 can include executing, storing, retrieving, and/or otherwise processing one or more therapy models for determining one or more therapies. Processing one or more therapy models is preferably based on microbiome features. For example, generating a therapy model can based on microbiome features associated with one or more sleep-related conditions, therapy-related aspects such as therapy efficacy in relation to microbiome characteristics, and/or other suitable data. Additionally or alternatively, processing therapy models can be based on any suitable data. In an example, processing a therapy model can include determining one or more therapies for a user based on one or more therapy models, user microbiome features (e.g., inputting user microbiome feature values into the one or more therapy models, etc.), supplementary data (e.g., prior knowledge associated with therapies such as in relation to microorganism-related metabolization; user medical history; user demographic data, such as describing demographic characteristics; etc.), and/or any other suitable data. However, processing therapy models can be based on any suitable data in any suitable manner.

Sleep-related characterization models can include one or more therapy models. In an example, determining one or more sleep-related characterizations (e.g., for one or more users, for one or more sleep-related conditions, etc.), can include determining one or more therapies, such as based on one or more therapy models (e.g., applying one or more therapy models, etc.) and/or other suitable data (e.g., microbiome features such as user microbiome features, microorganism dataset such as user microorganism datasets, etc.). In a specific example, determining one or more sleep-related characterizations can include determining a first sleep-related characterization for a user (e.g., describing propensity for one or more sleep-related conditions; etc.); and determining a second sleep-related characterization for the user based on the first sleep-related characterization (e.g., determining one or more therapies, such as for recommendation to a user, based on the propensity for one or more sleep-related conditions; etc.). In a specific example, a sleep-related characterization can include both propensity-related data (e.g., diagnostic data; associated microbiome composition, function, diversity, and/or other characteristics; etc.) and therapy-related data (e.g., recommended therapies; potential therapies; etc.). However, sleep-related characterizations can include any suitable data (e.g., any combination of data described herein, etc.).

Processing therapy models can include processing a plurality of therapy models. For example, different therapy models can be processed for different therapies (e.g., different models for different individual therapies; different models for different combinations and/or categories of therapies, such as a first therapy model for determining consumable therapies and a second therapy model for determining psychological-associated therapies; etc.). In an example, different therapy models can be processed for different sleep-related conditions, (e.g., different models for different individual sleep-related conditions; different models for different combinations and/or categories of sleep-related conditions, such as a first therapy model for determining therapies for insomnias, and a second therapy model for determining therapies for hypersomnias, etc.). Additionally or alternatively, processing a plurality of therapy models can be performed for (e.g., based on; processing different therapy models for; etc.) any suitable types of data and/or entities. However, processing a plurality of therapy models can be performed in any suitable manner, and determining and/or applying one or more therapy models can be performed in any suitable manner.

4.4 Processing a User Biological Sample.

The method 100 can additionally or alternatively include Block S150, which can include processing one or more biological samples from a user (e.g., biological samples from different collection sites of the user, etc.). Block S150 can function to facilitate generation of a microorganism dataset for a user, such as for use in deriving inputs for the characterization process (e.g., for generating a sleep-related characterization for the user, such as through applying one or more sleep-related characterization models, etc.). As such, Block S150 can include receiving, processing, and/or analyzing one or more biological samples from one or more users (e.g., multiple biological samples for the same user over time, different biological samples for different users, etc.). In Block S150, the biological sample is preferably generated from the user and/or an environment of the user in a non-invasive manner. In variations, non-invasive manners of sample reception can use any one or more of: a permeable substrate (e.g., a swab configured to wipe a region of a user's body, toilet paper, a sponge, etc.), a non-permeable substrate (e.g., a slide, tape, etc.) a container (e.g., vial, tube, bag, etc.) configured to receive a sample from a region of a user's body, and any other suitable sample-reception element. In a specific example, the biological sample can be collected from one or more of the user's nose, skin, genitals, mouth, and gut (e.g., through stool samples, etc.) in a non-invasive manner (e.g., using a swab and a vial). However, the biological sample can additionally or alternatively be received in a semi-invasive manner or an invasive manner. In variations, invasive manners of sample reception can use any one or more of: a needle, a syringe, a biopsy element, a lance, and any other suitable instrument for collection of a sample in a semi-invasive or invasive manner. In specific examples, samples can include blood samples, plasma/serum samples (e.g., to enable extraction of cell-free DNA), and tissue samples.

In the above variations and examples, the biological sample can be taken from the body of the user without facilitation by another entity (e.g., a caretaker associated with a user, a health care professional, an automated or semi-automated sample collection apparatus, etc.), or can alternatively be taken from the body of the user with the assistance of another entity. In one example, where the biological sample is taken from the user without facilitation by another entity in the sample extraction process, a sample-provision kit can be provided to the user. In the example, the kit can include one or more swabs for sample acquisition, one or more containers configured to receive the swab(s) for storage, instructions for sample provision and setup of a user account, elements configured to associate the sample(s) with the user (e.g., barcode identifiers, tags, etc.), and a receptacle that allows the sample(s) from the user to be delivered to a sample processing operation (e.g., by a mail delivery system). In another example, where the biological sample is extracted from the user with the help of another entity, one or more samples can be collected in a clinical or research setting from the user (e.g., during a clinical appointment). The biological sample can, however, be received from the user in any other suitable manner.

Furthermore, processing and analyzing biological samples (e.g., to generate a user microorganism dataset; etc.) from the user is preferably performed in a manner similar to that of one of the embodiments, variations, and/or examples of sample reception described in relation to Block 110 above, and/or any other suitable portions of the method 100 and/or system 200. As such, reception and processing of the biological sample in Block S150 can be performed for the user using similar processes as those for receiving and processing biological samples used to perform the characterization processes of the method 100, such as in order to provide consistency of process. However, biological sample reception and processing in Block S150 can additionally or alternatively be performed in any other suitable manner.

4.5 Determining a Sleep-Related Characterization.

The method 100 can additionally or alternatively include Block S160, which can include determining, with one or more characterization processes (e.g., one or more characterization processes described in relation to Block S130, etc.), a sleep-related characterization for the user, such as based upon processing one or more microorganism dataset (e.g., user microorganism sequence dataset, microbiome composition dataset, microbiome functional diversity dataset; processing of the microorganism dataset to extract user microbiome features that can be used to determine the one or more sleep-related characterizations; etc.) derived from the biological sample of the user. Block S160 can function to characterize one or more sleep-related conditions for a user, such as through extracting features from microbiome-derived data of the user, and using the features as inputs into an embodiment, variation, or example of the characterization process described in Block S130 above (e.g., using the user microbiome feature values as inputs into a microbiome-related condition characterization model, etc.). In an example, Block S160 can include generating a sleep-related characterization for the user based on user microbiome features and a sleep-related condition model (e.g., generated in Block S130). Sleep-related characterizations can be for any number and/or combination of sleep-related conditions (e.g., a combination of sleep-related conditions, a single sleep-related condition, and/or other suitable sleep-related conditions; etc.), users, collection sites, and/or other suitable entities. Sleep-related characterizations can include one or more of: diagnoses (e.g., presence or absence of a sleep-related condition; etc.); risk (e.g., risk scores for developing and/or the presence of a sleep-related condition; information regarding sleep-related characterizations (e.g., symptoms, signs, triggers, associated conditions, etc.); comparisons (e.g., comparisons with other subgroups, populations, users, historic health statuses of the user such as historic microbiome compositions and/or functional diversities; comparisons associated with sleep-related conditions; etc.); therapy determinations; other suitable outputs associated with characterization processes; and/or any other suitable data.

In another variation, a sleep-related characterization can include a microbiome diversity score (e.g., in relation to microbiome composition, function, etc.) associated with (e.g., correlated with; negatively correlated with; positively correlated with; etc.) a microbiome diversity score correlated with one or more sleep-related conditions. In examples, the sleep-related characterization can include microbiome diversity scores over time (e.g., calculated for a plurality of biological samples of the user collected over time), comparisons to microbiome diversity scores for other users, and/or any other suitable type of microbiome diversity score. However, processing microbiome diversity scores (e.g., determining microbiome diversity scores; using microbiome diversity scores to determine and/or provide therapies; etc.) can be performed in any suitable manner.

Determining a sleep-related characterization in Block S160 preferably includes determining features and/or combinations of features associated with the microbiome composition and/or functional features of the user (e.g., determining feature values associated with the user, the feature values corresponding to microbiome features determined in Block S130, etc.), inputting the features into the characterization process, and receiving an output that characterizes the user as belonging to one or more of: a behavioral group, a gender group, a dietary group, a disease-state group, and any other suitable group capable of being identified by the characterization process. Block S160 can additionally or alternatively include generation of and/or output of a confidence metric associated with the characterization of the user. For instance, a confidence metric can be derived from the number of features used to generate the characterization, relative weights or rankings of features used to generate the characterization, measures of bias in the characterization process, and/or any other suitable parameter associated with aspects of the characterization process. However, leveraging user microbiome features can be performed in any suitable manner to generate any suitable sleep-related characterizations.

In some variations, features extracted from the microorganism dataset of the user can be supplemented with supplementary features (e.g., extracted from supplementary data collected for the user; such as survey-derived features, medical history-derived features, sensor data, etc.), where such data, the user microbiome data, and/or other suitable data can be used to further refine the characterization process of Block S130, Block S160, and/or other suitable portions of the method 100.

Determining a sleep-related characterization preferably includes extracting and applying user microbiome features (e.g., user microbiome composition diversity features; user microbiome functional diversity features; etc.) for the user (e.g., based on a user microorganism dataset), characterization models, and/or other suitable components, such as by employing processes described in Block S130, and/or by employing any suitable approaches described herein.

Figure 6:
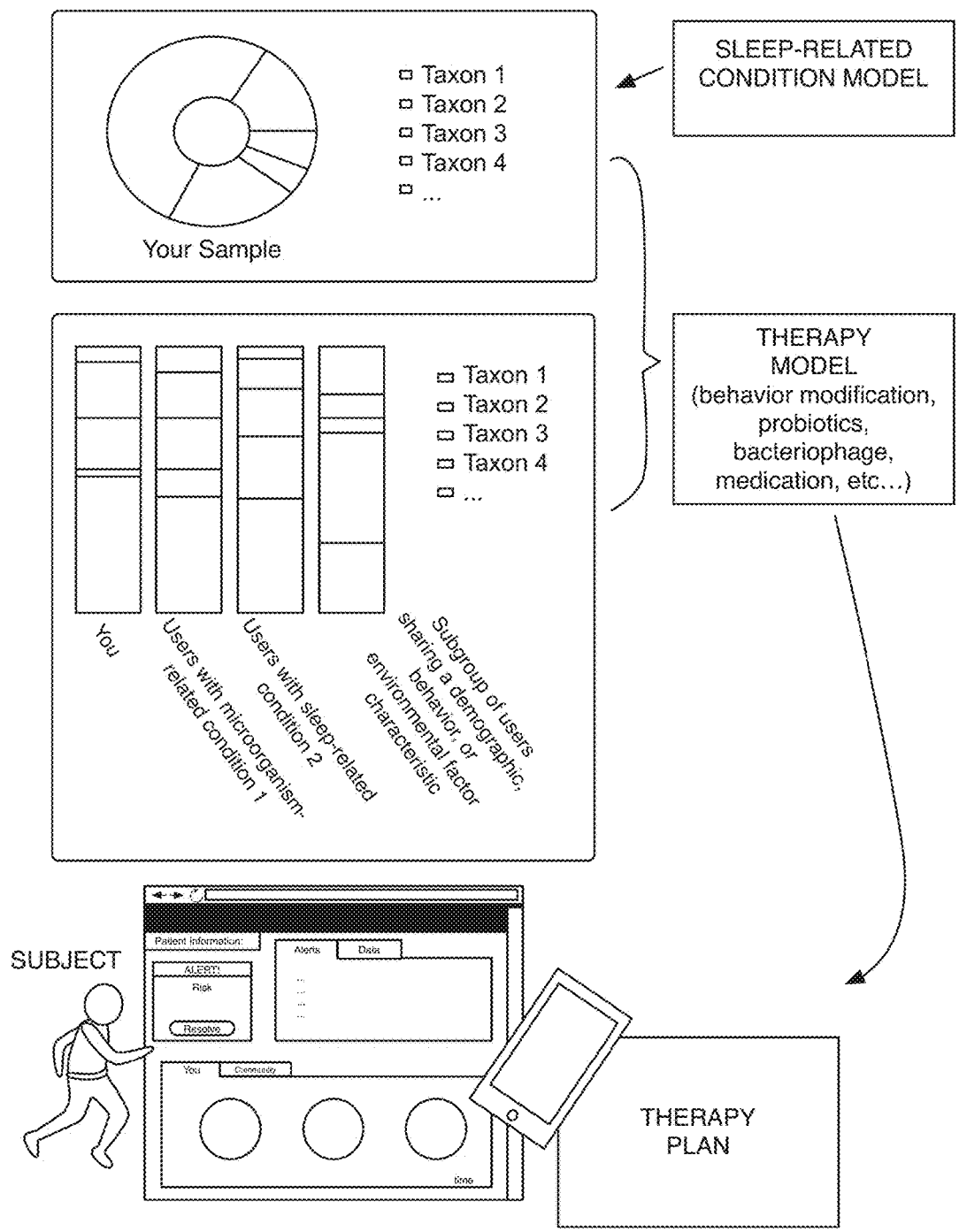
FIG. 6 depicts examples of notification provision.

In variations, as shown in FIG. 6, Block S160 can include presenting sleep-related characterizations (e.g., information extracted from the characterizations; as part of facilitating therapeutic intervention; etc.), such as at a web interface, a mobile application, and/or any other suitable interface, but presentation of information can be performed in any suitable manner. However, the microorganism dataset of the user can additionally or alternatively be used in any other suitable manner to enhance the models of the method 100, and Block S160 can be performed in any suitable manner.

4.6 Facilitating Therapeutic Intervention.

As shown in FIG. 9, the method 100 can additionally or alternatively include Block S170, which can include facilitating therapeutic intervention (e.g., promoting therapies, providing therapies, facilitating provision of therapies, etc.) for one or more sleep-related conditions for one or more users (e.g., based upon a sleep-related characterization and/or a therapy model). Block S170 can function to recommend, promote, provide, and/or otherwise facilitate therapeutic intervention in relation to one or more therapies for a user, such as to shift the microbiome composition and/or functional diversity of a user toward a desired equilibrium state (and/or otherwise improving a state of the sleep-related condition, etc.) in relation to one or more sleep-related conditions. Block S170 can include provision of a customized therapy to the user according to their microbiome composition and functional features, where the customized therapy can include a formulation of microorganisms configured to correct dysbiosis characteristic of users having the identified characterization. As such, outputs of Block S140 can be used to directly promote a customized therapy formulation and regimen (e.g., dosage, usage instructions) to the user based upon a trained therapy model. Additionally or alternatively, therapy provision can include recommendation of available therapeutic measures configured to shift microbiome composition and/or functional features toward a desired state. In variations, therapies can include any one or more of: consumables, topical therapies (e.g., lotions, ointments, antiseptics, etc.), medication (e.g., medications associated with any suitable medication type and/or dosage, etc.), bacteriophages, environmental treatments, behavioral modification (e.g., diet modification therapies, stress-reduction therapies, physical activity-related therapies, etc.), diagnostic procedures, other medical-related procedures, and/or any other suitable therapies associated with sleep-related conditions. Consumables can include any one or more of: food and/or beverage items (e.g., probiotic and/or prebiotic food and/or beverage items, etc.), nutritional supplements (e.g., vitamins, minerals, fiber, fatty acids, amino acids, prebiotics, probiotics, etc.), consumable medications, and/or any other suitable therapeutic measure.

For example, a combination of commercially available probiotic supplements can include a suitable probiotic therapy for the user according to an output of the therapy model. In another example, the method 100 can include determining a sleep-related condition risk for the user for the sleep-related condition based on a sleep-related condition model (e.g., and/or user microbiome features); and promoting a therapy to the user based on the sleep-related condition risk.

In a variation, facilitating therapeutic intervention can include promoting a diagnostic procedure (e.g., for facilitating detection of sleep-related conditions, which can motivate subsequent promotion of other therapies, such as for modulation of a user microbiome for improving a user health state associated with one or more sleep-related conditions; etc.). Diagnostic procedures can include any one or more of: medical history analyses, imaging examinations, cell culture tests, antibody tests, skin prick testing, patch testing, blood testing, challenge testing, performing portions of the method 100, and/or any other suitable procedures for facilitating the detecting (e.g., observing, predicting, etc.) of sleep-related conditions. Additionally or alternatively, diagnostic device-related information and/or other suitable diagnostic information can be processed as part of a supplementary dataset (e.g., in relation to Block S120, where such data can be used in determining and/or applying characterization models, therapy models, and/or other suitable models; etc.), and/or collected, used, and/or otherwise processed in relation to any suitable portions of the method 100 (e.g., administering diagnostic procedures for users for monitoring therapy efficacy in relation to Block S180; etc.)

In another variation, Block S170 can include promoting a bacteriophage-based therapy. In more detail, one or more populations (e.g., in terms of colony forming units) of bacteriophages specific to a certain bacteria (or other microorganism) represented in the user can be used to downregulate or otherwise eliminate populations of the certain bacteria. As such, bacteriophage-based therapies can be used to reduce the size(s) of the undesired population(s) of bacteria represented in the user. Complementarily, bacteriophage-based therapies can be used to increase the relative abundances of bacterial populations not targeted by the bacteriophage(s) used.

In another variation, facilitating therapeutic intervention (e.g., providing therapies, etc.) can include provision of notifications to a user regarding the recommended therapy, other forms of therapy, sleep-related characterizations, and/or other suitable data. In a specific example, providing a therapy to a user can include providing therapy recommendations (e.g., substantially concurrently with providing information derived from a sleep-related characterization for a user; etc.) and/or other suitable therapy-related information (e.g., therapy efficacy; comparisons to other individual users, subgroups of users, and/or populations of users; therapy comparisons; historic therapies and/or associated therapy-related information; psychological therapy guides such as for cognitive behavioral therapy; etc.), such as through presenting notifications at a web interface (e.g., through a user account associated with and identifying a user; etc.). Notifications can be provided to a user by way of an electronic device (e.g., personal computer, mobile device, tablet, wearable, head-mounted wearable computing device, wrist-mounted wearable computing device, etc.) that executes an application, web interface, and/or messaging client configured for notification provision. In one example, a web interface of a personal computer or laptop associated with a user can provide access, by the user, to a user account of the user, where the user account includes information regarding the user's sleep-related characterization, detailed characterization of aspects of the user's microbiome (e.g., in relation to correlations with sleep-related conditions; etc.), and/or notifications regarding suggested therapeutic measures (e.g., generated in Blocks S140 and/or S170, etc.). In another example, an application executing at a personal electronic device (e.g., smart phone, smart watch, head-mounted smart device) can be configured to provide notifications (e.g., at a display, haptically, in an auditory manner, etc.) regarding therapy suggestions generated by the therapy model of Block S170. Notifications and/or probiotic therapies can additionally or alternatively be provided directly through an entity associated with a user (e.g., a caretaker, a spouse, a significant other, a healthcare professional, etc.). In some further variations, notifications can additionally or alternatively be provided to an entity (e.g., healthcare professional) associated with a user, such as where the entity is able to facilitate provision of the therapy (e.g., by way of prescription, by way of conducting a therapeutic session, through a digital telemedicine session using optical and/or audio sensors of a computing device, etc.). Providing notifications and/or otherwise facilitating therapeutic, however, be performed in any suitable manner.

4.7 Monitoring Therapy Effectiveness.

Figure 7:
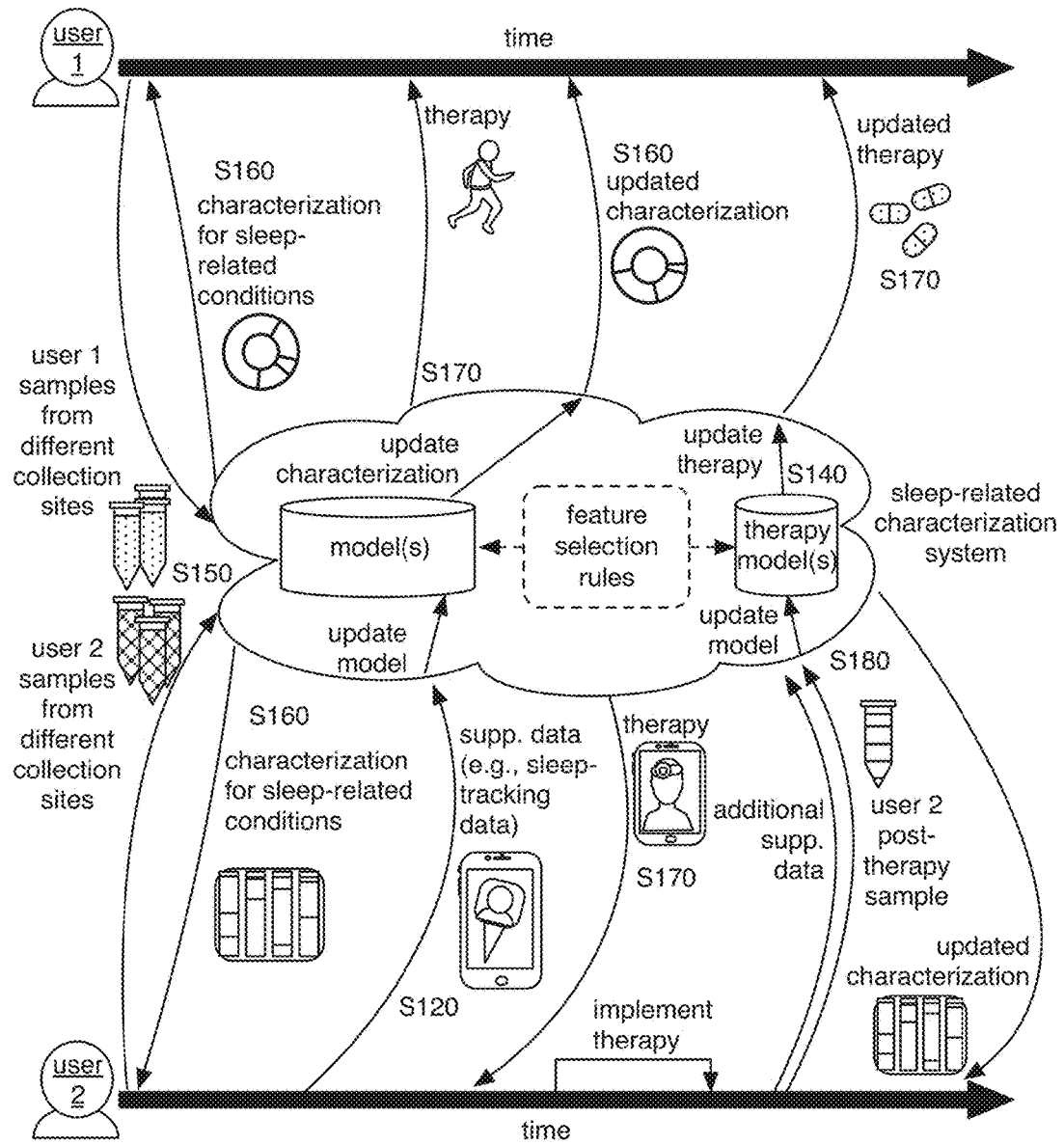
FIG. 7 depicts a schematic representation of variations of an embodiment of the method.

As shown in FIG. 7, the method can additionally or alternatively include Block S180, which can include: monitoring effectiveness of one or more therapies and/or monitoring other suitable components (e.g., microbiome characteristics, etc.) for the user (e.g., based upon processing a series of biological samples from the user), over time. Block S180 can function to gather additional data regarding positive effects, negative effects, and/or lack of effectiveness of one or more therapies (e.g., suggested by the therapy model for users of a given characterization, etc.) and/or monitoring microbiome characteristics (e.g., to assess microbiome composition and/or functional features for the user at a set of time points, etc.).

Monitoring of a user during the course of a therapy promoted by the therapy model (e.g., by receiving and analyzing biological samples from the user throughout therapy, by receiving survey-derived data from the user throughout therapy) can thus be used to generate a therapy-effectiveness model for each characterization provided by the characterization process of Block S130, and each recommended therapy measure provided in Blocks S140 and S170.

In Block S180, the user can be prompted to provide additional biological samples, supplementary data, and/or other suitable data at one or more key time points of a therapy regimen that incorporates the therapy, and the additional biological sample(s) can be processed and analyzed (e.g., in a manner similar to that described in relation to Block S120) to generate metrics characterizing modulation of the user's microbiome composition and/or functional features. For instance, metrics related to one or more of: a change in relative abundance of one or more taxonomic groups represented in the user's microbiome at an earlier time point, a change in representation of a specific taxonomic group of the user's microbiome, a ratio between abundance of a first taxonomic group of bacteria and abundance of a second taxonomic group of bacteria of the user's microbiome, a change in relative abundance of one or more functional families in a user's microbiome, and any other suitable metrics can be used to assess therapy effectiveness from changes in microbiome composition and/or functional features. Additionally or alternatively, survey-derived data from the user, pertaining to experiences of the user while on the therapy (e.g., experienced side effects, personal assessment of improvement, behavioral modifications, symptom improvement, etc.) can be used to determine effectiveness of the therapy in Block S180. For example, the method 100 can include receiving a post-therapy biological sample from the user; collecting a supplementary dataset from the user, where the supplementary dataset describes user adherence to a therapy (e.g., a determined and promoted therapy) and/or other suitable user characteristics (e.g., behaviors, conditions, etc.); generating a post-therapy sleep-related characterization of the first user in relation to the sleep-related condition based on the sleep-related characterization model and the post-therapy biological sample; and promoting an updated therapy to the user for the sleep-related condition based on the post-therapy sleep-related characterization (e.g., based on a comparison between the post-therapy sleep-related characterization and a pre-therapy sleep-related characterization; etc.) and/or the user adherence to the therapy (e.g., modifying the therapy based on positive or negative results for the user microbiome in relation to the sleep-related condition; etc.). Additionally or alternatively, other suitable data (e.g., supplementary data describing user behavior associated with one or more sleep-related conditions; supplementary data describing a sleep-related condition such as observed symptoms; etc.) can be used in determining a post-therapy characterization (e.g., degree of change from pre- to post-therapy in relation to the sleep-related condition; etc.), updated therapies (e.g., determining an updated therapy based on effectiveness and/or adherence to the promoted therapy, etc.).

In an example, the method 100 can include collecting first sleep-tracking data (e.g., at least one of first survey-derived data and first device data) and/or other suitable supplementary, where the first sleep-tracking data is associated with sleep quality of the user; determining the sleep-related characterization for the user based on the user microbiome features and the first sleep-tracking data; facilitating therapeutic intervention based on the sleep-related characterization; collecting a post-therapy biological sample from the user; collecting second sleep-tracking data (e.g., including at least one of second survey-derived data and second device data; etc.) and/or other suitable supplementary data, where the second sleep-tracking data is associated with the sleep quality of the user; and determining a post-therapy sleep-related characterization for the user for the sleep-related condition based on the second sleep-tracking data and post-therapy microbiome features associated with the post-therapy biological sample. In the example, the method 100 can include facilitating therapeutic intervention in relation to an updated therapy (e.g., a modification of the therapy; a different therapy; etc.) for the user for improving the sleep-related condition, based on the post-therapy sleep-related characterization, such as where the updated therapy can include at least one of a consumable, a device-related therapy, a surgical operation, a psychological-associated therapy, a behavior modification therapy, and an environmental factor modification therapy. In the example determining the post-therapy sleep-related characterization can include determining a comparison between microbiome characteristics of the user and reference microbiome characteristics corresponding to a user subgroup sharing at least one of a behavior and an environmental factor (and/or other suitable characteristic) associated with the sleep-related condition, based on the post-therapy microbiome features, and where facilitating therapeutic intervention in relation to the updated therapy can include presenting the comparison to the user for facilitating at least one of the behavior modification therapy and the environmental factor modification therapy and/or other suitable therapies. However, Block S180 can be performed in relation to additional biological samples, additional supplementary data, and/or other suitable additional data in any suitable manner.

Therapy effectiveness, processing of additional biological samples (e.g., to determine additional sleep-related characterizations, therapies, etc.), and/or other suitable aspects associated with continued biological sample collection, processing, and analysis in relation to sleep-related conditions can be performed at any suitable time and frequency for generating, updating, and/or otherwise processing models (e.g., characterization models, therapy models, etc.), and/or for any other suitable purpose (e.g., as inputs associated with other portions of the method 100). However, Block S180 can be performed in any suitable manner.

The method 100 can, however, include any other suitable blocks or steps configured to facilitate reception of biological samples from subjects, processing of biological samples from subjects, analyzing data derived from biological samples, and generating models that can be used to provide customized diagnostics and/or probiotic-based therapeutics according to specific microbiome compositions and/or functional features of subjects.

Embodiments of the system 200 and/or method 100 can include every combination and permutation of the various system components and the various method processes, including any variants (e.g., embodiments, variations, examples, specific examples, figures, etc.), where portions of the method 100 and/or processes described herein can be performed asynchronously (e.g., sequentially), concurrently (e.g., in parallel), or in any other suitable order by and/or using one or more instances, elements, components of, and/or other aspects of the system 200 and/or other entities described herein.

Any of the variants described herein (e.g., embodiments, variations, examples, specific examples, figures, etc.) and/or any portion of the variants described herein can be additionally or alternatively combined, aggregated, excluded, used, and/or otherwise applied.

The system 200 and/or method 100 and/or variants thereof can be embodied and/or implemented at least in part as a machine configured to receive a computer-readable medium storing computer-readable instructions. The instructions are preferably executed by computer-executable components preferably integrated with the system. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the system 200, method 100, and/or variants without departing from the scope defined in the following claims.

TABLE 1

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | Bacteroidaceae | f | + | g | Anaerobacter | g | − | n | Sphingomonas sp. 540 | s | − |
| g | Bacteroides | g | + | g | Cryobacterium | g | + | n | Corynebacterium epidermicanis | s | − |
| g | Bacteroides thetaiotaomicron | s | − | g | Enterococcus raffinosus | s | − | n | Mesorhizobium sp. mat916 | s | + |
| g | Bacteroides uniformis | s | + | g | Helicobacteraceae | f | + | n | Actinomyces sp. ICM58 | s | − |
| g | Bacteroides vulgatus | s | − | g | Elusimicrobia | p | + | n | Megasphaera sp. BV3C16-1 | s | − |
| g | Roseburia | g | + | g | Desulfovibrio sp. UNSW3caefatS | s | − | n | Sphingobium sp. LC341 | s | − |
| g | Faecalibacterium prausnitzii | s | − | g | Pseudomonas monteilii | s | − | n | Anaerococcus sp. PH9 | s | − |
| g | Desulfovibrio | g | + | g | Bifidobacterium merycicum | s | + | n | Leptotrichiaceae | f | + |
| g | Desulfovibrio sp. | s | − | g | Bifidobacterium pullorum | s | − | n | Faecalibacterium sp. canine oral taxon 147 | s | + |
| g | Bacteroidetes | p | + | g | Leuconostocaceae | f | + | n | Murdochiella | g | + |
| g | Proteobacteria | p | + | g | Anaerovibrio | g | − | n | Lachnoanaerobaculum | g | − |
| g | Firmicutes | p | − | g | Anaerosinus glycerini | s | − | n | Streptococcus sp. GMD6S | s | + |
| g | Sarcina | g | − | g | Aeromonadaceae | f | + | n | Varibaculum sp. CCUG 45114 | s | + |
| g | Streptococcaceae | f | + | g | Papillibacter | g | − | n | Dermabacter sp. HFH0086 | s | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | *Streptococcus* | g | + | g | *Coprobacillus* | g | − | n | *Propionibacterium* sp. KPL2005 | s | − |
| g | *Clostridium* | g | + | g | *Anaerostipes caccae* | s | + | n | *Stomatobaculum* | g | + |
| g | Actinobacteria | c | + | g | *Parasporobacterium paucivorans* | s | − | n | *Actinomyces* sp. S4-C9 | s | − |
| g | *Lachnospira* | g | − | g | *Bifidobacterium* sp. 65947 | s | − | n | *Atopobium* sp. S3PFAA1-4 | s | + |
| g | *Lachnospira pectinoschiza* | s | − | g | *Campylobacter faecalis* | s | + | n | *Atopobium* sp. S4-A11a | s | − |
| g | Betaproteobacteria | c | − | g | *Oscillospira guilliermondii* | s | + | n | *Gardnerella* sp. S3PF20 | s | + |
| g | Deltaproteobacteria | c | + | g | *Fusobacterium equinum* | s | + | n | *Prevotella* sp. S4-10 | s | + |
| g | *Asaccharospora irregularis* | s | − | g | Aeromonadales | o | − | n | *Corynebacterium* sp. jw37 | s | − |
| g | Clostridiaceae | f | − | g | *Bacillus* sp. HC15 | s | + | n | *Streptococcus* sp. 2011_Oral_MS_A3 | s | − |
| g | *Phascolarctobacterium* | g | − | g | *Weissella cibaria* | s | − | n | *Veillonella* sp. 2011_Oral_VSA_D3 | s | − |
| g | *Phascolarctobacterium faecium* | s | + | g | Brachyspiraceae | f | + | n | *Alloprevotella* | g | − |
| g | Lactobacillaceae | f | + | g | *Collinsella intestinalis* | s | − | n | *Dialister* sp. S7MSR5 | s | − |
| g | *Dorea formicigenerans* | s | − | g | *Anaerosinus* | g | − | n | *Stenotrophomonas* sp. N017 | s | + |
| g | *Sutterella* | g | − | g | *Dysgonomonas* | g | + | n | *Bradyrhizobium* sp. CCBAU 53380 | s | + |
| g | *Pseudobutyrivibrio* | g | − | g | *Bifidobacterium scardovii* | s | − | n | *Anaerococcus* sp. S8 87-3 | s | − |
| g | *Bacteroides caccae* | s | + | g | *Enterococcus pallens* | s | − | n | *Anaerococcus* sp. S8 F2 | s | + |
| g | Verrucomicrobiales | o | − | g | *Leuconostoc inhae* | s | + | n | *Finegoldia* sp. S9 AA1-5 | s | + |
| g | *Holdemania* | g | + | g | *Blautia schinkii* | s | − | n | *Murdochiella* sp. S9 PR-10 | s | + |
| g | *Holdemania filiformis* | s | + | g | Acholeplasmatales | o | + | n | *Peptoniphilus* sp. S9 PR-13 | s | − |
| g | Fibrobacteres | p | − | g | Eubacteriaceae | f | − | n | *Corynebacterium* sp. 713182/2012 | s | − |
| g | Verrucomicrobia | p | − | g | Thermoanaerobacteraceae | f | + | n | *Ralstonia* sp. A52 | s | − |
| g | Burkholderiales | o | − | g | Planococcaceae | f | + | n | *Staphylococcus* sp. 3348O2 | s | − |
| g | Coriobacteriaceae | f | − | g | *Gelria* | g | + | n | *Senegalimassilia* | g | + |
| g | *Eggerthella* | g | + | g | *Sedimentibacter* | g | + | n | *Peptoniphilus* sp. DNF00840 | s | + |
| g | Coriobacteriia | c | − | g | *Anaerofustis stercorihominis* | s | + | n | *Romboutsia* | g | + |
| g | Coriobacteriales | o | − | g | *Corynebacterium ciconiae* | s | + | n | *Veillonella seminalis* | s | + |
| g | *Bacteroides acidifaciens* | s | + | g | *Eggerthella sinensis* | s | − | n | *Terrisporobacter* | g | − |
| g | *Blautia luti* | s | − | g | *Slackia faecicanis* | s | − | n | Peptoniphilaceae | f | − |
| g | Bacilli | c | + | g | *Acetanaerobacterium* | g | − | n | Tissierellia | c | − |
| g | *Bacteroides* sp. AR20 | s | + | g | *Anaerosporobacter mobilis* | s | − | n | Tissierellales | o | − |
| g | *Bacteroides* sp. AR29 | s | + | g | *Anaerofustis* | g | + | n | Veillonellales | o | + |
| g | *Collinsella* | g | − | g | *Lactobacillus kefiranofaciens* | s | + | n | Selenomonadaceae | f | |
| g | *Oscillospira* | g | + | g | *Veillonella* sp. ADV 269.01 | s | + | n | Spirochaetales | o | − |
| g | Erysipelotrichaceae | f | + | g | *Catabacter* | g | − | n | *Deinococcus* | g | + |
| g | *Roseburia intestinalis* | s | + | g | *Catabacter hongkongensis* | s | + | n | *Lactococcus* | g | − |
| g | Bacteroidales | o | + | g | *Pseudoclavibacter bifida* | s | + | n | Deinococcaceae | f | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | Rikenellaceae | f | + | g | *Bacteroides* sp. Smarlab 3301643 | s | + | n | Spirochaetes | p | − |
| g | *Shuttleworthia* | g | + | g | Anaerolineaceae | f | + | n | Spirochaetia | c | − |
| g | Clostridia | c | − | g | Anaerolineales | o | + | n | *Campylobacter showae* | s | + |
| g | Clostridiales | o | − | g | *Proteiniphilum* | g | + | n | *Comamonas* | g | − |
| g | Lachnospiraceae | f | − | g | *Streptococcus* sp. S16-11 | s | − | n | *Neisseria flavescens* | s | |
| g | Peptostreptococcaceae | f | + | g | *Bacteroides* sp. WH302 | s | − | n | *Neisseria canis* | s | + |
| g | Lactobacillales | o | + | g | *Bacteroides* sp. 4072 | s | − | n | *Eikenella corrodens* | s | + |
| g | *Dorea* | g | − | g | *Alistipes onderdonkii* | s | − | n | *Aggregatibacter aphrophilus* | s | − |
| g | Desulfovibrionaceae | f | + | g | *Mitsuokella* sp. TM-10 | s | + | n | *Aggregatibacter segnis* | s | − |
| g | Bacteroidia | c | + | g | *Oscillibacter valericigenes* | s | − | n | *Rodentibacter pneumotropicus* | s | + |
| g | Actinobacteria | p | + | g | *Bifidobacterium tsurumiense* | s | + | n | Cardiobacteriaceae | f | + |
| g | Verrucomicrobiae | c | − | g | *Megasphaera* sp. TrE9262 | s | − | n | *Selenomonas* | g | − |
| g | Verrucomicrobiaceae | f | − | g | *Anaerococcus* sp. gpac137 | s | + | n | *Capnocytophaga* | g | − |
| g | Fibrobacteria | c | − | g | *Lactococcus* sp. D2 | s | − | n | *Capnocytophaga gingivalis* | s | − |
| g | Fibrobacteraceae | f | − | g | *Weissella* sp. H1a | s | − | n | *Capnocytophaga ochracea* | s | − |
| g | *Anaerostipes* | g | − | g | *Barnesiella viscericola* | s | + | n | *Capnocytophaga sputigena* | s | − |
| g | Desulfovibrionales | o | + | g | *Pediococcus* sp. MFC1 | s | − | n | Cyanobacteria | p | − |
| g | Oscillospiraceae | f | + | g | *Cronobacter dublinensis* | s | + | n | *Streptococcus mutans* | s | + |
| g | *Faecalibacterium* | g | − | g | *Cronobacter turicensis* | s | + | n | *Atopobium rimae* | s | + |
| g | Fibrobacterales | o | − | g | *Elusimicrobium* | g | + | n | *Lactobacillus paracasei* | s | + |
| g | *Alistipes* | g | − | g | Catabacteriaceae | f | − | n | *Actinomyces viscosus* | s | − |
| g | *Akkermansia* | g | − | g | *Cellulosilyticum ruminicola* | s | + | n | *Bifidobacterium adolescentis* | s | + |
| g | *Akkermansia muciniphila* | s | − | g | *Bacteroides* sp. CB57 | s | + | n | *Pseudopropionibacterium propionicum* | s | + |
| g | *Hespellia* | g | + | g | *Paraprevotella xylaniphila* | s | + | n | *Cardiobacterium* | g | + |
| g | *Anaerotruncus* | g | + | g | *Bacteroides* sp. 3_1_23 | s | + | n | *Cardiobacterium hominis* | s | + |
| g | *Marvinbryantia* | g | − | g | *Parabacteroides* sp. 20_3 | s | + | n | *Tannerella forsythia* | s | − |
| g | *Subdoligranulum* | g | − | g | *Nosocomiicoccus* | g | − | n | *Porphyromonas endodontalis* | s | − |
| g | *Flavonifractor plautii* | s | + | g | *Nosocomiicoccus ampullae* | s | − | n | *Prevotella intermedia* | s | − |
| g | *Bacteroides finegoldii* | s | − | g | *Megamonas rupellensis* | s | − | n | *Prevotella nigrescens* | s | + |
| g | *Roseburia inulinivorans* | s | + | g | *Butyricicoccus pullicaecorum* | s | + | n | *Prevotella oris* | s | − |
| g | *Blautia wexlerae* | s | − | g | *Cloacibacterium rupense* | s | + | n | *Prevotella oulorum* | s | − |
| g | *Lactonifactor* | g | + | g | *Fusobacterium* sp. DJF_B100 | s | + | n | *Dolosigranulum* | g | + |
| g | *Moryella* | g | + | g | *Mitsuokella* sp. DJF_RR21 | s | + | n | *Dolosigranulum pigrum* | s | − |
| g | *Adlercreutzia equolifaciens* | s | − | g | *Roseburia* sp. DJF_RR73 | s | − | n | *Acetitomaculum* | g | − |
| g | *Adlercreutzia* | g | − | g | Gracilibacteraceae | f | + | n | *Terrisporobacter glycolicus* | s | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | Erysipelotrichia | c | + | g | Pantoea sp. CWB304 | s | − | n | Leptotrichia buccalis | s | − |
| g | Erysipelotrichales | o | + | g | Butyricimonas synergistica | s | − | n | Porphyromonas catoniae | s | − |
| g | Ruminococcaceae | f | − | g | Selenomonas sp. Ycbo8 | s | + | n | Corynebacterium matruchotii | s | − |
| g | Clostridiales f XIII. Incertae Sedis | f | + | g | Asaccharobacter | g | + | n | Catonella | g | − |
| g | Blautia | g | − | g | Coprobacillus sp. D6 | s | − | n | Catonella morbi | s | − |
| g | Roseburia sp. 11SE39 | s | + | g | Bifidobacterium sp. 138 | s | + | n | Filifactor | g | − |
| g | Bacteroides sp. D22 | s | − | g | Bacteroides sp. S-17 | s | + | n | Actinomyces georgiae | s | − |
| g | Alistipes sp. RMA 9912 | s | + | g | Butyricicoccus | g | + | n | Actinomyces gerencseriae | s | + |
| g | Blautia faecis | s | − | g | Bacteroides sp. D20 | s | − | n | Acidobacteria | p | + |
| g | Selenomonadales | o | + | g | Hydrogenoanaerobacterium | g | + | n | Prevotella pallens | s | |
| g | Acidaminococcaceae | f | − | g | Bacteroides fluxus | s | − | n | Corynebacterium durum | s | + |
| g | Negativicutes | c | + | g | Bacteroides oleiciplenus | s | − | n | Alloprevotella tannerae | s | − |
| g | Eggerthella sp. HGA1 | s | + | g | Slackia piriformis | s | − | n | Centipeda | g | − |
| g | Flavonifractor | g | + | g | Collinsella tanakaei | s | − | n | Centipeda periodontii | s | − |
| g | Sutterellaceae | f | − | g | Christensenella minuta | s | + | n | Eggerthella lenta | s | + |
| g | Anaerostipes sp. 5_1_63FAA | s | − | g | Succinatimonas hippei | s | + | n | Cryptobacterium | g | + |
| g | Fusicatenibacter saccharivorans | s | − | g | Desulfovibrio sp. G11 | s | − | n | Cryptobacterium curtum | s | + |
| g | Intestinimonas | g | + | g | Pyramidobacter piscolens | s | − | n | Rothia sp. CCUG 25688 | s | − |
| g | Fusicatenibacter | g | + | g | Lactobacillus sp. S16 | s | + | n | Mogibacterium pumilum | s | − |
| g | Candidatus Soleaferrea | g | + | g | Elusimicrobia | c | + | n | Pseudoflavonifractor capillosus | s | + |
| g | Peptoclostridium | g | + | g | Elusimicrobiales | o | + | n | Sphingobacteriia | c | + |
| g | Asaccharospora | g | − | g | Elusimicrobiaceae | f | + | n | Cardiobacteriales | o | + |
| g | Erysipelatoclostridium | g | − | g | Bacteroides sp. TP-5 | s | − | n | Filifactor alocis | s | − |
| g | Flavobacterium | g | − | g | Anaerostipes butyraticus | s | − | n | Turicibacter sanguinis | s | + |
| g | Enterobacteriaceae | f | + | g | Aeromonas sp. B11 | s | + | n | Leptotrichia wadei | s | + |
| g | Kluyvera | g | + | g | Parabacteroides sp. D25 | s | − | n | Leptotrichia shahii | s | + |
| g | Pasteurellaceae | f | + | g | Desulfovibrio sp. 6_1_46AFAA | s | + | n | Rothia aeria | s | + |
| g | Haemophilus | g | + | g | Enterorhabdus caecimuris | s | − | n | Victivallis | g | − |
| g | Haemophilus parainfluenzae | s | + | g | Bacteroides faecis | s | − | n | Turicibacter | g | + |
| g | Bacteroides fragilis | s | + | g | Succinatimonas | g | + | n | Tannerella | g | − |
| g | Parabacteroides distasonis | s | + | g | Blautia sp. Ser5 | s | − | n | Sphingobacteriales | o | + |
| g | Butyrivibrio | g | − | g | Eubacterium sp. SA11 | s | + | n | Chloroflexi | p | − |
| g | Porphyromonas | g | + | g | Bacteroides rodentium | s | − | n | Acidobacteriia | c | − |
| g | Prevotella | g | + | g | Bacteroides chinchillae | s | + | n | Acidobacteriales | o | − |
| g | Gammaproteobacteria | c | + | g | Cellulosilyticum | g | + | n | Selenomonas genomosp. P5 | s | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | *Streptococcus thermophilus* | s | + | g | *Caldicoprobacter* | g | + | n | Victivallaceae | f | − |
| g | *Erysipelatoclostridium ramosum* | s | + | g | *Enterobacter* sp. UDC345 | s | − | n | Lentisphaerae | p | − |
| g | *Lactobacillus* | g | + | g | *Lactobacillus* sp. TAB-26 | s | + | n | Victivallales | o | − |
| g | Corynebacteriaceae | f | + | g | *Bifidobacterium biavatii* | s | + | n | *Capnocytophaga* genosp. AHN8471 | s | − |
| g | *Bifidobacterium* | g | − | g | *Megasphaera* sp. BS-4 | s | + | n | *Capnocytophaga* sp. AHN10044 | s | + |
| g | *Corynebacterium* | g | + | g | *Pseudomonas* sp. a101-18-2 | s | + | n | *Capnocytophaga* sp. AHN9756 | s | + |
| g | *Corynebacterium* sp. | s | + | g | *Rothia* sp. RV13 | s | + | n | *Aggregatibacter* | g | − |
| g | Actinomycetales | o | + | g | *Klebsiella* sp. SOR89 | s | − | n | *Prevotella nanceiensis* | s | − |
| g | Methanobacteriales | o | + | g | *Lactococcus* sp. MH5-2 | s | + | n | *Actinomyces massiliensis* | s | + |
| g | Methanobacteriaceae | f | + | g | *Campylobacter* sp. 0402694-C0078 | s | + | n | *Lachnoanaerobaculum saburreum* | s | + |
| g | *Methanobrevibacter* | g | + | g | *Lactobacillus* sp. C4I2 | s | − | n | *Bacteroides* sp. 2_2_4 | s | − |
| g | *Methanobrevibacter smithii* | s | + | g | *Leuconostoc* sp. C7I4 | s | + | n | *Olsenella* sp. F0004 | s | + |
| g | *Gardnerella* | g | + | g | Christensenellaceae | f | + | n | *Leptotrichia hongkongensis* | s | − |
| g | *Gardnerella vaginalis* | s | + | g | *Christensenella* | g | + | n | Chitinophagaceae | f | + |
| g | *Peptococcus* | g | + | g | *Bacteroides* sp. dnLKVg | s | − | n | *Bifidobacterium stercoris* | s | + |
| g | *Alistipes putredinis* | s | − | g | *Parabacteroides* sp. dnLKV8 | s | − | n | *Neisseria shayeganii* | s | + |
| g | *Odoribacter splanchnicus* | s | + | g | *Bacteroides* sp. HPS0048 | s | + | n | *Rhizobium* sp. T45 | s | + |
| g | Alphaproteobacteria | c | + | g | *Anaerovibrio* sp. 656 | s | + | n | *Fretibacterium fastidiosum* | s | − |
| g | Euryarchaeota | p | + | g | *Anaerovibrio* sp. 765 | s | − | n | *Oribacterium* sp. oral taxon 078 | s | + |
| g | Bifidobacteriaceae | f | − | g | *Acidaminococcus* sp. BV3L6 | s | − | n | *Leptotrichia* sp. oral taxon 225 | s | + |
| g | Mollicutes | c | + | g | *Finegoldia* sp. BV3C29 | s | + | n | *Alloprevotella rava* | s | + |
| g | *Bilophila* | g | − | g | *Lactococcus* sp. STM1 | s | − | n | *Prevotella* sp. WAL 2039G | s | − |
| g | *Sutterella wadsworthensis* | s | + | g | *Herbaspirillum* sp. YR522 | s | + | n | *Neisseria skkuensis* | s | + |
| g | Rhodospirillaceae | f | + | g | *Phascolarctobacterium* sp. canine oral taxon 149 | s | − | n | *Capnocytophaga* sp. oral taxon 329 | s | + |
| g | *Butyrivibrio crossotus* | s | − | g | *Peptococcus* sp. canine oral taxon 334 | s | + | n | *Capnocytophaga* sp. oral taxon 338 | s | + |
| g | *Parabacteroides merdae* | s | − | g | *Proteiniclasticum* | g | − | n | *Actinomyces* sp. oral taxon 448 | s | − |
| g | *Bacteroides stercoris* | s | + | g | *Bacteroides* sp. 14(A) | s | − | n | *Streptococcus* sp. oral taxon G63 | s | + |
| g | Flavobacteriaceae | f | − | g | *Turicibacter* sp. LA62 | s | + | n | *Tannerella* sp. oral taxon HOT-286 | s | − |
| g | *Kluyvera georgiana* | s | + | g | *Cloacibacillus porcorum* | s | + | n | *Capnocytophaga* sp. CM59 | s | − |
| g | *Collinsella aerofaciens* | s | + | g | *Propionibacterium* sp. KPL1844 | s | + | n | *Fusobacterium* sp. CM22 | s | + |
| g | *Slackia* | g | + | g | *Butyricimonas* sp. 180-3 | s | + | n | *Oribacterium* sp. CM12 | s | − |
| g | Bifidobacteriales | o | − | g | *Butyricimonas* sp. 214-4 | s | − | n | *Brevundimonas* sp. FXJ8.080 | s | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | Corynebacteriales | o | + | g | Olsenella sp. 1183 | s | + | n | Moraxella sp. WB19-16 | s | + |
| g | Dorea longicatena | s | − | g | Anaerostipes rhamnosivorans | s | + | n | Pseudomonas sp. KB23 | s | − |
| g | Enterobacterales | o | + | g | Butyricimonas sp. GD2 | s | − | n | Lysinibacillus sp. SJ2SN2 | s | + |
| g | Flavobacteriia | c | − | g | Streptococcus sp. 2011_Ileo_MS_A10 | s | + | n | Pseudoflavonifractor | g | + |
| g | Pasteurellales | o | + | g | Streptococcus sp. 2011_Oral_MS_D12 | s | + | n | Neisseria oralis | s | − |
| g | Peptoniphilus | g | + | g | Veillonella sp. 2011_Oral_VSA_D12 | s | − | n | Actinomyces sp. ph3 | s | − |
| g | Anaerococcus | g | + | g | Sutterella sp. 252 | s | − | n | Rothia sp. THG-N7 | s | − |
| g | Thalassospira | g | + | g | Roseburia sp. 499 | s | − | n | Lentisphaeria | c | − |
| g | Porphyromonadaceae | f | + | g | Anaerostipes sp. 992a | s | − | n | Tessaracoccus lapidicaptus | s | + |
| g | Prevotellaceae | f | + | g | Rahnella sp. FB303 | s | + | n | Fretibacterium | g | − |
| g | Methanobacteria | c | + | g | Citrobacter sp. HD4.9 | s | − | n | Dielma | g | − |
| g | Peptococcaceae | f | + | g | Megasphaera sp. DNF00872 | s | + | n | Alistipes inops | s | + |
| g | Flavobacteriales | o | − | g | Megasphaera sp. DNF00912 | s | − | n | Pseudomonas aeruginosa | s | − |
| g | Rhodospirillales | o | + | g | Megasphaera sp. S6-MB2 | s | − | n | Moraxella catarrhalis | s | − |
| g | Subdoligranulum variabile | s | − | g | Candidatus Methanomethylophilus | g | + | n | Enterobacter cloacae | s | + |
| g | Bifidobacterium longum | s | + | g | Rahnella sp. BSP18 | s | + | n | Klebsiella oxytoca | s | + |
| g | Peptoniphilus sp. 2002-2300004 | s | + | g | Bacteroides caecigallinarum | s | − | n | Aeromonas | g | − |
| g | Sutterella stercoricanis | s | − | g | Bacteroides sp. C13EG172 | s | − | n | Rhodobacter | g | + |
| g | Odoribacter | g | + | g | Pediococcus sp. 3107O2 | s | − | n | Oscillatoriales | o | − |
| g | Bacteroides salyersiae | s | + | g | Streptococcus sp. 3244O2 | s | + | n | Leuconostoc | g | + |
| g | Parabacteroides goldsteinii | s | + | g | Eggerthellales | o | − | n | Leuconostoc mesenteroides | s | + |
| g | Bacteroides sp. XB12B | s | + | g | Eggerthellaceae | f | − | n | Leuconostoc lactis | s | − |
| g | Parabacteroides | g | − | g | Acidaminococcales | o | − | n | Leuconostoc carnosum | s | + |
| g | Barnesiella | g | − | g | Odoribacteraceae | f | + | n | Pediococcus | g | + |
| g | Howardella | g | + | g | Clostridioides | g | − | n | Weissella confusa | s | − |
| g | Alistipes sp. EBA6-25cl2 | s | + | g | Barnesiellaceae | f | + | n | Lactobacillus delbrueckii | s | + |
| g | Oscillibacter | g | + | g | Klebsiella pneumoniae | s | + | n | Carnobacterium | g | |
| g | Alistipes sp. NML05A004 | s | + | g | Aeromonas salmonicida | s | + | n | Lactobacillus curvatus | s | + |
| g | Barnesiella intestinihominis | s | + | g | Streptococcus sobrinus | s | − | n | Bacteroides ovatus | s | + |
| g | Parasutterella excrementihominis | s | + | g | Nocardioides | g | − | n | Rahnella | g | − |
| g | Porphyromonas bennonis | s | − | g | Solanaceae | f | + | n | Weissella | g | − |
| g | Clostridiales f XI. Incertae Sedis | f | + | g | Acidovorax | g | + | n | Weissella hellenica | s | − |
| g | Tenericutes | p | + | g | Variovorax | g | + | n | Raoultella ornithinolytica | s | − |
| g | Butyricimonas | g | − | g | Pseudomonas citronellolis | s | + | n | Rhodocyclaceae | f | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | Parasutterella | g | + | g | Nocardioidaceae | f | − | n | Pseudomonas monteilii | s | − |
| g | Bifidobacterium kashiwanohense | s | − | g | Cytophagaceae | f | + | n | Leuconostocaceae | f | + |
| g | Anaerosporobacter | g | + | g | Massilia | g | − | n | Aeromonadaceae | f | − |
| g | Corynebacterium canis | s | + | g | Staphylococcus equorum | s | − | n | Fusobacterium equinum | s | + |
|   | Bilophila sp. 4_1_30 | s | − | g | Cytophagia | c | + | n | Aeromonadales | o | − |
| g | Blautia stercoris | s | + | g | Cytophagales | o | + | n | Raoultella | g | − |
| g | Alistipes sp. HGB5 | s | − | g | Aerococcus sp. B43(2010) | s | + | n | Planococcaceae | f | − |
| g | Bacteroides sp. SLC1-38 | s | + | g | Defluviimonas | g | − | n | Corynebacterium atypicum | s | + |
| g | Terrisporobacter | g | − | g | Yersinia | g | − | n | Acidobacteriaceae | f | − |
| g | Intestinibacter | g | + | g | Yersinia enterocolitica | s | − | n | Rhodocyclales | o | + |
| g | Lactococcus | g | − | g | Bacillus cereus | s | − | n | Pseudoclavibacter bifida | s | + |
| g | Bacteroides sp. XB44A | s | + | g | Planomicrobium | g | + | n | Paucibacter | g | + |
| g | Phascolarctobacterium succinatutens | s | − | g | Rothia sp. BBH4 | s | − | n | Cloacibacterium rupense | s | − |
| g | Asteroleplasma | g | − | g | Clostridiales f XII. Incertae Sedis | f | + | n | Acinetobacter sp. 423D | s | + |
| g | Acetitomaculum | g | + | g | Arthrospira | g | + | n | Pantoea gaviniae | s | − |
| g | Terrisporobacter glycolicus | s | − | g | Variovorax sp. TA_DQ | s | + | n | Bacillus sp. DHT-33 | s | − |
| g | Bifidobacterium sp. | s | + | g | Streptococcus australis | s | − | n | Lactobacillus sp. TAB-26 | s | + |
| g | Turicibacter sanguinis | s | + | g | Spirochaetaceae | f | + | n | Pseudomonas sp. a101-18-2 | s | − |
| g | Victivallis | g | + | g | Providencia | g | − | n | Lactococcus sp. MH5-2 | s | − |
| g | Anaeroplasmatales | o | + | g | Salmonella | g | + | n | Pseudomonas sp. CBMAI 1177 | s | − |
| g | Anaeroplasmataceae | f | + | g | Leuconostoc gelidum | s | + | n | Propionibacterium sp. KPL1844 | s | + |
| g | Turicibacter | g | + | g | Streptococcus suis | s | − | n | Streptococcus sp. 2011_Ileo_MS_A10 | s | + |
| R | Victivallaceae | f | + | g | Enterococcus faecium | s | − | n | Rahnella sp. BSP18 | s | − |
| R | Lentisphaerae | p | + | g | Enterococcus gallinarum | s | + | n | Myxococcales | o | + |
| R | Victivallales | o | + | g | Lactococcus raffinolactis | s | + | n | Lysobacter | g | − |
| g | Bacteroides nordii | s | + | g | Bacillus subtilis | s | + | n | Caulobacter | g |   |
| g | Howardella ureilytica | s | + | g | Salmonella enterica | s | + | n | Planctomycetales | o | + |
| g | Bacteroides sp. 2_2_4 | s | − | g | Peptoniphilus indolicus | s | + | n | Planctomycetaceae | f | + |
| g | Gordonibacter pamelaeae | s | + | g | Lactobacillus pontis | s | − | n | Brevundimonas diminuta | s | − |
| g | Bacteroides sp. DJF_B097 | s | − | g | Corynebacterium vitaeruminis | s | + | n | Xanthomonas campestris | s | + |
| g | Butyricimonas virosa | s | − | g | Helcococcus kunzii | s | + | n | Acetobacteraceae | f | + |
| g | Anaerotruncus sp. NML 070203 | s | + | g | Desulfovibrio fairfieldensis | s | + | n | Acinetobacter baumannii | s | − |
| g | Robinsoniella | g | + | g | Brachyspira pilosicoli | s | + | n | Moraxella nonliquefaciens | s | + |
| g | Bifidobacterium stercoris | s | − | g | Desulfovibrio intestinalis | s | − | n | Psychrobacter | g | − |
| g | Gordonibacter | g | + | g | Deinococcus geothermalis | s | + | n | Klebsiella pneumoniae | s | − |
| g | Caldicoprobacteraceae | f | − | g | Denitrobacterium | g | − | n | Aeromonas salmonicida | s | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | Lentisphaeria | c | + | g | Mannheimia varigena | s | + | n | Alloiococcus | g | + |
| g | Dielma | g | + | g | Dysgonomonas gadei | s | − | n | Alloiococcus otitis | s | + |
| g | Alistipes inops | s | − | g | Allobaculum | g | + | n | Nocardia | g | + |
| g | Alistipes massiliensis | s | + | g | Allobaculum stercoricanis | s | + | n | Nocardioides | g | − |
| g | Alistipes indistinctus | s | − | g | Cetobacterium | g | + | n | Pseudonocardia | g | − |
| g | Lactococcus sp. MH5-2 | s | − | g | Cetobacterium somerae | s | + | n | Streptomyces | g | − |
| g | Sutterella sp. 252 | s | + | g | Paraeggerthella hongkongensis | s | + | n | Aeromicrobium | g | + |
| ge | Bacteroidaceae | f | − | g | Desulfovibrio sp. LNB2 | s | + | n | Streptomycetaceae | f | − |
| ge | Bacteroides | g | − | g | Anaerostipes sp. AIP 183.04 | s | − | n | Pseudonocardiaceae | f | − |
| ge | Bacteroides thetaiotaomicron | s | − | g | Denitratisoma | g | − | n | Brochothrix | g | + |
| ge | Bacteroides uniformis | s | − | g | Bacteroides barnesiae | s | − | n | Solanaceae | f | + |
| ge | Bacteroides vulgatus | s | + | g | Bacteroides salanitronis | s | + | n | Basidiomycota | p | + |
| ge | Roseburia | g | + | g | Sphaerochaeta | g | + | n | Acidovorax | g | + |
| ge | Faecalibacterium prausnitzii | s | − | g | Puniceicoccaceae | f | + | n | Sphingobacterium | g | + |
| ge | Acidaminococcus | g | − | g | Pediococcus argentinicus | s | − | n | Staphylococcus saprophyticus | s | + |
| ge | Herbaspirillum | g | − | g | Slackia equolifaciens | s | + | n | Microlunatus | g | + |
| ge | Herbaspirillum seropedicae | s | + | g | Herbaspirillum sp. AU13035 | s | + | n | Cutibacterium granulosum | s | − |
| ge | Bacteroidetes | p | − | g | Vagococcus teuberi | s | − | n | Microbacterium lacticum | s | − |
| ge | Proteobacteria | p | − | g | Brachyspira sp. HIS5 | s | + | n | Exiguobacterium | g | + |
| ge | Firmicutes | p | + | g | Parabacteroides sp. D13 | s | + | n | Variovorax | g | + |
| ge | Sarcina | g | + | g | Enterorhabdus mucosicola | s | + | n | Dietzia | g | + |
| ge | Streptococcaceae | f | − | g | Paraeggerthella | g | + | n | Blastococcus | g | − |
| ge | Streptococcus | g | − | g | Lactobacillus sp. oral taxon 052 | s | + | n | Blastococcus aggregatus | s | − |
| ge | Clostridium | g | + | g | Bacteroides sartorii | s | + | n | Chlamydiales | o | + |
| ge | Actinobacteria | c | − | g | Lactococcus sp. TP1MJ | s | + | n | Pseudomonas citronellolis | s | + |
| ge | Lachnospira | g | + | g | Lactococcus sp. TP2MJ | s | + | n | Malassezia | g | + |
| ge | Lachnospira pectinoschiza | s | + | g | Bacteroides sp. D-2 | s | − | n | Dermacoccus | g | + |
| ge | Betaproteobacteria | c | − | g | Dysgonomonas oryzarvi | s | + | n | Brevundimonas subvibrioides | s | + |
| ge | Asaccharospora irregularis | s | + | g | Lactobacillus faecis | s | − | n | Malassezia restricta | s | − |
| ge | Clostridiaceae | f | + | g | Parabacteroides chinchillae | s | + | n | Sphingobacteriaceae | f | + |
| ge | Lactobacillaceae | f | + | g | Lactobacillus sp. Mbohs2t7 | s | + | n | Rubrobacteria | c | − |
| ge | Sutterella | g | − | g | Lactobacillus sp. Thmro2 | s | − | n | Pseudonocardiales | o | − |
| ge | Pseudobutyrivibrio | g | + | g | Bacillus sp. PrMC7 | s | − | n | Streptomycetales | o | − |
| ge | Verrucomicrobiales | o | + | g | Fusobacterium sp. CM1 | s | + | n | Frankiales | o | − |
| ge | Verrucomicrobia | p | + | g | Lactobacillus sp. C4I1 | s | − | n | Nocardioidaceae | f | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | Oxalobacteraceae | f | − | g | *Bacillus* sp. N-16 | s | − | n | Intrasporangiaceae | f | + |
| ge | Burkholderiales | o | − | g | *Methanosphaera cuniculi* | s | + | n | Dietziaceae | f | + |
| ge | Coriobacteriaceae | f | + | g | *Eggerthella* sp. E1 | s | − | n | Geodermatophilaceae | f | − |
| ge | Coriobacteriia | c | + | g | *Anaeroglobus* sp. S4-A15 | s | + | n | Nakamurellaceae | f | |
| ge | Coriobacteriales | o | + | g | *Murdochiella* sp. S5-A16 | s | − | n | *Facklamia tabacinasalis* | s | + |
| ge | *Bacteroides acidifaciens* | s | + | g | *Oscillibacter* sp. 1-3 | s | − | n | Cytophagaceae | f | − |
| ge | Bacilli | c | + | g | *Bacteroides* sp. 2011_Ileo_VSA_D7 | s | + | n | *Hymenobacter* | g | + |
| ge | *Bacteroides* sp. AR20 | s | − | g | *Corynebacterium* sp. full20 | s | − | n | *Acinetobacter ursingii* | s | − |
| ge | *Bacteroides* sp. AR29 | s | − | g | Oligosphaeria | c | − | n | *Dyadobacter* | g | + |
| ge | *Collinsella* | g | + | g | Oligosphaerales | o | − | n | *Corynebacterium felinum* | s | + |
| ge | *Oscillospira* | g | − | g | *Parabacteroides* sp. J1502 | s | + | n | Dermacoccaceae | f | + |
| ge | Erysipelotrichaceae | f | − | g | *Enterobacter* sp. SPSA1 | s | − | n | *Massilia* | g | + |
| ge | *Roseburia intestinalis* | s | + | g | *Anaerobacterium* | g | − | n | Malasseziales | o | + |
| ge | Bacteroidales | o | − | g | *Ruminiclostridium* | g | + | n | *Aurantimonas* | g | − |
| ge | Rikenellaceae | f | − | g | Sporomusaceae | f | − | n | *Sphingomonas aerolata* | s | + |
| ge | *Shuttleworthia* | g | + | g | Erwiniaceae | f | + | n | Listeriaceae | f | + |
| ge | Clostridia | c | + | m | Bacteroidaceae | f | + | n | *Dermacoccus* sp. Ellin183 | s | + |
| ge | Clostridiales | o | + | m | *Bacteroides* | g | + | n | *Dermacoccus* sp. Ellin185 | s | + |
| ge | Lachnospiraceae | f | + | m | *Bacteroides uniformis* | s | − | n | Thermomicrobia | c | − |
| ge | Peptostreptococcaceae | f | − | m | *Bacteroides vulgatus* | s | + | n | Planctomycetes | p | + |
| ge | Lactobacillales | o | + | m | *Roseburia* | g | + | n | Planctomycetia | c | + |
| ge | Bacteroidia | c | − | m | *Faecalibacterium prausnitzii* | s | + | n | Chlamydiae | p | + |
| ge | Actinobacteria | p | − | m | *Desulfovibrio* | g | + | n | Chlamydiia | c | + |
| ge | Verrucomicrobiae | c | + | m | *Herbaspirillum* | g | + | n | *Solirubrobacter* | g | − |
| ge | Verrucomicrobiaceae | f | + | m | *Herbaspirillum seropedicae* | s | + | n | *Brachybacterium muris* | s | − |
| ge | Oscillospiraceae | f | − | m | Bacteroidetes | p | + | n | Gemmatimonadales | o | + |
| ge | *Faecalibacterium* | g | − | m | Proteobacteria | p | − | n | Gemmatimonadaceae | f | + |
| ge | *Alistipes* | g | − | m | Firmicutes | p | + | n | *Kocuria marina* | s | − |
| ge | *Akkermansia* | g | + | m | *Sarcina* | g | + | n | *Jeotgalicoccus* | g | + |
| ge | *Akkermansia muciniphila* | s | + | m | Streptococcaceae | f | − | n | *Staphylococcus equorum* | s | − |
| ge | *Anaerotruncus* | g | − | m | *Streptococcus* | g | − | n | Aurantimonadaceae | f | − |
| ge | *Marvinbryantia* | g | + | m | *Clostridium* | g | + | n | *Rubellimicrobium* | g | − |
| ge | *Flavonifractor plautii* | s | − | m | Actinobacteria | c | − | n | *Burkholderia* sp. CBPB-HIM | s | + |
| ge | *Bacteroides finegoldii* | s | − | m | *Lachnospira* | g | + | n | *Sphingomonas oligophenolica* | s | + |
| ge | *Moryella* | g | + | m | *Lachnospira pectinoschiza* | s | − | n | Solirubrobacteraceae | f | − |
| ge | *Adlercreutzia equolifaciens* | s | + | m | Betaproteobacteria | c | − | n | Trueperaceae | f | − |
| ge | *Adlercreutzia* | g | + | m | Deltaproteobacteria | c | + | n | *Truepera* | g | − |
| ge | Erysipelotrichia | c | − | m | *Asaccharospora irregularis* | s | + | n | *Methylobacterium adhaesivum* | s | + |
| ge | Erysipelotrichales | o | − | m | Veillonellaceae | f | − | n | Patulibacteraceae | f | + |
| ge | Ruminococcaceae | f | + | m | Clostridiaceae | f | + | n | *Actinomycetospora* | g | + |
| ge | Clostridiales f XIII. Incertae Sedis | f | − | m | *Phascolarctobacterium* | g | + | n | *Acinetobacter* sp. RBE2CD-76 | s | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | *Acidaminococcus* sp. D21 | s | − | m | *Phascolarctobacterium faecium* | s | + | n | Exobasidiomycetes | c | + |
| ge | *Blautia* | g | + | m | Lactobacillaceae | f | − | n | *Dermacoccus* sp. SST-20 | s | + |
| ge | *Roseburia* sp. 11SE39 | s | + | m | *Dorea formicigenerans* | s | + | n | *Methylobacterium* sp. Gh-143 | s | + |
| ge | *Alistipes* sp. RMA 9912 | s | + | m | *Sutterella* | g | + | n | *Moraxella* sp. BBN2P-02d | s | + |
| ge | *Blautia* sp. Ser8 | s | − | m | *Pseudobutyrivibrio* | g | + | n | Solirubrobacterales | o | − |
| ge | *Blautia faecis* | s | + | m | *Bacteroides caccae* | s | + | n | *Acinetobacter kyonggiensis* | s | + |
| ge | Negativicutes | c | + | m | Verrucomicrobiales | o | + | n | *Acinetobacter* sp. T133 | s | + |
| ge | *Eggerthella* sp. HGA1 | s | + | m | *Holdemania* | g | | n | Iamiaceae | f | + |
| ge | *Flavonifractor* | g | − | m | *Holdemania filiformis* | s | | n | *Brevundimonas* sp. JW23.4a | s | − |
| ge | Sutterellaceae | f | − | m | Verrucomicrobia | p | + | n | Malasseziaceae | f | + |
| ge | *Intestinimonas* | g | − | m | Oxalobacteraceae | f | + | n | *Pseudomonas* sp. PcFRB119 | s | + |
| ge | *Peptoclostridium* | g | + | m | Burkholderiales | o | + | n | *Microbacterium* sp. PcRB024 | s | + |
| ge | *Asaccharospora* | g | + | m | Coriobacteriaceae | f | + | n | Cytophagia | c | − |
| ge | *Erysipelatoclostridium* | g | − | m | *Coriobacteriia* | c | + | n | Cytophagales | o | − |
| ge | *Campylobacter* | g | + | m | Coriobacteriales | o | + | n | *Novosphingobium* sp. THA_AIK7 | s | − |
| ge | *Campylobacter concisus* | s | − | m | *Bacteroides acidifaciens* | s | + | n | *Staphylococcus* sp. C-D-MA2 | s | + |
| ge | *Campylobacter rectus* | s | + | m | *Blautia luti* | s | + | n | *Aerococcus* sp. B43(2010) | s | + |
| ge | *Achromobacter* | g | + | m | Bacilli | c | + | n | *Pseudomonas* sp. PKG89 | s | − |
| ge | *Flavobacterium* | g | + | m | *Bacteroides* sp. AR20 | s | + | n | *Acinetobacter* sp. C049 | s | + |
| ge | *Pseudomonas* | g | − | m | *Bacteroides* sp. AR29 | s | + | n | *Acinetobacter* sp. WB22-23 | s | − |
| ge | *Ralstonia pickettii* | s | − | m | *Collinsella* | g | + | n | *Micrococcus* sp. WB18-01 | s | − |
| ge | Rhizobiales | o | − | m | *Oscillospira* | g | + | n | *Sphingomonas* sp. PDD-26b-16 | s | + |
| ge | *Rhizobium* | g | − | m | Erysipelotrichaceae | f | + | n | *Ferruginibacter* | g | + |
| ge | *Methylobacterium* | g | + | m | *Roseburia intestinalis* | s | − | n | *Amnibacterium* | g | + |
| ge | Moraxellaceae | f | + | m | Bacteroidales | o | + | n | *Aureimonas phyllosphaerae* | s | − |
| ge | *Acinetobacter* | g | − | m | Rikenellaceae | f | + | n | *Stenotrophomonas* sp. L_63-LFP1A9B1 | s | + |
| ge | *Moraxella* | g | + | m | *Shuttleworthia* | g | − | n | *Blastocatella fastidiosa* | s | + |
| ge | Neisseriaceae | f | − | m | Clostridia | c | + | n | *Acinetobacter* sp. HD5.2 | s | − |
| ge | *Neisseria* | g | + | m | Clostridiales | o | + | n | *Ochrobactrum* sp. FPY8 | s | + |
| ge | *Neisseria elongata* | s | + | m | Lachnospiraceae | f | + | n | *Chryseobacterium* sp. R064 | s | + |
| ge | Alcaligenaceae | f | − | m | Peptostreptococcaceae | f | − | n | *Rhizobium* sp. 10II | s | |
| ge | *Ochrobactrum* | g | − | m | Lactobacillales | o | − | n | *Brevibacterium* sp. MBTD_CMFRI_Br02 | s | − |
| ge | Enterobacteriaceae | f | − | m | *Dorea* | g | + | n | *Exiguobacterium* sp. icr3 | s | + |
| ge | *Citrobacter* | g | − | m | Desulfovibrionaceae | f | + | n | *Mycobacterium* sp. UNC410CL29Cvi84 | s | − |
| ge | *Enterobacter* | g | + | m | Bacteroidia | c | + | n | *Phenylobacterium* | g | + |
| ge | *Kluyvera* | g | − | m | Actinobacteria | p | − | n | *Planctomyces* | g | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | *Proteus* | g | + | m | Verrucomicrobiae | c | + | n | *Pirellula* | g | − |
| ge | *Proteus mirabilis* | s | − | m | Verrucomicrobiaceae | f | + | n | *Thermus* sp. | s | − |
| ge | *Serratia* | g | − | m | *Anaerostipes* | g | + | n | *Acidiphilium* | g | + |
| ge | *Haemophilus influenzae* | s | + | m | Desulfovibrionales | o | + | n | *Pantoea agglomerans* | s | + |
| ge | *Haemophilus parainfluenzae* | s | + | m | Oscillospiraceae | f | + | n | *Yersinia* | g | + |
| ge | *Bacteroides fragilis* | s | + | m | *Faecalibacterium* | g | + | n | *Yersinia enterocolitica* | s | + |
| ge | *Parabacteroides distasonis* | s | − | m | *Alistipes* | g | + | n | *Sphingobacterium mizutaii* | s | + |
| ge | *Campylobacter gracilis* | s | + | m | *Akkermansia* | g | + | n | *Dermacoccus nishinomiyaensis* | s | + |
| ge | *Campylobacter ureolyticus* | s | + | m | *Hespellia* | g | − | n | *Planococcus* | g | − |
| ge | *Porphyromonas* | g | − | m | *Anaerotruncus* | g | + | n | *Bacillus cereus* | s | − |
| ge | *Prevotella* | g | + | m | *Marvinbryantia* | g | − | n | *Sporosarcina* | g | − |
| ge | *Fusobacterium* | g | + | m | *Subdoligranulum* | g | + | n | *Cellulomonas* | g | − |
| ge | *Fusobacterium nucleatum* | s | + | m | *Flavonifractor plautii* | s | − | n | *Sphingomonas paucimobilis* | s | + |
| ge | *Fusobacterium periodonticum* | s | + | m | *Bacteroides finegoldii* | s | + | n | *Alicyclobacillus* | g | − |
| ge | *Megasphaera* | g | + | m | *Roseburia inulinivorans* | s | + | n | *Porphyromonas cangingivalis* | s | − |
| ge | *Weeksella* | g | + | m | *Blautia wexlerae* | s | + | n | *Porphyromonas canoris* | s | + |
| ge | *Weeksella virosa* | s | + | m | *Lactonifactor* | g | − | n | *Kocuria kristinae* | s | − |
| ge | Chromatiaceae | f | + | m | *Moryella* | g | + | n | *Pedomicrobium* | g | − |
| ge | *Rhodopseudomonas* | g | − | m | *Adlercreutzia equolifaciens* | s | − | n | *Bibersteinia trehalosi* | s | − |
| ge | Gammaproteobacteria | c | − | m | *Adlercreutzia* | g | − | n | Pleurocapsales | o | + |
| ge | *Peptostreptococcus* | g | − | m | Erysipelotrichia | c | + | n | *Janibacter* | g | + |
| ge | *Peptostreptococcus anaerobius* | s | − | m | Erysipelotrichales | o | + | n | *Chroococcidiopsis* | g | + |
| ge | Micrococcaceae | f | − | m | Ruminococcaceae | f | + | n | *Kytococcus* | g | + |
| ge | *Micrococcus* | g | + | m | *Blautia* | g | + | n | *Empedobacter* | g | − |
| ge | *Micrococcus luteus* | s | + | m | *Roseburia* sp. 11SE39 | s | + | n | *Rheinheimera* | g | |
| ge | *Staphylococcus* | g | + | m | *Bacteroides* sp. D22 | s | + | n | *Macrococcus* | g | + |
| ge | *Staphylococcus aureus* | s | − | m | *Alistipes* sp. RMA 9912 | s | + | n | *Luteimonas* | g | + |
| ge | *Staphylococcus epidermidis* | s | − | m | *Blautia faecis* | s | − | n | *Pedobacter* | g | + |
| ge | *Staphylococcus simulans* | s | + | m | Selenomonadales | o | − | n | Rubrobacterales | o | + |
| ge | *Deinococcus-Thermus* | p | − | m | Acidaminococcaceae | f | + | n | Rubrobacteraceae | f | + |
| ge | *Streptococcus gordonii* | s | − | m | Negativicutes | c | − | n | Sphaerobacterales | o | − |
| ge | *Streptococcus agalactiae* | s | − | m | *Eggerthella* sp. HGA1 | s | | n | Streptosporangiales | o | + |
| ge | *Streptococcus parasanguinis* | s | − | m | *Streptococcus* sp. BS35a | s | − | n | *Modestobacter* | g | − |
| ge | *Streptococcus anginosus* | s | − | m | *Flavonifractor* | g | + | n | *Modestobacter multiseptatus* | s | − |
| ge | *Streptococcus dysgalactiae* | s | − | m | Sutterellaceae | f | − | n | *Sphingomonas aquatilis* | s | + |
| ge | *Enterococcus* | g | + | m | *Anaerostipes* sp. 5_1_63FAA | s | + | n | *Ochrobactrum tritici* | s | − |
| ge | *Enterococcus faecalis* | s | + | m | *Fusicatenibacter saccharivorans* | s | + | n | *Ornithinimicrobium* | g | + |
| ge | *Lactococcus lactis* | s | + | m | *Blautia* sp. YHC-4 | s | − | n | *Planomicrobium* | g | + |
| ge | *Aerococcus* | g | + | m | *Intestinimonas* | g | + | n | *Microvirga* | g | − |
| ge | *Aerococcus urinae* | s | − | m | *Fusicatenibacter* | g | + | n | Alicyclobacillaceae | f | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | Gemella | g | − | m | Eisenbergiella | g | − | n | Albidovulum inexpectatum | s | − |
| ge | Atopobium | g | + | m | Eisenbergiella tayi | s | − | n | Ralstonia sp. CCUG 46389 | s | + |
| ge | Atopobium minutum | s | + | m | Candidatus Soleaferrea | g | | n | Albidovulum | g | − |
| ge | Bacillales | o | − | m | Peptoclostridium | g | − | n | Bdellovibrionales | o | |
| ge | Bacillus | g | − | m | Asaccharospora | g | + | n | Paucibacter toxinivorans | s | + |
| ge | Lysinibacillus sphaericus | s | − | m | Erysipelatoclostridium | g | + | n | Chthoniobacter | g | − |
| ge | Lactobacillus | g | + | m | Campylobacter | g | − | n | Conchiformibius | g | − |
| ge | Lactobacillus acidophilus | s | − | m | Campylobacter concisus | s | + | n | Erythrobacteraceae | f | − |
| ge | Lactobacillus plantarum | s | − | m | Campylobacter rectus | s | + | n | Sphingomonas dokdonensis | s | + |
| ge | Lactobacillus gasseri | s | + | m | Achromobacter | g | + | n | Staphylococcus sp. L10 | s | − |
| ge | Lactobacillus reuteri | s | − | m | Flavobacterium | g | − | n | Flavisolibacter | g | + |
| ge | Lactobacillus fermentum | s | | m | Pseudomonas | g | − | n | Aureimonas | g | − |
| ge | Lactobacillus vaginalis | s | − | m | Rhizobiales | o | − | n | Chryseobacterium haifense | s | + |
| ge | Corynebacteriaceae | f | − | m | Bradyrhizobium | g | − | n | Nocardioides mesophilus | s | + |
| ge | Actinomyces odontolyticus | s | − | m | Methylobacterium | g | − | n | Singulisphaera | g | + |
| ge | Arthrobacter | g | − | m | Moraxellaceae | f | + | n | Acidovorax sp. LR05 | s | − |
| ge | Bifidobacterium | g | − | m | Acinetobacter | g | + | n | Mycobacterium sp. KNUC297 | s | − |
| ge | Bifidobacterium bifidum | s | − | m | Moraxella | g | − | n | Pseudomonas sp. KNUC378 | s | + |
| ge | Bifidobacterium breve | s | + | m | Neisseriaceae | f | − | n | Nitrososphaera | g | + |
| ge | Bifidobacterium dentium | s | + | m | Neisseria | g | − | n | Brevibacterium pityocampae | s | + |
| ge | Brevibacterium | g | − | m | Neisseria mucosa | s | − | n | Sphingomonas sp. CS81 | s | + |
| ge | Corynebacterium | g | − | m | Neisseria elongata | s | − | n | Chryseobacterium sp. Y1D | s | + |
| ge | Corynebacterium diphtheriae | s | − | m | Neisseria macacae | s | − | n | Variovorax sp. IMER-B2-7 | s | − |
| ge | Corynebacterium sp. | s | − | m | Alcaligenaceae | f | + | n | Thaumarchaeota | p | − |
| ge | Propionibacterium | g | − | m | Enterobacteriaceae | f | + | n | Jeotgalicoccus aerolatus | s | + |
| ge | Cutibacterium acnes | s | + | m | Enterobacter | g | + | n | Pseudorhodoferax | g | − |
| ge | Mycobacteriaceae | f | + | m | Klebsiella | g | − | n | Burkholderia sp. S32 | s | − |
| ge | Mycobacterium | g | + | m | Kluyvera | g | − | n | Blastococcus sp. 0705C6-3 | s | + |
| ge | Rhodococcus | g | − | m | Pasteurellaceae | f | − | n | Pseudomonas sp. PcFRB100 | s | + |
| ge | Rhodococcus erythropolis | s | − | m | Actinobacillus | g | − | n | Chryseobacterium sp. IIL-Nv8 | s | + |
| ge | Actinomycetales | o | − | m | Haemophilus | g | − | n | Brevibacterium sp. A9C6 | s | + |
| ge | Actinomycetaceae | f | − | m | Haemophilus influenzae | s | − | n | Acinetobacter sp. C-S-PDA7 | s | + |
| ge | Mobiluncus | g | − | m | Haemophilus parainfluenzae | s | − | n | Janibacter sp. M3-5 | s | + |
| ge | Mobiluncus curtisii | s | − | m | Bacteroides fragilis | s | − | n | Blastococcus sp. FXJ6.383 | s | + |
| ge | Mobiluncus mulieris | s | − | m | Parabacteroides distasonis | s | − | n | Mesorhizobium sp. RE 62 | s | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | Mycoplasma | g | + | m | Campylobacter gracilis | s | − | n | Bacillus sp. CBMAI 1158 | s | − |
| ge | Mycoplasma hominis | s | + | m | Campylobacter ureolyticus | s | + | n | Shewanella sp. 8113 | s | + |
| ge | Ureaplasma | g | − | m | Butyrivibrio | g | − | n | Kocuria sp. FXJ6.339 | s | + |
| ge | Ureaplasma urealyticum | s | − | m | Porphyromonas | g | + | n | Acinetobacter sp. STE | s | − |
| ge | Methanobacteriales | o | − | m | Prevotella | g | − | n | Pseudomonas sp. PDD-31b-4 | s | |
| ge | Methanobacteriaceae | f | − | m | Fusobacterium | g | − | n | Nitrososphaerales | o | + |
| ge | Methanobrevibacter | g | − | m | Fusobacterium nucleatum | s | − | n | Nitrososphaeraceae | f | + |
| ge | Methanobrevibacter smithii | s | − | m | Fusobacterium periodonticum | s | + | n | Photobacterium sp. squidInt_04 | s | + |
| ge | Gardnerella | g | + | m | Megasphaera | g | + | n | Dermacoccus sp. D2.1 | s | + |
| ge | Gardnerella vaginalis | s | − | m | Gammaproteobacteria | c | − | n | Stenotrophomonas sp. Z2-S2 | s | − |
| ge | Peptococcus | g | − | m | Peptostreptococcus | g | − | n | Deinococcus antarcticus | s | − |
| ge | Peptococcus niger | s | − | m | Finegoldia magna | s | + | n | Deinococcus sp. UAC-77 | s | − |
| ge | Halomonas | g | − | m | Peptostreptococcus anaerobius | s | − | n | Staphylococcus sp. 335602 | s | − |
| ge | Globicatella | g | − | m | Micrococcaceae | f | − | n | Variovorax sp. MM43Nov | s | + |
| ge | Globicatella sanguinis | s | − | m | Staphylococcus | g | + | n | Janibacter sp. IARI-RP17 | s | + |
| ge | Sphingomonas | g | − | m | Staphylococcus epidermidis | s | − | n | Rhodobacter capsulatus | s | + |
| ge | Phyllobacterium | g | + | m | Deinococcus-Thermus | p | − | n | Thermomonosporaceae | f | + |
| ge | Bacteroides eggerthii | s | − | m | Streptococcus gordonii | s | − | n | Pedomicrobium ferrugineum | s | − |
| ge | Alistipes putredinis | s | + | m | Streptococcus thermophilus | s | + | n | Thermomonas | g | − |
| ge | Odoribacter splanchnicus | s | + | m | Streptococcus agalactiae | s | − | n | Alkanindiges | g | − |
| ge | Porphyromonas asaccharolytica | s | + | m | Streptococcus parasanguinis | s | − | n | Aureimonas altamirensis | s | − |
| ge | Prevotella bivia | s | − | m | Enterococcus | g | + | n | Rhodococcus sp. CO56 | s | + |
| ge | Prevotella buccalis | s | + | m | Lactococcus lactis | s | + | n | Pseudomonas syringae | s | + |
| ge | Prevotella disiens | s | − | m | Aerococcus | g | + | n | Acinetobacter calcoaceticus | s | − |
| ge | Cronobacter sakazakii | s | − | m | Gemella | g | + | n | Neisseria meningitidis | s | + |
| ge | Alphaproteobacteria | c | − | m | Atopobium | g | − | n | Pectobacterium carotovorum | s | + |
| ge | Halomonadaceae | f | − | m | Bacillales | o | + | n | Rickettsiales | o | − |
| ge | Arcanobacterium | g | + | m | Bacillus | g | − | n | Fusobacterium russii | s | − |
| ge | Arcanobacterium haemolyticum | s | + | m | Lysinibacillus sphaericus | s | − | n | Thiobacillus | g | − |
| ge | Euryarchaeota | p | − | m | Clostridioides difficile | s | − | n | Bergeyella zoohelcum | s | − |
| ge | Gemella morbillorum | s | − | m | Erysipelatoclostridium ramosum | s | − | n | Nitrosococcus | g | + |
| ge | Rhizobium etli | s | − | m | Lactobacillus | g | − | n | Streptococcus pneumoniae | s | − |
| ge | Veillonella | g | − | m | Lactobacillus plantarum | s | − | n | Aerococcus viridans | s | − |
| ge | Veillonella parvula | s | − | m | Lactobacillus gasseri | s | − | n | Actinomyces israelii | s | − |
| ge | Epsilonproteobacteria | c | + | m | Lactobacillus fermentum | s | − | n | Mycobacterium chelonae | s | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | Bifidobacteriaceae | f | + | m | Lactobacillus salivarius | s | + | n | Curtobacterium | g | |
| ge | Propionibacteriaceae | f | + | m | Lactobacillus vaginalis | s | − | n | Halobacteriales | o | + |
| ge | Mollicutes | c | + | m | Corynebacteriaceae | f | + | n | Halobacteriaceae | f | + |
| ge | Eggerthia catenaformis | s | − | m | Actinomyces | g | − | n | Chelatococcus | g | − |
| ge | Helcococcus | g | − | m | Actinomyces odontolyticus | s | + | n | Brachymonas | g | + |
| ge | Leptotrichia | g | + | m | Bifidobacterium bifidum | s | + | n | Microlunatus phosphovorus | s | + |
| ge | Rothia | g | − | m | Bifidobacterium dentium | s | − | n | Acinetobacter haemolyticus | s | + |
| ge | Actinomyces neuii | s | − | m | Corynebacterium | g | + | n | Arthrospira | g | − |
| ge | Cutibacterium avidum | s | − | m | Corynebacterium sp. | s | + | n | Rubrobacter | g | + |
| ge | Propionimicrobium lymphophilum | s | − | m | Propionibacterium | g | + | n | Johnsonella ignava | s | + |
| ge | Anaerococcus hydrogenalis | s | + | m | Cutibacterium acnes | s | + | n | Pseudomonas agarici | s | + |
| ge | Peptoniphilus lacrimalis | s | + | m | Mycobacteriaceae | f | + | n | Arthrospira fusiformis | s | − |
| ge | Anaerococcus lactolyticus | s | − | m | Mycobacterium | g | + | n | Macrococcus caseolyticus | s | + |
| ge | Anaerococcus prevotii | s | + | m | Actinomycetales | o | − | n | Aquabacterium commune | s | − |
| ge | Anaerococcus tetradius | s | + | m | Rothia dentocariosa | s | − | n | Staphylococcus vitulinus | s | − |
| ge | Anaerococcus vaginalis | s | + | m | Actinomycetaceae | f | − | n | Williamsia | g | − |
| ge | Microbacterium | g | − | m | Mobiluncus | g | + | n | Bacillus niacini | s | − |
| ge | Lactobacillus johnsonii | s | − | m | Mycoplasmatales | o | − | n | Moraxella lincolnii | s | + |
| ge | Dermabacter | g | + | m | Mycoplasmataceae | f | − | n | Parachlamydiaceae | f | + |
| ge | Dermabacter hominis | s | + | m | Mycoplasma | g | − | n | Alkalibacterium | g | + |
| ge | Veillonella atypica | s | − | m | Methanobacteriales | o | + | n | Alishewanella | g | − |
| ge | Corynebacterium glucuronolyticum | s | + | m | Methanobacteriaceae | f | + | n | Tepidimonas | g | − |
| ge | Dialister | g | − | m | Methanobrevibacter | g | + | n | Coxiellaceae | f | |
| ge | Sneathia sanguinegens | s | − | m | Methanobrevibacter smithii | s | + | n | Legionellales | o | + |
| ge | Sutterella wadsworthensis | s | − | m | Peptococcus | g | + | n | Rhodobiaceae | f | + |
| ge | Brevundimonas | g | + | m | Solanales | o | − | n | Salana | g | + |
| ge | Bradyrhizobiaceae | f | + | m | Bifidobacterium pseudocatenulatum | s | + | n | Salana multivorans | s | + |
| ge | Rhodospirillaceae | f | + | m | Phyllobacterium | g | − | n | Pectobacterium | g | + |
| ge | Sphingomonadaceae | f | − | m | Bacteroides eggerthii | s | + | n | Beutenbergiaceae | f | + |
| ge | Corynebacterium argentoratense | s | + | m | Alistipes putredinis | s | + | n | Bogoriellaceae | f | − |
| ge | Brachybacterium | g | + | m | Odoribacter splanchnicus | s | + | n | Xenophilus | g | − |
| ge | Rothia mucilaginosa | s | + | m | Porphyromonas asaccharolytica | s | + | n | Georgenia | g | − |
| ge | Abiotrophia | g | + | m | Prevotella bivia | s | − | n | Pseudomonas graminis | s | + |
| ge | Granulicatella adiacens | s | + | m | Prevotella buccalis | s | + | n | Neisseria sp. CCUG 45853 | s | + |
| ge | Abiotrophia defectiva | s | + | m | Prevotella disiens | s | − | n | Williamsiaceae | f | − |
| ge | Parabacteroides merdae | s | + | m | Arcanobacterium | g | − | n | Halobacteria | c | + |
| ge | Bacteroides stercoris | s | − | m | Euryarchaeota | p | + | n | Prevotella micans | s | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | Lactobacillus rhamnosus | s | + | m | Gemella morbillorum | s | + | n | Flavobacterium sp. EP372 | s | + |
| ge | Lactobacillus crispatus | s | + | m | Veillonella | g | − | n | Pseudospirillum | g | + |
| ge | Flavobacteriaceae | f | + | m | Veillonella parvula | s | + | n | Macrococcus brunensis | s | + |
| ge | Pantoea | g | + | m | Epsilonproteobacteria | c | − | n | Thermomonas brevis | s | − |
| ge | Anaerococcus octavius | s | + | m | Bifidobacteriaceae | f | − | n | Acinetobacter sp. 2002-2301217 | s | − |
| ge | Actinotignum schaalii | s | + | m | Propionibacteriaceae | f | + | n | Effusibacillus pohliae | s | − |
| ge | Trueperella bernardiae | s | − | m | Mollicutes | c | + | n | Corynebacterium caspium | s | − |
| ge | Chryseobacterium | g | + | m | Eggerthia catenaformis | s | − | n | Kocuria carniphila | s | + |
| ge | Bergeyella | g | + | m | Rhodobacteraceae | f | − | n | Candidatus Protochlamydia | g | − |
| ge | Corynebacterium ulcerans | s | − | m | Burkholderia | g | + | n | Adhaeribacter | g | − |
| ge | Meiothermus | g |  | m | Fusobacteria | p | − | n | Solibacteres | c | − |
| ge | Actinomyces europaeus | s | + | m | Leptotrichia | g | − | n | Solibacterales | o | − |
| ge | Facklamia | g | + | m | Rothia | g | − | n | Solibacteraceae | f | − |
| ge | Facklamia sp. 164-92 | s | + | m | Actinomyces neuii | s | + | n | Candidatus Solibacter | g | − |
| ge | Facklamia sp. 1440-97 | s | − | m | Peptoniphilus lacrimalis | s | − | n | Exiguobacterium sibiricum | s | + |
| ge | Mesorhizobium | g | + | m | Parvimonas micra | s | − | n | Epilithonimonas | g | − |
| ge | Thermales | o |  | m | Anaerococcus tetradius | s |  | n | Chryseobacterium sp. BBCT14 | s | + |
| ge | Phyllobacteriaceae | f | + | m | Anaerococcus vaginalis | s | + | n | Cryobacterium psychrotolerans | s | + |
| ge | Kocuria rhizophila | s | − | m | Streptophyta | p | − | n | Bradyrhizobium sp. P-45 | s | − |
| ge | Pseudomonadales | o | − | m | Bilophila | g | + | n | Comamonas sp. P-115 | s | − |
| ge | Campylobacteraceae | f | + | m | Bilophila wadsworthia | s | + | n | Leucobacter sp. LR-2006b | s | + |
| ge | Tessaracoccus | g | − | m | Veillonella atypica | s | − | n | Caldilineae | c | + |
| ge | Kluyvera georgiana | s | − | m | Corynebacterium glucuronolyticum | s | − | n | Caldilineales | o | + |
| ge | Collinsella aerofaciens | s | − | m | Dialister | g | − | n | Caldilineaceae | f | + |
| ge | Campylobacter hominis | s | − | m | Dialister pneumosintes | s | − | n | Sphingobium sp. MH60 | s | − |
| ge | Actinobaculum | g | + | m | Stenotrophomonas | g | + | n | Burkholderia lata | s | − |
| ge | Halomonas pacifica | s | − | m | Sneathia sanguinegens | s | − | n | Deinococcus sp. 3B1 | s | − |
| ge | Bacillus pseudofirmus | s | − | m | Sutterella wadsworthensis | s | + | n | Pseudonocardia sp. CC981102-15 | s | − |
| ge | Comamonadaceae | f | − | m | Bradyrhizobiaceae | f | − | n | Perlucidibaca | g | + |
| ge | Delftia | g | − | m | Rhodospirillaceae | f | + | n | Microvirga aerilata | s | − |
| ge | Enterococcaceae | f | + | m | Sphingomonadaceae | f | − | n | Bacillus nanhaiisediminis | s | − |
| ge | Rhizobiaceae | f | − | m | Rothia mucilaginosa | s | − | n | Planococcus sp. ljh-25 | s | − |
| ge | Facklamia languida | s | + | m | Abiotrophia | g | + | n | Frigoribacterium sp. 181 | s | + |
| ge | Slackia | g | + | m | Granulicatella adiacens | s | − | n | Porphyrobacter sp. NMC22 | s | + |
| ge | Slackia exigua | s | − | m | Abiotrophia defectiva | s | + | n | Microvirga sp. TSX10-2 | s | + |
| ge | Gemella sp. 933-88 | s | − | m | Parabacteroides merdae | s | + | n | Comamonas sp. RV_A09_23b | s | + |
| ge | Bifidobacteriales | o | + | m | Bacteroides stercoris | s | + | n | Pseudomonas sp. BM5 | s | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | Micrococcales | o | − | m | Lautropia | g | − | n | Brachybacterium sp. b110-100S | s | + |
| ge | Corynebacteriales | o | − | m | Lactobacillus rhamnosus | s | + | n | Methylobacterium sp. CCGE4019 | s | − |
| ge | Propionibacteriales | o | + | m | Lactobacillus crispatus | s | − | n | Actinomycetospora sp. CAP 335 | s | + |
| ge | Brevibacteriaceae | f | − | m | Ralstonia | g | + | n | Arthrobacter sp. T2-4 | s | + |
| ge | Dermabacteraceae | f | + | m | Flavobacteriaceae | f | + | n | Flavobacterium sp. bk_25 | s | − |
| ge | Microbacteriaceae | f | + | m | Actinobacillus porcinus | s | − | n | Massilia oculi | s | + |
| ge | Nocardiaceae | f | − | m | Meiothermus silvanus | s | − | n | Alishewanella sp. Mn5-6 | s | − |
| ge | Bosea | g | + | m | Pantoea | g | + | n | Rhodopseudomonas thermotolerans | s | + |
| ge | Achromobacter xylosoxidans | s | + | m | Anaerococcus octavius | s | + | n | Ornithinimicrobium sp. X1C | s | + |
| ge | Mogibacterium | g | − | m | Kocuria | g | + | n | Brachymonas sp. canine oral taxon 015 | s | + |
| ge | Propionibacterium sp. V07/12348 | s | − | m | Chryseobacterium | g | + | n | Tepidimonas sp. AK30 | s | − |
| ge | Aerococcus christensenii | s | + | m | Bergeyella | g | + | n | Microvirga sp. BR10193 | s | − |
| ge | Lactobacillus fornicalis | s | − | m | Corynebacterium ulcerans | s | + | n | Ornithinimicrobium sp. THG-GM43 | s | − |
| ge | Dorea longicatena | s | + | m | Phyllobacteriaceae | f | + | n | Kocuria sp. BRI 36 | s | + |
| ge | Oligella | g | − | m | Campylobacteraceae | f | − | n | Kocuria sp. LW2-LEVI2-W | s | + |
| ge | Oligella urethralis | s | − | m | Tessaracoccus | g | + | n | Stenotrophomonas sp. TV49May | s | − |
| ge | Staphylococcaceae | f | − | m | Kluyvera georgiana | s | − | n | Staphylococcus sp. 155b | s | + |
| ge | Enterobacterales | o | − | m | Collinsella aerofaciens | s | + | n | Geodermatophilales | o | + |
| ge | Aquabacterium | g | + | m | Campylobacter hominis | s | − | n | Hymenobacteraceae | f | + |
| ge | Aquabacterium sp. Aqua2 | s | + | m | Caulobacteraceae | f | + | n | Luteimonas mephitis | s | + |
| ge | Candidatus Saccharibacteria | p | + | m | Delftia | g | + | n | Dermatophilaceae | f | + |
| ge | Pseudoglutamicibacter albus | s | − | m | Enterococcaceae | f | + | n | Leucobacter aridicollis | s | + |
| ge | Solobacterium moorei | s | + | m | Rhizobiaceae | f | + | s | Bacteroidaceae | f | − |
| ge | Veillonella ratti | s | + | m | Slackia | g | + | s | Bacteroides | g | − |
| ge | Lactobacillus jensenii | s | − | m | Slackia exigua | s | + | s | Bacteroides thetaiotaomicron | s | + |
| ge | Granulicatella | g | − | m | Gemella sp. 933-88 | s | + | s | Bacteroides uniformis | s | − |
| ge | Flavobacteriia | c | + | m | Bifidobacteriales | o | − | s | Bacteroides vulgatus | s | − |
| ge | Bulleidia | g | − | m | Micrococcales | o | − | s | Roseburia | g | + |
| ge | Bulleidia extructa | s | + | m | Corynebacteriales | o | + | s | Faecalibacterium prausnitzii | s | − |
| ge | Brucellaceae | f | − | m | Propionibacteriales | o | + | s | Desulfovibrio | g | + |
| ge | Deinococcales | o | − | m | Achromobacter xylosoxidans | s | + | s | Acidaminococcus | g | + |
| ge | Methylobacteriaceae | f | + | m | Mogibacterium | g | − | s | Herbaspirillum | g | − |
| ge | Solobacterium | g | + | m | Propionibacterium sp. V07/12348 | s | + | s | Herbaspirillum seropedicae | s | − |
| ge | Pseudomonas brenneri | s | − | m | Aerococcus christensenii | s | + | s | Bacteroidetes | p | − |
| ge | Actinomyces radingae | s | + | m | Lactobacillus fornicalis | s | + | s | Proteobacteria | p | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | *Actinomyces turicensis* | s | − | m | *Dorea longicatena* | s | + | s | Firmicutes | p | − |
| ge | *Olsenella* | g | − | m | Staphylococcaceae | f | + | s | *Sarcina* | g | − |
| ge | Chromatiales | o | + | m | Enterobacterales | o | + | s | Streptococcaceae | f | + |
| ge | Oceanospirillales | o | − | m | *Aquabacterium* | g | + | s | *Streptococcus* | g | + |
| ge | Pseudomonadaceae | f | − | m | *Aquabacterium* sp. Aqua2 | s | + | s | *Clostridium* | g | − |
| ge | *Catenibacterium* | g | − | m | Candidatus Saccharibacteria | p | + | s | Actinobacteria | c | + |
| ge | *Globicatella sulfidifaciens* | s | + | m | *Solobacterium moorei* | s | + | s | *Lachnospira pectinoschiza* | s | + |
| ge | *Granulicatella elegans* | s | − | m | *Lactobacillus jensenii* | s | − | s | Betaproteobacteria | c | + |
| ge | *Lactobacillus iners* | s | − | m | *Granulicatella* | g | + | s | Deltaproteobacteria | c | − |
| ge | *Anaeroglobus* | g | − | m | Flavobacteriia | c | + | s | Veillonellaceae | f | − |
| ge | *Anaeroglobus geminatus* | s | − | m | Deinococcales | o | − | s | Clostridiaceae | f | − |
| ge | *Pseudoglutamicibacter cumminsii* | s | + | m | Methylobacteriaceae | f | − | s | *Phascolarctobacterium* | g | + |
| ge | *Megamonas* | g | − | m | Burkholderiaceae | f | − | s | *Phascolarctobacterium faecium* | s | + |
| ge | *Corynebacterium mastitidis* | s | − | m | *Solobacterium* | g | + | s | Lactobacillaceae | f | − |
| ge | *Peptoniphilus* | g | − | m | *Olsenella* | g | − | s | *Sutterella* | g | − |
| ge | *Sphingobium* | g | − | m | Pseudomonadaceae | f | + | s | *Bacteroides caccae* | s | + |
| ge | *Novosphingobium* | g | + | m | Pasteurellales | o | − | s | Verrucomicrobiales | o | − |
| ge | *Anaerococcus* | g | − | m | *Catenibacterium* | g | + | s | *Holdemania* | g | + |
| ge | *Sneathia* | g | − | m | *Aerosphaera* | g | + | s | Verrucomicrobia | p | − |
| ge | *Thalassospira* | g | + | m | *Aerosphaera taetra* | s | + | s | Oxalobacteraceae | f | + |
| ge | *Brevibacterium paucivorans* | s | + | m | *Granulicatella elegans* | s | + | s | Burkholderiales | o | + |
| ge | Porphyromonadaceae | f | − | m | *Finegoldia* | g | + | s | Coriobacteriaceae | f | + |
| ge | Prevotellaceae | f | + | m | *Anoxybacillus* | g | + | s | *Eggerthella* | g | + |
| ge | *Lactobacillus* sp. CR-609S | s | + | m | *Anaeroglobus geminatus* | s | + | s | Coriobacteriia | c | + |
| ge | *Actinomyces hongkongensis* | s | + | m | *Megamonas* | g |  | s | Coriobacteriales | o | + |
| ge | *Lactobacillus coleohominis* | s | − | m | *Peptoniphilus* | g | − | s | *Blautia luti* | s | − |
| ge | Methanobacteria | c | − | m | *Novosphingobium* | g | + | s | Bacilli | c | − |
| ge | *Varibaculum* | g | − | m | *Anaerococcus* | g | + | s | *Bacteroides* sp. AR20 | s | − |
| ge | *Varibaculum cambriense* | s | − | m | *Sneathia* | g | − | s | *Oscillospira* | g | + |
| ge | *Corynebacterium spheniscorum* | s | − | m | *Thalassospira* | g | + | s | Bacteroidales | o | − |
| ge | Peptococcaceae | f | − | m | Porphyromonadaceae | f | + | s | *Shuttleworthia* | g | + |
| ge | Bacillaceae | f | − | m | Prevotellaceae | f | − | s | Clostridia | c | − |
| ge | Aerococcaceae | f | + | m | Methanobacteria | c | + | s | Clostridiales | o | − |
| ge | Carnobacteriaceae | f | − | m | *Varibaculum* | g | + | s | Lachnospiraceae | f | + |
| ge | *Megasphaera micronuciformis* | s | + | m | Peptococcaceae | f | + | s | Peptostreptococcaceae | f | + |
| ge | *Acidaminococcus intestini* | s | + | m | Bacillaceae | f | − | s | Lactobacillies | o | − |
| ge | *Veillonella montpellierensis* | s | + | m | Aerococcaceae | f | + | s | Desulfovibrionaceae | f | + |
| ge | Thermaceae | f |  | m | Carnobacteriaceae | f | + | s | Bacteroidia | c | − |
| ge | Deinococci | c | − | m | *Megasphaera micronuciformis* | s | + | s | Actinobacteria | p | + |
| ge | *Dialister* sp. E2_20 | s | + | m | Deinococci | c | − | s | Verrucomicrobiae | c | − |
| ge | *Actinotignum urinale* | s | + | m | *Dialister* sp. E2_20 | s | − | s | Verrucomicrobiaceae | f | − |
| ge | *Propionibacterium* sp. MSP09A | s | − | m | *Propionibacterium* sp. MSP09A | s | + | s | *Anaerostipes* | g | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | Streptococcus pasteurianus | s | + | m | Flavobacteriales | o | + | s | Desulfovibrionales | o | + |
| ge | Flavobacteriales | o | + | m | Fusobacteriia | c | − | s | Oscillospiraceae | f | − |
| ge | Actinobaculum massiliense | s | − | m | Fusobacteriales | o | − | s | Faecalibacterium | g | − |
| ge | Propionimicrobium | g | + | m | Fusobacteriaceae | f | − | s | Akkermansia | g | − |
| ge | Fusobacteriaceae | f | + | m | Rhodospirillales | o | + | s | Akkermansia muciniphila | s | − |
| ge | Rhodospirillales | o | − | m | Rhodobacterales | o | − | s | Hespellia | g | − |
| ge | Sphingomonadales | o | − | m | Sphingomonadales | o | + | s | Marvinbryantia | g | − |
| ge | Bacteroides massiliensis | s | − | m | Caulobacterales | o | + | s | Subdoligranulum | g | − |
| ge | Neisseriales | o | − | m | Bacteroides massiliensis | s | + | s | Flavonifractor plautii | s | + |
| ge | Campylobacterales | o | + | m | Neisseriales | o | − | s | Bacteroides finegoldii | s | + |
| ge | Subdoligranulum variabile | s | + | m | Campylobacterales | o | − | s | Lactonifactor longoviformis | s | − |
| ge | Alistipes finegoldii | s | − | m | Subdoligranulum variabile | s | + | s | Roseburia inulinivorans | s | + |
| ge | Peptoniphilus sp. 2002-38328 | s | − | m | Bifidobacterium longum | s | − | s | Blautia wexlerae | s | − |
| ge | Peptoniphilus sp. 2002-2300004 | s | − | m | Dialister invisus | s | + | s | Lactonifactor | g | − |
| ge | Actinomyces sp. 2002-2301122 | s | + | m | Peptoniphilus sp. 2002-38328 | s | + | s | Ruminococcaceae | f | − |
| ge | Curvibacter gracilis | s | + | m | Peptoniphilus sp. 2002-2300004 | s | − | s | Clostridiales f XIII. Incertae Sedis | f | + |
| ge | Bacillus sp. T41 | s | − | m | Sutterella stercoricanis | s | + | s | Blautia | g | − |
| ge | Sutterella stercoricanis | s | − | m | Oribacterium | g | + | s | Roseburia sp. 11SE39 | s | + |
| ge | Fastidiosipila | g | − | m | Porphyromonas uenonis | s | − | s | Bacteroides sp. D22 | s | − |
| ge | Fastidiosipila sanguinis | s | − | m | Odoribacter | g | + | s | Blautia faecis | s | − |
| ge | Cloacibacterium normanense | s | + | m | Bacteroides salyersiae | s | + | s | Selenomonadales | o | − |
| ge | Helcococcus sueciensis | s | − | m | Roseburia hominis | s | + | s | Acidaminococcaceae | f | + |
| ge | Pseudoclavibacter | g | + | m | Roseburia faecis | s | + | s | Negativicutes | c | − |
| ge | Oribacterium | g | + | m | Dialister propionicifaciens | s | + | s | Streptococcus sp. BS35a | s | + |
| ge | Curvibacter | g | + | m | Bacteroides plebeius | s | + | s | Sutterellaceae | f | − |
| ge | Porphyromonas uenonis | s | − | m | Bacteroides coprocola | s | − | s | Fusicatenibacter saccharivorans | s | − |
| ge | Odoribacter | g | + | m | Porphyromonas somerae | s | − | s | Blautia sp. YHC-4 | s | + |
| ge | Corynebacterium sp. 2300500 | s | + | m | Shinella | g |  | s | Intestinimonas | g | + |
| ge | Bacteroides salyersiae | s | − | m | Alistipes shahii | s | + | s | Fusicatenibacter | g | − |
| ge | Roseburia hominis | s | + | m | Bacteroides intestinalis | s | + | s | Eisenbergiella | g |  |
| ge | Roseburia faecis | s | + | m | Peptostreptococcus stomatis | s | − | s | Eisenbergiella tayi | s |  |
| ge | Dialister propionicifaciens | s | − | m | Bergeyella sp. AF14 | s | + | s | Peptoclostridium | g | − |
| ge | Dialister micraerophilus | s | − | m | Bacteroides dorei | s | − | s | Erysipelatoclostridium | g | − |
| ge | Bacteroides plebeius | s | − | m | Peptoniphilus sp. gpac018A | s | + | s | Campylobacter | g | − |
| ge | Bacteroides coprocola | s | − | m | Bacteroides sp. XB12B | s | + | s | Achromobacter | g | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | Porphyromonas somerae | s | + | m | Parabacteroides | g | + | s | Flavobacterium | g | + |
| ge | Parabacteroides goldsteinii | s | − | m | Anoxybacillus sp. HT14 | s | + | s | Pseudomonas | g | − |
| ge | Alistipes shahii | s | − | m | Prevotella timonensis | s | − | s | Ralstonia pickettii | s | + |
| ge | Bacteroides intestinalis | s | − | m | Barnesiella | g | + | s | Rhizobiales | o | + |
| ge | Pelomonas | s | + | m | Lysinibacillus | g | − | s | Bradyrhizobium | g | + |
| ge | Bergeyella sp. AF14 | s | + | m | Howardella | g | + | s | Rhizobium | g | + |
| ge | Bacteroides dorei | s | − | m | Anaerococcus murdochii | s | − | s | Mesorhizobium loti | s | + |
| ge | Peptoniphilus sp. gpac018A | s | + | m | Acinetobacter sp. RBE2CD-114 | s | − | s | Methylobacterium | g | − |
| ge | Peptoniphilus sp. gpac018B | s | + | m | Streptococcus sp. 11aTha1 | s | + | s | Moraxellaceae | f | + |
| ge | Peptoniphilus sp.gpac148 | s | + | m | Prevotella amnii | s | − | s | Acinetobacter | g | − |
| ge | Bacteroides sp. XB12B | s | + | m | Alloscardovia | g | − | s | Moraxella | g | + |
| ge | Moryella indoligenes | s | − | m | Alloscardovia omnicolens | s | − | s | Neisseriaceae | f | + |
| ge | Parabacteroides | g | − | m | Veillonella rogosae | s | − | s | Neisseria | g | + |
| ge | Anoxybacillus sp. HT14 | s | + | m | Megamonas funiformis | s |  | s | Neisseria mucosa | s | + |
| ge | Prevotella timonensis | s | − | m | Alistipes sp. EBA6-25cl2 | s | + | s | Neisseria elongata | s | − |
| ge | Barnesiella | g | − | m | Bacteroides sp. EBA5-17 | s | + | s | Neisseria macacae | s | − |
| ge | Lysinibacillus | g | − | m | Paraprevotella clara | s | + | s | Alcaligenaceae | f | − |
| ge | Howardella | g | − | m | Oscillibacter | g | + | s | Ochrobactrum | g | + |
| ge | Citrobacter sp. BW4 | s | − | m | Anaerobacillus alkalidiazotrophicus | s | + | s | Enterobacteriaceae | f | − |
| ge | Anaerococcus murdochii | s | + | m | Alistipes sp. NML05A004 | s | + | s | Citrobacter | g | + |
| ge | Cronobacter | g | − | m | Barnesiella intestinihominis | s | + | s | Enterobacter | g | − |
| ge | Acinetobacter sp. RBE2CD-114 | s | − | m | Parasutterella excrementihominis | s | − | s | Klebsiella | g | − |
| ge | Streptococcus sp. 11Tha1 | s | + | m | Porphyromonas bennonis | s | + | s | Kluyvera | g | + |
| ge | Methylobacterium sp. CBMB45 | s | + | m | Cloacibacterium | g | + | s | Pasteurellaceae | f | − |
| ge | Prevotella amnii | s | − | m | Synergistetes | p | − | s | Actinobacillus | g | + |
| ge | Alloscardovia | g | + | m | Clostridiales f XI. Incertae Sedis | f | + | s | Haemophilus parainfluenzae | s | + |
| ge | Alloscardovia omnicolens | s | + | m | Parvimonas | g | − | s | Bacteroides fragilis | s | − |
| ge | Rhizobium sp. sc-w | s | − | m | Tenericutes | p | + | s | Campylobacter gracilis | s | − |
| ge | Veillonella rogosae | s | + | m | Corynebacterium freiburgense | s | + | s | Campylobacter ureolyticus | s | − |
| ge | Jonquetella | g | + | m | Delftia lacustris | s | + | s | Butyrivibrio | g | + |
| ge | Jonquetella anthropi | s | + | m | Novosphingobium sediminicola | s | + | s | Porphyromonas | g | − |
| ge | Megamonas funiformis | s | − | m | Butyricimonas | g | + | s | Prevotella | g | − |
| ge | Bacillus sp. CZb | s | − | m | Parasutterella | g | − | s | Fusobacterium | g | − |
| ge | Alistipes sp. EBA6-25cl2 | s | + | m | Enterorhabdus | g | − | s | Fusobacterium nucleatum | s | − |
| ge | Bacteroides sp. EBA5-17 | s |  | m | Phyllobacterium sp. T50 | s |  | s | Fusobacterium periodonticum | s | + |
| ge | Paraprevotella clara | s | + | m | Negativicoccus succinicivorans | s | − | s | Desulfovibrio piger | s | − |
| ge | Serratia nematodiphila | s | − | m | Bacteroides clarus | s | − | s | Megasphaera | g | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | Oscillibacter | g | − | m | Sutterella sp. YIT 12072 | s | − | s | Chromatiaceae | f | + |
| ge | Pantoea vagans | s | + | m | Bifidobacterium kashiwanohense | s | | s | Rhodopseudomonas | g | + |
| ge | Anaerobacillus alkalidiazotrophicus | s | − | m | Porphyromonas sp. 2024b | s | − | s | Gammaproteobacteria | c | − |
| ge | Rhodopseudomonas boonkerdii | s | − | m | Lautropia sp. TeTO | s | − | s | Peptostreptococcus | g | + |
| ge | Chryseobacterium sp. MH28 | s | + | m | Pyramidobacter | g | + | s | Finegoldia magna | s | − |
| ge | Alistipes sp. NML05A004 | s | + | m | Anaerostipes hadrus | s | − | s | Peptostreptococcus anaerobius | s | |
| ge | Brevibacterium ravenspurgense | s | − | m | Synergistia | c | − | s | Micrococcaceae | f | + |
| ge | Dialister succinatiphilus | s | − | m | Synergistales | o | − | s | Micrococcus | g | + |
| ge | Barnesiella intestinihominis | s | − | m | Synergistaceae | f | − | s | Micrococcus luteus | s | − |
| ge | Pseudomonas sp. GmFRB023 | s | + | m | Anaerosporobacter | g | + | s | Staphylococcus | g | − |
| ge | Porphyromonas bennonis | s | − | m | Lactobacillus sp. BL302 | s | + | s | Staphylococcus aureus | s | − |
| ge | Cloacibacterium | g | + | m | Campylobacter sp. 10_1_50 | s | − | s | Staphylococcus epidermidis | s | + |
| ge | Gemella asaccharolytica | s | + | m | Lactobacillus sp. 7_1_47FAA | s | + | s | Staphylococcus simulans | s | + |
| ge | Bosea sp. BIWAKO-01 | s | + | m | Veillonella sp. oral taxon 780 | s | + | s | Deinococcus-Thermus | p | + |
| ge | Peptoniphilus duerdenii | s | + | m | Bilophila sp. 4_1_30 | s | + | s | Streptococcus thermophilus | s | + |
| ge | Peptoniphilus koenoeneniae | s | + | m | Anaerobacillus | g | − | s | Streptococcus parasanguinis | s | + |
| ge | Murdochiella asaccharolytica | s | + | m | Corynebacterium sp. NML 97-0186 | s | + | s | Streptococcus dysgalactiae | s | − |
| ge | Synergistetes | p | + | m | Actinomyces sp. oral taxon 175 | s | + | s | Enterococcus | g | + |
| ge | Cloacibacillus | g | − | m | Peptococcus sp. oral taxon 168 | s | − | s | Aerococcus | g | + |
| ge | Cloacibacillus evryensis | s | − | m | Streptococcus sp. oral taxon G59 | s | − | s | Gemella | g | − |
| ge | Clostridiales f XI. Incertae Sedis | f | + | m | Stomatobaculum longum | s | + | s | Atopobium | g | + |
| ge | Parvimonas | g | + | m | Blautia stercoris | s | + | s | Bacillales | o | + |
| ge | Tenericutes | p | + | m | Peptoniphilus sp. 1-14 | s | + | s | Bacillus | g | + |
| ge | Corynebacterium freiburgense | s | + | m | Peptoniphilus sp. 7-2 | s | + | s | Lysinibacillus sphaericus | s | + |
| ge | Delftia lacustris | s | − | m | Ralstonia sp. S2.MAC.005 | s | + | s | Clostridioides difficile | s | + |
| ge | Novosphingobium sediminicola | s | + | m | Stenotrophomonas sp. KITS-1 | s | − | s | Lactobacillus | g | − |
| ge | Butyricimonas | g | − | m | Alistipes sp. HGB5 | s | | s | Lactobacillus plantarum | s | − |
| ge | Bifidobacterium sp. 120 | s | − | m | Negativicoccus | g | − | s | Lactobacillus salivarius | s | − |
| ge | Brevibacterium massiliense | s | + | m | Shinella sp. DR33 | s | | s | Corynebacteriaceae | f | + |
| ge | Paraprevotella | g | − | m | Bacteroides sp. SLC1-38 | s | + | s | Actinomyces | g | + |
| ge | Parasutterella | g | − | m | Lactobacillus sp. Akhmr01 | s | + | s | Actinomyces odontolyticus | s | + |
| ge | Enterorhabdus | g | + | m | Veillonella sp. CM60 | s | + | s | Arthrobacter | g | + |
| ge | Negativicoccus succinicivorans | s | + | m | Actinomyces sp. ICM54 | s | + | s | Bifidobacterium | g | − |
| ge | Mycobacterium sp. T126 | s | + | m | Bifidobacterium sp. MSX5B | s | + | s | Brevibacterium | g | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | *Bacteroides clarus* | s | − | m | *Campylobacter* sp. FOBRC15 | s | − | s | *Corynebacterium* | g | − |
| ge | *Bifidobacterium kashiwanohense* | s | − | m | *Fusobacterium* sp. ACB2 | s | − | s | *Corynebacterium diphtheriae* | s | + |
| ge | *Porphyromonas* sp. 2024b | s | − | m | *Fusobacterium* sp. AS2 | s | − | s | *Propionibacterium* | g | + |
| ge | *Porphyromonas* sp. 2026 | s | − | m | *Fusobacterium* sp. CM21 | s | − | s | *Cutibacterium acnes* | s | + |
| ge | *Pyramidobacter* | g | + | m | *Veillonella* sp. AS16 | s | − | s | Mycobacteriaceae | f | − |
| ge | *Pseudoclavibacter* sp. Timone | s | + | m | *Veillonella* sp. MSA12 | s | − | s | *Mycobacterium* | g | − |
| ge | *Anaerostipes hadrus* | s | + | m | *Anaerococcus* sp. 8404299 | s | + | s | *Rhodococcus* | g | − |
| ge | Synergistia | c | + | m | *Anaerococcus* sp. 8405254 | s | + | s | *Rhodococcus erythropolis* | s | − |
| ge | Synergistales | o | + | m | *Anaerococcus* sp. 9401487 | s | + | s | Actinomycetales | o | + |
| ge | Synergistaceae | f | + | m | *Anaerococcus provencensis* | s | + | s | *Rothia dentocariosa* | s | + |
| ge | *Anaerosporobacter* | g | − | m | *Bradyrhizobium* sp. 68A4SAPT | s | − | s | Actinomycetaceae | f | + |
| ge | *Lactobacillus* sp. BL302 | s | − | m | *Delftia* sp. BN-SKY3 | s | + | s | *Mobiluncus* | g | − |
| ge | *Ochrobactrum* sp. SCTS14 | s | − | m | *Methylobacterium* sp. RK-2008-1 | s | − | s | *Mobiluncus curtisii* | s | − |
| ge | *Anaerostipes* sp. 3_2_56FAA | s | − | m | *Staphylococcus* sp. C9I2 | s | + | s | *Mobiluncus mulieris* | s | + |
| ge | *Campylobacter* sp. 10_1_50 | s | + | m | *Enterobacter* sp. BS2-1 | s | + | s | Mycoplasmatales | o | + |
| ge | *Lactobacillus* sp. 7_1_47FAA | s | + | m | *Megasphaera* sp. UPII 199-6 | s | − | s | Mycoplasmataceae | f | + |
| ge | *Veillonella* sp. oral taxon 780 | s | − | m | *Sphingomonas* sp. 540 | s | + | s | *Mycoplasma* | g | + |
| ge | *Microbacterium yannicii* | s | + | m | *Coprobacter fastidiosus* | s | + | s | Methanobacteriales | o | − |
| ge | *Corynebacterium canis* | s | + | m | *Actinomyces* sp. ICM58 | s | + | s | Methanobacteriaceae | f | − |
| ge | *Tessaracoccus* sp. SL014B-79A | s | + | m | Leptotrichiaceae | f | − | s | *Methanobrevibacter* | g | − |
| ge | *Peptoniphilus* sp. JCM 8143 | s | + | m | *Faecalibacterium* sp. canine oral taxon 147 | s | − | s | *Methanobrevibacter smithii* | s | − |
| ge | *Corynebacterium* sp. NML96-0085 | s | + | m | *Murdochiella* | g | + | s | *Gardnerella* | g | − |
| ge | *Anaerobacillus* | g | − | m | *Lachnoanaerobaculum* | g | + | s | *Gardnerella vaginalis* | s | − |
| ge | *Corynebacterium* sp. NML 97-0186 | s | + | m | *Streptococcus* sp. GMD6S | s | + | s | *Peptococcus* | g | − |
| ge | *Peptoniphilus* sp. oral taxon 375 | s | + | m | *Varibaculum* sp. CCUG 45114 | s | + | s | *Halomonas* | g | + |
| ge | *Brevundimonas* sp. V3M6 | s | + | m | *Stomatobaculum* | g | + | s | Solanales | o | − |
| ge | *Lactobacillus* sp. TAB-22 | s | + | m | *Prevotella* sp. S4-10 | s | − | s | *Sphingomonas* | g | − |
| ge | *Peptoniphilus coxii* | s | + | m | *Solobacterium* sp. S4-A19 | s | + | s | *Phyllobacterium* | g | + |
| ge | *Stomatobaculum longum* | s | + | m | *Streptococcus* sp. 2011_Oral_MS_A3 | s | − | s | *Bacteroides eggerthii* | s | − |
| ge | *Herbaspirillum huttiense* | s | + | m | *Veillonella* sp. 2011_Oral_VSA_D3 | s | + | s | *Odoribacter splanchnicus* | s | + |
| ge | *Bacteroides stercorirosoris* | s | + | m | *Eggerthia* | g | − | s | *Porphyromonas asaccharolytica* | s | + |
| ge | *Peptoniphilus* sp. 1-14 | s | + | m | *Alloprevotella* | g | − | s | *Prevotella bivia* | s | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | Peptoniphilus sp. 7-2 | s | + | m | Anaerococcus sp. S8 87-3 | s | + | s | Prevotella buccalis | s | + |
| ge | Streptococcus sp. XQ-1 | s | − | m | Porphyromonas sp. S8 86-12 | s | − | s | Alphaproteobacteria | c | − |
| ge | Stenotrophomonas sp. KITS-1 | s | + | m | Slackia sp. S8 F4 | s | + | s | Halomonadaceae | f | + |
| ge | Alistipes sp. HGB5 | s | − | m | Finegoldia sp. S9 AA1-5 | s | + | s | Gemella morbillorum | s | − |
| ge | Negativicoccus | g | + | m | Murdochiella sp. S9 PR-10 | s | + | s | Rhizobium etli | s | + |
| ge | Bacteroides sp. SLC1-38 | s | + | m | Peptoniphilus sp. S9 PR-13 | s | + | s | Veillonella | g | − |
| ge | Lactobacillus sp. Akhmro1 | s | + | m | Coprobacter | g | + | s | Veillonella parvula | s | − |
| ge | Acinetobacter sp. C-S-NA3 | s | − | m | Staphylococcus sp. 334802 | s | + | s | Epsilonproteobacteria | c | − |
| ge | Stenotrophomonas sp. C-S-TSA3 | s | − | m | Senegalimassilia | g | − | s | Bifidobacteriaceae | f | − |
| ge | Acinetobacter sp. RE 51 | s | − | m | Romboutsia | g | + | s | Propionibacteriacae | f | + |
| ge | Veillonella sp. CM60 | s | + | m | Terrisporobacter | g | + | s | Mollicutes | c | + |
| ge | Actinomyces sp. ICM54 | s | + | m | Intestinibacter | g | + | s | Rhodobacteraceae | f | + |
| ge | Bifidobacterium sp. MSX5B | s | + | m | Peptoniphilaceae | f | + | s | Burkholderia | g | + |
| ge | Campylobacter sp. FOBRC15 | s | + | m | Atopobiaceae | f | − | s | Xanthomonadaceae | f | − |
| ge | Fusobacterium sp. ACB2 | s | − | m | Tissierellia | c | + | s | Leptotrichia | g | − |
| ge | Fusobacterium sp. AS2 | s | − | m | Tissierellales | o | + | s | Cutibacterium avidum | s | + |
| ge | Fusobacterium sp. CM21 | s | + | m | Veillonellales | o | + | s | Anaerococcus hydrogenalis | s | − |
| ge | Veillonella sp. AS16 | s | − | m | Selenomonadaceae | f | + | s | Peptoniphilus lacrimalis | s | − |
| ge | Veillonella sp. MSA12 | s | − | m | Cutibacterium | g |   | s | Anaerococcus lactolyticus | s |   |
| ge | Anaerococcus sp. 8404299 | s | − | m | Tannerellaceae | f | + | s | Parvimonas micra | s | − |
| ge | Anaerococcus provencensis | s | + | m | Spirochaetales | o | − | s | Anaerococcus prevotii | s | − |
| ge | Bradyrhizobium sp. 68A4SAPT | s | + | m | Deinococcus | g | − | s | Anaerococcus tetradius | s | + |
| ge | Sphingomonas sp. 24T | s | − | m | Lactococcus | g | + | s | Anaerococcus vaginalis | s | − |
| ge | Enterococcus sp. SI-4 | s | + | m | Johnsonella | g | + | s | Microbacterium | g | − |
| ge | Bosea sp. R-46060 | s | + | m | Deinococcaceae | f | − | s | Streptophyta | p | − |
| ge | Lactobacillus sp. MYMRS/TEN2 | s | − | m | Spirochaetes | p | − | s | Bilophila | g | + |
| ge | Delftia sp. BN-SKY3 | s | − | m | Spirochaetia | c | − | s | Dermabacter hominis | s | + |
| ge | Moraxella sp. 26 | s | − | m | Phascolarctobacterium succinatutens | s | − | s | Veillonella atypica | s | + |
| ge | Staphylococcus sp. WB18-16 | s | − | m | Campylobacter showae | s | + | s | Corynebacterium glucuronolyticum | s | − |
| ge | Methylobacterium sp. RK-2008-1 | s | + | m | Comamonas | g | − | s | Stenotrophomonas | g | − |
| ge | Enterococcus sp. C6I11 | s | + | m | Neisseria flavescens | s | − | s | Brevundimonas | g | − |
| ge | Staphylococcus sp. C9I2 | s | − | m | Neisseria sicca | s | + | s | Bradyrhizobiaceae | f | + |
| ge | Brachybacterium sp. NIO-27 | s | + | m | Neisseria canis | s | + | s | Rhodospirillaceae | f | − |
| ge | Megasphaera sp. UPII 199-6 | s | + | m | Bergeriella denitrificans | s | − | s | Sphingomonadaceae | f | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | Megasphaera sp. UPII 135-E | s | − | m | Kingella oralis | s | − | s | Corynebacterium argentoratense | s | + |
| ge | Sphingomonas sp. 540 | s | − | m | Eikenella | g | + | s | Brachybacterium | g | + |
| ge | Corynebacterium epidermidicanis | s | + | m | Eikenella corrodens | s | + | s | Abiotrophia | g | + |
| ge | Trueperella | g | − | m | Aggregatibacter aphrophilus | s | + | s | Granulicatella adiacens | s | + |
| ge | Mesorhizobium sp. mat916 | s | − | m | Aggregatibacter segnis | s | − | s | Abiotrophia defectiva | s | + |
| ge | Coprobacter fastidiosus | s | + | m | Pasteurella | g | − | s | Parabacteroides merdae | s | + |
| ge | Actinomyces sp. ICM58 | s | + | m | Rodentibacter pneumotropicus | s | − | s | Bacteroides stercoris | s | + |
| ge | Jonquetella sp. BV3C4 | s | + | m | Porphyromonas gingivalis | s | + | s | Lautropia | g | + |
| ge | Prevotella sp. BV3C7 | s | + | m | Cardiobacteriaceae | f | + | s | Lactobacillus crispatus | s | − |
|  | Peptoniphilus sp. BV3AC2 | s | − | m | Desulfobulbus | g | − | s | Ralstonia | g | + |
| ge | Megasphaera sp. BV3C16-1 | s | + | m | Selenomonas | g | − | s | Flavobacteriaceae | f | − |
| ge | Sphingobium sp. LC341 | s | − | m | Capnocytophaga | g | + | s | Actinobacillus porcinus | s | + |
| ge | Anaerococcus sp. PH9 | s | + | m | Capnocytophaga gingivalis | s | + | s | Pantoea | g | + |
| ge | Leptotrichiaceae | f | − | m | Capnocytophaga sputigena | s | − | s | Anaerococcus octavius | s | − |
| ge | Faecalibacterium sp. canine oral taxon 147 | s | − | m | Cyanobacteria | p | + | s | Kocuria | g | − |
| ge | Murdochiella | g | + | m | Streptococcus mutans | s | + | s | Chryseobacterium | g | − |
| ge | Lachnoanaerobaculum | g | + | m | Streptococcus intermedius | s | − | s | Bergeyella | g | + |
| ge | Streptococcus sp. GMD6S | s | + | m | Atopobium parvulum | s | − | s | Corynebacterium ulcerans | s | + |
| ge | Varibaculum sp. CCUG 45114 | s | − | m | Atopobium rimae | s | − | s | Facklamia | g | + |
| ge | Varibaculum sp. CCUG 61255 | s | + | m | Lactobacillus paracasei | s | − | s | Mesorhizobium | g | − |
| ge | Propionibacterium sp. KPL2005 | s | + | m | Actinomyces viscosus | s | − | s | Phyllobacteriaceae | f | − |
| ge | Stomatobaculum | g | + | m | Bifidobacterium adolescentis | s | − | s | Kocuria rhizophila | s | + |
| ge | Actinomyces sp. S4C9 | s | − | m | Pseudopropionibacterium propionicum | s | + | s | Pseudomonadales | o | − |
| ge | Atopobium sp. MVA9 | s | − | m | Anaeroplasma | g | + | s | Campylobacteraceae | f | − |
| ge | Atopobium sp. S3MV24 | s | + | m | Asteroleplasma | g | + | s | Tessaracoccus | g | − |
| ge | Atopobium sp. S3MV26 | s | + | m | Methanosphaera | g | + | s | Kluyvera georgiana | s | + |
| ge | Atopobium sp. S3PFAA1-4 | s | + | m | Methanosphaera stadtmanae | s | + | s | Collinsella aerofaciens | s | + |
| ge | Atopobium sp. S4-5 | s | − | m | Cardiobacterium | g | + | s | Caulobacteraceae | f | − |
| ge | Atopobium sp. S4-A11a | s | + | m | Vagococcus | g | + | s | Halomonas pacifica | s | + |
| ge | Dialister sp. S4-23 | s | + | m | Streptococcus mitis | s | − | s | Bacillus pseudofirmus | s | − |
| ge | Finegoldia sp. S3MVA9 | s | − | m | Tannerella forsythia | s | − | s | Comamonadaceae | f | + |
| ge | Gardnerella sp. S3PF20 | s | + | m | Porphyromonas endodontalis | s | − | s | Delftia | g | + |
| ge | Peptoniphilus sp. S4-13 | s | + | m | Prevotella intermedia | s | − | s | Enterococcaceae | f | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | *Prevotella* sp. S4-10 | s | + | m | *Prevotella oralis* | s | − | s | Rhizobiaceae | f | + |
| ge | *Solobacterium* sp. S4-A19 | s | + | m | *Prevotella oris* | s | − | s | *Facklamia languida* | s | + |
| ge | *Peptoniphilus* sp. S4-A10 | s | − | m | *Prevotella oulorum* | s | + | s | *Gemella* sp. 933-88 | s | + |
| ge | *Finegoldia* sp. S5-A7 | s | + | m | *Acetitomaculum* | g | − | s | Bifidobacteriales | o | − |
| ge | *Negativicoccus* sp. S5-A15 | s | − | m | *Kingella* | g | − | s | Micrococcales | o | + |
| ge | *Corynebacterium frankenforstense* | s | + | m | *Terrisporobacter glycolicus* | s | + | s | Propionibacteriales | o | + |
| ge | *Megasphaera massiliensis* | s | − | m | *Veillonella dispar* | s | − | s | Brevibacteriaceae | f | + |
| ge | *Corynebacterium* sp. jw37 | s | + | m | *Leptotrichia buccalis* | s | − | s | Dermabacteraceae | f | + |
| ge | *Streptococcus* sp. 2011_Oral_MS_A3 | s | − | m | *Porphyromonas catoniae* | s | + | s | Microbacteriaceae | f | − |
| ge | *Veillonella* sp. 2011_Oral_VSA_D3 | s | − | m | *Corynebacterium matruchotii* | s | + | s | Nocardiaceae | f | − |
| ge | *Eggerthia* | g | − | m | *Catonella* | g | − | s | *Bosea* | g | − |
| ge | *Alloprevotella* | g | + | m | *Catonella morbi* | s | − | s | *Achromobacter xylosoxidans* | s | − |
| ge | *Dialister* sp. S7MSR5 | s | − | m | *Filifactor* | g | − | s | *Mogibacterium* | g | + |
| ge | *Intestinimonas butyriciproducens* | s | − | m | *Capnocytophaga granulosa* | s | − | s | *Propionibacterium* sp. V07/12348 | s | − |
| ge | *Lactobacillus* sp. C30An8 | s | + | m | *Capnocytophaga haemolytica* | s | + | s | *Lactobacillus fornicalis* | s | + |
| ge | *Bradyrhizobium* sp. CCBAU 53380 | s | − | m | *Actinomyces georgiae* | s | − | s | Staphylococcaceae | f | − |
| ge | *Anaerococcus* sp. S8 87-3 | s | + | m | *Actinomyces meyeri* | s | − | s | Enterobacterales | o | − |
| ge | *Finegoldia* sp. S8 F7 | s | − | m | *Actinomyces graevenitzii* | s | + | s | *Aquabacterium* | g | + |
| ge | *Porphyromonas* sp. S8 86-12 | s | − | m | Acidobacteria | p | + | s | *Aquabacterium* sp. Aqua2 | s | + |
| ge | *Slackia* sp. S8 F4 | s | + | m | *Prevotella pallens* | s | + | s | Candidatus Saccharibacteria | p | + |
| ge | *Actinomyces* sp. S9 PR-21 | s | + | m | *Corynebacterium durum* | s | − | s | *Solobacterium moorei* | s | − |
| ge | *Anaerococcus* sp. S9 PR-16 | s | − | m | *Streptococcus peroris* | s | − | s | *Lactobacillus jensenii* | s | + |
| ge | *Anaerococcus* sp. S9 PR-5 | s | − | m | *Mannheimia* | g | + | s | *Granulicatella* | g | − |
| ge | *Finegoldia* sp. S9 AA1-5 | s | − | m | *Alloprevotella tannerae* | s | − | s | Flavobacteriia | c | − |
| ge | *Olsenella* sp. S9 HS-6 | s | − | m | *Centipeda* | g | + | s | Brucellaceae | f | + |
| ge | *Peptococcus* sp. S9 B-15 | s | − | m | *Centipeda periodontii* | s | + | s | Deinococcales | o | + |
| ge | *Peptococcus* sp. S9 Pr-12 | s | − | m | *Cryptobacterium* | g | − | s | Methylobacteriaceae | f | − |
| ge | *Peptoniphilus* sp. S9 PR-13 | s | + | m | *Cryptobacterium curtum* | s | − | s | Burkholderiaceae | f | + |
| ge | *Coprobacter* | g | + | m | *Rothia* sp. CCUG 25688 | s | − | s | *Solobacterium* | g | − |
| ge | *Corynebacterium* sp. 713182/2012 | s | − | m | *Mannheimia granulomatis* | s | − | s | *Pseudomonas brenneri* | s | − |
| ge | *Atopobium deltae* | s | − | m | *Mogibacterium pumilum* | s | + | s | *Actinomyces radingae* | s | − |
| ge | *Parvibacter* | g | − | m | *Mycoplasma falconis* | s | + | s | Chromatiales | o | + |
| ge | *Ralstonia* sp. A52 | s | − | m | *Mycoplasma subdolum* | s | − | s | Xanthomonadales | o | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| ge | *Helcococcus seattlensis* | s | + | m | *Pseudoflavonifractor capillosus* | s | + | s | Oceanospirillales | o | + |
| ge | *Staphylococcus* sp. 334802 | s | + | m | *Leptotrichia trevisanii* | s | + | s | Pseudomonadaceae | f | − |
| ge | *Senegalimassilia* | g | + | m | Sphingobacteriia | c | + | s | Pasteurellales | o | − |
| ge | *Peptoniphilus* sp. DNF00840 | s | − | m | Cardiobacteriales | o | + | s | *Aerosphaera* | g | − |
| ge | *Romboutsia* | g | + | m | *Filifactor alocis* | s | − | s | *Aerosphaera taetra* | s | − |
| ge | *Veillonella seminalis* | s | + | m | *Turicibacter sanguinis* | s | + | s | *Granulicatella elegans* | s | − |
| ge | *Terrisporobacter* | g | + | m | *Leptotrichia wadei* | s | + | s | *Lactobacillus iners* | s | + |
| ge | *Intestinibacter* | g | + | m | *Leptotrichia hofstadii* | s | − | s | *Finegoldia* | g | − |
| ge | Atopobiaceae | f | + | m | *Leptotrichia shahii* | s | + | s | *Anoxybacillus* | g | − |
| ge | *Actinotignum* | g | + | m | *Leptotrichia goodfellowii* | s | − | s | *Megamonas* | g | − |
| ge | Veillonellales | o | + | m | *Actinomyces* sp. oral strain Hal-1065 | s | − | s | *Corynebacterium mastitidis* | s | + |
| ge | Selenomonadaceae | f | − | m | *Anaerotruncus colihominis* | s |   | s | *Peptoniphilus* | g | − |
| ge | *Cutibacterium* | g | + | m | *Rothia aeria* | s | − | s | *Gallicola* | g | − |
| ge | Tannerellaceae | f | − | m | *Victivallis* | g | + | s | *Sphingobium* | g | + |
| ge | Spirochaetales | o | + | m | Anaeroplasmatales | o | + | s | *Novosphingobium* | g | + |
| ge | *Deinococcus* | g | + | m | Anaeroplasmataceae | f | + | s | *Anaerococcus* | g | + |
| ge | *Johnsonella* | g | − | m | *Turicibacter* | g | + | s | *Thalassospira* | g | − |
| ge | Deinococcaceae | f | − | m | *Alysiella* | g | − | s | Porphyromonadaceae | f | − |
| ge | Spirochaetes | p | + | m | *Cardiobacterium valvarum* | s | + | s | Prevotellaceae | f | − |
| ge | Spirochaetia | c | + | m | *Tannerella* | g | − | s | *Lactobacillus* sp. CR-609S | s | + |
| ge | *Bacteroides* sp. XB44A | s | − | m | *Scardovia* | g | − | s | Methanobacteria | c | − |
| ge | *Lactobacillus taiwanensis* | s | − | m | Sphingobacteriales | o | + | s | *Varibaculum* | g | + |
| g | Bacteroidaceae | f | − | m | Acidobacteriia | c | + | s | *Varibaculum cambriense* | s | + |
| g | *Bacteroides* | g | − | m | Acidobacteriales | o | + | s | *Corynebacterium spheniscorum* | s | + |
| g | *Bacteroides thetaiotaomicron* | s | − | m | Desulfobacterales | o | − | s | Peptococcaceae | f | + |
| g | *Bacteroides vulgatus* | s | − | m | Desulfobulbaceae | f | − | s | Bacillaceae | f | + |
| g | *Roseburia* | g | + | m | *Leptotrichia* genomosp. C1 | s | − | s | Aerococcaceae | f | + |
| g | *Faecalibacterium prausnitzii* | s | + | m | *Megasphaera* genomosp. C1 | s | − | s | Carnobacteriaceae | f | + |
| g | *Desulfovibrio* | g | − | m | *Scardovia wiggsiae* | s | − | s | Deinococci | c | + |
| g | *Desulfovibrio* sp. | s | − | m | *Selenomonas* genomosp. P5 | s | − | s | *Propionibacterium* sp. MSP09A | s | + |
| g | *Acidaminococcus* | g | − | m | Victivallaceae | f | + | s | Flavobacteriales | o | − |
| g | *Herbaspirillum* | g | + | m | Lentisphaerae | p | + | s | *Propionimicrobium* | g | + |
| g | *Herbaspirillum seropedicae* | s | + | m | *Neisseria bacilliformis* | s | − | s | Fusobacteriaceae | f | − |
| g | Bacteroidetes | p | − | m | *Actinomyces dentalis* | s | − | s | Rhodospirillales | o | − |
| g | Proteobacteria | p | − | m | Victivallales | o | + | s | Rhodobacterales | o | + |
| g | Firmicutes | p | + | m | *Bacteroides nordii* | s |   | s | Sphingomonadales | o | − |
| g | *Sarcina* | g | − | m | *Capnocytophaga* genosp. AHN8471 | s | − | s | Caulobacterales | o | − |
| g | *Clostridium* | g | + | m | *Capnocytophaga* sp. AHN10044 | s |   | s | *Bacteroides massiliensis* | s | + |
| g | Actinobacteria | c | + | m | *Capnocytophaga* sp. AHN9576 | s | − | s | Neisseriales | o | + |
| g | *Lachnospira* | g | + | m | *Capnocytophaga* sp. AHN9687 | s | + | s | Campylobacterales | o | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | *Lachnospira pectinoschiza* | s | + | m | *Bergeriella* | g | − | s | *Subdoligranulum variabile* | s | − |
| g | Betaproteobacteria | c | − | m | *Streptococcus dentirousetti* | s | + | s | *Alistipes finegoldii* | s | + |
| g | Deltaproteobacteria | c | − | m | *Parabacteroides johnsonii* | s | + | s | *Bifidobacterium longum* | s | − |
| g | Veillonellaceae | f | − | m | *Howardella ureilytica* | s |   | s | *Dialister invisus* | s | + |
| g | Clostridiaceae | f | + | m | Opitutae | c |   | s | *Peptoniphilus* sp. 2002-38328 | s | − |
| g | *Phascolarctobacterium* | g | − | m | Puniceicoccales | o |   | s | *Peptoniphilus* sp. 2002-2300004 | s | − |
| g | *Phascolarctobacterium faecium* | s |   | m | *Aggregatibacter* | g | − | s | *Curvibacter gracilis* | s | + |
| g | Lactobacillaceae | f | + | m | *Prevotella nanceiensis* | s | − | s | *Bacillus* sp. T41 | s | + |
| g | *Dorea formicigenerans* | s | − | m | *Prevotella maculosa* | s | + | s | *Sutterella stercoricanis* | s | − |
| g | *Pseudobutyrivibrio* | g | + | m | *Veillonella* sp. 6_1_27 | s | − | s | *Bacteroides* sp. 35AE37 | s | + |
| g | Verrucomicrobiales | o | − | m | *Actinomyces massiliensis* | s | + | s | *Pseudoclavibacter* | g | + |
| g | *Holdemania* | g | − | m | *Lachnoanaerobaculum saburreum* | s | + | s | *Oribacterium* | g | − |
| g | *Holdemania filiformis* | s | − | m | *Bacteroides* sp. 2_2_4 | s | + | s | *Curvibacter* | g | + |
| g | Fibrobacteres | p | − | m | *Bacteroides* sp. 3_1_40A | s | − | s | *Porphyromonas uenonis* | s | + |
| g | Verrucomicrobia | p | − | m | *Gordonibacter pamelaeae* | s |   | s | *Odoribacter* | g | + |
| g | Oxalobacteraceae | f | + | m | *Atopobium* sp. DMCT15023 | s | − | s | *Dialister propionicifaciens* | s | − |
| g | Burkholderiales | o | − | m | *Olsenella* sp. F0004 | s | − | s | *Dialister micraerophilus* | s | − |
| g | Coriobacteriaceae | f | + | m | *Blautia glucerasea* | s | + | s | *Bacteroides plebeius* | s | + |
| g | *Eggerthella* | g | − | m | *Bacteroides* sp. DJF_B097 | s | + | s | *Bacteroides coprocola* | s | − |
| g | Coriobacteriia | c | + | m | *Actinomyces oris* | s | − | s | *Alistipes shahii* | s | + |
| g | Coriobacteriales | o | + | m | *Butyricimonas virosa* | s | − | s | *Peptoniphilus* sp. gpac018A | s | + |
| g | *Blautia luti* | s | + | m | *Leptotrichia hongkongensis* | s | − | s | *Peptoniphilus* sp. gpac148 | s | − |
| g | *Bacteroides* sp. AR29 | s | − | m | Chitinophagaceae | f | + | s | *Bacteroides* sp. XB12B | s | − |
| g | *Collinsella* | g | + | m | *Robinsoniella* | g | + | s | *Moryella indoligenes* | s | − |
| g | *Oscillospira* | g | − | m | *Propionibacterium* sp. 'Oral Taxon 191' | s | + | s | *Anoxybacillus* sp. HT14 | s | − |
| g | Bacteroidales | o | − | m | *Prevotella aurantiaca* | s |   | s | *Prevotella timonensis* | s | − |
| g | Rikenellaceae | f | + | m | *Neisseria shayeganii* | s | + | s | *Barnesiella* | g | − |
| g | Clostridia | c | + | m | *Lachnoanaerobaculum umeaense* | s | − | s | *Lysinibacillus* | g | + |
| g | Clostridiales | o | + | m | *Odoribacter laneus* | s | + | s | *Citrobacter* sp. BW4 | s | + |
| g | Lachnospiraceae | f | + | m | *Gordonibacter* | g | + | s | *Pseudomonas* sp. G1116 | s | + |
| g | Peptostreptococcaceae | f | + | m | *Fretibacterium fastidiosum* | s | − | s | *Anaerococcus murdochii* | s | − |
| g | Lactobacillales | o | + | m | *Oribacterium* sp. oral taxon 078 | s | + | s | *Acinetobacter* sp. RBE2CD-114 | s | − |
| g | *Dorea* | g | + | m | *Prevotella* sp. oral taxon 299 | s | − | s | *Streptococcus* sp. 11aTha1 | s | + |
| g | Desulfovibrionaceae | f | − | m | *Leptotrichia* sp. oral taxon 225 | s | − | s | *Methylobacterium* sp. CBMB45 | s | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | Bacteroidia | c | − | m | Oribacterium sp. oral taxon 102 | s | − | s | Megamonas funiformis | s | − |
| g | Actinobacteria | p | + | m | Alloprevotella rava | s | + | s | Alistipes sp. EBA6-25cl2 | s | + |
| g | Verrucomicrobiae | c | − | m | Parvimonas sp. oral taxon 110 | s | − | s | Bacteroides sp. EBA5-17 | s | + |
| g | Verrucomicrobiaceae | f | − | m | Prevotella sp. WAL 2039G | s | − | s | Paraprevotella clara | s | − |
| g | Fibrobacteria | c | − | m | Neisseria skkuensis | s | − | s | Serratia nematodiphila | s | − |
| g | Fibrobacteraceae | f | − | m | Capnocytophaga sp. oral taxon 329 | s | + | s | Oscillibacter | g | − |
| g | Anaerostipes | g | + | m | Actinomyces sp. oral taxon 178 | s | + | s | Anaerobacillus alkalidiazotrophicus | s | + |
| g | Desulfovibrionales | o | − | m | Capnocytophaga sp. oral taxon 338 | s | − | s | Rhodopseudomonas boonkerdii | s | + |
| g | Oscillospiraceae | f | − | m | Actinomyces sp. oral taxon 170 | s | − | s | Alistipes sp. NML05A004 | s | + |
| g | Faecalibacterium | g | + | m | Actinomyces sp. oral taxon 448 | s | + | s | Dialister succinatiphilus | s | + |
| g | Fibrobacterales | o | − | m | Capnocytophaga sp. oral taxon 335 | s | + | s | Barnesiella intestinihominis | s | − |
| g | Alistipes | g | + | m | Capnocytophaga sp. oral taxon 336 | s | + | s | Parasutterella excrementihominis | s | − |
| g | Akkermansia | g | − | m | Desulfobulbus sp. oral taxon 041 | s | − | s | Pseudomonas sp. GmFRB023 | s | − |
| g | Akkermansia muciniphila | s | − | m | Leptotrichia sp. oral taxon 223 | s | + | s | Porphyromonas bennonis | s | − |
| g | Hespellia | g | − | m | Oribacterium sp. oral taxon 108 | s | + | s | Cloacibacterium | g | − |
| g | Anaerotruncus | g | + | m | Shuttleworthia sp. oral taxon G69 | s | − | s | Bosea sp. BIWAKO-01 | s | + |
| g | Marvinbryantia | g | − | m | Streptococcus sp. oral taxon G63 | s | + | s | Synergistetes | p | + |
| g | Subdoligranulum | g | + | m | Tannerella sp. oral taxon HOT-286 | s | + | s | Clostridiales f XI. Incertae Sedis | f | − |
| g | Flavonifractor plautii | s | − | m | Parvimonas sp. oral taxon 393 | s | − | s | Parvimonas | g | − |
| g | Lactonifactor longoviformis | s | − | m | Caldicoprobacteraceae | f | − | s | Tenericutes | p | + |
| g | Lactonifactor | g | − | m | Leptotrichia sp. PG10 | s | − | s | Corynebacterium freiburgense | s | + |
| g | Moryella | g | − | m | Leptotrichia sp. PTE15 | s | + | s | Delftia lacustris | s | + |
| g | Adlercreutzia equolifaciens | s | − | m | Methylobacterium longum | s | − | s | Novosphingobium sediminicola | s | + |
| g | Adlercreutzia | g | − | m | Capnocytophaga sp. CM59 | s | + | s | Paraprevotella | g | − |
| g | Erysipelotrichia | c | − | m | Mogibacterium sp. CM50 | s | − | s | Parasutterella | g | − |
| g | Erysipelotrichales | o | − | m | Mogibacterium sp. CM96 | s | − | s | Enterorhabdus | g | − |
| g | Ruminococcaceae | f | + | m | Selenomonas sp. CM52 | s | + | s | Phyllobacterium sp. T50 | s | − |
| g | Clostridiales f XIII. Incertae Sedis | f | + | m | Actinomyces sp. ICM41 | s | − | s | Negativicoccus succinicivorans | s | − |
| g | Acidaminococcus sp. D21 | s | − | m | Actinomyces sp. ICM47 | s | + | s | Bacteroides clarus | s | + |
| g | Blautia | g | + | m | Atopobium sp. ICM57 | s | + | s | Porphyromonas sp. 2024b | s | + |
| g | Roseburia sp. 11SE39 | s | + | m | Fusobacterium sp. CM22 | s | − | s | Lautropia sp. TeTO | s | − |
| g | Bacteroides sp. D22 | s | − | m | Oribacterium sp. CM12 | s | + | s | Pseudoclavibacter sp. Timone | s | + |
| g | Blautia sp. Ser8 | s | + | m | Oribacterium sp. OBRC12 | s | − | s | Anaerostipes hadrus | s | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | *Blautia faecis* | s | + | m | *Lachnoanaerobaculum* sp. OBRC5-5 | s | + | s | Synergistia | c | + |
| g | Selenomonadales | o | − | m | *Lachnoanaerobaculum* sp. MSX33 | s | + | s | Synergistales | o | + |
| g | Acidaminococca ceae | f | − | m | *Vagococcus* sp. SIX2(2011) | s | − | s | Synergistaceae | f | + |
| g | Negativicutes | c | − | m | *Lachnoanaerobaculum orale* | s | + | s | *Klebsiella* sp. B12 | s | − |
| g | *Eggerthella* sp. HGA1 | s | − | m | *Actinomyces* sp. ZSY-1 | s | + | s | *Anaerosporobacter* | g | − |
| g | *Flavonifractor* | g | − | m | *Pseudomonas* sp. KB23 | s | − | s | *Lactobacillus* sp. BL302 | s | + |
| g | Sutterellaceae | f | − | m | *Pseudoflavonifractor* | g | + | s | *Ochrobactrum* sp. SCTS14 | s | + |
| g | *Anaerostipes* sp. 5_1_63FAA | s | + | m | *Fusobacterium* sp. OBRC1 | s | − | s | *Lactobacillus* sp. 7_1_47FAA | s | + |
| g | *Fusicatenibacter saccharivorans* | s | + | m | *Dielma fastidiosa* | s | − | s | *Veillonella* sp. oral taxon 780 | s | + |
| g | *Blautia* sp. YHC-4 | s | − | m | *Veillonella* sp. JL-2 | s | − | s | *Microbacterium yannicii* | s | + |
| g | *Intestinimonas* | g | − | m | *Neisseria oralis* | s | − | s | *Corynebacterium canis* | s | + |
| g | *Fusicatenibacter* | g | + | m | *Veillonella tobetsuensis* | s | + | s | *Bilophila* sp. 4_1_30 | s | + |
| g | *Eisenbergiella* | g | − | m | *Actinomyces* sp. ph3 | s | − | s | *Anaerobacillus* | g | + |
| g | *Eisenbergiella tayi* | s | − | m | *Neisseria* sp. 104(2012) | s | + | s | *Corynebacterium* sp. NML 97-0186 | s | − |
| g | Candidatus Soleaferrea | g | + | m | *Phascolarctobacterium* sp. 377 | s | | s | *Actinomyces* sp. oral taxon 175 | s | − |
| g | *Campylobacter concisus* | s | − | m | *Streptococcus* sp. 2011_Oral_MS_H4 | s | + | s | *Peptococcus* sp. oral taxon 168 | s | − |
| g | *Campylobacter rectus* | s | − | m | *Veillonella* sp. 2011_Oral_VSA_B12 | s | + | s | *Peptoniphilus* sp. oral taxon 375 | s | − |
| g | *Achromobacter* | g | + | m | *Veillonella* sp. 2011_Oral_VSA_C9 | s | + | s | *Streptococcus* sp. oral taxon G59 | s | + |
| g | *Flavobacterium* | g | + | m | *Rothia* sp. THG-N7 | s | + | s | *Brevundimonas* sp. V3M6 | s | + |
| g | Rhizobiales | o | + | m | *Capnocytophaga* sp. HS5_2W_I24 | s | − | s | *Lactobacillus* sp. TAB-22 | s | − |
| g | *Rhizobium* | g | + | m | *Actinomyces* sp. S6-Spd3 | s | + | s | *Stomatobaculum longum* | s | + |
| g | *Mesorhizobium loti* | s | − | m | Lentisphaeria | c | + | s | *Herbaspirillum huttiense* | s | + |
| g | Moraxellaceae | f | + | m | Candidatus Saccharimonas | g | + | s | *Blautia stercoris* | s | + |
| g | *Acinetobacter* | g | + | m | *Bacteroides* sp. J1511 | s | + | s | *Peptoniphilus* sp. 1-14 | s | − |
| g | *Moraxella* | g | + | m | *Tessaracoccus lapidicaptus* | s | + | s | *Peptoniphilus* sp. 7-2 | s | + |
| g | Neisseriaceae | f | + | m | *Prevotella* sp. HJM029 | s | + | s | *Ralstonia* sp. S2.MAC.005 | s | + |
| g | *Neisseria* | g | + | m | *Fretibacterium* | g | − | s | *Stenotrophomonas* sp. KITS-1 | s | + |
| g | *Neisseria mucosa* | s | + | m | *Butyricimonas faecihominis* | s | + | s | *Negativicoccus* | g | − |
| g | Alcaligenaceae | f | − | m | *Butyricimonas paravirosa* | s | | s | *Shinella* sp. DR33 | s | + |
| g | *Ochrobactrum* | g | + | m | *Aeromonas* | g | + | s | *Acinetobacter* sp. C-S-NA3 | s | − |
| g | Enterobacteriaceae | f | − | m | *Roseburia cecicola* | s | − | s | *Stenotrophomonas* sp. C-S-TSA3 | s | + |
| g | *Citrobacter* | g | + | m | *Fusobacterium ulcerans* | s | − | s | *Veillonella* sp. CM60 | s | − |
| g | *Enterobacter* | g | − | m | *Rhodobacter* | g | + | s | *Actinomyces* sp. ICM54 | s | + |
| g | *Klebsiella* | g | − | m | Oscillatoriales | o | + | s | *Veillonella* sp. AS16 | s | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | Kluyvera | g | − | m | Leuconostoc | g | − | s | Veillonella sp. MSA12 | s | + |
| g | Proteus mirabilis | s | + | m | Blautia hansenii | s | − | s | Anaerococcus sp. 8405254 | s | + |
| g | Serratia | g | + | m | Streptococcus equinus | s | + | s | Anaerococcus sp. 9401487 | s | − |
| g | Haemophilus influenzae | s | + | m | Acholeplasmataceae | f | + | s | Anaerococcus provencensis | s | − |
| g | Bacteroides fragilis | s | − | m | Acholeplasma | g | + | s | Sphingomonas sp. 24T | s | + |
| g | Parabacteroides distasonis | s | − | m | Bifidobacterium animalis | s | + | s | Enterococcus sp. SI-4 | s | + |
| g | Campylobacter gracilis | s | − | m | Bacteroides ovatus | s | − | s | Bosea sp. R-46060 | s | − |
| g | Campylobacter ureolyticus | s | − | m | Leuconostocaceae | f | − | s | Delftia sp. BN-SKY3 | s | − |
| g | Porphyromonas | g | − | m | Aeromonadaceae | f | + | s | Moraxella sp. 26 | s | + |
| g | Prevotella | g | + | m | Aeromonadales | o | + | s | Staphylococcus sp. WB18-16 | s | + |
| g | Fusobacterium | g | + | m | Acholeplasmatales | o | + | s | Methylobacterium sp. RK-2008-1 | s | − |
| g | Fusobacterium mortiferum | s | + | m | Planococcaceae | f | + | s | Enterococcus sp. C6I11 | s | − |
| g | Fusobacterium nucleatum | s | + | m | Acidobacteriaceae | f |   | s | Staphylococcus sp. C9I2 | s | − |
| g | Fusobacterium periodonticum | s | + | m | Anaerosporobacter mobilis | s | − | s | Brachybacterium sp. NIO-27 | s | + |
| g | Megasphaera | g | − | m | Alistipes massiliensis | s | − | s | Sphingomonas sp. 540 | s | − |
| g | Gammaproteobacteria | c | − | m | Veillonella sp. ADV 269.01 | s | − | s | Corynebacterium epidermidicanis | s | − |
| g | Peptostreptococcus | g | − | m | Bacteroides coprophilus | s | − | s | Mesorhizobium sp. mat916 | s | − |
| g | Micrococcaceae | f | + | m | Paraprevotella xylaniphila | s | − | s | Murdochiella | g | + |
| g | Staphylococcus aureus | s | + | m | Alistipes indistinctus | s | + | s | Lachnoanaerobaculum | g | + |
| g | Streptococcus gordonii | s | + | m | Aeromonas sp. B11 | s | + | s | Streptococcus sp. GMD6S | s | + |
| g | Streptococcus parasanguinis | s | − | m | Pseudomonas sp. a111-5 | s | + | s | Varibaculum sp. CCUG 45114 | s | − |
| g | Streptococcus anginosus | s | + | m | Lactococcus sp. MH5-2 | s | − | s | Varibaculum sp. CCUG 61255 | s | + |
| g | Streptococcus dysgalactiae | s | − | m | Leuconostoc sp. C7I4 | s | − | s | Propionibacterium sp. KPL2005 | s | + |
| g | Enterococcus faecalis | s | − | m | Butyricimonas sp. 214-4 | s | + | s | Stomatobaculum | g | + |
| g | Aerococcus | g | + | m | Sutterella sp. 252 | s | + | s | Actinomyces sp. S4-C9 | s | − |
| g | Aerococcus urinae | s | − | m | Solanaceae | f | − | s | Atopobium sp. S3MV24 | s | + |
| g | Atopobium | g | + | m | Staphylococcus saprophyticus | s | − | s | Negativicoccus sp. S5-A15 | s | − |
| g | Atopobium minutum | s | + | m | Cutibacterium granulosum | s | + | s | Corynebacterium sp. jw37 | s | + |
| g | Bacillus | g | − | m | Intrasporangiaceae | f | + | s | Streptococcus sp. 2011_Oral_MS_A3 | s | − |
| g | Lysinibacillus sphaericus | s | − | m | Actinomyces genomosp. C1 | s | + | s | Veillonella sp. 2011_Oral_VSA_D3 | s | + |
| g | Erysipelatoclostridium ramosum | s | − | m | Cytophagia | c | − | s | Alloprevotella | g | + |
| g | Lactobacillus acidophilus | s | + | m | Cytophagales | o | − | s | Dialister sp. s7MSR5 | s | − |
| g | Lactobacillus plantarum | s | − | m | Simonsiella | g | + | s | Bradyrhizobium sp. CCBAU 53380 | s | + |
| g | Lactobacillus gasseri | s | + | m | Simonsiella muelleri | s | + | s | Anaerococcus sp. S8 F2 | s | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | *Lactobacillus fermentum* | s | − | m | *Streptobacillus* | g | + | s | *Finegoldia* sp. S8 F7 | s | − |
| g | *Lactobacillus salivarius* | s | − | m | *Kocuria kristinae* | s | − | s | *Finegoldia* sp. S9 AA1-5 | s | + |
| g | *Lactobacillus vaginalis* | s | − | m | *Janibacter* | g | + | s | *Murdochiella* sp. S9 PR-10 | s | + |
| g | Corynebacteriaceae | f | − | m | *Planomicrobium* | g | + | s | *Peptococcus* sp. S9 Pr-12 | s | − |
| g | *Actinomyces odontolyticus* | s | − | m | *Neisseria wadsworthii* | s | − | s | *Peptoniphilus* sp. S9 PR-13 | s | − |
| g | *Arthrobacter* | g | + | m | *Burkholderia* sp. S32 | s | + | s | *Corynebacterium* sp. 713182/2012 | s | + |
| g | *Arthrobacter* sp. | s | + | m | *Necropsobacter* | g | − | s | *Ralstonia* sp. A52 | s | + |
| g | *Bifidobacterium bifidum* | s | − | m | *Necropsobacter rosorum* | s | − | s | *Staphylococcus* sp. 3348O2 | s | + |
| g | *Bifidobacterium breve* | s | − | m | *Janibacter* sp. M3-5 | s | + | s | *Terrisporobacter* | g | − |
| g | *Bifidobacterium dentium* | s | − | m | *Pseudomonas syringae* | s | − | s | *Intestinibacter* | g | + |
| g | *Brevibacterium* | g | + | m | *Neisseria meningitidis* | s | + | s | Peptoniphilaceae | f | − |
| g | *Corynebacterium* | g | − | m | *Neisseria flava* | s | − | s | Tissierellia | c | − |
| g | *Corynebacterium diphtheriae* | s | + | m | *Arthrospira* | g | + | s | Tissierellales | o | − |
| g | *Corynebacterium* sp. | s | + | m | *Johnsonella ignava* | s | − | s | Veillonellales | o | − |
| g | *Cutibacterium acnes* | s | + | m | *Arthrospira fusiformis* | s | − | s | *Cutibacterium* | g | + |
| g | Mycobacteriaceae | f | + | m | *Neisseria* sp. CCUG 45853 | s | + | s | Spirochaetales | o | + |
| g | *Rhodococcus* | g | − | m | *Prevotella micans* | s | − | s | *Deinococcus* | g | + |
| g | Actinomycetales | o | + | m | *Campylobacter hyointestinalis* | s | − | s | *Lactococcus* | g | + |
| g | *Rothia dentocariosa* | s | + | m | *Neisseria cinerea* | s | − | s | *Johnsonella* | g | + |
| g | *Mobiluncus* | g | − | m | *Neisseria polysaccharea* | s | − | s | Deinococcaceae | f | + |
| g | *Mobiluncus curtisii* | s | + | m | *Aggregatibacter actinomycetemcomitans* | s | − | s | Spirochaetes | p | + |
| g | *Mobiluncus mulieris* | s | − | m | *Selenomonas sputigena* | s | + | s | Spirochaetia | c | + |
| g | Mycoplasmatales | o | + | m | *Trichococcus* | g | + | s | *Bacteroides* sp. XB44A | s | − |
| g | Mycoplasmataceae | f | + | m | *Porphyromonas gulae* | s | + | s | *Comamonas* | g | − |
| g | Methanobacteriales | o | − | m | *Streptococcus australis* | s | − | s | *Neisseria sicca* | s | + |
| g | Methanobacteriaceae | f | − | m | *Olsenella uli* | s | − | s | *Kingella oralis* | s | |
| g | *Methanobrevibacter* | g | − | m | *Capnocytophaga* sp. oral strain A47ROY | s | − | s | *Aggregatibacter aphrophilus* | s | − |
| g | *Methanobrevibacter smithii* | s | − | m | *Gemella* sp. oral strain C24KA | s | − | s | *Aggregatibacter segnis* | s | + |
| g | *Gardnerella* | g | − | m | *Actinomyces* sp. oral strain B19SC | s | − | s | *Pasteurella* | g | + |
| g | *Globicatella* | g | + | m | *Actinomyces cardiffensis* | s | − | s | *Capnocytophaga* | g | − |
| g | *Globicatella sanguinis* | s | + | m | *Prevotella* sp. Smarlab 121567 | s | − | s | *Capnocytophaga gingivalis* | s | + |
| g | *Sphingomonas* | g | + | m | *Eikenella* sp. MDA2346-4 | s | + | s | *Capnocytophaga ochracea* | s | − |
| g | *Bifidobacterium pseudocatenulatum* | s | + | m | *Veillonella rodentium* | s | + | s | Cyanobacteria | p | − |
| g | *Phyllobacterium* | g | − | m | *Capnocytophaga* sp. P2 oral strain P4P_12 | s | − | s | *Streptococcus mutans* | s | + |
| g | *Bacteroides eggerthii* | s | − | m | *Capnocytophaga leadbetteri* | s | + | s | *Vagococcus* | g | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | *Alistipes putredinis* | s | + | m | *Mycoplasma* sp. M221-9 | s | + | s | *Tannerella forsythia* | s | + |
| g | *Porphyromonas asaccharolytica* | s | − | m | *Propionibacterium acidifaciens* | s | − | s | *Porphyromonas endodontalis* | s | − |
| g | *Prevotella buccalis* | s | + | m | *Fusobacterium* sp. CM55 | s | + | s | *Prevotella intermedia* | s | + |
| g | Alphaproteobacteria | c | + | m | *Campylobacter* sp. FOBRC14 | s | + | s | *Prevotella nigrescens* | s | − |
| g | *Arcanobacterium haemolyticum* | s | − | m | *Stenotrophomonas* sp. NB3 | s | + | s | *Prevotella oris* | s | − |
| g | Euryarchaeota | p | − | m | *Snodgrassella* | g | − | s | *Prevotella oulorum* | s | − |
| g | *Veillonella parvula* | s | − | m | *Rothia* sp. THG-T3 | s | + | s | *Dolosigranulum* | g | + |
| g | Mollicutes | c | + | m | *Actinomyces* sp. canine oral taxon 417 | s | − | s | *Dolosigranulum pigrum* | s | + |
| g | *Helcococcus* | g | + | n | Bacteroidaceae | f | + | s | *Acetitomaculum* | g | − |
| g | Rhodobacteraceae | f | + | n | *Bacteroides* | g | + | s | *Kingella* | g | |
| g | Xanthomonadaceae | f | + | n | *Bacteroides thetaiotaomicron* | s | + | s | *Terrisporobacter glycolicus* | s | + |
| g | *Leptotrichia* | g | + | n | *Bacteroides uniformis* | s | + | s | *Leptotrichia buccalis* | s | − |
| g | *Rothia* | g | + | n | *Bacteroides vulgatus* | s | − | s | *Porphyromonas catoniae* | s | − |
| g | *Cutibacterium avidum* | s | − | n | *Roseburia* | g | + | s | *Catonella* | g | + |
| g | *Anaerococcus hydrogenalis* | s | − | n | *Faecalibacterium prausnitzii* | s | + | s | *Catonella morbi* | s | + |
| g | *Peptoniphilus lacrimalis* | s | − | n | *Desulfovibrio* | g | − | s | *Filifactor* | g | + |
| g | *Anaerococcus lactolyticus* | s | − | n | *Desulfovibrio* sp. | s | − | s | *Capnocytophaga granulosa* | s | + |
| g | *Parvimonas micra* | s | + | n | *Herbaspirillum seropedicae* | s | − | s | *Actinomyces georgiae* | s | + |
| g | *Anaerococcus prevotii* | s | + | n | Bacteroidetes | p | + | s | *Actinomyces gerencseriae* | s | + |
| g | *Anaerococcus tetradius* | s | + | n | Proteobacteria | p | + | s | *Actinomyces graevenitzii* | s | − |
| g | *Lactobacillus johnsonii* | s | + | n | Firmicutes | p | − | s | Acidobacteria | p | − |
| g | *Bilophila* | g | − | n | *Sarcina* | g | − | s | *Prevotella pallens* | s | + |
| g | *Bilophila wadsworthia* | s | − | n | Streptococcaceae | f | − | s | *Corynebacterium durum* | s | − |
| g | *Dermabacter* | g | − | n | *Streptococcus* | g | − | s | *Centipeda* | g | − |
| g | *Dermabacter hominis* | s | + | n | *Clostridium* | g | + | s | *Centipeda periodontii* | s | − |
| g | *Corynebacterium glucuronolyticum* | s | − | n | Actinobacteria | c | − | s | *Rothia* sp. CCUG 25688 | s | + |
| g | *Dialister pneumosintes* | s | + | n | *Lachnospira* | g | + | s | *Mogibacterium pumilum* | s | − |
| g | *Stenotrophomonas* | g | + | n | *Lachnospira pectinoschiza* | s | − | s | *Pseudoflavonifractor capillosus* | s | − |
| g | *Sneathia sanguinegens* | s | + | n | Betaproteobacteria | c | − | s | *Leptotrichia trevisanii* | s | + |
| g | *Sutterella wadsworthensis* | s | − | n | Deltaproteobacteria | c | − | s | Sphingobacteriia | c | − |
| g | Bradyrhizobiaceae | f | + | n | Veillonellaceae | f | − | s | *Leptotrichia wadei* | s | − |
| g | Rhodospirillaceae | f | + | n | Clostridiaceae | f | − | s | *Leptotrichia shahii* | s | + |
| g | Sphingomonadaceae | f | + | n | *Phascolarctobacterium* | g | − | s | *Leptotrichia goodfellowii* | s | − |
| g | *Corynebacterium argentoratense* | s | + | n | *Phascolarctobacterium faecium* | s | + | s | *Tannerella* | g | − |
| g | *Rothia mucilaginosa* | s | + | n | Lactobacillaceae | f | − | s | Sphingobacteriales | o | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | Butyrivibrio crossotus | s | − | n | Dorea formicigenerans | s | + | s | Chloroflexi | p | − |
| g | Abiotrophia | g | + | n | Sutterella | g | + | s | Acidobacteriia | c | − |
| g | Granulicatella adiacens | s | + | n | Pseudobutyrivibrio | g | + | s | Acidobacteriales | o | − |
| g | Abiotrophia defectiva | s | + | n | Bacteroides caccae | s | + | s | Megasphaera genomosp. C1 | s | + |
| g | Parabacteroides merdae | s | − | n | Verrucomicrobiales | o | − | s | Selenomonas genomosp. P5 | s | + |
| g | Bacteroides stercoris | s | + | n | Oxalobacteraceae | f | − | s | Actinomyces dentalis | s | − |
| g | Lautropia | g | + | n | Burkholderiales | o | − | s | Bacteroides nordii | s | − |
| g | Lactobacillus rhamnosus | s | + | n | Coriobacteriaceae | f | + | s | Capnocytophaga genosp. AHN8471 | s | − |
| g | Flavobacteriaceae | f | + | n | Eggerthella | g | + | s | Aggregatibacter | g | − |
| g | Pantoea | g | + | n | Coriobacteriia | c | + | s | Prevotella nanceiensis | s | + |
| g | Actinotignum schaalii | s | + | n | Coriobacteriales | o | + | s | Prevotella maculosa | s | − |
| g | Trueperella bernardiae | s | + | n | Bacteroides acidifaciens | s | + | s | Actinomyces massiliensis | s | + |
| g | Corynebacterium ulcerans | s | − | n | Blautia luti | s | + | s | Lachnoanaerobaculum saburreum | s | + |
| g | Facklamia sp. 164-92 | s | + | n | Bacteroides sp. AR20 | s | − | s | Bacteroides sp. 2_2_4 | s | + |
| g | Facklamia sp. 1440-97 | s | + | n | Bacteroides sp. AR29 | s | − | s | Gordonibacter pamelaeae | s | + |
| g | Mesorhizobium | g | − | n | Collinsella | g | + | s | Bacteroides sp. DJF_B097 | s | + |
| g | Phyllobacteriaceae | f | − | n | Erysipelotrichaceae | f | + | s | Butyricimonas virosa | s | + |
| g | Hydrogenophilus | g | − | n | Roseburia intestinalis | s | + | s | Leptotrichia hongkongensis | s | − |
| g | Pseudomonadales | o | + | n | Bacteroidales | o | − | s | Chitinophagaceae | f | − |
| g | Tessaracoccus | g | + | n | Rikenellaceae | f | + | s | Robinsoniella | g | + |
| g | Kluyvera georgiana | s | − | n | Shuttleworthia | g | + | s | Rhizobium sp. T45 | s | − |
| g | Collinsella aerofaciens | s | − | n | Clostridia | c | − | s | Oribacterium sp. oral taxon 078 | s | − |
| g | Campylobacter hominis | s | + | n | Clostridiales | o | − | s | Leptotrichia sp. oral taxon 225 | s | − |
| g | Bifidobacterium gallicum | s | + | n | Peptostreptococcaceae | f | + | s | Alloprevotellarava | s | + |
| g | Comamonadaceae | f | + | n | Dorea | g | + | s | Capnocytophaga sp. oral taxon 338 | s | + |
| g | Rhizobiaceae | f | + | n | Desulfovibrionaceae | f | + | s | Tannerella sp. oral taxon HOT-286 | s | − |
| g | Atopobium vaginae | s | + | n | Bacteroidia | c | − | s | Leptotrichia sp. PTE15 | s | − |
| g | Facklamia languida | s | + | n | Actinobacteria | p | − | s | Actinomyces sp. ICM41 | s | − |
| g | Slackia | g | − | n | Verrucomicrobiae | c | − | s | Oribacterium sp. CM12 | s | + |
| g | Gemella sp. 933-88 | s | + | n | Anaerostipes | g | − | s | Lachnoanaerobaculum sp. OBRC5-5 | s | + |
| g | Micrococcales | o | + | n | Desulfovibrionales | o | + | s | Moraxella sp. WB19-16 | s | + |
| g | Corynebacteriales | o | − | n | Oscillospiraceae | f | + | s | Lysinibacillus sp. SJ2SN2 | s | + |
| g | Brevibacteriaceae | f | + | n | Faecalibacterium | g | + | s | Pseudoflavonifractor | g | − |
| g | Dermabacteraceae | f | − | n | Alistipes | g | + | s | Neisseria oralis | s | + |
| g | Microbacteriaceae | f | − | n | Akkermansia muciniphila | s | − | s | Actinomyces sp. ph3 | s | + |
| g | Nocardiaceae | f | − | n | Hespellia | g | + | s | Rothia sp. THG-N7 | s | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | Bosea | g | + | n | Marvinbryantia | g | + | s | Candidatus Saccharimonas | g | − |
| g | Achromobacter xylosoxidans | s | + | n | Roseburia inulinivorans | s | + | s | Bacteroides sp. J1511 | s | − |
| g | Mogibacterium | g | + | n | Blautia wexlerae | s | + | s | Tessaracoccus lapidicaptus | s | − |
| g | Aerococcus christensenii | s | − | n | Moryella | g | + | s | Fretibacterium | g | + |
| g | Eremococcus coleocola | s | + | n | Erysipelotrichia | c | + | s | Candidatus Stoquefichus | g | + |
| g | Lactobacillus fornicalis | s | + | n | Erysipelotrichales | o | + | s | Pseudomonas aeruginosa | s | + |
| g | Dorea longicatena | s | − | n | Clostridiales f XIII. Incertae Sedis | f | + | s | Enterobacter cloacae | s | + |
| g | Oligella | g | − | n | Blautia | g | + | s | Vibrionaceae | f | − |
| g | Oligella urethralis | s | − | n | Roseburia sp. 11SE39 | s | − | s | Aeromonas | g | − |
| g | Enterobacterales | o | − | n | Bacteroides sp. D22 | s |  | s | Rhodobacter | g | + |
| g | Candidatus Saccharibacteria | p | + | n | Blautia faecis | s | + | s | Oscillatoriales | o | − |
| g | Veillonella ratti | s | − | n | Selenomonadales | o | − | s | Leuconostoc | g | + |
| g | Lactobacillus jensenii | s | − | n | Acidaminococcaceae | f | + | s | Leuconostoc lactis | s | − |
| g | Granulicatella | g | + | n | Negativicutes | c | − | s | Lactobacillus delbrueckii | s |  |
| g | Flavobacteriia | c | + | n | Streptococcus sp. BS35a | s | − | s | Bifidobacterium animalis | s | − |
| g | Brucellaceae | f | + | n | Flavonifractor | g | + | s | Lactobacillus curvatus | s | + |
| g | Deinococcales | o | + | n | Sutterellaceae | f | + | s | Bacteroides ovatus | s | − |
| g | Burkholderiaceae | f | + | n | Anaerostipes sp. 5_1_63FAA | s | + | s | Rahnella | g | + |
| g | Hydrogenophilales | o | − | n | Fusicatenibacter saccharivorans | s | + | s | Weissella | g | + |
| g | Solobacterium | g | + | n | Blautia sp. YHC-4 | s | − | s | Rhodocyclaceae | f | − |
| g | Actinomyces radingae | s | − | n | Fusicatenibacter | g | + | s | Pseudomonas monteilii | s | − |
| g | Actinomyces turicensis | s | + | n | Eisenbergiella | g | − | s | Leuconostocaceae | f | + |
| g | Xanthomonadales | o | − | n | Eisenbergiella tayi | s | − | s | Aeromonadaceae | f | − |
| g | Catenibacterium | g | + | n | Peptoclostridium | g | + | s | Papillibacter | g | + |
| g | Globicatella sulfidifaciens | s | − | n | Erysipelatoclostridium | g | + | s | Cupriavidus | g | + |
| g | Aerosphaera | g | + | n | Campylobacter | g | − | s | Vibrionales | o | − |
| g | Aerosphaera taetra | s | + | n | Campylobacter concisus | s | + | s | Aeromonadales | o | − |
| g | Granulicatella elegans | s | + | n | Achromobacter | g | − | s | Azospira | g | − |
| g | Lactobacillus iners | s | + | n | Flavobacterium | g | + | s | Collinsella intestinalis | s | + |
| g | Finegoldia | g | + | n | Pseudomonas | g | − | s | Leuconostoc inhae | s | − |
| g | Anaeroglobus geminatus | s | − | n | Ralstonia pickettii | s | + | s | Planococcaceae | f | + |
| g | Megamonas | g | − | n | Rhizobiales | o | − | s | Corynebacterium atypicum | s | − |
| g | Corynebacterium mastitidis | s | + | n | Rhizobium | g | + | s | Acidobacteriaceae | f | − |
| g | Peptoniphilus | g | + | n | Mesorhizobium loti | s | + | s | Rhodocyclales | o | − |
| g | Sphingobium | g | + | n | Methylobacterium | g | − | s | Corynebacterium ciconiae | s | + |
| g | Sneathia | g | + | n | Moraxellaceae | f | + | s | Pseudoclavibacter bifida | s | + |
| g | Thalassospira | g | + | n | Acinetobacter | g | − | s | Anaerolineales | o | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | *Brevibacterium paucivorans* | s | + | n | *Moraxella* | g | + | s | *Streptococcus* sp. S16-11 | s | + |
| g | *Eremococcus* | g | + | n | Neisseriaceae | f | + | s | *Cloacibacterium rupense* | s | + |
| g | Porphyromonadaceae | f | − | n | *Neisseria* | g | + | s | *Aeromonas* sp. B11 | s | + |
| g | *Lactobacillus* sp. CR-609S | s | − | n | *Neisseria mucosa* | s | − | s | *Acinetobacter* sp. 423D | s | + |
| g | Methanobacteria | c | − | n | *Neisseria elongata* | s | − | s | *Paucibacter* sp. 186 | s | + |
| g | *Varibaculum cambriense* | s | − | n | *Neisseria macacae* | s | − | s | *Pseudomonas* sp. a101-18-2 | s | − |
| g | *Corynebacterium spheniscorum* | s | − | n | Alcaligenaceae | f | − | s | *Lactococcus* sp. MH5-2 | s | + |
| g | Peptococcaceae | f | + | n | Enterobacteriaceae | f | + | s | *Pseudomonas* sp. CBMAI 1177 | s | + |
| g | Aerococcaceae | f | + | n | *Citrobacter* | g | + | s | *Finegoldia* sp. BV3C29 | s | − |
| g | Carnobacteriaceae | f | − | n | *Klebsiella* | g | − | s | *Comamonas jiangduensis* | s | + |
| g | *Megasphaera micronuciformis* | s | − | n | *Kluyvera* | g | − | s | *Propionibacterium* sp. KPL1844 | s | − |
| g | *Veillonella montpellierensis* | s | − | n | *Proteus* | g |  | s | *Sutterella* sp. 252 | s | + |
| g | *Dialister* sp. E2_20 | s | − | n | *Actinobacillus* | g | + | s | *Rahnella* sp. FB303 | s | + |
| g | *Propionibacterium* sp. MSP09A | s | + | n | *Haemophilus influenzae* | s | + | s | Hyphomicrobiaceae | f | − |
| g | *Streptococcus pasteurianus* | s | + | n | *Haemophilus parainfluenzae* | s | − | s | *Shewanella* | g | + |
| g | Flavobacteriales | o | + | n | *Bacteroides fragilis* | s | − | s | Myxococcales | o | − |
| g | *Actinobaculum massiliense* | s | − | n | *Parabacteroides distasonis* | s | + | s | *Lysobacter* | g | − |
| g | *Propionimicrobium* | g | − | n | *Campylobacter gracilis* | s | + | s | *Caulobacter* | g | + |
| g | Fusobacteriaceae | f | + | n | *Porphyromonas* | g | − | s | *Caulobacter* sp. | s | + |
| g | Rhodospirillales | o | + | n | *Prevotella* | g | − | s | Planctomycetales | o | − |
| g | Rhodobacterales | o | + | n | *Fusobacterium* | g | − | s | Planctomycetaceae | f | − |
| g | Sphingomonadales | o | + | n | *Fusobacterium nucleatum* | s | + | s | *Elizabethkingia meningoseptica* | s | − |
| g | *Bacteroides massiliensis* | s | − | n | *Fusobacterium periodonticum* | s | − | s | *Brevundimonas diminuta* | s | + |
| g | Hydrogenophilaceae | f | − | n | *Megasphaera* | g | + | s | *Xanthomonas campestris* | s | − |
| g | Neisseriales | o | + | n | Chromatiaceae | f | − | s | Acetobacteraceae | f | − |
| g | *Subdoligranulum variabile* | s | + | n | *Rhodopseudomonas* | g | + | s | *Acinetobacter baumannii* | s | − |
| g | *Bifidobacterium longum* | s | − | n | Gammaproteobacteria | c | + | s | *Moraxella nonliquefaciens* | s | + |
| g | *Dialister invisus* | s | − | n | *Peptostreptococcus* | g | + | s | *Psychrobacter* | g | + |
| g | *Peptoniphilus* sp. 2002-38328 | s | − | n | *Finegoldia magna* | s | − | s | *Zymomonas* | g | + |
| g | *Peptoniphilus* sp. 2002-2300004 | s | + | n | *Peptostreptococcus anaerobius* | s | + | s | *Klebsiella pneumoniae* | s | + |
| g | *Actinomyces* sp. 2002-2301122 | s | + | n | Micrococcaceae | f | − | s | *Aeromonas salmonicida* | s | − |
| g | *Sutterella stercoricanis* | s | − | n | *Micrococcus* | g | − | s | *Photobacterium* | g | − |
| g | *Fastidiosipila* | g | + | n | *Micrococcus luteus* | s | + | s | *Geobacillus stearothermophilus* | s | + |
| g | *Helcococcus sueciensis* | s | − | n | *Staphylococcus* | g | − | s | *Alloiococcus otitis* | s | − |
| g | *Bacteroides* sp. 35AE37 | s | − | n | *Staphylococcus aureus* | s | + | s | *Nocardioides* | g | − |
| g | *Pseudoclavibacter* | g | − | n | *Staphylococcus epidermidis* | s | + | s | *Pseudonocardia* | g | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | Oribacterium | g | + | n | Staphylococcus simulans | s | + | s | Streptomyces | g | + |
| g | Porphyromonas uenonis | s | − | n | Deinococcus-Thermus | p | + | s | Gordonia | g | + |
| g | Roseburia hominis | s | + | n | Streptococcus gordonii | s | − | s | Gordonia terrae | s | − |
| g | Dialister propionicifaciens | s | + | n | Streptococcus thermophilus | s | + | s | Brochothrix | g | + |
| g | Bacteroides plebeius | s | + | n | Streptococcus parasanguinis | s | − | s | Solanaceae | f | + |
| g | Bacteroides coprocola | s | − | n | Streptococcus dysgalactiae | s | + | s | Basidiomycota | p | + |
| g | Shinella | g | + | n | Enterococcus | g | + | s | Acidovorax | g | + |
| g | Alistipes shahii | s | + | n | Lactococcus lactis | s | − | s | Sphingobium yanoikuyae | s | + |
| g | Pelomonas | g | + | n | Aerococcus | g | + | s | Micromonosporaceae | f | + |
| g | Peptostreptococcus stomatis | s | − | n | Aerococcus urinae | s | + | s | Sphingobacterium | g | + |
| g | Peptoniphilus sp. gpac018A | s | − | n | Atopobium | g | + | s | Turicella otitidis | s | + |
| g | Bacteroides sp. XB12B | s | − | n | Atopobium minutum | s | − | s | Rhodoplanes | g | − |
| g | Parabacteroides | g | − | n | Bacillales | o | − | s | Cutibacterium granulosum | s | + |
| g | Barnesiella | g | − | n | Bacillus | g | − | s | Microbacterium lacticum | s | − |
| g | Lysinibacillus | g | − | n | Lysinibacillus sphaericus | s | + | s | Exiguobacterium | g | − |
| g | Howardella | g | − | n | Clostridioides difficile | s | + | s | Dietzia | g | + |
| g | Citrobacter sp. BW4 | s | + | n | Lactobacillus | g | − | s | Acinetobacter radioresistens | s | − |
| g | Streptococcus sp. 11aTha1 | s | + | n | Lactobacillus plantarum | s | + | s | Paenibacillus | g | + |
| g | Methylobacterium sp. CBMB45 | s | + | n | Lactobacillus gasseri | s | + | s | Pseudomonas citronellolis | s | − |
| g | Prevotella amnii | s | + | n | Lactobacillus salivarius | s | − | s | Malassezia | g | + |
| g | Alloscardovia | g | − | n | Lactobacillus vaginalis | s | − | s | Nesterenkonia | g | + |
| g | Alloscardovia omnicolens | s | − | n | Actinomyces | g | − | s | Dermacoccus | g | + |
| g | Jonquetella | g | − | n | Arthrobacter | g | − | s | Pseudoxanthomonas japonensis | s | + |
| g | Jonquetella anthropi | s | − | n | Bifidobacterium | g | − | s | Brevundimonas subvibrioides | s | − |
| g | Pelomonas aquatica | s | + | n | Brevibacterium | g | − | s | Malassezia restricta | s | + |
| g | Megamonas funiformis | s | − | n | Corynebacterium diphtheriae | s | − | s | Pseudoxanthomonas | g | + |
| g | Alistipes sp. EBA6-25cl2 | s | + | n | Corynebacterium sp. | s | − | s | Kineosporiaceae | f | + |
| g | Bacteroides sp. EBA5-17 | s | − | n | Propionibacterium | g | − | s | Sphingobacteriaceae | f | − |
| g | Paraprevotella clara | s | − | n | Cutibacterium acnes | s | + | s | Acidimicrobiia | c | − |
| g | Serratia nematodiphila | s | − | n | Mycobacteriaceae | f | + | s | Acidimicrobiales | o | − |
| g | Anaerobacillus alkalidiazotrophicus | s | + | n | Mycobacterium | g | + | s | Rubrobacteria | c | − |
| g | Alistipes sp. NML05A004 | s | + | n | Rhodococcus | g | + | s | Micromonosporales | o | + |
| g | Brevibacterium ravenspurgense | s | − | n | Rhodococcus erythropolis | s | + | s | Frankiales | o | − |
| g | Dialister succinatiphilus | s | + | n | Actinomycetales | o | − | s | Promicromonosporaceae | f | + |
| g | Barnesiella intestinihominis | s | − | n | Rothia dentocariosa | s | − | s | Intrasporangiaceae | f | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | *Parasutterella excrementihominis* | s | − | n | Actinomycetaceae | f | − | s | Gordoniaceae | f | + |
| g | *Porphyromonas bennonis* | s | − | n | *Mobiluncus* | g | + | s | Dietziaceae | f | + |
| g | *Cloacibacterium* | g | − | n | *Mobiluncus mulieris* | s | + | s | Geodermatophilaceae | f | − |
| g | *Gemella asaccharolytica* | s | + | n | Methanobacteriales | o | − | s | *Marmoricola* | g | − |
| g | *Peptoniphilus duerdenii* | s | + | n | Methanobacteriaceae | f | − | s | *Marmoricola aurantiacus* | s | − |
| g | *Peptoniphilus koenoeneniae* | s | − | n | *Methanobrevibacter* | g | − | s | Cytophagaceae | f | − |
| g | *Murdochiella asaccharolytica* | s | − | n | *Methanobrevibacter smithii* | s | − | s | *Hymenobacter* | g | − |
| g | Synergistetes | p | − | n | *Gardnerella* | g | + | s | *Xanthomonas gardneri* | s | + |
| g | *Cloacibacillus* | g | − | n | *Gardnerella vaginalis* | s | + | s | *Frigoribacterium* | g | + |
| g | *Cloacibacillus evryensis* | s | − | n | *Peptococcus* | g | + | s | *Acinetobacter ursingii* | s | − |
| g | *Atopobium* sp. F0209 | s | + | n | *Peptococcus niger* | s | + | s | *Roseomonas* | g | − |
| g | Clostridiales f XI. Incertae Sedis | f | + | n | *Halomonas* | g | − | s | *Geobacillus* | g | + |
| g | Tenericutes | p | + | n | Solanales | o | + | s | *Corynebacterium capitovis* | s | − |
| g | *Hydrogenophilus islandicus* | s | − | n | *Sphingomonas* | g | − | s | Verrucomicrobia subdivision 3 | f | − |
| g | *Corynebacterium freiburgense* | s | + | n | *Phyllobacterium* | g | − | s | Alteromonadales | o | + |
| g | *Delftia lacustris* | s | − | n | *Bacteroides eggerthii* | s | | s | Gemmatimonadetes | p | + |
| g | *Brevibacterium massiliense* | s | − | n | *Alistipes putredinis* | s | − | s | *Turicella* | g | + |
| g | *Paraprevotella* | g | − | n | *Porphyromonas asaccharolytica* | s | + | s | Dermacoccaceae | f | + |
| g | *Parasutterella* | g | − | n | *Prevotella bivia asaccharolytica* | s | − | s | *Massilia* | g | + |
| g | *Enterorhabdus* | g | + | n | *Prevotella buccalis* | s | + | s | *Microbacterium* sp. absalar | s | + |
| g | *Negativicoccus succinicivorans* | s | − | n | *Prevotella disiens* | s | + | s | *Cellulosimicrobium* | g | − |
| g | *Bacteroides clarus* | s | + | n | *Cronobacter sakazakii* | s | + | s | Malasseziales | o | + |
| g | *Sutterella* sp. YIT 12072 | s | + | n | Alphaproteobacteria | c | − | s | *Aurantimonas* | g | + |
| g | *Bifidobacterium kashiwanohense* | s | − | n | Halomonadaceae | f | − | s | Listeriaceae | f | + |
| g | *Porphyromonas* sp. 2024b | s | + | n | Euryarchaeota | p | − | s | Paenibacillaceae | f | + |
| g | *Lautropia* sp. TeTO | s | + | n | *Gemella morbillorum* | s | − | s | *Dermacoccus* sp. Ellin185 | s | + |
| g | *Pyramidobacter* | g | − | n | *Rhizobium etli* | s | + | s | Thermomicrobia | c | − |
| g | *Pseudoclavibacter* sp. Timone | s | − | n | *Veillonella* | g | − | s | Thermomicrobiales | o | + |
| g | *Anaerostipes hadrus* | s | + | n | Epsilonproteobacteria | c | − | s | Planctomycetes | p | − |
| g | Synergistia | c | − | n | Bifidobacteriaceae | f | − | s | Planctomycetia | c | − |
| g | Synergistales | o | − | n | Propionibacteriaceae | f | − | s | *Skermanella* | g | − |
| g | Synergistaceae | f | − | n | Rhodobacteraceae | f | − | s | *Roseomonas cervicalis* | s | − |
| g | *Klebsiella* sp. B12 | s | − | n | *Burkholderia* | g | − | s | *Solirubrobacter* | g | − |
| g | *Anaerosporobacter* | g | + | n | Xanthomonadaceae | f | − | s | Gemmatimonadetes | c | + |
| g | *Lactobacillus* sp. BL302 | s | + | n | Fusobacteria | p | + | s | *Jeotgalicoccus* | g | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | *Ochrobactrum* sp. SCTS14 | s | − | n | *Leptotrichia* | g | − | s | *Salinibacterium* | g | − |
| g | *Anaerostipes* sp. 3_2_56FAA | s | − | n | *Rothia* | g | − | s | *Staphylococcus equorum* | s | + |
| g | *Campylobacter* sp. 10_1_50 | s | + | n | *Actinomyces neuii* | s | + | s | Shewanellaceae | f | + |
| g | *Lactobacillus* sp. 7_1_47FAA | s | + | n | *Cutibacterium avidum* | s | − | s | *Rubellimicrobium* | g | + |
| g | *Peptoniphilus* sp. oral taxon 836 | s | + | n | *Propionimicrobium lymphophilum* | s | − | s | *Sphingomonas oligophenolica* | s | + |
| g | *Veillonella* sp. oral taxon 780 | s | + | n | *Anaerococcus hydrogenalis* | s | − | s | *Elizabethkingia* | g | − |
| g | *Corynebacterium canis* | s | − | n | *Peptoniphilus lacrimalis* | s | + | s | Solirubrobacteraceae | f | − |
| g | *Bilophila* sp. 4_1_30 | s | − | n | *Anaerococcus lactolyticus* | s | + | s | *Dietzia cinnamea* | s | − |
| g | *Peptoniphilus* sp. JCM 8143 | s | + | n | *Parvimonas micra* | s | − | s | Xanthobacteraceae | f | − |
| g | *Corynebacterium* sp. NML96-0085 | s | − | n | *Anaerococcus tetradius* | s | + | s | *Wautersiella* | g | + |
| g | *Corynebacterium* sp. NML 97-0186 | s | − | n | *Anaerococcus vaginalis* | s | + | s | *Empedobacter falsenii* | s | + |
| g | *Actinomyces* sp. oral taxon 175 | s | + | n | *Microbacterium* | g | − | s | *Patulibacter* | g | − |
| g | *Peptoniphilus* sp. oral taxon 375 | s | − | n | Streptophyta | p | + | s | *Nubsella zeaxanthinifaciens* | s | − |
| g | *Bacteroides stercorirosoris* | s | − | n | *Bilophila* | g | + | s | *Skermanella aerolata* | s | − |
| g | *Blautia stercoris* | s | + | n | *Bilophila wadsworthia* | s | + | s | *Acinetobacter* sp. RBE2CD-76 | s | − |
| g | *Peptoniphilus* sp. 1-14 | s | + | n | *Dermabacter hominis* | s | + | s | Exobasidiomycetes | c | + |
| g | *Peptoniphilus* sp. 7-2 | s | − | n | *Corynebacterium glucuronolyticum* | s | − | s | *Stenotrophomonas pavanii* | s | − |
| g | *Stenotrophomonas* sp. KITS-1 | s | + | n | *Dialister* | g | − | s | *Mycobacterium* sp. 18 GUW | s | + |
| g | *Shinella* sp. DR33 | s | + | n | *Dialister pneumosintes* | s | + | s | *Pseudolabrys* | g | + |
| g | *Bacteroides* sp. SLC1-38 | s | − | n | *Stenotrophomonas* | g | − | s | *Bacillus safensis* | s | + |
| g | *Lactobacillus* sp. Akhmro1 | s | + | n | *Brevundimonas* | g | − | s | *Nubsella* | g | − |
| g | *Stenotrophomonas* sp. C-S-TSA3 | s | + | n | Bradyrhizobiaceae | f | − | s | *Jeotgalicoccus nanhaiensis* | s | + |
| g | *Actinomyces* sp. ICM54 | s | − | n | Rhodospirillaceae | f | + | s | *Dermacoccus* sp. SST-20 | s | − |
| g | *Bifidobacterium* sp. MSX5B | s | + | n | Sphingomonadaceae | f | − | s | *Flavobacterium* sp. CS43 | s | − |
| g | *Fusobacterium* sp. ACB2 | s | − | n | *Brachybacterium* | g | + | s | *Moraxella* sp. BBN2P-02d | s | + |
| g | *Fusobacterium* sp. AS2 | s | − | n | *Rothia mucilaginosa* | s | + | s | Solirubrobacterales | o | − |
| g | *Fusobacterium* sp. CM21 | s | + | n | *Abiotrophia* | g | + | s | *Acinetobacter* sp. T133 | s | + |
| g | *Veillonella* sp. AS16 | s | + | n | *Granulicatella adiacens* | s | − | s | Kineosporiales | o | + |
| g | *Anaerococcus* sp. 8404299 | s | + | n | *Abiotrophia defectiva* | s | + | s | Iamiaceae | f | − |
| g | *Anaerococcus* sp. 8405254 | s | + | n | *Bacteroides stercoris* | s | + | s | *Rummeliibacillus* | g | + |
| g | *Anaerococcus* sp. 9401487 | s | + | n | *Lautropia* | g | + | s | *Pseudomonas baetica* | s | − |
| g | *Anaerococcus provencensis* | s | + | n | *Lactobacillus crispatus* | s | + | s | *Photobacterium* sp. CAIM 866 | s | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | *Bradyrhizobium* sp. 68A4SAPT | s | + | n | *Ralstonia* | g | − | s | *Chryseomicrobium imtechense* | s | − |
| g | *Sphingomonas* sp. 24T | s | + | n | Flavobacteriaceae | f | + | s | *Brevundimonas* sp. JW23.4a | s | + |
| g | *Enterococcus* sp. SI-4 | s | + | n | *Actinobacillus porcinus* | s | + | s | *Pseudomonas* sp. DQ-01 | s | + |
| g | *Delftia* sp. BN-SKY3 | s | − | n | *Meiothermus silvanus* | s | + | s | Malasseziaceae | f | + |
| g | *Methylobacterium* sp. RK-2008-1 | s | + | n | *Pantoea* | g | − | s | *Microbacterium* sp. PCRB024 | s | − |
| g | *Enterococcus* sp. C6I11 | s | − | n | *Anaerococcus octavius* | s | − | s | Cytophagia | c | − |
| g | *Staphylococcus* sp. C9I2 | s | − | n | *Kocuria* | g | + | s | Cytophagales | o | − |
| g | *Enterobacter* sp. BS2-1 | s | + | n | *Chryseobacterium* | g | + | s | *Chryseomicrobium* | g | − |
| g | *Megasphaera* sp. UPII 199-6 | s | + | n | *Bergeyella* | g | + | s | *Staphylococcus* sp. C-D-MA2 | s | − |
| g | *Megasphaera* sp. UPII 135-E | s | + | n | *Corynebacterium ulcerans* | s | − | s | *Pseudomonas* sp. KVS86 | s | + |
| g | *Corynebacterium epidermidicanis* | s | − | n | *Meiothermus* | g | + | s | *Pseudomonas* sp. PKG89 | s | − |
| g | *Trueperella* | g | + | n | *Actinomyces europaeus* | s | + | s | *Massilia* sp. MA5-1 | s | − |
| g | *Mesorhizobium* sp. mat916 | s | + | n | *Facklamia* | g | + | s | *Granulicella* | g | − |
| g | *Coprobacter fastidiosus* | s | − | n | *Facklamia* sp. 164-92 | s | + | s | *Micrococcus* sp. WB18-01 | s | + |
| g | *Actinomyces* sp. ICM58 | s | + | n | Thermales | o | + | s | *Dietzia* sp. ISA13 | s | + |
| g | *Peptoniphilus* sp. BV3AC2 | s | + | n | Phyllobacteriaceae | f | + | s | *Brochothrix* sp. MVP25 | s | + |
| g | *Megasphaera* sp. BV3C16-1 | s | + | n | *Hydrogenophilus* | g | + | s | *Sphingomonas* sp. PDD-26b-16 | s | − |
| g | *Anaerococcus* sp. PH9 | s | + | n | *Kocuria rhizophila* | s | − | s | *Sphingomonas* sp. KOPRI 25661 | s | − |
| g | Leptotrichiaceae | f | + | n | Pseudomonadales | o | + | s | *Ferruginibacter* | g | + |
| g | *Faecalibacterium* sp. canine oral taxon 147 | s | + | n | Campylobacteraceae | f | − | s | *Sphingobacterium* sp. HTc4-a | s | − |
| g | *Murdochiella* | g | − | n | *Tessaracoccus* | g | − | s | *Amnibacterium* | g | + |
| g | *Lachnoanaerobaculum* | g | + | n | *Kluyvera georgiana* | s | − | s | *Comamonas* sp.C HM_AF10 | s | − |
| g | *Streptococcus* sp. GMD6S | s | + | n | *Collinsella aerofaciens* | s | + | s | *Massilia* sp. hp37 | s | + |
| g | *Varibaculum* sp. CCUG 61255 | s | + | n | *Campylobacter hominis* | s | + | s | *Defluviimonas* | g | − |
| g | *Dermabacter* sp. HFH0086 | s | − | n | *Actinobaculum* | g | − | s | *Ochrobactrum* sp. LC498 | s | − |
| g | *Propionibacterium* sp. KPL2005 | s | − | n | Caulobacteraceae | f | − | s | Gaiellales | o | − |
| g | *Actinomyces* sp. S4-C9 | s | + | n | *Halomonas pacifica* | s | − | s | Gaiellaceae | f | − |
| g | *Atopobium* sp. MVA9 | s | + | n | *Bacillus pseudofirmus* | s | − | s | *Aureimonas phyllosphaerae* | s | + |
| g | *Atopobium* sp. S3MV24 | s | + | n | Comamonadaceae | f | − | s | *Stenotrophomonas* sp. L_63-LFP1A9B1 | s | − |
| g | *Atopobium* sp. S3MV26 | s | + | n | *Delftia* | g | − | s | *Salinibacterium* sp. MDT1-9-1 | s | − |
| g | *Dialister* sp. S4-23 | s | + | n | Enterococcaceae | f | + | s | *Blastocatella* | g | − |
| g | *Gardnerella* sp. S3PF20 | s | − | n | Rhizobiaceae | f | + | s | *Acinetobacter* sp. HD5.2 | s | + |
| g | *Prevotella* sp. S4-10 | s | + | n | *Atopobium vaginae* | s | + | s | *Rhizobium* sp. 10II | s | + |
| g | *Corynebacterium frankenforstense* | s | − | n | *Facklamia languida* | s | − | s | *Bosea* sp. B0.09-49 | s | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | *Megasphaera massiliensis* | s | + | n | *Gemella* sp. 933-88 88 | s | + | s | *Brevibacterium* sp. MBTD_CMFRI_Bro2 | s | + |
| g | *Streptococcus* sp. 2011_Oral_MS_A3 | s | − | n | Bifidobacteriales | o | − | s | *Exiguobacterium* sp. icr3 | s | − |
| g | *Veillonella* sp. 2011_Oral_VSA_D3 | s | − | n | Micrococcales | o | − | s | *Jatrophihabitans* | g | − |
| g | *Alloprevotella* | g | + | n | Propionibacteriales | o | − | s | *Chryseobacterium* sp. R31 | s | − |
| g | *Peptoniphilus* sp. DNF00192 | s | + | n | Brevibacteriaceae | f | − | s | *Phenylobacterium* | g | + |
| g | *Dialister* sp. S7MSR5 | s | + | n | Microbacteriaceae | f | + | s | Myxococcaceae | f | − |
| g | *Intestinimonas butyriciproducens* | s | + | n | Nocardiaceae | f | + | s | Polyangiaceae | f | − |
| g | *Lactobacillus* sp. C30An8 | s | + | n | *Bosea* | g | + | s | *Simonsiella* | g | + |
| g | *Anaerococcus* sp. S8 87-3 | s | − | n | *Achromobacter xylosoxidans* | s | − | s | *Simonsiella muelleri* | s | + |
| g | *Anaerococcus* sp. S8 F2 | s | − | n | *Mogibacterium* | g | + | s | *Spirosoma* | g | − |
| g | *Finegoldia* sp. S8 F7 | s | + | n | *Propionibacterium* sp. V07/12348 | s | − | s | *Aquaspirillum* | g | + |
| g | *Porphyromonas* sp. S8 86-12 | s | + | n | *Aerococcus christensenii* | s | + | s | *Pseudomonas fluorescens* | s | + |
| g | *Actinomyces* sp. S9 PR-21 | s | − | n | *Eremococcus coleocola* | s | + | s | *Moraxella* sp. | s | − |
| g | *Anaerococcus* sp. S9 PR-16 | s | + | n | *Lactobacillus fornicalis* | s | + | s | *Acidiphilium* | g | − |
| g | *Anaerococcus* sp. S9 PR-5 | s | + | n | *Dorea longicatena* | s | + | s | *Pantoea agglomerans* | s | + |
| g | *Finegoldia* sp. S9 AA1-5 | s | + | n | Staphylococcaceae | f | + | s | *Pasteurella multocida* | s | + |
| g | *Murdochiella* sp. S9 PR-10 | s | − | n | Enterobacterales | o | + | s | *Erythrobacter* | g | − |
| g | *Olsenella* sp. S9 HS-6 | s | − | n | *Aquabacterium* | g | − | s | *Dermacoccus nishinomiyaensis* | s | + |
| g | *Peptococcus* sp. S9 Pr-12 | s | + | n | *Aquabacterium* sp. Aqua2 | s | − | s | *Streptococcus pyogenes* | s | − |
| g | *Peptoniphilus* sp. S9 PR-13 | s | − | n | Candidatus Saccharibacteria | p | + | s | *Planococcus* | g | + |
| g | *Coprobacter* | g | − | n | *Solobacterium moorei* | s | − | s | *Bacillus cereus* | s | + |
| g | *Corynebacterium* sp. 713182/2012 | s | − | n | *Lactobacillus jensenii* | s | − | s | *Cellulomonas* | g | − |
| g | *Atopobium deltae* | s | − | n | *Granulicatella* | g | + | s | *Cellulosimicrobium cellulans* | s | − |
| g | *Helcococcus seattlensis* | s | − | n | Flavobacteriia | c | + | s | *Actinomadura* | g | − |
| g | *Senegalimassilia* | g | + | n | Deinococcales | o | + | s | *Capnocytophaga canimorsus* | s | + |
| g | *Peptoniphilus* sp. DNF00840 | s | + | n | Methylobacteriaceae | f | − | s | *Alicyclobacillus* | g | − |
| g | *Romboutsia* | g | − | n | Burkholderiaceae | f | − | s | *Filifactor villosus* | s | + |
| g | *Veillonella seminalis* | s | − | n | Hydrogenophilales | o | + | s | Methylocystaceae | f | − |
| g | *Terrisporobacter* | g | + | n | *Solobacterium* | g | − | s | *Agromyces* | g | − |
| g | *Intestinibacter* | g | + | n | *Pseudomonas brenneri* | s | − | s | *Gordonia sputi* | s | − |
| g | Peptoniphilaceae | f | − | n | *Actinomyces radingae* | s | + | s | *Porphyromonas cangingivalis* | s | − |
| g | Atopobiaceae | f | − | n | *Olsenella* | g | + | s | *Porphyromonas canoris* | s | − |
| g | Akkermansiaceae | f | + | n | Chromatiales | o | − | s | *Kocuria kristinae* | s | + |
| g | Tissierellia | c | − | n | Xanthomonadales | o | − | s | *Brachybacterium faecium* | s | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | Tissierellales | o | − | n | Oceanospirillales | o | − | s | Beijerinckiaceae | f | − |
| g | Veillonellales | o | − | n | Pseudomonadaceae | f | − | s | Devosia | g | + |
| g | Selenomonadaceae | f | + | n | Catenibacterium | g | + | s | Pedomicrobium | g | + |
| g | Tannerellaceae | f | + | n | Aerosphaera | g | − | s | Bibersteinia trehalosi | s | + |
| g | Spirochaetales | o | + | n | Aerosphaera taetra | s | − | s | Actinoplanes auranticolor | s | + |
| g | Deinococcus | g | + | n | Granulicatella elegans | s | + | s | Kineosporia | g | + |
| g | Deinococcaceae | f | + | n | Finegoldia | g | − | s | Polaromonas | g | − |
| g | Spirochaetes | p | − | n | Anoxybacillus | g | + | s | Friedmanniella | g | − |
| g | Spirochaetia | c | − | n | Anaeroglobus | g | − | s | Janib acteg | g | − |
| g | Comamonas | g | − | n | Anaeroglobus geminatus | s | − | s | Nakamurella | g | − |
| g | Neisseria flavescens | s | + | n | Corynebacterium mastitidis | s | − | s | Amaricoccus | g | − |
| g | Aggregatibacter aphrophilus | s | − | n | Peptoniphilus | g | − | s | Kytococcus | g | + |
| g | Aggregatibacter segnis | s | − | n | Gallicola | g | − | s | Aquamicrobium | g | − |
| g | Capnocytophaga | g | + | n | Novosphingobium | g | − | s | Planomicrobium alkanoclasticum | s | − |
| g | Capnocytophaga gingivalis | s | + | n | Anaerococcus | g | + | s | Duganella | g | − |
| g | Cyanobacteria | p | + | n | Thalassospira | g | − | s | Fusibacter | g | + |
| g | Streptococcus mutans | s | − | n | Brevibacterium paucivorans | s | − | s | Craurococcus | g | − |
| g | Atopobium rimae | s | − | n | Eremococcus | g | + | s | Chitinophaga | g | + |
| g | Lactobacillus paracasei | s | − | n | Porphyromonadaceae | f | − | s | Friedmanniella spumicola | s | − |
| g | Actinomyces viscosus | s | + | n | Prevotellaceae | f | − | s | Microbacterium oxydans | s | − |
| g | Bifidobacterium adolescentis | s | − | n | Lactobacillus sp. CR-609S | s | − | s | Luteimonas | g | + |
| g | Anaeroplasma | g | + | n | Facklamia hominis | s | + | s | Virgibacillus | g | + |
| g | Asteroleplasma | g | + | n | Methanobacteria | c | − | s | Pedobacter | g | + |
| g | Methanosphaera | g | − | n | Varibaculum | g | + | s | Rubrobacterales | o | − |
| g | Methanosphaera stadtmanae | s | − | n | Varibaculum cambriense | s | + | s | Rubrobacteraceae | f | − |
| g | Vagococcus | g | − | n | Corynebacterium spheniscorum | s | − | s | Cellulomonadaceae | f | − |
| g | Prevotella nigrescens | s | − | n | Bacillaceae | f | − | s | Bacillus flexus | s | − |
| g | Prevotella oris | s | − | n | Aerococcaceae | f | + | s | Modestobacter | g | − |
| g | Dolosigranulum | g | − | n | Carnobacteriaceae | f | + | s | Modestobacter multiseptatus | s | − |
| g | Dolosigranulum pigrum | s | − | n | Veillonella montpellierensis | s | − | s | Aquamicrobium lusatiense | s | − |
| g | Acetitomaculum | g | − | n | Thermaceae | f | + | s | Sphingomonas aquatilis | s | − |
| g | Mogibacterium timidum | s | + | n | Deinococci | c | + | s | Ochrobactrum tritici | s | + |
| g | Terrisporobacter glycolicus | s | + | n | Dialister sp. E2_20 | s | + | s | Leifsonia | g | − |
| g | Veillonella dispar | s | − | n | Propionibacterium sp. MSP09A | s | − | s | Ornithinimicrobium | g | + |
| g | Succiniclasticum | g | − | n | Flavobacteriales | o | + | s | Candidatus Xiphinematobacter | g | − |
| g | Bifidobacterium sp. | s | + | n | Actinobaculum massiliense | s | − | s | Knoellia | g | − |
| g | Corynebacterium matruchotii | s | + | n | Propionimicrobium | g | − | s | Conchiformibius steedae | s | + |
| g | Actinomyces graevenitzii | s | + | n | Fusobacteriia | c | + | s | Planomicrobium | g | − |
| g | Corynebacterium durum | s | + | n | Fusobacteriales | o | + | s | Oerskovia | g | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | Thermoanaerobacterales | o | − | n | Fusobacteriaceae | f | − | s | Microvirga | g | − |
| g | Streptococcus peroris | s | − | n | Rhodospirillales | o | + | s | Alicyclobacillaceae | f | − |
| g | Mannheimia | g | + | n | Rhodobacterales | o | − | s | Haematobacter massiliensis | s | − |
| g | Alloprevotella tannerae | s | + | n | Sphingomonadales | o | − | s | Albidovulum inexpectatum | s | + |
| g | Centipeda | g | + | n | Caulobacterales | o | − | s | Alkanindiges illinoisensis | s | − |
| g | Eggerthella lenta | s | − | n | Bacteroides massiliensis | s | − | s | Flammeovirgaceae | f | − |
| g | Catenibacterium mitsuokai | s | + | n | Hydrogenophilaceae | f | + | s | Ralstonia sp. CCUG 46389 | s | + |
| g | Pseudoflavonifractor capillosus | s | − | n | Neisseriales | o | + | s | Albidovulum | g | + |
| g | Anaerovorax | g | − | n | Campylobacterales | o | − | s | Bdellovibrionales | o | − |
| g | Parasporobacterium | g | − | n | Alistipes finegoldii | s | + | s | Bergeyella sp. h1971d | s | + |
| g | Sphingobacteriia | c | + | n | Bifidobacterium longum | s | − | s | Cellulomonas denverensis | s | + |
| g | Anaerotruncus colihominis | s | − | n | Dialister invisus | s | + | s | Serinicoccus | g | − |
| g | Anaeroplasmatales | o | + | n | Peptoniphilus sp. 2002-38328 | s | − | s | Paucibacter toxinivorans | s | − |
| g | Anaeroplasmataceae | f | + | n | Peptoniphilus sp. 2002-2300004 | s | + | s | Chthoniobacter | g | + |
| g | Sphingobacteriales | o | + | n | Curvibacter gracilis | s | + | s | Phyllobacterium trifolii | s | + |
| g | Chloroflexi | p | + | n | Bacillus sp. T41 | s | + | s | Sphingomonas yunnanensis | s | − |
| g | Thermodesulfobiaceae | f | − | n | Sutterella stercoricanis | s | + | s | Polaromonas aquatica | s | − |
| g | Megasphaera genomosp. C1 | s | − | n | Fastidiosipila sanguinis | s | + | s | Conchiformibius | g | − |
| g | Actinomyces dentalis | s | − | n | Bacteroides sp. 35AE37 | s | + | s | Methylobacterium sp. PB142 | s | + |
| g | Bacteroides nordii | s | − | n | Pseudoclavibacter | g | + | s | Candidatus Alysiosphaera | g | + |
| g | Anaerolineae | c | + | n | Oribacterium | g | − | s | Altererythrobacter | g | − |
| g | Streptococcus dentirousetti | s | − | n | Curvibacter | g | + | s | Bacillus pocheonensis | s | − |
| g | Parabacteroides johnsonii | s | − | n | Porphyromonas uenonis | s | + | s | Belnapia | g | − |
| g | Howardella ureilytica | s | − | n | Odoribacter | g | + | s | Haematobacter | g | − |
| g | Opitutae | c | + | n | Corynebacterium sp. 2300500 | s | + | s | Porphyromonas crevioricanis | s | − |
| g | Puniceicoccales | o | + | n | Bacteroides salyersiae | s | + | s | Flavobacterium ceti | s | + |
| g | Desulfovibrio sp. 3_1_syn3 | s | + | n | Roseburia faecis | s | + | s | Flavisolibacter | g | − |
| g | Bacteroides sp. 2_2_4 | s | − | n | Dialister propionicifaciens | s | − | s | Nocardioides daphniae | s | + |
| g | Gordonibacter pamelaeae | s | + | n | Bacteroides coprocola | s | − | s | Aureimonas | g | − |
| g | Atopobium sp. DMCT15023 | s | + | n | Shinella | g | + | s | Microbacterium lacus | s | − |
| g | Blautia glucerasea | s | − | n | Parabacteroides goldsteinii | s | − | s | Chryseobacterium haifense | s | + |
| g | Bacteroides sp. DJF_B097 | s | − | n | Alistipes shahii | s | + | s | Novosphingobium panipatense | s | + |
| g | Butyricimonas virosa | s | + | n | Pelomonas | g | − | s | Nocardioides mesophilus | s | + |
| g | Parabacteroides gordonii | s | + | n | Peptostreptococcus stomatis | s | − | s | Microlunatus aurantiacus | s | − |
| g | Robinsoniella | g | + | n | Bergeyella sp. AF14 | s | − | s | Luteimonas aestuarii | s | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | *Bifidobacterium stercoris* | s | + | n | *Peptoniphilus* sp. gpac018A | s | + | s | *Saccharibacillus* | g | + |
| g | *Rhizobium* sp. T45 | s | − | n | *Peptoniphilus* sp. gpac148 | s | − | s | *Singulisphaera* | g | − |
| g | *Gordonibacter* | g | + | n | *Anoxybacillus* sp. HT14 | s | + | s | *Iamia* | g | − |
| g | *Slackia* sp. NATTS | s | − | n | *Barnesiella* | g | − | s | *Duganella* sp. 5B | s | − |
| g | *Prevotella* sp. WAL 2039G | s | + | n | *Lysinibacillus* | g | + | s | *Mycobacterium* sp. KNUC297 | s | − |
| g | *Capnocytophaga* sp. oral taxon 329 | s | + | n | *Citrobacter* sp. BW4 | s | + | s | *Pseudomonas* sp. KNUC378 | s | − |
| g | *Parvimonas* sp. oral taxon 393 | s | + | n | *Pseudomonas* sp. G1116 | s | + | s | *Nitrososphaera* | g | − |
| g | *Caldicoprobacteraceae* | f | + | n | *Anaerococcus murdochii* | s | + | s | *Brevibacterium pityocampae* | s | + |
| g | *Actinomyces* sp. ICM47 | s | + | n | *Cronobacter* | g | + | s | *Clostridiales* f XII. Incertae Sedis | f | + |
| g | *Oribacterium* sp. CM12 | s | + | n | *Acinetobacter* sp. RBE2CD-114 | s | − | s | *Clostridiales* f XIX. Incertae Sedis | f | − |
| g | *Oribacterium* sp. OBRC12 | s | − | n | *Streptococcus* sp. 11aTha1 | s | − | s | *Dietzia lutea* | s | + |
| g | *Lachnoanaerobaculum* sp. OBRC5-5 | s | + | n | *Methylobacterium* sp. CBMB45 | s | + | s | *Sphingomonas* sp. CS81 | s | + |
| g | *Moraxella* sp. WB19-16 | s | + | n | *Rhizobium* sp. sc-w | s | + | s | *Chryseobacterium* sp. Y1D | s | − |
| g | *Lysinibacillus* sp. SJ2SN2 | s | − | n | *Veillonella rogosae* | s | + | s | *Spirosoma rigui* | s | − |
| g | *Pseudoflavonifractor* | g | − | n | *Jonquetella* | g | + | s | *Pedobacter* sp. DL5 | s | + |
| g | *Fusobacterium* sp. OBRC1 | s | + | n | *Jonquetella anthropi* | s | + | s | *Exiguobacterium* sp. YS1 | s | + |
| g | *Dielma fastidiosa* | s | + | n | *Pelomonas aquatica* | s | − | s | *Neisseria wadsworthii* | s | − |
| g | *Veillonella* sp. JL-2 | s | + | n | *Alistipes* sp. EBA6-25Cl2 | s | + | s | *Variovorax* sp. IMER-B2-7 | s | + |
| g | *Actinomyces* sp. ph3 | s | − | n | *Bacteroides* sp. EBA5-17 | s | + | s | *Thaumarchaeota* | p | − |
| g | *Phascolarctobacterium* sp. 377 | s | − | n | *Paraprevotella clara* | s | + | s | *Pseudomonas* sp. StFRB280 | s | + |
| g | *Parabacteroides faecis* | s | + | n | *Oscillibacter* | g | + | s | *Jeotgalicoccus* sp. AD9 | s | + |
| g | *Veillonella* sp. 2011_Oral_VSA_B12 | s | + | n | *Anaerobacillus alkalidiazotrophicus* | s | + | s | *Nocardioides ginsengagri* | s | − |
| g | *Veillonella* sp. 2011_Oral_VSA_C9 | s | + | n | *Rhodopseudomonas boonkerdii* | s |  | s | *Leifsonia psychrotolerans* | s | − |
| g | *Rothia* sp. THG-N7 | s | + | n | *Chryseobacterium* sp. MH28 | s | − | s | *Cellulosimicrobium* sp. 143-1 | s | − |
| g | *Actinomyces* sp. S6-Spd3 | s | − | n | *Alistipes* sp. NML05A004 | s | − | s | *Sphingomonas* sp. Z1-YC6841 | s | − |
| g | *Bacteroides* sp. J1511 | s | − | n | *Barnesiella intestinihominis* | s | − | s | *Acinetobacter* sp. S2(2009) | s | + |
| g | *Tessaracoccus lapidicaptus* | s | + | n | *Parasutterella excrementihominis* | s | + | s | *Jeotgalicoccus aerolatus* | s | − |
| g | *Robinsoniella* sp. KNHs210 | s | − | n | *Pseudomonas* sp. GmFRB023 | s | + | s | *Chryseobacterium* sp. sptzw36 | s | + |
| g | *Candidatus Stoquefichus* | g | − | n | *Porphyromonas bennonis* | s | − | s | *Pseudorhodoferax* | g | + |
| g | *Dielma* | g | + | n | *Cloacibacterium* | g | − | s | *Burkholderia* sp. S32 | s | − |
| g | *Alistipes inops* | s | − | n | *Bosea* sp. BIWAKO-01 | s | + | s | *Pseudomonas* sp. PcFRB068 | s | − |
| g | *Coprobacter secundus* | s | − | n | *Peptoniphilus duerdenii* | s | + | s | *Pseudomonas* sp. PcFRB100 | s | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | [Collinsella] massiliensis | s | + | n | Synergistetes | p | + | s | Psychrobacter sanguinis | s | − |
| g | Bifidobacterium choerinum | s | − | n | Clostridiales f XI. Incertae Sedis | f | − | s | Chryseobacterium sp. MC10-6 | s | + |
| g | Helicobacter | g | + | n | Parvimonas | g | + | s | Planomicrobium sp. TPD46 | s | − |
| g | Enterobacter cloacae | s | − | n | Hydrogenophilus islandicus | s | + | s | Comamonas sp. RV_F08_22d | s | + |
| g | Hafnia | g | + | n | Corynebacterium freiburgense | s | + | s | Exiguobacterium sp. Sh3 | s | + |
| g | Hafnia alvei | s | + | n | Delftia lacustris | s | + | s | Mo destobacter sp. R-36506 | s | − |
| g | Klebsiella oxytoca | s | + | n | Novosphingobium sediminicola | s | − | s | Brevundimonas sp. a001-4 | s | − |
| g | Morganella | g | + | n | Brevibacterium massiliense | s | + | s | Psychrobacter sp. b110-1 | s | − |
| g | Morganella morganii | s | + | n | Paraprevotella | g | + | s | Brevibacterium sp. A9C6 | s | + |
| g | Aeromonas | g | + | n | Parasutterella | g | + | s | Nitriliruptoria | c | − |
| g | Roseburia cecicola | s | − | n | Phyllobacterium sp. T50 | s | − | s | Euzebyales | o | − |
| g | Fusobacterium varium | s | + | n | Negativicoccus succinicivorans | s | − | s | Euzebyaceae | f | − |
| g | Fusobacterium necrogenes | s | + | n | Porphyromonas sp. 2026 | s | − | s | Euzebya | g | − |
| g | Fusobacterium ulcerans | s | − | n | Lautropia sp. TeTO | s | + | s | Methylobacterium sp. AMS64 | s | + |
| g | Desulfovibrio desulfuricans | s | − | n | Pseudoclavibacter sp. Timone | s | + | s | Acinetobacter sp. C-S-PDA7 | s | − |
| g | Acidaminococcus fermentans | s | − | n | Synergistia | c | + | s | Micrococcus sp. M12-2-2 | s | − |
| g | Oscillatoriales | o | + | n | Synergistales | o | + | s | Chryseobacterium sp. bk_19 | s | − |
| g | Leuconostoc | g | + | n | Synergistaceae | f | + | s | Rhodococcus sp. MARG10 | s | − |
| g | Leuconostoc mesenteroides | s | + | n | Anaerosporobacter | g | + | s | Rhodococcus sp. P52 | s | − |
| g | Leuconostoc lactis | s | + | n | Ochrobactrum sp. SCTS14 | s | + | s | Blastococcus sp. FXJ6.383 | s | − |
| g | Pediococcus | g | − | n | Lactobacillus sp. 7_1_47FAA | s | − | s | Mesorhizobium sp. RE 62 | s | + |
| g | Clostridium ventriculi | s | − | n | Peptoniphilus sp. oral taxon 836 | s | + | s | Knoellia sp. BA3(2011) | s | − |
| g | Blautia hansenii | s | − | n | Veillonella sp. oral taxon 780 | s | + | s | Nocardioides sp. BA32(2011) | s | − |
| g | Streptococcus equinus | s | − | n | Microbacterium yannicii | s | − | s | Bacillus sp. CBMAI 1158 | s | + |
| g | Enterococcus hirae | s | − | n | Corynebacterium canis | s | + | s | Rhizobium skierniewicense | s | + |
| g | Blautia coccoides | s | + | n | Tessaracoccus sp. SL014B-79A | s | − | s | Shewanella sp. 8113 | s | + |
| g | Romboutsia lituseburensis | s | + | n | Bilophila sp. 4_1_30 | s | − | s | Kocuria sp. FXJ6.339 | s | − |
| g | Weissella confusa | s | − | n | Peptoniphilus sp. JCM 8143 | s | + | s | Exiguobacterium sp. IT2 | s | − |
| g | Lactobacillus delbrueckii | s | + | n | Anaerobacillus | g | + | s | Arthrobacter sp. LM27(2011) | s | − |
| g | Lactobacillus animalis | s | − | n | Corynebacterium sp. NML 97-0186 | s | + | s | Staphylococcus sp. C5I16 | s | − |
| g | Lactobacillus ruminis | s | + | n | Actinomyces sp. oral taxon 175 | s | + | s | Arthrobacter sp. NIO-1057 | s | − |
| g | Bifidobacterium catenulatum | s | − | n | Peptococcus sp. oral taxon 168 | s | + | s | Frigoribacterium sp. PDD-31b-8 | s | − |
| g | Eubacterium | g | − | n | Streptococcus sp. oral taxon G59 | s | − | s | Methylobacterium sp. PDD-23b-14 | s | − |
| g | Eubacterium limosum | s | − | n | Brevundimonas sp. V3M6 | s | + | s | Pseudomonas sp. PDD-31b-4 | s | + |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | *Propionibacterium freudenreichii* | s | − | n | *Peptoniphilus coxii* | s | + | s | *Rhodococcus* sp. PDD-31b-7 | s | + |
| g | Acholeplasmataceae | f | + | n | *Herbaspirillum huttiense* | s | + | s | *Stenotrophomonas* sp. PDD-33b-8 | s | − |
| g | *Acholeplasma* | g | + | n | *Peptoniphilus* sp. 1-14 | s | − | s | *Sphingobacterium* sp. TB1 | s | − |
| g | *Sporomusa* | g | − | n | *Peptoniphilus* sp. 7-2 | s | − | s | *Moraxella* sp. 1967 | s | + |
| g | *Epulopiscium* | g | + | n | *Ralstonia* sp. S2.MAC.005 | s | − | s | Nitrososphaerales | o | − |
| g | *Carnobacterium* | g | − | n | *Stenotrophomonas* sp. KITS-1 | s | + | s | Nitrososphaeraceae | f | − |
| g | *Carnobacterium maltaromaticum* | s | − | n | *Negativicoccus* | g | + | s | *Photobacterium* sp. squidInt_04 | s | − |
| g | *Synergistes* | g | + | n | *Shinella* sp. DR33 | s | + | s | *Erythrobacter* sp. DHXJ15 | s | + |
| g | *Bifidobacterium animalis* | s | + | n | *Bacteroides* sp. SLC1-38 | s | + | s | *Deinococcus* sp. MN4-8 | s | − |
| g | *Lactobacillus curvatus* | s | − | n | *Lactobacillus* sp. Akhmr01 | s | − | s | *Bacteroides* sp. canine oral taxon 040 | s | − |
| g | *Bacteroides ovatus* | s | − | n | *Stenotrophomonas* sp. C-S-TSA3 | s | − | s | *Aquaspirillum* sp. canine oral taxon 091 | s | + |
| g | *Rikenella* | g | + | n | *Acinetobacter* sp. RE 51 | s | − | s | *Streptococcus* sp. canine oral taxon 279 | s | − |
| g | *Rikenella microfusus* | s | + | n | *Veillonella* sp. CM60 | s | − | s | *Peptococcus* sp. canine oral taxon 344 | s | − |
| g | *Cellulosilyticum lentocellum* | s | − | n | *Actinomyces* sp. ICM54 | s | + | s | *Stenotrophomonas* sp. Z2-S2 | s | + |
| g | *Brachyspira* | g | + | n | *Fusobacterium* sp. ACB2 | s | + | s | *Deinococcus antarcticus* | s | − |
| g | *Brachyspira aalborgi* | s | + | n | *Fusobacterium* sp. AS2 | s | + | s | *Hymenobacter* sp. MIC2056 | s | + |
| g | *Bacteroides* sp. | s | + | n | *Fusobacterium* sp. CM21 | s | + | s | *Knoellia* sp. Zs20 | s | − |
| g | *Blautia producta* | s | − | n | *Veillonella* sp. AS16 | s | − | s | *Oerskovia* sp. Tibet-YD4604-5 | s | + |
| g | *Lactobacillus kefiri* | s | + | n | *Veillonella* sp. MSA12 | s | + | s | *Staphylococcus* sp. 335602 | s | − |
| g | *Rahnella* | g | + | n | *Anaerococcus* sp. 8404299 | s | − | s | *Novosphingobium* sp. iMX1 | s | + |
| g | *Citrobacter amalonaticus* | s | + | n | *Anaerococcus* sp. 8405254 | s | + | s | *Variovorax* sp. MM43NoV | s | + |
| g | *Acetivibrio* | g | − | n | *Anaerococcus* sp. 9401487 | s | − | s | *Janibacter* sp. IARI-RP17 | s | + |
| g | *Sporobacter* | g | + | n | *Anaerococcus* sp. provencensis | s | − | s | *Kytococcus* sp. YB227 | s | + |
| g | *Pseudobutyrivibrio ruminis* | s | + | n | *Bradyrhizobium* sp. 68A4SAPT | s | − | s | Chromobacteriaceae | f | + |
| g | *Weissella* | g | − | n | *Sphingomonas* sp. 24T | s | − | s | *Luteococcus* | g | − |
| g | *Weissella hellenica* | s | + | n | *Enterococcus* sp. SI-4 | s | + | s | *Sorangium* | g | − |
| g | *Sporomusa sphaeroides* | s | − | n | *Bosea* sp. R-46060 | s | + | s | *Pedomicrobium ferrugineum* | s | + |
| g | *Mitsuokella* | g | − | n | *Delftia* sp. BN-SKY3 | s | − | s | *Friedmanniella* sp. Ellin171 | s | − |
| g | *Mitsuokella multacida* | s | + | n | *Staphylococcus* sp. WB18-16 | s | + | s | *Alkanindiges* | g | − |
| g | *Enterococcus durans* | s | − | n | *Methylobacterium* sp. RK-2008-1 | s | − | s | *Rheinheimera* sp. G3DM-27 | s | + |
| g | *Blautia hydrogenotrophica* | s | − | n | *Staphylococcus* sp. C9I2 | s | − | s | *Rhodococcus* sp. CO56 | s | − |

TABLE 1-continued

Taxa associated with individuals with sleep-related condition of bad sleep quality, where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals (good sleep quality); "−" corresponds to correlation and/or other association with condition group individuals (bad sleep quality)).

| s | n | r | c | s | n | r | c | s | n | r | c |
|---|---|---|---|---|---|---|---|---|---|---|---|
| g | Methanobrevibacter sp. | s | − | n | Brachybacterium sp. NIO-27 | s | + | s | Actinomyces sp. canine oral taxon 374 | s | − |
|   |   |   |   | n | Megasphaera sp. UPII 199-6 | s | + | s | Ornithinimicrobium sp. L5 | s | + |

TABLE 2

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Bacteroidaceae | f | − | g | Finegoldia sp. S5-A7 | s | + | n | Rhodobacteraceae | f | + |
| g | Bacteroides | g | − | g | Negativicoccus sp. S5-A15 | s | − | n | Xanthomonadaceae | f | + |
| g | Bacteroides thetaiotaomicron | s | + | g | Corynebacterium frankenforstense | s | + | n | Fusobacteria | p | + |
| g | Bacteroides uniformis | s | + | g | Megasphaera massiliensis | s | − | n | Leptotrichia | g | + |
| g | Bacteroides vulgatus | s | − | g | Corynebacterium sp. jw37 | s | − | n | Rothia | g | + |
| g | Roseburia | g | + | g | Streptococcus sp. 2011_Oral_MS_A3 | s | + | n | Actinomyces neuii | s | + |
| g | Faecalibacterium prausnitzii | s | + | g | Veillonella sp. 2011_Oral_VSA_D3 | s | + | n | Cutibacterium avidum | s | + |
| g | Desulfovibrio | g | + | g | Alloprevotella | g | + | n | Propionimicrobium lymphophilum | s | + |
| g | Desulfovibrio sp. | s | + | g | Dialister sp. S7MSR5 | s | − | n | Peptoniphilus lacrimalis | s | + |
| g | Acidaminococcus | g | − | g | Intestinimonas butyriciproducens | s | + | n | Anaerococcus lactolyticus | s | + |
| g | Herbaspirillum | g | − | g | Lactobacillus sp. C30An8 | s | + | n | Anaerococcus tetradius | s | − |
| g | Herbaspirillum seropedicae | s | − | g | Anaerococcus sp. S8 87-3 | s | − | n | Anaerococcus vaginalis | s | + |
| g | Bacteroidetes | p | − | g | Anaerococcus sp. S8 F2 | s | − | n | Microbacterium | g | − |
| g | Proteobacteria | p | + | g | Porphyromonas sp. S8 86-12 | s | − | n | Streptophyta | p | + |
| g | Firmicutes | p | + | g | Actinomyces sp. S9 PR-21 | s | − | n | Dermabacter | g | + |
| g | Sarcina | g | + | g | Anaerococcus sp. S9 PR-5 | s | − | n | Dermabacter hominis | s | + |
| g | Streptococcaceae | f | − | g | Finegoldia sp. S9 AA1-5 | s | + | n | Veillonella atypica | s | − |
| g | Streptococcus | g | + | g | Murdochiella sp. S9 PR-10 | s | − | n | Corynebacterium glucuronolyticum | s | − |
| g | Clostridium | g | − | g | Murdochiella sp. S9 PR-10 | s | − | n | Dialister | g | + |
| g | Actinobacteria | c | + | g | Olsenella sp. S9 HS-6 | s | + | n | Stenotrophomonas | g | − |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Lachnospira | g | + | g | Peptococcus sp. S9 Pr-12 | s | − | n | Brevundimonas | g | + |
| g | Lachnospira pectinoschiza | s | + | g | Peptoniphilus sp. S9 PR-13 | s | − | n | Bradyrhizobiaceae | f | + |
| g | Betaproteobacteria | c | + | g | Coprobacter | g | − | n | Rhodospirillaceae | f | + |
| g | Deltaproteobacteria | c | + | g | Coprobacter | g | − | n | Sphingomonadaceae | f | − |
| g | Asaccharospora irregularis | s | + | g | Corynebacterium sp. 713182/2012 | s | − | n | Corynebacterium argentoratense | s | − |
| g | Veillonellaceae | f | + | g | Atopobium deltae | s | + | n | Brachybacterium | g | + |
| g | Clostridiaceae | f | + | g | Helcococcus seattlensis | s | − | n | Abiotrophia | g | + |
| g | Phascolarctobacterium | g | − | g | Staphylococcus sp. 334802 | s | − | n | Granulicatella adiacens | s | − |
| g | Phascolarctobacterium faecium | s | − | g | Senegalimassilia | g | + | n | Abiotrophia defectiva | s | + |
| g | Lactobacillaceae | f | + | g | Peptoniphilus sp. DNF00840 | s | + | n | Lautropia | g | − |
| g | Dorea formicigenerans | s | + | g | Romboutsia | g | − | n | Lactobacillus rhamnosus | s | − |
| g | Sutterella | g | + | g | Romboutsia | g | − | n | Lactobacillus crispatus | s | + |
| g | Pseudobutyrivibrio | g | + | g | Veillonella seminalis | s | + | n | Ralstonia | g | − |
| g | Bacteroides caccae | s | + | g | Terrisporobacter | g | + | n | Flavobacteriaceae | f | + |
| g | Verrucomicrobiales | o | + | g | Terrisporobacter | g | + | n | Actinobacillus porcinus | s | − |
| g | Holdemania | g | + | g | Intestinibacter | g | + | n | Pantoea | g | − |
| g | Holdemania filiformis | s | + | g | Peptoniphilaceae | f | − | n | Anaerococcus octavius | s | − |
| g | Fibrobacteres | p | + | g | Peptoniphilaceae | f | − | n | Kocuria | g | + |
| g | Verrucomicrobia | p | + | g | Atopobiaceae | f | − | n | Actinotignum schaalii | s | + |
| g | Oxalobacteraceae | f | − | g | Akkermansiaceae | f | + | n | Trueperella bernardiae | s | − |
| g | Burkholderiales | o | + | g | Tissierellia | c | − | n | Chryseobacterium | g | + |
| g | Coriobacteriaceae | f | + | g | Tissierellia | c | − | n | Bergeyella | g | + |
| g | Eggerthella | g | + | g | Tissierellales | o | − | n | Corynebacterium ulcerans | s | + |
| g | Coriobacteriia | c | + | g | Tissierellales | o | − | n | Actinomyces europaeus | s | + |
| g | Coriobacteriales | o | + | g | Veillonellales | o | + | n | Facklamia | g | − |
| g | Bacteroides acidifaciens | s | − | g | Selenomonadaceae | f | + | n | Facklamia sp. 164-92 | s | − |
| g | Blautia luti | s | + | g | Tannerellaceae | f | + | n | Facklamia sp. 1440-97 | s | − |
| g | Bacilli | c | + | g | Spirochaetales | o | + | n | Mesorhizobium | g | − |
| g | Bacteroides sp. AR20 | s | − | g | Deinococcus | g | + | n | Phyllobacteriaceae | f | − |
| g | Bacteroides sp. AR29 | s | − | g | Lactococcus | g | + | n | Kocuria rhizophila | s | + |
| g | Collinsella | g | + | g | Lactococcus | g | + | n | Pseudomonadales | o | − |
| g | Oscillospira | g | − | g | Deinococcaceae | f | + | n | Campylobacteraceae | f | − |
| g | Erysipelotrichaceae | f | + | g | Spirochaetes | p | − | n | Tessaracoccus | g | + |
| g | Roseburia intestinalis | s | − | g | Spirochaetia | c | − | n | Kluyvera georgiana | s | + |
| g | Bacteroidales | o | − | g | Bacteroides sp. XB44A | s | − | n | Collinsella aerofaciens | s | + |
| g | Rikenellaceae | f | − | g | Phascolarctobacterium succinatutens | s | − | n | Actinobaculum | g | − |
| g | Shuttleworthia | g | + | g | Comamonas | g | − | n | Caulobacteraceae | f | + |
| g | Clostridia | c | + | g | Neisseria flavescens | s | + | n | Bacillus pseudofirmus | s | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Clostridiales | o | + | g | *Aggregatibacter aphrophilus* | s | + | n | Comamonadaceae | f | − |
| g | Lachnospiraceae | f | + | g | *Aggregatibacter segnis* | s | + | n | *Delftia* | g | − |
| g | Peptostreptococcaceae | f | + | g | *Pasteurella* | g | + | n | Enterococcaceae | f | + |
| g | Lactobacillales | o | + | g | *Rodentibacter pneumotropicus* | s | + | n | Rhizobiaceae | f | + |
| g | *Dorea* | g | + | g | *Fibrobacter* | g | − | n | *Facklamia languida* | s | + |
| g | Desulfovibrionaceae | f | + | g | *Selenomonas* | g | + | n | *Gemella* sp. 933-88 | s | + |
| g | Bacteroidia | c | − | g | *Capnocytophaga* | g | + | n | Bifidobacteriales | o | − |
| g | Actinobacteria | p | + | g | Cyanobacteria | p | + | n | Corynebacteriales | o | − |
| g | Verrucomicrobiae | c | + | g | *Actinomyces viscosus* | s | + | n | Propionibacteriales | o | − |
| g | Verrucomicrobiaceae | f | + | g | *Bifidobacterium adolescentis* | s | + | n | Brevibacteriaceae | f | − |
| g | Fibrobacteria | c | + | g | *Bifidobacterium adolescentis* | s | + | n | Dermabacteraceae | f | + |
| g | Fibrobacteraceae | f | + | g | *Anaeroplasma* | g | + | n | Microbacteriaceae | f | − |
| g | *Anaerostipes* | g | + | g | *Asteroleplasma* | g | + | n | Nocardiaceae | f | − |
| g | Desulfovibrionales | o | + | g | Methanosphaera | g | + | n | *Bosea* | g | + |
| g | Oscillospiraceae | f | − | g | *Methanosphaera stadtmanae* | s | + | n | *Achromobacter xylosoxidans* | s | + |
| g | *Faecalibacterium* | g | + | g | *Porphyromonas endodontalis* | s | + | n | *Mogibacterium* | g | − |
| g | Fibrobacterales | o | + | g | *Prevotella intermedia* | s | + | n | *Propionibacterium* sp. V07/12348 | s | + |
| g | *Alistipes* | g | − | g | *Prevotella nigrescens* | s | + | n | *Aerococcus christensenii* | s | + |
| g | *Akkermansia* | g | + | g | *Prevotella oris* | s | − | n | *Eremococcus coleocola* | s | + |
| g | *Akkermansia muciniphila* | s | + | g | *Dolosigranulum* | g | − | n | *Dorea longicatena* | s | + |
| g | *Hespellia* | g | − | g | *Dolosigranulum pigrum* | s | − | n | Staphylococcaceae | f | + |
| g | *Anaerotruncus* | g | − | g | *Acetitomaculum* | g | + | n | Enterobacterales | o | + |
| g | *Marvinbryantia* | g | + | g | *Mogibacterium timidum* | s | + | n | *Aquabacterium* | g | + |
| g | *Subdoligranulum* | g | + | g | Terrisporobacter glycolicus | s | − | n | *Aquabacterium* sp. Aqua2 | s | + |
| g | *Flavonifractor plautii* | s | − | g | *Veillonella dispar* | s | + | n | *Candidatus Saccharibacteria* | p | + |
| g | *Bacteroides finegoldii* | s | + | g | *Succiniclasticum* | g | − | n | *Pseudoglutamicibacter albus* | s | − |
| g | *Lactonifactor longoviformis* | s | + | g | *Bifidobacterium* sp. | s | + | n | *Solobacterium moorei* | s | + |
| g | *Roseburia inulinivorans* | s | + | g | *Porphyromonas catoniae* | s | − | n | *Granulicatella* | g | + |
| g | *Blautia wexlerae* | s | − | g | Acidobacteria | p | − | n | Flavobacteriia | c | + |
| g | *Lactonifactor* | g | + | g | *Prevotella pallens* | s | − | n | Brucellaceae | f | + |
| g | *Moryella* | g | − | g | Thermoanaerobacterales | o | + | n | Deinococcales | o | + |
| g | *Adlercreutzia equolifaciens* | s | − | g | *Streptococcus peroris* | s | + | n | Methylobacteriaceae | f | + |
| g | *Adlercreutzia* | g | − | g | *Eggerthella lenta* | s | + | n | Burkholderiaceae | f | − |
| g | Erysipelotrichia | c | + | g | *Catenibacterium mitsuokai* | s | − | n | *Solobacterium* | g | + |
| g | Erysipelotrichales | o | + | g | *Pseudoflavonifractor capillosus* | s | + | n | *Pseudomonas brenneri* | s | + |
| g | Ruminococcaceae | f | + | g | *Anaerovorax* | g | + | n | *Actinomyces radingae* | s | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Clostridiales f XIII. Incertae Sedis | f | − | g | Parasporobacterium | g | − | n | Chromatiales | o | + |
| g | Acidaminococcus sp. D21 | s | − | g | Sphingobacteriia | c | + | n | Xanthomonadales | o | + |
| g | Blautia | g | + | g | Turicibacter sanguinis | s | − | n | Oceanospirillales | o | − |
| g | Roseburia sp. 11SE39 | s | + | g | Actinomyces sp. oral strain Hal-1065 | s | + | n | Pseudomonadaceae | f | − |
| g | Bacteroides sp. D22 | s | − | g | Anaerotruncus colihominis | s | + | n | Pasteurellales | o | − |
| g | Alistipes sp. RMA 9912 | s | − | g | Victivallis | g | − | n | Aerosphaera | g | + |
| g | Blautia sp. Ser8 | s | + | g | Anaeroplasmatales | o | + | n | Aerosphaera taetra | s | + |
| g | Blautia faecis | s | + | g | Anaeroplasmataceae | f | + | n | Granulicatella elegans | s | + |
| g | Selenomonadales | o | − | g | Turicibacter | g | − | n | Lactobacillus iners | s | − |
| g | Acidaminococcaceae | f | − | g | Scardovia | g | + | n | Finegoldia | g | − |
| g | Negativicutes | c | − | g | Sphingobacteriales | o | + | n | Corynebacterium mastitidis | s | − |
| g | Eggerthella sp. HGA1 | s | + | g | Chloroflexi | p | + | n | Peptoniphilus | g | − |
| g | Streptococcus sp. BS35a | s | + | g | Acidobacteriia | c | − | n | Sphingobium | g | + |
| g | Flavonifractor | g | + | g | Acidobacteriales | o | − | n | Novosphingobium | g | |
| g | Sutterellaceae | f | + | g | Thermodesulfobiaceae | f | | n | Anaerococcus | g | − |
| g | Anaerostipes sp. 5_1_63FAA | s | + | g | Leptotrichia genomosp. C1 | s | − | n | Thalassospira | g | + |
| g | Fusicatenibacter saccharivorans | s | + | g | Megasphaera genomosp. C1 | s | − | n | Brevibacterium paucivorans | s | − |
| g | Blautia sp. YHC-4 | s | + | g | Scardovia wiggsiae | s | + | n | Eremococcus | g | + |
| g | Intestinimonas | g | − | g | Victivallaceae | f | − | n | Porphyromonadaceae | f | − |
| g | Fusicatenibacter | g | + | g | Lentisphaerae | p | + | n | Prevotellaceae | f | + |
| g | Eisenbergiella | g | − | g | Victivallales | o | − | n | Facklamia hominis | s | − |
| g | Eisenbergiella tayi | s | − | g | Bacteroides nordii | s | + | n | Varibaculum | g | − |
| g | Candidatus Soleaferrea | g | + | g | Anaerolineae | c | + | n | Varibaculum cambriense | s | − |
| g | Peptoclostridium | g | − | g | Streptococcus dentirousetti | s | + | n | Corynebacterium spheniscorum | s | − |
| g | Asaccharospora | g | + | g | Parabacteroides johnsonii | s | + | n | Peptococcaceae | f | + |
| g | Erysipelatoclostridium | g | + | g | Howardella ureilytica | s | + | n | Bacillaceae | f | + |
| ge | Bacteroidaceae | f | + | g | Opitutae | c | − | n | Aerococcaceae | f | − |
| ge | Bacteroides | g | + | g | Puniceicoccales | o | − | n | Carnobacteriaceae | f | + |
| ge | Bacteroides thetaiotaomicron | s | + | g | Aggregatibacter | g | + | n | Megasphaera micronuciformis | s | − |
| ge | Bacteroides vulgatus | s | + | g | Prevotella nanceiensis | s | − | n | Deinococci | c | + |
| ge | Roseburia | g | + | g | Desulfovibrio sp. 3_1_syn3 | s | + | n | Dialister sp. E2_20 | s | + |
| ge | Faecalibacterium prausnitzii | s | + | g | Bacteroides sp. 2_2_4 | s | − | n | Propionibacterium sp. MSP09A | s | + |
| ge | Herbaspirillum | g | − | g | Bacteroides sp. 3_1_40A | s | − | n | Flavobacteriales | o | + |
| ge | Herbaspirillum seropedicae | s | − | g | Gordonibacter pamelaeae | s | + | n | Propionimicrobium | g | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| ge | Bacteroidetes | p | + | g | *Gordonibacter pamelaeae* | s | + | n | Fusobacteriia | c | + |
| ge | Proteobacteria | p | + | g | *Blautia glucerasea* | s | + | n | Fusobacteriales | o | + |
| ge | Firmicutes | p | − | g | *Bacteroides* sp. DJF_B097 | s | − | n | Fusobacteriaceae | f | + |
| ge | *Sarcina* | g | + | g | *Bacteroides* sp. DJF_B097 | s | − | n | Rhodospirillales | o | + |
| ge | Streptococcaceae | f | − | g | *Actinomyces oris* | s | + | n | Rhodobacterales | o | + |
| ge | *Streptococcus* | g | + | g | *Butyricimonas virosa* | s | + | n | Sphingomonadales | o | − |
| ge | Actinobacteria | c | + | g | *Anaerotruncus* sp. NML 070203 | s | + | n | Caulobacterales | o | + |
| ge | *Lachnospira* | g | + | g | *Parabacteroides gordonii* | s | + | n | Neisseriales | o | − |
| ge | Betaproteobacteria | c | − | g | *Robinsoniella* | g | − | n | Campylobacterales | o | − |
| ge | Veillonellaceae | f | + | g | *Bifidobacterium stercoris* | s | − | n | *Subdoligranulum variabile* | s | + |
| ge | Clostridiaceae | f | − | g | *Rhizobium* sp. T45 | s | − | n | *Alistipes finegoldii* | s | + |
| ge | Lactobacillaceae | f | − | g | *Odoribacter laneus* | s | + | n | *Bifidobacterium longum* | s | − |
| ge | *Sutterella* | g | + | g | *Gordonibacter* | g | + | n | *Dialister invisus* | s | |
| ge | *Bacteroides caccae* | s | + | g | *Gordonibacter* | g | + | n | *Peptoniphilus* sp. 2002-38328 | s | + |
| ge | Verrucomicrobiales | o | + | g | *Slackia* sp. NATTS | s | − | n | *Peptoniphilus* sp. 2002-2300004 | s | − |
| ge | Verrucomicrobia | p | + | g | *Prevotella* sp. WAL 2039G | s | − | n | *Curvibacter gracilis* | s | − |
| ge | Oxalobacteraceae | f | − | g | Caldicoprobacteraceae | f | + | n | *Bacillus* sp. T41 | s | − |
| ge | Burkholderiales | o | − | g | *Leptotrichia* sp. PG10 | s | − | n | *Fastidiosipila sanguinis* | s | + |
| ge | Coriobacteriaceae | f | + | g | *Lactobacillus* sp. NRCT-KU 1 | s | + | n | *Helcococcus sueciensis* | s | − |
| ge | Coriobacteriia | c | + | g | *Actinomyces* sp. ICM47 | s | − | n | *Pseudoclavibacter* | g | − |
| ge | Coriobacteriales | o | + | g | *Atopobium* sp. ICM57 | s | − | n | *Oribacterium* | g | + |
| ge | *Blautia luti* | s | + | g | *Oribacterium* sp. OBRC12 | s | − | n | *Curvibacter* | g | − |
| ge | Bacilli | c | − | g | *Lachnoanaerobaculum* sp. MSX33 | s | + | n | *Odoribacter* | g | |
| ge | *Bacteroides* sp. AR20 | s | + | g | *Lachnoanaerobaculum orale* | s | + | n | *Roseburia faecis* | s | + |
| ge | *Collinsella* | g | + | g | *Pseudomonas* sp. KB23 | s | + | n | *Dialister propionicifaciens* | s | + |
| ge | Erysipelotrichaceae | f | + | g | *Pseudoflavonifractor* | g | + | n | *Dialister micraerophilus* | s | + |
| ge | Bacteroidales | o | + | g | *Fusobacterium* sp. OBRC1 | s | + | n | *Porphyromonas somerae* | s | − |
| ge | *Shuttleworthia* | g | − | g | *Dielma fastidiosa* | s | + | n | *Shinella* | g | + |
| ge | Clostridia | c | + | g | *Phascolarctobacterium* sp. 377 | s | − | n | *Pelomonas* | g | − |
| ge | Clostridiales | o | + | g | *Phascolarctobacterium* sp. 377 | s | − | n | *Peptostreptococcus stomatis* | s | |
| ge | Lachnospiraceae | f | − | g | *Parabacteroides faecis* | s | − | n | *Bergeyella* sp. AF14 | s | − |
| ge | Peptostreptococcaceae | f | + | g | *Veillonella* sp. 2011_Oral_VSA_B12 | s | − | n | *Bacteroides dorei* | s | + |
| ge | Lactobacillales | o | − | g | *Veillonella* sp. 2011_Oral_VSA_C9 | s | + | n | *Peptoniphilus* sp. gpaco18A | s | − |
| ge | Bacteroidia | c | + | g | *Rothia* sp. THG-N7 | s | + | n | *Peptoniphilus* sp. gpac148 | s | + |
| ge | Actinobacteria | p | + | g | *Actinomyces* sp. S6-Spd3 | s | − | n | *Prevotella timonensis* | s | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "–" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| ge | Verrucomicrobiae | c | + | g | Lentisphaeria | c | – | n | *Lysinibacillus* | g | + |
| ge | Verrucomicrobiaceae | f | + | g | *Bacteroides* sp. J1511 | s | – | n | *Citrobacter* sp. BW4 | s | + |
| ge | *Faecalibacterium* | g | + | g | *Bacteroides* sp. J1511 | s | – | n | *Pseudomonas* sp. G1116 | s | – |
| ge | *Akkermansia* | g | + | g | *Tessaracoccus lapidicaptus* | s | – | n | *Anaerococcus murdochii* | s | – |
| ge | *Akkermansia muciniphila* | s | + | g | *Fretibacterium* | g | + | n | *Acinetobacter* sp. RBE2CD-114 | s | + |
| ge | *Subdoligranulum* | g | + | g | *Robinsoniella* sp. KNHS210 | s | – | n | *Streptococcus* sp. 11aTha1 | s | + |
| ge | *Moryella* | g | + | g | *Candidatus Stoqueficus* | g | – | n | *Methylobacterium* sp. CBMB45 | s | + |
| ge | *Erysipelotrichia* | c | + | g | *Butyricimonas faecihominis* | s | – | n | *Veillonella rogosae* | s | + |
| ge | *Erysipelotrichales* | o | + | g | *Butyricimonas paravirosa* | s | – | n | *Jonquetella* | g | – |
| ge | *Ruminococcaceae* | f | + | g | *Dielma* | g | – | n | *Jonquetella anthropi* | s | – |
| ge | Clostridiales f XIII. Incertae Sedis | f | + | g | *Alistipes inops* | s | – | n | *Pelomonas aquatica* | s | – |
| ge | *Blautia* | g | + | g | *Coprobacter secundus* | s | + | n | *Pantoea vagans* | s | – |
| ge | *Bacteroides* sp. D22 | s | + | g | *Anaerofilum* | g | + | n | *Anaerobacillus alkalidiazotrophicus* | s | – |
| ge | *Selenomonadales* | o | + | g | [*Collinsella*] *massiliensis* | s | – | n | *Rhodopseudomonas boonkerdii* | s | + |
| ge | *Acidaminococcaceae* | f | + | g | *Bifidobacterium choerinum* | s | + | n | *Brevibacterium ravenspurgense* | s | – |
| ge | *Negativicutes* | c | + | g | *Campylobacter jejuni* | s | + | n | *Dialister succinatiphilus* | s | + |
| ge | *Streptococcus* sp. BS35a | s | + | g | *Moraxella catarrhalis* | s | – | n | *Pseudomonas* sp. GmFRB023 | s | + |
| ge | *Sutterellaceae* | f | + | g | *Hafnia* | g | + | n | *Porphyromonas bennonis* | s | – |
| ge | *Fusicatenibacter saccharivorans* | s | + | g | *Hafnia alvei* | s | + | n | *Peptoniphilus duerdenii* | s | – |
| ge | *Fusicatenibacter* | g | + | g | *Klebsiella oxytoca* | s | + | n | Synergistetes | p | – |
| ge | *Campylobacter* | g | + | g | *Morganella* | g | + | n | Clostridiales f XI. Incertae Sedis | f | – |
| ge | *Achromobacter* | g | – | g | *Morganella morganii* | s | + | n | *Parvimonas* | g | + |
| ge | *Pseudomonas* | g |   | g | *Proteus vulgaris* | s | + | n | *Corynebacterium freiburgense* | s | + |
| ge | *Ralstonia pickettii* | s | + | g | *Aeromonas* | g | + | n | *Delftia lacustris* | s | – |
| ge | *Rhizobiales* | o | + | g | *Fusobacterium perfoetens* | s | + | n | *Brevibacterium massiliense* | s | + |
| ge | *Rhizobium* | g | + | g | *Fusobacterium varium* | s | + | n | *Phyllobacterium* sp. T50 | s |   |
| ge | *Mesorhizobium loti* | s | – | g | *Fusobacterium necrogenes* | s | + | n | *Negativicoccus succinicivorans* | s | – |
| ge | *Methylobacterium* | g | + | g | *Fusobacterium ulcerans* | s | + | n | *Lautropia* sp. TeTO | s | – |
| ge | *Neisseria macacae* | s | + | g | *Acidaminococcus fermentans* | s | – | n | *Pseudoclavibacter* sp. *Timone* | s | – |
| ge | *Alcaligenaceae* | f | – | g | *Megasphaera elsdenii* | s | – | n | Synergistia | c | – |
| ge | *Ochrobactrum* | g | + | g | *Rhodobacter* | g | – | n | Synergistales | o | – |
| ge | *Enterobacteriaceae* | f | + | g | *Leuconostoc* | g | – | n | Synergistaceae | f | – |
| ge | *Citrobacter* | g |   | g | *Leuconostoc lactis* | s | – | n | *Klebsiella* sp. B12 | s | + |
| ge | *Kluyvera* | g | + | g | *Leuconostoc carnosum* | s | – | n | *Ochrobactrum* sp. SCTS14 | s | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| ge | Pasteurellaceae | f | + | g | Clostridium ventriculi | s | − | n | Lactobacillus sp. 7_1_47FAA | s | + |
| ge | Haemophilus | g | + | g | Blautia hansenii | s | − | n | Peptoniphilus sp. oral taxon 836 | s | + |
| ge | Haemophilus influenzae | s | + | g | Streptococcus equinus | s | − | n | Veillonella sp. oral taxon 780 | s | + |
| ge | Haemophilus parainfluenzae | s | + | g | Enterococcus hirae | s | + | n | Corynebacterium canis | s | + |
| ge | Campylobacter ureolyticus | s | + | g | Blautia coccoides | s | − | n | Tessaracoccus sp. SL014B-79A | s | + |
| ge | Porphyromonas | g | + | g | Romboutsia lituseburensis | s | − | n | Peptoniphilus sp. JCM 8143 | s | − |
| ge | Prevotella | g | + | g | Weissella confusa | s | − | n | Corynebacterium sp. NML96-0085 | s | − |
| ge | Fusobacterium | g | + | g | Lactobacillus delbrueckii | s | + | n | Anaerobacillus | g | − |
| ge | Rhodopseudomonas | g | + | g | Lactobacillus helveticus | s | − | n | Corynebacterium sp. NML 97-0186 | s | − |
| ge | Gammaproteobacteria | c | + | g | Lactobacillus animalis | s | + | n | Actinomyces sp. oral taxon 175 | s | + |
| ge | Peptostreptococcus | g | + | g | Lactobacillus ruminis | s | − | n | Peptococcus sp. oral taxon 168 | s | − |
| ge | Finegoldiamagna | s | + | g | Bifidobacterium catenulatum | s | − | n | Peptoniphilus sp. oral taxon 375 | s | − |
| ge | Peptostreptococcus anaerobius | s | + | g | Eubacterium | g | + | n | Streptococcus sp. oral taxon G59 | s | − |
| ge | Micrococcaceae | f | − | g | Eubacterium limosum | s | + | n | Brevundimonas sp. V3M6 | s | + |
| ge | Staphylococcus | g | + | g | Propionibacterium freudenreichii | s | − | n | Peptoniphilus coxii | s | − |
| ge | Streptococcus gordonii | s | + | g | Acholeplasmataceae | f | + | n | Stomatobaculum longum | s | − |
| ge | Streptococcus thermophilus | s | + | g | Acholeplasma | g | + | n | Peptoniphilus sp. 1-14 | s | − |
| ge | Streptococcus agalactiae | s | − | g | Sporomusa | g | − | n | Peptoniphilus sp. 7-2 | s | − |
| ge | Streptococcus parasanguinis | s | + | g | Carnobacterium | g | + | n | Ralstonia sp. S2.MAC.005 | s | − |
| ge | Streptococcus anginosus | s | + | g | Carnobacterium maltaromaticum | s | + | n | Stenotrophomonas sp. KITS-1 | s | + |
| ge | Streptococcus dysgalactiae | s | + | g | Synergistes | g | + | n | Negativicoccus | g | − |
| ge | Enterococcus | g | + | g | Bifidobacterium animalis | s | + | n | Shinella sp. DR33 | s | + |
| ge | Enterococcus faecalis | s | + | g | Bacteroides ovatus | s | − | n | Acinetobacter sp. C-S-NA3 | s | − |
| ge | Aerococcus | g | − | g | Bacteroides ovatus | s | − | n | Stenotrophomonas sp. C-S-TSA3 | s | + |
| ge | Aerococcus urinae | s | + | g | Rikenella | g | + | n | Veillonella sp. CM60 | s | − |
| ge | Gemella | g | + | g | Rikenella microfusus | s | + | n | Actinomyces sp. ICM54 | s | + |
| ge | Atopobium | g | + | g | Cellulosilyticum lentocellum | s | − | n | Fusobacterium sp. ACB2 | s | − |
| ge | Bacillales | o | + | g | Brachyspira | g | + | n | Fusobacterium sp. CM21 | s | + |
| ge | Bacillus | g | + | g | Brachyspira aalborgi | s | + | n | Veillonella sp. AS16 | s | + |
| ge | Lysinibacillus sphaericus | s | + | g | Bacteroides sp. | s | − | n | Anaerococcus sp. 8404299 | s | − |
| ge | Lactobacillus | g | − | g | Blautia producta | s | − | n | Anaerococcus sp. 8405254 | s | + |
| ge | Lactobacillus acidophilus | s | − | g | Lactobacillus kefiri | s | + | n | Anaerococcus sp. 9401487 | s | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| ge | *Lactobacillus gasseri* | s | + | g | *Rahnella* | g | − | n | *Anaerococcus provencensis* | s | − |
| ge | *Lactobacillus reuteri* | s | + | g | *Citrobacter amalonaticus* | s | + | n | *Bradyrhizobium* sp. 68A4SAPT | s | |
| ge | *Lactobacillus vaginalis* | s | + | g | *Acetivibrio* | g | − | n | *Sphingomonas* sp. 24T | s | − |
| ge | Corynebacteriaceae | f | + | g | *Sporobacter* | g | + | n | *Enterococcus* sp. SI-4 | s | + |
| ge | *Actinomyces* | g | + | g | *Sporobacter termitidis* | s | − | n | *Bosea* sp. R-46060 | s | + |
| ge | *Actinomyces odontolyticus* | s | + | g | *Dysgonomonas capnocytophagoides* | s | + | n | *Delftia* sp. BN-SKY3 | s | − |
| ge | *Arthrobacter* | g | − | g | *Pseudobutyrivibrio ruminis* | s | − | n | *Staphylococcus* sp. WB18-16 | s | + |
| ge | *Bifidobacterium* | g | + | g | *Weissella* | g | − | n | *Methylobacterium* sp. RK-2008-1 | s | |
| ge | *Bifidobacterium bifidum* | s | + | g | *Weissella hellenica* | s | + | n | *Staphylococcus* sp. C9I2 | s | + |
| ge | *Bifidobacterium breve* | s | + | g | *Sporomusa sphaeroides* | s | − | n | *Enterobacter* sp. BS2-1 | s | − |
| ge | *Brevibacterium* | g | − | g | *Mitsuokella* | g | − | n | *Megasphaera* sp. UPII 199-6 | s | + |
| ge | *Corynebacterium* | g | + | g | *Mitsuokella multacida* | s | + | n | *Sphingomonas* sp. 540 | s | + |
| ge | *Corynebacterium* sp. | s | | g | *Enterococcus durans* | s | + | n | *Trueperella* | g | − |
| ge | *Propionibacterium* | g | − | g | *Eubacterium callanderi* | s | + | n | *Mesorhizobium* sp. mat916 | s | − |
| ge | *Cutibacterium acnes* | s | + | g | *Blautia hydrogenotrophica* | s | − | n | *Actinomyces* sp. ICM58 | s | + |
| ge | Actinomycetales | o | + | g | *Raoultella ornithinolytica* | s | + | n | *Sphingobium* sp. LC341 | s | + |
| ge | Actinomycetaceae | f | + | g | *Enterobacter asburiae* | s | + | n | *Anaerococcus* sp. PH9 | s | + |
| ge | *Mobiluncus* | g | + | g | *Methanobrevibacter* sp. | s | − | n | Leptotrichiaceae | f | + |
| ge | *Mobiluncus curtisii* | s | + | g | *Anaerobacter* | s | + | n | *Murdochiella* | g | + |
| ge | *Mobiluncus mulieris* | s | + | g | *Desulfovibrio* sp. UNSW3caefatS | s | + | n | *Lachnoanaerobaculum* | g | − |
| ge | Mycoplasmatales | o | + | g | Rhodocyclaceae | f | − | n | *Varibaculum* sp. CCUG 45114 | s | − |
| ge | Mycoplasmataceae | f | + | g | *Pseudomonas monteilii* | s | − | n | *Dermabacter* sp. HFH0086 | s | + |
| ge | *Mycoplasma* | g | + | g | *Bifidobacterium merycicum* | s | − | n | *Propionibacterium* sp. KPL2005 | s | + |
| ge | *Mycoplasma hominis* | s | + | g | *Bifidobacterium pullorum* | s | + | n | *Stomatobaculum* | g | − |
| ge | *Ureaplasma* | g | + | g | Leuconostocaceae | f | − | n | *Actinomyces* sp. S4-C9 | s | + |
| ge | *Ureaplasma urealyticum* | s | + | g | *Anaerovibrio* | g | − | n | *Atopobium* sp. S3MV26 | s | + |
| ge | *Gardnerella* | g | + | g | *Anaerosinus glycerini* | s | + | n | *Atopobium* sp. S3PFAA1-4 | s | + |
| ge | *Gardnerella vaginalis* | s | + | g | Succinivibrionaceae | f | − | n | *Atopobium* sp. S4-A11a | s | + |
| ge | *Peptococcus* | g | + | g | *Succinivibrio* | g | − | n | *Gardnerella* sp. S3PF20 | s | − |
| ge | *Globicatella* | g | − | g | Aeromonadaceae | f | + | n | *Prevotella* sp. S4-10 | s | − |
| ge | *Globicatella sanguinis* | s | − | g | *Lactobacillus mucosae* | s | + | n | *Negativicoccus* sp. S5-A15 | s | + |
| ge | *Sphingomonas* | g | | g | *Papillibacter* | g | + | n | *Corynebacterium* sp. jw37 | s | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| ge | Prevotella bivia | s | + | g | Coprobacillus | g | + | n | Streptococcus sp. 2011_Oral_MS_A3 | s | − |
| ge | Prevotella buccalis | s | + | g | Proteus penneri | s | + | n | Alloprevotella | g | + |
| ge | Prevotella disiens | s | + | g | Lactobacillus algidus | s | − | n | Stenotrophomonas sp. N017 | s | + |
| ge | Alphaproteobacteria | c | + | g | Anaerostipes caccae | s | + | n | Bradyrhizobium sp. CCBAU 53380 | s | − |
| ge | Arcanobacterium | g | + | g | Pelistega | g | − | n | Anaerococcus sp. S8 87-3 | s | − |
| ge | Arcanobacterium haemolyticum | s | + | g | Cupriavidus | g | + | n | Anaerococcus sp. S8 F2 | s | − |
| ge | Gemella morbillorum | s | + | g | Parasporobacterium paucivorans | s | − | n | Finegoldia sp. S8 F7 | s | + |
| ge | Veillonella parvula | s | − | g | Campylobacter faecalis | s | − | n | Finegoldia sp. S9 AA1-5 | s | − |
| ge | Epsilonproteobacteria | c | + | g | Oscillospira guilliermondii | s | − | n | Murdochiella sp. S9 PR-10 | s | + |
| ge | Bifidobacteriaceae | f | + | g | Fusobacterium equinum | s | − | n | Peptoniphilus sp. S9 PR-13 | s | + |
| ge | Propionibacteriaceae | f | − | g | Aeromonadales | o | − | n | Corynebacterium sp. 713182/2012 | s | + |
| ge | Mollicutes | c | + | g | Bacillus sp. HC15 | s | − | n | Ralstonia sp. A52 | s | + |
| ge | Helcococcus | g | − | g | Weissella cibaria | s | + | n | Staphylococcus sp. 334802 | s | − |
| ge | Xanthomonadaceae | f | − | g | Brachyspiraceae | f | + | n | Peptoniphilus sp. DNF00840 | s | + |
| ge | Fusobacteria | p | + | g | Azospira | g | − | n | Veillonella seminalis | s | + |
| ge | Leptotrichia | g | + | g | Collinsella intestinalis | s | − | n | Intestinibacter | g | + |
| ge | Rothia | g |   | g | Anaerosinus | g | + | n | Peptoniphilaceae | f | − |
| ge | Actinomyces neuii | s | − | g | Dysgonomonas | g | + | n | Atopobiaceae | f | − |
| ge | Propionimicrobium lymphophilum | s | + | g | Bifidobacterium scardovii | s | + | n | Tissierellia | c | − |
| ge | Anaerococcus hydrogenalis | s | + | g | Enterococcus pallens | s | − | n | Tissierellales | o | − |
| ge | Peptoniphilus lacrimalis | s | + | g | Raoultella | g | + | n | Veillonellales | o | − |
| ge | Anaerococcus lactolyticus | s | + | g | Marvinbryantia formatexigens | s | + | n | Selenomonadaceae | f | − |
| ge | Anaerococcus prevotii | s | + | g | Victivallis vadensis | s | + | n | Cutibacterium | g | + |
| ge | Anaerococcus vaginalis | s | + | g | Blautia schinkii | s | + | n | Spirochaetales | o | − |
| ge | Lactobacillus johnsonii | s | + | g | Robinsoniella peoriensis | s | − | n | Deinococcus | g | − |
| ge | Dermabacter | g | + | g | Acholeplasmatales | o | + | n | Lactococcus | g | + |
| ge | Veillonella atypica | s | + | g | Eubacteriaceae | f | − | n | Deinococcaceae | f | + |
| ge | Dialister | g | + | g | Thermoanaerobacteraceae | f | − | n | Spirochaetes | p | − |
| ge | Stenotrophomonas | g | − | g | Planococcaceae | f | − | n | Spirochaetia | c | − |
| ge | Sneathia sanguinegens | s | + | g | Mitsuokella jalaludinii | s | − | n | Neisseria canis | s | + |
| ge | Bradyrhizobiaceae | f | − | g | Gelria | g | − | n | Aggregatibacter aphrophilus | s | − |
| ge | Sphingomonadaceae | f | + | g | Sedimentibacter | g | + | n | Aggregatibacter segnis | s | − |
| ge | Brachybacterium | g | + | g | Corynebacterium atypicum | s | + | n | Cardiobacteriaceae | f | + |
| ge | Abiotrophia | g | + | g | Acidobacteriaceae | f | − | n | Capnocytophaga | g | + |
| ge | Abiotrophia defectiva | s | + | g | Rhodocyclales | o | − | n | Capnocytophaga gingivalis | s | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| ge | Lactobacillus rhamnosus | s | − | g | Allisonella | g | − | n | Capnocytophaga sputigena | s | − |
| ge | Lactobacillus crispatus | s | + | g | Allisonella | g | − | n | Cyanobacteria | p | − |
| ge | Flavobacteriaceae | f | − | g | Allisonella histaminiformans | s | − | n | Actinomyces viscosus | s | + |
| ge | Anaerococcus octavius | s | + | g | Allisonella histaminiformans | s | − | n | Cardiobacterium | g | + |
| ge | Actinotignum schaalii | s | + | g | Anaerofustis stercorihominis | s | − | n | Cardiobacterium hominis | s | + |
| ge | Trueperella bernardiae | s | + | g | Methanomicrobia | c | − | n | Tannerella forsythia | s | + |
| ge | Actinomyces europaeus | s | + | g | Eggerthella sinensis | s | + | n | Porphyromonas endodontalis | s | + |
| ge | Facklamia | g | − | g | Bifidobacterium thermacidophilum | s | − | n | Prevotella nigrescens | s | + |
| ge | Facklamia sp. 164-92 | s | − | g | Bacteroides sp. 31SF15 | s | + | n | Prevotella oris | s | + |
| ge | Facklamia sp. 1440-97 | s | − | g | Slackia faecicanis | s | − | n | Prevotella oulorum | s | + |
| ge | Mesorhizobium | g | − | g | Anaerosporobacter mobilis | s | − | n | Dolosigranulum | g | + |
| ge | Phyllobacteriaceae | f | − | g | Anaerofustis | g | − | n | Dolosigranulum pigrum | s | + |
| ge | Pseudomonadales | o | | g | Alistipes massiliensis | s | − | n | Leptotrichia buccalis | s | − |
| ge | Campylobacteraceae | f | + | g | Veillonella sp. ADV 269.01 | s | + | n | Bifidobacterium sp. | s | − |
| ge | Tessaracoccus | g | − | g | Catabacter | g | + | n | Porphyromonas catoniae | s | − |
| ge | Kluyvera georgiana | s | + | g | Catabacter hongkongensis | s | + | n | Corynebacterium matruchotii | s | + |
| ge | Collinsella aerofaciens | s | + | g | Pseudoclavibacter bifida | s | − | n | Capnocytophaga granulosa | s | + |
| ge | Campylobacter hominis | s | + | g | Bacteroides sp. Smarlab 3301643 | s | + | n | Actinomyces georgiae | s | + |
| ge | Actinobaculum | g | + | g | Anaerolineaceae | f | + | n | Actinomyces graevenitzii | s | + |
| ge | Bifidobacterium gallicum | s | + | g | Anaerolineales | o | + | n | Prevotella pallens | s | + |
| ge | Bacillus pseudofirmus | s | + | g | Proteiniphilum | g | + | n | Corynebacterium durum | s | + |
| ge | Comamonadaceae | f | + | g | Streptococcus sp. S16-11 | s | − | n | Streptococcus peroris | s | + |
| ge | Delftia | g | + | g | Bacteroides sp. WH302 | s | + | n | Alloprevotella tannerae | s | + |
| ge | Enterococcaceae | f | + | g | Bacteroides sp. 4072 | s | − | n | Centipeda | g | + |
| ge | Rhizobiaceae | f | − | g | Paucibacter | g | + | n | Centipeda periodontii | s | + |
| ge | Atopobium vaginae | s | + | g | Alistipes onderdonkii | s | − | n | Mogibacterium pumilum | s | − |
| ge | Facklamia languida | s | + | g | Mitsuokella sp. TM-10 | s | + | n | Moraxella caprae | s | − |
| ge | Bifidobacteriales | o | + | g | Oscillibacter valericigenes | s | − | n | Sphingobacteriia | c | + |
| ge | Micrococcales | o | − | g | Bifidobacterium tsurumiense | s | − | n | Cardiobacteriales | o | + |
| ge | Corynebacteriales | o | + | g | Megasphaera sp. TrE9262 | s | − | n | Turicibacter sanguinis | s | − |
| ge | Propionibacteriales | o | − | g | Anaerococcus sp. gpac137 | s | − | n | Leptotrichia wadei | s | + |
| ge | Brevibacteriaceae | f | − | g | Weissella sp. H1a | s | − | n | Rothia aeria | s | − |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| ge | Dermabacteraceae | f | − | g | Bacteroides xylanisolvens | s | − | n | Turicibacter | g | − |
| ge | Microbacteriaceae | f | − | g | Barnesiella viscericola | s | + | n | Sphingobacteriales | o | + |
| ge | Bosea | g | − | g | Pediococcus sp. MFC1 | s | + | n | Acidobacteriia | c | + |
| ge | Achromobacter xylosoxidans | s | − | g | Cronobacter dublinensis | s | + | n | Acidobacteriales | o | + |
| ge | Mogibacterium | g | + | g | Cronobacter turicensis | s | − | n | Actinomyces dentalis | s | + |
| ge | Aerococcus christensenii | s | − | g | Catabacteriaceae | f | + | n | Aggregatibacter | g | − |
| ge | Lactobacillus fornicalis | s | + | g | Cellulosilyticum ruminicola | s | − | n | Prevotella nanceiensis | s | + |
| ge | Oligella | g | − | g | Bacteroides sp. CB57 | s | − | n | Lachnoanaerobaculum saburreum | s | − |
| ge | Oligella urethralis | s | − | g | Sutterella parvirubra | s | − | n | Leptotrichia hongkongensis | s | + |
| ge | Staphylococcaceae | f | + | g | Paraprevotella xylaniphila | s | + | n | Bifidobacterium stercoris | s | + |
| ge | Enterobacterales | o | + | g | Bacteroides sp. 3_1_23 | s | − | n | Rhizobium sp. T45 | s | + |
| ge | Candidatus Saccharibacteria | p | − | g | Parabacteroides sp. 20_3 | s | + | n | Leptotrichia sp. oral taxon 225 | s | + |
| ge | Pseudoglutamicibacter albus | s | − | g | Nosocomiicoccus | g | + | n | Alloprevotella rava | s | + |
| ge | Lactobacillus jensenii | s | − | g | Nosocomiicoccus ampullae | s | + | n | Neisseria skkuensis | s | + |
| ge | Granulicatella | g | + | g | Comamonas sp. j41 | s | + | n | Capnocytophaga sp. oral taxon 329 | s | + |
| ge | Flavobacteriia | c | − | g | Butyricicoccus pullicaecorum | s | + | n | Leptotrichia sp. PTE15 | s | − |
| ge | Bulleidia | g | + | g | Cloacibacterium rupense | s | − | n | Fusobacterium sp. CM22 | s | + |
| ge | Bulleidia extructa | s | + | g | Fusobacterium sp. DJF_B100 | s | + | n | Brevundimonas sp. FXJ8.080 | s | + |
| ge | Brucellaceae | f | + | g | Mitsuokella sp. DJF_RR21 | s | − | n | Moraxella sp. WB19-16 | s | − |
| ge | Methylobacteriaceae | f | + | g | Gracilibacteraceae | f | − | n | Pseudomonas sp. KB23 | s | − |
| ge | Burkholderiaceae | f | + | g | Butyricimonas synergistica | s | + | n | Lysinibacillus sp. SJ2SN2 | s | + |
| ge | Actinomyces turicensis | s | + | g | Selenomonas sp. Ycbo8 | s | − | n | Fusobacterium sp. OBRC1 | s | + |
| ge | Xanthomonadales | o | − | g | Streptococcus sp. TMO13 | s | − | n | Neisseria oralis | s | − |
| ge | Pseudomonadaceae | f |  | g | Asaccharobacter | g | + | n | Rothia sp. THG-N7 | s | + |
| ge | Pasteurellales | o | + | g | Coprobacillus sp. D6 | s | − | n | Candidatus Saccharimonas | g | + |
| ge | Globicatella sulfidifaciens | s | + | g | Bifidobacterium sp. 138 | s | − | n | Bacteroides sp. J1511 | s | + |
| ge | Aerosphaera | g | + | g | Butyricicoccus | s | + | n | Pseudomonas aeruginosa | s | + |
| ge | Aerosphaera taetra | s | + | g | Bacteroides sp. D20 | s | + | n | Moraxella catarrhalis | s | − |
| ge | Granulicatella elegans | s | + | g | Hydrogenoanaerobacterium | g | + | n | Enterobacter cloacae | s | + |
| ge | Lactobacillus iners | s | − | g | Bacteroides fluxus | s | − | n | Morganella | g | + |
| ge | Finegoldia | g | + | g | Bacteroides oleiciplenus | s | + | n | Morganella morganii | s | + |
| ge | Anaeroglobus | g | + | g | Alistipes indistinctus | s | + | n | Aeromonas | g | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| ge | *Anaeroglobus geminatus* | s | + | g | *Slackia piriformis* | s | − | n | *Rhodobacter* | g | + |
| ge | *Pseudoglutamicibacter cumminsii* | s | + | g | *Collinsella tanakaei* | s | − | n | *Leuconostoc* | g | + |
| ge | *Peptoniphilus* | g | + | g | *Pyramidobacter piscolens* | s | + | n | *Leuconostoc lactis* | s | + |
| ge | *Gallicola* | g | + | g | *Bacteroides* sp. TP-5 | s | + | n | *Weissella confusa* | s | + |
| ge | *Sphingobium* | g | + | g | *Anaerostipes butyraticus* | s | + | n | *Lactobacillus curvatus* | s | − |
| ge | *Anaerococcus* | g | + | g | *Aeromonas* sp. B11 | s | + | n | Rhodocyclaceae | f |  |
| ge | *Sneathia* | g | + | g | *Acinetobacter* sp. 423D | s | + | n | *Pseudomonas monteilii* | s | + |
| ge | *Brevibacterium paucivorans* | s | − | g | *Acinetobacter* sp. 81A1 | s | + | n | Leuconostocaceae | f | − |
| ge | *Porphyromonadaceae* | f | + | g | *Parabacteroides* sp. D25 | s | + | n | Aeromonadaceae | f | + |
| ge | Prevotellaceae | f | + | g | *Pantoea gaviniae* | s | − | n | Aeromonadales | o | + |
| ge | *Lactobacillus* sp. CR-609S | s | + | g | *Enterorhabdus caecimuris* | s | + | n | *Corynebacterium atypicum* | s | + |
| ge | *Facklamia hominis* | s | − | g | *Bacteroides faecis* | s | + | n | Acidobacteriaceae | f | + |
| ge | *Actinomyces hongkongensis* | s | − | g | *Bacteroides faecis* | s | + | n | Rhodocyclales | o |  |
| ge | *Lactobacillus coleohominis* | s | + | g | *Blautia* sp. Ser5 | s | + | n | *Pseudoclavibacter bifida* | s | + |
| ge | *Varibaculum* | g | + | g | *Eubacterium* sp. SA11 | s | − | n | *Nosocomiicoccus* | g | − |
| ge | *Varibaculum cambriense* | s | + | g | *Bacteroides rodentium* | s | − | n | *Nosocomiicoccus ampullae* | s | − |
| ge | *Corynebacterium spheniscorum* | s | + | g | *Paucibacter* sp. 186 | s | + | n | *Aeromonas* sp. B11 | s | − |
| ge | Peptococcaceae | f | + | g | *Cellulosilyticum* | g | − | n | *Acinetobacter* sp. 423D | s | + |
| ge | Bacillaceae | f | + | g | *Caldicoprobacter* | g | + | n | *Lactobacillus* sp. TAB-26 | s | + |
| ge | Aerococcaceae | f | − | g | *Enterobacter* sp. UDC345 | s | − | n | *Pseudomonas* sp. a101-18-2 | s | − |
| ge | Carnobacteriaceae | f | + | g | *Lactobacillus* sp. TAB-26 | s | + | n | *Pseudomonas* sp. a111-5 | s | − |
| ge | *Veillonella montpellierensis* | s | + | g | *Bifidobacterium biavatii* | s | + | n | *Lactococcus* sp. MH5-2 | s | + |
| ge | *Dialister* sp. E2_20 | s | + | g | *Megasphaera* sp. BS-4 | s | − | n | *Pseudomonas* sp. CBMAI 1177 | s | + |
| ge | *Propionibacterium* sp. MSP09A | s | − | g | *Pseudomonas* sp. a101-18-2 | s | + | n | *Propionibacterium* sp. KPL1844 | s | − |
| ge | *Streptococcus pasteurianus* | s | + | g | *Pseudomonas* sp. a111-5 | s | + | n | *Streptococcus* sp. 2011_Ileo_MS_A10 | s | − |
| ge | Flavobacteriales | o | − | g | *Rothia* sp. RV13 | s | − | n | *Rahnella* sp. BSP18 | s | + |
| ge | *Actinobaculum massiliense* | s | + | g | *Klebsiella* sp. SOR89 | s | + | n | *Shewanella* | g | − |
| ge | *Propionimicrobium* | g | + | g | *Lactococcus* sp. MH5-2 | s | + | n | *Caulobacter* | g | − |
| ge | Fusobacteriia | c | + | g | *Pseudomonas* sp. CBMAI 1177 | s | − | n | *Caulobacter* sp. | s | − |
| ge | Fusobacteriales | o | + | g | *Campylobacter* sp. 0402694-C0078 | s | − | n | Planctomycetales | o | + |
| ge | Fusobacteriaceae | f | + | g | *Lactobacillus* sp. C4I2 | s | + | n | Planctomycetaceae | f | + |
| ge | Sphingomonadales | o | + | g | *Leuconostoc* sp. C7I4 | s | + | n | *Brevundimonas diminuta* | s | + |
| ge | *Bacteroides massiliensis* | s | + | g | *Bacteroides* sp. dnLKV9 | s | + | n | Acetobacteraceae | f | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| ge | Campylobacterales | o | + | g | Parabacteroides sp. dnLKV8 | s | − | n | Aeromonas salmonicida | s | + |
| ge | Bifidobacterium longum | s | − | g | Bacteroides sp. HPS0048 | s | + | n | Streptococcus sobrinus | s | − |
| ge | Peptoniphilus sp. 2002-38328 | s | + | g | Methanomassiliicoccus | s | − | n | Alloiococcus | g | + |
| ge | Peptoniphilus sp. 2002-2300004 | s | + | g | Anaerovibrio sp. 656 | s | + | n | Alloiococcus otitis | s | + |
| ge | Actinomyces sp. 2002-2301122 | s | + | g | Anaerovibrio sp. 765 | s | − | n | Pseudonocardia | g | − |
| ge | Curvibacter gracilis | s | + | g | Acidaminococcus sp. BV3L6 | s | − | n | Pseudonocardiaceae | f | + |
| ge | Bacillus sp. T41 | s | + | g | Finegoldia sp. BV3C29 | s | + | n | Brochothrix | g | − |
| ge | Sutterella stercoricanis | s | + | g | Cruoricaptor ignavus | s | − | n | Solanum lycopersicum | s | − |
| ge | Fastidiosipila | g | + | g | Lactococcus sp. STM1 | s | + | n | Solanum | g | − |
| ge | Fastidiosipila sanguinis | s | + | g | Herbaspirillum sp. YR522 | s | − | n | Acidovorax | g | + |
| ge | Helcococcus sueciensis | s | − | g | Phascolarctobacterium sp. canine oral taxon 149 | s | − | n | Sphingobium yanoikuyae | s | + |
| ge | Pseudoclavibacter | g | − | g | Peptococcus sp. canine oral taxon 334 | s | + | n | Micromonosporaceae | f | + |
| ge | Curvibacter | g | + | g | Proteiniclasticum | g | − | n | Turicella otitidis | s | − |
| ge | Porphyromonas uenonis | s | + | g | Bacteroides sp. 14(A) | s | + | n | Staphylococcus saprophyticus | s | − |
| ge | Dialister propionicifaciens | s | + | g | Comamonas jiangduensis | s | − | n | Janthinobacterium | g | − |
| ge | Dialister micraerophilus | s | + | g | Turicibacter sp. LA62 | s | − | n | Cutibacterium granulosum | s | − |
| ge | Porphyromonas somerae | s | + | g | Acidaminococcus sp. HPA0509 | s | + | n | Microbacterium lacticum | s | − |
| ge | Pelomonas | g | + | g | Propionibacterium sp. KPL1844 | s | − | n | Variovorax | g | + |
| ge | Peptoniphilus sp. gpaco18A | s | + | g | Brachybacterium sp. S26 | s | + | n | Blastococcus aggregatus | s | − |
| ge | Peptoniphilus sp.gpac148 | s | + | g | Butyricimonas sp. 180-3 | s | + | n | Acinetobacter radioresistens | s | − |
| ge | Prevotella timonensis | s | + | g | Butyricimonas sp. 214-4 | s | + | n | Leucobacter | g | + |
| ge | Lysinibacillus | g | + | g | Anaerostipes rhamnosivorans | s | + | n | Nesterenkonia | g | − |
| ge | Howardella | g | + | g | Butyricimonas sp. GD2 | s | + | n | Dermacoccus | g | − |
| ge | Citrobacter sp. BW4 | s | | g | Streptococcus sp. 2011_Ileo_MS_A10 | s | + | n | Acidimicrobiia | c | + |
| ge | Anaerococcus murdochii | s | + | g | Streptococcus sp. 2011_Oral_MS_D12 | s | + | n | Acidimicrobiales | o | + |
| ge | Arcanobacterium sp. NML 06501 | s | | g | Veillonella sp. 2011_Oral_VSA_D12 | | | n | Rubrobacteria | c | + |
| ge | Streptococcus sp. 11aTha1 | s | + | g | Sutterella sp. 252 | s | − | n | Micromonosporales | o | + |
| ge | Methylobacterium sp. CBMB45 | s | + | g | Roseburia sp. 499 | s | + | n | Pseudonocardiales | o | + |
| ge | Prevotella amnii | s | + | g | Anaerostipes sp. 494a | s | + | n | Frankiales | o | + |
| ge | Alloscardovia | g | + | g | Anaerostipes sp. 992a | s | + | n | Nocardioidaceae | f | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| ge | *Alloscardovia omnicolens* | s | + | g | *Rahnella* sp. FB303 | s | − | n | Intrasporangiaceae | f | + |
| ge | *Rhizobium* sp. sc-w | s | + | g | *Citrobacter* sp. HD4.9 | s | − | n | Geodermatophilaceae | f | + |
| ge | *Jonquetella* | g | + | g | *Megasphaera* sp. DNF00912 | s | − | n | Cytophagaceae | f | + |
| ge | *Pelomonas aquatica* | s | + | g | *Megasphaera* sp. S6-MB2 | s | − | n | *Hymenobacter* | g | + |
| ge | *Anaerobacillus alkalidiazotrophicus* | s | + | g | Candidatus *Methanomethylophilus* | g | − | n | *Acinetobacter ursingii* | s | + |
| ge | *Rhodopseudomonas boonkerdii* | s | + | g | *Rahnella* sp. BSP15 | s | − | n | *Dyadobacter* | g | + |
| ge | *Brevibacterium ravenspurgense* | s | − | g | *Rahnella* sp. BSP18 | s | + | n | Alteromonadales | o | − |
| ge | *Dialister succinatiphilus* | s | + | g | *Bacteroides caecigallinarum* | s | + | n | *Turicella* | g | − |
| ge | *Porphyromonas bennonis* | s | + | g | *Pelistega indica* | s | − | n | Dermacoccaceae | f | + |
| ge | *Bosea* sp. BIWAKO-01 | s | + | g | *Cruoricaptor* | g | − | n | *Massilia* | g | + |
| ge | *Peptoniphilus duerdenii* | s | + | g | *Terrisporobacter petrolearius* | s | + | n | *Sphingomonas aerolata* | s | + |
| ge | *Murdochiella asaccharolytica* | s | + | g | Acidaminococcales | o | − | n | Listeriaceae | f | − |
| ge | Synergistetes | p | + | g | Odoribacteraceae | f | + | n | *Dermacoccus* sp. Ellin183 | s | + |
| ge | *Atopobium* sp. F0209 | s | + | g | Odoribacteraceae | f | + | n | Planctomycetes | p | + |
| ge | *Clostridiales* f XI. Incertae Sedis | f | + | g | Barnesiellaceae | f | + | n | Planctomycetia | c | + |
| ge | *Parvimonas* | g | + | g | Barnesiellaceae | f | + | n | *Solirubrobacter* | g | + |
| ge | Tenericutes | p | + | g | Hyphomicrobiaceae | f | − | n | *Brachybacterium muris* | s | + |
| ge | *Corynebacterium freiburgense* | s | + | m | *Bacteroides thetaiotaomicron* | s | + | n | *Actinomyces* genomosp. C1 | s | − |
| ge | *Delftia lacustris* | s | + | m | *Bacteroides uniformis* | s | − | n | *Staphylococcus equorum* | s | − |
| ge | *Bifidobacterium* Sp. 120 | s | − | m | *Bacteroides vulgatus* | s | + | n | Shewanellaceae | f | − |
| ge | *Brevibacterium massiliense* | s | + | m | *Roseburia* | g | + | n | *Rubellimicrobium* | g | + |
| ge | *Porphyromonas* sp. 2024b | s | + | m | *Faecalibacterium prausnitzii* | s | + | n | *Burkholderia* sp. CBPB-HIM | s | − |
| ge | *Pseudoclavibacter* sp. Timone | s | + | m | *Herbaspirillum* | g | + | n | *Sphingomonas oligophenolica* | s | + |
| ge | *Synergistia* | c | + | m | *Herbaspirillum seropedicae* | s | + | n | Solirubrobacteraceae | f | + |
| ge | *Synergistales* | o | + | m | Bacteroidetes | p | − | n | *Methylobacterium adhaesivum* | s | − |
| ge | Synergistaceae | f | + | m | Proteobacteria | p | + | n | Patulibacteraceae | f | + |
| ge | *Lactobacillus* sp. BL302 | s | + | m | Firmicutes | p | − | n | *Dermacoccus* sp. SST-20 | s | − |
| ge | *Lactobacillus* sp. BL304 | s | + | m | *Sarcina* | g | + | n | *Flavobacterium* sp. CS43 | s | − |
| ge | *Ochrobactrum* sp. SCTS14 | s | + | m | Streptococcaceae | f | − | n | *Moraxella* sp. BBN2P-02d | s | + |
| ge | *Lactobacillus* sp. 7_1_47FAA | s | − | m | *Streptococcus* | g | − | n | Solirubrobacterales | o | + |
| ge | *Peptoniphilus* sp. oral taxon 836 | s | + | m | *Clostridium* | g | − | n | *Kocuria* sp. M2T9B2 | s | + |
| ge | *Corynebacterium canis* | s | + | m | Actinobacteria | c | − | n | *Brevundimonas* sp. JW23.4a | s | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| ge | *Tessaracoccus* sp. SL014B-79A | s | − | m | *Lachnospira* | g | + | n | *Pseudomonas* sp. DQ-01 | s | − |
| ge | *Staphylococcus* sp. FXY54 | s | − | m | *Lachnospira pectinoschiza* | s | + | n | *Microbacterium* sp. PCRB024 | s | + |
| ge | *Peptoniphilus* sp. JCM 8143 | s | | m | Betaproteobacteria | c | + | n | *Cytophagia* | c | + |
| ge | *Corynebacterium* sp. NML96-0085 | s | + | m | Deltaproteobacteria | c | + | n | *Cytophagales* | o | + |
| ge | *Anaerobacillus* | g | + | m | *Asaccharospora irregularis* | s | − | n | *Aerococcus* sp. B43(2010) | s | − |
| ge | *Peptoniphilus* sp. oral taxon 375 | s | + | m | Veillonellaceae | f | + | n | *Acinetobacter* sp. WB22-23 | s | + |
| ge | *Peptoniphilus coxii* | s | + | m | Clostridiaceae | f | − | n | *Micrococcus* sp. WB18-01 | s | + |
| ge | *Herbaspirillum huttiense* | s | + | m | *Phascolarctobacterium faecium* | s | + | n | *Nesterenkonia* sp. JS3 | s | − |
| ge | *Peptoniphilus* sp. 1-14 | s | + | m | Lactobacillaceae | f | − | n | *Pseudomonas* sp. PDD-27b-3 | s | − |
| ge | *Peptoniphilus* sp. 7-2 | s | + | m | *Dorea formicigenerans* | s | + | n | *Sphingomonas* sp. PDD-26b-16 | s | |
| ge | *Stenotrophomonas* sp. KITS-1 | s | − | m | *Sutterella* | g | − | n | *Sphingomonas* sp. KOPRI 25661 | s | + |
| ge | *Negativicoccus* | g | + | m | *Pseudobutyrivibrio* | g | − | n | *Ferruginibacter* | g | + |
| ge | *Lactobacillus* sp. Akhmr01 | s | + | m | *Bacteroides caccae* | s | + | n | *Massilia* sp. hp37 | s | + |
| ge | *Fusobacterium* sp. ACB2 | s | + | m | Verrucomicrobiales | o | + | n | *Defluviimonas* | g | + |
| ge | *Fusobacterium* sp. CM21 | s | + | m | Fibrobacteres | p | + | n | *Ochrobactrum* sp. LC498 | s | + |
| ge | *Anaerococcus* sp. 8404299 | s | + | m | Oxalobacteraceae | f | + | n | *Acinetobacter* sp. HD5.2 | s | − |
| ge | *Anaerococcus* sp. 8405254 | s | + | m | Burkholderiales | o | + | n | *Rhizobium* sp. 10II | s | − |
| ge | *Anaerococcus* sp. 9401487 | s | + | m | Coriobacteriaceae | f | − | n | *Brevibacterium* sp. MBTD_CMFRI_Br02 | s | + |
| ge | *Anaerococcus provencensis* | s | + | m | *Eggerthella* | g | + | n | *Moraxella* sp. | s | − |
| ge | *Enterococcus* sp. SI-4 | s | + | m | Coriobacteriia | c | − | n | *Yersinia* | g | + |
| ge | *Bosea* sp. R-46060 | s | − | m | Coriobacteriales | o | − | n | *Yersinia enterocolitica* | s | + |
| ge | *Lactobacillus* sp. MYMRS/TEN2 | s | + | m | *Bacteroides acidifaciens* | s | + | n | *Streptococcus oralis* | s | + |
| ge | *Delftia* sp. BN-SKY3 | s | − | m | *Blautia luti* | s | + | n | *Bacillus cereus* | s | − |
| ge | *Staphylococcus* sp. C9I2 | s | + | m | Bacilli | c | − | n | *Peredibacter starrii* | s | + |
| ge | *Megasphaera* sp. UPII 199-6 | s | − | m | *Bacteroides* sp. AR20 | s | + | n | *Brachybacterium faecium* | s | + |
| ge | *Megasphaera* sp. UPII 135-E | s | − | m | *Bacteroides* sp. AR29 | s | + | n | *Kytococcus* | g | + |
| ge | *Corynebacterium epidermidicanis* | s | + | m | *Collinsella* | g | − | n | *Duganella* | g | − |
| ge | *Trueperella* | g | + | m | *Oscillospira* | g | − | n | *Fusibacter* | g | − |
| ge | *Mesorhizobium* sp. mat916 | s | + | m | Erysipelotrichaceae | f | − | n | Cellulomonadaceae | f | − |
| ge | *Actinomyces* sp. ICM58 | s | + | m | *Roseburia intestinalis* | s | + | n | *Sphingomonas aquatilis* | s | − |
| ge | *Jonquetella* sp. BV3C4 | s | + | m | Rikenellaceae | f | − | n | *Ochrobactrum tritici* | s | − |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| ge | *Prevotella* sp. BV3C7 | s | + | m | *Shuttleworthia* | g | − | n | Spartobacteria | c | + |
| ge | *Peptoniphilus* sp. BV3AC2 | s | + | m | Clostridia | c | + | n | *Candidatus Xiphinematobacter* | g | − |
| ge | *Megasphaera* sp. BV3C16-1 | s | + | m | Clostridiales | o | + | n | *Albidovulum inexpectatum* | s | + |
| ge | *Sphingobium* sp. LC341 | s | + | m | Lachnospiraceae | f | + | n | *Alkanindiges illinoisensis* | s | − |
| ge | *Anaerococcus* sp. PH9 | s | + | m | Peptostreptococcaceae | f | − | n | *Albidovulum* | g | + |
| ge | Leptotrichiaceae | f | + | m | Lactobacillales | o | − | n | Bdellovibrionales | o | + |
| ge | *Faecalibacterium* sp. *canine* oral taxon 147 | s | + | m | *Dorea* | g | + | n | Bacteriovoracaceae | f | + |
| ge | *Murdochiella* | g | + | m | Desulfovibrionaceae | f | + | n | *Peredibacter* | g | + |
| ge | *Varibaculum* sp. CCUG 45114 | s | + | m | Actinobacteria | p | − | n | *Conchiformibius* | g | − |
| ge | *Varibaculum* sp. CCUG 61255 | s |   | m | Verrucomicrobiae | c | + | n | Erythrobacteraceae | f | + |
| ge | *Propionibacterium* sp. KPL2005 | s | + | m | Verrucomicrobiaceae | f | + | n | *Staphylococcus* sp. L10 | s | + |
| ge | *Actinomyces* sp. S4-C9 | s | + | m | Fibrobacteria | c | + | n | *Rothia* sp. BBH4 | s | − |
| ge | *Atopobium* sp. MVA9 | s | + | m | Fibrobacteraceae | f | + | n | *Luteimonas aestuarii* | s | − |
| ge | *Atopobium* sp. S3MV24 | s | + | m | *Anaerostipes* | g | + | n | *Acidovorax* sp. LR05 | s | + |
| ge | *Atopobium* sp. S4-A11a | s | + | m | Desulfovibrionales | o | + | n | Clostridiales f XII. Incertae Sedis | f | − |
| ge | *Dialister* sp. S4-23 | s | + | m | Oscillospiraceae | f | − | n | *Chryseobacterium* sp. Y1D | s | − |
| ge | *Finegoldia* sp. S3MVA9 | s | + | m | *Faecalibacterium* | g | + | n | *Pseudomonas* sp. PcFRB100 | s | − |
| ge | *Gardnerella* sp. S3PF20 | s | + | m | Fibrobacterales | o | + | n | *Chryseobacterium* sp. IIL-Nv8 | s | + |
| ge | *Prevotella* sp. S4-10 | s | + | m | *Alistipes* | g | + | n | *Kocuria* sp. M1-36 | s | + |
| ge | *Peptoniphilus* sp. S4-A10 | s | + | m | *Akkermansia* | g | + | n | *Stenotrophomonas* sp. Z2-S2 | s | + |
| ge | *Finegoldia* sp. S5-A7 | s | + | m | *Akkermansia muciniphila* | s | + | n | *Deinococcus* sp. UAC-77 | s | + |
| ge | *Negativicoccus* sp. S5-A15 | s | + | m | *Anaerotruncus* | g | + | n | *Variovorax* sp. MM43Nov | s | + |
| ge | *Corynebacterium frankenforstense* | s | + | m | *Marvinbryantia* | g | − | n | *Kytococcus* sp. YB227 | s | + |
| ge | *Megasphaera massiliensis* | s | + | m | *Subdoligranulum* | g | + | n | *Alkanindiges* | g | + |
| ge | *Corynebacterium* sp. jw37 | s | + | m | *Flavonifractor plautii* | s | + | n | *Campylobacter sputorum* | s | + |
| ge | *Streptococcus* sp. 2011_Oral_MS_A3 | s | + | m | *Roseburia inulinivorans* | s | + | n | *Pseudomonas syringae* | s | − |
| ge | *Veillonella* sp. 2011_Oral_VSA_D3 | s | + | m | *Blautia wexlerae* | s | + | n | *Bordetella* | g | + |
| ge | *Peptoniphilus* sp. DNF00192 | s | + | m | *Moryella* | g | + | n | *Pedobacter heparinus* | s | − |
| ge | *Dialister* sp. S7MSR5 | s |   | m | Erysipelotrichia | c | − | n | *Bergeyella zoohelcum* | s | − |
| ge | *Stenotrophomonas* sp. N017 | s | + | m | Erysipelotrichales | o | − | n | *Porphyrobacter* | g | + |
| ge | *Lactobacillus* sp. C30An8 | s | − | m | Ruminococcaceae | f | + | n | *Streptococcus pneumoniae* | s | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| ge | *Bradyrhizobium* sp. CCBAU 53380 | s | − | m | Clostridiales f XIII. Incertae *Sedis* | f | − | n | *Aerococcus viridans* | s | − |
| ge | *Anaerococcus* sp. S8 87-3 | s | + | m | *Blautia* | g | + | n | *Actinomyces israelii* | s | + |
| ge | *Finegoldia* sp. S8 F7 | s | + | m | *Roseburia* sp. 11SE39 | s | + | n | *Mycobacterium chelonae* | s | + |
| ge | *Porphyromonas* sp. S8 86-12 | s | + | m | *Bacteroides* sp. D22 | s | + | n | *Brachymonas* | g | − |
| ge | *Actinomyces* sp. S9 PR-21 | s | + | m | *Alistipes* sp. RMA 9912 | s | + | n | *Pseudomonas agarici* | s | − |
| ge | *Anaerococcus* sp. S9 PR-16 | s | + | m | *Blautia faecis* | s | + | n | *Staphylococcus vitulinus* | s | − |
| ge | *Anaerococcus* sp. S9 PR-5 | s | + | m | Selenomonadales | o | − | n | *Moraxella lincolnii* | s | + |
| ge | *Finegoldia* sp. S9 AA1-5 | s | + | m | Negativicutes | c | − | n | *Alkalibacterium* | g | + |
| ge | *Murdochiella* sp. S9 PR-10 | s | + | m | *Streptococcus* sp. BS35a | s | + | n | *Xenophilus* | g | + |
| ge | *Peptococcus* sp. S9 Pr-12 | s | + | m | *Flavonifractor* | g | + | n | *Flavobacterium* sp. EP372 | s | − |
| ge | *Peptoniphilus* sp. S9 PR-13 | s | + | m | Sutterellaceae | f | − | n | *Corynebacterium caspium* | s | + |
| ge | *Corynebacterium* sp. 713182/2012 | s | + | m | *Anaerostipes* sp. 5_1_63FAA | s | + | n | *Epilithonimonas* | g | − |
| ge | *Atopobium deltae* | s | + | m | *Fusicatenibacter saccharivorans* | s | − | n | *Porphyrobacter* sp. NMC22 | s | + |
| ge | *Parvibacter* | g | + | m | *Blautia* sp. YHC-4 | s | + | n | *Brevundimonas* sp. a101-97 | s | + |
| ge | *Ralstonia* sp. A52 | s | + | m | Intestinimonas | g | + | n | *Massilia oculi* | s | + |
| ge | *Helcococcus seattlensis* | s | − | m | *Fusicatenibacter* | g | − | n | *Xenophilus* sp. XB36 | s | + |
| ge | *Staphylococcus* sp. 334802 | s | + | m | *Eisenbergiella* | g | + | n | *Kocuria* sp. LW2-LEVI2-W | s |  |
| ge | *Senegalimassilia* | g | − | m | *Eisenbergiella tayi* | s | + | n | *Pseudochrobactrum* | g | + |
| ge | *Veillonella seminalis* | s | − | m | *Candidatus Soleaferrea* | g | + | n | *Pseudochrobactrum* sp. a001-58 | s | + |
| ge | Intestinibacter | g | + | m | *Peptoclostridium* | g | + | n | *Flavobacterium johnsoniae* | s | − |
| ge | Peptoniphilaceae | f | + | m | *Asaccharospora* | g | − | n | *Brochothrix thermosphacta* | s | − |
| ge | Tissierellia | c | + | m | *Erysipelatoclostridium* | g | − | n | *Capnocytophaga cynodegmi* | s | − |
| ge | Tissierellales | o | + | m | *Campylobacter* | g | − | n | *Microbacterium xylanilyticum* | s | + |
| ge | Spirochaetales | o | + | m | *Campylobacter concisus* | s | − | n | *Pseudomonas* sp. GmFRB014 | s | + |
| ge | Spirochaetes | p | + | m | *Achromobacter* | g | + | n | *Flavobacterium rivuli* | s | + |
| ge | Spirochaetia | c | + | m | *Flavobacterium* | g | + | n | *Chryseobacterium anthropi* | s | + |
| ge | *Lactobacillus taiwanensis* | s | − | m | Rhizobiales | o | − | n | *Deinococcus taklimakanensis* | s | + |
| ge | *Phascolarctobacterium succinatutens* | s | + | m | *Rhizobium* | g | − | n | *Halomonas* sp. VS-102 | s | − |
| ge | *Leptotrichia hongkongensis* | s | + | m | *Methylobacterium* | g | + | n | *Alkalibacterium* sp. I-5 | s | + |
| ge | *Methylobacterium organophilum* | s | + | m | Moraxellaceae | f | + | n | *Methylobacterium* sp. JC86 | s | + |
| ge | *Bifidobacterium choerinum* | s | + | m | *Moraxella* | g | + | n | *Shewanella* sp. bk_8 | s | − |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| ge | Mycoplasma spermatophilum | s | + | m | Neisseriaceae | f | + | n | Sphingobacterium sp. KB45 | s | − |
| ge | Aerococcus sanguinicola | s | + | m | Neisseria | g | + | n | Bradyrhizobium sp. MG-2011-42-CD | s | + |
| ge | Brevibacterium sp. 10-1 | s | − | m | Neisseria mucosa | s | + | n | Pseudonocardia sp. MB03-A | s | + |
| ge | Lactobacillus sp. B164 | s | + | m | Neisseria elongata | s | − | n | Chryseobacterium sp. PYR2 | s | + |
| g | Bacteroidaceae | f | − | m | Neisseria macacae | s | + | n | Myroides | g | − |
| g | Bacteroides | g | − | m | Alcaligenaceae | f | + | n | Kocuria sp. PDM-7 | s | − |
| g | Bacteroides thetaiotaomicron | s | + | m | Enterobacteriaceae | f | − | n | Flavobacterium sp. ICM 1082 | s | + |
| g | Bacteroides thetaiotaomicron | s | + | m | Kluyvera | g | − | s | Bacteroidaceae | f | − |
| g | Bacteroides uniformis | s | − | m | Pasteurellaceae | f | + | s | Bacteroides | g | − |
| g | Bacteroides uniformis | s | − | m | Actinobacillus | g | + | s | Bacteroides uniformis | s | − |
| g | Bacteroides vulgatus | s | − | m | Haemophilus | g | + | s | Bacteroides vulgatus | s | − |
| g | Bacteroides vulgatus | s | − | m | Haemophilus influenzae | s | − | s | Roseburia | g | + |
| g | Roseburia | g | − | m | Haemophilus parainfluenzae | s | + | s | Faecalibacterium prausnitzii | s | + |
| g | Roseburia | g | − | m | Bacteroides fragilis | s | + | s | Herbaspirillum | g | + |
| g | Faecalibacterium prausnitzii | s | − | m | Parabacteroides distasonis | s | + | s | Bacteroidetes | p | − |
| g | Desulfovibrio | g | − | m | Campylobacter gracilis | s | − | s | Proteobacteria | p | − |
| g | Desulfovibrio sp. | s | + | m | Campylobacter ureolyticus | s | + | s | Firmicutes | p | + |
| g | Acidaminococcus | g | − | m | Butyrivibrio | g | − | s | Sarcina | g | + |
| g | Herbaspirillum | g | + | m | Porphyromonas | g | + | s | Streptococcaceae | f | + |
| g | Herbaspirillum seropedicae | s | + | m | Prevotella | g | − | s | Streptococcus | g | + |
| g | Bacteroidetes | p | + | m | Fusobacterium | g | − | s | Clostridium | g | + |
| g | Bacteroidetes | p | + | m | Fusobacterium nucleatum | s | − | s | Actinobacteria | c | − |
| g | Proteobacteria | p | + | m | Fusobacterium periodonticum | s | + | s | Lachnospira | g | + |
| g | Proteobacteria | p | + | m | Megasphaera | g | − | s | Lachnospira pectinoschiza | s | + |
| g | Firmicutes | p | − | m | Gammaproteobacteria | c | + | s | Betaproteobacteria | c | + |
| g | Sarcina | g | + | m | Peptostreptococcus | g | − | s | Veillonellaceae | f | − |
| g | Sarcina | g | + | m | Micrococcaceae | f | − | s | Clostridiaceae | f | + |
| g | Streptococcaceae | f | − | m | Staphylococcus | g | + | s | Phascolarctobacterium | g | |
| g | Streptococcaceae | f | − | m | Staphylococcus epidermidis | s | − | s | Phascolarctobacterium faecium | s | |
| g | Streptococcus | g | − | m | Streptococcus gordonii | s | − | s | Lactobacillaceae | f | + |
| g | Streptococcus | g | − | m | Streptococcus thermophilus | s | − | s | Dorea formicigenerans | s | |
| g | Clostridium | g | + | m | Streptococcus parasanguinis | s | + | s | Sutterella | g | |
| g | Clostridium | g | + | m | Enterococcus | g | + | s | Pseudobutyrivibrio | g | + |
| g | Actinobacteria | c | − | m | Aerococcus | g | + | s | Bacteroides caccae | s | |
| g | Actinobacteria | c | − | m | Gemella | g | − | s | Verrucomicrobiales | o | + |
| g | Lachnospira | g | + | m | Atopobium | g | − | s | Verrucomicrobia | p | + |
| g | Lachnospira pectinoschiza | s | − | m | Bacillales | o | + | s | Oxalobacteraceae | f | − |
| g | Lachnospira pectinoschiza | s | − | m | Clostridioides difficile | s | + | s | Burkholderiales | o | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "–" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Betaproteobacteria | c | – | m | Erysipelatoclostridium ramosum | s | + | s | Coriobacteriaceae | f | + |
| g | Betaproteobacteria | c | – | m | Lactobacillus | g | – | s | Coriobacteriia | c | + |
| g | Deltaproteobacteria | c | – | m | Lactobacillus salivarius | s | + | s | Coriobacteriales | o | + |
| g | Asaccharospora irregularis | s | – | m | Lactobacillus vaginalis | s | – | s | Bacteroides acidifaciens | s | |
| g | Veillonellaceae | f | – | m | Corynebacteriaceae | f | + | s | Blautia luti | s | + |
| g | Veillonellaceae | f | – | m | Actinomyces | g | – | s | Bacilli | c | + |
| g | Clostridiaceae | f | + | m | Actinomyces odontolyticus | s | + | s | Bacteroides sp. AR20 | s | + |
| g | Clostridiaceae | f | + | m | Bifidobacterium | g | + | s | Bacteroides sp. AR29 | s | + |
| g | Phascolarctobacterium | g | – | m | Corynebacterium | g | + | s | Collinsella | g | + |
| g | Phascolarctobacterium | g | – | m | Corynebacterium sp. | s | + | s | Erysipelotrichaceae | f | + |
| g | Phascolarctobacterium faecium | s | – | m | Propionibacterium | g | + | s | Roseburia intestinalis | s | |
| g | Lactobacillaceae | f | + | m | Cutibacterium acnes | s | + | s | Bacteroidales | o | – |
| g | Dorea formicigenerans | s | – | m | Mycobacteriaceae | f | + | s | Rikenellaceae | f | |
| g | Dorea formicigenerans | s | – | m | Mycobacterium | g | – | s | Shuttleworthia | g | – |
| g | Sutterella | g | – | m | Actinomycetales | o | – | s | Clostridia | c | + |
| g | Pseudobutyrivibrio | g | + | m | Rothia dentocariosa | s | – | s | Clostridiales | o | + |
| g | Pseudobutyrivibrio | g | + | m | Actinomycetaceae | f | – | s | Lachnospiraceae | f | + |
| g | Bacteroides caccae | s | – | m | Methanobacteriales | o | – | s | Peptostreptococcaceae | f | + |
| g | Bacteroides caccae | s | – | m | Methanobacteriaceae | f | – | s | Lactobacillales | o | + |
| g | Verrucomicrobiales | o | + | m | Methanobrevibacter | g | – | s | Dorea | g | + |
| g | Holdemania | g | + | m | Methanobrevibacter smithii | s | – | s | Desulfovibrionaceae | f | |
| g | Holdemania | g | + | m | Gardnerella | g | – | s | Bacteroidia | c | – |
| g | Holdemania filiformis | s | + | m | Gardnerella vaginalis | s | – | s | Actinobacteria | p | – |
| g | Holdemania filiformis | s | + | m | Peptococcus | g | + | s | Verrucomicrobiae | c | + |
| g | Fibrobacteres | p | + | m | Solanales | o | + | s | Verrucomicrobiaceae | f | + |
| g | Verrucomicrobia | p | + | m | Sphingomonas | g | | s | Anaerostipes | g | + |
| g | Oxalobacteraceae | f | + | m | Bacteroides eggerthii | s | + | s | Desulfovibrionales | o | |
| g | Burkholderiales | o | – | m | Alistipes putredinis | s | + | s | Oscillospiraceae | f | |
| g | Burkholderiales | o | – | m | Odoribacter splanchnicus | s | + | s | Faecalibacterium | g | + |
| g | Coriobacteriaceae | f | – | m | Prevotella bivia | s | + | s | Alistipes | g | |
| g | Eggerthella | g | + | m | Prevotella disiens | s | + | s | Akkermansia | g | + |
| g | Coriobacteriia | c | – | m | Alphaproteobacteria | c | – | s | Anaerotruncus | g | + |
| g | Coriobacteriales | o | – | m | Euryarchaeota | p | – | s | Subdoligranulum | g | + |
| g | Bacteroides acidifaciens | s | – | m | Gemella morbillorum | s | – | s | Blautia wexlerae | s | + |
| g | Blautia luti | s | – | m | Veillonella | g | + | s | Moryella | g | |
| g | Blautia luti | s | – | m | Veillonella parvula | s | + | s | Erysipelotrichia | c | + |
| g | Bacilli | c | – | m | Epsilonproteobacteria | c | – | s | Erysipelotrichales | o | + |
| g | Bacteroides sp. AR20 | s | + | m | Bifidobacteriaceae | f | – | s | Ruminococcaceae | f | + |
| g | Bacteroides sp. AR20 | s | + | m | Propionibacteriacea | f | + | s | Clostridiales f XIII. Incertaee Sedis | f | + |
| g | Bacteroides sp. AR29 | s | – | m | Mollicutes | c | + | s | Blautia | g | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | *Bacteroides* sp. AR29 | s | − | m | *Eggerthia catenaformis* | s | + | s | *Roseburia* sp. 11SE39 | s | + |
| g | *Collinsella* | g | − | m | *Leptotrichia* | g | + | s | *Blautia faecis* | s | + |
| g | *Collinsella* | g | − | m | *Rothia* | g | − | s | Selenomonadales | o | − |
| g | *Oscillospira* | g | + | m | *Parvimonas micra* | s | + | s | Acidaminococcaceae | f | |
| g | *Oscillospira* | g | + | m | Streptophyta | p | + | s | Negativicutes | c | |
| g | Erysipelotrichaceae | f | − | m | *Bilophila* | g | + | s | *Streptococcus* sp. BS35a | s | + |
| g | *Roseburia intestinalis* | s | − | m | *Bilophila wadsworthia* | s | + | s | *Flavonifractor* | g | |
| g | *Roseburia intestinalis* | s | − | m | *Veillonella atypica* | s | − | s | Sutterellaceae | f | + |
| g | Bacteroidales | o | + | m | *Corynebacterium glucuronolyticum* | s | + | s | *Anaerostipes* sp. 5_1_63FAA | s | + |
| g | Bacteroidales | o | + | m | *Dialister* | g | − | s | *Fusicatenibacter saccharivorans* | s | + |
| g | Rikenellaceae | f | + | m | *Dialister pneumosintes* | s | − | s | *Fusicatenibacter* | g | + |
| g | Rikenellaceae | f | + | m | *Sutterella wadsworthensis* | s | − | s | *Peptoclostridium* | g | + |
| g | *Shuttleworthia* | g | − | m | *Brevundimonas* | g | + | s | *Erysipelatoclostridium* | g | + |
| g | Clostridia | c | + | m | Bradyrhizobiaceae | f | + | s | *Campylobacter* | g | + |
| g | Clostridia | c | + | m | Sphingomonadaceae | f | | s | *Flavobacterium* | g | + |
| g | Clostridiales | o | + | m | *Rothia mucilaginosa* | s | − | s | *Pseudomonas* | g | − |
| g | Clostridiales | o | + | m | *Butyrivibrio crossotus* | s | | s | Rhizobiales | o | + |
| g | Lachnospiraceae | f | − | m | *Abiotrophia* | g | + | s | *Bradyrhizobium* | g | + |
| g | Lachnospiraceae | f | − | m | *Granulicatella adiacens* | s | − | s | *Rhizobium* | g | − |
| g | Peptostreptococcaceae | f | + | m | *Abiotrophia defectiva* | s | + | s | *Mesorhizobium loti* | s | − |
| g | Peptostreptococcaceae | f | + | m | *Parabacteroides merdae* | s | + | s | *Methylobacterium* | g | + |
| g | Lactobacillales | o | − | m | *Bacteroides stercoris* | s | − | s | Moraxellaceae | f | + |
| g | *Dorea* | g | − | m | *Lautropia* | g | + | s | *Acinetobacter* | g | + |
| g | *Dorea* | g | − | m | *Lactobacillus crispatus* | s | + | s | Neisseriaceae | f | + |
| g | Desulfovibrionaceae | f | − | m | Flavobacteriaceae | f | + | s | *Neisseria* | g | + |
| g | Bacteroidia | c | + | m | *Actinobacillus porcinus* | s | + | s | *Neisseria mucosa* | s | + |
| g | Bacteroidia | c | + | m | *Pantoea* | g | + | s | *Neisseria macacae* | s | + |
| g | Actinobacteria | p | − | m | *Chryseobacterium* | g | − | s | *Ochrobactrum* | g | + |
| g | Actinobacteria | p | − | m | *Bergeyella* | g | + | s | Enterobacteriaceae | f | − |
| g | Verrucomicrobiae | c | + | m | *Corynebacterium ulcerans* | s | − | s | *Citrobacter* | g | − |
| g | Verrucomicrobiaceae | f | + | m | Phyllobacteriaceae | f | | s | *Enterobacter* | g | − |
| g | Fibrobacteria | c | + | m | Pseudomonadales | o | + | s | *Klebsiella* | g | − |
| g | Fibrobacteraceae | f | + | m | Campylobacteraceae | f | − | s | *Kluyvera* | g | − |
| g | *Anaerostipes* | g | − | m | *Tessaracoccus* | g | + | s | *Proteus* | g | |
| g | *Anaerostipes* | g | − | m | *Kluyvera georgiana* | s | − | s | *Serratia* | g | + |
| g | Desulfovibrionales | o | − | m | *Collinsella aerofaciens* | s | + | s | Pasteurellaceae | f | + |
| g | Oscillospiraceae | f | + | m | Caulobacteraceae | f | + | s | *Actinobacillus* | g | + |
| g | Oscillospiraceae | f | + | m | Comamonadaceae | f | − | s | *Haemophilus* | g | + |
| g | *Faecalibacterium* | g | − | m | *Delftia* | g | − | s | *Haemophilus influenzae* | s | + |
| g | Fibrobacterales | o | + | m | Enterococcaceae | f | + | s | *Haemophilus parainfluenzae* | s | + |
| g | *Alistipes* | g | + | m | Rhizobiaceae | f | − | s | *Parabacteroides distasonis* | s | − |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Alistipes | g | + | m | Gemella sp. 933-88 | s | + | s | Campylobacter ureolyticus | s | + |
| g | Akkermansia | g | + | m | Bifidobacteriales | o | − | s | Porphyromonas | g | − |
| g | Akkermansia muciniphila | s | + | m | Micrococcales | o | − | s | Prevotella | g | − |
| g | Hespellia | g | + | m | Corynebacteriales | o | + | s | Fusobacterium | g | + |
| g | Hespellia | g | + | m | Propionibacteriales | o | + | s | Fusobacterium nucleatum | s | + |
| g | Anaerotruncus | g | + | m | Mogibacterium | g | − | s | Gammaproteobacteria | c | − |
| g | Anaerotruncus | g | + | m | Aerococcus christensenii | s | + | s | Peptostreptococcus | g | − |
| g | Marvinbryantia | g | + | m | Dorea longicatena | s | + | s | Finegoldia magna | s | − |
| g | Marvinbryantia | g | + | m | Staphylococcaceae | f | + | s | Peptostreptococcus anaerobius | s | − |
| g | Subdoligranulum | g | − | m | Enterobacterales | o | − | s | Micrococcaceae | f | − |
| g | Flavonifractor plautii | s | + | m | Candidatus Saccharibacteria | p | − | s | Micrococcus | g | + |
| g | Bacteroides finegoldii | s | − | m | Solobacterium moorei | s | − | s | Micrococcus luteus | s | − |
| g | Lactonifactor longoviformis | s | + | m | Granulicatella | g | − | s | Staphylococcus | g | + |
| g | Roseburia inulinivorans | s | − | m | Flavobacteriia | c | + | s | Staphylococcus aureus | s | + |
| g | Roseburia inulinivorans | s | − | m | Methylobacteriaceae | f | − | s | Staphylococcus epidermidis | s | + |
| g | Blautia wexlerae | s | − | m | Burkholderiaceae | f | + | s | Deinococcus-Thermus | p | + |
| g | Blautia wexlerae | s | − | m | Solobacterium | g | − | s | Streptococcus gordonii | s | + |
| g | Lactonifactor | g | + | m | Olsenella | g | − | s | Streptococcus thermophilus | s | + |
| g | Moryella | g | + | m | Pseudomonadaceae | f | − | s | Streptococcus parasanguinis | s | + |
| g | Adlercreutzia equolifaciens | s | + | m | Pasteurellales | o | + | s | Enterococcus | g | + |
| g | Adlercreutzia equolifaciens | s | + | m | Catenibacterium | g | + | s | Aerococcus | g | + |
| g | Adlercreutzia | g | + | m | Granulicatella elegans | s | − | s | Gemella | g | + |
| g | Adlercreutzia | g | + | m | Finegoldia | g | + | s | Bacillales | o | + |
| g | Erysipelotrichia | c | − | m | Anaeroglobus | g | − | s | Bacillus | g | − |
| g | Erysipelotrichales | o | − | m | Anaeroglobus geminatus | s | − | s | Lysinibacillus sphaericus | s | + |
| g | Ruminococcaceae | f | + | m | Megamonas | g | − | s | Lactobacillus | g | + |
| g | Ruminococcaceae | f | + | m | Anaerococcus | g | + | s | Corynebacteriaceae | f | + |
| g | Clostridiales f XIII. Incertae Sedis | f | + | m | Porphyromonadaceae | f | + | s | Actinomyces | g | − |
| g | Clostridiales f XIII. Incertae Sedis | f | + | m | Prevotellaceae | f | − | s | Actinomyces odontolyticus | s | − |
| g | Acidaminococcus sp. D21 | s | − | m | Methanobacteria | c | − | s | Bifidobacterium | g | |
| g | Blautia | g | − | m | Varibaculum cambriense | s | + | s | Brevibacterium | g | − |
| g | Blautia | g | − | m | Corynebacterium spheniscorum | s | + | s | Corynebacterium | g | + |
| g | Roseburia sp. 11SE39 | s | − | m | Peptococcaceae | f | − | s | Corynebacterium diphtheriae | s | + |
| g | Roseburia sp. 11SE39 | s | − | m | Bacillaceae | f | + | s | Corynebacterium sp. | s | − |
| g | Bacteroides sp. D22 | s | − | m | Aerococcaceae | f | + | s | Propionibacterium | g | − |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | *Alistipes* sp. RMA 9912 | s | + | m | Carnobacteriaceae | f | + | s | *Cutibacterium acnes* | s | − |
| g | *Blautia* sp. Ser8 | s | − | m | *Megasphaera micronuciformis* | s | − | s | Mycobacteriaceae | f | − |
| g | *Blautia faecis* | s | + | m | *Propionibacterium* sp. MSP09A | s | − | s | *Mycobacterium* | g | − |
| g | *Blautia faecis* | s | + | m | Flavobacteriales | o | + | s | *Rhodococcus* | g | + |
| g | Selenomonadales | o | − | m | Fusobacteriaceae | f | − | s | *Rhodococcus erythropolis* | s | + |
| g | Selenomonadales | o | − | m | Sphingomonadales | o | + | s | Actinomycetales | o | − |
| g | Acidaminococcaceae | f | − | m | Caulobacterales | o | + | s | *Rothia dentocariosa* | s | − |
| g | Acidaminococcaceae | f | − | m | *Bacteroides massiliensis* | s | + | s | Actinomycetaceae | f | − |
| g | Negativicutes | c | − | m | Neisseriales | o | + | s | *Gardnerella* | g | + |
| g | Negativicutes | c | − | m | Campylobacterales | o | − | s | *Gardnerella vaginalis* | s | + |
| g | *Eggerthella* sp. HGA1 | s | + | m | *Subdoligranulum variabile* | s | + | s | *Halomonas* | g | + |
| g | *Streptococcus* sp. BS35a | s | − | m | *Alistipes finegoldii* | s | − | s | *Globicatella* | g | − |
| g | *Flavonifractor* | g | + | m | *Bifidobacterium longum* | s | + | s | *Globicatella sanguinis* | s | − |
| g | *Flavonifractor* | g | + | m | *Dialister invisus* | s | − | s | *Phyllobacterium* | g | |
| g | Sutterellaceae | f | − | m | *Peptoniphilus* sp. 2002-2300004 | s | + | s | *Alistipes putredinis* | s | |
| g | Sutterellaceae | f | − | m | *Sutterella stercoricanis* | s | + | s | *Odoribacter splanchnicus* | s | |
| g | *Anaerostipes* sp. 5_1_63FAA | s | − | m | *Oribacterium* | g | − | s | *Porphyromonas asaccharolytica* | s | − |
| g | *Anaerostipes* sp. 5_1_63FAA | s | − | m | *Porphyromonas uenonis* | s | − | s | *Prevotella buccalis* | s | − |
| g | *Fusicatenibacter saccharivorans* | s | − | m | *Odoribacter* | g | − | s | *Prevotella disiens* | s | − |
| g | *Fusicatenibacter saccharivorans* | s | − | m | *Roseburia hominis* | s | − | s | Alphaproteobacteria | c | + |
| g | *Blautia* sp. YHC-4 | s | − | m | *Roseburia faecis* | s | + | s | Halomonadaceae | f | + |
| g | *Intestinimonas* | g | + | m | *Dialister micraerophilus* | s | + | s | *Arcanobacterium* | g | + |
| g | *Intestinimonas* | g | + | m | *Bacteroides plebeius* | s | + | s | *Gemella morbillorum* | s | + |
| g | *Fusicatenibacter* | g | − | m | *Bacteroides coprocola* | s | + | s | *Rhizobium etli* | s | + |
| g | *Fusicatenibacter* | g | − | m | *Parabacteroides goldsteinii* | s | + | s | *Veillonella* | g | + |
| g | *Eisenbergiella* | g | − | m | *Bacteroides intestinalis* | s | + | s | *Veillonella parvula* | s | + |
| g | *Eisenbergiella tayi* | s | − | m | *Peptostreptococcus stomatis* | s | − | s | Epsilonproteobacteria | c | + |
| g | *Candidatus Soleaferrea* | g | + | m | *Peptoniphilus* sp. gpac018A | s | | s | Propionibacteriaceae | f | − |
| g | *Peptoclostridium* | g | − | m | *Bacteroides* sp. XB12B | s | + | s | *Helcococcus* | g | − |
| g | *Asaccharospora* | g | − | m | *Parabacteroides* | g | + | s | Xanthomonadaceae | f | − |
| g | *Erysipelatoclostridium* | g | − | m | *Barnesiella* | g | − | s | *Fusobacteria* | p | + |
| g | *Erysipelatoclostridium* | g | − | m | *Howardella* | g | − | s | *Leptotrichia* | g | − |
| g | *Campylobacter* | g | − | m | *Streptococcus* sp. 11aTha1 | s | − | s | *Rothia* | g | − |
| g | *Achromobacter* | g | − | m | *Alloscardovia* | g | | s | *Actinomyces neuii* | s | − |
| g | *Flavobacterium* | g | − | m | *Alloscardovia omnicolens* | s | | s | *Cutibacterium avidum* | s | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Pseudomonas | g | + | m | Veillonella rogosae | s | − | s | Propionimicrobium lymphophilum | s | + |
| g | Rhizobiales | o | + | m | Megamonas funiformis | s | − | s | Anaerococcus hydrogenalis | s | + |
| g | Bradyrhizobium | g | + | m | Alistipes sp. EBA6-25cl2 | s | − | s | Peptoniphilus lacrimalis | s | + |
| g | Moraxella | g | − | m | Bacteroides sp. EBA5-17 | s | − | s | Anaerococcus lactolyticus | s | + |
| g | Neisseriaceae | f | − | m | Oscillibacter | g | − | s | Parvimonas micra | s | + |
| g | Neisseria | g | − | m | Alistipes sp. NML05A004 | s | − | s | Anaerococcus prevotii | s | + |
| g | Neisseria mucosa | s | − | m | Barnesiella intestinihominis | s | − | s | Anaerococcus tetradius | s | |
| g | Neisseria macacae | s | − | m | Parasutterella excrementihominis | s | + | s | Microbacterium | g | − |
| g | Alcaligenaceae | f | + | m | Porphyromonas bennonis | s | | s | Dermabacter | g | + |
| g | Ochrobactrum | g | + | m | Synergistetes | p | − | s | Dermabacter hominis | s | + |
| g | Enterobacteriaceae | f | − | m | Clostridiales f XI. Incertae Sedis | f | + | s | Corynebacterium glucuronolyticum | s | − |
| g | Citrobacter | g | − | m | Parvimonas | g | − | s | Dialister | g | − |
| g | Klebsiella | g | − | m | Tenericutes | p | + | s | Stenotrophomonas | g | − |
| g | Kluyvera | g | − | m | Delftia lacustris | s | + | s | Brevundimonas | g | − |
| g | Proteus | g | + | m | Butyricimonas | g | + | s | Bradyrhizobiaceae | f | + |
| g | Proteus mirabilis | s | + | m | Paraprevotella | g | + | s | Rhodospirillaceae | f | + |
| g | Pasteurellaceae | f | − | m | Parasutterella | g | + | s | Corynebacterium argentoratense | s | − |
| g | Pasteurellaceae | f | − | m | Enterorhabdus | g | + | s | Brachybacterium | g | + |
| g | Actinobacillus | g | + | m | Bacteroides clarus | s | + | s | Rothia mucilaginosa | s | + |
| g | Haemophilus | g | − | m | Bifidobacterium kashiwanohense | s | − | s | Granulicatella adiacens | s | + |
| g | Haemophilus | g | − | m | Lautropia sp. TeTO | s | + | s | Bacteroides stercoris | s | − |
| g | Haemophilus influenzae | s | + | m | Anaerostipes hadrus | s | − | s | Lactobacillus crispatus | s | + |
| g | Haemophilus parainfluenzae | s | − | m | Synergistia | c | − | s | Ralstonia | g | + |
| g | Haemophilus parainfluenzae | s | − | m | Synergistales | o | − | s | Flavobacteriaceae | f | − |
| g | Bacteroides fragilis | s | + | m | Synergistaceae | f | − | s | Actinobacillus porcinus | s | + |
| g | Bacteroides fragilis | s | + | m | Anaerosporobacter | g | − | s | Meiothermus silvanus | s | + |
| g | Parabacteroides distasonis | s | − | m | Lactobacillus sp. BL302 | s | − | s | Pantoea | g | − |
| g | Parabacteroides distasonis | s | − | m | Campylobacter sp. 10_1_50 | s | − | s | Anaerococcus octavius | s | + |
| g | Campylobacter gracilis | s | + | m | Lactobacillus sp. 7_1_47FAA | s | − | s | Kocuria | g | + |
| g | Campylobacter ureolyticus | s | + | m | Veillonella sp. oral taxon 780 | s | + | s | Trueperella bernardiae | s | − |
| g | Butyrivibrio | g | − | m | Anaerobacillus | g | + | s | Chryseobacterium | g | − |
| g | Porphyromonas | g | − | m | Actinomyces sp. oral taxon 175 | s | − | s | Meiothermus | g | + |
| g | Prevotella | g | − | m | Peptococcus sp. oral taxon 168 | s | − | s | Facklamia | g | + |
| g | Fusobacterium | g | + | m | Streptococcus sp. oral taxon G59 | s | − | s | Facklamia sp. 164-92 | s | + |
| g | Fusobacterium mortiferum | s | + | m | Stomatobaculum longum | s | + | s | Mesorhizobium | g | − |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Fusobacterium nucleatum | s | + | m | Bacteroides stercorirosoris | s | + | s | Phyllobacteriaceae | f | − |
| g | Fusobacterium periodonticum | s | + | m | Blautia stercoris | s | + | s | Kocuria rhizophila | s | + |
| g | Desulfovibrio piger | s | + | m | Alistipes sp. HGB5 | s | − | s | Pseudomonadales | o | − |
| g | Megasphaera | g | − | m | Bacteroides sp. SLC1-38 | s | + | s | Campylobacteraceae | f | + |
| g | Weeksella | g | − | m | Lactobacillus sp. Akhmro1 | s | + | s | Tessaracoccus | g | + |
| g | Weeksella virosa | s | − | m | Veillonella sp. CM60 | s | − | s | Kluyvera georgiana | s | − |
| g | Gammaproteobacteria | c | − | m | Actinomyces sp. ICM54 | s | − | s | Collinsella aerofaciens | s | + |
| g | Peptostreptococcus | g | + | m | Bifidobacterium sp. MSX5B | s | + | s | Actinobaculum | g | + |
| g | Finegoldia magna | s | − | m | Campylobacter sp. FOBRC15 | s | − | s | Caulobacteraceae | f | − |
| g | Finegoldia magna | s | − | m | Fusobacterium sp. AS2 | s | + | s | Bacillus pseudofirmus | s | + |
| g | Peptostreptococcus anaerobius | s | + | m | Fusobacterium sp. CM21 | s | − | s | Comamonadaceae | f | + |
| g | Staphylococcus | g | − | m | Bradyrhizobium sp. 68A4SAPT | s | + | s | Delftia | g | + |
| g | Staphylococcus simulans | s | − | m | Delftia sp. BN-SKY3 | s | − | s | Enterococcaceae | f | + |
| g | Deinococcus-Thermus | p | + | m | Methylobacterium sp. RK-2008-1 | s | | s | Rhizobiaceae | f | − |
| g | Streptococcus gordonii | s | + | m | Staphylococcus sp. C9I2 | s | + | s | Gemella sp. 933-88 | s | + |
| g | Streptococcus thermophilus | s | − | m | Megasphaera sp. UPII 199-6 | s | − | s | Micrococcales | o | − |
| g | Streptococcus thermophilus | s | − | m | Coprobacter fastidiosus | s | + | s | Corynebacteriales | o | + |
| g | Streptococcus parasanguinis | s | + | m | Actinomyces sp. ICM58 | s | − | s | Propionibacteriales | o | − |
| g | Enterococcus | g | + | m | Leptotrichiaceae | f | + | s | Brevibacteriaceae | f | − |
| g | Enterococcus faecalis | s | − | m | Faecalibacterium sp. canine oral taxon 147 | s | − | s | Dermabacteraceae | f | + |
| g | Lactococcus lactis | s | + | m | Lachnoanaerobaculum | g | − | s | Microbacteriaceae | f | − |
| g | Lactococcus lactis | s | + | m | Streptococcus sp. GMD6S | s | + | s | Bosea | g | − |
| g | Aerococcus | g | + | m | Stomatobaculum | g | + | s | Achromobacter xylosoxidans | s | + |
| g | Gemella | g | − | m | Solobacterium sp. S4-A19 | s | − | s | Propionibacterium sp. V07/12348 | s | − |
| g | Atopobium | g | − | m | Megasphaera massiliensis | s | − | s | Aerococcus christensenii | s | − |
| g | Atopobium minutum | s | + | m | Streptococcus sp. 2011_Oral_MS_A3 | s | + | s | Lactobacillus fornicalis | s | − |
| g | Bacillales | o | − | m | Veillonella sp. 2011_Oral_VSA_D3 | s | − | s | Dorea longicatena | s | + |
| g | Bacillus | g | + | m | Eggerthia | g | + | s | Staphylococcaceae | f | + |
| g | Clostridioides difficile | s | − | m | Alloprevotella | g | − | s | Enterobacterales | o | − |
| g | Erysipelatoclostridium ramosum | s | − | m | Finegoldia sp. S8 F7 | s | − | s | Candidatus Saccharibacteria | p | + |
| g | Lactobacillus | g | − | m | Finegoldia sp. S9 AA1-5 | s | + | s | Pseudoglutamicibacter albus | s | − |
| g | Lactobacillus acidophilus | s | − | m | Coprobacter | g | + | s | Solobacterium moorei | s | − |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "–" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | *Lactobacillus gasseri* | s | + | m | *Staphylococcus* sp. 3348O2 | s | + | s | *Granulicatella* | g | + |
| g | *Lactobacillus reuteri* | s | + | m | *Terrisporobacter* | g | – | s | Flavobacteriia | c | – |
| g | *Lactobacillus salivarius* | s | + | m | *Intestinibacter* | g | + | s | Brucellaceae | f | + |
| g | *Lactobacillus vaginalis* | s | – | m | Peptoniphilaceae | f | + | s | Deinococcales | o | + |
| g | Corynebacteriaceae | f | – | m | Tissierellia | c | + | s | Methylobacteriaceae | f | + |
| g | Corynebacteriaceae | f | – | m | Tissierellales | o | + | s | Burkholderiaceae | f | + |
| g | *Actinomyces* | g | – | m | Veillonellales | o | + | s | *Solobacterium* | g | – |
| g | *Actinomyces odontolyticus* | s | + | m | Spirochaetales | o | – | s | *Actinomyces radingae* | s | – |
| g | *Arthrobacter* | g | – | m | *Johnsonella* | g | + | s | Xanthomonadales | o | – |
| g | *Arthrobacter* sp. | s | – | m | Spirochaetes | p | – | s | Oceanospirillales | o | + |
| g | *Bifidobacterium* | g | – | m | Spirochaetia | c | – | s | Pseudomonadaceae | f | – |
| g | *Bifidobacterium* | g | – | m | *Bacteroides* sp. XB44A | s | – | s | Pasteurellales | o | + |
| g | *Bifidobacterium bifidum* | s | + | m | *Phascolarctobacterium succinatutens* | s | – | s | *Aerosphaera* | g | + |
| g | *Bifidobacterium bifidum* | s | + | m | *Campylobacter showae* | s | + | s | *Aerosphaera taetra* | s | + |
| g | *Bifidobacterium breve* | s | + | m | *Comamonas* | g | + | s | *Lactobacillus iners* | s | + |
| g | *Bifidobacterium dentium* | s | + | m | *Neisseria flavescens* | s | – | s | *Finegoldia* | g | – |
| g | *Brevibacterium* | g | – | m | *Neisseria sicca* | s | – | s | *Corynebacterium mastitidis* | s | + |
| g | *Corynebacterium* | g | – | m | *Bergeriella denitrificans* | s | – | s | *Peptoniphilus* | g | – |
| g | *Corynebacterium* | g | – | m | *Kingella oralis* | s | + | s | *Gallicola* | g | + |
| g | *Corynebacterium diphtheriae* | s | + | m | *Eikenella* | g | – | s | *Novosphingobium* | g | + |
| g | *Corynebacterium diphtheriae* | s | + | m | *Eikenella corrodens* | s | – | s | *Anaerococcus* | g | + |
| g | *Corynebacterium* sp. | s | – | m | *Aggregatibacter aphrophilus* | s | + | s | *Brevibacterium paucivorans* | s | – |
| g | *Propionibacterium* | g | – | m | *Aggregatibacter segnis* | s | – | s | Porphyromonadaceae | f | – |
| g | *Cutibacterium acnes* | s | – | m | *Pasteurella* | g | – | s | Prevotellaceae | f | + |
| g | Mycobacteriaceae | f | – | m | *Rodentibacter pneumotropicus* | s | – | s | *Corynebacterium spheniscorum* | s | – |
| g | *Mycobacterium* | g | + | m | *Fibrobacter* | g | + | s | Bacillaceae | f | + |
| g | *Rhodococcus* | g | + | m | *Porphyromonas gingivalis* | s | + | s | Carnobacteriaceae | f | + |
| g | Actinomycetales | o | – | m | Cardiobacteriaceae | f | + | s | Deinococci | c | + |
| g | Actinomycetales | o | – | m | *Desulfobulbus* | g | + | s | *Propionibacterium* sp. MSP09A | s | – |
| g | *Rothia dentocariosa* | s | + | m | *Selenomonas* | g | + | s | Flavobacteriales | o | – |
| g | Actinomycetaceae | f | – | m | *Capnocytophaga* | g | – | s | Fusobacteriia | c | + |
| g | *Mobiluncus* | g | – | m | *Capnocytophaga gingivalis* | s | + | s | Fusobacteriales | o | + |
| g | *Mobiluncus curtisii* | s | + | m | *Capnocytophaga ochracea* | s | + | s | Fusobacteriaceae | f | + |
| g | *Mobiluncus mulieris* | s | – | m | *Capnocytophaga sputigena* | s | + | s | Rhodospirillales | o | + |
| g | Mycoplasmatales | o | + | m | Cyanobacteria | p | – | s | Caulobacterales | o | – |
| g | Mycoplasmataceae | f | + | m | *Streptococcus mutans* | s | + | s | Neisseriales | o | + |
| g | *Mycoplasma* | g | + | m | *Streptococcus intermedius* | s | – | s | Campylobacterales | o | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Mycoplasma hominis | s | + | m | Atopobium parvulum | s | − | s | Subdoligranulum variabile | s | + |
| g | Ureaplasma | g | − | m | Atopobium rimae | s | − | s | Peptoniphilus sp. 2002-38328 | s | − |
| g | Ureaplasma urealyticum | s | − | m | Lactobacillus paracasei | s | + | s | Peptoniphilus sp. 2002-2300004 | s | + |
| g | Methanobacteriales | o | + | m | Actinomyces naeslundii | s | + | s | Bacillus sp. T41 | s | + |
| g | Methanobacteriaceae | f | + | m | Actinomyces viscosus | s | + | s | Fastidiosipila | g | − |
| g | Methanobrevibacter | g | + | m | Bifidobacterium adolescentis | s | + | s | Fastidiosipila sanguinis | s | − |
| g | Methanobrevibacter smithii | s | + | m | Pseudopropionibacterium propionicum | s | − | s | Cloacibacterium normanense | s | − |
| g | Gardnerella | g | + | m | Anaeroplasma | g | + | s | Helcococcus sueciensis | s | − |
| g | Gardnerella vaginalis | s | − | m | Mycoplasma salivarium | s | + | s | Pseudoclavibacter | g | − |
| g | Peptococcus | g | − | m | Methanosphaera | g | + | s | Odoribacter | g | |
| g | Peptococcus | g | − | m | Methanosphaera stadtmanae | s | + | s | Roseburia faecis | s | + |
| g | Peptococcus niger | s | − | m | Cardiobacterium | g | + | s | Dialister propionicifaciens | s | − |
| g | Solanales | o | − | m | Cardiobacterium hominis | s | + | s | Porphyromonas somerae | s | − |
| g | Bifidobacterium pseudocatenulatum | s | − | m | Vagococcus | g | + | s | Pelomonas | g | + |
| g | Phyllobacterium | g | + | m | Streptococcus mitis | s | − | s | Peptoniphilus sp. gpaco18A | s | − |
| g | Bacteroides eggerthii | s | + | m | Tannerella forsythia | s | − | s | Peptoniphilus sp. gpac148 | s | + |
| g | Alistipes putredinis | s | + | m | Porphyromonas endodontalis | s | − | s | Parabacteroides | g | − |
| g | Alistipes putredinis | s | + | m | Prevotella intermedia | s | − | s | Lysinibacillus | g | + |
| g | Odoribacter splanchnicus | s | + | m | Prevotella nigrescens | s | − | s | Citrobacter sp. BW4 | s | − |
| g | Odoribacter splanchnicus | s | + | m | Prevotella oralis | s | − | s | Pseudomonas sp. G1116 | s | − |
| g | Porphyromonas asaccharolytica | s | + | m | Prevotella oris | s | − | s | Anaerococcus murdochii | s | − |
| g | Prevotella buccalis | s | − | m | Prevotella oulorum | s | + | s | Acinetobacter sp. RBE2CD-114 | s | + |
| g | Prevotella disiens | s | + | m | Actinomyces sp. | s | + | s | Streptococcus sp. 11aTha1 | s | + |
| g | Cronobacter sakazakii | s | + | m | Dolosigranulum | g | + | s | Methylobacterium sp. CBMB45 | s | − |
| g | Alphaproteobacteria | c | + | m | Dolosigranulum pigrum | s | + | s | Rhizobium sp. sc-w | s | + |
| g | Arcanobacterium | g | + | m | Acetitomaculum | g | − | s | Pelomonas aquatica | s | + |
| g | Arcanobacterium haemolyticum | s | + | m | Kingella | g | + | s | Bacteroides sp. EBA5-17 | s | + |
| g | Euryarchaeota | p | + | m | Mogibacterium timidum | s | − | s | Pantoea vagans | s | − |
| g | Veillonella | g | + | m | Terrisporobacter glycolicus | s | − | s | Anaerobacillus alkalidiazotrophicus | s | + |
| g | Veillonella | g | + | m | Veillonella dispar | s | + | s | Brevibacterium ravenspurgense | s | − |
| g | Veillonella parvula | s | + | m | Leptotrichia buccalis | s | − | s | Parasutterella excrementihominis | s | + |
| g | Epsilonproteobacteria | c | − | m | Porphyromonas catoniae | s | + | s | Porphyromonas bennonis | s | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Bifidobacteriaceae | f | − | m | *Corynebacterium matruchotii* | s | + | s | *Clostridiales* f XI. *Incertae Sedis* | f | + |
| g | Bifidobacteriaceae | f | − | m | *Catonella* | g | − | s | *Parvimonas* | g | + |
| g | Propionibacteriaceae | f | − | m | *Catonella morbi* | s | − | s | *Corynebacterium freiburgense* | s | + |
| g | Mollicutes | c | + | m | *Filifactor* | g | − | s | *Delftia lacustris* | s | + |
| g | *Helcococcus* | g | − | m | *Capnocytophaga granulosa* | s | + | s | *Butyricimonas* | g | |
| g | Rhodobacteraceae | f | − | m | *Capnocytophaga haemolytica* | s | + | s | *Parasutterella* | g | + |
| g | *Leptotrichia* | g | − | m | *Actinomyces georgiae* | s | + | s | *Phyllobacterium* sp. T50 | s | |
| g | *Rothia* | g | + | m | *Actinomyces gerencseriae* | s | + | s | *Porphyromonas* sp. 2024b | s | − |
| g | *Actinomyces neuii* | s | + | m | *Actinomyces meyeri* | s | − | s | *Pseudoclavibacter* sp. *Timone* | s | − |
| g | *Cutibacterium avidum* | s | + | m | *Actinomyces graevenitzii* | s | + | s | *Klebsiella* sp. B12 | s | − |
| g | *Propionimicrobium lymphophilum* | s | + | m | Acidobacteria | p | − | s | *Ochrobactrum* sp. SCTS14 | s | + |
| g | *Anaerococcus hydrogenalis* | s | + | m | *Prevotella pallens* | s | − | s | *Lactobacillus* sp. 7_1_47FAA | s | |
| g | *Peptoniphilus lacrimalis* | s | − | m | *Corynebacterium durum* | s | − | s | *Veillonella* sp. oral taxon 780 | s | + |
| g | *Anaerococcus lactolyticus* | s | + | m | Thermoanaerobacterales | o | + | s | *Microbacterium yannicii* | s | + |
| g | *Parvimonas micra* | s | − | m | *Streptococcus peroris* | s | + | s | *Corynebacterium canis* | s | + |
| g | *Anaerococcus prevotii* | s | + | m | *Streptococcus infantis* | s | − | s | *Tessaracoccus* sp. SL014B-79A | s | + |
| g | *Anaerococcus tetradius* | s | + | m | *Alloprevotella tannerae* | s | − | s | *Staphylococcus* sp. FXY54 | s | − |
| g | *Anaerococcus vaginalis* | s | − | m | *Parascardovia denticolens* | s | − | s | *Anaerobacillus* | g | + |
| g | *Anaerococcus vaginalis* | s | − | m | *Centipeda* | g | − | s | *Corynebacterium* sp. NML 97-0186 | s | + |
| g | *Lactobacillus johnsonii* | s | + | m | *Centipeda periodontii* | s | − | s | *Actinomyces* sp. oral taxon 175 | s | |
| g | Streptophyta | p | − | m | *Eggerthella lenta* | s | + | s | *Peptoniphilus* sp. oral taxon 375 | s | − |
| g | *Bilophila* | g | − | m | *Gemella sanguinis* | s | + | s | *Streptococcus* sp. oral taxon G59 | s | |
| g | *Bilophila wadsworthia* | s | − | m | *Cryptobacterium* | g | − | s | *Brevundimonas* sp. V3M6 | s | + |
| g | *Dermabacter* | g | + | m | *Cryptobacterium curtum* | s | − | s | *Stomatobaculum longum* | s | − |
| g | *Veillonella atypica* | s | + | m | *Rothia* sp. CCUG 25688 | s | + | s | *Herbaspirillums huttiense* | s | − |
| g | *Corynebacterium glucuronolyticum* | s | + | m | *Mannheimia granulomatis* | s | − | s | *Peptoniphilus* sp. 7-2 | s | + |
| g | *Dialister* | g | − | m | *Mogibacterium pumilum* | s | − | s | *Ralstonia* sp. S2.MAC.005 | s | + |
| g | *Dialister* | g | − | m | *Mycoplasma falconis* | s | + | s | *Stenotrophomonas* sp. KITS-1 | s | + |
| g | *Dialister pneumosintes* | s | + | m | *Mycoplasma subdolum* | s | − | s | *Negativicoccus* | g | − |
| g | *Sneathia sanguinegens* | s | − | m | *Catenibacterium mitsuokai* | s | + | s | *Shinella* sp. DR33 | s | − |
| g | *Sutterella wadsworthensis* | s | + | m | *Anaerovorax* | g | − | s | *Acinetobacter* sp. C-S-NA3 | s | − |
| g | Bradyrhizobiaceae | f | + | m | *Leptotrichia trevisanii* | s | + | s | *Stenotrophomonas* sp. C-S-TSA3 | s | + |
| g | Rhodospirillaceae | f | + | m | *Parasporobacterium* | g | − | s | *Veillonella* sp. CM60 | s | − |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | *Corynebacterium argentoratense* | s | + | m | Sphingobacteriia | c | + | s | *Actinomyces* sp. ICM54 | s | |
| g | *Brachybacterium* | g | + | m | Cardiobacteriales | o | + | s | *Fusobacterium* sp. ACB2 | s | + |
| g | *Rothia mucilaginosa* | s | + | m | *Filifactor alocis* | s | − | s | *Veillonella* sp. MSA12 | s | |
| g | *Butyrivibrio crossotus* | s | − | m | *Leptotrichia wadei* | s | + | s | *Anaerococcus* sp. 8404299 | s | |
| g | *Abiotrophia* | g | − | m | *Leptotrichia hofstadii* | s | + | s | *Anaerococcus* sp. 8405254 | s | + |
| g | *Granulicatella adiacens* | s | − | m | *Leptotrichia shahii* | s | + | s | *Anaerococcus* sp. 9401487 | s | + |
| g | *Abiotrophia defectiva* | s | − | m | *Leptotrichia goodfellowii* | s | − | s | *Anaerococcus provencensis* | s | + |
| g | *Parabacteroides merdae* | s | + | m | *Actinomyces* sp. oral strain Hal-1065 | s | + | s | *Bradyrhizobium* sp. 68A4SAPT | s | − |
| g | *Parabacteroides merdae* | s | + | m | *Rothia aeria* | s | − | s | *Delftia* sp. BN-SKY3 | s | − |
| g | *Bacteroides stercoris* | s | − | m | *Victivallis* | g | + | s | *Methylobacterium* sp. RK-2008-1 | s | + |
| g | *Lautropia* | g | + | m | Anaeroplasmatales | o | − | s | *Staphylococcus* sp. C9I2 | s | + |
| g | *Lactobacillus rhamnosus* | s | − | m | Anaeroplasmataceae | f | − | s | *Megasphaera* sp. UPII 199-6 | s | + |
| g | Flavobacteriaceae | f | − | m | *Alysiella* | g | + | s | *Sphingomonas* sp. 540 | s | |
| g | *Actinobacillus porcinus* | s | + | m | *Tannerella* | g | − | s | *Corynebacterium epidermidicanis* | s | − |
| g | *Pantoea* | g | + | m | *Scardovia* | g | − | s | *Trueperella* | g | − |
| g | *Anaerococcus octavius* | s | − | m | *Parascardovia* | g | − | s | *Mesorhizobium* sp. mat916 | s | + |
| g | *Actinotignum schaalii* | s | − | m | Sphingobacteriales | o | + | s | *Peptoniphilus* sp. BV3AC2 | s | − |
| g | *Trueperella bernardiae* | s | − | m | Chloroflexi | p | − | s | *Sphingobium* sp. LC341 | s | − |
| g | *Bergeyella* | g | − | m | Acidobacteriia | c | − | s | *Anaerococcus* sp. PH9 | s | − |
| g | *Corynebacterium ulcerans* | s | + | m | Acidobacteriales | o | + | s | Leptotrichiaceae | f | − |
| g | *Facklamia* | g | + | m | Desulfobacterales | o | + | s | *Faecalibacterium* sp. canine oral taxon 147 | s | + |
| g | *Facklamia* sp. 164-92 | s | + | m | Desulfobulbaceae | f | + | s | *Murdochiella* | g | + |
| g | *Facklamia* sp. 1440-97 | s | + | m | Thermodesulfobiaceae | f | + | s | *Varibaculum* sp. CCUG 45114 | s | + |
| g | Phyllobacteriaceae | f | + | m | *Leptotrichia genomo* sp. C1 | s | + | s | *Dermabacter* sp. HFH0086 | s | − |
| g | Pseudomonadales | o | − | m | *Megasphaera genomo* sp. C1 | s | − | s | *Propionibacterium* sp. KPL2005 | s | + |
| g | Campylobacteraceae | f | − | m | *Scardovia wiggsiae* | s | − | s | *Stomatobaculum* | g | + |
| g | *Tessaracoccus* | g | − | m | *Selenomonas genomo* sp. P5 | s | + | s | *Negativicoccus* sp. S5-A15 | s | − |
| g | *Kluyvera georgiana* | s | − | m | Victivallaceae | f | + | s | *Corynebacterium* sp. jw37 | s | + |
| g | *Collinsella aerofaciens* | s | − | m | Lentisphaerae | p | + | s | *Veillonella* sp. 2011_Oral_VSA_D3 | s | + |
| g | *Collinsella aerofaciens* | s | − | m | *Neisseria bacilliformis* | s | + | s | *Alloprevotella* | g | + |
| g | *Campylobacter hominis* | s | − | m | *Actinomyces dentalis* | s | + | s | *Peptoniphilus* sp. DNF00192 | s | − |
| g | *Actinobaculum* | g | − | m | Victivallales | o | + | s | *Stenotrophomonas* sp. N017 | s | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Bifidobacterium gallicum | s | + | m | Bacteroides nordii | s | + | s | Bradyrhizobium sp. CCBAU 53380 | s | + |
| g | Comamonadaceae | f | + | m | Anaerolineae | c | − | s | Anaerococcus sp. S8 87-3 | s | − |
| g | Delftia | g | − | m | Capnocytophaga sp. AHN9576 | s | − | s | Anaerococcus sp. S9 PR-16 | s | − |
| g | Enterococcaceae | f | + | m | Capnocytophaga sp. AHN9687 | s | + | s | Finegoldia sp. S9 AA1-5 | s | + |
| g | Atopobium vaginae | s | + | m | Bergeriella | g | − | s | Peptococcus sp. S9 Pr-12 | s | + |
| g | Slackia | g | − | m | Capnocytophaga sp. AHN9756 | s | − | s | Peptoniphilus sp. S9 PR-13 | s | − |
| g | Gemella sp. 933-88 | s | − | m | Streptococcus dentirousetti | s | + | s | Ralstonia sp. A52 | s | − |
| g | Bifidobacteriales | o | − | m | Parabacteroides johnsonii | s | − | s | Staphylococcus sp. 334802 | s | + |
| g | Bifidobacteriales | o | − | m | Opitutae | c | − | s | Terrisporobacter | g | |
| g | Micrococcales | o | − | m | Puniceicoccales | o | − | s | Intestinibacter | g | + |
| R | Corynebacteriales | o | − | m | Aggregatibacter | g | + | s | Peptoniphilaceae | f | − |
| R | Corynebacteriales | o | − | m | Prevotella nanceiensis | s | + | s | Tissierellia | c | − |
| R | Propionibacteriales | o | − | m | Veillonella sp. 6_1_27 | s | + | s | Tissierellales | o | − |
| g | Brevibacteriaceae | f | − | m | Desulfovibrio sp. 3_1_syn3 | s | + | s | Veillonellales | o | − |
| g | Dermabacteraceae | f | − | m | Actinomyces massiliensis | s | − | s | Selenomonadaceae | f | + |
| g | Microbacteriaceae | f | − | m | Lachnoanaerobaculum saburreum | s | − | s | Cutibacterium | g | + |
| g | Nocardiaceae | f | + | m | Bacteroides sp. 3_1_40A | s | − | s | Deinococcus | g | + |
| g | Achromobacter xylosoxidans | s | − | m | Gordonibacter pamelaeae | s | + | s | Lactococcus | g | + |
| g | Mogibacterium | g | − | m | Atopobium sp. DMCT15023 | s | − | s | Johnsonella | g | − |
| g | Aerocoecus christensenii | s | + | m | Olsenella sp. F0004 | s | − | s | Deinococcaceae | f | + |
| g | Eremococcus coleocola | s | + | m | Bacteroides sp. DJF_B097 | s | − | s | Comamonas | g | − |
| g | Lactobacillus fornicalis | s | − | m | Actinomyces oris | s | − | s | Selenomonas | g | − |
| g | Dorea longicatena | s | − | m | Butyricimonas virosa | s | + | s | Capnocytophaga | g | + |
| g | Dorea longicatena | s | − | m | Anaerotruncus sp. NML 070203 | s | + | s | Cyanobacteria | p | + |
| g | Oligella | g | + | m | Leptotrichia hongkongensis | s | + | s | Actinomyces viscosus | s | − |
| g | Oligella urethralis | s | + | m | Chitinophagaceae | f | + | s | Prevotella oulorum | s | − |
| g | Staphylococcaceae | f | − | m | Parabacteroides gordonii | s | − | s | Dolosigranulum | g | − |
| g | Enterobacterales | o | − | m | Prevotella aurantiaca | s | + | s | Dolosigranulum pigrum | s | − |
| g | Candidatus Saccharibacteria | p | − | m | Neisseria shayeganii | s | + | s | Corynebacterium matruchotii | s | − |
| g | Pseudoglutamicibacter albus | s | − | m | Lachnoanaerobaculum umeaense | s | − | s | Actinomyces georgiae | s | − |
| g | Solobacterium moorei | s | − | m | Rhizobium sp. T45 | s | − | s | Actinomyces gerencseriae | s | − |
| g | Veillonella ratti | s | + | m | Odoribacter laneus | s | − | s | Acidobacteria | p | − |
| g | Lactobacillus jensenii | s | + | m | Gordonibacter | g | + | s | Corynebacterium durum | s | − |
| g | Granulicatella | g | − | m | Slackia sp. NATTS | s | + | s | Streptococcus peroris | s | − |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Flavobacteriia | c | − | m | *Fretibacterium fastidiosum* | s | − | s | *Centipeda* | g | − |
| g | Brucellaceae | f | + | m | *Oribacterium* sp. oral taxon 078 | s | − | s | *Centipeda periodontii* | s | − |
| g | Deinococcales | o | + | m | *Prevotella* sp. oral taxon 299 | s | + | s | Sphingobacteriia | c | − |
| g | *Solobacterium* | g | + | m | *Leptotrichia* sp. oral taxon 225 | s | + | s | *Leptotrichia wadei* | s | + |
| g | *Actinomyces radingae* | s | − | m | *Oribacterium* sp. oral taxon 102 | s | − | s | *Leptotrichia hofstadii* | s | − |
| g | *Actinomyces turicensis* | s | − | m | *Alloprevotella rava* | s | − | s | Sphingobacteriales | o | − |
| g | *Olsenella* | g | + | m | *Prevotella* sp. WAL 2039G | s | + | s | Chloroflexi | p | − |
| g | Xanthomonadales | o | + | m | *Neisseria skkuensis* | s | + | s | Acidobacteriia | c | + |
| g | Pseudomonadaceae | f | + | m | *Actinomyces* sp. oral taxon 178 | s | + | s | Acidobacteriales | o | − |
| g | Pasteurellales | o | − | m | *Capnocytophaga* sp. oral taxon 338 | s | − | s | *Selenomonas genomo* sp. P5 | s | − |
| g | Pasteurellales | o | − | m | *Actinomyces* sp. oral taxon 170 | s | − | s | *Actinomyces dentalis* | s | − |
| g | *Catenibacterium* | g | − | m | *Actinomyces* sp. oral taxon 448 | s | − | s | *Aggregatibacter* | g | + |
| g | *Catenibacterium* | g | − | m | *Capnocytophaga* sp. oral taxon 335 | s | + | s | *Lachnoanaerobaculum saburreum* | s | − |
| g | *Globicatella sulfidifaciens* | s | + | m | *Capnocytophaga* sp. oral taxon 336 | s | + | s | *Rhizobium* sp. T45 | s | − |
| g | *Aerosphaera* | g | − | m | *Desulfobulbus* sp. oral taxon 041 | s | + | s | *Actinomyces* sp. oral taxon 448 | s | − |
| g | *Aerosphaera taetra* | s | − | m | *Leptotrichia* sp. oral taxon 223 | s | + | s | *Brevundimonas* sp FXJ8.080 | s | + |
| g | *Lactobacillus iners* | s | + | m | *Oribacterium* sp. oral taxon 108 | s | − | s | *Pseudomonas* sp. KB23 | s | + |
| g | *Finegoldia* | g | + | m | *Prevotella* sp. oral taxon G60 | s | + | s | *Lysinibacillus* sp. SJ2SN2 | s |  |
| g | *Finegoldia* | g | + | m | *Shuttleworthia* sp. oral taxon G69 | s | − | s | *Rothia* sp. THG-N7 | s | + |
| g | *Anaeroglobus* | g | + | m | *Streptococcus* sp. oral taxon G63 | s | + | s | *Bacteroides* sp. J1511 | s | − |
| g | *Anaeroglobus geminatus* | s | + | m | *Tannerella* sp. oral taxon HOT-286 | s | + | s | *Moraxella catarrhalis* | s | − |
| g | *Pseudoglutamicibacter cumminsii* | s | + | m | *Parvimonas* sp. oral taxon 393 | s | − | s | *Enterobacter cloacae* | s | + |
| g | *Megamonas* | g | − | m | Caldicoprobacteraceae | f | + | s | *Morganella* | g |  |
| g | *Corynebacterium mastitidis* | s | − | m | *Leptotrichia* sp. PG10 | s | + | s | *Morganella morganii* | s |  |
| g | *Peptoniphilus* | g | − | m | *Leptotrichia* sp. PTE15 | s | − | s | *Aeromonas* | g | − |
| g | *Gallicola* | g | − | m | *Lactobacillus* sp. NRCT-KU 1 | s | − | s | *Leuconostoc* | g | + |
| g | *Novosphingobium* | g | − | m | *Methylobacterium longum* | s | − | s | *Weissella* | g | + |
| g | *Anaerococcus* | g | − | m | *Capnocytophaga* sp. CM59 | s | − | s | Rhodocyclaceae | f | − |
| g | *Sneathia* | g | − | m | *Mogibacterium* sp. CM50 | s | − | s | *Pseudomonas monteilii* | s | − |
| g | *Thalassospira* | g | + | m | *Mogibacterium* sp. CM96 | s | − | s | Leuconostocaceae | f | + |
| g | *Brevibacterium paucivorans* | s | − | m | *Selenomonas* sp. CM52 | s | − | s | Aeromonadaceae | f | − |
| g | *Eremococcus* | g | + | m | *Actinomyces* sp. ICM34 | s | + | s | Aeromonadales | o | − |
| g | Porphyromonadaceae | f | + | m | *Actinomyces* sp. ICM41 | s | − | s | *Azospira* | g | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Porphyromonadaceae | f | + | m | *Actinomyces* sp. ICM47 | s | − | s | *Raoultella* | g | − |
| g | Prevotellaceae | f | − | m | *Atopobium* sp. ICM57 | s | − | s | Planococcaceae | f | + |
| g | Prevotellaceae | f | − | m | *Fusobacterium* sp. CM22 | s | + | s | Acidobacteriaceae | f | − |
| g | *Lactobacillus* sp. CR-609S | s | − | m | *Oribacterium* sp. CM12 | s | − | s | Rhodocyclales | o | − |
| g | *Facklamia hominis* | s | − | m | *Lachnoanaerobaculum* sp. OBRC5-5 | s | + | s | *Paucibacter* | g | − |
| g | *Actinomyces hongkongensis* | s | + | m | *Lachnoanaerobaculum* sp. MSX33 | s | − | s | *Paucibacter* sp. 186 | s | − |
| g | *Lactobacillus coleohominis* | s | + | m | *Brevundimonas* sp. FXJ8.080 | s | + | s | *Pseudomonas* sp. a101-18-2 | s | − |
| g | Methanobacteria | c | + | m | *Vagococcus* sp. SIX2(2011) | s | + | s | *Pseudomonas* sp. a111-5 | s | − |
| g | *Varibaculum* | g | − | m | *Moraxella* sp. WB19-16 | s | − | s | *Finegoldia* sp. BV3C29 | s | − |
| g | *Varibaculum* | g | − | m | *Lachnoanaerobaculum orale* | s | + | s | *Comamonas jiangduensis* | s | − |
| g | *Varibaculum cambriense* | s | − | m | *Actinomyces* sp. ZSY-1 | s | − | s | *Propionibacterium* sp. KPL1844 | s | − |
| g | Peptococcaceae | f | + | m | *Pseudomonas* sp. KB23 | s | − | s | Hyphomicrobiaceae | f | + |
| g | Peptococcaceae | f | + | m | *Lysinibacillus* sp. SJ2SN2 | s | + | s | *Shewanella* | g | + |
| g | Bacillaceae | f | + | m | *Fusobacterium* sp. OBRC1 | s | + | s | *Lysobacter* | g | − |
| g | Aerococcaceae | f | + | m | *Veillonella* sp. JL-2 | s |   | s | *Caulobacter* | g | + |
| g | Carnobacteriaceae | f | − | m | *Neisseria oralis* | s | + | s | Planctomycetales | o | + |
| g | *Megasphaera micronuciformis* | s | + | m | *Veillonella tobetsuensis* | s | − | s | *Gemmata* | g | − |
| g | *Acidaminococcus intestini* | s | − | m | *Actinomyces* sp. ph3 | s | + | s | Planctomycetaceae | f | + |
| g | *Veillonella montpellierensis* | s | − | m | *Neisseria* sp. 104(2012) | s | + | s | *Elizabethkingia meningoseptica* | s | − |
| g | Deinococci | c | + | m | *Phascolarctobacterium* sp. 377 | s | − | s | *Brevundimonas diminuta* | s | + |
| g | *Dialister* sp. E2_20 | s | − | m | *Parabacteroides faecis* | s | + | s | *Xanthomonas* | g | + |
| g | *Dialister* sp. E2_20 | s | − | m | *Streptococcus* sp. 2011_Oral_MS_H4 | s | − | s | Acetobacteraceae | f | − |
| g | *Propionibacterium* sp. MSP09A | s | − | m | *Veillonella* sp. 2011_Oral_VSA_B12 | s | + | s | *Acinetobacter baumannii* | s | + |
| g | Flavobacteriales | o | − | m | *Rothia* sp. THG-N7 | s | + | s | *Moraxella nonliquefaciens* | s | + |
| g | *Propionimicrobium* | g | + | m | *Capnocytophaga* sp. HS5_2W_I24 | s | + | s | *Zymomonas* | g | − |
| g | Fusobacteriaceae | f | + | m | *Actinomyces* sp. S6-Spd3 | s | − | s | *Aeromonas salmonicida* | s | − |
| g | Rhodospirillales | o | + | m | Lentisphaeria | c | + | s | *Streptococcus sobrinus* | s | + |
| g | Rhodobacterales | o | − | m | *Candidatus Saccharimonas* | g | + | s | *Bacillus megaterium* | s | − |
| g | *Bacteroides massiliensis* | s | − | m | *Bacteroides* sp. J1511 | s | + | s | *Geobacillus stearothermophilus* | s | − |
| g | Neisseriales | o | − | m | *Tessaracoccus lapidicaptus* | s | + | s | *Kurthia* | g | − |
| g | Campylobacterales | o | − | m | *Fretibacterium* | g | − | s | *Nocardioides* | g | − |
| g | *Subdoligranulum variabile* | s | − | m | *Robinsoniella* sp. KNHS210 | s | + | s | *Pseudonocardia* | g | + |
| g | *Alistipes finegoldii* | s | − | m | *Butyricimonas faecihominis* | s | + | s | *Streptomyces* | g | − |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | *Alistipes finegoldii* | s | − | m | *Butyricimonas paravirosa* | s | + | s | *Gordonia terrae* | s | − |
| g | *Bifidobacterium longum* | s | − | m | *Alistipes inops* | s | + | s | Streptomycetaceae | f | − |
| g | *Bifidobacterium longum* | s | − | m | [*Collinsella*] *massiliensis* | s | − | s | Pseudonocardiaceae | f | − |
| g | *Dialister invisus* | s | − | n | Bacteroidaceae | f | + | s | Solanaceae | f | − |
| g | *Peptoniphilus* sp. 2002-38328 | s | + | n | *Bacteroides* | g | + | s | *Solanum lycopersicum* | s | − |
| g | *Peptoniphilus* sp. 2002-2300004 | s | − | n | *Bacteroides vulgatus* | s | + | s | *Solanum* | g | − |
| g | *Actinomyces* sp. 2002-2301122 | s | − | n | *Roseburia* | g | + | s | *Basidiomycota* | p | − |
| g | *Sutterella stercoricanis* | s | − | n | *Faecalibacterium prausnitzii* | s | + | s | *Acidovorax* | g | − |
| g | *Fastidiosipila* | g | − | n | *Herbaspirillum* | g | + | s | *Acidothermus* | g | − |
| g | *Fastidiosipila sanguinis* | s | − | n | Bacteroidetes | p | + | s | *Sphingobacterium* | g | − |
| g | *Helcococcus sueciensis* | s | − | n | Proteobacteria | p | − | s | *Turicella otitidis* | s | + |
| g | *Bacteroides* sp. 35AE37 | s | + | n | Firmicutes | p | + | s | *Staphylococcus saprophyticus* | s | − |
| g | *Pseudoclavibacter* | g | − | n | *Sarcina* | g | + | s | *Microlunatus* | g | + |
| g | *Oribacterium* | g | + | n | Streptococcaceae | f | + | s | *Rhodoplanes* | g | + |
| g | *Porphyromonas uenonis* | s | + | n | *Streptococcus* | g | + | s | *Janthinobacterium* | g | + |
| g | *Odoribacter* | g | + | n | *Clostridium* | g | | s | *Cutibacterium granulosum* | s | + |
| g | *Odoribacter* | g | + | n | Actinobacteria | c | − | s | *Microbacterium lacticum* | s | − |
| g | *Corynebacterium* sp. 2300500 | s | + | n | *Lachnospira* | g | | s | *Exiguobacterium* | g | − |
| g | *Bacteroides salyersiae* | s | + | n | *Lachnospira pectinoschiza* | s | | s | *Variovorax* | g | − |
| g | *Bacteroides salyersiae* | s | + | n | Betaproteobacteria | c | − | s | *Dietzia* | g | + |
| g | *Roseburia hominis* | s | − | n | Deltaproteobacteria | c | + | s | *Blastococcus aggregatus* | s | − |
| g | *Roseburia hominis* | s | − | n | Veillonellaceae | f | + | s | *Acinetobacter radioresistens* | s | + |
| g | *Roseburia faecis* | s | − | n | Clostridiaceae | f | + | s | *Paenibacillus* | g | − |
| g | *Roseburia faecis* | s | − | n | Lactobacillaceae | f | − | s | Chlamydiales | o | − |
| g | *Dialister propionicifaciens* | s | − | n | *Dorea formicigenerans* | s | + | s | *Pseudomonas citronellolis* | s | − |
| g | *Dialister micraerophilus* | s | − | n | *Pseudobutyrivibrio* | g | + | s | *Malassezia* | g | − |
| g | *Bacteroides plebeius* | s | − | n | Verrucomicrobiales | o | + | s | *Leucobacter* | g | + |
| g | *Parabacteroides goldsteinii* | s | − | n | Verrucomicrobia | p | + | s | *Dermacoccus* | g | + |
| g | *Alistipes shahii* | s | + | n | Oxalobacteraceae | f | + | s | *Malassezia restricta* | s | − |
| g | *Alistipes shahii* | s | + | n | Burkholderiales | o | − | s | Sphingobacteriaceae | f | − |
| g | *Bacteroides intestinalis* | s | + | n | Coriobacteriaceae | f | + | s | Acidimicrobiia | c | + |
| g | *Pelomonas* | g | + | n | Coriobacteriia | c | + | s | Acidimicrobiales | o | + |
| g | *Peptostreptococcus stomatis* | s | + | n | Coriobacteriales | o | + | s | Rubrobacteria | c | − |
| g | *Bergeyella* sp. AF14 | s | − | n | *Blautia luti* | s | + | s | Pseudonocardiales | o | − |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | *Bacteroides dorei* | s | + | n | Bacilli | c | + | s | Streptomycetales | o | − |
| g | *Bacteroides dorei* | s | + | n | *Bacteroides* sp. AR20 | s | + | s | Frankiales | o | − |
| g | *Peptoniphilus* sp. gpac018A | s | − | n | *Bacteroides* sp. AR29 | s |   | s | Nocardioidaceae | f | − |
| g | *Peptoniphilus* sp. gpac148 | s | − | n | *Collinsella* | g | + | s | Promicromonosporaceae | f | − |
| g | *Bacteroides* sp. XB12B | s | + | n | *Roseburia intestinalis* | s | + | s | Dietziaceae | f | + |
| g | *Moryella indoligenes* | s | − | n | Bacteroidales | o | + | s | Nakamurellaceae | f | − |
| g | *Parabacteroides* | g | − | n | Rikenellaceae | f | + | s | Acidothermaceae | f | − |
| g | *Parabacteroides* | g | − | n | *Shuttleworthia* | g | − | s | *Marmoricola* | g | + |
| g | *Prevotella timonensis* | s | − | n | Clostridia | c | + | s | *Marmoricola aurantiacus* | s | − |
| g | *Barnesiella* | g | + | n | Clostridiales | o | + | s | *Facklamia tabacinasalis* | s | + |
| g | *Barnesiella* | g | + | n | Lachnospiraceae | f | + | s | Cytophagaceae | f | − |
| g | *Howardella* | g | + | n | Peptostreptococcaceae | f | + | s | *Hymenobacter* | g | − |
| g | *Citrobacter* sp. BW4 | s | − | n | Lactobacillales | o | + | s | *Frigoribacterium* | g | − |
| g | *Anaerococcus murdochii* | s | − | n | *Dorea* | g | + | s | *Acinetobacter ursingii* | s | − |
| g | *Arcanobacterium* sp. NML 06501 | s | + | n | Bacteroidia | c | + | s | *Dyadobacter* | g | − |
| g | *Cronobacter* | g | + | n | Actinobacteria | p | − | s | *Roseomonas* | g | − |
| g | *Streptococcus* sp. 11aTha1 | s | + | n | Verrucomicrobiae | c | + | s | *Geobacillus* | g | − |
| g | *Prevotella amnii* | s | − | n | Verrucomicrobiaceae | f |   | s | *Corynebacterium capitovis* | s | + |
| g | *Alloscardovia* | g | − | n | *Anaerostipes* | g | + | s | *Corynebacterium felinum* | s | + |
| g | *Alloscardovia omnicolens* | s | − | n | Oscillospiraceae | f |   | s | Verrucomicrobia subdivision 3 | f | + |
| g | *Veillonella rogosae* | s | + | n | *Faecalibacterium* | g | + | s | Alteromonadales | o | + |
| g | *Jonquetella anthropi* | s | + | n | *Alistipes* | g | + | s | Gemmatimonadetes | p | − |
| g | *Pelomonas aquatica* | s | + | n | *Akkermansia* | g | + | s | *Turicella* | g | + |
| g | *Megamonas funiformis* | s | − | n | *Akkermansia muciniphila* | s | + | s | Dermacoccaceae | f | + |
| g | *Alistipes* sp. EBA6-25cl2 | s | + | n | *Anaerotruncus* | g |   | s | *Massilia* | g | − |
| g | *Bacteroides* sp. EBA5-17 | s | − | n | *Subdoligranulum* | g | + | s | *Microbacterium* sp. *absalar* | s | + |
| g | *Bacteroides* sp. EBA5-17 | s | + | n | *Roseburia inulinivorans* | s | + | s | *Cellulosimicrobium* | g | − |
| g | *Paraprevotella clara* | s | − | n | *Blautia wexlerae* | s | + | s | Malasseziales | o | − |
| g | *Oscillibacter* | g | + | n | *Moryella* | g |   | s | *Gemmatimonas* | g | − |
| g | *Oscillibacter* | g | + | n | Ruminococcaceae | f | + | s | *Aurantimonas* | g | − |
| g | *Alistipes* sp. NML05A004 | s | + | n | Clostridiales f XIII. Incertae Sedis | f | − | s | *Sphingomonas aerolata* | s | − |
| g | *Alistipes* sp. NML05A004 | s | + | n | *Blautia* | g | + | s | Paenibacillaceae | f | − |
| g | *Brevibacterium ravenspurgense* | s | + | n | *Roseburia* sp. 11SE39 | s | + | s | Thermoactinomycetaceae | f | + |
| g | *Dialister succinatiphilus* | s | + | n | *Blautia faecis* | s | + | s | *Dermacoccus* sp. Ellin183 | s | − |
| g | *Barnesiella intestinihominis* | s | + | n | Selenomonadales | o | + | s | Thermomicrobiales | o | − |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Barnesiella intestinihominis | s | + | n | Negativicutes | c | + | s | Microbacterium paraoxydans | s | − |
| g | Parasutterella excrementihominis | s | − | n | Streptococcus sp. BS35a | s | + | s | Planctomycetes | p | + |
| g | Parasutterella excrementihominis | s | − | n | Flavonifractor | g |   | s | Planctomycetia | c | + |
| g | Porphyromonas bennonis | s | + | n | Anaerostipes sp. 5_1_63FAA | s | + | s | Chlamydiae | p | − |
| g | Cloacibacterium | g | − | n | Fusicatenibacter saccharivorans | s | + | s | Chlamydiia | c | − |
| g | Gemella asaccharolytica | s | + | n | Fusicatenibacter | g | + | s | Skermanella | g | + |
| g | Peptoniphilus duerdenii | s | + | n | Erysipelatoclostridium | g | + | s | Roseomonas cervicalis | s | − |
| g | Peptoniphilus koenoeneniae | s | + | n | Campylobacter | g | − | s | Solirubrobacter | g | − |
| g | Murdochiella asaccharolytica | s | + | n | Achromobacter | g | + | s | Brachybacterium muris | s | − |
| g | Synergistetes | p | + | n | Flavobacterium | g | + | s | Gemmatimonadetes | c | − |
| g | Cloacibacillus | g | + | n | Pseudomonas | g | − | s | Gemmatimonadales | o | − |
| g | Cloacibacillus evryensis | s | + | n | Rhizobiales | o | + | s | Gemmatimonadaceae | f | − |
| g | Atopobium sp. F0209 | s | − | n | Bradyrhizobium | g | − | s | Kocuria marina | s | − |
| g | Clostridiales f XI. Incertae Sedis | f | − | n | Rhizobium | g | + | s | Actinomyces genomo sp. C1 | s | − |
| g | Parvimonas | g | − | n | Mesorhizobium loti | s | + | s | Salinibacterium | g | + |
| g | Tenericutes | p | + | n | Methylobacterium | g | + | s | Cryomorphaceae | f | − |
| g | Corynebacterium freiburgense | s | + | n | Moraxellaceae | f | − | s | Aurantimonadaceae | f | − |
| g | Delftia lacustris | s | + | n | Acinetobacter | g | + | s | Lysobacter brunescens | s | − |
| g | Butyricimonas | g | − | n | Moraxella | g | + | s | Shewanellaceae | f | + |
| g | Bifidobacterium sp. 120 | s | + | n | Neisseriaceae | f | − | s | Rubellimicrobium | g | − |
| g | Brevibacterium massiliense | s | − | n | Neisseria | g | − | s | Elizabethkingia | g | − |
| g | Paraprevotella | g | + | n | Neisseria mucosa | s | − | s | Solirubrobacteraceae | f | − |
| g | Parasutterella | g | − | n | Neisseria elongata | s | − | s | Dietzia cinnamea | s | − |
| g | Parasutterella | g | − | n | Neisseria macacae | s | − | s | Fluviicola | g | − |
| g | Enterorhabdus | g | + | n | Alcaligenaceae | f | + | s | Trueperaceae | f | − |
| g | Bacteroides clarus | s | + | n | Ochrobactrum | g | + | s | Truepera | g | − |
| g | Bacteroides clarus | s | + | n | Enterobacteriaceae | f | + | s | Methylobacterium adhaesivum | s | − |
| g | Sutterella sp. YIT 12072 | s | − | n | Citrobacter | g | + | s | Xanthobacteraceae | f | − |
| g | Bifidobacterium kashiwanohense | s | + | n | Enterobacter | g | − | s | Patulibacteraceae | f | − |
| g | Porphyromonas sp. 2024b | s | + | n | Klebsiella | g | + | s | Patulibacter | g | − |
| g | Lautropia sp. TeTO | s | + | n | Kluyvera | g | + | s | Solirubrobacter sp. Gsoil 921 | s | − |
| g | Pseudoclavibacter sp. Timone | s | + | n | Proteus | g | + | s | Sphingomonas anadarae | s | − |
| g | Anaerostipes hadrus | s | − | n | Pasteurellaceae | f | − | s | Nubsella zeaxanthinifaciens | s | − |
| g | Anaerostipes hadrus | s | − | n | Actinobacillus | g | − | s | Skermanella aerolata | s | + |
| g | Synergistia | c | + | n | Haemophilus | g | − | s | Actinomycetospora | g | − |
| g | Synergistales | o | + | n | Haemophilus influenzae | s | − | s | Acinetobacter sp. RBE2CD-76 | s | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Synergistaceae | f | + | n | Haemophilus parainfluenzae | s | + | s | Flavobacterium lindanitolerans | s | + |
| g | Klebsiella sp. B12 | s | − | n | Campylobacter ureolyticus | s | − | s | Sphingomonas mathurensis | s | + |
| g | Anaerosporobacter | g | − | n | Porphyromonas | g | − | s | Exobasidiomycetes | c | − |
| g | Lactobacillus sp. BL302 | s | + | n | Prevotella | g | + | s | Stenotrophomonas pavanii | s | − |
| g | Ochrobactrum sp. SCTS14 | s | + | n | Fusobacterium | g | + | s | Mycobacterium sp. 18 GUW | s | − |
| g | Anaerostipes sp. 3_2_56FAA | s | + | n | Fusobacterium nucleatum | s | + | s | Pseudolabrys | g | − |
| g | Lactobacillus sp. 7_1_47FAA | s | − | n | Fusobacterium periodonticum | s | − | s | Bacillus safensis | s | − |
| g | Peptoniphilus sp. oral taxon 836 | s | + | n | Megasphaera | g | + | s | Nubsella | g | − |
| g | Veillonella sp. oral taxon 780 | s | − | n | Rhodopseudomonas | g | + | s | Microbacterium sp. GGC-P2D | s | − |
| g | Corynebacterium canis | s | − | n | Gammaproteobacteria | c | − | s | Dermacoccus sp. SST-20 | s | − |
| g | Tessaracoccus sp. SL014B-79A | s | − | n | Peptostreptococcus | g | + | s | Flavobacterium sp. CS43 | s | + |
| g | Bilophila sp. 4_1_30 | s | − | n | Finegoldia magna | s | + | s | Methylobacterium sp. Gh-143 | s | − |
| g | Peptoniphilus sp. JCM 8143 | s | + | n | Peptostreptococcus anaerobius | s | + | s | Solirubrobacterales | o | − |
| g | Anaerobacillus | g | − | n | Micrococcaceae | f | + | s | Acinetobacter kyonggiensis | s | + |
| g | Corynebacterium sp. NML 97-0186 | s | − | n | Micrococcus | g | + | s | Acinetobacter sp. T133 | s | + |
| g | Peptoniphilus sp. oral taxon 375 | s | + | n | Micrococcus luteus | s | + | s | Iamiaceae | f | + |
| g | Streptococcus sp. oral taxon G59 | s | − | n | Staphylococcus | g | + | s | Rummeliibacillus | g | − |
| g | Streptococcus sp. oral taxon G59 | s | − | n | Staphylococcus aureus | s | + | s | Chryseomicrobium imtechense | s | + |
| g | Lactobacillus sp. TAB-22 | s | + | n | Deinococcus-Thermus | p | + | s | Brevundimonas sp. JW23.4a | s | − |
| g | Peptoniphilus coxii | s | + | n | Streptococcus thermophilus | s | − | s | Pseudomonas sp. DQ-01 | s | − |
| g | Stomatobaculum longum | s | + | n | Streptococcus parasanguinis | s | + | s | Malasseziaceae | f | − |
| g | Bacteroides stercorirosoris | s | + | n | Enterococcus | g | + | s | Pseudomonas sp. PcFRB119 | s | − |
| g | Blautia stercoris | s | − | n | Enterococcus faecalis | s | − | s | Methylobacterium sp. 399 | s | − |
| g | Blautia stercoris | s | − | n | Lactococcus lactis | s | + | s | Methylobacterium sp. 57 | s | − |
| g | Peptoniphilus sp. 1-14 | s | − | n | Aerococcus | g | + | s | Cytophagia | c | − |
| g | Peptoniphilus sp. 1-14 | s | − | n | Aerococcus urinae | s | − | s | Cytophagales | o | − |
| g | Peptoniphilus sp. 7-2 | s | + | n | Gemella | g | + | s | Pseudomonas sp. PcFRB072 | s | − |
| g | Ralstonia sp. S2.MAC.005 | s | + | n | Bacillales | o | + | s | Chryseomicrobium | g | + |
| g | Alistipes sp. HGB5 | s | + | n | Bacillus | g | + | s | Bryobacter | g | − |
| g | Negativicoccus | g | − | n | Lysinibacillus sphaericus | s | + | s | Novosphingobium sp. THA_AIK7 | s | + |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "–" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | *Bacteroides* sp. SLC1-38 | s | + | n | *Lactobacillus* | g | – | s | *Staphylococcus* sp. C-D-MA2 | s | + |
| g | *Lactobacillus* sp. Akhmro1 | s | + | n | *Lactobacillus plantarum* | s | – | s | *Pseudomonas* sp. KVS86 | s | + |
| g | *Stenotrophomonas* sp. C-S-TSA3 | s | + | n | *Lactobacillus reuteri* | s | + | s | *Pseudomonas* sp. PKG89 | s | + |
| g | *Actinomyces* sp. ICM54 | s | + | n | *Lactobacillus salivarius* | s | – | s | *Acinetobacter* sp. C049 | s | – |
| g | *Bifidobacterium* sp. MSX5B | s | + | n | Corynebacteriaceae | f | – | s | *Granulicella* | g | + |
| g | *Fusobacterium* sp. AS2 | s | – | n | *Actinomyces* | g | + | s | *Mycobacterium* sp. CO183 | s | – |
| g | *Fusobacterium* sp. CM21 | s | + | n | *Actinomyces odontolyticus* | s | – | s | *Acinetobacter* sp. WB22-23 | s | + |
| g | *Veillonella* sp. AS16 | s | + | n | *Arthrobacter* | g | + | s | *Micrococcus* sp. WB18-01 | s | + |
| g | *Veillonella* sp. MSA12 | s | + | n | *Bifidobacterium bifidum* | s | + | s | *Dietzia* sp. ISA13 | s | – |
| g | *Anaerococcus* sp. 8404299 | s | + | n | *Brevibacterium* | g | – | s | *Psychrobacter* sp. S1-1 | s | + |
| g | *Anaerococcus* sp. 8405254 | s | – | n | *Corynebacterium* | g | – | s | *Pseudomonas* sp. PDD-27b-3 | s | + |
| g | *Anaerococcus provencensis* | s | – | n | *Corynebacterium diphtheriae* | s | – | s | *Sphingomonas* sp. KOPRI 25661 | s | – |
| g | *Enterococcus* sp. SI-4 | s | – | n | *Corynebacterium* sp. | s | + | s | *Gaiella occulta* | s | – |
| g | *Delftia* sp. BN-SKY3 | s | – | n | *Propionibacterium* | g | – | s | *Ferruginibacter* | g | – |
| g | *Enterococcus* sp. C6I11 | s | + | n | *Cutibacterium acnes* | s | + | s | *Sphingobacterium* sp. HTc4-a | s | – |
| g | *Brachybacterium* sp. NIO-27 | s | + | n | Mycobacteriaceae | f | + | s | *Amnibacterium* | g | – |
| g | *Enterobacter* sp. BS2-1 | s | + | n | *Rhodococcus* | g | + | s | *Rhizobium nepotum* | s | – |
| g | *Megasphaera* sp. UPII 199-6 | s | – | n | *Rhodococcus erythropolis* | s | – | s | Sandaracinaceae | f | – |
| g | *Corynebacterium epidermidicanis* | s | + | n | Actinomycetales | o | – | s | *Comamonas* sp. HM_AF10 | s | – |
| g | *Trueperella* | g | – | n | *Rothia dentocariosa* | s | + | s | *Massilia* sp. hp37 | s | – |
| g | *Coprobacter fastidiosus* | s | – | n | *Mobiluncus mulieris* | s | + | s | *Defluviimonas* | g | + |
| g | *Coprobacter fastidiosus* | s | – | n | *Gardnerella* | g | + | s | *Ochrobactrum* sp. LC498 | s | – |
| g | *Actinomyces* sp. ICM58 | s | + | n | *Gardnerella vaginalis* | s | + | s | Gaiellales | o | – |
| g | *Jonquetella* sp. BV3C4 | s | – | n | *Peptococcus* | g | – | s | Gaiellaceae | f | – |
| g | *Prevotella* sp. BV3C7 | s | + | n | *Halomonas* | g | – | s | *Gaiella* | g | – |
| g | *Peptoniphilus* sp. BV3AC2 | s | – | n | Solanales | o | + | s | *Aureimonas phyllosphaerae* | s | – |
| g | *Megasphaera* sp. BV3C16-1 | s | – | n | *Globicatella* | g | – | s | *Massilia* sp. S5-252-1 | s | + |
| g | *Anaerococcus* sp. PH9 | s | – | n | *Globicatella sanguinis* | s | – | s | *Stenotrophomonas* sp. I_35-G5PA9A1 | s | – |
| g | Leptotrichiaceae | f | – | n | *Sphingomonas* | g | – | s | *Stenotrophomonas* sp. I_63-LFP1A9B1 | s | – |
| g | *Faecalibacterium* sp. canine oral taxon 147 | s | – | n | *Phyllobacterium* | g | | s | *Sphingomonas* sp. HEXBA01 | s | – |

TABLE 2-continued

Taxa associated with individuals with sleep-related condition of shift work (e.g., night shift work, with daytime sleeping periods, etc.), where the first through fourth columns are a set corresponding to each other, the fifth through eighth columns are a set corresponding to each other, and the ninth through twelfth columns are a set corresponding to each other. Column header "s" corresponds to site ("g" corresponds to gut, "ge" corresponds to genitals", "n" corresponds to nose, "s" corresponds to skin, "m" corresponds to mouth"); column header "n" corresponds to taxon name; column header "r" corresponds to taxon rank ("f" corresponds to family, "g" corresponds to genus, "s" corresponds to species, "p" corresponds to phylum, "c" corresponds to class, "o" corresponds to order); column header "c" corresponds to correlation ("+" corresponds to correlation and/or other association with control group individuals; "−" corresponds to correlation and/or other association with condition group individuals (sleep-relation condition of shift work)).

| s | n | r | c | s | n | r | c | s | n | r | c |
|---|---|---|---|---|---|---|---|---|---|---|---|
| g | Faecalibacterium sp. canine oral taxon 147 | s | − | n | Alistipes putredinis | s | | s | Chryseobacterium sp. SOZ3-3181 | s | − |
| g | Murdochiella | g | + | n | Odoribacter splanchnicus | s | | s | Blastocatella fastidiosa | s | + |
| g | Lachnoanaerobaculum | g | + | n | Porphyromonas asaccharolytica | s | + | s | Massilia sp. TMT4-34 | s | − |
| g | Streptococcus sp. GMD6S | s | + | n | Prevotella bivia | s | + | s | Salinibacterium sp. MDT1-9-1 | s | + |
| g | Varibaculum sp. CCUG 45114 | s | + | n | Prevotella buccalis | s | + | s | Blastocatella | g | − |
| g | Varibaculum sp. CCUG 45114 | s | + | n | Prevotella disiens | s | + | s | Acinetobacter sp. HD5.2 | s | + |
| g | Dermabacter sp. HFH0086 | s | + | n | Alphaproteobacteria | c | + | s | Sphingomonas sp. DS-3PS-11 | s | − |
| g | Stomatobaculum | g | + | n | Halomonadaceae | f | − | s | Chryseobacterium sp. R064 | s | − |
| g | Actinomyces sp. S4-C9 | s | − | n | Euryarchaeota | p | + | s | Rhizobium sp. 10II | s | − |
| g | Atopobium sp. S3MV24 | s | − | n | Gemella morbillorum | s | − | s | Bosea sp. B0.09-49 | s | − |
| g | Atopobium sp. S3MV26 | s | − | n | Rhizobium etli | s | + | s | Sphingomonas sp. URHD0057 | s | − |
| g | Atopobium sp. S3PFAA1-4 | s | + | n | Veillonella | g | − | s | Exiguobacterium sp. icr3 | s | − |
| g | Dialister sp. S4-23 | s | − | n | Veillonella parvula | s | − | s | Jatrophihabitans | g | + |
| g | Gardnerella sp. S3PF20 | s | + | n | Epsilonproteobacteria | c | − | s | Chryseobacterium sp. R31 | s | − |
| g | Prevotella sp. S4-10 | s | + | n | Bifidobacteriaceae | f | − | s | Flavobacterium qiangtangense | s | + |
| g | Solobacterium sp. S4-A19 | s | + | n | Propionibacteriaceae | f | − | s | Mycobacterium sp. UNC410CL29Cvi84 | s | − |
| | | | | n | Helcococcus | g | − | s | Pseudonocardia sp. ARG1 | s | + |

We claim:

1. A method for characterizing a sleep-related condition associated with microorganisms, the method comprising:
   determining a microorganism sequence dataset associated with a set of subjects, based on microorganism nucleic acids from samples associated with the set of subjects, wherein the microorganism nucleic acids are associated with the sleep-related condition;
   collecting, for the set of subjects, supplementary data associated with the sleep-related condition;
   determining at least one of a set of microbiome composition features and a set of microbiome functional features associated with the set of subjects, based on the microorganism sequence dataset;
   generating a sleep-related characterization model based on the supplementary data and the at least one of the set of microbiome composition features and the set of microbiome functional features, wherein the sleep-related characterization model is associated with the sleep-related condition;
   determining a sleep-related characterization for a user for the sleep-related condition based on the sleep-related characterization model; and
   providing a therapy to the user for facilitating improvement of the sleep-related condition, based on the sleep-related characterization.

2. The method of claim 1, wherein determining the microorganism sequence dataset comprises:
   identifying a first primer type compatible with a first genetic target associated with the sleep-related condition; and
   generating the microorganism sequence dataset for the set of subjects based on the microorganism nucleic acids and first primers corresponding to the first primer type.

3. The method of claim 2, wherein the samples correspond to a set of collection sites comprising at least two of a gut site, a skin site, a nose site, a mouth site, and a genitals site, and wherein determining the microorganism sequence dataset comprises:

identifying the first primer type compatible with the first genetic target associated with the sleep-related condition and a first collection site of the set of collection sites;

identifying a second primer type compatible with a second genetic target associated with the sleep-related condition and a second collection site of the set of collection sites; and generating the microorganism sequence dataset for the set of subjects based on the microorganism nucleic acids, the first primers corresponding to the first primer type, and second primers corresponding to the second primer type.

4. The method of claim 3, wherein the first collection site comprises the gut site, wherein determining the microorganism sequence dataset comprises determining at least one of a metagenomic library and a metatranscriptomic library based on a subset of the microorganism nucleic acids and the first primers, and wherein determining the at least one of the set of microbiome composition features and the set of microbiome functional features comprises determining the at least one of the set of microbiome composition features and the set of microbiome functional features based on the at least one of the metagenomic library and the metatranscriptomic library.

5. The method of claim 2, wherein determining the microorganism sequence dataset comprises:
fragmenting the microorganism nucleic acids; and
generating amplified microorganism nucleic acids through at least one of a singleplex amplification process and a multiplex amplification process for the fragmented microorganism nucleic acids, based on the first primers corresponding to the first primer type compatible with the first genetic target associated with the sleep-related condition; and
determining, with a next-generation sequencing system, the microorganism sequence dataset based on the amplified microorganism nucleic acids.

6. The method of claim 1, wherein determining the at least one of the set of microbiome composition features and the set of microbiome functional features comprises applying a set of analytical techniques comprising at least one of a univariate statistical test, a multivariate statistical test, a dimensionality reduction technique, and an artificial intelligence approach, based on the microorganism sequence dataset, and wherein the at least one of the set of microbiome composition features and the set of microbiome functional features is configured to improve computing system-related functionality associated with the determining of the sleep-related characterization for the user.

7. The method of claim 6,
wherein determining the at least one of the set of microbiome composition features and the set of microbiome functional features comprises determining a set of cross-condition features associated with the sleep-related condition and a second sleep-related condition, based on the set of analytical techniques,
wherein determining the sleep-related characterization comprises determining the sleep-related characterization for a user for the sleep-related condition and the second sleep-related condition based on the sleep-related characterization model, and
wherein the set of cross-condition features is configured to improve the computing system-related functionality associated with the determining of the sleep-related characterization for the user for the sleep-related condition and the second sleep-related condition.

8. The method of claim 1, wherein the generating the sleep-related characterization model comprises generating the sleep-related characterization model based on the supplementary data and the set of microbiome composition features, and wherein the set of microbiome composition features comprises features associated at least one of: *Acetitomaculum* (genus), Acidaminococcaceae (family), *Acidaminococcus* (genus), *Acidaminococcus* sp. D21 (species), Actinobacteria (class), Actinobacteria (phylum), *Actinomyces* (genus), *Actinomyces* sp. ICM47 (species), *Actinomyces* sp. ICM54 (species), *Actinomyces* sp. S9 PR-21 (species), *Akkermansia muciniphila* (species), Alcaligenaceae (family), *Alistipes indistinctus* (species), *Alistipes* sp. 627 (species), *Anaerococcus* (genus), *Anaerococcus hydrogenalis* (species), *Anaerococcus octavius* (species), *Anaerococcus* sp. 8404299 (species), *Anaerococcus* sp. 8405254 (species), *Anaerococcus tetradius* (species), *Anaerofustis* (genus), *Anaerofustis stercorihominis* (species), *Anaeroplasma* (genus), *Anaerosporobacter* (genus), *Anaerostipes* sp. 1y-2 (species), *Anaerostipes* sp. 3_2_56FAA (species), *Anaerotruncus colihominis* (species), *Anaerotruncus* sp. NML 070203 (species), *Atopobium* (genus), *Atopobium vaginae* (species), *Bacteroides clarus* (species), *Bacteroides coprocola* (species), *Bacteroides nordii* (species), *Bacteroides plebeius* (species), *Bacteroides* sp. 2_2_4 (species), *Bacteroides* sp. CB57 (species), *Bacteroides* sp. DJF_B097 (species), *Bacteroides* sp. EBA5-17 (species), *Bacteroides* sp. SLC1-38 (species), *Bacteroides* sp. XB12B (species), *Bacteroides stercorirosoris* (species), Bifidobacteriaceae (family), Bifidobacteriales (order), *Bifidobacterium* (genus), *Bifidobacterium biavatii* (species), *Bifidobacterium bifidum* (species), *Bifidobacterium choerinum* (species), *Bifidobacterium longum* (species), *Bifidobacterium merycicum* (species), *Bifidobacterium* sp. MSX5B (species), *Bifidobacterium stercoris* (species), *Blautia glucerasea* (species), *Blautia hydrogenotrophica* (species), *Blautia* sp. Ser8 (species), *Blautia* sp. YHC-4 (species), *Brevibacterium massiliense* (species), *Butyricicoccus* (genus), *Butyricicoccus pullicaecorum* (species), *Butyricimonas synergistica* (species), *Butyrivibrio* (genus), *Butyrivibrio crossotus* (species), *Campylobacter* (genus), *Campylobacter hominis* (species), *Campylobacter ureolyticus* (species), Campylobacteraceae (family), Campylobacterales (order), *Candidatus Soleaferrea* (genus), *Candidatus Stoquefichus* (genus), *Catabacter hongkongensis* (genus), *Catenibacterium mitsuokai* (species), *Cellulosilyticum* (genus), *Collinsella aerofaciens* (species), *Collinsella intestinalis* (species), *Coprobacillus* (genus), *Coprobacillus* sp. D6 (species), *Coprobacter* (genus), *Coprobacter fastidiosus* (species), *Corynebacterium* sp. (species), *Corynebacterium ulcerans* (species), Cyanobacteria (phylum), *Dermabacter* (genus), *Dermabacter hominis* (species), Dermabacteraceae (family), *Desulfovibrio desulfuricans* (species), *Desulfovibrio piger* (species), *Desulfovibrio* sp. (species), *Dialister* (genus), *Dialister invisus* (species), *Dialister propionicifaciens* (species), *Dielma* (genus), *Dielma fastidiosa* (species), *Eggerthella* (genus), *Eggerthella* sp. HGA1 (species), *Eisenbergiella tayi* (species), *Enterobacter* (genus), *Enterobacter* sp. BS2-1 (species), *Enterococcus* sp. C6I11 (species), Epsilonproteobacteria (class), *Erysipelatoclostridium ramosum* (species), Eubacteriaceae (family), *Eubacterium* (genus), *Eubacterium callanderi* (species), *Eubacterium* sp. SA11 (species), *Facklamia* sp. 1440-97 (species), *Fibrobacter* (genus), *Flavobacterium* (genus), *Flavonifractor plautii* (species), Fusobacteria (phylum), Fusobacteriaceae (family), Fusobacteriales (order), Fusobacteriia (class), *Fusobacterium* (genus), *Fusobacterium equinum* (species),

*Fusobacterium ulcerans* (species), *Gardnerella* (genus), *Gardnerella vaginalis* (species), *Gelria* (genus), *Gordonibacter* (genus), *Gordonibacter pamelaeae* (species), *Granulicatella* (genus), *Granulicatella adiacens* (species), *Haemophilus* (genus), *Haemophilus parainfluenzae* (species), *Herbaspirillum* (genus), *Herbaspirillum seropedicae* (species), *Holdemania* (genus), *Holdemania filiformis* (species), *Howardella* (genus), *Hydrogenoanaerobacterium* (genus), *Intestinibacter* (genus), *Klebsiella* (genus), *Kluyvera georgiana* (species), *Lachnospira* (genus), *Lactobacillus crispatus* (species), *Lactobacillus rhamnosus* (species), *Lactobacillus* sp. 66c (species), *Lactobacillus* sp. Akhmr01 (species), *Lactobacillus* sp. BL302 (species), *Lactobacillus* sp. TAB-30 (species), *Lactonifactor* (genus), *Lactonifactor longoviformis* (species), Leptotrichiaceae (family), *Leuconostoc* (genus), Leuconostocaceae (family), *Megamonas* (genus), *Megamonas funiformis* (species), *Megasphaera* (genus), *Megasphaera* genomosp. C1 (species), *Megasphaera* sp. S6-MB2 (species), *Megasphaera* sp. UPII 199-6 (species), *Mobiluncus* (genus), *Mobiluncus mulieris* (species), *Moryella* (genus), *Negativicoccus* (genus), *Negativicoccus succinicivorans* (species), Negativicutes (class), *Oligella* (genus), *Oligella urethralis* (species), *Olsenella* sp. 1183 (species), Oscillospiraceae (family), *Pantoea* (genus), *Papillibacter* (genus), *Parabacteroides goldsteinii* (species), *Parabacteroides* sp. 157 (species), *Paraprevotella clara* (species), *Parvimonas micra* (species), Pasteurellaceae (family), Pasteurellales (order), *Peptoniphilus* (genus), *Peptoniphilus coxii* (species), *Peptoniphilus* sp. 2002-2300004 (species), *Peptoniphilus* sp. 7-2 (species), *Peptoniphilus* sp. gpac018A (species), *Phascolarctobacterium* (genus), *Phascolarctobacterium succinatutens* (species), Phyllobacteriaceae (family), *Phyllobacterium* (genus), *Porphyromonas uenonis* (species), *Prevotella bivia* (species), *Prevotella disiens* (species), Propionibacteriaceae (family), *Propionibacterium* (genus), Proteobacteria (phylum), *Pseudobutyrivibrio* (genus), *Pseudoclavibacter* sp. Timone (species), Rhizobiales (order), *Roseburia* (genus), Ruminococcaceae (family), *Sarcina ventriculi* (species), Selenomonadales order *Shuttleworthia* (genus), Sphingomonadaceae (family), Sphingomonadales (order), *Stenotrophomonas* (genus), *Stenotrophomonas* sp. C-S-TSA3 (species), *Streptococcus agalactiae* (species), *Streptococcus gordonii* (species), *Streptococcus pasteurianus* (species), *Streptococcus peroris* (species), *Streptococcus* sp. BS35a (species), *Streptococcus* sp. oral taxon G59 (species), *Sutterella* (genus), *Sutterella* sp. YIT 12072 (species), *Sutterella stercoricanis* (species), *Sutterella wadsworthensis* (species), *Terrisporobacter glycolicus* (species), Thermoanaerobacteraceae (family), Thermoanaerobacterales (order), *Turicibacter* (genus), *Turicibacter sanguinis* (species), *Varibaculum* (genus), *Varibaculum cambriense* (species), *Veillonella* sp. AS16 (species), Veillonellaceae (family), *Weissella hellenica* (species), Xanthomonadaceae (family), Xanthomonadales (order), *Alistipes massiliensis* (species), *Butyricimonas virosa* (species), *Alistipes putredinis* (species), *Actinobacillus porcinus* (species), *Actinobacillus* (genus), *Butyricimonas* (genus), *Howardella ureilytica* (species), Firmicutes (phylum), *Clostridium* (genus), Lentisphaeria (class), Anaeroplasmataceae (family), Pseudomonadaceae (family), Victivallaceae (family), *Blautia* (genus), *Asteroleplasma* (genus), *Delftia* (genus), *Victivallis* (genus), *Peptostreptococcus* (genus), *Pseudomonas* (genus), *Alloprevotella* (genus), *Catenibacterium* (genus), Anaeroplasmatales (order), Pseudomonadales (order), Lentisphaerae (phylum), *Veillonella* sp. CM60 (species), *Porphyromonas* sp. 2026 (species), *Delftia* sp. BN-SKY3 (species), *Peptostreptococcus anaerobius* (species), *Citrobacter* sp. BW4 (species), *Alistipes* sp. RMA 9912 (species), *Bacteroides vulgatus* (species), *Lactobacillus* sp. BL302 (species), *Lactobacillus* sp. TAB-26 (species), *Bifidobacterium kashiwanohense* (species), and *Butyricimonas* sp. JCM 18677 (species).

9. The method of claim 1, wherein the therapy comprises a consumable comprising at least one of a probiotic therapy and a prebiotic therapy, and wherein the at least one of the probiotic therapy and the prebiotic therapy is associated with at least one of *Anaerococcus* sp. 8405254, *Bacteroides nordii*, *Bacteroides* sp. SLC1-38, *Bifidobacterium merycicum*, *Blautia glucerasea*, *Blautia* sp. YHC-4, *Butyrivibrio crossotus*, *Catabacter hongkongensis*, *Catenibacterium mitsuokai*, *Collinsella aerofaciens*, *Collinsella intestinalis*, *Desulfovibrio piger*, *Eubacterium* sp. SA11, *Fusobacterium ulcerans*, *Lactobacillus* sp. TAB-30, *Megamonas funiformis*, *Megasphaera* sp. S6-MB2, *Olsenella* sp. 1183, *Phascolarctobacterium succinatutens*, *Streptococcus gordonii*, *Sutterella* sp. YIT 12072, *Sutterella wadsworthensis*, *Veillonella* sp. AS16, *Fusobacterium equinum*, *Facklamia* sp. 1440-97, *Anaerostipes* sp. 3_2_56FAA, *Pseudoclavibacter* sp. Timone, *Parvimonas micra*, *Lactobacillus* sp. 66c, *Bacteroides coprocola*, *Corynebacterium ulcerans*, *Anaerostipes* sp. 1y-2, *Sarcina ventriculi*, *Lactonifactor longoviformis*, *Enterococcus* sp. C6I11, *Eubacterium callanderi*, *Dialister invisus*, *Blautia* sp. Ser8, *Bacteroides plebeius*, *Bacteroides* sp. 2_2_4, *Anaerotruncus colihominis*, *Varibaculum cambriense*, *Actinomyces* sp. S9 PR-21, *Desulfovibrio* sp., *Prevotella disiens*, *Mobiluncus mulieris*, *Lactobacillus rhamnosus*, *Bifidobacterium* sp. MSX5B, *Acidaminococcus* sp. D21, *Bifidobacterium bifidum*, *Bacteroides* sp. EBA5-17, *Anaerococcus hydrogenalis*, *Alistipes* sp. 627, *Negativicoccus succinicivorans*, *Anaerococcus* sp. 8404299, *Butyricimonas synergistica*, *Actinomyces* sp. ICM54, *Turicibacter sanguinis*, *Blautia hydrogenotrophica*, *Parabacteroides goldsteinii*, *Bifidobacterium biavatii*, *Erysipelatoclostridium ramosum*, *Anaerofustis stercorihominis*, *Gardnerella vaginalis*, *Gordonibacter pamelaeae*, *Campylobacter hominis*, *Lactobacillus* sp. BL302, *Megasphaera* sp. UPII 199-6, *Peptoniphilus* sp. gpac018A, *Bifidobacterium stercoris*, *Butyricicoccus pullicaecorum*, *Megasphaera* sp. S6-MB2, *Corynebacterium* sp., *Dialister propionicifaciens*, *Anaerococcus tetradius*, *Eggerthella* sp. HGA1, *Peptoniphilus* sp. 7-2, *Terrisporobacter glycolicus*, *Peptoniphilus* sp. 2002-2300004, *Bacteroides* sp. CB57, *Streptococcus pasteurianus*, *Megasphaera* genomosp. C1, *Holdemania filiformis*, *Coprobacillus* sp. D6, *Dielma fastidiosa*, *Sutterella stercoricanis*, *Brevibacterium massiliense*, *Bacteroides stercorirosoris*, *Lactobacillus* sp. Akhmr01, *Actinomyces* sp. ICM47, *Lactobacillus crispatus*, *Prevotella bivia*, *Enterobacter* sp. BS2-1, *Streptococcus* sp. BS35a, *Anaerotruncus* sp. NML 070203, *Haemophilus parainfluenzae*, *Peptoniphilus coxii*, *Granulicatella adiacens*, *Campylobacter ureolyticus*, *Bifidobacterium longum*, *Bacteroides clarus*, *Bacteroides* sp. XB12B, *Streptococcus agalactiae*, *Kluyvera georgiana*, *Flavonifractor plautii*, *Paraprevotella clara*, *Stenotrophomonas* sp. C-S-TSA3, *Bacteroides* sp. DJF_B097, *Herbaspirillum seropedicae*, *Streptococcus* sp. oral taxon G59, *Eisenbergiella tayi*, *Coprobacter fastidiosus*, *Oligella urethralis*, *Akkermansia muciniphila*, *Desulfovibrio desulfuricans*, *Streptococcus peroris*, *Anaerococcus octavius*, *Atopobium vaginae*, *Parabacteroides* sp. 157, *Bifidobacterium choerinum*, *Porphyromonas uenonis*, *Dermabacter hominis*, *Alistipes indistinctus*, *Weissella hellenica*, *Alistipes massiliensis*, *Butyricimonas virosa*, *Alistipes putredinis*, *Actinobacillus porcinus*, *Howardella ureilytica*, *Veillonella* sp. CM60, *Porphyromonas* sp. 2026, *Delftia* sp.

BN-SKY3, *Peptostreptococcus anaerobius, Citrobacter* sp. BW4, *Alistipes* sp. RMA 9912, *Bacteroides vulgatus, Lactobacillus* sp. TAB-26, *Bifidobacterium* sp., *Bifidobacterium kashiwanohense,* and *Butyricimonas* sp. JCM 18677.

10. The method of claim 1, wherein the supplementary data comprises at least one of survey-derived data, user data, site-specific data, and device data, wherein the method further comprises determining a set of supplementary features based on the at least one of the survey-derived data, the user data, the site-specific data, and the device data, and wherein generating the sleep-related characterization model comprises generating the sleep-related characterization model based on the set of supplementary features and the at least one of the set of microbiome composition features and the set of microbiome functional features.

11. The method of claim 1, further comprising determining a set of user microbiome features for the user based on a user sample from the user,
wherein the set of user microbiome features is associated with the at least one of the set of microbiome composition features and the set of microbiome functional features,
wherein the sleep-related characterization model comprises a therapy model,
wherein determining the sleep-related characterization comprises determining the therapy for the user for the sleep-related condition based on the therapy model and the set of user microbiome features, and
wherein providing the therapy comprises providing a recommendation for the therapy to the user at a computing device associated with the user.

12. A method for characterizing a first sleep-related condition associated with microorganisms, the method comprising:
collecting a sample from a user, wherein the sample comprises microorganism nucleic acids associated with the first sleep-related condition;
determining a microorganism dataset associated with the user based on the microorganism nucleic acids of the sample;
determining user microbiome features comprising at least one of user microbiome composition features and user microbiome functional features, based on the microorganism dataset, wherein the user microbiome features are associated with the first sleep-related condition;
determining a sleep-related characterization for the user for the first sleep-related condition based on the user microbiome features; and
providing a therapy for the user for facilitating improvement of the first sleep-related condition, based on the sleep-related characterization.

13. The method of claim 12, further comprising collecting first sleep-tracking data comprising at least one of first survey-derived data and first device data, wherein the first sleep-tracking data is associated with sleep quality of the user, wherein determining the sleep-related characterization comprises determining the sleep-related characterization for the user based on the user microbiome features and the first sleep-tracking data, and wherein the method further comprises, after providing the therapy:
collecting a post-therapy sample from the user;
collecting second sleep-tracking data comprising at least one of second survey-derived data and second device data, wherein the second sleep-tracking data is associated with the sleep quality of the user; and
determining a post-therapy sleep-related characterization for the user for the first sleep-related condition based on the second sleep-tracking data and post-therapy microbiome features associated with the post-therapy sample.

14. The method of claim 13, further comprising facilitating therapeutic intervention in relation to an updated therapy for the user for improving the first sleep-related condition, based on the post-therapy sleep-related characterization, and wherein the updated therapy comprises at least one of a consumable, a device-related therapy, a surgical operation, a psychological-associated therapy, a behavior modification therapy, and an environmental factor modification therapy.

15. The method of claim 14, wherein determining the post-therapy sleep-related characterization comprises determining a comparison between microbiome characteristics of the user and reference microbiome characteristics corresponding to a user subgroup sharing at least one of a behavior and an environmental factor associated with the first sleep-related condition, based on the post-therapy microbiome features, and wherein facilitating therapeutic intervention in relation to the updated therapy comprises presenting the comparison to the user for facilitating at least one of the behavior modification therapy and the environmental factor modification therapy.

16. The method of claim 12, wherein determining user microbiome features comprises determining the user microbiome composition features comprising a first set of composition features associated with at least one of: *Acetitomaculum* (genus), Acidaminococcaceae (family), *Acidaminococcus* (genus), *Acidaminococcus* sp. D21 (species), Actinobacteria (class), Actinobacteria (phylum), *Actinomyces* (genus), *Actinomyces* sp. ICM47 (species), *Actinomyces* sp. ICM54 (species), *Actinomyces* sp. S9 PR-21 (species), *Akkermansia muciniphila* (species), Alcaligenaceae (family), *Alistipes indistinctus* (species), *Alistipes* sp. 627 (species), *Anaerococcus* (genus), *Anaerococcus hydrogenalis* (species), *Anaerococcus octavius* (species), *Anaerococcus* sp. 8404299 (species), *Anaerococcus* sp. 8405254 (species), *Anaerococcus tetradius* (species), *Anaerofustis* (genus), *Anaerofustis stercorihominis* (species), *Anaeroplasma* (genus), *Anaerosporobacter* (genus), *Anaerostipes* sp. 1y-2 (species), *Anaerostipes* sp. 3_2_56FAA (species), *Anaerotruncus colihominis* (species), *Anaerotruncus* sp. NML 070203 (species), *Atopobium* (genus), *Atopobium vaginae* (species), *Bacteroides clarus* (species), *Bacteroides coprocola* (species), *Bacteroides nordii* (species), *Bacteroides plebeius* (species), *Bacteroides* sp. 2_2_4 (species), *Bacteroides* sp. CB57 (species), *Bacteroides* sp. DJF_B097 (species), *Bacteroides* sp. EBA5-17 (species), *Bacteroides* sp. SLC1-38 (species), *Bacteroides* sp. XB12B (species), *Bacteroides stercorirosoris* (species), Bifidobacteriaceae (family), Bifidobacteriales (order), *Bifidobacterium* (genus), *Bifidobacterium biavatii* (species), *Bifidobacterium bifidum* (species), *Bifidobacterium choerinum* (species), *Bifidobacterium longum* (species), *Bifidobacterium merycicum* (species), *Bifidobacterium* sp. MSX5B (species), *Bifidobacterium stercoris* (species), *Blautia glucerasea* (species), *Blautia hydrogenotrophica* (species), *Blautia* sp. Ser8 (species), *Blautia* sp. YHC-4 (species), *Brevibacterium massiliense* (species), *Butyricicoccus* (genus), *Butyricicoccus pullicaecorum* (species), *Butyricimonas synergistica* (species), *Butyrivibrio* (genus), *Butyrivibrio crossotus* (species), *Campylobacter* (genus), *Campylobacter hominis* (species), *Campylobacter ureolyticus* (species), Campylobacteraceae (family), Campylobacterales (order), *Candidatus Soleaferrea* (genus), *Candidatus Stoquefichus* (genus), *Catabacter hongkongensis* (species), *Catenibacterium mitsuokai* (species), *Cellulosilyticum* (genus), *Collinsella aerofaciens* (species), *Collinsella intestinalis* (species), *Coprobacillus* (genus), *Coprobacillus* sp. D6 (species), *Coprobacter* (genus), *Coprobacter fastidiosus* (species), *Corynebacterium* sp. (species), *Corynebacterium ulcerans* (species), Cyanobacteria (phylum), *Dermabacter* (genus), *Dermabacter hominis* (species), Dermabacteraceae (family), *Desulfovibrio desulfuricans* (species), *Desulfovibrio piger* (species), *Desulfovibrio* sp. (species), *Dialister* (genus), *Dialister invisus* (species), *Dialister propionicifaciens* (species), *Dielma* (genus), *Dielma fastidiosa* (species), *Eggerthella* (genus), *Eggerthella* sp. HGA1 (species), *Eisenbergiella tayi* (species), *Enterobacter* (genus), *Enterobacter* sp. BS2-1 (species), *Enterococcus* sp. C6I11 (species), Epsilonproteobacteria (class), *Erysipelatoclostridium ramosum* (species), Eubacteriaceae (family), *Eubacterium* (genus), *Eubacterium callanderi* (species), *Eubacterium* sp. SA11 (species), *Facklamia* sp. 1440-97 (species), *Fibrobacter* (genus), *Flavobacterium* (genus), *Flavonifractor plautii* (species), Fusobacteria (phylum), Fusobacteriaceae (family), Fusobacteriales (order), Fusobacteriia (class), *Fusobacterium* (genus), *Fusobacterium equinum* (species), *Fusobacterium ulcerans* (species), *Gardnerella* (genus), *Gardnerella vaginalis* (species), *Gelria* (genus), *Gordonibacter* (genus), *Gordonibacter pamelaeae* (species), *Granulicatella* (genus), *Granulicatella adiacens* (species), *Haemophilus* (genus), *Haemophilus parainfluenzae* (species), *Herbaspirillum* (genus), *Herbaspirillum seropedicae* (species), *Holdemania* (genus), *Holdemania filiformis* (species), *Howardella* (genus), *Hydrogenoanaerobacterium* (genus), *Intestinibacter* (genus), *Klebsiella* (genus), *Kluyvera georgiana* (species), *Lachnospira* (genus), *Lactobacillus crispatus* (species), *Lactobacillus rhamnosus* (species), *Lactobacillus* sp. 66c (species), *Lactobacillus* sp. Akhmr01 (species), *Lactobacillus* sp. BL302 (species), *Lactobacillus* sp. TAB-30 (species), *Lactonifactor* (genus), *Lactonifactor longoviformis* (species), Leptotrichiaceae (family), *Leuconostoc* (genus), Leuconostocaceae (family), *Megamonas* (genus), *Megamonas funiformis* (species), *Megasphaera* (genus), *Megasphaera* genomosp. C1 (species), *Megasphaera* sp. S6-MB2 (species), *Megasphaera* sp. UPII 199-6 (species), *Mobiluncus* (genus), *Mobiluncus mulieris* (species), *Moryella* (genus), *Negativicoccus* (genus), *Negativicoccus succinicivorans* (species), Negativicutes (class), *Oligella* (genus), *Oligella urethralis* (species), *Olsenella* sp. 1183 (species), Oscillospiraceae (family), *Pantoea* (genus), *Papillibacter* (genus), *Parabacteroides goldsteinii* (species), *Parabacteroides* sp. 157 (species), *Paraprevotella clara* (species), *Parvimonas micra* (species), Pasteurellaceae (family), Pasteurellales (order), *Peptoniphilus* (genus), *Peptoniphilus coxii* (species), *Peptoniphilus* sp. 2002-2300004 (species), *Peptoniphilus* sp. 7-2 (species), *Peptoniphilus* sp. gpac018A (species), *Phascolarctobacterium* (genus), *Phascolarctobacterium succinatutens* (species), Phyllobacteriaceae (family), *Phyllobacterium* (genus), *Porphyromonas uenonis* (species), *Prevotella bivia* (species), *Prevotella disiens* (species), Propionibacteriaceae (family), *Propionibacterium* (genus), Proteobacteria (phylum), *Pseudobutyrivibrio* (genus), *Pseudoclavibacter* sp. *Timone* (species), Rhizobiales (order), *Roseburia* (genus), Ruminococcaceae (family), *Sarcina ventriculi* (species), Selenomonadales order *Shuttleworthia* (genus), Sphingomonadaceae (family), Sphingomonadales (order), *Stenotrophomonas* (genus), *Stenotrophomonas* sp. C-S-TSA3 (species), *Streptococcus agalactiae* (species), *Streptococcus gordonii* (species), *Streptococcus pasteurianus* (species), *Streptococcus peroris* (species), *Streptococcus* sp. BS35a (species), *Streptococcus* sp. oral taxon G59 (species), *Sutterella* (genus), *Sutterella* sp. YIT 12072 (species), *Sutterella stercoricanis* (species), *Sutterella wadsworthensis* (species), *Terrisporobacter glycolicus* (species), Thermoanaerobacteraceae (family), Thermoanaerobacterales (order), *Turicibacter* (genus), *Turicibacter sanguinis* (species), *Varibaculum* (genus), *Varibaculum cambriense* (species), *Veillonella* sp. AS16 (species), Veillonellaceae (family), *Weissella hellenica* (species), Xanthomonadaceae (family), and Xanthomonadales (order).

17. The method of claim 16, wherein determining the user microbiome features comprises determining the user microbiome composition features comprising a second set of composition features associated with at least one of: *Alistipes massiliensis* (species), *Butyricimonas virosa* (species), *Alistipes putredinis* (species), *Actinobacillus porcinus* (species), *Actinobacillus* (genus), *Butyricimonas* (genus), *Howardella ureilytica* (species), Firmicutes (phylum), *Clostridium* (genus), Lentisphaeria (class), Anaeroplasmataceae (family), Pseudomonadaceae (family), Victivallaceae (family), *Blautia* (genus), *Asteroleplasma* (genus), *Delftia* (genus), *Victivallis* (genus), *Peptostreptococcus* (genus), *Pseudomonas* (genus), *Alloprevotella* (genus), *Catenibacterium* (genus), Anaeroplasmatales (order), Pseudomonadales (order), Lentisphaerae (phylum), *Veillonella* sp. CM60 (species), *Porphyromonas* sp. 2026 (species), *Delftia* sp. BN-SKY3 (species), *Peptostreptococcus anaerobius* (species), *Citrobacter* sp. BW4 (species), *Alistipes* sp. RMA 9912 (species), *Bacteroides vulgatus* (species), *Lactobacillus* sp. BL302 (species), *Lactobacillus* sp. TAB-26 (species), *Bifidobacterium kashiwanohense* (species), *Butyricimonas* sp. JCM 18677 (species).

18. The method of claim 17, wherein determining the sleep-related characterization comprises determining the sleep-related characterization for the user for the first sleep-related condition and a second sleep-related condition based on the first set of composition features, a first sleep-related characterization model, the second set of composition features, and a second sleep-related characterization model, wherein the first sleep-related characterization model is associated with the first sleep-related condition, and wherein the second sleep-related characterization model is associated with the second sleep-related condition.

19. The method of claim 18, wherein determining the user microbiome features comprises:
   determining first user microbiome functional features associated with first functions from at least one of Cluster of Orthologous Groups (COG) database and Kyoto Encyclopedia of Genes and Genomes (KEGG) database, wherein the first user microbiome functional features are associated with the first sleep-related condition; and
   determining second user microbiome functional features associated with second functions from at least one of the COG database and the KEGG database, wherein the second user microbiome functional features are associated with the second sleep-related condition,
   wherein determining the sleep-related characterization comprises determining the sleep-related characterization for the user for the first sleep-related condition and the second sleep-related condition based on the first set of composition features, the first user microbiome functional features, the first sleep-related characterization model, the second set of composition features, the second user microbiome functional features, and the second sleep-related characterization model.

20. The method of claim 12,
wherein determining the user microbiome features comprises applying a set of analytical techniques to determine at least one of presence of at least one of a microbiome composition diversity feature and a microbiome functional diversity feature, absence of the at least one of the microbiome composition diversity feature and the microbiome functional diversity feature, a relative abundance feature describing relative abundance of different taxonomic groups associated with the first sleep-related condition, a ratio feature describing a ratio between at least two microbiome features associated with the different taxonomic groups, an interaction feature describing an interaction between the different taxonomic groups, and a phylogenetic distance feature describing phylogenetic distance between the different taxonomic groups, based on the microorganism dataset, and
wherein the set of analytical techniques comprises at least one of a univariate statistical test, a multivariate statistical test, a dimensionality reduction technique, and an artificial intelligence approach.

21. The method of claim 12, wherein the first sleep-related condition comprises a bad sleep quality condition, wherein determining user microbiome features comprises determining the user microbiome composition features comprising a set of composition features associated with a genital site and with at least one of: Abiotrophia defectiva, Achromobacter xylosoxidans, Acidaminococcus intestini, Acidaminococcus sp. D21, Acinetobacter sp. C-S-NA3, Acinetobacter sp. RBE2CD-114, Acinetobacter sp. RE 51, Actinobaculum massiliense, Actinomyces europaeus, Actinomyces hongkongensis, Actinomyces neuii, Actinomyces odontolyticus, Actinomyces radingae, Actinomyces sp. 2002-2301122, Actinomyces sp. ICM54, Actinomyces sp. ICM58, Actinomyces sp. S4-C9, Actinomyces sp. S9 PR-21, Actinomyces turicensis, Actinotignum schaalii, Actinotignum urinale, Adlercreutzia equolifaciens, Aerococcus christensenii, Aerococcus urinae, Akkermansia muciniphila, Alistipes finegoldii, Alistipes putredinis, Alistipes shahii, Alistipes sp. EBA6-25cl2, Alistipes sp. HGB5, Alistipes sp. NML05A004, Alistipes sp. RMA 9912, Alloscardovia omnicolens, Anaerobacillus alkalidiazotrophicus, Anaerococcus hydrogenalis, Anaerococcus lactolyticus, Anaerococcus murdochii, Anaerococcus octavius, Anaerococcus prevotii, Anaerococcus provencensis, Anaerococcus sp. 8404299, Anaerococcus sp. PH9, Anaerococcus sp. S8 87-3, Anaerococcus sp. S9 PR-16, Anaerococcus sp. S9 PR-5, Anaerococcus tetradius, Anaerococcus vaginalis, Anaeroglobus geminatus, Anaerostipes hadrus, Anaerostipes sp. 3_2_56FAA, Anoxybacillus sp. HT14, Aquabacterium sp. Aqua2, Arcanobacterium haemolyticum, Asaccharospora irregularis, Atopobium deltae, Atopobium minutum, Atopobium sp. MVA9, Atopobium sp. S3MV24, Atopobium sp. S3MV26, Atopobium sp. S3PFAA1-4, Atopobium sp. S4-5, Atopobium sp. S4-A11a, Bacillus pseudofirmus, Bacillus sp. CZb, Bacillus sp. T41, Bacteroides acidifaciens, Bacteroides clarus, Bacteroides coprocola, Bacteroides dorei, Bacteroides eggerthii, Bacteroides finegoldii, Bacteroides fragilis, Bacteroides intestinalis, Bacteroides massiliensis, Bacteroides plebeius, Bacteroides salyersiae, Bacteroides sp. AR20, Bacteroides sp. AR29, Bacteroides sp. EBA5-17, Bacteroides sp. SLC1-38, Bacteroides sp. XB12B, Bacteroides sp. XB44A, Bacteroides stercorirosoris, Bacteroides stercoris, Bacteroides thetaiotaomicron, Bacteroides uniformis, Bacteroides vulgatus, Barnesiella intestinihominis, Bergeyella sp. AF14, Bifidobacterium bifidum, Bifidobacterium breve, Bifidobacterium dentium, Bifidobacterium kashiwanohense, Bifidobacterium sp. 120, Bifidobacterium sp. MSX5B, Blautia faecis, Blautia sp. Ser8, Bosea sp. BIWAKO-01, Bosea sp. R-46060, Brachybacterium sp. NIO-27, Bradyrhizobium sp. 68A4SAPT, Bradyrhizobium sp. CCBAU 53380, Brevibacterium massiliense, Brevibacterium paucivorans, Brevibacterium ravenspurgense, Brevundimonas sp. V3M6, Bulleidia extructa, Campylobacter concisus, Campylobacter gracilis, Campylobacter hominis, Campylobacter rectus, Campylobacter sp. 10_1_50, Campylobacter sp. FOBRC15, Campylobacter ureolyticus, Chryseobacterium sp. MH28, Citrobacter sp. BW4, Cloacibacillus evryensis, Cloacibacterium normanense, Collinsella aerofaciens, Coprobacter fastidiosus, Corynebacterium argentoratense, Corynebacterium canis, Corynebacterium diphtheriae, Corynebacterium epidermidicanis, Corynebacterium frankenforstense, Corynebacterium freiburgense, Corynebacterium glucuronolyticum, Corynebacterium mastitidis, Corynebacterium sp., Corynebacterium sp. 2300500, Corynebacterium sp. 713182/2012, Corynebacterium sp. NML 97-0186, Corynebacterium sp. NML96-0085, Corynebacterium sp. jw37, Corynebacterium spheniscorum, Corynebacterium ulcerans, Cronobacter sakazakii, Curvibacter gracilis, Cutibacterium acnes, Cutibacterium avidum, Delftia lacustris, Delftia sp. BN-SKY3, Dermabacter hominis, Dialister micraerophilus, Dialister propionicifaciens, Dialister sp. E2_20, Dialister sp. S4-23, Dialister sp. S7MSR5, Dialister succinatiphilus, Dorea longicatena, Eggerthella sp. HGA1, Eggerthia catenaformis, Enterococcus faecalis, Enterococcus sp. C6I11, Enterococcus sp. SI-4, Facklamia languida, Facklamia sp. 1440-97, Facklamia sp. 164-92, Faecalibacterium prausnitzii, Faecalibacterium sp. canine oral taxon 147, Fastidiosipila sanguinis, Finegoldia sp. S3MVA9, Finegoldia sp. S5-A7, Finegoldia sp. S8 F7, Finegoldia sp. S9 AA1-5, Flavonifractor plautii, Fusobacterium nucleatum, Fusobacterium periodonticum, Fusobacterium sp. ACB2, Fusobacterium sp. AS2, Fusobacterium sp. CM21, Gardnerella sp. S3PF20, Gardnerella vaginalis, Gemella asaccharolytica, Gemella morbillorum, Gemella sp. 933-88, Globicatella sanguinis, Globicatella sulfidifaciens, Granulicatella adiacens, Granulicatella elegans, Haemophilus influenzae, Haemophilus parainfluenzae, Halomonas pacifica, Helcococcus seattlensis, Helcococcus suecensis, Herbaspirillum huttiense, Herbaspirillum seropedicae, Intestinimonas butyriciproducens, Jonquetella anthropi, Jonquetella sp. BV3C4, Kluyvera georgiana, Kocuria rhizophila, Lachnospira pectinoschiza, Lactobacillus acidophilus, Lactobacillus coleohominis, Lactobacillus crispatus, Lactobacillus fermentum, Lactobacillus fornicalis, Lactobacillus gasseri, Lactobacillus iners, Lactobacillus jensenii, Lactobacillus johnsonii, Lactobacillus plantarum, Lactobacillus reuteri, Lactobacillus rhamnosus, Lactobacillus sp. 7_1_47FAA, Lactobacillus sp. Akhmr01, Lactobacillus sp. BL302, Lactobacillus sp. C30An8, Lactobacillus sp. CR-609S, Lactobacillus sp. MYMRS/TEN2, Lactobacillus sp. TAB-22, Lactobacillus taiwanensis, Lactobacillus vaginalis, Lactococcus lactis, Lysinibacillus sphaericus, Megamonas funiformis, Megasphaera massiliensis, Megasphaera micronuciformis, Megasphaera sp. BV3C16-1, Megasphaera sp. UPII 135-E, Megasphaera sp. UPII 199-6, Mesorhizobium sp. mat916, Methanobrevibacter smithii, Methylobacterium sp. CBMB45, Methylobacterium sp. RK-2008-1, Microbacterium yannicii, Micrococcus luteus, Mobiluncus curtisii, Mobiluncus mulieris, Moraxella sp. 26, Moryella indoligenes, Murdochiella asaccharolytica, Mycobacterium sp. T126, Mycoplasma hominis, Negativicoccus sp. S5-A15, Negativicoccus succinicivorans, Neisseria elongata, *Novosphingobium sediminicola, Ochrobactrum* sp. SCTS14, *Odoribacter splanchnicus, Oligella urethralis, Olsenella* sp. S9 HS-6, *Pantoea vagans, Parabacteroides distasonis, Parabacteroides goldsteinii, Parabacteroides merdae, Paraprevotella clara, Peptococcus niger, Peptococcus* sp. S9 B-15, *Peptococcus* sp. S9 Pr-12, *Peptoniphilus coxii, Peptoniphilus duerdenii, Peptoniphilus koenoeneniae, Peptoniphilus lacrimalis, Peptoniphilus* sp. 1-14, *Peptoniphilus* sp. 2002-2300004, *Peptoniphilus* sp. 2002-38328, *Peptoniphilus* sp. 7-2, *Peptoniphilus* sp. BV3AC2, *Peptoniphilus* sp. DNF00840, *Peptoniphilus* sp. JCM 8143, *Peptoniphilus* sp. S4-13, *Peptoniphilus* sp. S4-A10, *Peptoniphilus* sp. S9 PR-13, *Peptoniphilus* sp. gpac018A, *Peptoniphilus* sp. gpac018B, *Peptoniphilus* sp. gpac148, *Peptoniphilus* sp. oral taxon 375, *Peptostreptococcus anaerobius, Porphyromonas asaccharolytica, Porphyromonas bennonis, Porphyromonas somerae, Porphyromonas* sp. 2024b, *Porphyromonas* sp. 2026, *Porphyromonas* sp. S8 86-12, *Porphyromonas uenonis, Prevotella amnii, Prevotella bivia, Prevotella buccalis, Prevotella disiens, Prevotella* sp. BV3C7, *Prevotella* sp. S4-10, *Prevotella timonensis, Propionibacterium* sp. KPL2005, *Propionibacterium* sp. MSP09A, *Propionibacterium* sp. V07/12348, *Propionimicrobium lymphophilum, Proteus mirabilis, Pseudoclavibacter* sp. *Timone, Pseudoglutamicibacter albus, Pseudoglutamicibacter cumminsii, Pseudomonas brenneri, Pseudomonas* sp. GmFRB023, *Ralstonia pickettii, Ralstonia* sp. A52, *Rhizobium etli, Rhizobium* sp. sc-w, *Rhodococcus erythropolis, Rhodopseudomonas boonkerdii, Roseburia faecis, Roseburia hominis, Roseburia intestinalis, Roseburia* sp. 11SE39, *Rothia mucilaginosa, Serratia nematodiphila, Slackia exigua, Slackia* sp. S8 F4, *Sneathia sanguinegens, Solobacterium moorei, Solobacterium* sp. S4-A19, *Sphingobium* sp. LC341, *Sphingomonas* sp. 24T, *Sphingomonas* sp. 540, *Staphylococcus aureus, Staphylococcus epidermidis, Staphylococcus simulans, Staphylococcus* sp. 334802, *Staphylococcus* sp. C912, *Staphylococcus* sp. WB18-16, *Stenotrophomonas* sp. C-S-TSA3, *Stenotrophomonas* sp. KITS-1, *Stomatobaculum longum, Streptococcus agalactiae, Streptococcus anginosus, Streptococcus dysgalactiae, Streptococcus gordonii, Streptococcus parasanguinis, Streptococcus pasteurianus, Streptococcus* sp. 11aTha1, *Streptococcus* sp. 2011_Oral_MS_A3, *Streptococcus* sp. GMD6S, *Streptococcus* sp. XQ-1, *Subdoligranulum variabile, Sutterella stercoricanis, Sutterella wadsworthensis, Tessaracoccus* sp. SL014B-79A, *Trueperella bernardiae, Ureaplasma urealyticum, Varibaculum cambriense, Varibaculum* sp. CCUG 45114, *Varibaculum* sp. CCUG 61255, *Veillonella atypica, Veillonella montpellierensis, Veillonella parvula, Veillonella ratti, Veillonella rogosae, Veillonella seminalis, Veillonella* sp. 2011_Oral_VSA_D3, *Veillonella* sp. AS16, *Veillonella* sp. CM60, *Veillonella* sp. MSA12, *Veillonella* sp. oral taxon 780, *Weeksella virosa, Abiotrophia, Achromobacter, Acidaminococcus, Acinetobacter, Actinobaculum, Actinotignum, Adlercreutzia, Aerococcus, Akkermansia, Alistipes, Alloprevotella, Alloscardovia, Anaerobacillus, Anaerococcus, Anaeroglobus, Anaerosporobacter, Anaerotruncus, Aquabacterium, Arcanobacterium, Arthrobacter, Asaccharospora, Atopobium, Bacillus, Bacteroides, Barnesiella, Bergeyella, Bifidobacterium, Blautia, Bosea, Brachybacterium, Brevibacterium, Brevundimonas, Bulleidia, Butyricimonas, Campylobacter, Catenibacterium, Chryseobacterium, Citrobacter, Cloacibacillus, Cloacibacterium, Clostridium, Collinsella, Coprobacter, Corynebacterium, Cronobacter, Curvibacter, Cutibacterium, Deinococcus, Delftia, Dermabacter, Dialister, Eggerthia, Enterobacter, Enterococcus, Enterorhabdus, Erysipelatoclostridium, Facklamia, Faecalibacterium, Fastidiosipila, Flavobacterium, Flavonifractor, Fusobacterium, Gardnerella, Gemella, Globicatella, Granulicatella, Halomonas, Helcococcus, Herbaspirillum, Howardella, Intestinibacter, Intestinimonas, Johnsonella, Jonquetella, Kluyvera, Lachnoanaerobaculum, Lachnospira, Lactobacillus, Leptotrichia, Lysinibacillus, Marvinbryantia, Megamonas, Megasphaera, Meiothermus, Mesorhizobium, Methanobrevibacter, Methylobacterium, Microbacterium, Micrococcus, Mobiluncus, Mogibacterium, Moraxella, Moryella, Murdochiella, Mycobacterium, Mycoplasma, Negativicoccus, Neisseria, Novosphingobium, Ochrobactrum, Odoribacter, Oligella, Olsenella, Oribacterium, Oscillibacter, Oscillospira, Pantoea, Parabacteroides, Paraprevotella, Parasutterella, Parvibacter, Parvimonas, Pelomonas, Peptoclostridium, Peptococcus, Peptoniphilus, Peptostreptococcus, Phyllobacterium, Porphyromonas, Prevotella, Propionibacterium, Propionimicrobium, Proteus, Pseudobutyrivibrio, Pseudoclavibacter, Pseudomonas, Pyramidobacter, Rhizobium, Rhodococcus, Rhodopseudomonas, Romboutsia, Roseburia, Rothia, Sarcina, Senegalimassilia, Serratia, Shuttleworthia, Slackia, Sneathia, Solobacterium, Sphingobium, Sphingomonas, Staphylococcus, Stomatobaculum, Streptococcus, Sutterella, Terrisporobacter, Tessaracoccus, Thalassospira, Trueperella, Ureaplasma, Varibaculum, Veillonella, Weeksella*.

22. The method of claim 12, wherein the first sleep-related condition comprises a bad sleep quality condition, wherein determining user microbiome features comprises determining the user microbiome composition features comprising a set of composition features associated with a gut site and with at least one of: *Abiotrophia defectiva, Achromobacter xylosoxidans, Acidaminococcus fermentans, Acidaminococcus* sp. BV3L6, *Acidaminococcus* sp. D21, *Actinobaculum massiliense, Actinomyces dentalis, Actinomyces graevenitzii, Actinomyces odontolyticus, Actinomyces radingae, Actinomyces* sp. 2002-2301122, *Actinomyces* sp. ICM47, *Actinomyces* sp. ICM54, *Actinomyces* sp. ICM58, *Actinomyces* sp. S4-C9, *Actinomyces* sp. S6-Spd3, *Actinomyces* sp. S9 PR-21, *Actinomyces* sp. oral taxon 175, *Actinomyces* sp. ph3, *Actinomyces turicensis, Actinomyces viscosus, Actinotignum schaalii, Adlercreutzia equolifaciens, Aerococcus christensenii, Aerococcus* sp. B43(2010), *Aerococcus urinae, Aeromonas salmonicida, Aeromonas* sp. B11, *Aerosphaera taetra, Aggregatibacter aphrophilus, Aggregatibacter segnis, Akkermansia muciniphila, Alistipes indistinctus, Alistipes inops, Alistipes massiliensis, Alistipes onderdonkii, Alistipes putredinis, Alistipes shahii, Alistipes* sp. EBA6-25cl2, *Alistipes* sp. HGB5, *Alistipes* sp. NML05A004, *Alistipes* sp. RMA 9912, *Allobaculum stercoricanis, Alloprevotella tannerae, Alloscardovia omnicolens, Anaerobacillus alkalidiazotrophicus, Anaerococcus hydrogenalis, Anaerococcus lactolyticus, Anaerococcus prevotii, Anaerococcus provencensis, Anaerococcus* sp. 8404299, *Anaerococcus* sp. 8405254, *Anaerococcus* sp. 9401487, *Anaerococcus* sp. PH9, *Anaerococcus* sp. S8 87-3, *Anaerococcus* sp. S8 F2, *Anaerococcus* sp. S9 PR-16, *Anaerococcus* sp. S9 PR-5, *Anaerococcus* sp. gpac137, *Anaerococcus tetradius, Anaerofustis stercorihominis, Anaeroglobus geminatus, Anaeroglobus* sp. S4-A15, *Anaerosinus glycerini, Anaerosporobacter mobilis, Anaerostipes butyraticus, Anaerostipes caccae, Anaerostipes hadrus, Anaerostipes rhamnosivorans, Anaerostipes* sp. 3_2_56FAA, *Anaerostipes* sp. 5_1_63FAA, *Anaerostipes* sp. 992a, *Anaerostipes* sp. AIP 183.04, *Anaerotruncus colihominis, Anaerotruncus* sp. NML 070203, *Anaerovibrio* sp. 656,

*Anaerovibrio* sp. 765, *Arcanobacterium haemolyticum*, *Arthrobacter* sp., *Asaccharospora irregularis*, *Atopobium deltae*, *Atopobium minutum*, *Atopobium rimae*, *Atopobium* sp. DMCT15023, *Atopobium* sp. F0209, *Atopobium* sp. MVA9, *Atopobium* sp. S3MV24, *Atopobium* sp. S3MV26, *Atopobium vaginae*, *Bacillus cereus*, *Bacillus* sp. HC15, *Bacillus* sp. N-16, *Bacillus* sp. PrMC7, *Bacillus subtilis*, *Bacteroides acidifaciens*, *Bacteroides barnesiae*, *Bacteroides caccae*, *Bacteroides caecigallinarum*, *Bacteroides chinchillae*, *Bacteroides clarus*, *Bacteroides coprocola*, *Bacteroides eggerthii*, *Bacteroides faecis*, *Bacteroides finegoldii*, *Bacteroides fluxus*, *Bacteroides fragilis*, *Bacteroides massiliensis*, *Bacteroides nordii*, *Bacteroides oleiciplenus*, *Bacteroides ovatus*, *Bacteroides plebeius*, *Bacteroides rodentium*, *Bacteroides salanitronis*, *Bacteroides salyersiae*, *Bacteroides sartorii*, *Bacteroides* sp., *Bacteroides* sp. 14(A), *Bacteroides* sp. 2011_Ileo_VSA_D7, *Bacteroides* sp. 2_2_4, *Bacteroides* sp. 35AE37, *Bacteroides* sp. 3_1_23, *Bacteroides* sp. 4072, *Bacteroides* sp. AR20, *Bacteroides* sp. AR29, *Bacteroides* sp. C13EG172, *Bacteroides* sp. CB57, *Bacteroides* sp. D-2, *Bacteroides* sp. D20, *Bacteroides* sp. D22, *Bacteroides* sp. DJF_B097, *Bacteroides* sp. EBA5-17, *Bacteroides* sp. HPS0048, *Bacteroides* sp. J1511, *Bacteroides* sp. S-17, *Bacteroides* sp. SLC1-38, *Bacteroides* sp. Smarlab 3301643, *Bacteroides* sp. TP-5, *Bacteroides* sp. WH302, *Bacteroides* sp. XB12B, *Bacteroides* sp. XB44A, *Bacteroides* sp. dnLKV9, *Bacteroides stercorirosoris*, *Bacteroides stercoris*, *Bacteroides thetaiotaomicron*, *Bacteroides uniformis*, *Bacteroides vulgatus*, *Barnesiella intestinihominis*, *Barnesiella viscericola*, *Bifidobacterium adolescentis*, *Bifidobacterium animalis*, *Bifidobacterium biavatii*, *Bifidobacterium bifidum*, *Bifidobacterium breve*, *Bifidobacterium catenulatum*, *Bifidobacterium choerinum*, *Bifidobacterium dentium*, *Bifidobacterium gallicum*, *Bifidobacterium kashiwanohense*, *Bifidobacterium longum*, *Bifidobacterium merycicum*, *Bifidobacterium pseudocatenulatum*, *Bifidobacterium pullorum*, *Bifidobacterium scardovii*, *Bifidobacterium* sp., *Bifidobacterium* sp. 138, *Bifidobacterium* sp. 65947, *Bifidobacterium* sp. MSX5B, *Bifidobacterium stercoris*, *Bifidobacterium tsurumiense*, *Bilophila* sp. 4_1_30, *Bilophila wadsworthia*, *Blautia coccoides*, *Blautia faecis*, *Blautia glucerasea*, *Blautia hansenii*, *Blautia hydrogenotrophica*, *Blautia luti*, *Blautia producta*, *Blautia schinkii*, *Blautia* sp. Ser5, *Blautia* sp. Ser8, *Blautia* sp. YHC-4, *Blautia stercoris*, *Blautia wexlerae*, *Brachyspira aalborgi*, *Brachyspira pilosicoli*, *Brachyspira* sp. HIS5, *Bradyrhizobium* sp. 68A4SAPT, *Brevibacterium massiliense*, *Brevibacterium paucivorans*, *Brevibacterium ravenspurgense*, *Butyricicoccus pullicaecorum*, *Butyricimonas* sp. 180-3, *Butyricimonas* sp. 214-4, *Butyricimonas* sp. GD2, *Butyricimonas synergistica*, *Butyricimonas virosa*, *Butyrivibrio crossotus*, *Campylobacter concisus*, *Campylobacter faecalis*, *Campylobacter gracilis*, *Campylobacter hominis*, *Campylobacter rectus*, *Campylobacter* sp. 0402694-C0078, *Campylobacter* sp. 10_1_50, *Campylobacter ureolyticus*, *Capnocytophaga gingivalis*, *Capnocytophaga* sp. oral taxon 329, *Carnobacterium maltaromaticum*, *Catabacter hongkongensis*, *Catenibacterium mitsuokai*, *Cellulosilyticum lentocellum*, *Cellulosilyticum ruminicola*, *Cetobacterium somerae*, *Christensenella minuta*, *Citrobacter amalonaticus*, *Citrobacter* sp. BW4, *Citrobacter* sp. HD4.9, *Cloacibacillus evryensis*, *Cloacibacillus porcorum*, *Cloacibacterium rupense*, *Clostridium ventriculi*, *Collinsella aerofaciens*, *Collinsella intestinalis*, *Collinsella tanakaei*, *Coprobacillus* sp. D6, *Coprobacter fastidiosus*, *Coprobacter secundus*, *Corynebacterium argentoratense*, *Corynebacterium canis*, *Corynebacterium ciconiae*, *Corynebacterium diphtheriae*, *Corynebacterium durum*, *Corynebacterium epidermidicanis*, *Corynebacterium frankenforstense*, *Corynebacterium freiburgense*, *Corynebacterium glucuronolyticum*, *Corynebacterium mastitidis*, *Corynebacterium matruchotii*, *Corynebacterium* sp., *Corynebacterium* sp. 713182/2012, *Corynebacterium* sp. NML 97-0186, *Corynebacterium* sp. NML96-0085, *Corynebacterium* sp. full20, *Corynebacterium spheniscorum*, *Corynebacterium ulcerans*, *Corynebacterium vitaeruminis*, *Cronobacter dublinensis*, *Cronobacter turicensis*, *Cutibacterium acnes*, *Cutibacterium avidum*, *Deinococcus geothermalis*, *Delftia lacustris*, *Delftia* sp. BN-SKY3, *Dermabacter hominis*, *Dermabacter* sp. HFH0086, *Desulfovibrio desulfuricans*, *Desulfovibrio fairfieldensis*, *Desulfovibrio intestinalis*, *Desulfovibrio* sp., *Desulfovibrio* sp. 3_1_syn3, *Desulfovibrio* sp. 6_1_46AFAA, *Desulfovibrio* sp. G11, *Desulfovibrio* sp. LNB2, *Desulfovibrio* sp. UNSW3caefatS, *Dialister invisus*, *Dialister pneumosintes*, *Dialister propionicifaciens*, *Dialister* sp. E2_20, *Dialister* sp. S4-23, *Dialister* sp. S7MSR5, *Dialister succinatiphilus*, *Dielma fastidiosa*, *Dolosigranulum pigrum*, *Dorea formicigenerans*, *Dorea longicatena*, *Dysgonomonas gadei*, *Dysgonomonas oryzarvi*, *Eggerthella lenta*, *Eggerthella sinensis*, *Eggerthella* sp. E1, *Eggerthella* sp. HGA1, *Eisenbergiella tayi*, *Enterobacter cloacae*, *Enterobacter* sp. BS2-1, *Enterobacter* sp. SPSA1, *Enterobacter* sp. UDC345, *Enterococcus durans*, *Enterococcus faecalis*, *Enterococcus faecium*, *Enterococcus gallinarum*, *Enterococcus hirae*, *Enterococcus pallens*, *Enterococcus raffinosus*, *Enterococcus* sp. C6I11, *Enterococcus* sp. SI-4, *Enterorhabdus caecimuris*, *Enterorhabdus mucosicola*, *Eremococcus coleocola*, *Erysipelatoclostridium ramosum*, *Eubacterium limosum*, *Eubacterium* sp. SA11, *Facklamia languida*, *Facklamia* sp. 1440-97, *Facklamia* sp. 164-92, *Faecalibacterium prausnitzii*, *Faecalibacterium* sp. canine oral taxon 147, *Finegoldia* sp. BV3C29, *Finegoldia* sp. S8 F7, *Finegoldia* sp. S9 AA1-5, *Flavonifractor plautii*, *Fusicatenibacter saccharivorans*, *Fusobacterium equinum*, *Fusobacterium mortiferum*, *Fusobacterium necrogenes*, *Fusobacterium nucleatum*, *Fusobacterium periodonticum*, *Fusobacterium* sp. ACB2, *Fusobacterium* sp. AS2, *Fusobacterium* sp. CM1, *Fusobacterium* sp. CM21, *Fusobacterium* sp. DJF_B100, *Fusobacterium* sp. OBRC1, *Fusobacterium ulcerans*, *Fusobacterium varium*, *Gardnerella* sp. S3PF20, *Gardnerella vaginalis*, *Gemella asaccharolytica*, *Gemella* sp. 933-88, *Globicatella sanguinis*, *Globicatella sulfidifaciens*, *Gordonibacter pamelaeae*, *Granulicatella adiacens*, *Granulicatella elegans*, *Haemophilus influenzae*, *Haemophilus parainfluenzae*, *Hafnia alvei*, *Helcococcus kunzii*, *Helcococcus seattlensis*, *Helcococcus sueciensis*, *Herbaspirillum seropedicae*, *Herbaspirillum* sp. AU13035, *Herbaspirillum* sp. YR522, *Holdemania filiformis*, *Howardella ureilytica*, *Hydrogenophilus islandicus*, *Intestinimonas butyriciproducens*, *Jonquetella anthropi*, *Klebsiella oxytoca*, *Klebsiella pneumoniae*, *Klebsiella* sp. B12, *Klebsiella* sp. SOR89, *Kluyvera georgiana*, *Lachnoanaerobaculum* sp. OBRC5-5, *Lachnospira pectinoschiza*, *Lactobacillus acidophilus*, *Lactobacillus animalis*, *Lactobacillus curvatus*, *Lactobacillus delbrueckii*, *Lactobacillus faecis*, *Lactobacillus fermentum*, *Lactobacillus fornicalis*, *Lactobacillus gasseri*, *Lactobacillus iners*, *Lactobacillus jensenii*, *Lactobacillus johnsonii*, *Lactobacillus kefiranofaciens*, *Lactobacillus kefiri*, *Lactobacillus paracasei*, *Lactobacillus plantarum*, *Lactobacillus pontis*, *Lactobacillus* rhamnosus, *Lactobacillus ruminis*, *Lactobacillus salivarius*, *Lactobacillus* sp. 7_1_47FAA, *Lactobacillus* sp. Akhmr01, *Lactobacillus* sp. BL302, *Lactobacillus* sp. C30An8, *Lactobacillus* sp. C4I1, *Lactobacillus* sp. C4I2, *Lactobacillus* sp.

CR-609S, *Lactobacillus* sp. Mbohs2t7, *Lactobacillus* sp. S16, *Lactobacillus* sp. TAB-26, *Lactobacillus* sp. Thmr02, *Lactobacillus* sp. oral taxon 052, *Lactobacillus vaginalis, Lactococcus raffinolactis, Lactococcus* sp. D2, *Lactococcus* sp. MH5-2, *Lactococcus* sp. STM1, *Lactococcus* sp. TPIMJ, *Lactococcus* sp. TP2MJ, *Lactonifactor longoviformis, Lautropia* sp. TeTO, *Leuconostoc gelidum, Leuconostoc inhae, Leuconostoc lactis, Leuconostoc mesenteroides, Leuconostoc* sp. C714, *Lysinibacillus* sp. SJ2SN2, *Lysinibacillus sphaericus, Mannheimia varigena, Megamonas funiformis, Megamonas rupellensis, Megasphaera* genomosp. C1, *Megasphaera massiliensis, Megasphaera micronuciformis, Megasphaera* sp. BS-4, *Megasphaera* sp. BV3C16-1, *Megasphaera* sp. DNF00872, *Megasphaera* sp. DNF00912, *Megasphaera* sp. S6-MB2, *Megasphaera* sp. TrE9262, *Megasphaera* sp. UPII 135-E, *Megasphaera* sp. UPII 199-6, *Mesorhizobium loti, Mesorhizobium* sp. mat916, *Methanobrevibacter smithii, Methanobrevibacter* sp., *Methanosphaera cuniculi, Methanosphaera stadtmanae, Methylobacterium* sp. CBMB45, *Methylobacterium* sp. RK-2008-1, *Mitsuokella multacida, Mitsuokella* sp. DJF_RR21, *Mitsuokella* sp. TM-10, *Mobiluncus curtisii, Mobiluncus mulieris, Mogibacterium timidum, Moraxella* sp. WB19-16, *Morganella morganii, Murdochiella asaccharolytica, Murdochiella* sp. S5-A16, *Murdochiella* sp. S9 PR-10, *Negativicoccus succinicivorans, Neisseria flavescens, Neisseria mucosa, Nosocomiicoccus ampullae, Ochrobactrum* sp. SCTS14, *Odoribacter splanchnicus, Oligella urethralis, Olsenella* sp. 1183, *Olsenella* sp. S9 HS-6, *Oribacterium* sp. CM12, *Oribacterium* sp. OBRC12, *Oscillibacter* sp. 1-3, *Oscillibacter valericigenes, Oscillospira guilliermondii, Pantoea* sp. CWB304, *Parabacteroides chinchillae, Parabacteroides distasonis, Parabacteroides faecis, Parabacteroides goldsteinii, Parabacteroides gordonii, Parabacteroides johnsonii, Parabacteroides merdae, Parabacteroides* sp. 20_3, *Parabacteroides* sp. D13, *Parabacteroides* sp. D25, *Parabacteroides* sp. J1502, *Parabacteroides* sp. dnLKV8, *Paraeggerthella hongkongensis, Paraprevotella clara, Paraprevotella xylaniphila, Parasporobacterium paucivorans, Parasutterella excrementihominis, Parvimonas micra, Parvimonas* sp. oral taxon 393, *Pediococcus argenticus, Pediococcus* sp. 310702, *Pediococcus* sp. MFC1, *Pelomonas aquatica, Peptococcus* sp. S9 Pr-12, *Peptococcus* sp. canine oral taxon 334, *Peptoniphilus duerdenii, Peptoniphilus indolicus, Peptoniphilus koenoeneniae, Peptoniphilus lacrimalis, Peptoniphilus* sp. 1-14, *Peptoniphilus* sp. 2002-2300004, *Peptoniphilus* sp. 2002-38328, *Peptoniphilus* sp. 7-2, *Peptoniphilus* sp. BV3AC2, *Peptoniphilus* sp. DNF00192, *Peptoniphilus* sp. DNF00840, *Peptoniphilus* sp. JCM 8143, *Peptoniphilus* sp. S9 PR-13, *Peptoniphilus* sp. gpac018A, *Peptoniphilus* sp. oral taxon 375, *Peptoniphilus* sp. oral taxon 836, *Peptostreptococcus stomatis, Phascolarctobacterium faecium, Phascolarctobacterium* sp. 377, *Phascolarctobacterium* sp. canine oral taxon 149, *Phascolarctobacterium succinatutens, Porphyromonas asaccharolytica, Porphyromonas bennonis, Porphyromonas* sp. 2024b, *Porphyromonas* sp. S8 86-12, *Porphyromonas uenonis, Prevotella amnii, Prevotella buccalis, Prevotella nigrescens, Prevotella oris, Prevotella* sp. S4-10, *Prevotella* sp. WAL 2039G, *Propionibacterium freudenreichii, Propionibacterium* sp. KPL1844, *Propionibacterium* sp. KPL2005, *Propionibacterium* sp. MSP09A, *Proteus mirabilis, Pseudobutyrivibrio ruminis, Pseudoclavibacter bifida, Pseudoclavibacter* sp. Timone, *Pseudoflavonifractor capillosus, Pseudomonas citronellolis, Pseudomonas monteilii, Pseudomonas* sp. a101-18-2, *Pyramidobacter piscolens, Rahnella* sp. BSP18, *Rahnella* sp. FB303, *Rhizobium* sp. T45, *Rikenella microfusus, Robinsoniella* sp. KNHs210, *Romboutsia lituseburensis, Roseburia cecicola, Roseburia hominis, Roseburia intestinalis, Roseburia inulinivorans, Roseburia* sp. 11SE39, *Roseburia* sp. 499, *Roseburia* sp. DJF_RR73, *Rothia dentocariosa, Rothia mucilaginosa, Rothia* sp. BBH4, *Rothia* sp. RV13, *Rothia* sp. THG-N7, *Salmonella enterica, Selenomonas* sp. Ycb08, *Serratia nematodiphila, Shinella* sp. DR33, *Slackia equolifaciens, Slackia faecicanis, Slackia piriformis, Slackia* sp. NATTS, *Sneathia sanguinegens, Sphingomonas* sp. 24T, *Sporomusa sphaeroides, Staphylococcus aureus, Staphylococcus equorum, Staphylococcus* sp. C912, *Stenotrophomonas* sp. C-S-TSA3, *Stenotrophomonas* sp. KITS-1, *Streptococcus anginosus, Streptococcus australis, Streptococcus dentirousetti, Streptococcus dysgalactiae, Streptococcus equinus, Streptococcus gordonii, Streptococcus mutans, Streptococcus parasanguinis, Streptococcus pasteurianus, Streptococcus peroris, Streptococcus sobrinus, Streptococcus* sp. 11aTha1, *Streptococcus* sp. 2011_Ileo_MS_A10, *Streptococcus* sp. 2011_Oral_MS_A3, *Streptococcus* sp. 2011_Oral_MS_D12, *Streptococcus* sp. 324402, *Streptococcus* sp. GMD6S, *Streptococcus* sp. S16-11, *Streptococcus suis, Streptococcus thermophilus, Subdoligranulum variabile, Succinatimonas hippei, Sutterella* sp. 252, *Sutterella* sp. YIT 12072, *Sutterella stercoricanis, Sutterella wadsworthensis, Terrisporobacter glycolicus, Tessaracoccus lapidicaptus, Trueperella bernardiae, Turicibacter sanguinis, Turicibacter* sp. LA62, *Vagococcus teuberi, Varibaculum cambriense, Varibaculum* sp. CCUG 61255, *Variovorax* sp. TA_DQ, *Veillonella dispar, Veillonella montpellierensis, Veillonella parvula, Veillonella ratti, Veillonella seminalis, Veillonella* sp. 2011_Oral_VSA_B12, *Veillonella* sp. 2011_Oral_VSA_C9, *Veillonella* sp. 2011_Oral_VSA_D12, *Veillonella* sp. 2011_Oral_VSA_D3, *Veillonella* sp. ADV 269.01, *Veillonella* sp. AS16, *Veillonella* sp. JL-2, *Veillonella* sp. oral taxon 780, *Weissella cibaria, Weissella confusa, Weissella hellenica, Weissella* sp. H1a, *Yersinia enterocolitica*, [*Collinsella*] *massiliensis*, *Abiotrophia, Acetanaerobacterium, Acetitomaculum, Acetivibrio, Acholeplasma, Achromobacter, Acidaminococcus, Acidovorax, Acinetobacter, Adlercreutzia, Aerococcus, Aeromonas, Aerosphaera, Akkermansia, Alistipes, Allobaculum, Alloprevotella, Alloscardovia, Anaerobacter, Anaerobacterium, Anaerococcus, Anaerofustis, Anaeroplasma, Anaerosinus, Anaerosporobacter, Anaerostipes, Anaerotruncus, Anaerovibrio, Anaerovorax, Arthrobacter, Arthrospira, Asaccharobacter, Asaccharospora, Asteroleplasma, Atopobium, Bacillus, Bacteroides, Barnesiella, Bifidobacterium, Bilophila, Blautia, Bosea, Brachyspira, Brevibacterium, Butyriciccus, icous, Butyricimonas, Butyrivibrio, Caldicoprobacter, Candidatus Methanomethylophilus, Candidatus Soleaferrea, Candidatus Stoquefichus, Capnocytophaga, Carnobacterium, Catabacter, Catenibacterium, Cellulosilyticum, Centipeda, Cetobacterium, Christensenella, Citrobacter, Cloacibacillus, Cloacibacterium, Clostridioides, Clostridium, Collinsella, Comamonas, Coprobacillus, Coprobacter, Corynebacterium, Cryobacterium, Defluviimonas, Deinococcus, Denitratisoma, Denitrobacterium, Dermabacter, Desulfovibrio, Dielma, Dolosigranulum, Dorea, Dysgonomonas, Eggerthella, Eisenbergiella, Elusimicrobium, Enterobacter, Enterorhabdus, Epulopiscium, Eremococcus, Erysipelatoclostridium, Eubacterium, Faecalibacterium, Fastidiosipila, Finegoldia, Flavobacterium, Flavonifractor, Fusicatenibacter, Fusobacterium, Gardnerella, Gelria, Globicatella, Gordonibacter, Granulicatella, Haemophilus, Hafnia, Helcococcus, Helicobacter, Herbaspirillum, Hespellia, Holdemania, Howardella,*

*Hydrogenoanaerobacterium, Hydrogenophilus, Intestinibacter, Intestinimonas, Jonquetella, Klebsiella, Kluyvera, Lachnoanaerobaculum, Lachnospira, Lactobacillus, Lactococcus, Lactonifactor, Lautropia, Leptotrichia, Leuconostoc, Lysinibacillus, Mannheimia, Marvinbryantia, Massilia, Megamonas, Megasphaera, Mesorhizobium, Methanobrevibacter, Methanosphaera, Mitsuokella, Mobiluncus, Mogibacterium, Moraxella, Morganella, Moryella, Murdochiella, Neisseria, Nocardioides, Nosocomiicoccus, Ochrobactrum, Odoribacter, Oligella, Oribacterium, Oscillibacter, Oscillospira, Pantoea, Papillibacter, Parabacteroides, Paraeggerthella, Paraprevotella, Parasporobacterium, Parasutterella, Pediococcus, Pelomonas, Peptoclostridium, Peptococcus, Peptoniphilus, Peptostreptococcus, Phascolarctobacterium, Phyllobacterium, Planomicrobium, Porphyromonas, Prevotella, Propionimicrobium, Proteiniclasticum, Proteiniphilum, Providencia, Pseudobutyrivibrio, Pseudoclavibacter, Pseudoflavonifractor, Pyramidobacter, Rahnella, Rhizobium, Rhodococcus, Rikenella, Robinsoniella, Romboutsia, Roseburia, Rothia, Ruminiclostridium, Salmonella, Sarcina, Sedimentibacter, Senegalimassilia, Serratia, Shinella, Shuttleworthia, Slackia, Sneathia, Solobacterium, Sphaerochaeta, Sphingobium, Sphingomonas, Sporobacter, Sporomusa, Stenotrophomonas, Streptococcus, Subdoligranulum, Succinatimonas, Succiniclasticum, Sutterella, Synergistes, Terrisporobacter, Tessaracoccus, Thalassospira, Trueperella, Turicibacter, Vagococcus, Variovorax, Victivallis, Weissella, Yersinia.*

23. The method of claim 12, wherein the first sleep-related condition comprises a bad sleep quality condition, wherein determining user microbiome features comprises determining the user microbiome composition features comprising a set of composition features associated with a mouth site and with at least one of: *Abiotrophia defectiva, Achromobacter xylosoxidans, Acinetobacter* sp. RBE2CD-114, *Actinobacillus porcinus, Actinomyces cardiffensis, Actinomyces dentalis, Actinomyces* genomosp. C1, *Actinomyces georgiae, Actinomyces graevenitzii, Actinomyces massiliensis, Actinomyces meyeri, Actinomyces neuii, Actinomyces odontolyticus, Actinomyces oris, Actinomyces* sp. ICM41, *Actinomyces* sp. ICM47, *Actinomyces* sp. ICM54, *Actinomyces* sp. ICM58, *Actinomyces* sp. S6-Spd3, *Actinomyces* sp. ZSY-1, *Actinomyces* sp. canine oral taxon 417, *Actinomyces* sp. oral strain B19SC, *Actinomyces* sp. oral strain Hal-1065, *Actinomyces* sp. oral taxon 170, *Actinomyces* sp. oral taxon 175, *Actinomyces* sp. oral taxon 178, *Actinomyces* sp. oral taxon 448, *Actinomyces* sp. ph3, *Actinomyces viscosus, Adlercreutzia equolifaciens, Aerococcus christensenii, Aeromonas* sp. B11, *Aerosphaera taetra, Aggregatibacter actinomycetemcomitans, Aggregatibacter aphrophilus, Aggregatibacter segnis, Alistipes indistinctus, Alistipes massiliensis, Alistipes putredinis, Alistipes shahii, Alistipes* sp. EBA6-25cl2, *Alistipes* sp. HGB5, *Alistipes* sp. NML05A004, *Alistipes* sp. RMA 9912, *Alloprevotella rava, Alloprevotella tannerae, Alloscardovia omnicolens, Anaerobacillus alkalidiazotrophicus, Anaerococcus murdochii, Anaerococcus octavius, Anaerococcus provencensis, Anaerococcus* sp. 8404299, *Anaerococcus* sp. 8405254, *Anaerococcus* sp. 9401487, *Anaerococcus* sp. S8 87-3, *Anaerococcus tetradius, Anaerococcus vaginalis, Anaeroglobus geminatus, Anaerosporobacter mobilis, Anaerostipes hadrus, Anaerostipes* sp. 5_1_63FAA, *Anaerotruncus colihominis, Anoxybacillus* sp. HT14, *Aquabacterium* sp. Aqua2, *Arthrospira fusiformis, Asaccharospora irregularis, Atopobium parvulum, Atopobium rimae, Atopobium* sp. DMCT15023, *Atopobium* sp. ICM57, *Bacteroides acidifaciens, Bacteroides caccae, Bacteroides clarus, Bacteroides coprocola, Bacteroides coprophilus, Bacteroides dorei, Bacteroides eggerthii, Bacteroides finegoldii, Bacteroides fragilis, Bacteroides intestinalis, Bacteroides massiliensis, Bacteroides nordii, Bacteroides ovatus, Bacteroides plebeius, Bacteroides salyersiae, Bacteroides* sp. 2_2_4, *Bacteroides* sp. 3_1_40A, *Bacteroides* sp. AR20, *Bacteroides* sp. AR29, *Bacteroides* sp. D22, *Bacteroides* sp. DJF_B097, *Bacteroides* sp. EBA5-17, *Bacteroides* sp. J1511, *Bacteroides* sp. SLC1-38, *Bacteroides* sp. XB12B, *Bacteroides stercoris, Bacteroides uniformis, Bacteroides vulgatus, Barnesiella intestinihominis, Bergeriella denitrificans, Bergeyella* sp. AF14, *Bifidobacterium adolescentis, Bifidobacterium animalis, Bifidobacterium bifidum, Bifidobacterium dentium, Bifidobacterium kashiwanohense, Bifidobacterium longum, Bifidobacterium pseudocatenulatum, Bifidobacterium* sp. MSX5B, *Bilophila* sp. 4_1_30, *Bilophila wadsworthia, Blautia faecis, Blautia glucerasea, Blautia hansenii, Blautia luti, Blautia* sp. YHC-4, *Blautia stercoris, Blautia wexlerae, Bradyrhizobium* sp. 68A4SAPT, *Burkholderia* sp. S32, *Butyricimonas faecihominis, Butyricimonas paravirosa, Butyricimonas* sp. 214-4, *Butyricimonas virosa, Campylobacter concisus, Campylobacter gracilis, Campylobacter hominis, Campylobacter hyointestinalis, Campylobacter rectus, Campylobacter showae, Campylobacter* sp. 10_1_50, *Campylobacter* sp. FOBRC14, *Campylobacter* sp. FOBRC15, *Campylobacter ureolyticus, Capnocytophaga* genosp. AHN8471, *Capnocytophaga gingivalis, Capnocytophaga granulosa, Capnocytophaga haemolytica, Capnocytophaga leadbetteri, Capnocytophaga* sp. AHN10044, *Capnocytophaga* sp. AHN9576, *Capnocytophaga* sp. AHN9687, *Capnocytophaga* sp. CM59, *Capnocytophaga* sp. HS5_2W_I24, *Capnocytophaga* sp. P2 oral strain P4P_12, *Capnocytophaga* sp. oral strain A47ROY, *Capnocytophaga* sp. oral taxon 329, *Capnocytophaga* sp. oral taxon 335, *Capnocytophaga* sp. oral taxon 336, *Capnocytophaga* sp. oral taxon 338, *Capnocytophaga sputigena, Cardiobacterium valvarum, Catonella morbi, Centipeda periodontii, Clostridioides difficile, Collinsella aerofaciens, Coprobacter fastidiosus, Corynebacterium durum, Corynebacterium freiburgense, Corynebacterium glucuronolyticum, Corynebacterium matruchotii, Corynebacterium* sp., *Corynebacterium* sp. NML 97-0186, *Corynebacterium ulcerans, Cryptobacterium curtum, Cutibacterium acnes, Cutibacterium granulosum, Delftia lacustris, Delftia* sp. BN-SKY3, *Desulfobulbus* sp. oral taxon 041, *Dialister invisus, Dialister pneumosintes, Dialister propionicifaciens, Dialister* sp. E2_20, *Dielma fastidiosa, Dorea formicigenerans, Dorea longicatena, Eggerthella* sp. HGA1, *Eggerthia catenaformis, Eikenella corrodens, Eikenella* sp. MDA2346-4, *Eisenbergiella tayi, Enterobacter* sp. BS2-1, *Erysipelatoclostridium ramosum, Faecalibacterium prausnitzii, Faecalibacterium* sp. canine oral taxon 147, *Filifactor alocis, Finegoldia magna, Finegoldia* sp. S9 AA1-5, *Flavonifractor plautii, Fretibacterium fastidiosum, Fusicatenibacter saccharivorans, Fusobacterium nucleatum, Fusobacterium periodonticum, Fusobacterium* sp. ACB2, *Fusobacterium* sp. AS2, *Fusobacterium* sp. CM21, *Fusobacterium* sp. CM22, *Fusobacterium* sp. CM55, *Fusobacterium* sp. OBRC1, *Fusobacterium ulcerans, Gemella morbillorum, Gemella* sp. 933-88, *Gemella* sp. oral strain C24KA, *Gordonibacter pamelaeae, Granulicatella adiacens, Granulicatella elegans, Haemophilus influenzae, Haemophilus parainfluenzae, Herbaspirillum seropedicae, Holdemania filiformis, Howardella ureilytica, Janibacter* sp. M3-5, *Johnsonella ignava, Kingella oralis, Kluyvera georgiana, Kocuria kristinae, Lachnoanaerobaculum orale, Lachnoanaerobaculum saburreum, Lachnoanaerobaculum* sp. MSX33, *Lachnoanaerobaculum* sp. OBRC5-5, *Lachnoanaerobaculum umeaense*, *Lachnospira pectinoschiza*, *Lactobacillus crispatus*, *Lactobacillus fermentum*, *Lactobacillus fornicalis*, *Lactobacillus gasseri*, *Lactobacillus jensenii*, *Lactobacillus paracasei*, *Lactobacillus plantarum*, *Lactobacillus rhamnosus*, *Lactobacillus salivarius*, *Lactobacillus* sp. 7_1_47FAA, *Lactobacillus* sp. Akhmr01, *Lactobacillus* sp. BL302, *Lactobacillus vaginalis*, *Lactococcus lactis*, *Lactococcus* sp. MH5-2, *Lautropia* sp. TeTO, *Leptotrichia buccalis*, *Leptotrichia* genomosp. C1, *Leptotrichia goodfellowii*, *Leptotrichia hofstadii*, *Leptotrichia hongkongensis*, *Leptotrichia shahii*, *Leptotrichia* sp. PG10, *Leptotrichia* sp. PTE15, *Leptotrichia* sp. oral taxon 223, *Leptotrichia* sp. oral taxon 225, *Leptotrichia* trevisanii, *Leptotrichia wadei*, *Leuconostoc* sp. C7I4, *Lysinibacillus sphaericus*, *Mannheimia granulomatis*, *Megamonas funiformis*, *Megasphaera* genomosp. C1, *Megasphaera micronuciformis*, *Megasphaera* sp. UPII 199-6, *Meiothermus silvanus*, *Methanobrevibacter smithii*, *Methanosphaera stadtmanae*, *Methylobacterium longum*, *Methylobacterium* sp. RK-2008-1, *Mogibacterium pumilum*, *Mogibacterium* sp. CM50, *Mogibacterium* sp. CM96, *Murdochiella* sp. S9 PR-10, *Mycoplasma falconis*, *Mycoplasma* sp. M221-9, *Mycoplasma subdolum*, *Necropsobacter rosorum*, *Negativicoccus succinicivorans*, *Neisseria bacilliformis*, *Neisseria canis*, *Neisseria cinerea*, *Neisseria elongata*, *Neisseria flava*, *Neisseria flavescens*, *Neisseria macacae*, *Neisseria meningitidis*, *Neisseria mucosa*, *Neisseria oralis*, *Neisseria polysaccharea*, *Neisseria shayeganii*, *Neisseria sicca*, *Neisseria skkuensis*, *Neisseria* sp. 104(2012), *Neisseria* sp. CCUG 45853, *Neisseria wadsworthii*, *Novosphingobium sediminicola*, *Odoribacter laneus*, *Odoribacter splanchnicus*, *Olsenella* sp. F0004, *Olsenella uli*, *Oribacterium* sp. CM12, *Oribacterium* sp. OBRC12, *Oribacterium* sp. oral taxon 078, *Oribacterium* sp. oral taxon 102, *Oribacterium* sp. oral taxon 108, *Parabacteroides distasonis*, *Parabacteroides johnsonii*, *Parabacteroides merdae*, *Paraprevotella clara*, *Paraprevotella xylaniphila*, *Parasutterella excrementihominis*, *Parvimonas micra*, *Parvimonas* sp. oral taxon 110, *Parvimonas* sp. oral taxon 393, *Peptococcus* sp. oral taxon 168, *Peptoniphilus lacrimalis*, *Peptoniphilus* sp. 1-14, *Peptoniphilus* sp. 2002-2300004, *Peptoniphilus* sp. 2002-38328, *Peptoniphilus* sp. 7-2, *Peptoniphilus* sp. S9 PR-13, *Peptoniphilus* sp. gpac018A, *Peptostreptococcus anaerobius*, *Peptostreptococcus stomatis*, *Phascolarctobacterium faecium*, *Phascolarctobacterium* sp. 377, *Phascolarctobacterium succinatutens*, *Phyllobacterium* sp. T50, *Porphyromonas asaccharolytica*, *Porphyromonas bennonis*, *Porphyromonas catoniae*, *Porphyromonas endodontalis*, *Porphyromonas gingivalis*, *Porphyromonas gulae*, *Porphyromonas somerae*, *Porphyromonas* sp. 2024b, *Porphyromonas* sp. S8 86-12, *Porphyromonas uenonis*, *Prevotella amnii*, *Prevotella aurantiaca*, *Prevotella bivia*, *Prevotella buccalis*, *Prevotella disiens*, *Prevotella intermedia*, *Prevotella maculosa*, *Prevotella micans*, *Prevotella nanceiensis*, *Prevotella oralis*, *Prevotella oris*, *Prevotella oulorum*, *Prevotella pallens*, *Prevotella* sp. HJM029, *Prevotella* sp. S4-10, *Prevotella* sp. Smarlab 121567, *Prevotella* sp. WAL 2039G, *Prevotella* sp. oral taxon 299, *Prevotella timonensis*, *Propionibacterium acidifaciens*, *Propionibacterium* sp. 'Oral Taxon 191', *Propionibacterium* sp. MSP09A, *Propionibacterium* sp. V07/12348, *Pseudoflavonifractor capillosus*, *Pseudomonas* sp. KB23, *Pseudomonas* sp. a111-5, *Pseudomonas syringae*, *Pseudopropionibacterium propionicum*, *Ralstonia* sp. S2.MAC.005, *Rodentibacter pneumotropicus*, *Roseburia cecicola*, *Roseburia faecis*, *Roseburia hominis*, *Roseburia intestinalis*, *Roseburia inulinivorans*, *Roseburia* sp. 11SE39, *Rothia aeria*, *Rothia dentocariosa*, *Rothia mucilaginosa*, *Rothia* sp. CCUG 25688, *Rothia* sp. THG-N7, *Rothia* sp. THG-T3, *Scardovia wiggsiae*, *Selenomonas* genomosp. P5, *Selenomonas* sp. CM52, *Selenomonas sputigena*, *Shinella* sp. DR33, *Shuttleworthia* sp. oral taxon G69, *Simonsiella muelleri*, *Slackia exigua*, *Slackia* sp. S8 F4, *Sneathia sanguinegens*, *Solobacterium moorei*, *Solobacterium* sp. S4-A19, *Sphingomonas* sp. 540, *Staphylococcus epidermidis*, *Staphylococcus saprophyticus*, *Staphylococcus* sp. 334802, *Staphylococcus* sp. C9I2, *Stenotrophomonas* sp. KITS-1, *Stenotrophomonas* sp. NB3, *Stomatobaculum longum*, *Streptococcus agalactiae*, *Streptococcus australis*, *Streptococcus dentirousetti*, *Streptococcus equinus*, *Streptococcus gordonii*, *Streptococcus intermedius*, *Streptococcus mitis*, *Streptococcus mutans*, *Streptococcus parasanguinis*, *Streptococcus peroris*, *Streptococcus* sp. 11aTha1, *Streptococcus* sp. 2011_Oral_MS_A3, *Streptococcus* sp. 2011_Oral_MS_H4, *Streptococcus* sp. BS35a, *Streptococcus* sp. GMD6S, *Streptococcus* sp. oral taxon G59, *Streptococcus* sp. oral taxon G63, *Streptococcus thermophilus*, *Subdoligranulum variabile*, *Sutterella* sp. 252, *Sutterella* sp. YIT 12072, *Sutterella stercoricanis*, *Sutterella wadsworthensis*, *Tannerella forsythia*, *Tannerella* sp. oral taxon HOT-286, *Terrisporobacter glycolicus*, *Tessaracoccus lapidicaptus*, *Turicibacter sanguinis*, *Vagococcus* sp. SIX2(2011), *Varibaculum* sp. CCUG 45114, *Veillonella atypica*, *Veillonella dispar*, *Veillonella parvula*, *Veillonella rodentium*, *Veillonella rogosae*, *Veillonella* sp. 2011_Oral_VSA_B12, *Veillonella* sp. 2011_Oral_VSA_C9, *Veillonella* sp. 2011_Oral_VSA_D3, *Veillonella* sp. 6_1_27, *Veillonella* sp. ADV 269.01, *Veillonella* sp. AS16, *Veillonella* sp. CM60, *Veillonella* sp. JL-2, *Veillonella* sp. MSA12, *Veillonella* sp. oral taxon 780, *Veillonella tobetsuensis*, *Abiotrophia*, *Acetitomaculum*, *Acholeplasma*, *Achromobacter*, *Acinetobacter*, *Actinobacillus*, *Actinomyces*, *Adlercreutzia*, *Aerococcus*, *Aeromonas*, *Aerosphaera*, *Aggregatibacter*, *Akkermansia*, *Alistipes*, *Alloprevotella*, *Alloscardovia*, *Alysiella*, *Anaerobacillus*, *Anaerococcus*, *Anaeroplasma*, *Anaerosporobacter*, *Anaerostipes*, *Anaerotruncus*, *Anoxybacillus*, *Aquabacterium*, *Arcanobacterium*, *Arthrospira*, *Asaccharospora*, *Asteroleplasma*, *Atopobium*, *Bacillus*, *Bacteroides*, *Barnesiella*, *Bergeriella*, *Bergeyella*, *Bilophila*, *Blautia*, *Bradyrhizobium*, *Burkholderia*, *Butyricimonas*, *Butyrivibrio*, *Campylobacter*, *Candidatus Saccharimonas*, *Candidatus Soleaferrea*, *Capnocytophaga*, *Cardiobacterium*, *Catenibacterium*, *Catonella*, *Centipeda*, *Chryseobacterium*, *Cloacibacterium*, *Clostridium*, *Collinsella*, *Comamonas*, *Coprobacter*, *Corynebacterium*, *Cryptobacterium*, *Cutibacterium*, *Deinococcus*, *Delftia*, *Desulfobulbus*, *Desulfovibrio*, *Dialister*, *Dorea*, *Eggerthia*, *Eikenella*, *Eisenbergiella*, *Enterobacter*, *Enterococcus*, *Enterorhabdus*, *Erysipelatoclostridium*, *Faecalibacterium*, *Filifactor*, *Finegoidia*, *Flavobacterium*, *Flavonifractor*, *Fretibacterium*, *Fusicatenibacter*, *Fusobacterium*, *Gemella*, *Gordonibacter*, *Granulicatella*, *Haemophilus*, *Herbaspirillum*, *Hespellia*, *Holdemania*, *Howardella*, *Intestinibacter*, *Intestinimonas*, *Janibacter*, *Johnsonella*, *Kingella*, *Klebsiella*, *Kluyvera*, *Kocuria*, *Lachnoanaerobaculum*, *Lachnospira*, *Lactobacillus*, *Lactococcus*, *Lactonifactor*, *Lautropia*, *Leptotrichia*, *Leuconostoc*, *Lysinibacillus*, *Mannheimia*, *Marvinbryantia*, *Megamonas*, *Megasphaera*, *Methanobrevibacter*, *Methanosphaera*, *Methylobacterium*, *Mobiluncus*, *Mogibacterium*, *Moraxella*, *Moryella*, *Murdochiella*, *Mycobacterium*, *Mycoplasma*, *Necropsobacter*, *Negativicoccus*, *Neisseria*, *Novosphingobium*, *Odoribacter*, *Olsenella*, *Oribacterium*, *Oscillibacter*, *Oscillospira*, *Pantoea*, *Parabacteroides*, *Parasutterella*, *Parvimonas*, *Pasteurella*, *Peptoclostridium*,

*Peptococcus, Peptoniphilus, Peptostreptococcus, Phascolarctobacterium, Phyllobacterium, Planomicrobium, Porphyromonas, Prevotella, Propionibacterium, Pseudobutyrivibrio, Pseudoflavonifractor, Pseudomonas, Pyramidobacter, Ralstonia, Rhodobacter, Robinsoniella, Romboutsia, Roseburia, Rothia, Sarcina, Scardovia, Selenomonas, Senegalimassilia, Shinella, Shuttleworthia, Simonsiella, Slackia, Sneathia, Snodgrassella, Solobacterium, Staphylococcus, Stenotrophomonas, Stomatobaculum, Streptobacillus, Streptococcus, Subdoligranulum, Sutterella, Tannerella, Terrisporobacter, Tessaracoccus, Thalassospira, Trichococcus, Turicibacter, Vagococcus, Varibaculum, Veillonella, Victivallis, Abiotrophia defectiva, Achromobacter xylosoxidans, Acidovorax sp. LR05, Acinetobacter baumannii, Acinetobacter calcoaceticus, Acinetobacter haemolyticus, Acinetobacter kyonggiensis, Acinetobacter sp. 2002-2301217, Acinetobacter sp. 423D, Acinetobacter sp. C-S-PDA7, Acinetobacter sp. C049, Acinetobacter sp. HD5.2, Acinetobacter sp. RBE2CD-114, Acinetobacter sp. RBE2CD-76, Acinetobacter sp. RE 51, Acinetobacter sp. STE, Acinetobacter sp. T133, Acinetobacter sp. WB22-23, Acinetobacter ursingii, Actinobacillus porcinus, Actinobaculum massiliense, Actinomyces europaeus, Actinomyces georgiae, Actinomyces gerencseriae, Actinomyces israelii, Actinomyces massiliensis, Actinomyces neuii, Actinomyces radingae, Actinomyces sp. ICM54, Actinomyces sp. ICM58, Actinomyces sp. S4-C9, Actinomyces sp. oral taxon 175, Actinomyces sp. oral taxon 448, Actinomyces sp. ph3, Actinomyces viscosus, Actinomycetospora sp. CAP 335, Aerococcus christensenii, Aerococcus sp. B43(2010), Aerococcus urinae, Aerococcus viridans, Aeromonas salmonicida, Aerosphaera taetra, Aggregatibacter aphrophilus, Aggregatibacter segnis, Akkermansia muciniphila, Albidovulum inexpectatum, Alishewanella sp. Mn5-6, Alistipes finegoldii, Alistipes inops, Alistipes putredinis, Alistipes shahii, Alistipes sp. EBA6-25cl2, Alistipes sp. NML05A004, Alloiococcus otitis, Alloprevotella rava, Alloprevotella tannerae, Anaerobacillus alkalidiazotrophicus, Anaerococcus hydrogenalis, Anaerococcus lactolyticus, Anaerococcus murdochii, Anaerococcus octavius, Anaerococcus provencensis, Anaerococcus sp. 8404299, Anaerococcus sp. 8405254, Anaerococcus sp. 9401487, Anaerococcus sp. PH9, Anaerococcus sp. S8 87-3, Anaerococcus sp. S8 F2, Anaerococcus tetradius, Anaerococcus vaginalis, Anaeroglobus geminatus, Anaerostipes sp. 5_1_63FAA, Anoxybacillus sp. HT14, Aquabacterium commune, Aquabacterium sp. Aqua2, Arthrobacter sp. T2-4, Arthrospira fusiformis, Atopobium minutum, Atopobium rimae, Atopobium sp. S3PFAA1-4, Atopobium sp. S4-A11a, Atopobium vaginae, Aureimonas altamirensis, Aureimonas phyllosphaerae, Bacillus cereus, Bacillus nanhaiisediminis, Bacillus niacini, Bacillus pseudofirmus, Bacillus sp. CBMAI 1158, Bacillus sp. DHT-33, Bacillus sp. T41, Bacteroides acidifaciens, Bacteroides caccae, Bacteroides coprocola, Bacteroides eggerthii, Bacteroides fragilis, Bacteroides massiliensis, Bacteroides ovatus, Bacteroides salyersiae, Bacteroides sp. 2_2_4, Bacteroides sp. 35AE37, Bacteroides sp. AR20, Bacteroides sp. AR29, Bacteroides sp. D22, Bacteroides sp. EBA5-17, Bacteroides sp. SLC1-38, Bacteroides stercoris, Bacteroides thetaiotaomicron, Bacteroides uniformis, Bacteroides vulgatus, Barnesiella intestinihominis, Bergeyella sp. AF14, Bergeyella zoohelcum, Bibersteinia trehalosi, Bifidobacterium adolescentis, Bifidobacterium longum, Bifidobacterium stercoris, Bilophila sp. 4_1_30, Bilophila wadsworthia, Blastocatella fastidiosa, Blastococcus aggregatus, Blastococcus sp. 0705C6-3, Blastococcus sp. FXJ6.383, Blautia faecis, Blautia luti, Blautia sp. YHC-4, Blautia wexlerae, Bosea sp. BIWAKO-01, Bosea sp. R-46060, Brachybacterium muris, Brachybacterium sp. NIO-27, Brachybacterium sp. b110-100S, Brachymonas sp. canine oral taxon 015, Bradyrhizobium sp. 68A4SAPT, Bradyrhizobium sp. CCBAU 53380, Bradyrhizobium sp. P-45, Brevibacterium massiliense, Brevibacterium paucivorans, Brevibacterium pityocampae, Brevibacterium sp. A9C6, Brevibacterium sp. MBTD_CMFRI_Br02, Brevundimonas diminuta, Brevundimonas sp. FXJ8.080, Brevundimonas sp. JW23.4a, Brevundimonas sp. V3M6, Brevundimonas subvibrioides, Burkholderia lata, Burkholderia sp. CBPB-HIM, Burkholderia sp. S32, Campylobacter concisus, Campylobacter gracilis, Campylobacter hominis, Campylobacter showae, Capnocytophaga genosp. AHN8471, Capnocytophaga gingivalis, Capnocytophaga ochracea, Capnocytophaga sp. AHN10044, Capnocytophaga sp. AHN9756, Capnocytophaga sp. CM59, Capnocytophaga sp. oral taxon 329, Capnocytophaga sp. oral taxon 338, Capnocytophaga sputigena, Cardiobacterium hominis, Catonella morbi, Centipeda periodontii, Chryseobacterium haifense, Chryseobacterium sp. BBCT14, Chryseobacterium sp. IIL-Nv8, Chryseobacterium sp. MH28, Chryseobacterium sp. R064, Chryseobacterium sp. Y1D, Citrobacter sp. BW4, Cloacibacterium rupense, Clostridioides difficile, Collinsella aerofaciens, Comamonas sp. P-115, Comamonas sp. RV A09_23b, Corynebacterium atypicum, Corynebacterium canis, Corynebacterium caspium, Corynebacterium diphtheriae, Corynebacterium durum, Corynebacterium epidermidicanis, Corynebacterium felinum, Corynebacterium freiburgense, Corynebacterium glucuronolyticum, Corynebacterium mastitidis, Corynebacterium matruchotii, Corynebacterium sp., Corynebacterium sp. 2300500, Corynebacterium sp. 713182/2012, Corynebacterium sp. NML 97-0186, Corynebacterium sp. jw37, Corynebacterium spheniscorum, Corynebacterium ulcerans, Cronobacter sakazakii, Cryobacterium psychrotolerans, Cryptobacterium curtum, Curvibacter gracilis, Cutibacterium acnes, Cutibacterium avidum, Cutibacterium granulosum, Deinococcus antarcticus, Deinococcus sp. 3B1, Deinococcus sp. UAC-77, Delftia lacustris, Delftia sp. BN-SKY3, Dermabacter hominis, Dermabacter sp. HFH0086, Dermacoccus nishinomiyaensis, Dermacoccus sp. D2.1, Dermacoccus sp. Ellin183, Dermacoccus sp. Ellin185, Dermacoccus sp. SST-20, Desulfovibrio sp., Dialister invisus, Dialister pneumosintes, Dialister propionicifaciens, Dialister sp. E2_200, Dialister sp. S7MSR5, Dolosigranulum pigrum, Dorea formicigenerans, Dorea longicatena, Effusibacillus pohliae, Eggerthella lenta, Eikenella corrodens, Eisenbergiella tayi, Enterobacter cloacae, Enterococcus sp. SI-4, Eremococcus coleocola, Exiguobacterium sibiricum, Exiguobacterium sp. icr3, Facklamia hominis, Facklamia languida, Facklamia sp. 164-92, Facklamia tabacinasalis, Faecalibacterium prausnitzii, Faecalibacterium sp. canine oral taxon 147, Fastidiosipila sanguinis, Filifactor alocis, Finegoldia magna, Finegoldia sp. S9 AA1-5, Flavobacterium sp. EP372, Flavobacterium sp. bk_25, Fretibacterium fastidiosum, Frigoribacterium sp. 181, Fusicatenibacter saccharivorans, Fusobacterium equinum, Fusobacterium nucleatum, Fusobacterium periodonticum, Fusobacterium russii, Fusobacterium sp. ACB2, Fusobacterium sp. AS2, Fusobacterium sp. CM21, Fusobacterium sp. CM22, Gardnerella sp. S3PF20, Gardnerella vaginalis, Gemella morbillorum, Gemella sp. 933-88, Granulicatella adiacens, Granulicatella elegans, Haemophilus influenzae, Haemophilus parainfluenzae, Halomonas pacifica, Herbaspirillum huttiense, Herbaspirillum seropedicae, Hydrogenophilus* islandicus, Janibacter sp. IARI-RP17, Janibacter sp. M3-5, Jeotgalicoccus aerolatus, Johnsonella ignava, Jonquetella anthropi, Klebsiella oxytoca, Klebsiella pneumoniae, Kluyvera georgiana, Kocuria carniphila, Kocuria kristinae, Kocuria marina, Kocuria rhizophila, Kocuria sp. BRI 36, Kocuria sp. FXJ6.339, Kocuria sp. LW2-LEV12-W, Lachnoanaerobaculum saburreum, Lachnospira pectinoschiza, Lactobacillus crispatus, Lactobacillus curvatus, Lactobacillus delbrueckii, Lactobacillus fornicalis, Lactobacillus gasseri, Lactobacillus jensenii, Lactobacillus paracasei, Lactobacillus plantarum, Lactobacillus salivarius, Lactobacillus sp. 7_1_47FAA, Lactobacillus sp. Akhmr01, Lactobacillus sp. CR-609S, Lactobacillus sp. TAB-26, Lactobacillus vaginalis, Lactococcus lactis, Lactococcus sp. MH5-2, Lautropia sp. TeTO, Leptotrichia buccalis, Leptotrichia hongkongensis, Leptotrichia shahii, Leptotrichia sp. oral taxon 225, Leptotrichia wadei, Leucobacter aridicollis, Leucobacter sp. LR-2006b, Leuconostoc carnosum, Leuconostoc lactis, Leuconostoc mesenteroides, Luteimonas mephitis, Lysinibacillus sp. SJ2SN2, Lysinibacillus sphaericus, Macrococcus brunensis, Macrococcus caseolyticus, Malassezia restricta, Massilia oculi, Megasphaera sp. BV3C16-1, Megasphaera sp. UPII 199-6, Meiothermus silvanus, Mesorhizobium loti, Mesorhizobium sp. RE 62, Mesorhizobium sp. mat916, Methanobrevibacter smithii, Methylobacterium adhaesivum, Methylobacterium sp. CBMB45, Methylobacterium sp. CCGE4019, Methylobacterium sp. Gh-143, Methylobacterium sp. RK-200008-1, Microbacterium lacticum, Microbacterium sp. PcRB024, Microbacterium yannicii, Micrococcus luteus, Micrococcus sp. WB18-01, Microlunatus phosphovorus, Microvirga aerilata, Microvirga sp. BR10193, Microvirga sp. TSX10-2, Mobiluncus mulieris, Modestobacter multiseptatus, Mogibacterium pumilum, Moraxella catarrhalis, Moraxella lincolnii, Moraxella nonliquefaciens, Moraxella sp. BBN2P-02d, Moraxella sp. WB19-16, Murdochiella sp. S9 PR-10, Mycobacterium chelonae, Mycobacterium sp. KNUC297, Mycobacterium sp. UNC410CL29Cvi84, Negativicoccus succinicivorans, Neisseria canis, Neisseria elongata, Neisseria flavescens, Neisseria macacae, Neisseria meningitidis, Neisseria mucosa, Neisseria oralis, Neisseria shayeganii, Neisseria skkuensis, Neisseria sp. CCUG 45853, Nocardioides mesophilus, Novosphingobium sediminicola, Novosphingobium sp. THA_AIK7, Ochrobactrum sp. FPY8, Ochrobactrum sp. SCTS14, Ochrobactrum tritici, Olsenella sp. F0004, Oribacterium sp. CM12, Oribacterium sp. oral taxon 078, Ornithinimicrobium sp. THG-GM43, Ornithinimicrobium sp. X1C, Pantoea agglomerans, Pantoea gaviniae, Parabacteroides distasonis, Parabacteroides goldsteinii, Paraprevotella clara, Parasutterella excrementihominis, Parvimonas micra, Paucibacter toxinivorans, Pectobacterium carotovorum, Pedomicrobium ferrugineum, Pelomonas aquatica, Peptococcus niger, Peptococcus sp. oral taxon 168, Peptoniphilus coxii, Peptoniphilus duerdenii, Peptoniphilus lacrimalis, Peptoniphilus sp. 1-14, Peptoniphilus sp. 2002-2300004, Peptoniphilus sp. 2002-38328, Peptoniphilus sp. 7-2, Peptoniphilus sp. DNF00840, Peptoniphilus sp. JCM 8143, Peptoniphilus sp. S9 PR-13, Peptoniphilus sp. gpac018A, Peptoniphilus sp. gpac148, Peptoniphilus sp. oral taxon 836, Peptostreptococcus anaerobius, Peptostreptococcus stomatis, Phascolarctobacterium faecium, Photobacterium sp. squidInt_04, Phyllobacterium sp. T50, Planococcus sp. ljh-25, Porphyrobacter sp. NMC22, Porphyromonas asaccharolytica, Porphyromonas bennonis, Porphyromonas cangingivalis, Porphyromonas canoris, Porphyromonas catoniae, Porphyromonas endodontalis, Porphyromonas sp. 2026, Porphyromonas uenonis, Prevotella bivia, Prevotella buccalis, Prevotella disiens, Prevotella intermedia, Prevotella micans, Prevotella nanceiensis, Prevotella nigrescens, Prevotella oris, Prevotella oulorum, Prevotella pallens, Prevotella sp. S4-10, Prevotella sp. WAL 2039G, Propionibacterium sp. KPL1844, Propionibacterium sp. KPL2005, Propionibacterium sp. MSP09A, Propionibacterium sp. V07/12348, Propionimicrobium lymphophilum, Pseudoclavibacter bifida, Pseudoclavibacter sp. Timone, Pseudoflavonifractor capillosus, Pseudomonas aeruginosa, Pseudomonas agarici, Pseudomonas brenneri, Pseudomonas citronellolis, Pseudomonas graminis, Pseudomonas monteilii, Pseudomonas sp. BM5, Pseudomonas sp. CBMAI 1177, Pseudomonas sp. G1116, Pseudomonas sp. GmFRB023, Pseudomonas sp. KB23, Pseudomonas sp. KNUC378, Pseudomonas sp. PDD-31b-4, Pseudomonas sp. PKG89, Pseudomonas sp. PcFRB100, Pseudomonas sp. PcFRBllg9, Pseudomonas sp. a101-18-2, Pseudomonas syringae, Pseudonocardia sp. CC981102-15, Pseudopropionibacterium propionicum, Rahnella sp. BSP18, Ralstonia pickettii, Ralstonia sp. A52, Ralstonia sp. CCUG 46389, Ralstonia sp. S2.MAC.005, Raoultella ornithinolytica, Rhizobium etli, Rhizobium sp. 10II, Rhizobium sp. T45, Rhizobium sp. sc-w, Rhodobacter capsulatus, Rhodococcus erythropolis, Rhodococcus sp. C056, Rhodopseudomonas boonkerdii, Rhodopseudomonas thermotolerans, Rodentibacter pneumotropicus, Roseburia faecis, Roseburia intestinalis, Roseburia inulinivorans, Roseburia sp. 11SE39, Rothia aeria, Rothia dentocariosa, Rothia mucilaginosa, Rothia sp. CCUG 25688, Rothia sp. THG-N7, Salana multivorans, Selenomonas genomosp. P5, Shewanella sp. 8113, Shinella sp. DR33, Solobacterium moorei, Sphingobacterium mizutaii, Sphingobium sp. LC341, Sphingobium sp. MH60, Sphingomonas aerolata, Sphingomonas aquatilis, Sphingomonas dokdonensis, Sphingomonas oligophenolica, Sphingomonas paucimobilis, Sphingomonas sp. 24T, Sphingomonas sp. 540, Sphingomonas sp. CS81, Sphingomonas sp. PDD-26b-16, Staphylococcus aureus, Staphylococcus epidermidis, Staphylococcus equorum, Staphylococcus saprophyticus, Staphylococcus simulans, Staphylococcus sp. 155b, Staphylococcus sp. 334802, Staphylococcus sp. 335602, Staphylococcus sp. C-D-MA2, Staphylococcus sp. C912, Staphylococcus sp. L10, Staphylococcus sp. WB18-16, Staphylococcus vitulinus, Stenotrophomonas sp. C-S-TSA3, Stenotrophomonas sp. I_63-LFP1A9B1, Stenotrophomonas sp. KITS-1, Stenotrophomonas sp. N017, Stenotrophomonas sp. TV49May, Stenotrophomonas sp. Z2-S2, Streptococcus dysgalactiae, Streptococcus gordonii, Streptococcus mutans, Streptococcus parasanguinis, Streptococcus pneumoniae, Streptococcus sp. 11aTha1, Streptococcus sp. 2011_Ileo_MS_A10, Streptococcus sp. 2011_Oral_MS_A3, Streptococcus sp. BS35a, Streptococcus sp. GMD6S, Streptococcus sp. oral taxon G59, Streptococcus sp. oral taxon G63, Streptococcus thermophilus, Sutterella stercoricanis, Tannerella forsythia, Tannerella sp. oral taxon HOT-286, Tepidimonas sp. AK30, Terrisporobacter glycolicus, Tessaracoccus lapidicaptus, Tessaracoccus sp. SL014B-79A, Thermomo nas brevis, Thermus sp., Turicibacter sanguinis, Varibaculum cambriense, Varibaculum sp. CCUG 45114, Variovorax sp. IMER-B2-7, Variovorax sp. MM43Nov, Veillonella montpellierensis, Veillonella rogosae, Veillonella seminalis, Veillonella sp. 2011_Oral_VSA_D3, Veillonella sp. AS16, Veillonella sp. CM60, Veillonella sp. MSA12, Veillonella sp. oral taxon 780, Weissella confusa, Weissella hellenica, Xanthomonas campestris, Yersinia enterocolitica, Abiotrophia, Acetitomaculum, Achromobacter, Acidiphilium, Acidovorax,

*Acinetobacter, Actinobacillus, Actinobaculum, Actinomyces, Actinomycetospora, Adhaeribacter, Aerococcus, Aeromicrobium, Aeromonas, Aerosphaera, Aggregatibacter, Albidovulum, Alicyclobacillus, Alishewanella, Alistipes, Alkalibacterium, Alkanindiges, Alloiococcus, Alloprevotella, Amnibacterium, Anaerobacillus, Anaerococcus, Anaeroglobus, Anaerosporobacter, Anaerostipes, Anoxybacillus, Aquabacterium, Arthrobacter, Arthrospira, Atopobium, Aurantimonas, Aureimonas, Bacillus, Bacteroides, Barnesiella, Bergeyella, Bifidobacterium, Bilophila, Blastococcus, Blautia, Bosea, Brachybacterium, Brachymonas, Brevibacterium, Brevundimonas, Brochothrix, Burkholderia, Campylobacter, Candidatus Protochlamydia, Candidatus Solibacter, Capnocytophaga, Cardiobacterium, Carnobacterium, Catenibacterium, Catonella, Caulobacter, Cellulomonas, Centipeda, Chelatococcus, Chroococcidiopsis, Chryseobacterium, Chthoniobacter, Citrobacter, Cloacibacterium, Clostridium, Collinsella, Comamonas, Conchiformibius, Cronobacter, Cryptobacterium, Curtobacterium, Curvibacter, Deinococcus, Delftia, Dermacoccus, Desulfovibrio, Dialister, Dielma, Dietzia, Dolosigranulum, Dorea, Dyadobacter, Eggerthella, Eisenbergiella, Empedobacter, Enterococcus, Epilithonimonas, Eremococcus, Erysipelatoclostridium, Exiguobacterium, Facklamia, Faecalibacterium, Ferruginibacter, Filifactor, Finegoldia, Flavisolibacter, Flavobacterium, Flavonifractor, Fretibacterium, Fusicatenibacter, Fusobacterium, Gallicola, Gardnerella, Georgenia, Granulicatella, Halomonas, Hespellia, Hydrogenophilus, Hymenobacter, Janibacter, Jeotgalicoccus, Jonquetella, Klebsiella, Kluyvera, Kocuria, Kytococcus, Lachnoanaerobaculum, Lachnospira, Lactobacillus, Lactococcus, Lautropia, Leptotrichia, Leuconostoc, Luteimonas, Lysinibacillus, Lysobacter, Macrococcus, Malassezia, Marvinbryantia, Massilia, Megasphaera, Meiothermus, Methanobrevibacter, Methylobacterium, Microbacterium, Micrococcus, Microlunatus, Microvirga, Mobiluncus, Modestobacter, Mogibacterium, Moraxella, Moryella, Murdochiella, Mycobacterium, Negativicoccus, Neisseria, Nitrosococcus, Nitrososphaera, Nocardia, Nocardioides, Novosphingobium, Odoribacter, Olsenella, Oribacterium, Ornithinimicrobium, Oscillibacter, Pantoea, Paraprevotella, Parasutterella, Parvimonas, Paucibacter, Pectobacterium, Pediococcus, Pedobacter, Pedomicrobium, Pelomonas, Peptoclostridium, Peptococcus, Peptoniphilus, Peptostreptococcus, Perlucidibaca, Phascolarctobacterium, Phenylobacterium, Phyllobacterium, Pirellula, Planctomyces, Planococcus, Planomicrobium, Porphyromonas, Prevotella, Propionibacterium, Propionimicrobium, Proteus, Pseudobutyrivibrio, Pseudoclavibacter, Pseudoflavonifractor, Pseudomonas, Pseudonocardia, Pseudorhodoferax, Pseudospirillum, Psychrobacter, Rahnella, Ralstonia, Raoultella, Rheinheimera, Rhizobium, Rhodobacter, Rhodococcus, Rhodopseudomonas, Romboutsia, Roseburia, Rothia, Rubellimicrobium, Rubrobacter, Salana, Sarcina, Selenomonas, Senegalimassilia, Shinella, Shuttleworthia, Singulisphaera, Solirubrobacter, Solobacterium, Sphingobacterium, Sphingomonas, Sporosarcina, Staphylococcus, Stenotrophomonas, Stomatobaculum, Streptococcus, Streptomyces, Sutterella, Tannerella, Tepidimonas, Terrisporobacter, Tessaracoccus, Thalassospira, Thermomonas, Thiobacillus, Truepera, Turicibacter, Varibaculum, Variovorax, Veillonella, Victivallis, Weissella, Williamsia, Xenophilus, Yersinia.*

24. The method of claim 12, wherein the first sleep-related condition comprises a bad sleep quality condition, wherein determining user microbiome features comprises determining the user microbiome composition features comprising a set of composition features associated with a nose site and with at least one of: *Abiotrophia defectiva, Achromobacter xylosoxidans, Acidovorax* sp. LR05, *Acinetobacter baumannii, Acinetobacter calcoaceticus, Acinetobacter haemolyticus, Acinetobacter kyonggiensis, Acinetobacter* sp. 2002-2301217, *Acinetobacter* sp. 423D, *Acinetobacter* sp. C-S-PDA7, *Acinetobacter* sp. C049, *Acinetobacter* sp. HD5.2, *Acinetobacter* sp. RBE2CD-114, *Acinetobacter* sp. RBE2CD-76, *Acinetobacter* sp. RE 51, *Acinetobacter* sp. STE, *Acinetobacter* sp. T133, *Acinetobacter* sp. WB22-23, *Acinetobacter ursingii, Actinobacillus porcinus, Actinobaculum massiliense, Actinomyces europaeus, Actinomyces georgiae, Actinomyces gerencseriae, Actinomyces israelii, Actinomyces massiliensis, Actinomyces neuii, Actinomyces radingae, Actinomyces* sp. ICM54, *Actinomyces* sp. ICM58, *Actinomyces* sp. S4-C9, *Actinomyces* sp. oral taxon 175, *Actinomyces* sp. oral taxon 448, *Actinomyces* sp. ph3, *Actinomyces viscosus, Actinomycetospora* sp. CAP 335, *Aerococcus christensenii, Aerococcus* sp. B43(2010), *Aerococcus urinae, Aerococcus viridans, Aeromonas salmonicida, Aerosphaera taetra, Aggregatibacter aphrophilus, Aggregatibacter segnis, Akkermansia muciniphila, Albidovulum inexpectatum, Alishewanella* sp. Mn5-6, *Alistipes finegoldii, Alistipes inops, Alistipes putredinis, Alistipes shahii, Alistipes* sp. EBA6-25cl2, *Alistipes* sp. NML05A004, *Alloiococcus otitis, Alloprevotella rava, Alloprevotella tannerae, Anaerobacillus alkalidiazotrophicus, Anaerococcus hydrogenalis, Anaerococcus lactolyticus, Anaerococcus murdochii, Anaerococcus octavius, Anaerococcus provencensis, Anaerococcus* sp. 8404299, *Anaerococcus* sp. 8405254, *Anaerococcus* sp. 9401487, *Anaerococcus* sp. PH9, *Anaerococcus* sp. S8 87-3, *Anaerococcus* sp. S8 F2, *Anaerococcus tetradius, Anaerococcus vaginalis, Anaeroglobus geminatus, Anaerostipes* sp. 5_1_63FAA, *Anoxybacillus* sp. HT14, *Aquabacterium commune, Aquabacterium* sp. Aqua2, *Arthrobacter* sp. T2-4, *Arthrospira fusiformis, Atopobium minutum, Atopobium rimae, Atopobium* sp. S3PFAA1-4, *Atopobium* sp. S4-A11a, *Atopobium vaginae, Aureimonas altamirensis, Aureimonas phyllosphaerae, Bacillus cereus, Bacillus nanhaiisediminis, Bacillus niacini, Bacillus pseudofirmus, Bacillus* sp. CBMAI 1158, *Bacillus* sp. DHT-33, *Bacillus* sp. T41, *Bacteroides acidifaciens, Bacteroides caccae, Bacteroides coprocola, Bacteroides eggerthii, Bacteroides fragilis, Bacteroides massiliensis, Bacteroides ovatus, Bacteroides salyersiae, Bacteroides* sp. 2_2_4, *Bacteroides* sp. 35AE37, *Bacteroides* sp. AR20, *Bacteroides* sp. AR29, *Bacteroides* sp. D22, *Bacteroides* sp. EBA5-17, *Bacteroides* sp. SLC1-38, *Bacteroides stercoris, Bacteroides thetaiotaomicron, Bacteroides uniformis, Bacteroides vulgatus, Barnesiella intestinihominis, Bergeyella* sp. AF14, *Bergeyella zoohelcum, Bibersteinia trehalosi, Bifidobacterium adolescentis, Bifidobacterium longum, Bifidobacterium stercoris, Bilophila* sp. 4_1_30, *Bilophila wadsworthia, Blastocatella fastidiosa, Blastococcus aggregatus, Blastococcus* sp. 0705C6-3, *Blastococcus* sp. FXJ6.383, *Blautia faecis, Blautia luti, Blautia* sp. YHC-4, *Blautia wexlerae, Bosea* sp. BIWAKO-01, *Bosea* sp. R-46060, *Brachybacterium muris, Brachybacterium* sp. NIO-27, *Brachybacterium* sp. b110-100S, *Brachymonas* sp. canine oral taxon 015, *Bradyrhizobium* sp. 68A4SAPT, *Bradyrhizobium* sp. CCBAU 53380, *Bradyrhizobium* sp. P-45, *Brevibacterium massiliense, Brevibacterium paucivorans, Brevibacterium pityocampae, Brevibacterium* sp. A9C6, *Brevibacterium* sp. MBTD_CMFRI_Br02, *Brevundimonas diminuta, Brevundimonas* sp. FXJ8.080, *Brevundimonas* sp. JW23.4a, *Brevundimonas* sp. V3M6, *Brevundimonas subvibrioides, Burkholderia lata, Burkholderia* sp.

CBPB-HIM, *Burkholderia* sp. S32, *Campylobacter concisus*, *Campylobacter gracilis*, *Campylobacter hominis*, *Campylobacter showae*, *Capnocytophaga* genosp. AHN8471, *Capnocytophaga gingivalis*, *Capnocytophaga ochracea*, *Capnocytophaga* sp. AHN10044, *Capnocytophaga* sp. AHN9756, *Capnocytophaga* sp. CM59, *Capnocytophaga* sp. oral taxon 329, *Capnocytophaga* sp. oral taxon 338, *Capnocytophaga sputigena*, *Cardiobacterium hominis*, *Catonella morbi*, *Centipeda periodontii*, *Chryseobacterium haifense*, *Chryseobacterium* sp. BBCT14, *Chryseobacterium* sp. IIL-Nv8, *Chryseobacterium* sp. MH28, *Chryseobacterium* sp. R064, *Chryseobacterium* sp. Y1D, *Citrobacter* sp. BW4, *Cloacibacterium rupense*, *Clostridioides difficile*, *Collinsella aerofaciens*, *Comamonas* sp. P-115, *Comamonas* sp. RV A09_23b, *Corynebacterium atypicum*, *Corynebacterium canis*, *Corynebacterium caspium*, *Corynebacterium diphtheriae*, *Corynebacterium durum*, *Corynebacterium epidermidicanis*, *Corynebacterium felinum*, *Corynebacterium freiburgense*, *Corynebacterium glucuronolyticum*, *Corynebacterium mastitidis*, *Corynebacterium matruchotii*, *Corynebacterium* sp., *Corynebacterium* sp. 2300500, *Corynebacterium* sp. 713182/2012, *Corynebacterium* sp. NML 97-0186, *Corynebacterium* sp. jw37, *Corynebacterium spheniscorum*, *Corynebacterium ulcerans*, *Cronobacter sakazakii*, *Cryobacterium psychrotolerans*, *Cryptobacterium curtum*, *Curvibacter gracilis*, *Cutibacterium acnes*, *Cutibacterium avidum*, *Cutibacterium granulosum*, *Deinococcus antarcticus*, *Deinococcus* sp. 3B1, *Deinococcus* sp. UAC-77, *Delftia lacustris*, *Delftia* sp. BN-SKY3, *Dermabacter hominis*, *Dermabacter* sp. HFH0086, *Dermacoccus nishinomiyaensis*, *Dermacoccus* sp. D2.1, *Dermacoccus* sp. Ellin183, *Dermacoccus* sp. Ellin185, *Dermacoccus* sp. SST-20, *Desulfovibrio* sp., *Dialister invisus*, *Dialister pneumosintes*, *Dialister propionicifaciens*, *Dialister* sp. E2_20, *Dialister* sp. S7MSR5, *Dolosigranulum pigrum*, *Dorea formicigenerans*, *Dorea longicatena*, *Effusibacillus pohliae*, *Eggerthella lenta*, *Eikenella corrodens*, *Eisenbergiella tayi*, *Enterobacter cloacae*, *Enterococcus* sp. SI-4, *Eremococcus coleocola*, *Exiguobacterium sibiricum*, *Exiguobacterium* sp. icr3, *Facklamia hominis*, *Facklamia languida*, *Facklamia* sp. 164-92, *Facklamia tabacinasalis*, *Faecalibacterium prausnitzii*, *Faecalibacterium* sp. canine oral taxon 147, *Fastidiosipila sanguinis*, *Filifactor alocis*, *Finegoldia magna*, *Finegoldia* sp. S9 AA1-5, *Flavobacterium* sp. EP372, *Flavobacterium* sp. bk_25, *Fretibacterium fastidiosum*, *Frigoribacterium* sp. 181, *Fusicatenibacter saccharivorans*, *Fusobacterium equinum*, *Fusobacterium nucleatum*, *Fusobacterium periodonticum*, *Fusobacterium russii*, *Fusobacterium* sp. ACB2, *Fusobacterium* sp. AS2, *Fusobacterium* sp. CM21, *Fusobacterium* sp. CM22, *Gardnerella* sp. S3PF20, *Gardnerella vaginalis*, *Gemella morbillorum*, *Gemella* sp. 933-88, *Granulicatella adiacens*, *Granulicatella elegans*, *Haemophilus influenzae*, *Haemophilus parainfluenzae*, *Halomonas pacifica*, *Herbaspirillum huttiense*, *Herbaspirillum seropedicae*, *Hydrogenophilus islandicus*, *Janibacter* sp. IARI-RP17, *Janibacter* sp. M3-5, *Jeotgalicoccus aerolatus*, *Johnsonella ignava*, *Jonquetella anthropi*, *Klebsiella oxytoca*, *Klebsiella pneumoniae*, *Kluyvera georgiana*, *Kocuria carniphila*, *Kocuria kristinae*, *Kocuria marina*, *Kocuria rhizophila*, *Kocuria* sp. BRI 36, *Kocuria* sp. FXJ6.339, *Kocuria* sp. LW2-LEVI2-W, *Lachnoanaerobaculum saburreum*, *Lachnospira pectinoschiza*, *Lactobacillus crispatus*, *Lactobacillus curvatus*, *Lactobacillus delbrueckii*, *Lactobacillus fornicalis*, *Lactobacillus gasseri*, *Lactobacillus jensenii*, *Lactobacillus paracasei*, *Lactobacillus plantarum*, *Lactobacillus salivarius*, *Lactobacillus* sp. 7_1_47FAA, *Lactobacillus* sp. Akhmr01, *Lactobacillus* sp. CR-609S, *Lactobacillus* sp. TAB-26, *Lactobacillus vaginalis*, *Lactococcus lactis*, *Lactococcus* sp. MH5-2, *Lautropia* sp. TeTO, *Leptotrichia buccalis*, *Leptotrichia hongkongensis*, *Leptotrichia shahii*, *Leptotrichia* sp. oral taxon 225, *Leptotrichia wadei*, *Leucobacter aridicollis*, *Leucobacter* sp. LR-2006b, *Leuconostoc carnosum*, *Leuconostoc lactis*, *Leuconostoc mesenteroides*, *Luteimonas mephitis*, *Lysinibacillus* sp. SJ2SN2, *Lysinibacillus sphaericus*, *Macrococcus brunensis*, *Macrococcus caseolyticus*, *Malassezia restricta*, *Massilia oculi*, *Megasphaera* sp. BV3C16-1, *Megasphaera* sp. UPII 199-6, *Meiothermus silvanus*, *Mesorhizobium loti*, *Mesorhizobium* sp. RE 62, *Mesorhizobium* sp. mat916, *Methanobrevibacter smithii*, *Methylobacterium adhaesivum*, *Methylobacterium* sp. CBMB45, *Methylobacterium* sp. CCGE4019, *Methylobacterium* sp. Gh-143, *Methylobacterium* sp. RK-200008-1, *Microbacterium lacticum*, *Microbacterium* sp. PcRB024, *Microbacterium yannicii*, *Micrococcus luteus*, *Micrococcus* sp. WB18-01, *Microlunatus phosphovorus*, *Microvirga aerilata*, *Microvirga* sp. BR10193, *Microvirga* sp. TSX10-2, *Mobiluncus mulieris*, *Modestobacter multiseptatus*, *Mogibacterium pumilum*, *Moraxella catarrhalis*, *Moraxella lincolnii*, *Moraxella nonliquefaciens*, *Moraxella* sp. BBN2P-02d, *Moraxella* sp. WB19-16, *Murdochiella* sp. S9 PR-10, *Mycobacterium chelonae*, *Mycobacterium* sp. KNUC297, *Mycobacterium* sp. UNC410CL29Cvi84, *Negativicoccus succinicivorans*, *Neisseria canis*, *Neisseria elongata*, *Neisseria flavescens*, *Neisseria macacae*, *Neisseria meningitidis*, *Neisseria mucosa*, *Neisseria oralis*, *Neisseria shayeganii*, *Neisseria skkuensis*, *Neisseria* sp. CCUG 45853, *Nocardioides mesophilus*, *Novosphingobium sediminicola*, *Novosphingobium* sp. THA_AIK7, *Ochrobactrum* sp. FPY8, *Ochrobactrum* sp. SCTS14, *Ochrobactrum tritici*, *Olsenella* sp. F0004, *Oribacterium* sp. CM12, *Oribacterium* sp. oral taxon 078, *Ornithinimicrobium* sp. THG-GM43, *Ornithinimicrobium* sp. X1C, *Pantoea agglomerans*, *Pantoea gaviniae*, *Parabacteroides distasonis*, *Parabacteroides goldsteinii*, *Paraprevotella clara*, *Parasutterella excrementihominis*, *Parvimonas micra*, *Paucibacter toxinivorans*, *Pectobacterium carotovorum*, *Pedomicrobium ferrugineum*, *Pelomonas aquatica*, *Peptococcus niger*, *Peptococcus* sp. oral taxon 168, *Peptoniphilus coxii*, *Peptoniphilus duerdenii*, *Peptoniphilus lacrimalis*, *Peptoniphilus* sp. 1-14, *Peptoniphilus* sp. 2002-2300004, *Peptoniphilus* sp. 2002-38328, *Peptoniphilus* sp. 7-2, *Peptoniphilus* sp. DNF00840, *Peptoniphilus* sp. JCM 8143, *Peptoniphilus* sp. S9 PR-13, *Peptoniphilus* sp. gpac018A, *Peptoniphilus* sp. gpac148, *Peptoniphilus* sp. oral taxon 836, *Peptostreptococcus anaerobius*, *Peptostreptococcus stomatis*, *Phascolarctobacterium faecium*, *Photobacterium* sp. squidInt_04, *Phyllobacterium* sp. T50, *Planococcus* sp. ljh-25, *Porphyrobacter* sp. NMC22, *Porphyromonas asaccharolytica*, *Porphyromonas bennonis*, *Porphyromonas cangingivalis*, *Porphyromonas canoris*, *Porphyromonas catoniae*, *Porphyromonas endodontalis*, *Porphyromonas* sp. 2026, *Porphyromonas uenonis*, *Prevotella bivia*, *Prevotella buccalis*, *Prevotella disiens*, *Prevotella intermedia*, *Prevotella micans*, *Prevotella nanceiensis*, *Prevotella nigrescens*, *Prevotella oris*, *Prevotella oulorum*, *Prevotella pallens*, *Prevotella* sp. S4-10, *Prevotella* sp. WAL 2039G, *Propionibacterium* sp. KPL1844, *Propionibacterium* sp. KPL2005, *Propionibacterium* sp. MSP09A, *Propionibacterium* sp. V07/12348, *Propionimicrobium lymphophilum*, *Pseudoclavibacter bifida*, *Pseudoclavibacter* sp. Timone, *Pseudoflavonifractor capillosus*, *Pseudomonas aeruginosa*, *Pseudomonas agarici*, *Pseudomonas brenneri*, *Pseudomonas citronellolis*, Pseudomonas graminis, Pseudomonas monteilii, Pseudomonas sp. BM5, Pseudomonas sp. CBMAI 1177, Pseudomonas sp. G1116, Pseudomonas sp. GmFRB023, Pseudomonas sp. KB23, Pseudomonas sp. KNUC378, Pseudomonas sp. PDD-31b-4, Pseudomonas sp. PKG89, Pseudomonas sp. PcFRB100, Pseudomonas sp. PcFRB119, Pseudomonas sp. a101-18-2, Pseudomonas syringae, Pseudonocardia sp. CC981102-15, Pseudopropionibacterium propionicum, Rahnella sp. BSP18, Ralstonia pickettii, Ralstonia sp. A52, Ralstonia sp. CCUG 46389, Ralstonia sp. S2.MAC.005, Raoultella ornithinolytica, Rhizobium etli, Rhizobium sp. 10II, Rhizobium sp. T45, Rhizobium sp. sc-w, Rhodobacter capsulatus, Rhodococcus erythropolis, Rhodococcus sp. C056, Rhodopseudomonas boonkerdii, Rhodopseudomonas thermotolerans, Rodentibacter pneumotropicus, Roseburia faecis, Roseburia intestinalis, Roseburia inulinivorans, Roseburia sp. 11SE39, Rothia aeria, Rothia dentocariosa, Rothia mucilaginosa, Rothia sp. CCUG 25688, Rothia sp. THG-N7, Salana multivorans, Selenomonas genomosp. P5, Shewanella sp. 8113, Shinella sp. DR33, Solobacterium moorei, Sphingobacterium mizutaii, Sphingobium sp. LC341, Sphingobium sp. MH60, Sphingomonas aerolata, Sphingomonas aquatilis, Sphingomonas dokdonensis, Sphingomonas oligophenolica, Sphingomonas paucimobilis, Sphingomonas sp. 24T, Sphingomonas sp. 540, Sphingomonas sp. CS81, Sphingomonas sp. PDD-26b-16, Staphylococcus aureus, Staphylococcus epidermidis, Staphylococcus equorum, Staphylococcus saprophyticus, Staphylococcus simulans, Staphylococcus sp. 155b, Staphylococcus sp. 334802, Staphylococcus sp. 335602, Staphylococcus sp. C-D-MA2, Staphylococcus sp. C912, Staphylococcus sp. L10, Staphylococcus sp. WB18-16, Staphylococcus vitulinus, Stenotrophomonas sp. C-S-TSA3, Stenotrophomonas sp. I_63-LFP1A9B1, Stenotrophomonas sp. KITS-1, Stenotrophomonas sp. N017, Stenotrophomonas sp. TV49May, Stenotrophomonas sp. Z2-S2, Streptococcus dysgalactiae, Streptococcus gordonii, Streptococcus mutans, Streptococcus parasanguinis, Streptococcus pneumoniae, Streptococcus sp. 11aTha1, Streptococcus sp. 2011_Ileo_MS_A10, Streptococcus sp. 2011_Oral_MS_A3, Streptococcus sp. BS35a, Streptococcus sp. GMD6S, Streptococcus sp. oral taxon G59, Streptococcus sp. oral taxon G63, Streptococcus thermophilus, Sutterella stercoricanis, Tannerella forsythia, Tannerella sp. oral taxon HOT-286, Tepidimonas sp. AK30, Terrisporobacter glycolicus, Tessaracoccus lapidicaptus, Tessaracoccus sp. SL014B-79A, Thermomo nas brevis, Thermus sp., Turicibacter sanguinis, Varibaculum cambriense, Varibaculum sp. CCUG 45114, Variovorax sp. IMER-B2-7, Variovorax sp. MM43Nov, Veillonella montpellierensis, Veillonella rogosae, Veillonella seminalis, Veillonella sp. 2011_Oral_VSA_D3, Veillonella sp. AS16, Veillonella sp. CM60, Veillonella sp. MSA12, Veillonella sp. oral taxon 780, Weissella confusa, Weissella hellenica, Xanthomonas campestris, Yersinia enterocolitica, Abiotrophia, Acetitomaculum, Achromobacter, Acidiphilium, Acidovorax, Acinetobacter, Actinobacillus, Actinobaculum, Actinomyces, Actinomycetospora, Adhaeribacter, Aerococcus, Aeromicrobium, Aeromonas, Aerosphaera, Aggregatibacter, Albidovulum, Alicyclobacillus, Alishewanella, Alistipes, Alkalibacterium, Alkanindiges, Alloiococcus, Alloprevotella, Amnibacterium, Anaerobacillus, Anaerococcus, Anaeroglobus, Anaerosporobacter, Anaerostipes, Anoxybacillus, Aquabacterium, Aureimonas, Arthrobacter, Arthrospira, Atopobium, Aurantimonas, Aureimonas, Bacillus, Bacteroides, Barnesiella, Bergeyella, Bifidobacterium, Bilophila, Blastococcus, Blautia, Bosea, Brachybacterium, Brachymonas, Brevibacterium, Brevundimonas, Brochothrix, Burkholderia, Campylobacter, Candidatus Protochlamydia, Candidatus Solibacter, Capnocytophaga, Cardiobacterium, Carnobacterium, Catenibacterium, Catonella, Caulobacter, Cellulomonas, Centipeda, Chelatococcus, Chroococcidiopsis, Chryseobacterium, Chthoniobacter, Citrobacter, Cloacibacterium, Clostridium, Collinsella, Comamonas, Conchiformibius, Cronobacter, Cryptobacterium, Curtobacterium, Curvibacter, Deinococcus, Delftia, Dermacoccus, Desulfovibrio, Dialister, Dielma, Dietzia, Dolosigranulum, Dorea, Dyadobacter, Eggerthella, Eisenbergiella, Empedobacter, Enterococcus, Epilithonimonas, Eremococcus, Erysipelatoclostridium, Exiguobacterium, Facklamia, Faecalibacterium, Ferruginibacter, Filifactor, Finegoldia, Flavisolibacter, Flavobacterium, Flavonifractor, Fretibacterium, Fusicatenibacter, Fusobacterium, Gallicola, Gardnerella, Georgenia, Granulicatella, Halomonas, Hespellia, Hydrogenophilus, Hymenobacter, Janibacter, Jeotgalicoccus, Jonquetella, Klebsiella, Kluyvera, Kocuria, Kytococcus, Lachnoanaerobaculum, Lachnospira, Lactobacillus, Lactococcus, Lautropia, Leptotrichia, Leuconostoc, Luteimonas, Lysinibacillus, Lysobacter, Macrococcus, Malassezia, Marvinbryantia, Massilia, Megasphaera, Meiothermus, Methanobrevibacter, Methylobacterium, Microbacterium, Micrococcus, Microlunatus, Microvirga, Mobiluncus, Modestobacter, Mogibacterium, Moraxella, Moryella, Murdochiella, Mycobacterium, Negativicoccus, Neisseria, Nitrosococcus, Nitrososphaera, Nocardia, Nocardioides, Novosphingobium, Odoribacter, Olsenella, Oribacterium, Ornithinimicrobium, Oscillibacter, Pantoea, Paraprevotella, Parasutterella, Parvimonas, Paucibacter, Pectobacterium, Pediococcus, Pedobacter, Pedomicrobium, Pelomonas, Peptoclostridium, Peptococcus, Peptoniphilus, Peptostreptococcus, Perlucidibaca, Phascolarctobacterium, Phenylobacterium, Phyllobacterium, Pirellula, Planctomyces, Planococcus, Planomicrobium, Porphyromonas, Prevotella, Propionibacterium, Propionimicrobium, Proteus, Pseudobutyrivibrio, Pseudoclavibacter, Pseudoflavonifractor, Pseudomonas, Pseudonocardia, Pseudorhodoferax, Pseudospirillum, Psychrobacter, Rahnella, Ralstonia, Raoultella, Rheinheimera, Rhizobium, Rhodobacter, Rhodococcus, Rhodopseudomonas, Romboutsia, Roseburia, Rothia, Rubellimicrobium, Rubrobacter, Salana, Sarcina, Selenomonas, Senegalimassilia, Shinella, Shuttleworthia, Singulisphaera, Solirubrobacter, Solobacterium, Sphingobacterium, Sphingomonas, Sporosarcina, Staphylococcus, Stenotrophomonas, Stomatobaculum, Streptococcus, Streptomyces, Sutterella, Tannerella, Tepidimonas, Terrisporobacter, Tessaracoccus, Thalassospira, Thermomonas, Thiobacillus, Truepera, Turicibacter, Varibaculum, Variovorax, Veillonella, Victivallis, Weissella, Williamsia, Xenophilus, Yersinia.

25. The method of claim 12, wherein the first sleep-related condition comprises a bad sleep quality condition, wherein determining user microbiome features comprises determining the user microbiome composition features comprising a set of composition features associated with a skin site and with at least one of: Abiotrophia defectiva, Achromobacter xylosoxidans, Acinetobacter baumannii, Acinetobacter radioresistens, Acinetobacter sp. 423D, Acinetobacter sp. C-S-NA3, Acinetobacter sp. C-S-PDA7, Acinetobacter sp. HD5.2, Acinetobacter sp. RBE2CD-114, Acinetobacter sp. RBE2CD-76, Acinetobacter sp. S2(2009), Acinetobacter sp. T133, Acinetobacter ursingii, Actinobacillus porcinus, Actinomyces dentalis, Actinomyces georgiae, Actinomyces gerencseriae, Actinomyces graevenitzii, Actinomyces massiliensis, Actinomyces odontolyticus, Actinomyces rad-

*ingae, Actinomyces* sp. ICM41, *Actinomyces* sp. ICM54, *Actinomyces* sp. S4-C9, *Actinomyces* sp. canine oral taxon 374, *Actinomyces* sp. oral taxon 175, *Actinomyces* sp. ph3, *Actinoplanes auranticolor, Aeromonas salmonicida, Aeromonas* sp. B11, *Aerosphaera taetra, Aggregatibacter aphrophilus, Aggregatibacter segnis, Akkermansia muciniphila, Albidovulum inexpectatum, Alistipes finegoldii, Alistipes shahii, Alistipes* sp. EBA6-25cl2, *Alistipes* sp. NML05A004, *Alkanindiges illinoisensis, Alloiococcus otitis, Alloprevotella rava, Anaerobacillus alkalidiazotrophicus, Anaerococcus hydrogenalis, Anaerococcus lactolyticus, Anaerococcus murdochii, Anaerococcus octavius, Anaerococcus prevotii, Anaerococcus provencensis, Anaerococcus* sp. 8405254, *Anaerococcus* sp. 9401487, *Anaerococcus* sp. S8 F2, *Anaerococcus tetradius, Anaerococcus vaginalis, Anaerostipes hadrus, Anoxybacillus* sp. HT14, *Aquabacterium* sp. Aqua2, *Aquamicrobium lusatiense, Aquaspirillum* sp. canine oral taxon 091, *Arthrobacter* sp. LM27(2011), *Arthrobacter* sp. NIO-1057, *Atopobium* sp. S3MV24, *Aureimonas phyllosphaerae, Bacillus cereus, Bacillus flexus, Bacillus pocheonensis, Bacillus pseudofirmus, Bacillus safensis, Bacillus* sp. CBMAI 1158, *Bacillus* sp. T41, *Bacteroides caccae, Bacteroides clarus, Bacteroides coprocola, Bacteroides eggerthii, Bacteroides finegoldii, Bacteroides fragilis, Bacteroides massiliensis, Bacteroides nordii, Bacteroides ovatus, Bacteroides plebeius, Bacteroides* sp. 2_2_4, *Bacteroides* sp. 35AE37, *Bacteroides* sp. AR20, *Bacteroides* sp. D22, *Bacteroides* sp. DJF_B097, *Bacteroides* sp. EBA5-17, *Bacteroides* sp. J1511, *Bacteroides* sp. XB12B, *Bacteroides* sp. XB44A, *Bacteroides* sp. canine oral taxon 040, *Bacteroides stercoris, Bacteroides thetaiotaomicron, Bacteroides uniformis, Bacteroides vulgatus, Barnesiella intestinihominis, Bergeyella* sp. h1971d, *Bibersteinia trehalosi, Bifidobacterium animalis, Bifidobacterium longum, Bilophila* sp. 4_1_30, *Blastococcus* sp. FXJ6.383, *Blautia faecis, Blautia luti, Blautia* sp. YHC-4, *Blautia stercoris, Blautia wexlerae, Bosea* sp. B0.09-49, *Bosea* sp. BIWAKO-01, *Bosea* sp. R-46060, *Brachybacterium faecium, Brachybacterium* sp. NIO-27, *Bradyrhizobium* sp. CCBAU 53380, *Brevibacterium pityocampae, Brevibacterium* sp. A9C6, *Brevibacterium* sp. MBTD_CMFRI_Br02, *Brevundimonas diminuta, Brevundimonas* sp. JW23.4a, *Brevundimonas* sp. V3M6, *Brevundimonas* sp. a001-4, *Brevundimonas subvibrioides, Brochothrix* sp. MVP25, *Burkholderia* sp. S32, *Butyricimonas virosa, Campylobacter gracilis, Campylobacter ureolyticus, Capnocytophaga canimorsus, Capnocytophaga* genosp. AHN8471, *Capnocytophaga gingivalis, Capnocytophaga granulosa, Capnocytophaga ochracea, Capnocytophaga* sp. oral taxon 338, *Catonella morbi, Caulobacter* sp., *Cellulomonas denverensis, Cellulosimicrobium cellulans, Cellulosimicrobium* sp. 143-1, *Centipeda periodontii, Chryseobacterium haifense, Chryseobacterium* sp. MC10-6, *Chryseobacterium* sp. R31, *Chryseobacterium* sp. Y1D, *Chryseobacterium* sp. bk_19, *Chryseobacterium* sp. sptzw36, *Chryseomicrobium imtechense, Citrobacter* sp. BW4, *Cloacibacterium rupense, Clostridioides difficile, Collinsella aerofaciens, Collinsella intestinalis, Comamonas jiangduensis, Comamonas* sp. HM_AF10, *Comamonas* sp. RV_F08_22d, *Conchiformibius steedae, Corynebacterium argentoratense, Corynebacterium atypicum, Corynebacterium canis, Corynebacterium capitovis, Corynebacterium ciconiae, Corynebacterium diphtheriae, Corynebacterium durum, Corynebacterium epidermidicanis, Corynebacterium freiburgense, Corynebacterium glucuronolyticum, Corynebacterium mastitidis, Corynebacterium* sp. 713182/2012, *Corynebacterium* sp. NML 97-0186, *Corynebacterium* sp. jw37, *Corynebacterium spheniscorum, Corynebacterium ulcerans, Curvibacter gracilis, Cutibacterium acnes, Cutibacterium avidum, Cutibacterium granulosum, Deinococcus antarcticus, Deinococcus* sp. MN4-8, *Delftia lacustris, Delftia* sp. BN-SKY3, *Dermabacter hominis, Dermacoccus nishinomiyaensis, Dermacoccus* sp. Ellin185, *Dermacoccus* sp. SST-20, *Desulfovibrio piger, Dialister invisus, Dialister micraerophilus, Dialister propionicifaciens, Dialister* sp. S7MSR5, *Dialister succinatiphilus, Dietzia cinnamea, Dietzia lutea, Dietzia* sp. ISA13, *Dolosigranulum pigrum, Duganella* sp. 5B, *Eisenbergiella tayi, Elizabethkingia meningoseptica, Empedobacter falsenii, Enterobacter cloacae, Enterococcus* sp. C6I11, *Enterococcus* sp. SI-4, *Erythrobacter* sp. DHXJ15, *Exiguobacterium* sp. IT2, *Exiguobacterium* sp. Sh3, *Exiguobacterium* sp. YS1, *Exiguobacterium* sp. icr3, *Facklamia languida, Faecalibacterium prausnitzii, Filifactor villosus, Finegoldia magna, Finegoldia* sp. BV3C29, *Finegoldia* sp. S8 F7, *Finegoldia* sp. S9 AA1-5, *Flavobacterium ceti, Flavobacterium* sp. CS43, *Flavonifractor plautii, Friedmanniella* sp. Ellin171, *Friedmanniella spumicola, Frigoribacterium* sp. PDD-31b-8, *Fusicatenibacter saccharivorans, Fusobacterium nucleatum, Fusobacterium periodonticum, Gardnerella vaginalis, Gemella morbillorum, Gemella* sp. 933-88, *Geobacillus stearothermophilus, Gordonia sputi, Gordonia terrae, Gordonibacter pamelaeae, Granulicatella adiacens, Granulicatella elegans, Haematobacter massiliensis, Haemophilus parainfluenzae, Halomonas pacifica, Herbaspirillum huttiense, Herbaspirillum seropedicae, Hymenobacter* sp. MIC2056, *Janibacter* sp. IARI-RP17, *Jeotgalicoccus aerolatus, Jeotgalicoccus nanhaiensis, Jeotgalicoccus* sp. AD9, *Kingella oralis, Klebsiella pneumoniae, Klebsiella* sp. B12, *Kluyvera georgiana, Knoellia* sp. BA3(2011), *Knoellia* sp. Zs20, *Kocuria kristinae, Kocuria rhizophila, Kocuria* sp. FXJ6.339, *Kytococcus* sp. YB227, *Lachnoanaerobaculum saburreum, Lachnoanaerobaculum* sp. OBRC5-5, *Lachnospira pectinoschiza, Lactobacillus crispatus, Lactobacillus curvatus, Lactobacillus delbrueckii, Lactobacillus fornicalis, Lactobacillus iners, Lactobacillus jensenii, Lactobacillus plantarum, Lactobacillus salivarius, Lactobacillus* sp. 7_1_47FAA, *Lactobacillus* sp. BL302, *Lactobacillus* sp. CR-609S, *Lactobacillus* sp. TAB-22, *Lactococcus* sp. MH5-2, *Lactonifactor longoviformis, Lautropia* sp. TeTO, *Leifsonia psychrotolerans, Leptotrichia buccalis, Leptotrichia goodfellowii, Leptotrichia hongkongensis, Leptotrichia shahii, Leptotrichia* sp. PTE15, *Leptotrichia* sp. oral taxon 225, *Leptotrichia trevisanii, Leptotrichia wadei, Leuconostoc inhae, Leuconostoc lactis, Luteimonas aestuarii, Lysinibacillus* sp. SJ2SN2, *Lysinibacillus sphaericus, Malassezia restricta, Marmoricola aurantiacus, Massilia* sp. MAS-1, *Massilia* sp. hp37, *Megamonas funiformis, Megasphaera* genomosp. C1, *Mesorhizobium loti, Mesorhizobium* sp. RE 62, *Mesorhizobium* sp. mat916, *Methanobrevibacter smithii, Methylobacterium* sp. AMS64, *Methylobacterium* sp. CBMB45, *Methylobacterium* sp. PB142, *Methylobacterium* sp. PDD-23b-14, *Methylobacterium* sp. RK-2008-1, *Microbacterium lacticum, Microbacterium lacus, Microbacterium oxydans, Microbacterium* sp. PcRB024, *Microbacterium* sp. absalar, *Microbacterium yannicii, Micrococcus luteus, Micrococcus* sp. M12-2-2, *Micrococcus* sp. WB18-01, *Microlunatus aurantiacus, Mobiluncus curtisii, Mobiluncus mulieris, Modestobacter multiseptatus, Modestobacter* sp. R-36506, *Mogibacterium pumilum, Moraxella nonliquefaciens, Moraxella* sp., *Moraxella* sp. 1967, *Moraxella* sp. 26, *Moraxella* sp. BBN2P-02d, *Moraxella* sp. WB19-16, *Moryella indoligenes, Murdochiella* sp. S9 PR-10, *Mycobacterium* sp. 18 GUW, *Mycobacterium* sp. KNUC297, *Negativi-* coccus sp. S5-A15, *Negativicoccus succinicivorans, Neisseria elongata, Neisseria macacae, Neisseria mucosa, Neisseria oralis, Neisseria sicca, Neisseria wadsworthii, Nocardioides daphniae, Nocardioides ginsengagri, Nocardioides mesophilus, Nocardioides* sp. BA32(2011), *Novosphingobium panipatense, Novosphingobium sediminicola, Novosphingobium* sp. iMX1, *Nubsella zeaxanthinifaciens, Ochrobactrum* sp. LC498, *Ochrobactrum* sp. SCTS14, *Ochrobactrum tritici, Odoribacter splanchnicus, Oerskovia* sp. Tibet-YD4604-5, *Oribacterium* sp. CM12, *Oribacterium* sp. oral taxon 078, *Ornithinimicrobium* sp. L5, *Pantoea agglomerans, Parabacteroides merdae, Paraprevotella clara, Parasutterella excrementihominis, Parvimonas micra, Pasteurella multocida, Paucibacter* sp. 186, *Paucibacter toxinivorans, Pedobacter* sp. DL5, *Pedomicrobium ferrugineum, Peptococcus* sp. S9 Pr-12, *Peptococcus* sp. canine oral taxon 344, *Peptococcus* sp. oral taxon 168, *Peptoniphilus lacrimalis, Peptoniphilus* sp. 1-14, *Peptoniphilus* sp. 2002-2300004, *Peptoniphilus* sp. 2002-38328, *Peptoniphilus* sp. 7-2, *Peptoniphilus* sp. S9 PR-13, *Peptoniphilus* sp. gpac018A, *Peptoniphilus* sp. gpac148, *Peptoniphilus* sp. oral taxon 375, *Peptostreptococcus anaerobius, Phascolarctobacterium faecium, Photobacterium* sp. CAIM 866, *Photobacterium* sp. squidInt_04, *Phyllobacterium* sp. T50, *Phyllobacterium trifolii, Planomicrobium alkanoclasticum, Planomicrobium* sp. TPD46, *Polaromonas aquatica, Porphyromonas asaccharolytica, Porphyromonas bennonis, Porphyromonas cangingivalis, Porphyromonas canoris, Porphyromonas catoniae, Porphyromonas crevioricanis, Porphyromonas endodontalis, Porphyromonas* sp. 2024b, *Porphyromonas uenonis, Prevotella bivia, Prevotella buccalis, Prevotella intermedia, Prevotella maculosa, Prevotella nanceiensis, Prevotella nigrescens, Prevotella oris, Prevotella oulorum, Prevotella pallens, Prevotella timonensis, Propionibacterium* sp. KPL1844, *Propionibacterium* sp. KPL2005, *Propionibacterium* sp. MSP09A, *Propionibacterium* sp. V07/12348, *Pseudoclavibacter bifida, Pseudoclavibacter* sp. Timone, *Pseudoflavonifractor capillosus, Pseudomonas aeruginosa, Pseudomonas baetica, Pseudomonas brenneri, Pseudomonas citronellolis, Pseudomonas fluorescens, Pseudomonas monteilii, Pseudomonas* sp. CBMAI 1177, *Pseudomonas* sp. DQ-01, *Pseudomonas* sp. G1116, *Pseudomonas* sp. GmFRB023, *Pseudomonas* sp. KNUC378, *Pseudomonas* sp. KVS86, *Pseudomonas* sp. PDD-31b-4, *Pseudomonas* sp. PKG89, *Pseudomonas* sp. PcFRB068, *Pseudomonas* sp. PcFRB100, *Pseudomonas* sp. StFRB280, *Pseudomonas* sp. a101-18-2, *Pseudoxanthomonas japonensis, Psychrobacter sanguinis, Psychrobacter* sp. b110-1, *Rahnella* sp. FB303, *Ralstonia pickettii, Ralstonia* sp. A52, *Ralstonia* sp. CCUG 46389, *Ralstonia* sp. S2.MAC.005, *Rheinheimera* sp. G3DM-27, *Rhizobium etli, Rhizobium skierniewicense, Rhizobium* sp. 10II, *Rhizobium* sp. T45, *Rhodococcus erythropolis, Rhodococcus* sp. CO56, *Rhodococcus* sp. MARG10, *Rhodococcus* sp. PDD-31b-7, *Rhodococcus* sp. p52, *Rhodopseudomonas boonkerdii, Roseburia inulinivorans, Roseburia* sp. 11SE39, *Roseomonas cervicalis, Rothia dentocariosa, Rothia* sp. CCUG 25688, *Rothia* sp. THG-N7, *Salinibacterium* sp. MDT1-9-1, *Selenomonas* genomosp. P5, *Serratia nematodiphila, Shewanella* sp. 8113, *Shinella* sp. DR33, *Simonsiella muelleri, Skermanella aerolata, Solobacterium moorei, Sphingobacterium* sp. HTc4-a, *Sphingobacterium* sp. TB1, *Sphingobium yanoikuyae, Sphingomonas aquatilis, Sphingomonas oligophenolica, Sphingomonas* sp. 24T, *Sphingomonas* sp. 540, *Sphingomonas* sp. CS81, *Sphingomonas* sp. KOPRI 25661, *Sphingomonas* sp. PDD-26b-16, *Sphingomonas* sp. Z1-YC6841, *Sphingomonas yunnanensis, Spirosoma rigui, Staphylococcus aureus, Staphylococcus epidermidis, Staphylococcus equorum, Staphylococcus simulans, Staphylococcus* sp. 334802, *Staphylococcus* sp. 335602, *Staphylococcus* sp. C-D-MA2, *Staphylococcus* sp. C5I16, *Staphylococcus* sp. C9I2, *Staphylococcus* sp. WB18-16, *Stenotrophomonas pavanii, Stenotrophomonas* sp. C-S-TSA3, *Stenotrophomonas* sp. I_63-LFP1A9B1, *Stenotrophomonas* sp. KITS-1, *Stenotrophomonas* sp. PDD-33b-8, *Stenotrophomonas* sp. Z2-S2, *Stomatobaculum longum, Streptococcus dysgalactiae, Streptococcus mutans, Streptococcus parasanguinis, Streptococcus pyogenes, Streptococcus* sp. 11aTha1, *Streptococcus* sp. 2011_Oral_MS_A3, *Streptococcus* sp. BS35a, *Streptococcus* sp. GMD6S, *Streptococcus* sp. S16-11, *Streptococcus* sp. canine oral taxon 279, *Streptococcus* sp. oral taxon G59, *Streptococcus thermophilus, Subdoligranulum variabile, Sutterella* sp. 252, *Sutterella stercoricanis, Tannerella forsythia, Tannerella* sp. oral taxon HOT-286, *Terrisporobacter glycolicus, Tessaracoccus lapidicaptus, Turicella otitidis, Varibaculum cambriense, Varibaculum* sp. CCUG 45114, *Varibaculum* sp. CCUG 61255, *Variovorax* sp. IMER-B2-7, *Variovorax* sp. MM43Nov, *Veillonella atypica, Veillonella parvula, Veillonella* sp. 2011_Oral_VSA_D3, *Veillonella* sp. AS16, *Veillonella* sp. CM60, *Veillonella* sp. MSA12, *Veillonella* sp. oral taxon 780, *Xanthomonas campestris, Xanthomonas gardneri, Abiotrophia, Acetitomaculum, Achromobacter, Acidaminococcus, Acidiphilium, Acidovorax, Acinetobacter, Actinobacillus, Actinomadura, Actinomyces, Aerococcus, Aeromonas, Aerosphaera, Aggregatibacter, Agromyces, Akkermansia, Albidovulum, Alicyclobacillus, Alkanindiges, Alloprevotella, Altererythrobacter, Amaricoccus, Amnibacterium, Anaerobacillus, Anaerococcus, Anaerosporobacter, Anaerostipes, Anoxybacillus, Aquabacterium, Aquamicrobium, Aquaspirillum, Arthrobacter, Atopobium, Aurantimonas, Aureimonas, Azospira, Bacillus, Bacteroides, Barnesiella, Belnapia, Bergeyella, Bifidobacterium, Bilophila, Blastocatella, Blautia, Bosea, Brachybacterium, Bradyrhizobium, Brevibacterium, Brevundimonas, Brochothrix, Burkholderia, Butyrivibrio, Campylobacter, Candidatus Alysiosphaera, Candidatus Saccharimonas, Candidatus Stoquefichus, Candidatus Xiphinematobacter, Capnocytophaga, Catonella, Caulobacter, Cellulomonas, Cellulosimicrobium, Centipeda, Chitinophaga, Chryseobacterium, Chryseomicrobium, Chthoniobacter, Citrobacter, Cloacibacterium, Clostridium, Comamonas, Conchiformibius, Corynebacterium, Craurococcus, Cupriavidus, Curvibacter, Cutibacterium, Defluviimonas, Deinococcus, Delftia, Dermacoccus, Desulfovibrio, Devosia, Dietzia, Dolosigranulum, Duganella, Eggerthella, Eisenbergiella, Elizabethkingia, Enterobacter, Enterococcus, Enterorhabdus, Erysipelatoclostridium, Erythrobacter, Euzebya, Exiguobacterium, Facklamia, Faecalibacterium, Ferruginibacter, Filifactor, Finegoldia, Flavisolibacter, Flavobacterium, Fretibacterium, Friedmanniella, Frigoribacterium, Fusibacter, Fusicatenibacter, Fusobacterium, Gallicola, Gardnerella, Gemella, Geobacillus, Gordonia, Granulicatella, Granulicella, Haematobacter, Halomonas, Herbaspirillum, Hespellia, Holdemania, Hymenobacter, Iamia, Intestinibacter, Intestinimonas, Janibacter, Jatrophihabitans, Jeotgaalicus, Johnsonella, Kineosporia, Kingella, Klebsiella, Kluyvera, Knoellia, Kocuria, Kytococcus, Lachnoanaerobaculum, Lactobacillus, Lactococcus, Lactonifactor, Lautropia, Leifsonia, Leptotrichia, Leuconostoc, Luteimonas, Luteococcus, Lysinibacillus, Lysobacter, Malassezia, Marmoricola, Marvinbryantia, Massilia, Megamonas, Megasphaera, Mesorhizobium, Methanobrevibacter, Methylobac-* terium, Microbacterium, Micrococcus, Microvirga, Mobiluncus, Modestobacter, Mogibacterium, Moraxella, Murdochiella, Mycobacterium, Mycoplasma, Nakamurella, Negativicoccus, Neisseria, Nesterenkonia, Nitrososphaera, Nocardioides, Novosphingobium, Nubsella, Ochrobactrum, Odoribacter, Oerskovia, Oribacterium, Ornithinimicrobium, Oscillibacter, Oscillospira, Paenibacillus, Pantoea, Papillibacter, Paraprevotella, Parasutterella, Parvimonas, Pasteurella, Patulibacter, Pedobacter, Pedomicrobium, Peptoclostridium, Peptococcus, Peptoniphilus, Peptostreptococcus, Phascolarctobacterium, Phenylobacterium, Photobacterium, Phyllobacterium, Planococcus, Planomicrobium, Polaromonas, Porphyromonas, Prevotella, Propionibacterium, Propionimicrobium, Pseudoclavibacter, Pseudoflavonifractor, Pseudolabrys, Pseudomonas, Pseudonocardia, Pseudorhodoferax, Pseudoxanthomonas, Psychrobacter, Rahnella, Ralstonia, Rhizobium, Rhodobacter, Rhodococcus, Rhodoplanes, Rhodopseudomonas, Robinsoniella, Roseburia, Roseomonas, Rubellimicrobium, Rummeliibacillus, Saccharibacillus, Salinibacterium, Sarcina, Serinicoccus, Shewanella, Shuttleworthia, Simonsiella, Singulisphaera, Skermanella, Solirubrobacter, Solobacterium, Sorangium, Sphingobacterium, Sphingobium, Sphingomonas, Spirosoma, Staphylococcus, Stenotrophomonas, Stomatobaculum, Streptococcus, Streptomyces, Subdoligranulum, Sutterella, Tannerella, Terrisporobacter, Tessaracoccus, Thalassospira, Turicella, Vagococcus, Varibaculum, Veillonella, Virgibacillus, Wautersiella, Weissella, Zymomonas.

26. The method of claim 12, wherein the first sleep-related condition comprises a shift work condition, wherein determining user microbiome features comprises determining the user microbiome composition features comprising a set of composition features associated with a genital site and with at least one of: Abiotrophia defectiva, Achromobacter xylosoxidans, Actinobaculum massiliense, Actinomyces europaeus, Actinomyces hongkongensis, Actinomyces neuii, Actinomyces odontolyticus, Actinomyces sp. 2002-2301122, Actinomyces sp. ICM58, Actinomyces sp. S4-C9, Actinomyces sp. S9 PR-21, Actinomyces turicensis, Actinotignum schaalii, Aerococcus christensenii, Aerococcus sanguinicola, Aerococcus urinae, Aerosphaera taetra, Akkermansia muciniphila, Alloscardovia omnicolens, Anaerobacillus alkalidiazotrophicus, Anaerococcus hydrogenalis, Anaerococcus lactolyticus, Anaerococcus murdochii, Anaerococcus octavius, Anaerococcus prevotii, Anaerococcus provencensis, Anaerococcus sp. 8404299, Anaerococcus sp. 8405254, Anaerococcus sp. 9401487, Anaerococcus sp. PH9, Anaerococcus sp. S8 87-3, Anaerococcus sp. S9 PR-16, Anaerococcus sp. S9 PR-5, Anaerococcus vaginalis, Anaeroglobus geminatus, Arcanobacterium haemolyticum, Arcanobacterium sp. NML 06501, Atopobium deltae, Atopobium sp. F0209, Atopobium sp. MVA9, Atopobium sp. S3MV24, Atopobium sp. S4-A1a, Atopobium vaginae, Bacillus pseudofirmus, Bacillus sp. T41, Bacteroides caccae, Bacteroides massiliensis, Bacteroides sp. AR20, Bacteroides sp. D22, Bacteroides thetaiotaomicron, Bacteroides vulgatus, Bifidobacterium bifidum, Bifidobacterium breve, Bifidobacterium choerinum, Bifidobacterium gallicum, Bifidobacterium longum, Bifidobacterium sp. 120, Blautia luti, Bosea sp. BIWAKO-01, Bosea sp. R-46060, Bradyrhizobium sp. CCBAU 53380, Brevibacterium massiliense, Brevibacterium paucivorans, Brevibacterium ravenspurgense, Brevibacterium sp. 10-1, Bulleidia extructa, Campylobacter hominis, Campylobacter ureolyticus, Citrobacter sp. BW4, Collinsella aerofaciens, Corynebacterium canis, Corynebacterium epidermicanis, Corynebacterium frankenfor- stense, Corynebacterium freiburgense, Corynebacterium sp., Corynebacterium sp. 713182/2012, Corynebacterium sp. NML96-0085, Corynebacterium sp. jw37, Corynebacterium spheniscorum, Curvibacter gracilis, Cutibacterium acnes, Delftia lacustris, Delftia sp. BN-SKY3, Dialister micraerophilus, Dialister propionicifaciens, Dialister sp. E2_20, Dialister sp. S4-23, Dialister sp. S7MSR5, Dialister succinatiphilus, Enterococcus faecalis, Enterococcus sp. SI-4, Facklamia hominis, Facklamia languida, Facklamia sp. 1440-97, Facklamia sp. 164-92, Faecalibacterium prausnitzii, Faecalibacterium sp. canine oral taxon 147, Fastidiosipila sanguinis, Finegoldia magna, Finegoldia sp. S3MVA9, Finegoldia sp. S5-A7, Finegoldia sp. S8 F7, Finegoldia sp. S9 AA1-5, Fusicatenibacter saccharivorans, Fusobacterium sp. ACB2, Fusobacterium sp. CM21, Gardnerella sp. S3PF20, Gardnerella vaginalis, Gemella morbillorum, Globicatella sanguinis, Globicatella sulfidifaciens, Granulicatella elegans, Haemophilus influenzae, Haemophilus parainfluenzae, Helcococcus seattlensis, Helcococcus sueciensis, Herbaspirillum huttiense, Herbaspirillum seropedicae, Jonquetella sp. BV3C4, Kluyvera georgiana, Lactobacillus acidophilus, Lactobacillus coleohominis, Lactobacillus crispatus, Lactobacillus fornicalis, Lactobacillus gasseri, Lactobacillus iners, Lactobacillus jensenii, Lactobacillus johnsonii, Lactobacillus reuteri, Lactobacillus rhamnosus, Lactobacillus sp. 7_1_47FAA, Lactobacillus sp. Akhmr01, Lactobacillus sp. B164, Lactobacillus sp. BL302, Lactobacillus sp. BL304, Lactobacillus sp. C30An8, Lactobacillus sp. CR-609S, Lactobacillus sp. MYMRS/TEN2, Lactobacillus taiwanensis, Lactobacillus vaginalis, Leptotrichia hongkongensis, Lysinibacillus sphaericus, Megasphaera massiliensis, Megasphaera sp. BV3C16-1, Megasphaera sp. UPII 135-E, Megasphaera sp. UPII 199-6, Mesorhizobium loti, Mesorhizobium sp. mat916, Methylobacterium organophilum, Methylobacterium sp. CBMB45, Mobiluncus curtisii, Mobiluncus mulieris, Murdochiella asaccharolytica, Murdochiella sp. S9 PR-10, Mycoplasma hominis, Mycoplasma spermatophilum, Negativicoccus sp. S5-A15, Neisseria macacae, Ochrobactrum sp. SCTS14, Oligella urethralis, Pelomonas aquatica, Peptococcus sp. S9 Pr-12, Peptoniphilus coxii, Peptoniphilus duerdenii, Peptoniphilus lacrimalis, Peptoniphilus sp. 1-14, Peptoniphilus sp. 2002-2300004, Peptoniphilus sp. 2002-38328, Peptoniphilus sp. 7-2, Peptoniphilus sp. BV3AC2, Peptoniphilus sp. DNF00192, Peptoniphilus sp. JCM 8143, Peptoniphilus sp. S4-A10, Peptoniphilus sp. S9 PR-13, Peptoniphilus sp. gpac018A, Peptoniphilus sp. gpac148, Peptoniphilus sp. oral taxon 375, Peptoniphilus sp. oral taxon 836, Peptostreptococcus anaerobius, Phascolarctobacterium succinatutens, Porphyromonas bennonis, Porphyromonas somerae, Porphyromonas sp. 20024b, Porphyromonas sp. S8 86-12, Porphyromonas uenonis, Prevotella amnii, Prevotella bivia, Prevotella buccalis, Prevotella disiens, Prevotella sp. BV3C7, Prevotella sp. S4-10, Prevotella timonensis, Propionibacterium sp. KPL2005, Propionibacterium sp. MSP09A, Propionimicrobium lymphophilum, Pseudoclavibacter sp. Timone, Pseudoglutamicibacter albus, Pseudoglutamicibacter cumminsii, Ralstonia pickettii, Ralstonia sp. A52, Rhizobium sp. sc-w, Rhodopseudomonas boonkerdii, Sneathia sanguinegens, Sphingobium sp. LC341, Staphylococcus sp. 334802, Staphylococcus sp. C912, Staphylococcus sp. FXY54, Stenotrophomonas sp. KITS-1, Stenotrophomonas sp. N017, Streptococcus agalactiae, Streptococcus anginosus, Streptococcus dysgalactiae, Streptococcus gordonii, Streptococcus parasanguinis, Streptococcus pasteurianus, Streptococcus sp. 11aTha1, Streptococcus sp. 2011_Oral_MS_A3,

*Streptococcus* sp. BS35a, *Streptococcus thermophilus*, *Sutterella stercoricanis*, *Tessaracoccus* sp. SL014B-79A, *Trueperella bernardiae*, *Ureaplasma urealyticum*, *Varibaculum cambriense*, *Varibaculum* sp. CCUG 45114, *Varibaculum* sp. CCUG 61255, *Veillonella atypica*, *Veillonella montpellierensis*, *Veillonella parvula*, *Veillonella seminalis*, *Veillonella* sp. 2011_Oral_VSA_D3, *Abiotrophia*, *Achromobacter*, *Actinobaculum*, *Actinomyces*, *Aerococcus*, *Aerosphaera*, *Akkermansia*, *Alloscardovia*, *Anaerobacillus*, *Anaerococcus*, *Anaeroglobus*, *Arcanobacterium*, *Arthrobacter*, *Atopobium*, *Bacillus*, *Bacteroides*, *Bifidobacterium*, *Blautia*, *Bosea*, *Brachybacterium*, *Brevibacterium*, *Bulleidia*, *Campylobacter*, *Citrobacter*, *Collinsella*, *Corynebacterium*, *Curvibacter*, *Delftia*, *Dermabacter*, *Dialister*, *Enterococcus*, *Facklamia*, *Faecalibacterium*, *Fastidiosipila*, *Finegoldia*, *Fusicatenibacter*, *Fusobacterium*, *Gallicola*, *Gardnerella*, *Gemella*, *Globicatella*, *Granulicatella*, *Haemophilus*, *Helcococcus*, *Herbaspirillum*, *Howardella*, *Intestinibacter*, *Jonquetella*, *Kluyvera*, *Lachnospira*, *Lactobacillus*, *Leptotrichia*, *Lysinibacillus*, *Mesorhizobium*, *Methylobacterium*, *Mobiluncus*, *Mogibacterium*, *Moryella*, *Murdochiella*, *Mycoplasma*, *Negativicoccus*, *Ochrobactrum*, *Oligella*, *Parvibacter*, *Parvimonas*, *Pelomonas*, *Peptococcus*, *Peptoniphilus*, *Peptostreptococcus*, *Porphyromonas*, *Prevotella*, *Propionibacterium*, *Propionimicrobium*, *Pseudoclavibacter*, *Pseudomonas*, *Rhizobium*, *Rhodopseudomonas*, *Roseburia*, *Rothia*, *Sarcina*, *Senegalimassilia*, *Shuttleworthia*, *Sneathia*, *Sphingobium*, *Sphingomonas*, *Staphylococcus*, *Stenotrophomonas*, *Streptococcus*, *Subdoligranulum*, *Sutterella*, *Tessaracoccus*, *Trueperella*, *Ureaplasma*, *Varibaculum*.

27. The method of claim 12, wherein the first sleep-related condition comprises a shift work condition, wherein determining user microbiome features comprises determining the user microbiome composition features comprising a set of composition features associated with a gut site and with at least one of: *Abiotrophia defectiva*, *Achromobacter xylosoxidans*, *Acidaminococcus fermentans*, *Acidaminococcus intestini*, *Acidaminococcus* sp. BV3L6, *Acidaminococcus* sp. D21, *Acidaminococcus* sp. HPA0509, *Acinetobacter* sp. 423D, *Acinetobacter* sp. 81A1, *Actinobacillus porcinus*, *Actinomyces hongkongensis*, *Actinomyces neuii*, *Actinomyces odontolyticus*, *Actinomyces oris*, *Actinomyces radingae*, *Actinomyces* sp. 2002-2301122, *Actinomyces* sp. ICM47, *Actinomyces* sp. ICM54, *Actinomyces* sp. ICM58, *Actinomyces* sp. S4-C9, *Actinomyces* sp. S6-Spd3, *Actinomyces* sp. S9 PR-21, *Actinomyces* sp. oral strain Hal-1065, *Actinomyces turicensis*, *Actinomyces viscosus*, *Actinotignum schaalii*, *Adlercreutzia equolifaciens*, *Aerococcus christensenii*, *Aeromonas* sp. B11, *Aerosphaera taetra*, *Aggregatibacter aphrophilus*, *Aggregatibacter segnis*, *Akkermansia muciniphila*, *Alistipes finegoldii*, *Alistipes indistinctus*, *Alistipes inops*, *Alistipes massiliensis*, *Alistipes onderdonkii*, *Alistipes putredinis*, *Alistipes shahii*, *Alistipes* sp. EBA6-25cl2, *Alistipes* sp. HGB5, *Alistipes* sp. NML05A004, *Alistipes* sp. RMA 9912, *Allisonella histaminiformans*, *Alloscardovia omnicolens*, *Anaerococcus hydrogenalis*, *Anaerococcus lactolyticus*, *Anaerococcus murdochii*, *Anaerococcus octavius*, *Anaerococcus prevotii*, *Anaerococcus provencensis*, *Anaerococcus* sp. 8404299, *Anaerococcus* sp. 8405254, *Anaerococcus* sp. PH9, *Anaerococcus* sp. S8 87-3, *Anaerococcus* sp. S8 F2, *Anaerococcus* sp. S9 PR-5, *Anaerococcus* sp. gpac137, *Anaerococcus tetradius*, *Anaerococcus vaginalis*, *Anaerofustis stercorihominis*, *Anaeroglobus geminatus*, *Anaerosinus glycerini*, *Anaerosporobacter mobilis*, *Anaerostipes butyraticus*, *Anaerostipes caccae*, *Anaerostipes hadrus*, *Anaerostipes rhamnosivorans*, *Anaerostipes* sp. 3_2_56FAA, *Anaerostipes* sp. 494a, *Anaerostipes* sp. 5_1_63FAA, *Anaerostipes* sp. 992a, *Anaerotruncus colihominis*, *Anaerotruncus* sp. NML 070203, *Anaerovibrio* sp. 656, *Anaerovibrio* sp. 765, *Arcanobacterium haemolyticum*, *Arcanobacterium* sp. NML 065001, *Arthrobacter* sp., *Asaccharospora irregularis*, *Atopobium deltae*, *Atopobium minutum*, *Atopobium* sp. F02009, *Atopobium* sp. ICM57, *Atopobium* sp. S3MV24, *Atopobium* sp. S3MV26, *Atopobium* sp. S3PFAA1-4, *Atopobium vaginae*, *Bacillus* sp. HC15, *Bacteroides acidifaciens*, *Bacteroides caccae*, *Bacteroides caecigallinarum*, *Bacteroides clarus*, *Bacteroides dorei*, *Bacteroides eggerthii*, *Bacteroides faecis*, *Bacteroides finegoldii*, *Bacteroides fluxus*, *Bacteroides fragilis*, *Bacteroides intestinalis*, *Bacteroides massiliensis*, *Bacteroides nordii*, *Bacteroides oleiciplenus*, *Bacteroides ovatus*, *Bacteroides plebeius*, *Bacteroides rodentium*, *Bacteroides salyersiae*, *Bacteroides* sp., *Bacteroides* sp. 14(A), *Bacteroides* sp. 2_2_4, *Bacteroides* sp. 31SF15, *Bacteroides* sp. 35AE37, *Bacteroides* sp. 3_1_23, *Bacteroides* sp. 3_1_40A, *Bacteroides* sp. 4072, *Bacteroides* sp. AR20, *Bacteroides* sp. AR29, *Bacteroides* sp. CB57, *Bacteroides* sp. D20, *Bacteroides* sp. D22, *Bacteroides* sp. DJF_B097, *Bacteroides* sp. EBA5-17, *Bacteroides* sp. HPS0048, *Bacteroides* sp. J1511, *Bacteroides* sp. SLC1-38, *Bacteroides* sp. Smarlab 3301643, *Bacteroides* sp. TP-5, *Bacteroides* sp. WH302, *Bacteroides* sp. XB12B, *Bacteroides* sp. XB44A, *Bacteroides* sp. dnLKV9, *Bacteroides stercorirosoris*, *Bacteroides stercoris*, *Bacteroides thetaiotaomicron*, *Bacteroides uniformis*, *Bacteroides vulgatus*, *Bacteroides xylanisolvens*, *Barnesiella intestinihominis*, *Barnesiella viscericola*, *Bergeyella* sp. AF14, *Bifidobacterium adolescentis*, *Bifidobacterium animalis*, *Bifidobacterium biavatii*, *Bifidobacterium bifidum*, *Bifidobacterium breve*, *Bifidobacterium catenulatum*, *Bifidobacterium choerinum*, *Bifidobacterium dentium*, *Bifidobacterium gallicum*, *Bifidobacterium kashiwanohense*, *Bifidobacterium longum*, *Bifidobacterium merycicum*, *Bifidobacterium pseudocatenulatum*, *Bifidobacterium pullorum*, *Bifidobacterium scardovii*, *Bifidobacterium* sp., *Bifidobacterium* sp. 120, *Bifidobacterium* sp. 138, *Bifidobacterium* sp. MSX5B, *Bifidobacterium stercoris*, *Bifidobacterium thermacidophilum*, *Bifidobacterium tsurumiense*, *Bilophila* sp. 4_1_30, *Bilophila wadsworthia*, *Blautia coccoides*, *Blautia faecis*, *Blautia glucerasea*, *Blautia hansenii*, *Blautia hydrogenotrophica*, *Blautia luti*, *Blautia producta*, *Blautia schinkii*, *Blautia* sp. Ser5, *Blautia* sp. Ser8, *Blautia* sp. YHC-4, *Blautia stercoris*, *Blautia wexlerae*, *Brachybacterium* sp. NIO-27, *Brachybacterium* sp. S26, *Brachyspira aalborgi*, *Brevibacterium massiliense*, *Brevibacterium paucivorans*, *Brevibacterium ravenspurgense*, *Butyricicoccus pullicaecorum*, *Butyricimonas faecihominis*, *Butyricimonas paravirosa*, *Butyricimonas* sp. 180-3, *Butyricimonas* sp. 214-4, *Butyricimonas* sp. GD2, *Butyricimonas synergistica*, *Butyricimonas virosa*, *Butyrivibrio crossotus*, *Campylobacter faecalis*, *Campylobacter gracilis*, *Campylobacter hominis*, *Campylobacter jejuni*, *Campylobacter* sp. 0402694-C0078, *Campylobacter ureolyticus*, *Carnobacterium maltaromaticum*, *Catabacter hongkongensis*, *Catenibacterium mitsuokai*, *Cellulosilyticum lentocellum*, *Cellulosilyticum ruminicola*, *Citrobacter amalonaticus*, *Citrobacter* sp. BW4, *Citrobacter* sp. HD4.9, *Cloacibacillus evryensis*, *Cloacibacterium rupense*, *Clostridioides difficile*, *Clostridium ventriculi*, *Collinsella aerofaciens*, *Collinsella intestinalis*, *Collinsella tanakaei*, *Comamonas jiangduensis*, *Comamonas* sp. j41, *Coprobacillus* sp. D6, *Coprobacter fastidiosus*, *Coprobacter secundus*, *Corynebacterium argentoratense*, *Corynebacterium atypicum*, *Corynebacterium canis*, *Corynebacterium diphtheriae*, *Corynebacterium epidermidicanis*, *Corynebacte-* rium frankenforstense, Corynebacterium freiburgense, Corynebacterium glucuronolyticum, Corynebacterium mastitidis, Corynebacterium sp., Corynebacterium sp. 2300500, Corynebacterium sp. 713182/2012, Corynebacterium sp. NML 97-0186, Corynebacterium sp. jw37, Corynebacterium ulcerans, Cronobacter dublinensis, Cronobacter sakazakii, Cronobacter turicensis, Cruoricaptor ignavus, Cutibacterium acnes, Cutibacterium avidum, Delftia lacustris, Delftia sp. BN-SKY3, Dermabacter sp. HFH0086, Desulfovibrio piger, Desulfovibrio sp., Desulfovibrio sp. 3_1_syn3, Desulfovibrio sp. UNSW3caefatS, Dialister invisus, Dialister micraerophilus, Dialister pneumosintes, Dialister propionicifaciens, Dialister sp. E2_20, Dialister sp. S4-23, Dialister sp. S7MSR5, Dialister succinatiphilus, Dielma fastidiosa, Dolosigranulum pigrum, Dorea formicigenerans, Dorea longicatena, Dysgonomonas capnocytophagoides, Eggerthella lenta, Eggerthella sinensis, Eggerthella sp. HGA1, Eisenbergiella tayi, Enterobacter asburiae, Enterobacter sp. BS2-1, Enterobacter sp. UDC345, Enterococcus durans, Enterococcus faecalis, Enterococcus hirae, Enterococcus pallens, Enterococcus sp. C6I11, Enterococcus sp. SI-4, Enterorhabdus caecimuris, Eremococcus coleocola, Erysipelatoclostridium ramosum, Eubacterium callanderi, Eubacterium limosum, Eubacterium sp. SA11, Facklamia hominis, Facklamia sp. 1440-97, Facklamia sp. 164-92, Faecalibacterium prausnitzii, Faecalibacterium sp. canine oral taxon 147, Fastidiosipila sanguinis, Finegoldia magna, Finegoldia sp. BV3C29, Finegoldia sp. S5-A7, Finegoldia sp. S9 AA1-5, Flavonifractor plautii, Fusicatenibacter saccharivorans, Fusobacterium equinum, Fusobacterium mortiferum, Fusobacterium necrogenes, Fusobacterium nucleatum, Fusobacterium perfoetens, Fusobacterium periodonticum, Fusobacterium sp. AS2, Fusobacterium sp. CM21, Fusobacterium sp. DJF_B100, Fusobacterium sp. OBRC1, Fusobacterium ulcerans, Fusobacterium varium, Gardnerella sp. S3PF20, Gardnerella vaginalis, Gemella asaccharolytica, Gemella sp. 933-88, Globicatella sulfidifaciens, Gordonibacter pamelaeae, Granulicatella adiacens, Haemophilus influenzae, Haemophilus parainfluenzae, Hafnia alvei, Helcococcus seattlensis, Helcococcus sueciensis, Herbaspirillum seropedicae, Herbaspirillum sp. YR522, Holdemania filiformis, Howardella ureilytica, Intestinimonas butyriciproducens, Jonquetella anthropi, Jonquetella sp. BV3C4, Klebsiella oxytoca, Klebsiella sp. B12, Klebsiella sp. SOR89, Kluyvera georgiana, Lachnoanaerobaculum orale, Lachnoanaerobaculum sp. MSX33, Lachnospira pectinoschiza, Lactobacillus acidophilus, Lactobacillus algidus, Lactobacillus animalis, Lactobacillus coleohominis, Lactobacillus delbrueckii, Lactobacillus fornicalis, Lactobacillus gasseri, Lactobacillus helveticus, Lactobacillus iners, Lactobacillus jensenii, Lactobacillus johnsonii, Lactobacillus kefiri, Lactobacillus mucosae, Lactobacillus reuteri, Lactobacillus rhamnosus, Lactobacillus ruminis, Lactobacillus salivarius, Lactobacillus sp. 7_1_47FAA, Lactobacillus sp. Akhmr01, Lactobacillus sp. BL302, Lactobacillus sp. C30An8, Lactobacillus sp. C412, Lactobacillus sp. CR-609S, Lactobacillus sp. NRCT-KU 1, Lactobacillus sp. TAB-22, Lactobacillus sp. TAB-26, Lactobacillus vaginalis, Lactococcus lactis, Lactococcus sp. MH5-2, Lactococcus sp. STM1, Lactonifactor longoviformis, Lautropia sp. TeTO, Leptotrichia genomosp. C1, Leptotrichia sp. PG10, Leuconostoc carnosum, Leuconostoc lactis, Leuconostoc sp. C714, Marvinbryantia formatexigens, Megamonas funiformis, Megasphaera elsdenii, Megasphaera genomosp. C1, Megasphaera massiliensis, Megasphaera micronuciformis, Megasphaera sp. BS-4, Megasphaera sp. BV3C16-1, Megasphaera sp. DNF00912, Megasphaera sp. S6-MB2, Megasphaera sp. TrE9262, Megasphaera sp. UPII 199-6, Methanobrevibacter smithii, Methanobrevibacter sp., Methanosphaera stadtmanae, Mitsuokella jalaludinii, Mitsuokella multacida, Mitsuokella sp. DJF_RR21, Mitsuokella sp. TM-10, Mobiluncus curtisii, Mobiluncus mulieris, Mogibacterium timidum, Moraxella catarrhalis, Morganella morganii, Moryella indoligenes, Murdochiella asaccharolytica, Murdochiella sp. S9 PR-10, Mycoplasma hominis, Negativicoccus sp. S5-A15, Neisseria flavescens, Neisseria macacae, Neisseria mucosa, Nosocomiicoccus ampullae, Ochrobactrum sp. SCTS14, Odoribacter laneus, Odoribacter splanchnicus, Oligella urethralis, Olsenella sp. S9 HS-6, Oribacterium sp. OBRC12, Oscillibacter valericigenes, Oscillospira guilliermondii, Pantoea gaviniae, Parabacteroides distasonis, Parabacteroides faecis, Parabacteroides goldsteinii, Parabacteroides gordonii, Parabacteroides johnsonii, Parabacteroides merdae, Parabacteroides sp. 20_3, Parabacteroides sp. D25, Parabacteroides sp. dnLKV8, Paraprevotella clara, Paraprevotella xylaniphila, Parasporobacterium paucivorans, Parasutterella excrementihominis, Parvimonas micra, Paucibacter sp. 186, Pediococcus sp. MFC1, Pelistega indica, Pelomonas aquatica, Peptococcus niger, Peptococcus sp. S9 Pr-12, Peptococcus sp. canine oral taxon 334, Peptoniphilus coxii, Peptoniphilus duerdenii, Peptoniphilus koenoeneniae, Peptoniphilus lacrimalis, Peptoniphilus sp. 1-14, Peptoniphilus sp. 2002-2300004, Peptoniphilus sp. 2002-38328, Peptoniphilus sp. 7-2, Peptoniphilus sp. BV3AC2, Peptoniphilus sp. DNF00840, Peptoniphilus sp. JCM 8143, Peptoniphilus sp. S9 PR-13, Peptoniphilus sp. gpac018A, Peptoniphilus sp. gpac148, Peptoniphilus sp. oral taxon 375, Peptoniphilus sp. oral taxon 836, Peptostreptococcus anaerobius, Peptostreptococcus stomatis, Phascolarctobacterium faecium, Phascolarctobacterium sp. 377, Phascolarctobacterium sp. canine oral taxon 149, Phascolarctobacterium succinatutens, Porphyromonas asaccharolytica, Porphyromonas bennonis, Porphyromonas catoniae, Porphyromonas endodontalis, Porphyromonas sp. 20024b, Porphyromonas sp. S8 86-12, Porphyromonas uenonis, Prevotella amnii, Prevotella buccalis, Prevotella disiens, Prevotella intermedia, Prevotella nanceiensis, Prevotella nigrescens, Prevotella oris, Prevotella pallens, Prevotella sp. BV3C7, Prevotella sp. S4-10, Prevotella sp. WAL 2039G, Prevotella timonensis, Propionibacterium freudenreichii, Propionibacterium sp. KPL1844, Propionibacterium sp. MSP09A, Propionimicrobium lymphophilum, Proteus mirabilis, Proteus penneri, Proteus vulgaris, Pseudobutyrivibrio ruminis, Pseudoclavibacter bifida, Pseudoclavibacter sp. Timone, Pseudoflavonifractor capillosus, Pseudoglutamicibacter albus, Pseudoglutamicibacter cumminsii, Pseudomonas monteilii, Pseudomonas sp. CBMAI 1177, Pseudomonas sp. KB23, Pseudomonas sp. a101-18-2, Pseudomonas sp. a111-5, Pyramidobacter piscolens, Rahnella sp. BSP15, Rahnella sp. BSP18, Rahnella sp. FB303, Ralstonia sp. S2.MAC.005, Raoultella ornithinolytica, Rhizobium sp. T45, Rikenella microfusus, Robinsoniella peoriensis, Robinsoniella sp. KNHs210, Rodentibacter pneumotropicus, Romboutsia lituseburensis, Roseburia faecis, Roseburia hominis, Roseburia intestinalis, Roseburia inulinivorans, Roseburia sp. 11SE39, Roseburia sp. 499, Rothia dentocariosa, Rothia mucilaginosa, Rothia sp. RV13, Rothia sp. THG-N7, Scardovia wiggsiae, Selenomonas sp. Ycb08, Slackia faecicanis, Slackia piriformis, Slackia sp. NATTS, Sneathia sanguinegens, Solobacterium moorei, Solobacterium sp. S4-A19, Sporobacter termitidis, Sporomusa sphaeroides, Staphylococcus simulans, Staphylococcus sp. 334802, *Stenotrophomonas* sp. C-S-TSA3, *Stomatobaculum longum*, *Streptococcus dentirousetti*, *Streptococcus equinus*, *Streptococcus gordonii*, *Streptococcus parasanguinis*, *Streptococcus peroris*, *Streptococcus* sp. 11aTha1, *Streptococcus* sp. 2011_Ileo_MS_A10, *Streptococcus* sp. 2011_Oral_MS_A3, *Streptococcus* sp. 2011_Oral_MS_D12, *Streptococcus* sp. BS35a, *Streptococcus* sp. GMD6S, *Streptococcus* sp. S16-11, *Streptococcus* sp. TM013, *Streptococcus* sp. oral taxon G59, *Streptococcus thermophilus*, *Subdoligranulum variabile*, *Sutterella parvirubra*, *Sutterella* sp. 252, *Sutterella* sp. YIT 12072, *Sutterella stercoricanis*, *Sutterella wadsworthensis*, *Terrisporobacter glycolicus*, *Terrisporobacter petrolearius*, *Tessaracoccus lapidicaptus*, *Tessaracoccus* sp. SL014B-79A, *Trueperella bernardiae*, *Turicibacter sanguinis*, *Turicibacter* sp. LA62, *Ureaplasma urealyticum*, *Varibaculum cambriense*, *Varibaculum* sp. CCUG 45114, *Veillonella atypica*, *Veillonella dispar*, *Veillonella montpellierensis*, *Veillonella parvula*, *Veillonella ratti*, *Veillonella rogosae*, *Veillonella seminalis*, *Veillonella* sp. 2011_Oral_VSA_B12, *Veillonella* sp. 2011_Oral_VSA_C9, *Veillonella* sp. 2011_Oral_VSA_D12, *Veillonella* sp. 2011_Oral_VSA_D3, *Veillonella* sp. ADV 269.01, *Veillonella* sp. AS16, *Veillonella* sp. MSA12, *Veillonella* sp. oral taxon 780, *Victivallis vadensis*, *Weeksella virosa*, *Weissella cibaria*, *Weissella confusa*, *Weissella hellenica*, *Weissella* sp. H1a, [*Collinsella*] *massiliensis*, *Abiotrophia*, *Acetitomaculum*, *Acetivibrio*, *Acholeplasma*, *Achromobacter*, *Acidaminococcus*, *Actinobacillus*, *Actinobaculum*, *Actinomyces*, *Adlercreutzia*, *Aerococcus*, *Aeromonas*, *Aerosphaera*, *Aggregatibacter*, *Akkermansia*, *Alistipes*, *Allisonella*, *Alloprevotella*, *Alloscardovia*, *Anaerobacillus*, *Anaerobacter*, *Anaerococcus*, *Anaerofilum*, *Anaerofustis*, *Anaeroglobus*, *Anaeroplasma*, *Anaerosinus*, *Anaerosporobacter*, *Anaerostipes*, *Anaerotruncus*, *Anaerovibrio*, *Anaerovorax*, *Arcanobacterium*, *Arthrobacter*, *Asaccharobacter*, *Asaccharospora*, *Asteroleplasma*, *Atopobium*, *Azospira*, *Bacillus*, *Bacteroides*, *Barnesiella*, *Bergeyella*, *Bifidobacterium*, *Bilophila*, *Blautia*, *Brachybacterium*, *Brachyspira*, *Bradyrhizobium*, *Brevibacterium*, *Butyricicoccus*, *Butyricimonas*, *Butyrivibrio*, *Caldicoprobacter*, *Campylobacter*, *Candidatus Methanomethylophilus*, *Candidatus Soleaferrea*, *Candidatus Stoquefichus*, *Capnocytophaga*, *Carnobacterium*, *Catabacter*, *Catenibacterium*, *Cellulosilyticum*, *Citrobacter*, *Cloacibacillus*, *Cloacibacterium*, *Clostridium*, *Collinsella*, *Comamonas*, *Coprobacillus*, *Coprobacter*, *Corynebacterium*, *Cronobacter*, *Cruoricaptor*, *Cupriavidus*, *Deinococcus*, *Delftia*, *Dermabacter*, *Desulfovibrio*, *Dialister*, *Dielma*, *Dolosigranulum*, *Dorea*, *Dysgonomonas*, *Eggerthella*, *Eisenbergiella*, *Enterococcus*, *Enterorhabdus*, *Eremococcus*, *Erysipelatoclostridium*, *Eubacterium*, *Facklamia*, *Faecalibacterium*, *Fastidiosipila*, *Fibrobacter*, *Finegoldia*, *Flavobacterium*, *Flavonifractor*, *Fretibacterium*, *Fusicatenibacter*, *Fusobacterium*, *Gallicola*, *Gardnerella*, *Gelria*, *Gemella*, *Gordonibacter*, *Granulicatella*, *Haemophilus*, *Hafnia*, *Helcococcus*, *Herbaspirillum*, *Hespellia*, *Holdemania*, *Howardella*, *Hydrogenoanaerobacterium*, *Intestinibacter*, *Intestinimonas*, *Klebsiella*, *Kluyvera*, *Lachnoanaerobaculum*, *Lachnospira*, *Lactobacillus*, *Lactococcus*, *Lactonifactor*, *Lautropia*, *Leptotrichia*, *Leuconostoc*, *Marvinbryantia*, *Megamonas*, *Megasphaera*, *Methanobrevibacter*, *Methanomassiliicoccus*, *Methanosphaera*, *Mitsuokella*, *Mobiluncus*, *Mogibacterium*, *Moraxella*, *Morganella*, *Moryella*, *Murdochiella*, *Mycobacterium*, *Mycoplasma*, *Negativicoccus*, *Neisseria*, *Nosocomiicoccus*, *Novosphingobium*, *Ochrobactrum*, *Odoribacter*, *Oligella*, *Olsenella*, *Oribacterium*, *Oscillibacter*, *Oscillospira*, *Pantoea*, *Papillibacter*, *Parabacteroides*, *Paraprevotella*, *Parasporobacterium*, *Parasutterella*, *Parvimonas*, *Pasteurella*, *Paucibacter*, *Pelistega*, *Pelomonas*, *Peptoclostridium*, *Peptococcus*, *Peptoniphilus*, *Peptostreptococcus*, *Phascolarctobacterium*, *Phyllobacterium*, *Porphyromonas*, *Prevotella*, *Propionibacterium*, *Propionimicrobium*, *Proteiniclasticum*, *Proteiniphilum*, *Proteus*, *Pseudobutyrivibrio*, *Pseudoclavibacter*, *Pseudoflavonifractor*, *Pseudomonas*, *Rahnella Raoultella*, *Rhodobacter*, *Rhodococcus*, *Rikenella*, *Robinsoniella*, *Romboutsia*, *Roseburia*, *Rothia*, *Sarcina*, *Scardovia*, *Sedimentibacter*, *Selenomonas*, *Senegalimassilia*, *Shuttleworthia*, *Slackia*, *Sneathia*, *Solobacterium*, *Sporobacter*, *Sporomusa*, *Staphylococcus*, *Stomatobaculum*, *Streptococcus*, *Subdoligranulum*, *Succiniclasticum*, *Succinivibrio*, *Sutterella*, *Synergistes*, *Terrisporobacter*, *Tessaracoccus*, *Thalassospira*, *Trueperella*, *Turicibacter*, *Ureaplasma*, *Varibaculum*, *Veillonella*, *Victivallis*, *Weeksella*, *Weissella*.

28. The method of claim 12, wherein the first sleep-related condition comprises a shift work condition, wherein determining user microbiome features comprises determining the user microbiome composition features comprising a set of composition features associated with a mouth site and with at least one of: *Abiotrophia defectiva*, *Actinobacillus porcinus*, *Actinomyces dentalis*, *Actinomyces georgiae*, *Actinomyces gerencseriae*, *Actinomyces graevenitzii*, *Actinomyces massiliensis*, *Actinomyces meyeri*, *Actinomyces naeslundii*, *Actinomyces odontolyticus*, *Actinomyces oris*, *Actinomyces* sp., *Actinomyces* sp. ICM34, *Actinomyces* sp. ICM41, *Actinomyces* sp. ICM47, *Actinomyces* sp. ICM54, *Actinomyces* sp. ICM58, *Actinomyces* sp. S6-Spd3, *Actinomyces* sp. ZSY-1, *Actinomyces* sp. oral strain Hal-1065, *Actinomyces* sp. oral taxon 170, *Actinomyces* sp. oral taxon 175, *Actinomyces* sp. oral taxon 178, *Actinomyces* sp. oral taxon 448, *Actinomyces* sp. ph3, *Actinomyces viscosus*, *Aerococcus christensenii*, *Aggregatibacter aphrophilus*, *Aggregatibacter segnis*, *Akkermansia muciniphila*, *Alistipes finegoldii*, *Alistipes inops*, *Alistipes putredinis*, *Alistipes* sp. EBA6-25c12, *Alistipes* sp. HGB5, *Alistipes* sp. NML05A004, *Alistipes* sp. RMA 9912, *Alloprevotella rava*, *Alloprevotella tannerae*, *Alloscardovia omnicolens*, *Anaeroglobus geminatus*, *Anaerostipes hadrus*, *Anaerostipes* sp. 5_1_63FAA, *Anaerotruncus* sp. NML 070203, *Asaccharospora irregularis*, *Atopobium parvulum*, *Atopobium rimae*, *Atopobium* sp. DMCT15023, *Atopobium* sp. ICM57, *Bacteroides acidifaciens*, *Bacteroides caccae*, *Bacteroides clarus*, *Bacteroides coprocola*, *Bacteroides eggerthii*, *Bacteroides fragilis*, *Bacteroides intestinalis*, *Bacteroides massiliensis*, *Bacteroides nordii*, *Bacteroides plebeius*, *Bacteroides* sp. 3_1_40A, *Bacteroides* sp. AR20, *Bacteroides* sp. AR29, *Bacteroides* sp. D22, *Bacteroides* sp. DJF_B097, *Bacteroides* sp. EBA5-17, *Bacteroides* sp. J1511, *Bacteroides* sp. SLC1-38, *Bacteroides* sp. XB12B, *Bacteroides* sp. XB44A, *Bacteroides stercorirosoris*, *Bacteroides stercoris*, *Bacteroides thetaiotaomicron*, *Bacteroides uniformis*, *Bacteroides vulgatus*, *Barnesiella intestinihominis*, *Bergeriella denitrificans*, *Bifidobacterium adolescentis*, *Bifidobacterium kashiwanohense*, *Bifidobacterium longum*, *Bifidobacterium* sp. MSX5B, *Bilophila wadsworthia*, *Blautia faecis*, *Blautia luti*, *Blautia* sp. YHC-4, *Blautia stercoris*, *Blautia wexlerae*, *Bradyrhizobium* sp. 68A4SAPT, *Brevundimonas* sp. FXJ8.080, *Butyricimonas faecihominis*, *Butyricimonas paravirosa*, *Butyricimonas virosa*, *Butyrivibrio crossotus*, *Campylobacter concisus*, *Campylobacter gracilis*, *Campylobacter showae*, *Campylobacter* sp. 10_1_50, *Campylobacter* sp. FOBRC15, *Campylobacter ureolyticus*, *Capnocytophaga gingivalis*, *Capnocytophaga granulosa*, *Capnocytophaga haemolytica*, *Capnocytophaga ochracea*,

*Capnocytophaga* sp. AHN9576, *Capnocytophaga* sp. AHN9687, *Capnocytophaga* sp. AHN9756, *Capnocytophaga* sp. CM59, *Capnocytophaga* sp. HS5_2W_I24, *Capnocytophaga* sp. oral taxon 335, *Capnocytophaga* sp. oral taxon 336, *Capnocytophaga* sp. oral taxon 338, *Capnocytophaga sputigena*, *Cardiobacterium hominis*, *Catenibacterium mitsuokai*, *Catonella morbi*, *Centipeda periodontii*, *Clostridioides difficile*, *Collinsella aerofaciens*, *Coprobacter fastidiosus*, *Corynebacterium durum*, *Corynebacterium glucuronolyticum*, *Corynebacterium matruchotii*, *Corynebacterium* sp., *Corynebacterium spheniscorum*, *Corynebacterium ulcerans*, *Cryptobacterium curtum*, *Cutibacterium acnes*, *Delftia lacustris*, *Delftia* sp. BN-SKY3, *Desulfobulbus* sp. oral taxon 041, *Desulfovibrio* sp. 3_1_syn3, *Dialister invisus*, *Dialister micraerophilus*, *Dialister pneumosintes*, *Dolosigranulum pigrum*, *Dorea formicigenerans*, *Dorea longicatena*, *Eggerthella lenta*, *Eggerthia catenaformis*, *Eikenella corrodens*, *Eisenbergiella tayi*, *Erysipelatoclostridium ramosum*, *Faecalibacterium prausnitzii*, *Faecalibacterium* sp. canine oral taxon 147, *Filifactor alocis*, *Finegoldia* sp. S8 F7, *Finegoldia* sp. S9 AA1-5, *Flavonifractor plautii*, *Fretibacterium fastidiosum*, *Fusicatenibacter saccharivorans*, *Fusobacterium nucleatum*, *Fusobacterium periodonticum*, *Fusobacterium* sp. AS2, *Fusobacterium* sp. CM21, *Fusobacterium* sp. CM22, *Fusobacterium* sp. OBRC1, *Gardnerella vaginalis*, *Gemella morbillorum*, *Gemella sanguinis*, *Gemella* sp. 933-88, *Gordonibacter pamelaeae*, *Granulicatella adiacens*, *Granulicatella elegans*, *Haemophilus influenzae*, *Haemophilus parainfluenzae*, *Herbaspirillum seropedicae*, *Kingella oralis*, *Kluyvera georgiana*, *Lachnoanaerobaculum orale*, *Lachnoanaerobaculum saburreum*, *Lachnoanaerobaculum* sp. MSX33, *Lachnoanaerobaculum* sp. OBRC5-5, *Lachnoanaerobaculum umeaense*, *Lachnospira pectinoschiza*, *Lactobacillus crispatus*, *Lactobacillus paracasei*, *Lactobacillus salivarius*, *Lactobacillus* sp. 7_1_47FAA, *Lactobacillus* sp. Akhmr01, *Lactobacillus* sp. BL302, *Lactobacillus* sp. NRCT-KU 1, *Lactobacillus vaginalis*, *Lautropia* sp. TeTO, *Leptotrichia buccalis*, *Leptotrichia* genomosp. C1, *Leptotrichia goodfellowii*, *Leptotrichia hofstadii*, *Leptotrichia hongkongensis*, *Leptotrichia shahii*, *Leptotrichia* sp. PG10, *Leptotrichia* sp. PTE15, *Leptotrichia* sp. oral taxon 223, *Leptotrichia* sp. oral taxon 225, *Leptotrichia trevisanii*, *Leptotrichia wadei*, *Lysinibacillus* sp. SJ2SN2, *Mannheimia granulomatis*, *Megamonas funiformis*, *Megasphaera* genomosp. C1, *Megasphaera massiliensis*, *Megasphaera micronuciformis*, *Megasphaera* sp. UPII 199-6, *Methanobrevibacter smithii*, *Methanosphaera stadtmanae*, *Methylobacterium longum*, *Methylobacterium* sp. RK-2008-1, *Mogibacterium pumilum*, *Mogibacterium* sp. CM50, *Mogibacterium* sp. CM96, *Mogibacterium timidum*, *Moraxella* sp. WB19-16, *Mycoplasma falconis*, *Mycoplasma salivarium*, *Mycoplasma subdolum*, *Neisseria bacilliformis*, *Neisseria elongata*, *Neisseria flavescens*, *Neisseria macacae*, *Neisseria mucosa*, *Neisseria oralis*, *Neisseria shayeganii*, *Neisseria sicca*, *Neisseria skkuensis*, *Neisseria* sp. 104(2012), *Odoribacter laneus*, *Odoribacter splanchnicus*, *Olsenella* sp. F000004, *Oribacterium* sp. CM12, *Oribacterium* sp. oral taxon 078, *Oribacterium* sp. oral taxon 102, *Oribacterium* sp. oral taxon 108, *Parabacteroides distasonis*, *Parabacteroides faecis*, *Parabacteroides goldsteinii*, *Parabacteroides gordonii*, *Parabacteroides johnsonii*, *Parabacteroides merdae*, *Parascardovia denticolens*, *Parasutterella excrementihominis*, *Parvimonas micra*, *Parvimonas* sp. oral taxon 393, *Peptococcus* sp. oral taxon 168, *Peptoniphilus* sp. 2002-2300004, *Peptoniphilus* sp. gpac018A, *Peptostreptococcus stomatis*, *Phascolarctobacterium faecium*, *Phascolarctobacterium* sp. 377, *Phascolarctobacterium succinatutens*, *Porphyromonas bennonis*, *Porphyromonas catoniae*, *Porphyromonas endodontalis*, *Porphyromonas gingivalis*, *Porphyromonas uenonis*, *Prevotella aurantiaca*, *Prevotella bivia*, *Prevotella disiens*, *Prevotella intermedia*, *Prevotella nanceiensis*, *Prevotella nigrescens*, *Prevotella oralis*, *Prevotella oris*, *Prevotella oulorum*, *Prevotella pallens*, *Prevotella* sp. WAL 2039G, *Prevotella* sp. oral taxon 299, *Prevotella* sp. oral taxon G60, *Propionibacterium* sp. MSP09A, *Pseudomonas* sp. KB23, *Pseudopropionibacterium propionicum*, *Rhizobium* sp. T45, *Robinsoniella* sp. KNHs210, *Rodentibacter pneumotropicus*, *Roseburia faecis*, *Roseburia hominis*, *Roseburia intestinalis*, *Roseburia inulinivorans*, *Roseburia* sp. 11SE39, *Rothia aeria*, *Rothia dentocariosa*, *Rothia mucilaginosa*, *Rothia* sp. CCUG 25688, *Rothia* sp. THG-N7, *Scardovia wiggsiae*, *Selenomonas* genomosp. P5, *Selenomonas* sp. CM52, *Shuttleworthia* sp. oral taxon G69, *Slackia* sp. NATTS, *Solobacterium moorei*, *Solobacterium* sp. S4-A19, *Staphylococcus epidermidis*, *Staphylococcus* sp. 334802, *Staphylococcus* sp. C912, *Stomatobaculum longum*, *Streptococcus dentirousetti*, *Streptococcus gordonii*, *Streptococcus infantis*, *Streptococcus intermedius*, *Streptococcus mitis*, *Streptococcus mutans*, *Streptococcus parasanguinis*, *Streptococcus peroris*, *Streptococcus* sp. 11aTha1, *Streptococcus* sp. 2011_Oral_MS_A3, *Streptococcus* sp. 2011_Oral_MS_H4, *Streptococcus* sp. BS35a, *Streptococcus* sp. GMD6S, *Streptococcus* sp. oral taxon G59, *Streptococcus* sp. oral taxon G63, *Streptococcus thermophilus*, *Subdoligranulum variabile*, *Sutterella stercoricanis*, *Sutterella wadsworthensis*, *Tannerella forsythia*, *Tannerella* sp. oral taxon HOT-286, *Terrisporobacter glycolicus*, *Tessaracoccus lapidicaptus*, *Vagococcus* sp. SIX2(2011), *Varibaculum cambriense*, *Veillonella atypica*, *Veillonella dispar*, *Veillonella parvula*, *Veillonella rogosae*, *Veillonella* sp. 2011_Oral_VSA_B12, *Veillonella* sp. 2011_Oral_VSA_D3, *Veillonella* sp. 6_1_27, *Veillonella* sp. CM60, *Veillonella* sp. JL-2, *Veillonella* sp. oral taxon 780, *Veillonella tobetsuensis*, [*Collinsella*] *massiliensis*, *Abiotrophia*, *Acetitomaculum*, *Achromobacter*, *Actinobacillus*, *Actinomyces*, *Aerococcus*, *Aggregatibacter*, *Akkermansia*, *Alistipes*, *Alloprevotella*, *Alloscardovia*, *Alysiella*, *Anaerobacillus*, *Anaerococcus*, *Anaeroglobus*, *Anaeroplasma*, *Anaerosporobacter*, *Anaerostipes*, *Anaerotruncus*, *Anaerovorax*, *Asaccharospora*, *Atopobium*, *Barnesiella*, *Bergeriella*, *Bergeyella*, *Bifidobacterium*, *Bilophila*, *Blautia*, *Brevundimonas*, *Butyricimonas*, *Butyrivibrio*, *Campylobacter*, *Candidatus Saccharimonas*, *Candidatus Soleaferrea*, *Capnocytophaga*, *Cardiobacterium*, *Catenibacterium*, *Catonella*, *Centipeda*, *Chryseobacterium*, *Clostridium*, *Collinsella*, *Comamonas*, *Coprobacter*, *Corynebacterium*, *Cryptobacterium*, *Delftia*, *Desulfobulbus*, *Dialister*, *Dolosigranulum*, *Dorea*, *Eggerthella*, *Eggerthia*, *Eikenella*, *Eisenbergiella*, *Enterococcus*, *Enterorhabdus*, *Erysipelatoclostridium*, *Faecalibacterium*, *Fibrobacter*, *Filifactor*, *Finegoldia*, *Flavobacterium*, *Flavonifractor*, *Fretibacterium*, *Fusicatenibacter*, *Fusobacterium*, *Gardnerella*, *Gemella*, *Gordonibacter*, *Granulicatella*, *Haemophilus*, *Herbaspirillum*, *Howardella*, *Intestinibacter*, *Intestinimonas*, *Johnsonella*, *Kingella*, *Kluyvera*, *Lachnoanaerobaculum*, *Lachnospira*, *Lactobacillus*, *Lautropia*, *Leptotrichia*, *Marvinbryantia*, *Megamonas*, *Megasphaera*, *Methanobrevibacter*, *Methanosphaera*, *Methylobacterium*, *Mogibacterium*, *Moraxella*, *Moryella*, *Mycobacterium*, *Neisseria*, *Odoribacter*, *Olsenella*, *Oribacterium*, *Oscillibacter*, *Oscillospira*, *Pantoea*, *Parabacteroides*, *Paraprevotella*, *Parascardovia*, *Parasporobacterium*, *Parasutterella*, *Parvimonas*, *Pasteurella*,

*Peptoclostridium, Peptococcus, Peptostreptococcus, Porphyromonas, Prevotella, Propionibacterium, Pseudobutyrivibrio, Rhizobium, Roseburia, Rothia, Sarcina, Scardovia, Selenomonas, Shuttleworthia, Solobacterium, Sphingomonas, Staphylococcus, Stomatobaculum, Streptococcus, Subdoligranulum, Sutterella, Tannerella, Terrisporobacter, Tessaracoccus, Vagococcus, Veillonella, Victivallis.*

29. The method of claim 12, wherein the first sleep-related condition comprises a shift work condition, wherein determining user microbiome features comprises determining the user microbiome composition features comprising a set of composition features associated with a nose site and with at least one of: *Abiotrophia defectiva, Achromobacter xylosoxidans, Acidovorax* sp. LR05, *Acinetobacter radioresistens, Acinetobacter* sp. 423D, *Acinetobacter* sp. C-S-NA3, *Acinetobacter* sp. HD5.2, *Acinetobacter* sp. RBE2CD-114, *Acinetobacter* sp. WB22-23, *Acinetobacter ursingii, Actinobacillus porcinus, Actinomyces dentalis, Actinomyces europaeus, Actinomyces* genomosp. C1, *Actinomyces georgiae, Actinomyces graevenitzii, Actinomyces israelii, Actinomyces neuii, Actinomyces odontolyticus, Actinomyces radingae, Actinomyces* sp. ICM54, *Actinomyces* sp. ICM58, *Actinomyces* sp. S4-C9, *Actinomyces* sp. oral taxon 175, *Actinomyces viscosus, Actinotignum schaalii, Aerococcus christensenii, Aerococcus* sp. B43(2010), *Aerococcus urinae, Aerococcus viridans, Aeromonas salmonicida, Aeromonas* sp. B11, *Aerosphaera taetra, Aggregatibacter aphrophilus, Aggregatibacter segnis, Akkermansia muciniphila, Albidovulum inexpectatum, Alistipes finegoldii, Alistipes putredinis, Alkalibacterium* sp. 1-5, *Alkanindiges illinoisensis, Alloiococcus otitis, Alloprevotella rava, Alloprevotella tannerae, Anaerobacillus alkalidiazotrophicus, Anaerococcus lactolyticus, Anaerococcus murdochii, Anaerococcus octavius, Anaerococcus provencensis, Anaerococcus* sp. 8404299, *Anaerococcus* sp. 8405254, *Anaerococcus* sp. 9401487, *Anaerococcus* sp. PH9, *Anaerococcus* sp. S8 87-3, *Anaerococcus* sp. S8 F2, *Anaerococcus tetradius, Anaerococcus vaginalis, Anaerostipes* sp. 5_1_63FAA, *Aquabacterium* sp. Aqua2, *Atopobium* sp. S3MV26, *Atopobium* sp. S3PFAA1-4, *Atopobium* sp. S4-A11a, *Bacillus cereus, Bacillus pseudofirmus, Bacillus* sp. T41, *Bacteroides dorei, Bacteroides* sp. AR20, *Bacteroides* sp. AR29, *Bacteroides* sp. J1511, *Bacteroides vulgatus, Bergeyella* sp. AF14, *Bergeyella zoohelcum, Bifidobacterium bifidum, Bifidobacterium longum, Bifidobacterium* sp., *Bifidobacterium stercoris, Blastococcus aggregatus, Blautia faecis, Blautia luti, Blautia wexlerae, Bosea* sp. R-46060, *Brachybacterium faecium, Brachybacterium muris, Bradyrhizobium* sp. 68A4SAPT, *Bradyrhizobium* sp. CCBAU 53380, *Bradyrhizobium* sp. MG-2011-42-CD, *Brevibacterium massiliense, Brevibacterium paucivorans, Brevibacterium ravenspurgense, Brevibacterium* sp. MBTD_CMFRI_Br02, *Brevundimonas diminuta, Brevundimonas* sp. FXJ8.080, *Brevundimonas* sp. JW23.4a, *Brevundimonas* sp. V3M6, *Brevundimonas* sp. a101-97, *Brochothrix thermosphacta, Burkholderia* sp. CBPB-HIM, *Campylobacter sputorum, Campylobacter ureolyticus, Capnocytophaga cynodegmi, Capnocytophaga gingivalis, Capnocytophaga granulosa, Capnocytophaga* sp. oral taxon 329, *Capnocytophaga sputigena, Cardiobacterium hominis, Caulobacter* sp., *Centipeda periodontii, Chryseobacterium anthropi, Chryseobacterium* sp. IIL-Nv8, *Chryseobacterium* sp. PYR2, *Chryseobacterium* sp. Y1D, *Citrobacter* sp. BW4, *Collinsella aerofaciens, Corynebacterium argentoratense, Corynebacterium atypicum, Corynebacterium canis, Corynebacterium caspium, Corynebacterium diphtheriae, Corynebacterium durum, Corynebacterium freiburgense, Corynebacterium glucuronolyticum, Corynebacterium mastitidis, Corynebacterium matruchotii, Corynebacterium* sp., *Corynebacterium* sp. 713182/2012, *Corynebacterium* sp. NML 97-0186, *Corynebacterium* sp. NML96-0085, *Corynebacterium* sp. jw37, *Corynebacterium spheniscorum, Corynebacterium ulcerans, Curvibacter gracilis, Cutibacterium acnes, Cutibacterium avidum, Cutibacterium granulosum, Deinococcus* sp. UAC-77, *Deinococcus taklimakanensis, Delftia lacustris, Delftia* sp. BN-SKY3, *Dermabacter hominis, Dermabacter* sp. HFH0086, *Dermacoccus* sp. Ellin183, *Dermacoccus* sp. SST-20, *Dialister invisus, Dialister micraerophilus, Dialister propionicifaciens, Dialister* sp. E2_20, *Dialister succinatiphilus, Dolosigranulum pigrum, Dorea formicigenerans, Dorea longicatena, Enterobacter cloacae, Enterobacter* sp. BS2-1, *Enterococcus faecalis, Enterococcus* sp. SI-4, *Eremococcus coleocola, Facklamia hominis, Facklamia languida, Facklamia* sp. 1440-97, *Facklamia* sp. 164-92, *Faecalibacterium prausnitzii, Fastidiosipila sanguinis, Finegoldia magna, Finegoldia* sp. S8 F7, *Finegoldia* sp. S9 AA1-5, *Flavobacterium johnsoniae, Flavobacterium rivuli, Flavobacterium* sp. CS43, *Flavobacterium* sp. EP372, *Flavobacterium* sp. ICM 1082, *Fusicatenibacter saccharivorans, Fusobacterium nucleatum, Fusobacterium periodonticum, Fusobacterium* sp. ACB2, *Fusobacterium* sp. CM21, *Fusobacterium* sp. CM22, *Fusobacterium* sp. OBRC1, *Gardnerella* sp. S3PF20, *Gardnerella vaginalis, Gemella morbillorum, Gemella* sp. 933-88, *Globicatella sanguinis, Granulicatella adiacens, Granulicatella elegans, Haemophilus influenzae, Haemophilus parainfluenzae, Halomonas* sp. VS-102, *Helcococcus sueciensis, Jonquetella anthropi, Klebsiella* sp. B12, *Kluyvera georgiana, Kocuria rhizophila, Kocuria* sp. LW2-LEV12-W, *Kocuria* sp. M1-36, *Kocuria* sp. M2T9B2, *Kocuria* sp. PDM-7, *Kytococcus* sp. YB227, *Lachnoanaerobaculum saburreum, Lachnospira pectinoschiza, Lactobacillus crispatus, Lactobacillus curvatus, Lactobacillus iners, Lactobacillus plantarum, Lactobacillus reuteri, Lactobacillus rhamnosus, Lactobacillus salivarius, Lactobacillus* sp. 7_1_47FAA, *Lactobacillus* sp. TAB-26, *Lactococcus lactis, Lactococcus* sp. MH5-2, *Lautropia* sp. TeTO, *Leptotrichia buccalis, Leptotrichia hongkongensis, Leptotrichia* sp. PTE15, *Leptotrichia* sp. oral taxon 225, *Leptotrichia wadei, Leuconostoc lactis, Luteimonas aestuarii, Lysinibacillus* sp. SJ2SN2, *Lysinibacillus sphaericus, Massilia oculi, Massilia* sp. hp37, *Megasphaera micronuciformis, Megasphaera* sp. UPII 199-6, *Mesorhizobium loti, Mesorhizobium* sp. mat916, *Methylobacterium adhaesivum, Methylobacterium* sp. CBMB45, *Methylobacterium* sp. JC86, *Methylobacterium* sp. RK-200008-1, *Microbacterium lacticum, Microbacterium* sp. PcRB024, *Microbacterium xylanilyticum, Micrococcus luteus, Micrococcus* sp. WB18-01, *Mobiluncus mulieris, Mogibacterium pumilum, Moraxella caprae, Moraxella catarrhalis, Moraxella lincolnii, Moraxella* sp., *Moraxella* sp. BBN2P-02d, *Moraxella* sp. WB19-16, *Morganella morganii, Murdochiella* sp. S9 PR-10, *Mycobacterium chelonae, Negativicoccus* sp. S5-A15, *Negativicoccus succinicivorans, Neisseria canis, Neisseria elongata, Neisseria macacae, Neisseria mucosa, Neisseria oralis, Neisseria skkuensis, Nesterenkonia* sp. JS3, *Nosocomiicoccus ampullae, Ochrobactrum* sp. LC498, *Ochrobactrum* sp. SCTS14, *Ochrobactrum tritici, Odoribacter splanchnicus, Pantoea vagans, Pedobacter heparinus, Pelomonas aquatica, Peptococcus* sp. oral taxon 168, *Peptoniphilus coxii, Peptoniphilus duerdenii, Peptoniphilus lacrimalis, Peptoniphilus* sp. 1-14, *Peptoniphilus* sp. 2002-2300004, *Peptoniphilus* sp. 2002-38328, *Peptoniphilus* sp. 7-2, *Peptoniphilus* sp. DNF00840, *Peptoniphilus* sp. JCM 8143, *Peptoniphilus* sp. S9 PR-13, *Peptoniphilus* sp. gpac018A, *Peptoniphilus* sp. gpac148, *Peptoniphilus* sp. oral taxon 375, *Peptoniphilus* sp. oral taxon 836, *Peptostreptococcus anaerobius*, *Peptostreptococcus stomatis*, *Peredibacter starrii*, *Phyllobacterium* sp. T50, *Porphyrobacter* sp. NMC22, *Porphyromonas asaccharolytica*, *Porphyromonas bennonis*, *Porphyromonas catoniae*, *Porphyromonas endodontalis*, *Porphyromonas somerae*, *Prevotella bivia*, *Prevotella buccalis*, *Prevotella disiens*, *Prevotella nanceiensis*, *Prevotella nigrescens*, *Prevotella oris*, *Prevotella oulorum*, *Prevotella pallens*, *Prevotella* sp. S4-10, *Prevotella timonensis*, *Propionibacterium* sp. KPL1844, *Propionibacterium* sp. KPL2005, *Propionibacterium* sp. MSP09A, *Propionibacterium* sp. V07/12348, *Propionimicrobium lymphophilum*, *Pseudochrobactrum* sp. a001-58, *Pseudoclavibacter bifida*, *Pseudoclavibacter* sp. Timone, *Pseudoglutamicibacter albus*, *Pseudomonas aeruginosa*, *Pseudomonas agarici*, *Pseudomonas brenneri*, *Pseudomonas monteilii*, *Pseudomonas* sp. CBMAI 1177, *Pseudomonas* sp. DQ-01, *Pseudomonas* sp. G1116, *Pseudomonas* sp. GmFRB014, *Pseudomonas* sp. GmFRB023, *Pseudomonas* sp. KB23, *Pseudomonas* sp. PDD-27b-3, *Pseudomonas* sp. PcFRB100, *Pseudomonas* sp. a101-18-2, *Pseudomonas* sp. a111-5, *Pseudomonas syringae*, *Pseudonocardia* sp. MB03-A, *Rahnella* sp. BSP18, *Ralstonia* sp. A52, *Ralstonia* sp. S2.MAC.005, *Rhizobium etli*, *Rhizobium* sp. 10II, *Rhizobium* sp. T45, *Rhodococcus erythropolis*, *Rhodopseudomonas boonkerdii*, *Roseburia faecis*, *Roseburia intestinalis*, *Roseburia inulinivorans*, *Roseburia* sp. 11SE39, *Rothia aeria*, *Rothia dentocariosa*, *Rothia* sp. BBH4, *Rothia* sp. THG-N7, *Shewanella* sp. bk_8, *Shinella* sp. DR33, *Solanum lycopersicum*, *Solobacterium moorei*, *Sphingobacterium* sp. KB45, *Sphingobium* sp. LC341, *Sphingobium yanoikuyae*, *Sphingomonas aerolata*, *Sphingomonas aquatilis*, *Sphingomonas oligophenolica*, *Sphingomonas* sp. 24T, *Sphingomonas* sp. 540, *Sphingomonas* sp. KOPRI 25661, *Sphingomonas* sp. PDD-26b-16, *Staphylococcus aureus*, *Staphylococcus equorum*, *Staphylococcus saprophyticus*, *Staphylococcus* sp. 334802, *Staphylococcus* sp. C9I2, *Staphylococcus* sp. L10, *Staphylococcus* sp. WB18-16, *Staphylococcus vitulinus*, *Stenotrophomonas* sp. C-S-TSA3, *Stenotrophomonas* sp. KITS-1, *Stenotrophomonas* sp. N017, *Stenotrophomonas* sp. Z2-S2, *Stomatobaculum longum*, *Streptococcus oralis*, *Streptococcus parasanguinis*, *Streptococcus peroris*, *Streptococcus pneumoniae*, *Streptococcus sobrinus*, *Streptococcus* sp. 11aTha1, *Streptococcus* sp. 2011_Ileo_MS_A10, *Streptococcus* sp. 2011_Oral_MS_A3, *Streptococcus* sp. BS35a, *Streptococcus* sp. oral taxon G59, *Streptococcus thermophilus*, *Subdoligranulum variabile*, *Tannerella forsythia*, *Tessaracoccus* sp. SL014B-79A, *Trueperella bernardiae*, *Turicella otitidis*, *Turicibacter sanguinis*, *Varibaculum cambriense*, *Varibaculum* sp. CCUG 45114, *Variovorax* sp. MM43Nov, *Veillonella atypica*, *Veillonella parvula*, *Veillonella rogosae*, *Veillonella seminalis*, *Veillonella* sp. AS16, *Veillonella* sp. CM60, *Veillonella* sp. oral taxon 780, *Weissella confusa*, *Xenophilus* sp. XB36, *Yersinia enterocolitica* Abiotrophia, Achromobacter, Acidovorax, Acinetobacter, Actinobacillus, Actinobaculum, Actinomyces, Aerococcus, Aeromonas, Aerosphaera, Aggregatibacter, Akkermansia, Albidovulum, Alistipes, Alkalibacterium, Alkanindiges, Alloiococcus, Alloprevotella, Anaerobacillus, Anaerococcus, Anaerostipes, Anaerotruncus, Aquabacterium, Arthrobacter, Bacillus, Bacteroides, Bergeyella, Blautia, Bordetella, Bosea, Brachybacterium, Brachymonas, Bradyrhizobium, Brevibacterium, Brevundimonas, Brochothrix, Campylobacter, Candidatus Saccharimonas, Candidatus Xiphinematobacter, Capnocytophaga, Cardiobacterium, Caulobacter, Centipeda, Chryseobacterium, Citrobacter, Clostridium, Collinsella, Conchiformibius, Corynebacterium, Curvibacter, Cutibacterium, Defluviimnas, Deinococcus, Delftia, Dermabacter, Dermacoccus, Dialister, Dolosigranulum, Dorea, Duganella, Dyadobacter, Enterobacter, Enterococcus, Epilithonimonas, Eremococcus, Erysipelao stridium, Facklamia, Faecalibacterium, Ferruginibacter, Finegoldia, Flavobacterium, Flavonifractor, Fusibacter, Fusicatenibacter, Fusobacterium, Gardnerella, Gemella, Globicatella, Granulicatella, Haemophilus, Halomonas, Helcococcus, Herbaspirillum, Hymenobacter, Intestinibacter, Janthinobacterium, Jonquetella, Klebsiella, Kluyvera, Kocuria, Kytococcus, Lachnoanaerobaculum, Lachnospira, Lactobacillus, Lactococcus, Lautropia, Leptotrichia, Leucobacter, Leuconostoc, Lysinibacillus, Massilia, Megasphaera, Mesorhizobium, Methylobacterium, Microbacterium, Micrococcus, Mogibacterium, Moraxella, Morganella, Moryella, Murdochiella, Myroides, Negativicoccus, Neisseria, Nesterenkonia, Nosocomiicoccus, Novosphingobium, Ochrobactrum, Odoribacter, Oribacterium, Pantoea, Parvimonas, Pelomonas, Peptococcus, Peptoniphilus, Peptostreptococcus, Peredibacter, Phyllobacterium, Porphyrobacter, Porphyromonas, Prevotella, Propionibacterium, Propionimicrobium, Proteus, Pseudobutyrivibrio, Pseudochrobactrum, Pseudoclavibacter, Pseudomonas, Pseudonocardia, Ralstonia, Rhizobium, Rhodobacter, Rhodococcus, Rhodopseudomonas, Roseburia, Rothia, Rubellimicrobium, Sarcina, Shewanella, Shinella, Shuttleworthia, Solanum, Solirubrobacter, Solobacterium, Sphingobium, Sphingomonas, Staphylococcus, Stenotrophomonas, Stomatobaculum, Streptococcus, Subdoligranulum, Tessaracoccus, Thalassospira, Trueperella, Turicella, Turicibacter, Varibaculum, Variovorax, Veillonella, Xenophilus, Yersinia.

30. The method of claim 12, wherein the first sleep-related condition comprises a shift work condition, wherein determining user microbiome features comprises determining the user microbiome composition features comprising a set of composition features associated with a skin site and with at least one of: *Achromobacter xylosoxidans*, *Acinetobacter baumannii*, *Acinetobacter kyonggiensis*, *Acinetobacter radioresistens*, *Acinetobacter* sp. C-S-NA3, *Acinetobacter* sp. C049, *Acinetobacter* sp. HD5.2, *Acinetobacter* sp. RBE2CD-114, *Acinetobacter* sp. RBE2CD-76, *Acinetobacter* sp. T133, *Acinetobacter* sp. WB22-23, *Acinetobacter ursingii*, *Actinobacillus porcinus*, *Actinomyces dentalis*, *Actinomyces* genomosp. C1, *Actinomyces georgiae*, *Actinomyces gerencseriae*, *Actinomyces neuii*, *Actinomyces odontolyticus*, *Actinomyces radingae*, *Actinomyces* sp. ICM54, *Actinomyces* sp. oral taxon 175, *Actinomyces* sp. oral taxon 448, *Actinomyces viscosus*, *Aerococcus christensenii*, *Aeromonas salmonicida*, *Aerosphaera taetra*, *Alistipes putredinis*, *Anaerobacillus alkalidiazotrophicus*, *Anaerococcus hydrogenalis*, *Anaerococcus lactolyticus*, *Anaerococcus murdochii*, *Anaerococcus octavius*, *Anaerococcus prevotii*, *Anaerococcus provencensis*, *Anaerococcus* sp. 8404299, *Anaerococcus* sp. 8405254, *Anaerococcus* sp. 9401487, *Anaerococcus* sp. PH9, *Anaerococcus* sp. S8 87-3, *Anaerococcus* sp. S9 PR-16, *Anaerococcus tetradius*, *Anaerostipes* sp. 5_1_63FAA, *Aureimonas phyllosphaerae*, *Bacillus megaterium*, *Bacillus pseudofirmus*, *Bacillus safensis*, *Bacillus* sp. T41, *Bacteroides acidifaciens*, *Bacteroides caccae*, *Bacteroides* sp. AR20, *Bacteroides* sp. AR29, *Bacteroides* sp. EBA5-17, *Bacteroides* sp. J1511, *Bacteroides stercoris*, *Bacteroides uniformis*, *Bacteroides vulgatus*, *Blastocatella fastidiosa*, *Blastococcus aggregatus*, *Blautia faecis*, *Blautia luti*, *Blautia wexlerae*, *Bosea* sp. B0.09-49,

*Brachybacterium muris, Bradyrhizobium* sp. 68A4SAPT, *Bradyrhizobium* sp. CCBAU 53380, *Brevibacterium paucivorans, Brevibacterium ravenspurgense, Brevundimonas diminuta, Brevundimonas* sp. FXJ8.080, *Brevundimonas* sp. JW23.4a, *Brevundimonas* sp. V3M6, *Campylobacter ureolyticus, Centipeda periodontii, Chryseobacterium* sp. R064, *Chryseobacterium* sp. R31, *Chryseobacterium* sp. SOZ3-3181, *Chryseomicrobium imtechense, Citrobacter* sp. BW4, *Cloacibacterium normanense, Collinsella aerofaciens, Comamonas jiangduensis, Comamonas* sp. HM_AF10, *Corynebacterium argentoratense, Corynebacterium canis, Corynebacterium capitovis, Corynebacterium diphtheriae, Corynebacterium durum, Corynebacterium epidermicanis, Corynebacterium felinum, Corynebacterium freiburgense, Corynebacterium glucuronolyticum, Corynebacterium mastitidis, Corynebacterium matruchotii, Corynebacterium* sp., *Corynebacterium* sp. NML 97-0186, *Corynebacterium* sp. jw37, *Corynebacterium spheniscorum, Cutibacterium acnes, Cutibacterium avidum, Cutibacterium granulosum, Delftia lacustris, Delftia* sp. BN-SKY3, *Dermabacter hominis, Dermabacter* sp. HFH0086, *Dermacoccus* sp. Ellin183, *Dermacoccus* sp. SST-20, *Dialister propionicifaciens, Dietzia cinnamea, Dietzia* sp. ISA13, *Dolosigranulum pigrum, Dorea formicigenerans, Dorea longicatena, Elizabethkingia meningoseptica, Enterobacter cloacae, Exiguobacterium* sp. icr3, *Facklamia* sp. 164-92, *Facklamia tabacinasalis, Faecalibacterium prausnitzii, Faecalibacterium* sp. canine oral taxon 147, *Fastidiosipila sanguinis, Finegoldia magna, Finegoldia* sp. BV3C29, *Finegoldia* sp. S9 AA1-5, *Flavobacterium lindanitolerans, Flavobacterium qiangtangense, Flavobacterium* sp. CS43, *Fusicatenibacter saccharivorans, Fusobacterium nucleatum, Fusobacterium* sp. ACB2, *Gaiella occulta, Gardnerella vaginalis, Gemella morbillorum, Gemella* sp. 933-88, *Geobacillus stearothermophilus, Globicatella sanguinis, Gordonia terrae, Granulicatella adiacens, Haemophilus influenzae, Haemophilus parainfluenzae, Helcococcus sueciensis, Herbaspirillum huttiense, Klebsiella* sp. B12, *Kluyvera georgiana, Kocuria marina, Kocuria rhizophila, Lachnoanaerobaculum saburreum, Lachnospira pectinoschiza, Lactobacillus crispatus, Lactobacillus fornicalis, Lactobacillus iners, Lactobacillus* sp. 7_1_47FAA, *Leptotrichia hofstadii, Leptotrichia wadei, Lysinibacillus* sp. SJ2SN2, *Lysinibacillus sphaericus, Lysobacter brunescens, Malassezia restricta, Marmoricola aurantiacus, Massilia* sp. S5-252-1, *Massilia* sp. TMT4-34, *Massilia* sp. hp37, *Megasphaera* sp. UPII 199-6, *Meiothermus silvanus, Mesorhizobium loti, Mesorhizobium* sp. mat916, *Methylobacterium adhaesivum, Methylobacterium* sp. 399, *Methylobacterium* sp. 57, *Methylobacterium* sp. CBMB45, *Methylobacterium* sp. Gh-143, *Methylobacterium* sp. RK-2008-1, *Microbacterium lacticum, Microbacterium paraoxydans, Microbacterium* sp. GGC-P2D, *Microbacterium* sp. absalar, *Microbacterium yannicii, Micrococcus luteus, Micrococcus* sp. WB18-01, *Moraxella catarrhalis, Moraxella nonliquefaciens, Morganella morganii, Mycobacterium* sp. 18 GUW, *Mycobacterium* sp. C0183, *Mycobacterium* sp. UNC410CL29Cvi84, *Negativicoccus* sp. S5-A15, *Neisseria macacae, Neisseria mucosa, Novosphingobium* sp. THA_AIK7, *Nubsella zeaxanthinifaciens, Ochrobactrum* sp. LC498, *Ochrobactrum* sp. SCTS14, *Odoribacter splanchnicus, Pantoea vagans, Parabacteroides distasonis, Parasutterella excrementihominis, Parvimonas micra, Paucibacter* sp. 186, *Pelomonas aquatica, Peptococcus* sp. S9 Pr-12, *Peptoniphilus lacrimalis, Peptoniphilus* sp. 2002-2300004, *Peptoniphilus* sp. 2002-38328, *Peptoniphilus* sp. 7-2, *Peptoniphilus* sp. BV3AC2, *Peptoniphilus* sp. DNF00192, *Peptoniphilus* sp. S9 PR-13, *Peptoniphilus* sp. gpac018A, *Peptoniphilus* sp. gpac148, *Peptoniphilus* sp. oral taxon 375, *Peptostreptococcus anaerobius, Phascolarctobacterium faecium, Phyllobacterium* sp. T50, *Porphyromonas asaccharolytica, Porphyromonas bennonis, Porphyromonas somerae, Porphyromonas* sp. 2024b, *Prevotella buccalis, Prevotella disiens, Prevotella oulorum, Propionibacterium* sp. KPL1844, *Propionibacterium* sp. KPL2005, *Propionibacterium* sp. MSP09A, *Propionibacterium* sp. V07/12348, *Propionimicrobium lymphophilum, Pseudoclavibacter* sp. Timone, *Pseudoglutamicibacter albus, Pseudomonas citronellolis, Pseudomonas monteilii, Pseudomonas* sp. DQ-01, *Pseudomonas* sp. G1116, *Pseudomonas* sp. KB23, *Pseudomonas* sp. KVS86, *Pseudomonas* sp. PDD-27b-3, *Pseudomonas* sp. PKG89, *Pseudomonas* sp. PcFRB072, *Pseudomonas* sp. PcFRB119, *Pseudomonas* sp. a101-18-2, *Pseudomonas* sp. a111-5, *Pseudonocardia* sp. ARG1, *Psychrobacter* sp. S1-1, *Ralstonia* sp. A52, *Ralstonia* sp. S2.MAC.005, *Rhizobium etli, Rhizobium nepotum, Rhizobium* sp. 10II, *Rhizobium* sp. T45, *Rhizobium* sp. sc-w, *Rhodococcus erythropolis, Roseburia faecis, Roseburia intestinalis, Roseburia* sp. 11SE39, *Roseomonas cervicalis, Rothia dentocariosa, Rothia mucilaginosa, Rothia* sp. THG-N7, *Salinibacterium* sp. MDT1-9-1, *Selenomonas* genomosp. P5, *Shinella* sp. DR33, *Skermanella aerolata, Solanum lycopersicum, Solirubrobacter* sp. Gsoil 921, *Solobacterium moorei, Sphingobacterium* sp. HTc4-a, *Sphingobium* sp. LC341, *Sphingomonas aerolata, Sphingomonas anadarae, Sphingomonas mathurensis, Sphingomonas* sp. 540, *Sphingomonas* sp. DS-3PS-11, *Sphingomonas* sp. HEXBA01, *Sphingomonas* sp. KOPRI 25661, *Sphingomonas* sp. URHD0057, *Staphylococcus aureus, Staphylococcus epidermidis, Staphylococcus saprophyticus, Staphylococcus* sp. 334802, *Staphylococcus* sp. C-D-MA2, *Staphylococcus* sp. C9I2, *Staphylococcus* sp. FXY54, *Stenotrophomonas pavanii, Stenotrophomonas* sp. C-S-TSA3, *Stenotrophomonas* sp. I_35-G5PA9A1, *Stenotrophomonas* sp. I_63-LFP1A9B1, *Stenotrophomonas* sp. KITS-1, *Stenotrophomonas* sp. N017, *Stomatobaculum longum, Streptococcus gordonii, Streptococcus parasanguinis, Streptococcus peroris, Streptococcus sobrinus, Streptococcus* sp. 11aTha1, *Streptococcus* sp. BS35a, *Streptococcus* sp. oral taxon G59, *Streptococcus thermophilus, Subdoligranulum variabile, Tessaracoccus* sp. SL014B-79A, *Trueperella bernardiae, Turicella otitidis, Varibaculum* sp. CCUG 45114, *Veillonella parvula, Veillonella* sp. 2011_Oral_VSA_D3, *Veillonella* sp. CM60, *Veillonella* sp. MSA12, *Veillonella* sp. oral taxon 780, *Acidothermus, Acidovorax, Acinetobacter, Actinobacillus, Actinobaculum, Actinomyces, Actinomycetospora, Aerococcus, Aeromonas, Aerosphaera, Aggregatibacter, Akkermansia, Alistipes, Aloprevotella, Amnibacterium, Anaerobacillus, Anaerococcus, Anaerostipes, Anaerotruncus, Arcanobacterium, Aurantimonas, Azospira, Bacillus, Bacteroides, Bifidobacterium, Blastocatella, Blautia, Bosea, Brachybacterium, Bradyrhizobium, Brevibacterium, Brevundimonas, Bryobacter, Butyricimonas, Campylobacter, Capnocytophaga, Caulobacter, Cellulosimicrobium, Centipeda, Chryseobacterium, Chryseomicrobium, Citrobacter, Clostridium, Collinsella, Comamonas, Corynebacterium, Cutibacterium, Defluviimonas, Deinococcus, Delftia, Dermabacter, Dermacoccus, Dialister, Dietzia, Dolosigranulum, Dorea, Dyadobacter, Elizabethkingia, Enterobacter, Enterococcus, Erysipelatoclostridium, Exiguobacterium, Facklamia, Faecalibacterium, Fastidiosipila, Ferruginibacter, Finegoldia, Flavobacterium, Flavonifractor, Fluviicola, Frigoribacterium, Fusicatenibacter, Fusobacterium, Gaiella, Gallicola, Gard-* nerella, Gemella, Gemmata, Gemmatimonas, Geobacillus, Globicatella, Granulicatella, Granulicella, Haemophilus, Halomonas, Helcococcus, Herbaspirillum, Hymenobacter, Intestinibacter, Janthinobacterium, Jatrophihabitans, Johnsonella, Klebsiella, Kluyvera, Kocuria, Kurthia, Lachnospira, Lactobacillus, Lactococcus, Leptotrichia, Leucobacter, Leuconostoc, Lysinibacillus, Lysobacter, Malassezia, Marmoricola, Massilia, Meiothermus, Mesorhizobium, Methylobacterium, Microbacterium, Micrococcus, Microlunatus, Morganella, Moryella, Murdochiella, Mycobacterium, Negativicoccus, Neisseria, Nocardioides, Novosphingobium, Nubsella, Ochrobactrum, Odoribacter, Paenibacillus, Pantoea, Parabacteroides, Parasutterella, Parvimonas, Patulibacter, Paucibacter, Pelomonas, Peptoclostridium, Peptoniphilus, Peptostreptococcus, Phascolarctobacterium, Phyllobacterium, Porphyromonas, Prevotella, Propionibacterium, Proteus, Pseudobutyrivibrio, Pseudoclavibacter, Pseudolabrys, Pseudomonas, Pseudonocardia, Ralstonia, Raoultella, Rhizobium, Rhodococcus, Rhodoplanes, Roseburia, Roseomonas, Rothia, Rubellimicrobium, Rummeliibacillus, Salinibacterium, Sarcina, Selenomonas, Serratia, Shewanella, Shuttleworthia, Skermanella, Solanum, Solirubrobacter, Solobacterium, Sphingobacterium, Staphylococcus, Stenotrophomonas, Stomatobaculum, Streptococcus, Streptomyces, Subdoligranulum, Sutterella, Terrisporobacter, Tessaracoccus, Truepera, Trueperella, Turicella, Variovorax, Veillonella, Weissella, Xanthomonas, Zymomonas.

* * * * *